United States Patent
Xiao et al.

(10) Patent No.: US 10,865,191 B2
(45) Date of Patent: Dec. 15, 2020

(54) HETEROCYCLIC COMPOUNDS USEFUL AS MODULATORS OF TNF ALPHA

(71) Applicant: BRISTOL-MYERS SQUIBB COMPANY, Princeton, NJ (US)

(72) Inventors: Hai-Yun Xiao, Belle Mead, NJ (US); T. G. Murali Dhar, Newtown, PA (US); Ning Li, Basking Ridge, NJ (US); Jingwu Duan, Yardley, PA (US); Bin Jiang, Bryn Mawr, PA (US); Zhonghui Lu, King of Prussia, PA (US); Khehyong Ngu, Pennington, NJ (US); William J. Pitts, Newtown, PA (US); Joseph A. Tino, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/887,214

(22) PCT Filed: Aug. 2, 2016

(86) PCT No.: PCT/US2016/045110
§ 371 (c)(1),
(2) Date: Feb. 2, 2018

(87) PCT Pub. No.: WO2017/023905
PCT Pub. Date: Feb. 9, 2017

(65) Prior Publication Data
US 2018/0222883 A1    Aug. 9, 2018

Related U.S. Application Data

(60) Provisional application No. 62/200,424, filed on Aug. 3, 2015.

(51) Int. Cl.
| | | |
|---|---|---|
| *C07D 401/00* | (2006.01) | |
| *C07D 401/04* | (2006.01) | |
| *C07D 401/14* | (2006.01) | |
| *C07D 405/14* | (2006.01) | |
| *C07D 413/14* | (2006.01) | |
| *C07D 215/42* | (2006.01) | |
| *C07D 405/12* | (2006.01) | |
| *C07D 409/12* | (2006.01) | |
| *C07D 413/12* | (2006.01) | |
| *C07D 417/12* | (2006.01) | |
| *C07D 471/04* | (2006.01) | |
| *C07D 215/44* | (2006.01) | |
| *C07D 401/12* | (2006.01) | |

(52) U.S. Cl.
CPC ......... *C07D 401/04* (2013.01); *C07D 215/42* (2013.01); *C07D 215/44* (2013.01); *C07D 401/12* (2013.01); *C07D 401/14* (2013.01); *C07D 405/12* (2013.01); *C07D 405/14* (2013.01); *C07D 409/12* (2013.01); *C07D 413/12* (2013.01); *C07D 413/14* (2013.01); *C07D 417/12* (2013.01); *C07D 471/04* (2013.01)

(58) Field of Classification Search
CPC .................................................... C07D 401/00
See application file for complete search history.

(56) References Cited

U.S. PATENT DOCUMENTS

| | | |
|---|---|---|
| 5,391,553 A | 2/1995 | Shutske et al. |
| 7,294,624 B2 | 11/2007 | Duan et al. |
| 2017/0037025 A1 | 2/2017 | Brown et al. |

(Continued)

FOREIGN PATENT DOCUMENTS

| | | |
|---|---|---|
| WO | WO02096879 A1 | 12/2002 |
| WO | WO03053969 A1 | 7/2003 |
| WO | WO05009969 A1 | 2/2005 |

(Continued)

OTHER PUBLICATIONS

American Chemical Society Chemical Abstract Service. STN RN 856095-09-5. (Entered into STN/first available to public on Jul. 20, 2005). (Year: 2005).*

American Chemical Society Chemical Abstract Service. CAS RN #: 82240-91-3. First available to public/entered into STN: Nov. 16, 1984. (Year: 1984).*

American Chemical Society Chemical Abstract Service. CAS RN#: 82240-89-9. First available to public/entered into STN: Nov. 16, 1984. (Year: 1984).*

(Continued)

*Primary Examiner* — John S Kenyon
(74) *Attorney, Agent, or Firm* — Gary Greenblatt

(57) ABSTRACT

Disclosed are compounds of Formula (I) or a salt thereof, wherein: A is $CR_1$ or N; B is $CR_3$ or N; D is $CR_4$ or N; $L_1$ is —$(CR_7R_7)_m$—; $L_2$ is —$(CR_7R_7)_n$—; and X, Z, $R_1$, $R_2$, $R_3$, $R_4$, $R_5$, and $R_6$ are define herein. Also disclosed are methods of using such compounds as modulators of TNFα, and pharmaceutical compositions comprising such compounds. These compounds are useful in treating inflammatory and autoimmune diseases.

(I)

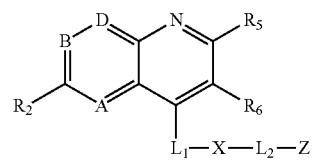

4 Claims, 5 Drawing Sheets

(56) References Cited

U.S. PATENT DOCUMENTS

2017/0233380 A1   8/2017   Das et al.

FOREIGN PATENT DOCUMENTS

| WO | WO 2009/155121 A2 | 12/2009 | |
| --- | --- | --- | --- |
| WO | WO-2012016082 A1 * | 2/2012 | ........... C07D 409/04 |
| WO | WO 2014/009295 A1 | 1/2014 | |
| WO | WO14071109 A1 | 5/2014 | |
| WO | WO14159837 A1 | 10/2014 | |
| WO | WO2017021384 A1 | 2/2017 | |
| WO | WO2017167993 A1 | 10/2017 | |

OTHER PUBLICATIONS

Degorce, Sébastien L., et al., "Discovery of Novel 3-Quinoline Carboxamides as Potent, Selective, and Orally Bioavailable Inhibitors of Ataxia Telangiectasia Mutated (ATM) Kinase", Journal of Medicinal Chemistry, Jun. 3, 2016, vol. 59, pp. 6281-6292.

Ochiana, Stefan O., et al., "Repurposing human PDE4 inhibitors for neglected tropical diseases. Evaluation of analogs of the human PDE4 inhibitor GSK-256066 as inhibitors of PDEB1 of Trypanosoma brucei", Chemical Biology and Drug Design, May 1, 2015, vol. 85, pp. 549-564.

Staderini, Matteo, et al., "Lewis Acid-Catalyzed Generation of C—C and C—N Bonds on pi-Deficient Heterocyclic Substrates", Advanced Synthesis and Catalysis, Dec. 8, 2014, vol. 357, No. 1, pp. 185-195.

Green, Neal, et al., "Inhibitors of Tumor Progression Loci-2 (Tpl2) Kinase and Tumor Necrosis Factor alpha (TNF-alpha) Production: Selectivity and in Vivo Antiinflammatory Activity of Novel 8-Substituted-4-anilino-6-aminoquinoline-3-carbonitriles", J. Med. Chem., 2007, vol. 50, pp. 4728-4745.

Teli, Mahesh Kumar, et al., "Pharmacophore generation and atom-based 3D-QSAR of novel quinoline-3-carbonitrile derivatives as Tpl2 kinase inhibitors", Journal of Enzyme Inhibition and Medicinal Chemistry, 2012, vol. 27, No. 4, pp. 558-570.

* cited by examiner

HETEROCYCLIC COMPOUNDS USEFUL AS MODULATORS OF TNF ALPHA

CROSS-REFERENCE TO RELATED APPLICATIONS

This application is a national phase application under 35 U.S.C. § 371 of International Patent Application No. PCT/US2016/045110, filed Aug. 2, 2016, which claims priority to U.S. Provisional Application No. 62/200,424, filed Aug. 3, 2015, which are expressly incorporated fully herein by reference.

The present invention generally relates to heterocyclic compounds useful as modulators of TNFα signaling. Provided herein are heterocyclic compounds, compositions comprising such compounds, and methods of their use. The invention further pertains to pharmaceutical compositions containing at least one compound according to the invention that are useful for the treatment of conditions related to TNFα activity, including inflammatory and autoimmune disorders.

TNFα is the first and archetypical member of the TNF superfamily (TNFSF) of ligands. TNFSF ligands are involved in the regulation of several key biological processes including cell differentiation, cell survival, cell death, and inflammation. Ligands of the TNF superfamily play a pivotal role in the regulation and orchestration of the immune and inflammatory responses at multiple levels. A common structural feature of TNFSF ligands is the formation of trimeric complexes that can bind to and activate specific TNFSF receptors. Similar to several other family members, TNFα is a type II transmembrane protein that can be secreted as a soluble form following proteolytic cleavage by a metalloprotease. Both the transmembrane and soluble forms of TNFα form biologically active trimeric complexes that signal through TNF receptors 1 and 2. TNFα can act on multiple cell types (T cells, monocytes, endothelial cells) through TNFRs to induce activation of the immune system, production of inflammatory cytokines, osteoclastogenesis, and cell death.

Based on their physiological and pathophysiological functions, TNF and TNFSF ligands are implicated in the pathogenesis of a number of inflammatory and autoimmune disorders (see, for example, E. C. Keystone et al., *J Rheumatol*, 2010, 37, 27-39; and L. M. Sedger & M. F. McDermott, *Cytokine Growth Factor Rev*, 2014, 25(4), 453-72). To date, a number of TNFα modulating agents have been developed and are commercially available. The mechanism of action of clinically-proven protein-based therapeutic agents directed against TNFα is to act as competitive antagonists to inhibit TNFα from binding to TNFR1 and TNFR2. These agents include antibodies specific to TNFα including adalimumab, golimumab, certolizumab pegol, and infliximab. Another approved agent for the treatment of TNFα-mediated disorders is etanercept, a chimera of the immunoglobulin molecule and the TNFR2 ectodomain which also prevents TNFα from binding to the cellular receptors.

Being modulators of human TNFα activity, the heterocyclic compounds are beneficial in the treatment and/or prevention of a number of human maladies. These include inflammatory and autoimmune disorders, neurological and neurodegenerative disorders, pain and nociceptive disorders, cardiovascular disorders, metabolic disorders, ocular disorders, and oncological disorders.

WO 2013/186229, WO 2014/009295, and WO 2014/009296 disclose compounds useful as modulators of TNFα.

In view of the numerous conditions that are contemplated to benefit by treatment involving modulation of TNF, it is immediately apparent that new compounds capable of modulating the signaling of TNFα and methods of using these compounds should provide substantial therapeutic benefits to a wide variety of patients.

The present invention relates to a new class of heterocyclic compounds found to be effective inhibitors of TNFα activity. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of TNFα, and are useful for the treatment of inflammatory and autoimmune disorders, neurological and neurodegenerative disorders, cardiovascular disorders, metabolic disorders, ocular disorders, and oncological disorders; or stereoisomers, tautomers, pharmaceutically acceptable salts, solvates or prodrugs thereof.

The present invention also provides pharmaceutical compositions comprising a pharmaceutically acceptable carrier and at least one of the compounds of Formula (I) or stereoisomers, tautomers, pharmaceutically acceptable salts, solvates, or prodrugs thereof.

The present invention also provides a method for modulation of TNFα comprising administering to a host in need of such treatment a therapeutically effective amount of at least one of the compounds of Formula (I) or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of Formula (I) or stereoisomers, tautomers, pharmaceutically acceptable salts, solvates, or prodrugs thereof.

One embodiment provides a method for treating inflammatory and autoimmune diseases. Particular, inflammatory and autoimmune diseases include, but are not limited to, systemic lupus erythematosus, psoriasis, Crohn's disease, ulcerative colitis, asthma, graft versus host disease, allograft rejection, chronic obstructive pulmonary disease, Graves' disease, rheumatoid arthritis, lupus nephritis, cutaneous lupus, ankylosing spondylitis, cryopyrin-associated periodic syndromes (CAPS), TNF receptor associated periodic syndrome (TRAPS), Wegener's granulomatosis, sarcoidosis, familial Mediterranean fever (FMF), adult onset stills, systemic onset juvenile idiopathic arthritis, psoriatic arthritis, multiple sclerosis, neuropathic pain, gout, and gouty arthritis.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of inflammatory and autoimmune diseases.

The present invention also provides a compound of Formula (I) or a pharmaceutical composition in a kit with instructions for using the compound or composition.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

BRIEF DESCRIPTION OF THE DRAWINGS

The invention is illustrated by reference to the accompanying drawings described below.

DETAILED DESCRIPTION

Figure 1:
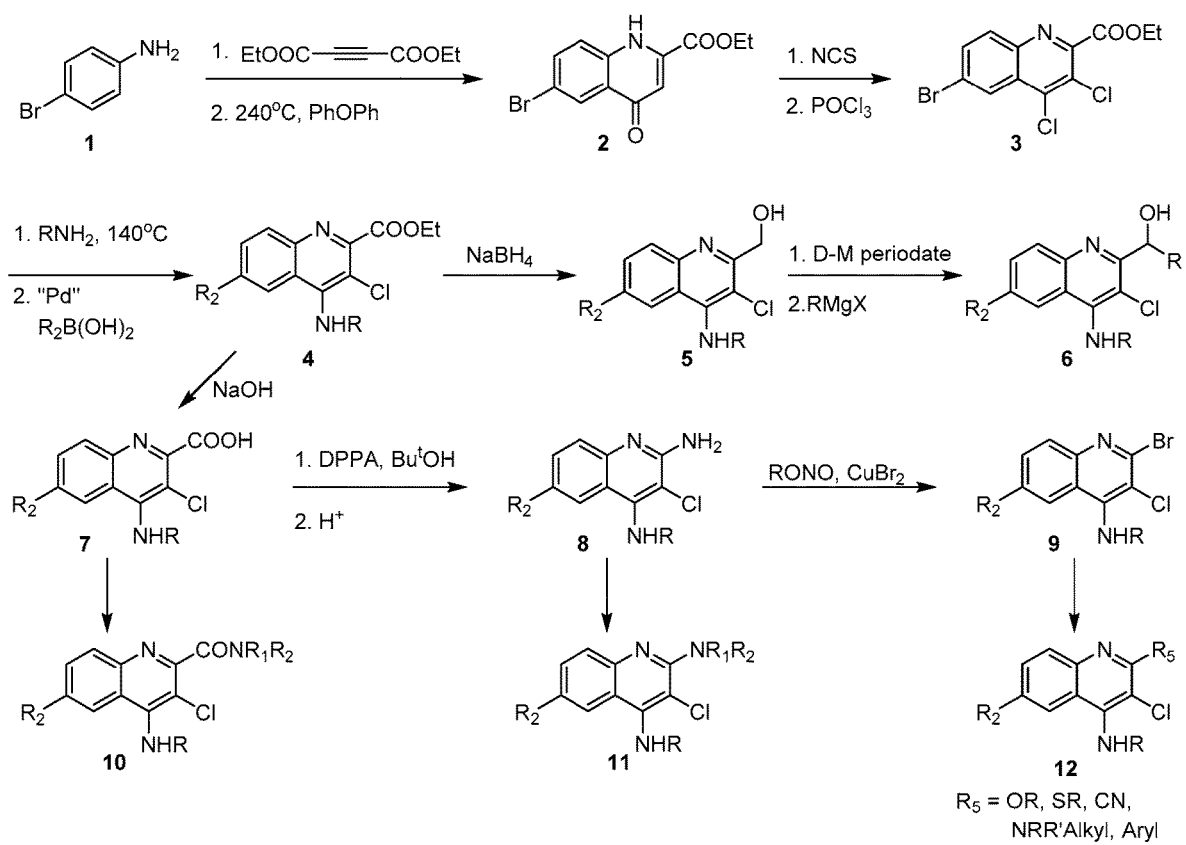
FIG. 1 shows the general synthesis of compounds of Formula (I) according to Scheme 1.

The first aspect of the present invention provides at least one compound of Formula (I):

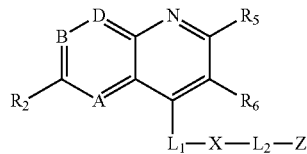

(I)

or a salt thereof, wherein:
A is $CR_1$ or N;
B is $CR_3$ or N;
D is $CR_4$ or N;
X is a bond, —O—, —S—, or —$NR_8$—;
$L_1$ is —$(CR_7R_7)_m$—;
$L_2$ is —$(CR_7R_7)_n$—;
Z is a cyclic group selected from carbocyclyl, heterocyclyl, aryl, and heteroaryl, wherein said cyclic group is substituted with zero to 3 $R_a$;
$R_1$ is H, halo, —CN, $C_{1-4}$ alkyl, $C_{1-6}$ haloalkyl, or $C_{1-3}$ alkoxy;
$R_2$ is H, $R_{1a}$, $C_{1-6}$ haloalkyl, $C_{2-6}$ alkenyl substituted with zero to 6 $R_{1a}$, $C_{2-6}$ alkynyl substituted with zero to 4 $R_{1a}$, —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 7-membered heterocyclyl substituted with zero to 3 $R_{1a}$), or —$(CR_gR_g)_r$(mono- or bicyclic heteroaryl substituted with zero to 3 $R_{1a}$);
$R_3$ is H, halo, —CN, —$CF_3$, —$OCF_3$, —$NO_2$, $C_{1-6}$ alkyl substituted with zero to 6 $R_{1a}$, —$(CR_gR_g)_rOR_e$, —$(CR_gR_g)_rNR_cR_c$, —$(CR_gR_g)_rS(O)_pR_b$, —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 7-membered heterocyclyl substituted with zero to 3 $R_{1a}$), or —$(CR_gR_g)_r$(monocyclic heteroaryl substituted with zero to 3 $R_{1a}$);
$R_4$ is H, halo, —CN, $C_{1-4}$ alkyl, $C_{1-6}$ haloalkyl, or $C_{1-3}$ alkoxy;
$R_5$ and $R_6$ are independently H, halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —C(O)$OR_h$, —C(O)$NR_hR_h$, —$NR_hR_h$, —$NR_hC(O)NR_cR_c$, —$NR_hC(O)R_y$, —$NR_hC(O)OR_h$, —$NR_hS(O)_2NR_cR_c$, or —$NR_hS(O)_2R_y$; or $R_5$ and $R_6$ together with the carbons to which they are attached form a 5- to 7-membered carbocyclic or a heterocyclic ring;
each $R_7$ is independently H, —OH, $C_{1-3}$ alkyl, $C_{1-3}$ fluoroalkyl, $C_{1-3}$ hydroxyalkyl, $C_{1-2}$ aminoalkyl, —$CH_2CH$=$CH_2$, $C_{3-6}$ cycloalkyl, phenyl or —$NR_hR_h$; or two $R_7$ along with the carbon atom to which they are attached form a 3- to 7-membered spirocarbocyclyl or spiroheterocyclyl group;
$R_8$ is H or $C_{1-3}$ alkyl;
each $R_{1a}$ is independently F, Cl, Br, —CN, $C_{1-6}$ alkyl substituted with zero to 6 $R_a$, $C_{3-6}$ cycloalkyl substituted with zero to 6 $R_a$, $C_{1-3}$ alkoxy substituted with zero to 7 $R_a$, heterocyclyl substituted with zero to 6 $R_a$, aryl substituted with zero to 6 $R_a$, mono- or bicyclic heteroaryl substituted with zero to 6 $R_a$, —C(O)$R_b$, —C(O)$OR_b$, —C(O)$NR_cR_c$, —OC(O)$R_b$, —OC(O)$NR_cR_c$, —OC(O)$OR_d$, —$NR_cR_c$, —$NR_bC(O)R_d$, —$NR_bC(O)OR_d$, —$NR_bS(O)_pR_d$, —$NR_bC(O)NR_cR_c$, —$NR_bS(O)_pNR_cR_c$, —$S(O)_pR_b$, —$S(O)_pNR_cR_c$, or —C(O)$NR_b(CH_2)_{1-3}NR_cR_c$;
each $R_a$ is independently halo, —CN, —OH, —$NO_2$, —$NH_2$, —$N_3$, $C_{1-7}$ alkyl substituted with zero to 6 $R_w$; $C_{2-4}$ alkenyl, $C_{2-4}$ alkynyl, $C_{1-3}$ alkoxy, $C_{1-3}$ fluoroalkoxy, $C_{1-3}$ hydroxyalkoxy, —O(CH=$CH_2$), —$(CH_2)_rC(O)OH$, —O$(CH_2)_rC(O)OH$, —$(CH_2)_rC(O)(C_{1-6}$ alkyl), —C(O)O$(C_{1-4}$ alkyl), —OC(O)$(C_{1-3}$ alkyl), —NH$(C_{1-6}$ alkyl), —N$(C_{1-3}$ alkyl$)_2$, —$(CH_2)_{0-2}C(O)NH_2$, —$(CH_2)_{0-2}C(O)$ NH$(C_{1-3}$ alkyl), —$(CH_2)_{0-2}C(O)N(C_{1-3}$ alkyl$)_2$, —OC(O) NH$(C_{1-3}$ alkyl), —C(O)CH$(NH_2)(CH_2)_{1-2}C(O)OH$, —C(O)CH$(NH_2)(CH_2)_{1-2}OH$, —C(O)$(CH_2)_{1-2}C(O)OH$, —C(O)$(C_{2-4}$ alkenyl), —C(O)$(C_{2-4}$ alkynyl), —C≡CH, —C≡C(phenyl), —NHC(O)$NH_2$, —NHC(O)NH$(C_{1-3}$ alkyl), —CH=NOH, —C(=NH)$(NH_2)$, $C_{3-7}$ carbocyclyl, aryl, 5- to 7-membered heterocyclyl, monocyclic or bicyclic heteroaryl, —$(CH_2)_r$(aryl), —$(CH_2)_r$(heteroaryl), —O(aryl), —O(benzyl), —O(heterocyclyl), —O(heteroaryl), —$S(O)_2NH_2$, —$S(O)_2CH_2CH_2C(O)OC_{1-3}$ alkyl), —$S(O)_p(C_{1-3}$ alkyl), —$S(O)_p$(aryl), —$S(O)_p$(heterocyclyl), —$NHS(O)_2$(aryl), —$NHS(O)_2$(heterocyclyl), —$NHS(O)_2NH$(aryl), —$NHS(O)_2NH$(heterocyclyl), —NH(aryl substituted with zero to 3 $R_x$), —NH(heterocyclyl), —NHC(O)(aryl), —NHC(O)$(C_{1-3}$ alkyl), —NHC(O)(heterocyclyl), —OC(O)(aryl), —OC(O)(heterocyclyl), —NHC(O)NH(aryl), —NHC(O)NH(heterocyclyl), —OC(O)O$(C_{1-3}$ alkyl), —OC(O)O(aryl), —OC(O)O (heterocyclyl), —OC(O)NH(aryl), —OC(O)NH(heterocyclyl), —NHC(O)O(aryl), —NHC(O)O(heterocyclyl), —NHC(O)O$(C_{1-4}$ alkyl), —C(O)NH(aryl), —C(O)NH (heterocyclyl), —C(O)O(aryl), —C(O)O(heterocyclyl), —N$(C_{1-3}$ alkyl)$S(O)_2$(aryl), —N$(C_{1-3}$ alkyl)$S(O)_2$(heterocyclyl), —N$(C_{1-3}$ alkyl)$S(O)_2NH$(aryl), —N$(C_{1-3}$ alkyl)$S$ $(O)_2NH$(heterocyclyl), —N$(C_{1-3}$ alkyl)(aryl), —N$(C_{1-3}$ alkyl)(heterocyclyl), —N$(C_{1-3}$ alkyl)C(O)(aryl), —N$(C_{1-3}$ alkyl)C(O)(heterocyclyl), —N$(C_{1-3}$ alkyl)C(O) NH(aryl), —$(CH_2)_{0-3}C(O)NH$(heterocyclyl), —OC(O)N $(C_{1-3}$ alkyl)(aryl), —OC(O)N$(C_{1-3}$ alkyl)(heterocyclyl), —N$(C_{1-3}$ alkyl)C(O)O(aryl), —N$(C_{1-3}$ alkyl)C(O)O(heterocyclyl), —C(O)N$(C_{1-3}$ alkyl)(aryl), —C(O)N$(C_{1-3}$ alkyl)(heterocyclyl), —$NHS(O)_2N(C_{1-3}$ alkyl)(aryl), —$NHS(O)_2N(C_{1-3}$ alkyl)(heterocyclyl), —$NHP(O)_2N$ $(C_{1-3}$ alkyl)(aryl), —NHC(O)N$(C_{1-3}$ alkyl)(aryl), —NHC (O)N(C$_{1-3}$ alkyl)(heterocyclyl), —N(C$_{1-3}$ alkyl)S(O)$_2$N(C$_{1-3}$ alkyl)(aryl), —(CH$_2$)$_{0-2}$C(O)NHS(O)$_2$(C$_{1-3}$ alkyl), —N(C$_{1-3}$ alkyl)S(O)$_2$N(C$_{1-3}$ alkyl)(heterocyclyl), —N(C$_{1-3}$ alkyl)C(O)N(C$_{1-3}$ alkyl)(aryl), —N(C$_{1-3}$ alkyl)C(O)N(C$_{1-3}$ alkyl)(heterocyclyl), or —Si(C$_{1-3}$ alkyl)$_3$, wherein each of said carbocyclyl, aryl, heterocyclyl, and heteroaryl is substituted with zero to 4 R$_z$; or two R$_a$ attached to the same carbon atom form =O;

each R$_b$ is independently H, C$_{1-6}$ alkyl substituted with zero to 6 R$_f$, C$_{3-7}$ cycloalkyl substituted with zero to 6 R$_f$, heterocyclyl substituted with zero to 6 R$_f$, aryl substituted with zero to 3 R$_f$, or mono- or bicyclic heteroaryl substituted with zero to 3 R$_f$;

each R$_c$ is independently H, C$_{1-6}$ alkyl substituted with zero to 6 R$_f$, C$_{3-7}$ cycloalkyl substituted with zero to 6 R$_f$, heterocyclyl substituted with zero to 6 R$_f$, aryl substituted with zero to 3 R$_f$, or mono- or bicyclic heteroaryl substituted with zero to 3 R$_f$; or two R$_c$ attached to the same nitrogen atom form a 4- to 8-membered heterocyclic ring substituted with zero to 3 R$_g$;

each R$_d$ is independently H, C$_{1-6}$ alkyl substituted with zero to 6 R$_f$, C$_{3-7}$ cycloalkyl substituted with zero to 6 R$_f$, heterocyclyl substituted with zero to 6 R$_f$, aryl substituted with zero to 3 R$_f$, or mono- or bicyclic heteroaryl substituted with zero to 3 R$_f$;

each R$_e$ is independently H, C$_{1-6}$ alkyl substituted with zero to 7 R$_f$, C$_{3-7}$ cycloalkyl substituted with zero to 6 R$_f$, heterocyclyl substituted with zero to 6 R$_f$, aryl substituted with zero to 3 R$_f$, or mono- or bicyclic heteroaryl substituted with zero to 3 R$_f$;

each R$_f$ is independently H, halo, —OH, —CN, —NH$_2$, C$_{1-6}$ alkyl substituted with zero to 6 R$_a$, C$_{1-3}$ alkoxy substituted with zero to 7 R$_a$, C$_{3-7}$ cycloalkyl substituted with zero to 6 R$_a$, heterocyclyl substituted with zero to 6 R$_a$, aryl substituted with zero to 3 R$_a$, or mono- or bicyclic heteroaryl substituted with zero to 3 R$_a$;

each R$_g$ is independently H, F, —OH, —CN, C$_{1-3}$ alkyl, —CF$_3$, or phenyl;

each R$_h$ is independently H, C$_{1-5}$ alkyl substituted with zero to 2 R$_x$, C$_{3-7}$ cycloalkyl substituted with zero to 2 R$_x$, mono- or bicyclic heterocyclyl substituted with zero to 2 R$_x$, aryl substituted with zero to 2 R$_x$, or mono- or bicyclic heteroaryl substituted with zero to 2 R$_x$;

each R$_w$ is independently F, —OH, —CN, —NH$_2$, —C(O)OH, —C(O)(C$_{1-3}$ alkyl), —C(O)NH$_2$, —C(O)NH(C$_{1-3}$ alkyl), —NHC(O)(C$_{1-3}$ alkyl), or —C(O)NHS(O)$_2$(C$_{1-3}$ alkyl);

each R$_x$ is independently H, halo, —CN, C$_{1-4}$ alkyl, C$_{1-6}$ haloalkyl, or C$_{1-3}$ alkoxy;

each R$_y$ is independently C$_{1-5}$ alkyl;

each R$_z$ is independently H, halo, —CN, C$_{1-4}$ alkyl, C$_{1-4}$ hydroxyalkyl, C$_{1-6}$ haloalkyl, C$_{1-3}$ alkoxy, —NH$_2$, —NH(C$_{1-3}$ alkyl), —N(C$_{1-3}$ alkyl)$_2$, —OC(O)(C$_{1-4}$ alkyl), —C(O)OH, —CH$_2$C(O)OH, —CH$_2$(phenyl), —CH$_2$CH$_2$(morpholinyl), —C(O)(morpholinyl), C$_{3-6}$ cycloalkyl, and morpholinyl; or two R$_z$ attached to the same carbon atom form =O;

m is zero, 1, 2, 3, or 4;
n is zero, 1, 2, 3, or 4;
each p is independently zero, 1, or 2; and
each r is independently zero, 1, 2, 3, or 4;
with the proviso that when at least one of R$_5$ and R$_6$ is H, then X is —O—, —S—, or —NR$_8$—, one of m and n is 1, 2, 3, or 4, and the other m and n is zero, 1, 2, 3, or 4.

The second aspect of the present invention provides at least one compound of Formula (I):

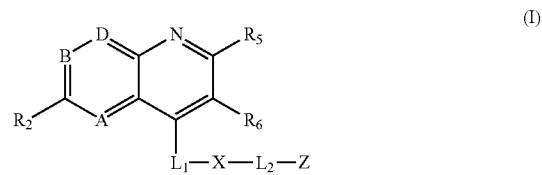

or a salt thereof, wherein:

A is CR$_1$ or N;
B is CR$_3$ or N;
D is CR$_4$ or N;
X is a bond, —O—, —S—, or —NR$_8$—;
L$_1$ is —(CR$_7$R$_7$)$_m$—;
L$_2$ is —(CR$_7$R$_7$)$_n$—;
Z is a cyclic group selected from carbocyclyl, heterocyclyl, aryl, and heteroaryl, wherein said cyclic group is substituted with zero to 3 R$_a$;
R$_1$ is H, halo, —CN, C$_{1-4}$ alkyl, C$_{1-6}$ haloalkyl, or C$_{1-3}$ alkoxy;
R$_2$ is H, R$_{1a}$, C$_{1-6}$ haloalkyl, C$_{2-6}$ alkenyl substituted with zero to 6 R$_{1a}$, C$_{2-6}$ alkynyl substituted with zero to 4 R$_{1a}$, —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 7-membered heterocyclyl substituted with zero to 3 R$_{1a}$), or —(CR$_g$R$_g$)$_r$(mono- or bicyclic heteroaryl substituted with zero to 3 R$_{1a}$);
R$_3$ is H, halo, —CN, —CF$_3$, —OCF$_3$, —NO$_2$, C$_{1-6}$ alkyl substituted with zero to 6 R$_{1a}$, —(CR$_g$R$_g$)$_r$OR$_e$, —(CR$_g$R$_g$)$_r$NR$_c$R$_c$, —(CR$_g$R$_g$)$_r$S(O)$_p$R$_b$, —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 7-membered heterocyclyl substituted with zero to 3 R$_{1a}$), or —(CR$_g$R$_g$)$_r$(monocyclic heteroaryl substituted with zero to 3 R$_{1a}$);
R$_4$ is H, halo, —CN, C$_{1-4}$ alkyl, C$_{1-6}$ haloalkyl, or C$_{1-3}$ alkoxy;
R$_5$ and R$_6$ are independently H, halo, —OH, —CN, C$_{1-5}$ alkyl substituted with zero to 6 R$_a$, C$_{3-6}$ cycloalkyl substituted with zero to 6 R$_a$, C$_{1-5}$ alkylthio substituted with zero to 6 R$_a$, arylthio substituted with zero to 6 R$_a$, C$_{1-5}$ alkoxy substituted with zero to 6 R$_a$, aryloxy substituted with zero to 6 R$_a$, —NR$_b$R$_h$, —NR$_b$C(O)NR$_c$R$_c$, —NR$_h$C(O)R$_y$, —NR$_b$S(O)$_2$NR$_c$R$_c$, or —NR$_h$S(O)$_2$R$_y$; or R$_5$ and R$_6$ together with the carbons to which they are attached form a 5- to 7-membered carbocyclic or a heterocyclic ring; each R$_7$ is independently H, C$_{1-3}$ alkyl, —OH, or —NR$_h$R$_h$; or two R$_7$ along with the carbon atom to which they are attached form a 3- to 7-membered spirocarbocyclyl or spiroheterocyclyl group;
R$_8$ is H or C$_{1-3}$ alkyl;
each R$_{1a}$ is independently F, Cl, —CN, C$_{1-6}$ alkyl substituted with zero to 6 R$_a$, C$_{3-6}$ cycloalkyl substituted with zero to 6 R$_a$, C$_{1-3}$ alkoxy substituted with zero to 7 R$_a$, heterocyclyl substituted with zero to 6 R$_a$, aryl substituted with zero to 6 R$_a$, mono- or bicyclic heteroaryl substituted with zero to 6 R$_a$, —C(O)R$_b$, —C(O)OR$_b$, —C(O)NR$_c$R$_c$, —OC(O)R$_b$, —OC(O)NR$_c$R$_c$, —OC(O)OR$_d$, —NR$_c$R$_c$, —NR$_b$C(O)R$_d$, —NR$_b$C(O)OR$_d$, —NR$_b$S(O)$_p$R$_d$, —NR$_b$C(O)NR$_c$R$_c$, —NR$_b$S(O)$_p$NR$_c$R$_c$, —S(O)$_p$R$_b$, —S(O)$_p$NR$_c$R$_c$, or —C(O)NR$_b$(CH$_2$)$_{1-3}$NR$_c$R$_c$;
each R$_a$ is independently halo, —CN, —OH, —NO$_2$, —NH$_2$, C$_{1-3}$ alkyl, C$_{1-3}$ fluoroalkyl, C$_{2-4}$ alkenyl, C$_{2-4}$ alkynyl, C$_{1-3}$ alkoxy, C$_{1-3}$ fluoroalkoxy, —(CH$_2$)$_r$C(O)OH, —C(O)(C$_{1-3}$ alkyl), —C(O)O(C$_{1-4}$ alkyl), —OC(O)

(C$_{1-3}$ alkyl), —NH(C$_{1-3}$ alkyl), —N(C$_{1-3}$ alkyl)$_2$, —C(O)NH(C$_{1-3}$ alkyl), —OC(O)NH(C$_{1-3}$ alkyl), —NHC(O)NH(C$_{1-3}$ alkyl), —C(=NH)(NH$_2$), C$_{3-7}$ carbocyclyl, aryl, 5- to 7-membered heterocyclyl, monocyclic or bicyclic heteroaryl, —O(aryl), —O(benzyl), —O(heterocyclyl), —S(O)$_p$(C$_{1-3}$ alkyl), —S(O)$_p$(aryl), —S(O)$_p$(heterocyclyl), —NHS(O)$_2$(aryl), —NHS(O)$_2$(heterocyclyl), —NHS(O)$_2$NH(aryl), —NHS(O)$_2$NH(heterocyclyl), —NH(aryl substituted with zero to 3 R$_x$), —NH(heterocyclyl), —NHC(O)(aryl), —NHC(O)(C$_{1-3}$ alkyl), —NHC(O)(heterocyclyl), —OC(O)(aryl), —OC(O)(heterocyclyl), —NHC(O)NH(aryl), —NHC(O)NH(heterocyclyl), —OC(O)O(C$_{1-3}$ alkyl), —OC(O)O(aryl), —OC(O)O(heterocyclyl), —OC(O)NH(aryl), —OC(O)NH(heterocyclyl), —NHC(O)O(aryl), —NHC(O)O(heterocyclyl), —NHC(O)O(C$_{1-3}$ alkyl), —C(O)NH(aryl), —C(O)NH(heterocyclyl), —C(O)O(aryl), —C(O)O(heterocyclyl), —N(C$_{1-3}$ alkyl)S(O)$_2$(aryl), —N(C$_{1-3}$ alkyl)S(O)$_2$(heterocyclyl), —N(C$_{1-3}$ alkyl)S(O)$_2$NH(aryl), —N(C$_{1-3}$ alkyl)S(O)$_2$NH(heterocyclyl), —N(C$_{1-3}$ alkyl)(aryl), —N(C$_{1-3}$ alkyl)(heterocyclyl), —N(C$_{1-3}$ alkyl)C(O)(aryl), —N(C$_{1-3}$ alkyl)C(O)(heterocyclyl), —N(C$_{1-3}$ alkyl)C(O)NH(aryl), —(CH$_2$)$_{0-3}$C(O)NH(heterocyclyl), —OC(O)N(C$_{1-3}$ alkyl)(aryl), —OC(O)N(C$_{1-3}$ alkyl)(heterocyclyl), —N(C$_{1-3}$ alkyl)C(O)O(aryl), —N(C$_{1-3}$ alkyl)C(O)O(heterocyclyl), —C(O)N(C$_{1-3}$ alkyl)(aryl), —C(O)N(C$_{1-3}$ alkyl)(heterocyclyl), —NHS(O)$_2$N(C$_{1-3}$ alkyl)(aryl), —NHS(O)$_2$N(C$_{1-3}$ alkyl)(heterocyclyl), —NHP(O)$_2$N(C$_{1-3}$ alkyl)(aryl), —NHC(O)N(C$_{1-3}$ alkyl)(aryl), —NHC(O)N(C$_{1-3}$ alkyl)(heterocyclyl), —N(C$_{1-3}$ alkyl)S(O)$_2$N(C$_{1-3}$ alkyl)(aryl), —N(C$_{1-3}$ alkyl)S(O)$_2$N(C$_{1-3}$ alkyl)(heterocyclyl), —N(C$_{1-3}$ alkyl)C(O)N(C$_{1-3}$ alkyl)(aryl), —N(C$_{1-3}$ alkyl)C(O)N(C$_{1-3}$ alkyl)(heterocyclyl), or —Si(C$_{1-3}$ alkyl)$_3$; or two R$_a$ attached to the same carbon atom form =O;

each R$_b$ is independently H, C$_{1-6}$ alkyl substituted with zero to 6 R$_f$, C$_{3-7}$ cycloalkyl substituted with zero to 6 R$_f$, heterocyclyl substituted with zero to 6 R$_f$, aryl substituted with zero to 3 R$_f$, or mono- or bicyclic heteroaryl substituted with zero to 3 R$_f$;

each R$_c$ is independently H, C$_{1-6}$ alkyl substituted with zero to 6 R$_f$, C$_{3-7}$ cycloalkyl substituted with zero to 6 R$_f$, heterocyclyl substituted with zero to 6 R$_f$, aryl substituted with zero to 3 R$_f$, or mono- or bicyclic heteroaryl substituted with zero to 3 R$_f$; or two R$_c$ attached to the same nitrogen atom form a 4- to 8-membered heterocyclic ring substituted with zero to 3 R$_g$;

each R$_d$ is independently H, C$_{1-6}$ alkyl substituted with zero to 6 R$_f$, C$_{3-7}$ cycloalkyl substituted with zero to 6 R$_f$, heterocyclyl substituted with zero to 6 R$_f$, aryl substituted with zero to 3 R$_f$, or mono- or bicyclic heteroaryl substituted with zero to 3 R$_f$;

each R$_e$ is independently H, C$_{1-6}$ alkyl substituted with zero to 7 R$_f$, C$_{3-7}$ cycloalkyl substituted with zero to 6 R$_f$, heterocyclyl substituted with zero to 6 R$_f$, aryl substituted with zero to 3 R$_f$, or mono- or bicyclic heteroaryl substituted with zero to 3 R$_f$;

each R$_f$ is independently H, halo, —OH, —CN, C$_{1-6}$ alkyl substituted with zero to 6 R$_a$, C$_{1-3}$ alkoxy substituted with zero to 7 R$_a$, C$_{3-7}$ cycloalkyl substituted with zero to 6 R$_a$, heterocyclyl substituted with zero to 6 R$_a$, aryl substituted with zero to 3 R$_a$, or mono- or bicyclic heteroaryl substituted with zero to 3 R$_a$;

each R$_g$ is independently H, F, —OH, —CN, C$_{1-3}$ alkyl, —CF$_3$, or phenyl;

each R$_h$ is independently H, C$_{1-5}$ alkyl substituted with zero to 2 R$_x$, C$_{3-7}$ cycloalkyl substituted with zero to 2 R$_x$, mono- or bicyclic heterocyclyl substituted with zero to 2 R$_x$, aryl substituted with zero to 2 R$_x$, or mono- or bicyclic heteroaryl substituted with zero to 2 R$_x$;

each R$_x$ is independently H, halo, —CN, C$_{1-4}$ alkyl, C$_{1-6}$ haloalkyl, or C$_{1-3}$ alkoxy;

each R$_y$ is independently C$_{1-5}$ alkyl;

m is zero, 1, 2, 3, or 4;

n is zero, 1, 2, 3, or 4;

each p is independently zero, 1, or 2; and each r is independently zero, 1, 2, 3, or 4;

with the proviso that when at least one of R$_5$ and R$_6$ is H, then X is —O—, —S—, or —NR$_8$—; one of m and n is zero, 1, 2, 3, or 4, and the other m and n is 1, 2, 3, or 4.

The third aspect of the present invention provides at least one compound of Formula (I):

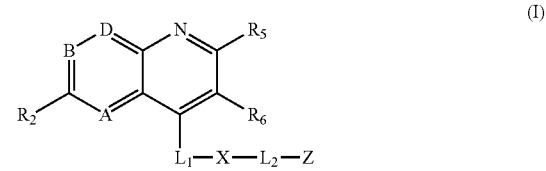

or a salt thereof, wherein:

A is CR$_1$ or N;
B is CR$_3$ or N;
D is CR$_4$ or N;
X is a —C(OH)—, —C(O)—, —C(NH$_2$)—, or —NR$_8$—;
L$_1$ is —(CR$_7$R$_7$)$_m$—;
L$_2$ is —(CR$_7$R$_7$)$_n$—;
Z is C$_{4-8}$ alkyl substituted with zero to 6 R$_q$;
R$_1$ is H, halo, —CN, C$_{1-4}$ alkyl, C$_{1-6}$ haloalkyl, or C$_{1-3}$ alkoxy;
R$_2$ is H, R$_{1a}$, C$_{1-6}$ haloalkyl, C$_{2-6}$ alkenyl substituted with zero to 6 R$_{1a}$, C$_{2-6}$ alkynyl substituted with zero to 4 R$_{1a}$, —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 7-membered heterocyclyl substituted with zero to 3 R$_{1a}$), or —(CR$_g$R$_g$)$_r$(mono- or bicyclic heteroaryl substituted with zero to 3 R$_{1a}$);
R$_3$ is H, halo, —CN, —CF$_3$, —OCF$_3$, —NO$_2$, C$_{1-6}$ alkyl substituted with zero to 6 R$_{1a}$, —(CR$_g$R$_g$)$_r$OR$_e$, —(CR$_g$R$_g$)$_r$NR$_c$R$_c$, —(CR$_g$R$_g$)$_r$S(O)$_p$R$_b$, —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 7-membered heterocyclyl substituted with zero to 3 R$_{1a}$), or —(CR$_g$R$_g$)$_r$(monocyclic heteroaryl substituted with zero to 3 R$_{1a}$);
R$_4$ is H, halo, —CN, C$_{1-4}$ alkyl, C$_{1-6}$ haloalkyl, or C$_{1-3}$ alkoxy;
R$_5$ and R$_6$ are independently H, halo, —OH, —CN, C$_{1-5}$ alkyl substituted with zero to 6 R$_a$, C$_{3-6}$ cycloalkyl substituted with zero to 6 R$_a$, C$_{1-5}$ alkylthio substituted with zero to 6 R$_a$, arylthio substituted with zero to 6 R$_a$, C$_{1-5}$ alkoxy substituted with zero to 6 R$_a$, aryloxy substituted with zero to 6 R$_a$, —C(O)OR$_h$, —C(O)NR$_h$R$_h$, —NR$_h$R$_h$, —NR$_b$C(O)NR$_c$R$_c$, —NR$_h$C(O)R$_y$, —NR$_b$C(O)OR$_b$, —NR$_b$S(O)$_2$NR$_c$R$_c$, or —NR$_h$S(O)$_2$R$_y$; or R$_5$ and R$_6$ together with the carbons to which they are attached form a 5- to 7-membered carbocyclic or a heterocyclic ring;
each R$_7$ is independently H, —OH, C$_{1-3}$ alkyl, C$_{1-3}$ fluoroalkyl, C$_{1-3}$ hydroxyalkyl, C$_{1-2}$ aminoalkyl, —CH$_2$CH=CH$_2$, C$_{3-6}$ cycloalkyl, phenyl or —NR$_h$R$_h$; or two $R_7$ along with the carbon atom to which they are attached form a 3- to 7-membered spirocarbocyclyl or spiroheterocyclyl group;

$R_8$ is H or $C_{1-3}$ alkyl;

each $R_{1a}$ is independently F, Cl, Br, —CN, $C_{1-6}$ alkyl substituted with zero to 6 $R_a$, $C_{3-6}$ cycloalkyl substituted with zero to 6 $R_a$, $C_{1-3}$ alkoxy substituted with zero to 7 $R_a$, heterocyclyl substituted with zero to 6 $R_a$, aryl substituted with zero to 6 $R_a$, mono- or bicyclic heteroaryl substituted with zero to 6 $R_a$, —C(O)$R_b$, —C(O)O$R_b$, —C(O)N$R_cR_c$, —OC(O)$R_b$, —OC(O)N$R_cR_c$, —OC(O)O$R_d$, —N$R_cR_c$, —N$R_bC(O)R_d$, —N$R_bC(O)OR_d$, —N$R_bS(O)_pR_d$, —N$R_bC(O)NR_cR_c$, —N$R_bS(O)_pNR_cR_c$, —S(O)$_pR_b$, —S(O)$_pNR_cR_c$, or —C(O)N$R_b$(CH$_2$)$_{1-3}$ N$R_cR_c$;

each $R_a$ is independently halo, —CN, —OH, —NO$_2$, —NH$_2$, —N$_3$, $C_{1-7}$ alkyl substituted with zero to 6 $R_w$; $C_{2-4}$ alkenyl, $C_{2-4}$ alkynyl, $C_{1-3}$ alkoxy, $C_{1-3}$ fluoroalkoxy, $C_{1-3}$ hydroxyalkoxy, —O(CH═CH$_2$), —(CH$_2$)$_r$C(O)OH, —O(CH$_2$)$_r$C(O)OH, —(CH$_2$)$_r$C(O)($C_{1-6}$ alkyl), —C(O)O ($C_{1-4}$ alkyl), —OC(O)($C_{1-3}$ alkyl), —NH($C_{1-6}$ alkyl), —N($C_{1-3}$ alkyl)$_2$, —(CH$_2$)$_{0-2}$C(O)NH$_2$, —(CH$_2$)$_{0-2}$C(O)NH($C_{1-3}$ alkyl), —(CH$_2$)$_{0-2}$C(O)N($C_{1-3}$ alkyl)$_2$, —OC(O)NH($C_{1-3}$ alkyl), —C(O)CH(NH$_2$)(CH$_2$)$_{1-2}$C(O)OH, —C(O)CH(NH$_2$)(CH$_2$)$_{1-2}$OH, —C(O)(CH$_2$)$_{1-2}$C(O)OH, —C(O)($C_{2-4}$ alkenyl), —C(O)($C_{2-4}$ alkynyl), —C≡CH, —C≡C(phenyl), —NHC(O)NH$_2$, —NHC(O)NH($C_{1-3}$ alkyl), —CH═NOH, —C(═NH)(NH$_2$), $C_{3-7}$ carbocyclyl, aryl, 5- to 7-membered heterocyclyl, monocyclic or bicyclic heteroaryl, —(CH$_2$)$_r$(aryl), —(CH$_2$)$_r$(heteroaryl), —O(aryl), —O(benzyl), —O(heterocyclyl), —O(heteroaryl), —S(O)$_2$NH$_2$, —S(O)$_2$CH$_2$CH$_2$C(O)O($C_{1-3}$ alkyl), —S(O)$_p$($C_{1-3}$ alkyl), —S(O)$_p$(aryl), —S(O)$_p$(heterocyclyl), —NHS(O)$_2$(aryl), —NHS(O)$_2$(heterocyclyl), —NHS(O)$_2$NH(aryl), —NHS(O)$_2$NH(heterocyclyl), —NH(aryl substituted with zero to 3 $R_x$), —NH(heterocyclyl), —NHC(O)(aryl), —NHC(O)($C_{1-3}$ alkyl), —NHC(O)(heterocyclyl), —OC(O)(aryl), —OC(O)(heterocyclyl), —NHC(O)NH(aryl), —NHC(O)NH(heterocyclyl), —OC(O)O($C_{1-3}$ alkyl), —OC(O)O(aryl), —OC(O)O (heterocyclyl), —OC(O)NH(aryl), —OC(O)NH(heterocyclyl), —NHC(O)O(aryl), —NHC(O)O(heterocyclyl), —NHC(O)O($C_{1-4}$ alkyl), —C(O)NH(aryl), —C(O)NH (heterocyclyl), —C(O)O(aryl), —C(O)O(heterocyclyl), —N($C_{1-3}$ alkyl)S(O)$_2$(aryl), —N($C_{1-3}$ alkyl)S(O)$_2$(heterocyclyl), —N($C_{1-3}$ alkyl)S(O)$_2$NH(aryl), —N($C_{1-3}$ alkyl)S (O)$_2$NH(heterocyclyl), —N($C_{1-3}$ alkyl)(aryl), —N($C_{1-3}$ alkyl)(heterocyclyl), —N($C_{1-3}$ alkyl)C(O)(aryl), —N($C_{1-3}$ alkyl)C(O)(heterocyclyl), —N($C_{1-3}$ alkyl)C(O) NH(aryl), —(CH$_2$)$_{0-3}$C(O)NH(heterocyclyl), —OC(O)N ($C_{1-3}$ alkyl)(aryl), —OC(O)N($C_{1-3}$ alkyl)(heterocyclyl), —N($C_{1-3}$ alkyl)C(O)O(aryl), —N($C_{1-3}$ alkyl)C(O)O(heterocyclyl), —C(O)N($C_{1-3}$ alkyl)(aryl), —C(O)N($C_{1-3}$ alkyl)(heterocyclyl), —NHS(O)$_2$N($C_{1-3}$ alkyl)(aryl), —NHS(O)$_2$N($C_{1-3}$ alkyl)(heterocyclyl), —NHP(O)$_2$N ($C_{1-3}$ alkyl)(aryl), —NHC(O)N($C_{1-3}$ alkyl)(aryl), —NHC (O)N($C_{1-3}$ alkyl)(heterocyclyl), —N($C_{1-3}$ alkyl)S(O)$_2$N ($C_{1-3}$ alkyl)(aryl), —(CH$_2$)$_{0-2}$C(O)NHS(O)$_2$($C_{1-3}$ alkyl), —N($C_{1-3}$ alkyl)S(O)$_2$N($C_{1-3}$ alkyl)(heterocyclyl), —N($C_{1-3}$ alkyl)C(O)N($C_{1-3}$ alkyl)(aryl), —N($C_{1-3}$ alkyl) C(O)N($C_{1-3}$ alkyl)(heterocyclyl), or —Si($C_{1-3}$ alkyl)$_3$, wherein each of said carbocyclyl, aryl, heterocyclyl, and heteroaryl is substituted with zero to 4 $R_z$; or two $R_a$ attached to the same carbon atom form ═O;

each $R_b$ is independently H, $C_{1-6}$ alkyl substituted with zero to 6 $R_f$, $C_{3-7}$ cycloalkyl substituted with zero to 6 $R_f$, heterocyclyl substituted with zero to 6 $R_f$, aryl substituted with zero to 3 $R_f$, or mono- or bicyclic heteroaryl substituted with zero to 3 $R_f$;

each $R_c$ is independently H, $C_{1-6}$ alkyl substituted with zero to 6 $R_f$, $C_{3-7}$ cycloalkyl substituted with zero to 6 $R_f$, heterocyclyl substituted with zero to 6 $R_f$, aryl substituted with zero to 3 $R_f$, or mono- or bicyclic heteroaryl substituted with zero to 3 $R_f$; or two $R_c$ attached to the same nitrogen atom form a 4- to 8-membered heterocyclic ring substituted with zero to 3 $R_g$;

each $R_d$ is independently H, $C_{1-6}$ alkyl substituted with zero to 6 $R_f$, $C_{3-7}$ cycloalkyl substituted with zero to 6 $R_f$, heterocyclyl substituted with zero to 6 $R_f$, aryl substituted with zero to 3 $R_f$, or mono- or bicyclic heteroaryl substituted with zero to 3 $R_f$;

each $R_e$ is independently H, $C_{1-6}$ alkyl substituted with zero to 7 $R_f$, $C_{3-7}$ cycloalkyl substituted with zero to 6 $R_f$, heterocyclyl substituted with zero to 6 $R_f$, aryl substituted with zero to 3 $R_f$, or mono- or bicyclic heteroaryl substituted with zero to 3 $R_f$;

each $R_f$ is independently H, halo, —OH, —CN, —NH$_2$, $C_{1-6}$ alkyl substituted with zero to 6 $R_a$, $C_{1-3}$ alkoxy substituted with zero to 7 $R_a$, $C_{3-7}$ cycloalkyl substituted with zero to 6 $R_a$, heterocyclyl substituted with zero to 6 $R_a$, aryl substituted with zero to 3 $R_a$, or mono- or bicyclic heteroaryl substituted with zero to 3 $R_a$;

each $R_g$ is independently H, F, —OH, —CN, $C_{1-3}$ alkyl, —CF$_3$, or phenyl; each $R_h$ is independently H, $C_{1-5}$ alkyl substituted with zero to 2 $R_x$, $C_{3-7}$ cycloalkyl substituted with zero to 2 $R_x$, mono- or bicyclic heterocyclyl substituted with zero to 2 $R_x$, aryl substituted with zero to 2 $R_x$, or mono- or bicyclic heteroaryl substituted with zero to 2 $R_x$;

each $R_q$ is independently H, halo, —CN, —OH, $C_{1-3}$ haloalkyl, or $C_{1-3}$ alkoxy;

each $R_w$ is independently F, —OH, —CN, —NH$_2$, —C(O) OH, —C(O)($C_{1-3}$ alkyl), —C(O)NH$_2$, —C(O)NH($C_{1-3}$ alkyl), —NHC(O)($C_{1-3}$ alkyl), or —C(O)NHS(O)$_2$($C_{1-3}$ alkyl);

each $R_x$ is independently H, halo, —CN, $C_{1-4}$ alkyl, $C_{1-6}$ haloalkyl, or $C_{1-3}$ alkoxy;

each $R_y$ is independently $C_{1-5}$ alkyl;

each $R_z$ is independently H, halo, —CN, $C_{1-4}$ alkyl, $C_{1-4}$ hydroxyalkyl, $C_{1-6}$ haloalkyl, $C_{1-3}$ alkoxy, —NH$_2$, —NH ($C_{1-3}$ alkyl), —N($C_{1-3}$ alkyl)$_2$, —OC(O)($C_{1-4}$ alkyl), —C(O)OH, —CH$_2$C(O)OH, —CH$_2$(phenyl), —CH$_2$CH$_2$ (morpholinyl), —C(O)(morpholinyl), $C_{3-6}$ cycloalkyl, and morpholinyl; or two $R_z$ attached to the same carbon atom form ═O;

m is zero, 1, 2, 3, or 4;

n is zero, 1, 2, 3, or 4;

each p is independently zero, 1, or 2; and each r is independently zero, 1, 2, 3, or 4.

One embodiment provides a compound of Formula (I) or a salt thereof, wherein A is CR$_1$; B is CR$_3$; D is CR$_4$; and R$_1$, R$_2$, R$_3$, R$_4$, R$_5$, R$_6$, L$_1$, L$_2$, X and Z are defined in the first or second aspect. The compounds of this embodiment have the structure of Formula (I-a):

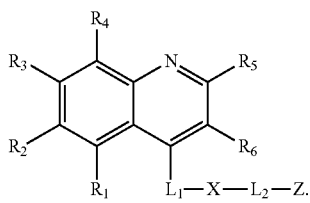

(I-a)

One embodiment provides a compound of Formula (I) or a salt thereof, wherein A is N; B is $CR_3$; D is $CR_4$; and $R_2$, $R_3$, $R_4$, $R_5$, $R_6$, $L_1$, $L_2$, X and Z are defined in the first or second aspect. The compounds of this embodiment have the structure of Formula (I-b):

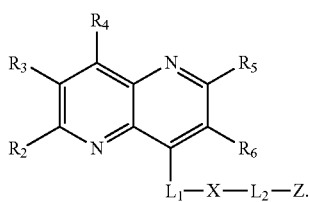

(I-b)

One embodiment provides a compound of Formula (I) or a salt thereof, wherein A is $CR_1$; B is N; D is $CR_4$; and $R_1$, $R_2$, $R_4$, $R_5$, $R_6$, $L_1$, $L_2$, X and Z are defined in the first or second aspect. The compounds of this embodiment have the structure of Formula (I-c):

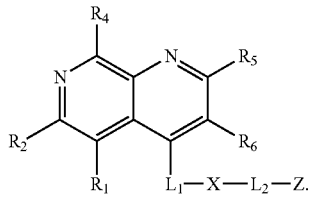

(I-c)

One embodiment provides a compound of Formula (I) or a salt thereof, wherein A is $CR_1$; B is $CR_3$; D is N; and $R_1$, $R_2$, $R_3$, $R_5$, $R_6$, $L_1$, $L_2$, X and Z are defined in the first or second aspect. The compounds of this embodiment have the structure of Formula (I-d):

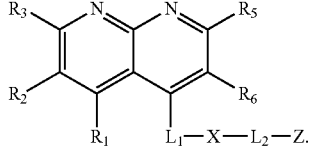

(I-d)

One embodiment provides a compound of Formula (I) or a salt thereof, wherein A is N; B is N; D is $CR_4$; and $R_2$, $R_4$, $R_5$, $R_6$, $L_1$, $L_2$, X and Z are defined in the first or second aspect. The compounds of this embodiment have the structure of Formula (I-e):

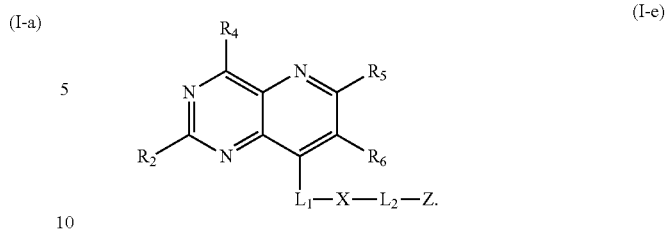

(I-e)

One embodiment provides a compound of Formula (I) or a salt thereof, wherein A is N; B is $CR_3$; D is N; and $R_2$, $R_3$, $R_5$, $R_6$, $L_1$, $L_2$, X and Z are defined in the first or second aspect. The compounds of this embodiment have the structure of Formula (I-f):

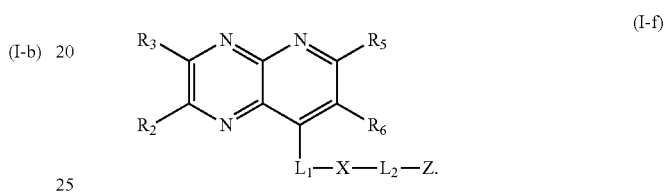

(I-f)

One embodiment provides a compound of Formula (I) or a salt thereof, wherein A is $CR_1$; B is N; D is N; and $R_1$, $R_2$, $R_5$, $R_6$, $L_1$, $L_2$, X and Z are defined in the first or second aspect. The compounds of this embodiment have the structure of Formula (I-g):

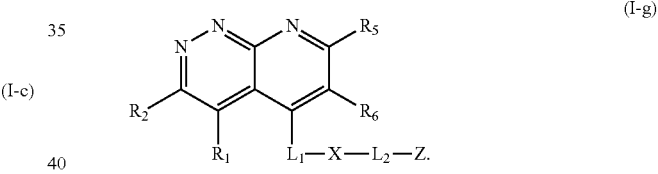

(I-g)

One embodiment provides a compound of Formula (I) or a salt thereof, wherein A is $CR_1$ or N; B is $CR_3$ or N; D is $CR_4$ or N; with the proviso that only one of A, B, and D is N; and $R_1$, $R_2$, $R_3$, $R_4$, $R_5$, $R_6$, $L_1$, $L_2$, X and Z are defined in the first or second aspect.

The compounds of this embodiment have the structures of Formula (I-b), Formula (I-c), and Formula (I-d).

One embodiment provides a compound of Formula (I) or a salt thereof, wherein A is $CR_1$ or N; B is $CR_3$ or N; D is $CR_4$ or N; with the proviso that only two of A, B, and D are N; and $R_1$, $R_2$, $R_3$, $R_4$, $R_5$, $R_6$, $L_1$, $L_2$, X and Z are defined in the first or second aspect. The compounds of this embodiment have the structures of Formula (I-e), Formula (I-f), and Formula (I-g).

One embodiment provides a compound of Formula (I) or a salt thereof, wherein A is $CR_1$ or N; B is $CR_3$ or N; D is $CR_4$ or N; provided that zero or one of A, B, and D is N; and wherein:

X is a bond, —O—, —S—, or —$NR_8$—;
Z is a cyclic group selected from $C_{3-6}$ cycloalkyl, $C_{4-6}$ cycloalkenyl, 5- to 10-membered heterocyclyl, phenyl, and 5- to 10-membered heteroaryl, wherein said cyclic group is substituted with zero to 3 $R_a$;
$R_1$ is H, F, Cl, —CN, —$CH_3$, —$CH_2F$, —$CHF_2$, —$CF_3$, or —$OCH_3$;

$R_2$ is H, $R_{1a}$, $C_{1-3}$ fluoroalkyl, $C_{2-4}$ alkenyl substituted with zero to 6 $R_{1a}$, $C_{2-4}$ alkynyl substituted with zero to 4 $R_{1a}$, $-(CR_gR_g)_r$(3- to 14-membered carbocyclyl substituted with zero to 3 $R_{1a}$), $-(CR_gR_g)_r$(phenyl substituted with zero to 3 $R_{1a}$), $-(CR_gR_g)_r$(5- to 7-membered heterocyclyl substituted with zero to 3 $R_{1a}$), or $-(CR_gR_g)_r$(mono- or bicyclic heteroaryl substituted with zero to 3 $R_{1a}$);

$R_3$ is H, F, Cl, $-CN$, $-OH$, $C_{1-2}$ alkyl, $-CF_3$, $-OCH_3$, $-OCF_3$, $-NH_2$, $-(CH_2)_r$(phenyl substituted with zero to 3 $R_{1a}$), $-(CH_2)_r$(3- to 14-membered carbocyclyl substituted with zero to 3 $R_{1a}$), $-(CH_2)_r$(phenyl substituted with zero to 3 $R_{1a}$), $-(CH_2)_r$(5- to 7-membered heterocyclyl substituted with zero to 3 $R_{1a}$), or $-(CH_2)_r$(monocyclic heteroaryl substituted with zero to 3 $R_{1a}$);

$R_4$ is H, F, Cl, $-CN$, $C_{1-2}$ alkyl, $C_{1-2}$ fluoroalkyl, or $C_{1-2}$ alkoxy;

$R_5$ and $R_6$ are independently H, F, Cl, $-OH$, $C_{1-3}$ alkyl substituted with zero to 6 $R_a$, $C_{3-6}$ cycloalkyl substituted with zero to 6 $R_a$, $C_{1-3}$ alkoxy substituted with zero to 6 $R_a$, $-C(O)OR_h$, $-C(O)NR_hR_h$, or $-NR_hR_h$;

each $R_7$ is independently H, $-OH$, $C_{1-3}$ alkyl, $C_{1-3}$ fluoroalkyl, $C_{1-3}$ hydroxyalkyl, $C_{1-2}$ aminoalkyl, $-CH_2CH=CH_2$, $C_{3-6}$ cycloalkyl, phenyl or $-NR_hR_h$; or two $R_7$ along with the carbon atom to which they are attached form a 3- to 7-membered spirocarbocyclyl group;

m is zero, 1, or 2;

n is zero, 1, 2, or 3;

each r is zero, 1, or 2; and $L_1$, $L_2$, $R_8$, $R_{1a}$, $R_a$, $R_g$, $R_h$, and r are defined in the first aspect.

One embodiment provides a compound of Formula (I) or a salt thereof, wherein:

X is a bond or $-NR_8-$;

$L_1$ is a bond or $-CH_2$;

$L_2$ is a bond, $-CH_2-$, $-CH(CH_3)-$, $-C(CH_3)_2-$, $-CH(CH_2F)-$, $-CH(CHF_2)-$, $-CH(CF_3)-$, $-CH(CH_2CH_3)-$, $-CH(CH_2CH_2F)-$, $-CH(CH_2CHF_2)-$, $-CH(CH_2CF_3)-$, $-CH(CH_2CH_2OH)-$, $-CH(CH_2N(CH_3)_2)-$, $-CH(C(CH_3)_2OH)-$, $-CH(CH_2CH=CH_2)-$, $-CH(CH_3)CH_2-$, $-CH(cyclopropyl)-$, $-CH(CH(CH_3)_2)-$, $-CH(C(CH_3)_2F)-$, $-CH(CH_3)CH_2CH_2-$, $-CH(CH_3)CH_2C(OH)(phenyl)-$, cyclopropyl, or cyclobutyl;

Z is a cyclic group selected from $C_{3-6}$ cycloalkyl, cyclopentenyl, phenyl, furanyl, imidazolyl, indolinyl, isoquinolinyl, isothiazolyl, isoxazolyl, oxazolyl, piperidinyl, pyrazinyl, pyrazolyl, pyridinyl, pyrimidinyl, thiazolyl, and thiophenyl, wherein said cyclic group is substituted with zero to 3 $R_a$;

$R_1$ is H or F;

$R_2$ is:
(i) H, F, Cl, or Br; or
(ii) dihydropyridinonyl, phenyl, piperidinyl, pyrazinyl, pyrazolyl, pyridinyl, or pyrimidinyl, each substituted with zero to 3 $R_{1a}$;

$R_3$ is H, F, or Cl;

$R_4$ is H, F, or Cl;

$R_5$ is H, $-OH$, $-CH_3$, $-CH_2OH$, $-CH_2NH_2$, $-CH_2N_3$, $-C(O)OH$, $-C(O)NH(CH_3)$, $-C(O)N(CH_3)_2$, $-C(O)OCH_2CH_3$, $-CH_2NH(dimethylphenyl)$, $-C(O)NH(pyridinyl)$, $-C(O)NH(phenyl)$, or $-CH_2O(pyridinyl)$;

$R_6$ is H, F, Cl, or $-CH_3$;

$R_8$ is H, $-CH_3$, or $-CH_2CH_3$;

each $R_{1a}$ is independently F, $-CN$, $-CH_3$, $-CH_2CH_3$, $-CH_2OH$, $-C(CH_3)_2OH$, $-CH(OH)CH_2OH$, $-CH(CH_3)(OH)CH_2OH$, $-C(CH_2F)_2OH$, $-C(CH_3)_2NHC(O)CH_3$, $-C(O)NH_2$, $-C(O)NHCH_2CH_2CH_2NH_2$, $-C(O)NHCH_3$, $-C(O)OH$, $-CH(C(O)OCH_3)CH_2NH_2$, $-CH(CH_2OH)NHC(O)CH_3$, $-CH(NH_2)CH_2OH$, $-CH(NH_2)CH_2C(O)OH$, $-CH_2CH(NH_2)C(O)OH$, $-CH_2NH(CH_2CH_3)$, $-CH_2NHC(O)CH_3$, $-CH_2NHC(O)NH_2$, $-CH(OH)CH_2NH(CH_3)$, $-NH(CH_3)$, $-NHCH_2CH_2OH$, $-NHCH_2CH(OH)CH_2OH$, $-NHCH_2C(CH_3)_2OH$, $-NHCH(CH_2OH)_2$, $-NHCH_2C(O)NH_2$, $-NHCH_2C(O)OH$, $-NHCH(CH_3)C(O)NH_2$, $-NHCH_2CH(OH)CH_2OH$, $-N(CH_3)C(O)CH=CH_2$, $-OCH_2CH_3$, $-S(O)_2CH_3$, $-S(O)_2NH(CH_3)$, $-CH_2(azetidinyl)$, $-CH_2(piperazinyl)$, $-CH_2(butoxycarbonyl piperazinyl)$, $-CH(OH)(cyclopropyl)$, $-CH(OH)CH_2(morpholinyl)$, $-CH(OH)CH_2(carboxypyrrolidinyl)$, $-NH(carbamoylcyclopropyl)$, $C_{3-6}$ cycloalkyl substituted with 1 to 2 substituents independently selected from $-OH$, $-NH_2$, $-NHC(O)NH_2$, $-NHC(O)CH_3$, $-NHCH_2CH_2OH$, $-NHS(O)_2CH_3$, $-CH_2OH$, $-C(O)OH$, and $-C(O)CH_3$; hydroxybutanonyl, hydroxypyrrolidinyl, carboxypyrrolidinyl, methoxycarbonylpyrrolidinyl, hydroxypropylpyrrolidinyl, hydroxypyranyl, hydroxyoxetanyl, hydroxymethylmorpholinyl, dioxohydroxytetrahydrothiopyranyl, piperidinyl substituted with 1 to 2 substituents independently selected from $-NH_2$, $-C(O)OH$, $-CH_2C(O)OH$, $-C(CH_3)_2OH$, and $-C(O)OCH_2CH_3$; piperazinyl substituted with zero or 1 substituent selected from $-CH_2OH$, $-CH_2CN$, $-CH_2C(O)OH$, $-CH_2C(O)OCH_3$, $-CH_2C(O)NH_2$, $-CH_2C(O)NHCH_3$, $-CH(C(O)OCH_3)CH_2NHC(O)CH_3$, $-CH(C(O)OH)CH_2NH_2$, $-CH_2C(O)NHS(O)_2CH_3$, $-CH_2C(O)NHCH_2C(O)OH$, $-CH(C(O)OH)CH_2NHC(O)CH_3$, $-CH(C(O)OH)CH_2NHC(O)OC(CH_3)_3$, $-C(O)OH$, $-C(O)CH(CH_3)OH$, $-C(O)CH(NH_2)CH_2C(O)OH$, $-C(O)CH(NH_2)CH_2OH$, $-C(O)CH_2CH_2C(O)OH$, $-C(O)CH=CH_2$, $-C(O)C\equiv CH$, $-CH_2(tetrazolyl)$, and pyrrolidinonyl; piperazinonyl, carboxymethylpiperazinonyl, morpholinyl, dioxothiomorpholinyl, carboxy-azabicyclo[3.2.1]octanyl, or pyridinyl;

each $R_a$ is independently F, Cl, Br, $-CN$, $-OH$, $-CH_3$, $-CH_2CH_3$, $-CH=CH_2$, $-C\equiv C(phenyl)$, $-CF_3$, $-CH_2OH$, $-CH_2CH_2OH$, $-CH(CH_3)OH$, $-CH_2CH_2CH_2OH$, $-C(CH_3)_2OH$, $-CH(OH)CH_2OH$, $-CH_2CH(OH)CH_2OH$, $-C(CH_3)(OH)CH_2OH$, $-CH(OH)CH(CH_3)CH_2CH(CH_3)_2$, $-CH_2NH_2$, $-CH(NH_2)CH_2OH$, $-CH(NH_2)CH(CH_3)CH_2CH_3$, $-CH_2C(O)NH_2$, $-CH_2CH_2C(O)NH_2$, $-CH_2(phenyl)$, $-C(O)CH_3$, $-C(O)NH_2$, $-C(O)NH(CH_3)$, $-C(O)NH(CH_2CH_3)$, $-C(O)N(CH_3)_2$, $-C(O)CH(CH_3)CH_2CH_3$, $-C(O)(pyrazolyl)$, $-C(O)(pyridinyl)$, $-C(O)NH(phenyl)$, $-C(O)OH$, $-CH_2C(O)OH$, $-CH_2CH_2C(O)OH$, $-C(O)OCH_3$, $-C(O)OC(CH_3)_3$, $-CH=NOH$, $-OCHF_2$, $-OCH_3$, $-OCF_3$, $-OCH_2CH_2OH$, $-OCH_2CH_2CH_2OH$, $-OCH_2C(O)OH$, $-OCH=CH_2$, $-NH_2$, $-NHC(O)OC(CH_3)_3$, $-NHCH(CH_3)CH_2CH(CH_3)CH_3$, $-S(O)CH_3$, $-S(O)_2NH_2$, $-S(O)_2CH_2CH_2C(O)OCH_3$, $S(O)_2(methylpyrazolyl)$, oxazolidinonyl, cyclopentenyl, imidazolidine-2,4-dionyl, imidazolinonyl, methylimidazolyl, indolyl, morpholinonyl, morpholinyl, pyrazinyl, pyridazinyl, methylpyridazinyl, dimethoxypyridazinyl, pyrrolidinonyl, pyrrolidinyl, pyrrolo[2,3-b]pyridinyl, tetrahydropyridinyl, tetrazolyl, methyltetrazolyl, thiazolyl, triazolyl, methyltriazolyl, phenyl substituted with zero to 2 substituents independently selected from F, Cl, $-CN$, $-CH_3$, $-NH_2$, $-OCH_3$, and $-OC(O)C(CH_3)_3$; pyrazolyl substituted with zero to 2 substituents independently selected from $-CH_3$, $-CH_2CH_3$, $-CHF_2$, $-CF_3$, —C(O)OH, —CH₂C(O)OH, —CH₂C(CH₃)₂OH, —CH₂(phenyl), and —CH₂CH₂(morpholinyl); pyridinyl substituted with zero to 2 substituents independently selected from —CN, —CH₃, —CH₂CH₃, —OCH₃, —NH₂, —NH(CH₃), —N(CH₃)₂, and —C(O)(morpholinyl); or pyrimidinyl substituted with zero to 1 substituent selected from —CH₃, —C(CH₃)₂OH, —OCH₃, —NH₂, —N(CH₃)₂, cyclopropyl, and morpholinyl;

and A, B, and D are defined in the first aspect.

One embodiment provides a compound of Formula (I) or a salt thereof, wherein

X is a bond or —NR₈—;

L₁ is a bond or —CH₂;

L₂ is a bond, —CH₂—, —CH(CH₃)—, —C(CH₃)₂—, —CH(CH₂F)—, —CH(CHF₂)—, —CH(CF₃)—, —CH(CH₂CH₃)—, —CH(CH₂CH₂F)—, —CH(CH₂CHF₂)—, —CH(CH₂CF₃)—, —CH(CH₂CH₂OH)—, —CH(CH₂N(CH₃)₂)—, —CH(C(CH₃)₂OH)—, —CH(CH₂CH=CH₂)—, —CH(CH₃)CH₂—, —CH(cyclopropyl)-, —CH(CH(CH₃)₂)—, —CH(C(CH₃)₂F)—, —CH(CH₃)CH₂CH₂—, —CH(CH₃)CH₂C(OH)(phenyl)-, cyclopropyl, or cyclobutyl;

Z is a cyclic group selected from C₃₋₆ cycloalkyl, cyclopentenyl, phenyl, furanyl, imidazolyl, indolinyl, isoquinolinyl, isothiazolyl, isoxazolyl, oxazolyl, piperidinyl, pyrazinyl, pyrazolyl, pyridinyl, pyrimidinyl, thiazolyl, and thiophenyl, wherein said cyclic group is substituted with zero to 3 R_a;

R₁ is H or F;

R₂ is:
(i) H, F, Cl, or Br; or
(ii) dihydropyridinonyl, phenyl, piperidinyl, pyrazinyl, pyrazolyl, pyridinyl, or pyrimidinyl, each substituted with zero to 3 R_{1a};

R₃ is H, F, or Cl;

R₄ is H, F, or Cl;

R₅ is H, —OH, —CH₃, —CH₂OH, —CH₂NH₂, —CH₂N₃, —C(O)OH, —C(O)NH(CH₃), —C(O)N(CH₃)₂, —C(O)OCH₂CH₃, —CH₂NH(dimethylphenyl), —C(O)NH(pyridinyl), —C(O)NH(phenyl), or —CH₂O(pyridinyl);

R₆ is H, F, Cl, or —CH₃;

R₈ is H, —CH₃, or —CH₂CH₃;

each R_{1a} is independently F, —CN, —CH₃, —CH₂CH₃, —CH₂OH, —C(CH₃)₂OH, —CH(OH)CH₂OH, —CH(CH₃)(OH)CH₂OH, —C(CH₂F)₂OH, —C(CH₃)₂NHC(O)CH₃, —C(O)NH₂, —C(O)NHCH₂CH₂CH₂NH₂, —C(O)NHCH₃, —C(O)OH, —CH(C(O)OCH₃)CH₂NH₂, —CH(CH₂OH)NHC(O)CH₃, —CH(NH₂)CH₂OH, —CH(NH₂)CH₂C(O)OH, —CH₂CH(NH₂)C(O)OH, —CH₂NH(CH₂CH₃), —CH₂NHC(O)CH₃, —CH₂NHC(O)NH₂, —CH(OH)CH₂NH(CH₃), —NH(CH₃), —NHCH₂CH₂OH, —NHCH₂CH(OH)CH₂OH, —NHCH₂C(CH₃)₂OH, —NHCH(CH₂OH)₂, —NHCH₂C(O)NH₂, —NHCH₂C(O)OH, —NHCH(CH₃)C(O)NH₂, —NHCH₂CH(OH)CH₂OH, —N(CH₃)C(O)CH=CH₂, —OCH₂CH₃, —S(O)₂CH₃, —S(O)₂NH(CH₃), —CH₂(azetidinyl), —CH₂(piperazinyl), —CH₂(butoxycarbonyl piperazinyl), —CH(OH)(cyclopropyl), —CH(OH)CH₂(morpholinyl), —CH(OH)CH₂(carboxypyrrolidinyl), —NH(carbamoylcyclopropyl), C₃₋₆ cycloalkyl substituted with 1 to 2 substituents independently selected from —OH, —NH₂, —NHC(O)NH₂, —NHC(O)CH₃, —NHCH₂CH₂OH, —NHS(O)₂CH₃, —CH₂OH, —C(O)OH, and —C(O)CH₃; hydroxybutanonyl, hydroxypyrrolidinyl, carboxypyrrolidinyl, methoxycarbonylpyrrolidinyl, hydroxypropylpyrrolidinyl, hydroxypyranyl, hydroxyoxetanyl, hydroxymethylmorpholinyl, dioxohydroxytetrahydrothiopyranyl, piperidinyl substituted with 1 to 2 substituents independently selected from —NH₂, —C(O)OH, —CH₂C(O)OH, —C(CH₃)₂OH, and —C(O)OCH₂CH₃; piperazinyl substituted with zero or 1 substituent selected from —CH₂OH, —CH₂CN, —CH₂C(O)OH, —CH₂C(O)OCH₃, —CH₂C(O)NH₂, —CH₂C(O)NHCH₃, —CH(C(O)OCH₃)CH₂NHC(O)CH₃, —CH(C(O)OH)CH₂NH₂, —CH₂C(O)NHS(O)₂CH₃, —CH₂C(O)NHCH₂C(O)OH, —CH(C(O)OH)CH₂NHC(O)CH₃, —CH(C(O)OH)CH₂NHC(O)OC(CH₃)₃, —C(O)OH, —C(O)CH(CH₃)OH, —C(O)CH(NH₂)CH₂C(O)OH, —C(O)CH(NH₂)CH₂OH, —C(O)CH₂CH₂C(O)OH, —C(O)CH=CH₂, —C(O)C≡CH, —CH₂(tetrazolyl), and pyrrolidinonyl; piperazinonyl, carboxymethylpiperazinonyl, morpholinyl, dioxothiomorpholinyl, carboxy-azabicyclo[3.2.1]octanyl, or pyridinyl;

each R_a is independently F, Cl, Br, —CN, —OH, —CH₃, —CH₂CH₃, —CH=CH₂, —C≡C(phenyl), —CF₃, —CH₂OH, —CH₂CH₂OH, —CH(CH₃)OH, —CH₂CH₂CH₂OH, —C(CH₃)₂OH, —CH(OH)CH₂OH, —CH₂CH(OH)CH₂OH, —C(CH₃)(OH)CH₂OH, —CH(OH)CH(CH₃)CH(CH₃)₂, —CH₂NH₂, —CH(NH₂)CH₂OH, —CH(NH₂)CH(CH₃)CH₂CH₃, —CH₂C(O)NH₂, —CH₂CH₂C(O)NH₂, —CH₂(phenyl), —C(O)CH₃, —C(O)NH₂, —C(O)NH(CH₃), —C(O)NH(CH₂CH₃), —C(O)N(CH₃)₂, —C(O)CH(CH₃)CH₂CH₃, —C(O)(pyrazolyl), —C(O)(pyridinyl), —C(O)NH(phenyl), —C(O)OH, —CH₂C(O)OH, —CH₂CH₂C(O)OH, —C(O)OCH₃, —C(O)OC(CH₃)₃, —CH=NOH, —OCHF₂, —OCH₃, —OCF₃, —OCH₂CH₂OH, —OCH₂CH₂CH₂OH, —OCH₂C(O)OH, —OCH=CH₂, —NH₂, —NHC(O)OC(CH₃)₃, —NHCH(CH₃)CH₂CH(CH₃)CH₃, —S(O)CH₃, —S(O)₂NH₂, —S(O)₂CH₂CH₂C(O)OCH₃, S(O)₂(methylpyrazolyl), oxazolidinonyl, cyclopentenyl, imidazolidine-2,4-dionyl, imidazolinonyl, methylimidazolyl, indolyl, morpholinonyl, morpholinyl, pyrazinyl, pyridazinyl, methylpyridazinyl, dimethoxypyridazinyl, pyrrolidinonyl, pyrrolidinyl, pyrrolo[2,3-b]pyridinyl, tetrahydropyridinyl, tetrazolyl, methyltetrazolyl, thiazolyl, triazolyl, methyltriazolyl, phenyl substituted with zero to 2 substituents independently selected from F, Cl, —CN, —CH₃, —NH₂, —OCH₃, and —OC(O)C(CH₃)₃; pyrazolyl substituted with zero to 2 substituents independently selected from —CH₃, —CH₂CH₃, —CHF₂, —CF₃, —C(O)OH, —CH₂C(O)OH, —CH₂C(CH₃)₂OH, —CH₂(phenyl), and —CH₂CH₂(morpholinyl); pyridinyl substituted with zero to 2 substituents independently selected from —CN, —CH₃, —CH₂CH₃, —OCH₃, —NH₂, —NH(CH₃), —N(CH₃)₂, and —C(O)(morpholinyl); or pyrimidinyl substituted with zero to 1 substituent selected from —CH₃, —C(CH₃)₂OH, —OCH₃, —NH₂, —N(CH₃)₂, cyclopropyl, and morpholinyl.

and A, B, and D are defined in the first aspect.

One embodiment provides a compound of Formula (I) or a salt thereof, wherein

L₁ is a bond;

L₂ is a —CH₂—, —CH(CH₃)—, —C(CH₃)₂—, —CH(CH₂F)—, —CH(CHF₂)—, —CH(CF₃)—, —CH(CH₂CH₃)—, —CH(CH₂CH₂F)—, —CH(CH₂CHF₂)—, —CH(CH₂CF₃)—, —CH(CH₂CH₂OH)—, —CH(CH₂N(CH₃)₂)—, —CH(C(CH₃)₂OH)—, —CH(CH₃)CH₂—, —CH(cyclopropyl)-, —CH(CH(CH₃)₂)—, —CH(C(CH₃)₂F)—, or —CH(CH₃)CH₂CH₂—;

X is —NR₈—;

Z is a cyclic group selected from phenyl, piperidinyl, pyrazinyl, pyrazolyl, or pyridinyl, pyrimidinyl, each substituted with zero to 3 substituents selected from F, Cl, Br, —CN, —OH, $C_{1-2}$ alkyl, —$CF_3$, —CH=$CH_2$, —$CH_2OH$, —$CH_2CH_2OH$, —CH($CH_3$)OH, —$CH_2CH_2CH_2OH$, —C($CH_3$)$_2$OH, —C($CH_3$)(OH)$CH_2OH$, —CH(OH)$CH_2OH$, —$CH_2$CH(OH)$CH_2OH$, —$CH_2CH_2$C(O)OH, —CH($NH_2$)$CH_2OH$, —$CH_2$(phenyl), —$CH_2$C(O)$NH_2$, —$CH_2$C(O)OH, —$CH_2CH_2$C(O)$NH_2$, —$OCH_3$, —$OCHF_2$, —$OCF_3$, —$OCH_2CH_2OH$, —$OCH_2CH_2CH_2OH$, —$OCH_2$C(O)OH, —OCH=$CH_2$, —C≡C(phenyl), —CH=N—OH, —C(O)OH, —C(O)$CH_3$, —C(O)$OCH_3$, —C(O)OC($CH_3$)$_3$, —C(O)$NH_2$, —C(O)NH($CH_3$), —C(O)NH($CH_2CH_3$), —C(O)N($CH_3$)$_2$, —C(O)NH(phenyl), —C(O)(pyrazolyl), —C(O)(pyridinyl), —$NH_2$, —$CH_2NH_2$, —NHC(O)OC($CH_3$)$_3$, —S(O)$_2CH_3$, —S(O)$_2NH_2$, —S(O)$_2CH_2CH_2$C(O)$OCH_3$, —S(O)$_2$(methylpyrazolyl), cyclopentenyl, phenyl, methylphenyl, cyanophenyl, aminophenyl butoxycarbonyl phenyl, methoxyphenyl, oxazolidinonyl, indolyl, methylimidazolyl, imidazolinonyl, imidazolidine-2,4-dionyl, pyrazinyl, pyridazinyl, methylpyridazinyl, dimethoxypyridazinyl, pyrrolidinyl, pyrrolidinonyl, chlorophenyl, fluorophenyl, morpholinyl, morpholinonyl, methyltriazolyl, triazolyl, tetrazolyl, methyltetrazolyl, tetrahydropyridinyl, pyrrolo[2,3-b]pyridinyl, pyrazolyl substituted with zero to 2 substituents independently selected from —$CH_3$, —$CH_2CH_3$, —$CHF_2$, —$CF_3$, —$CH_2$C($CH_3$)$_2$OH, —$CH_2$C(O)OH, —$CH_2$(phenyl), —C(O)OH, and —$CH_2CH_2$(morpholinyl); pyrimidinyl substituted with zero to one substituent selected from —$NH_2$, —N($CH_3$)$_2$, —$CH_3$, —C($CH_3$)$_2$OH, —$OCH_3$, cyclopropyl, and morpholinyl; or pyrazolyl substituted with zero to 2 substituents independently selected from —CN, —$CH_3$, —$CH_2CH_3$, —$OCH_3$, —$NH_2$, —NH($CH_3$), —N($CH_3$)$_2$, and —C(O)(morpholinyl);

$R_2$ is dihydropyridinonyl, phenyl, piperidinyl, pyrazinyl, pyrazolyl, pyridinyl, or pyrimidinyl, each substituted with zero to 3 $R_{1a}$;

$R_8$ is H, —$CH_3$, or —$CH_2CH_3$; and A, B, D, $R_5$ and $R_6$ are defined in the first aspect.

One embodiment provides a compound of Formula (I) or a salt thereof, wherein $R_5$ and $R_6$ are independently halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_b$C(O)$NR_cR_c$, —$NR_h$C(O)$R_y$, —$NR_b$C(O)$OR_b$, —$NR_h$S(O)$_2NR_cR_c$, or —$NR_h$S(O)$_2R_y$; or $R_5$ and $R_6$ together with the carbons to which they are attached form a 5- to 7-membered carbocyclic or a heterocyclic ring; X is a bond, —O—, —S—, or —$NR_8$—; m is zero, 1, 2, 3, or 4; n is zero, 1, 2, 3, or 4; and A, B, D, $L_1$, $L_2$, Z, $R_2$, $R_8$, $R_a$, $R_b$, $R_c$, $R_h$, and $R_y$ are defined in the first aspect.

One embodiment provides a compound of Formula (I) or a salt thereof, wherein X is —O—, —S—, or —$NR_8$—; one of m and n is zero, 1, 2, 3, or 4, and the other m and n is 1, 2, 3, or 4; and A, B, D, $L_1$, $L_2$, Z, $R_2$, $R_5$, $R_6$, and $R_8$ are defined in the first aspect.

One embodiment provides a compound of Formula (I) or a salt thereof, wherein: one of $R_5$ and $R_6$ is H; and the other of $R_5$ and $R_6$ is H, halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_b$C(O)$NR_cR_c$, —$NR_h$C(O)$R_y$, —$NR_b$C(O)$OR_b$, —$NR_b$S(O)$_2NR_cR_c$, or —$NR_h$S(O)$_2R_y$; or $R_5$ and $R_6$ together with the carbons to which they are attached form a 5- to 7-membered carbocyclic or a heterocyclic ring; X is —O—, —S—, or —$NR_8$—; one of m and n is zero, 1, 2, 3, or 4, and the other m and n is 1, 2, 3, or 4; and A, B, D, $L_1$, $L_2$, Z, $R_2$, $R_8$, $R_a$, $R_b$, $R_e$, $R_h$, and $R_y$ are defined in the first aspect.

One embodiment provides a compound of Formula (I) or a salt thereof, wherein X is a bond; $R_5$ and $R_6$ are independently halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_b$C(O)$NR_cR_c$, —$NR_h$C(O)$R_y$, —$NR_b$C(O)$OR_b$, —$NR_h$S(O)$_2NR_cR_c$, or —$NR_h$S(O)$_2R_y$; or $R_5$ and $R_6$ together with the carbons to which they are attached form a 5- to 7-membered carbocyclic or a heterocyclic ring; m is zero, 1, 2, 3, or 4; n is zero, 1, 2, 3, or 4; and A, B, D, $L_1$, $L_2$, Z, $R_2$, $R_8$, $R_a$, $R_b$, $R_c$, $R_h$, and $R_y$ are defined in the first aspect. This embodiment includes compounds having the structures of Formula (II) in which the sum of m+n is 1, 2, or 3; and Formula (III) in which both m and n are zero.

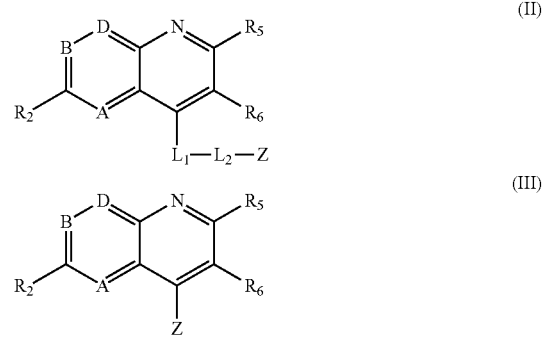

Included in this embodiment are compounds of Formula (II). Also included in this embodiment are compounds having the structure of Formula (III).

One embodiment provides a compound of Formula (I) or a salt thereof, wherein m is 1, 2, 3, or 4; n is zero; $R_5$ and $R_6$ are independently H, halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_b$C(O)$NR_cR_c$, —$NR_h$C(O)$R_y$, —$NR_b$C(O)$OR_b$, —$NR_b$S(O)$_2NR_cR_c$, or —$NR_h$S(O)$_2R_y$; or $R_5$ and $R_6$ together with the carbons to which they are attached form a 5- to 7-membered carbocyclic or a heterocyclic ring; and A, B, D, X, $L_1$, $L_2$, Z, $R_2$, $R_a$, $R_b$, $R_c$, $R_h$, $R_y$, and m are defined in the first aspect. Compounds of this embodiment have the structure of Formula (IV-a):

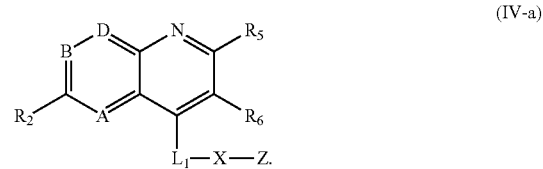

Included in this embodiment are compounds in which m is 1 or 2. Also included in this embodiment are compounds in which m is 1.

One embodiment provides a compound of Formula (I) or a salt thereof, wherein m is zero; n is 1, 2, 3, or 4; $R_5$ and $R_6$ are independently H, halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_bC(O)NR_cR_c$, —$NR_hC(O)R_y$, —$NR_bC(O)OR_b$, —$NR_bS(O)_2NR_cR_c$, or —$NR_hS(O)_2R_y$; or $R_5$ and $R_6$ together with the carbons to which they are attached form a 5- to 7-membered carbocyclic or a heterocyclic ring; and A, B, D, X, $L_1$, $L_2$, Z, $R_2$, $R_a$, $R_b$, $R_c$, $R_h$, $R_y$, and n are defined in the first aspect. Compounds of this embodiment have the structure of Formula (IV-b):

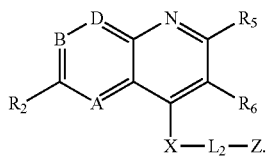

(IV-b)

Included in this embodiment are compounds in which n is 1 or 2. Also included in this embodiment are compounds in which n is 1.

One embodiment provides a compound of Formula (I) or a salt thereof, wherein m is zero; n is zero; and $R_5$ and $R_6$ are independently halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_bC(O)NR_cR_c$, —$NR_hC(O)R_y$, —$NR_bC(O)OR_b$, —$NR_bS(O)_2NR_cR_c$, or —$NR_hS(O)_2R_y$; or $R_5$ and $R_6$ together with the carbons to which they are attached form a 5- to 7-membered carbocyclic or a heterocyclic ring; and A, B, D, X, $L_1$, $L_2$, Z, $R_2$, $R_a$, $R_b$, $R_c$, $R_h$, and $R_y$ are defined in the first aspect. Compounds of this embodiment have the structure of Formula (IV-c):

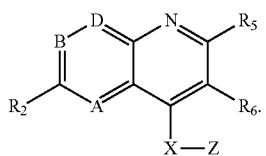

(IV-c)

One embodiment provides a compound of Formula (I) or a salt thereof, wherein X is a —O—, —S—, or —$NR_8$—; $R_5$ and $R_6$ are independently halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_bC(O)NR_cR_c$, —$NR_hC(O)R_y$, —$NR_bC(O)OR_b$, —$NR_bS(O)_2NR_cR_c$, or —$NR_hS(O)_2R_y$; or $R_5$ and $R_6$ together with the carbons to which they are attached form a 5- to 7-membered carbocyclic or a heterocyclic ring; m is zero, 1, 2, 3, or 4; n is zero, 1, 2, 3, or 4; and A, B, D, $L_1$, $L_2$, Z, $R_2$, $R_8$, $R_a$, $R_b$, $R_c$, $R_h$, and $R_y$ are defined in the first aspect. This embodiment includes compounds having the structures of Formula (IV-a), Formula (IV-b), and Formula (IV-c). Included in this embodiment are compounds of Formula (IV-a) in which m is 1 or 2. Also included in this embodiment are compounds having the structure of Formula (IV-b) in which n is 1 or 2.

One embodiment provides a compound of Formula (I) or a salt thereof, wherein X is a —O—; and A, B, D, $R_2$, $R_5$, $R_6$, $L_1$, $L_2$, and Z are defined in the first aspect. Included in this embodiment are compounds in which at least one of $R_5$ and $R_6$ is H; and one of m and n is zero, 1, 2, 3, or 4, and the other of m and n is 1, 2, 3, or 4. Also included in this embodiment are compounds in which $R_5$ and $R_6$ are independently halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_bC(O)NR_cR_c$, —$NR_hC(O)R_y$, —$NR_bC(O)OR_b$, —$NR_bS(O)_2NR_cR_c$, or —$NR_hS(O)_2R_y$; or $R_5$ and $R_6$ together with the carbons to which they are attached form a 5- to 7-membered carbocyclic or a heterocyclic ring; m is zero, 1, 2, 3, or 4; and n is zero, 1, 2, 3, or 4.

One embodiment provides a compound of Formula (I) or a salt thereof, wherein X is a —S—; and A, B, D, $R_2$, $R_5$, $R_6$, $L_1$, $L_2$, and Z are defined in the first aspect. Included in this embodiment are compounds in which at least one of $R_5$ and $R_6$ is H; and one of m and n is zero, 1, 2, 3, or 4, and the other of m and n is 1, 2, 3, or 4. Also included in this embodiment are compounds in which $R_5$ and $R_6$ are independently halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_bC(O)NR_cR_c$, —$NR_hC(O)R_y$, —$NR_bC(O)OR_b$, —$NR_bS(O)_2NR_cR_c$, or —$NR_hS(O)_2R_y$; or $R_5$ and $R_6$ together with the carbons to which they are attached form a 5- to 7-membered carbocyclic or a heterocyclic ring; m is zero, 1, 2, 3, or 4; and n is zero, 1, 2, 3, or 4.

One embodiment provides a compound of Formula (I) or a salt thereof, wherein X is a —$NR_8$—; and A, B, D, $R_2$, $R_5$, $R_6$, $R_8$, $L_1$, $L_2$, and Z are defined in the first aspect. Included in this embodiment are compounds in which at least one of $R_5$ and $R_6$ is H; and one of m and n is zero, 1, 2, 3, or 4, and the other of m and n is 1, 2, 3, or 4. Also included in this embodiment are compounds in which $R_5$ and $R_6$ are independently halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_bC(O)NR_cR_c$, —$NR_hC(O)R_y$, —$NR_bC(O)OR_b$, —$NR_bS(O)_2NR_cR_c$, or —$NR_hS(O)_2R_y$; or $R_5$ and $R_6$ together with the carbons to which they are attached form a 5- to 7-membered carbocyclic or a heterocyclic ring; m is zero, 1, 2, 3, or 4; and n is zero, 1, 2, 3, or 4.

One embodiment provides a compound of Formula (I) or a salt thereof, wherein X is a —O—, —S—, or —$NR_8$—; and A, B, D, $R_2$, $R_5$, $R_6$, $R_8$, $L_1$, $L_2$, and Z are defined in the first aspect. Included in this embodiment are compounds in which at least one of $R_5$ and $R_6$ is H; and one of m and n is zero, 1, 2, 3, or 4, and the other of m and n is 1, 2, 3, or 4. Also included in this embodiment are compounds in which $R_5$ and $R_6$ are independently halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6

$R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_bC(O)NR_cR_c$, —$NR_hC(O)R_y$, —$NR_bC(O)OR_b$, —$NR_bS(O)_2NR_cR_c$, or —$NR_hS(O)_2R_y$; or $R_5$ and $R_6$ together with the carbons to which they are attached form a 5- to 7-membered carbocyclic or a heterocyclic ring; m is zero, 1, 2, 3, or 4; and n is zero, 1, 2, 3, or 4.

One embodiment provides a compound of Formula (I) or a salt thereof, wherein X is a —O— or —$NR_8$—; and A, B, D, $R_2$, $R_5$, $R_6$, $R_8$, $L_1$, $L_2$, and Z are defined in the first aspect. Included in this embodiment are compounds in which at least one of $R_5$ and $R_6$ is H; and one of m and n is zero, 1, 2, 3, or 4, and the other of m and n is 1, 2, 3, or 4. Also included in this embodiment are compounds in which $R_5$ and $R_6$ are independently halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_bC(O)NR_cR_c$, —$NR_hC(O)R_y$, —$NR_bC(O)OR_b$, —$NR_bS(O)_2NR_cR_c$, or —$NR_hS(O)_2R_y$; or $R_5$ and $R_6$ together with the carbons to which they are attached form a 5- to 7-membered carbocyclic or a heterocyclic ring; m is zero, 1, 2, 3, or 4; and n is zero, 1, 2, 3, or 4.

One embodiment provides a compound of Formula (I) or a salt thereof, wherein X is a —O— or —S—; and A, B, D, $R_2$, $R_5$, $R_6$, $L_1$, $L_2$, and Z are defined in the first aspect. Included in this embodiment are compounds in which at least one of $R_5$ and $R_6$ is H; and one of m and n is zero, 1, 2, 3, or 4, and the other of m and n is 1, 2, 3, or 4. Also included in this embodiment are compounds in which $R_5$ and $R_6$ are independently halo, —OH, —CN, $C_{1-5}$ alkyl substituted with zero to 6 $R_a$, $C_{3-6}$ cycloalkyl substituted with zero to 6 $R_a$, $C_{1-5}$ alkylthio substituted with zero to 6 $R_a$, arylthio substituted with zero to 6 $R_a$, $C_{1-5}$ alkoxy substituted with zero to 6 $R_a$, aryloxy substituted with zero to 6 $R_a$, —$NR_hR_h$, —$NR_bC(O)NR_cR_c$, —$NR_hC(O)R_y$, —$NR_bC(O)OR_b$, —$NR_bS(O)_2NR_cR_c$, or —$NR_hS(O)_2R_y$; or $R_5$ and $R_6$ together with the carbons to which they are attached form a 5- to 7-membered carbocyclic or a heterocyclic ring; m is zero, 1, 2, 3, or 4; and n is zero, 1, 2, 3, or 4.

One embodiment provides a compound of Formula (I) or a salt thereof, wherein $L_1$ is —$(CR_7R_7)_m$—; m is 1, 2, 3, or 4; each $R_7$ is independently H, $C_{1-3}$ alkyl, —OH, or —$NR_hR_h$; and A, B, D, $R_2$, $R_5$, $R_6$, $R_7$, $L_2$, X, and Z are defined in the first aspect. Included in this embodiment are compounds in which each $R_7$ is independently H, —$CH_3$, —OH, —$NH_2$, —$NH(CH_3)$, or —$N(CH_3)_2$. Also included in this embodiment are compounds in which $R_7$ is H, —$CH_3$, or —OH.

One embodiment provides a compound of Formula (I) or a salt thereof, wherein $L_2$ is —$(CR_7R_7)_n$—; n is 1, 2, 3, or 4; each $R_7$ is independently H, $C_{1-3}$ alkyl, —OH, or —$NR_hR_h$; and A, B, D, $R_2$, $R_5$, $R_6$, $R_7$, $L_1$, X, and Z are defined in the first aspect. Included in this embodiment are compounds in which each $R_7$ is independently H, —$CH_3$, —OH, —$NH_2$, —$NH(CH_3)$, or —$N(CH_3)_2$. Also included in this embodiment are compounds in which $R_7$ is H, —$CH_3$, or —OH.

One embodiment provides a compound of Formula (I) or a salt thereof, wherein Z is a cyclic group selected from 3- to 14-membered carbocyclyl, 5- to 10-membered heterocyclyl, aryl, and mono- and bicyclic heteroaryl, wherein said cyclic group is substituted with zero to 3 $R_a$; and A, B, D, $R_2$, $R_5$, $R_6$, $R_a$, $L_1$, $L_2$, X, and Z are defined in the first aspect. Included in this embodiment are compounds in which Z is a cyclic group selected from $C_{3-7}$ cycloalkyl, 5- to 7-membered heterocyclyl, phenyl, naphthalenyl, and mono- and bicyclic heteroaryl, each substituted with zero to 3 $R_a$. Also included in this embodiment are compounds in which Z is a cyclic group selected from $C_{3-6}$ cycloalkyl, 5- to 7-membered heterocyclyl, phenyl, and mono- and bicyclic heteroaryl, each substituted with zero to 3 $R_a$.

One embodiment provides a compound of Formula (I) or a salt thereof, wherein Z is a 3- to 14-membered carbocyclyl substituted with zero to 3 $R_a$; and A, B, D, $R_2$, $R_5$, $R_6$, $R_a$, $L_1$, $L_2$, X, and Z are defined in the first aspect. Included in this embodiment are compounds in which Z is $C_{3-7}$ cycloalkyl substituted with zero to 3 $R_a$. Also included are compounds in which Z is $C_{3-6}$ cycloalkyl substituted with zero to 3 $R_a$.

One embodiment provides a compound of Formula (I) or a salt thereof, wherein Z is a 5- to 10-membered heterocyclyl substituted with zero to 3 $R_a$; and A, B, D, $R_2$, $R_5$, $R_6$, $R_a$, $L_1$, $L_2$, X, and Z are defined in the first aspect. Included in this embodiment are compounds in which Z is 5- to 7-membered heterocyclyl substituted with zero to 3 $R_a$. Also included are compounds in which Z is pyrrolidinyl, piperidinyl, piperazinyl, azepanyl, diazepanyl, morpholinyl, tetrahydrofuranyl, and tetrahydropyranyl, each substituted with zero to 3 $R_a$.

One embodiment provides a compound of Formula (I) or a salt thereof, wherein Z is aryl or mono- or bicyclic heteroaryl, each substituted with zero to 3 $R_a$; and A, B, D, $R_2$, $R_5$, $R_6$, $R_a$, $L_1$, $L_2$, X, and Z are defined in the first aspect. Included in this embodiment are compounds in which Z is phenyl, naphthalenyl, or mono- or bicyclic heteroaryl, each substituted with zero to 3 $R_a$. Also included in this embodiment are compounds in which Z is phenyl, pyrrolyl, furanyl, thiophenyl, oxazolyl, thiazolyl, imidazolyl, pyrazolyl, isoxazolyl, isothiazolyl, oxadiazolyl, thiadiazolyl, triazolyl, tetrazolyl, pyridinyl, pyrazinyl, pyrimidinyl, pyridazinyl, benzofuranyl, benzothiophenyl, benzoxazolyl, benzothiazolyl, indolyl, benzimidazolyl, indazolyl, benzotriazolyl, pyrrolopyridinyl, triazinyl, pyrrolopyridinyl, triazolopyridinyl, pyrrolopyrimidinyl, pyrrolopyrazinyl, pyrrolopyridazinyl, imidazopyridinyl, pyrazolopyridinyl, imidazopyridazinyl, imidazopyrimidinyl, imidazopyrazinyl, triazolopyridinyl, quinolinyl, isoquinolinyl, cinnolinyl, quinazolinyl, or quinoxalinyl, each substituted with zero to 3 $R_a$.

One embodiment provides a compound of Formula (I) or a salt thereof, wherein Z is aryl substituted with zero to 3 $R_a$; and A, B, D, $R_2$, $R_5$, $R_6$, $R_a$, $L_1$, $L_2$, X, and Z are defined in the first aspect. Included in this embodiment are compounds in which Z is phenyl or naphthalenyl, each substituted with zero to 3 $R_a$. Also included in this embodiment are compounds in which Z is phenyl substituted with zero to 3 $R_a$.

One embodiment provides a compound of Formula (I) or a salt thereof, wherein Z is mono- or bicyclic heteroaryl substituted with zero to 3 $R_a$; and A, B, D, $R_2$, $R_5$, $R_6$, $R_a$, $L_1$, $L_2$, X, and Z are defined in the first aspect. Included in this embodiment are compounds in which Z is monocyclic heteroaryl substituted with zero to 3 $R_a$. Examples of suitable monocyclic heteroaryls include pyrrolyl, furanyl, thiophenyl, oxazolyl, thiazolyl, imidazolyl, pyrazolyl, isoxazolyl, isothiazolyl, oxadiazolyl, thiadiazolyl, triazolyl, tetrazolyl, pyridinyl, pyrazinyl, pyrimidinyl, and pyridazinyl. Also included in this embodiment are compounds in which Z is a bicyclic heteroaryl substituted with zero to 3 $R_a$. Examples of suitable bicyclic heteroaryls include benzofuranyl, benzothiophenyl, benzoxazolyl, benzothiazolyl, indolyl, benzimidazolyl, indazolyl, benzotriazolyl, pyrrolopyridinyl, triazinyl, pyrrolopyridinyl, triazolopyridinyl, pyrrolopyrimidinyl, pyrrolopyrazinyl, pyrrolopyridazinyl, imidazopyridinyl, pyrazolopyridinyl, imidazopyridazinyl, imidazopyrimidinyl, imidazopyrazinyl, triazolopyridinyl, quinolinyl, isoquinolinyl, cinnolinyl, quinazolinyl, and quinoxalinyl.

One embodiment provides a compound of Formula (I) or a salt thereof, wherein A is $CR_1$; $R_1$ is H, F, Cl, Br, —CN, $C_{1-4}$ alkyl, $C_{1-6}$ fluoroalkyl, or $C_{1-3}$ alkoxy; and B, D, $R_2$, $R_5$, $R_6$, $L_1$, $L_2$, X, and Z are defined in the first aspect. Included in this embodiment are compounds in which $R_1$ is H, F, Cl, —CN, $C_{1-2}$ alkyl, $C_{1-3}$ fluoroalkyl, or $C_{1-2}$ alkoxy. Also included in this embodiment are compounds in which $R_1$ is H, F, —CN, —$CH_3$, —$CF_3$, or —$OCH_3$; compounds in which $R_1$ is H, F, —CN, or —$CH_3$; compounds in which $R_1$ is H, F, or —$CH_3$; compounds in which $R_1$ is H or —$CH_3$; and compounds in which $R_1$ is H.

One embodiment provides a compound of Formula (I) or a salt thereof, wherein $R_2$ is H, $R_{1a}$, $C_{1-4}$ haloalkyl, $C_{2-4}$ alkenyl substituted with zero to 6 $R_{1a}$, $C_{2-4}$ alkynyl substituted with zero to 4 $R_{1a}$, —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 7-membered heterocyclyl substituted with zero to 3 $R_{1a}$), or —$(CR_gR_g)_r$(mono- or bicyclic heteroaryl substituted with zero to 3 $R_{1a}$); and A, B, D, $R_5$, $R_6$, $R_{1a}$, $R_g$, r, $L_1$, $L_2$, X, and Z are defined in the first aspect. Included in this embodiment are compounds in which $R_2$ is H, $R_{1a}$, $C_{1-4}$ fluoroalkyl, —$(CR_gR_g)_r$($C_{3-7}$ cycloalkyl substituted with zero to 3 $R_{1a}$), —$(CR_gR_g)_r$(phenyl substituted with zero to 3 $R_{1a}$), —$(CR_gR_g)_r$(5- to 7-membered heterocyclyl substituted with zero to 3 $R_{1a}$), or —$(CR_gR_g)_r$(mono- or bicyclic heteroaryl substituted with zero to 3 $R_{1a}$). Also included in this embodiment are compounds in which $R_2$ is H, $R_{1a}$, $C_{1-3}$ fluoroalkyl, —$(CH_2)_r$($C_{3-7}$ cycloalkyl substituted with zero to 3 $R_{1a}$), —$(CH_2)_r$(phenyl substituted with zero to 3 $R_{1a}$), —$(CH_2)_r$(5- to 7-membered heterocyclyl substituted with zero to 3 $R_{1a}$), or —$(CH_2)_r$(mono- or bicyclic heteroaryl substituted with zero to 3 $R_{1a}$). Additionally, included in this embodiment are compounds in which $R_2$ is H, F, Cl, —CN, $C_{1-2}$ alkyl substituted with zero to 6 $R_a$, $C_{3-6}$ cycloalkyl substituted with zero to 6 $R_a$, $C_{1-3}$ alkoxy substituted with zero to 7 $R_a$, —$C(O)R_b$, —$C(O)O(C_{1-3}$ alkyl), —$C(O)NH_2$, —$C(O)NH(C_{1-3}$ alkyl), —$C(O)N(C_{1-3}$ alkyl)$_2$, —$OC(O)$ ($C_{1-3}$ alkyl), —$OC(O)NH_2$, —$OC(O)NH(C_{1-3}$ alkyl), —$OC(O)N(C_{1-3}$ alkyl)$_2$, —$OC(O)OH$, —$OC(O)O(C_{1-3}$ alkyl), —$NH_2$, —$NH(C_{1-3}$ alkyl), —$N(C_{1-3}$ alkyl)$_2$, —$NHC(O)$ ($C_{1-3}$ alkyl), —$NHC(O)O(C_{1-3}$ alkyl), —$NHS(O)_p(C_{1-3}$ alkyl), —$NHC(O)NH_2$, —$NHC(O)NH(C_{1-3}$ alkyl), —$NHC(O)N(C_{1-3}$ alkyl)$_2$, —$NHS(O)_pNH_2$, —$NHS(O)_pNH(C_{1-3}$ alkyl), —$NHS(O)_pN(C_{1-3}$ alkyl)$_2$, —$S(O)_p(C_{1-3}$ alkyl), —$S(O)_pNH_2$, —$S(O)_pNH(C_{1-3}$ alkyl), —$S(O)_pN(C_{1-3}$ alkyl)$_2$, —$C(O)NH(CH_2)_{1-3}NH_2$, —$C(O)NH(CH_2)_{1-3}NH(C_{1-3}$ alkyl), or —$C(O)NH(CH_2)_{1-3}N(C_{1-3}$ alkyl)$_2$; wherein p is defined in the first aspect.

One embodiment provides a compound of Formula (I) or a salt thereof, wherein B is $CR_3$; $R_3$ is H, F, Cl, Br, —CN, —$CF_3$, —$OCF_3$, —$NO_2$, $C_{1-4}$ alkyl substituted with zero to 6 $R_{1a}$, —$(CR_gR_g)_rOR_e$, —$(CR_gR_g)_rNR_cR_c$, —$(CR_gR_g)_rS(O)_pR_b$, —$(CR_gR_g)_r$(3- to 14- membered carbocyclyl substituted with zero to 3 $R_{1a}$), —$(CR_gR_g)_r$(phenyl substituted with zero to 3 $R_{1a}$), —$(CR_gR_g)_r$(5- to 7-membered heterocyclyl substituted with zero to 3 $R_{1a}$), or —$(CR_gR_g)_r$(monocyclic heteroaryl substituted with zero to 3 $R_{1a}$); and A, D, $R_2$, $R_5$, $R_6$, $R_{1a}$, $R_b$, $R_c$, $R_e$, $R_g$, p, r, $L_1$, $L_2$, X, and Z are defined in the first aspect. Included in this embodiment are compounds in which $R_3$ is H, F, Cl, —CN, —$CF_3$, —$OCF_3$, —$NO_2$, $C_{1-3}$ alkyl substituted with zero to 6 $R_{1a}$, —$(CR_gR_g)_rOH$, —$(CR_gR_g)_rO(C_{1-3}$ alkyl), —$(CR_gR_g)_rNH_2$, —$(CR_gR_g)_rNH(C_{1-3}$ alkyl), —$(CR_gR_g)_rN(C_{1-3}$ alkyl)$_2$, —$(CR_gR_g)_rS(O)_p(C_{1-3}$ alkyl), —$(CR_gR_g)_r$($C_{3-7}$ cycloalkyl substituted with zero to 3 $R_{1a}$), —$(CR_gR_g)_r$(phenyl substituted with zero to 3 $R_{1a}$), —$(CR_gR_g)_r$(5- to 7-membered heterocyclyl substituted with zero to 3 $R_{1a}$), or —$(CR_gR_g)_r$(monocyclic heteroaryl substituted with zero to 3 $R_{1a}$). Also included in this embodiment are compounds in which $R_3$ is H, F, —CN, —$CF_3$, —$OCF_3$, —$NO_2$, $C_{1-3}$ alkyl substituted with zero to 6 $R_{1a}$, —$(CH_2)_rOH$, —$(CH_2)_rO$ ($C_{1-3}$ alkyl), —$(CH_2)_rNH_2$, —$(CH_2)_rNH(C_{1-3}$ alkyl), —$(CH_2)_rN(C_{1-3}$ alkyl)$_2$, —$(CH_2)_rS(O)_p(C_{1-3}$ alkyl), —$(CH_2)_r$($C_{3-7}$ cycloalkyl substituted with zero to 3 $R_{1a}$), —$(CH_2)_r$(phenyl substituted with zero to 3 $R_{1a}$), —$(CH_2)_r$ (5- to 7-membered heterocyclyl substituted with zero to 3 $R_{1a}$), or —$(CH_2)_r$(monocyclic heteroaryl substituted with zero to 3 $R_{1a}$).

One embodiment provides a compound of Formula (I) or a salt thereof, wherein D is $CR_4$; $R_4$ is H, F, Cl, Br, —CN, $C_{1-4}$ alkyl, $C_{1-4}$ haloalkyl, or $C_{1-3}$ alkoxy; and A, B, $R_2$, $R_5$, $R_6$, $L_1$, $L_2$, X, and Z are defined in the first aspect. Included in this embodiment are compounds in which $R_4$ is H, F, Cl, —CN, $C_{1-3}$ alkyl, $C_{1-4}$ fluoroalkyl, or $C_{1-2}$ alkoxy. Also included in this embodiment are compounds in which $R_4$ is H, F, —CN, —$CH_3$, —$CF_3$, or —$OCH_3$.

One embodiment provides a compound of Formula (I) or a salt thereof, wherein the sum of m+n is not zero; each $R_7$ is independently H, $C_{1-3}$ alkyl, —OH, —$NH_2$, —$NH(C_{1-3}$ alkyl), or —$N(C_{1-3}$ alkyl)$_2$; and A, B, D, $R_2$, $R_5$, $R_6$, $L_1$, $L_2$, X, and Z are defined in the first aspect. Included in this embodiment are compounds in which $R_7$ is H, —$CH_3$, —OH, or —$NH_2$. Also included are compounds in which $R_7$ is H or —$CH_3$.

One embodiment provides a compound of Formula (I) or a salt thereof, wherein the sum of m+n is not zero; two $R_7$ along with the carbon atom to which they are attached form a 3- to 7-membered spirocarbocyclyl or spiroheterocyclyl group; and A, B, D, $R_2$, $R_5$, $R_6$, $L_1$, $L_2$, X, and Z are defined in the first aspect. Included in this embodiment are compounds in which $R_7$ is a 3- to 7-membered spirocarbocyclyl group. Also included in this embodiment are compounds in which $R_7$ is a 3- to 7-member spiroheterocyclyl group.

One embodiment provides a compound of Formula (I) or a salt thereof, wherein X is —$NR_8$—; $R_8$ is H or $C_{1-2}$ alkyl; and A, B, D, $R_2$, $R_5$, $R_6$, $R_8$, $L_1$, $L_2$, and Z are defined in the first aspect. Included in this embodiment are compounds in which $R_8$ is H or —$CH_3$. Also included in this embodiment are compounds in which $R_8$ is H.

One embodiment provides a compound of Formula (I) or a salt thereof, wherein each $R_{1a}$ is independently F, Cl, —CN, $C_{1-3}$ alkyl substituted with zero to 6 $R_a$, $C_{3-6}$ cycloalkyl substituted with zero to 6 $R_a$, $C_{1-3}$ alkoxy substituted with zero to 7 $R_a$, 5- to 7-membered heterocyclyl substituted with zero to 6 $R_a$, phenyl substituted with zero to 6 $R_a$, mono- or bicyclic heteroaryl substituted with zero to 6 $R_a$, —$C(O)R_b$, —$C(O)OR_b$, —$C(O)NR_cR_c$, —$OC(O)R_b$, —$OC(O)NR_cR_c$, —$OC(O)OR_d$, —$NR_cR_c$, —$NR_bC(O)R_d$, —$NR_bC(O)OR_d$, —$NR_bS(O)_pR_d$, —$NR_bC(O)NR_cR_c$, —$NR_bS(O)_pNR_cR_c$, —$S(O)_pR_b$, —$S(O)_pNR_cR_c$, or —$C(O)NR_b(CH_2)_{1-3}NR_cR_c$; and A, B, D, $R_2$, $R_5$, $R_6$, $R_a$, $R_b$, $R_c$, $R_d$, p, $L_1$, $L_2$, X, and Z are defined in the first aspect. Included in this embodiment are compounds in which each $R_{1a}$ is independently F, Cl, —CN, $C_{1-3}$ alkyl substituted with zero to 6 $R_a$, $C_{1-3}$ alkoxy substituted with zero to 7 $R_a$, —$C(O)$ ($C_{1-3}$ alkyl), —$C(O)OH$, —$C(O)O(C_{1-3}$ alkyl), —$C(O)NH_2$, —$C(O)NH(C_{1-3}$ alkyl), —$C(O)N(C_{1-3}$ alkyl)$_2$, —$OC(O)$ ($C_{1-3}$ alkyl), —OC(O)NH$_2$, —OC(O)NH($C_{1-3}$ alkyl), —OC(O)N($C_{1-3}$ alkyl)$_2$, —OC(O)O($C_{1-3}$ alkyl), —NH$_2$, —NH($C_{1-3}$ alkyl), —N($C_{1-3}$ alkyl)$_2$, —NR$_b$C(O)($C_{1-3}$ alkyl), —NHC(O)O($C_{1-3}$ alkyl), —NHS(O)$_p$($C_{1-3}$ alkyl), —NHC(O)NH$_2$, —NHC(O)NH($C_{1-3}$ alkyl), —NHC(O)N($C_{1-3}$ alkyl)$_2$, —NHS(O)$_p$NH$_2$, —NHS(O)$_p$NH($C_{1-3}$ alkyl), —NHS(O)$_p$N($C_{1-3}$ alkyl)$_2$, —S(O)$_p$($C_{1-3}$ alkyl), —S(O)$_p$NH$_2$, —S(O)$_p$NH($C_{1-3}$ alkyl), —S(O)$_p$N($C_{1-3}$ alkyl)$_2$, or —C(O)NH(CH$_2$)$_{1-3}$NH$_2$, —C(O)NH(CH$_2$)$_{1-3}$NH($C_{1-3}$ alkyl), or —C(O)NH(CH$_2$)$_{1-3}$N($C_{1-3}$ alkyl)$_2$. Also included in this embodiment are compounds in which each $R_{1a}$ is independently $C_{3-6}$ cycloalkyl substituted with zero to 6 $R_a$, 5- to 7-membered heterocyclyl substituted with zero to 6 $R_a$, phenyl substituted with zero to 6 $R_a$, or mono- or bicyclic heteroaryl substituted with zero to 6 $R_a$.

One embodiment provides a compound of Formula (I) or a salt thereof, wherein each $R_a$ is independently F, Cl, Br, —CN, —OH, —NO$_2$, —NH$_2$, $C_{1-3}$ alkyl, $C_{1-3}$ fluoroalkyl, $C_{2-4}$ alkenyl, $C_{2-4}$ alkynyl, $C_{1-3}$ alkoxy, $C_{1-3}$ fluoroalkoxy, —(CH$_2$)$_r$C(O)OH, —C(O)($C_{1-3}$ alkyl), —C(O)O($C_{1-4}$ alkyl), —OC(O)($C_{1-3}$ alkyl), —NH($C_{1-3}$ alkyl), —N($C_{1-3}$ alkyl)$_2$, —C(O)NH($C_{1-3}$ alkyl), —OC(O)NH($C_{1-3}$ alkyl), —NHC(O)NH($C_{1-3}$ alkyl), —C(=NH)(NH$_2$), $C_{3-7}$ cycloalkyl, phenyl, 5- to 7-membered heterocyclyl, monocyclic or bicyclic heteroaryl, —O(phenyl), —O(benzyl), —O(heterocyclyl), —S(O)$_p$($C_{1-3}$ alkyl), —S(O)$_p$(phenyl), —S(O)$_p$(heterocyclyl), —NHS(O)$_2$(phenyl), —NHS(O)$_2$(heterocyclyl), —NHS(O)$_2$NH(phenyl), —NHS(O)$_2$NH(heterocyclyl), —NH(aryl substituted with zero to 3 $R_x$), —NH(heterocyclyl), —NHC(O)(phenyl), —NHC(O)($C_{1-3}$ alkyl), —NHC(O)(heterocyclyl), —OC(O)(phenyl), —OC(O)(heterocyclyl), —NHC(O)NH(phenyl), —NHC(O)NH(heterocyclyl), —OC(O)O($C_{1-3}$ alkyl), —OC(O)O(phenyl), —OC(O)O(heterocyclyl), —OC(O)NH(phenyl), —OC(O)NH(heterocyclyl), —NHC(O)O(phenyl), —NHC(O)O(heterocyclyl), —NHC(O)O($C_{1-3}$ alkyl), —C(O)NH(phenyl), —C(O)NH(heterocyclyl), —C(O)O(phenyl), —C(O)O(heterocyclyl), —N($C_{1-3}$ alkyl)S(O)$_2$(phenyl), —N($C_{1-3}$ alkyl)S(O)$_2$(heterocyclyl), —N($C_{1-3}$ alkyl)S(O)$_2$NH(phenyl), —N($C_{1-3}$ alkyl)S(O)$_2$NH(heterocyclyl), —N($C_{1-3}$ alkyl)(phenyl), —N($C_{1-3}$ alkyl)(heterocyclyl), —N($C_{1-3}$ alkyl)C(O)(phenyl), —N($C_{1-3}$ alkyl)C(O)(heterocyclyl), —N($C_{1-3}$ alkyl)C(O)NH(phenyl), —(CH$_2$)$_{0-3}$C(O)NH(heterocyclyl), —OC(O)N($C_{1-3}$ alkyl)(phenyl), —OC(O)N($C_{1-3}$ alkyl)(heterocyclyl), —N($C_{1-3}$ alkyl)C(O)O(phenyl), —N($C_{1-3}$ alkyl)C(O)O(heterocyclyl), —C(O)N($C_{1-3}$ alkyl)(phenyl), —C(O)N($C_{1-3}$ alkyl)(heterocyclyl), —NHS(O)$_2$N($C_{1-3}$ alkyl)(phenyl), —NHS(O)$_2$N($C_{1-3}$ alkyl)(heterocyclyl), —NHP(O)$_2$N($C_{1-3}$ alkyl)(phenyl), —NHC(O)N($C_{1-3}$ alkyl)(phenyl), —NHC(O)N($C_{1-3}$ alkyl)(heterocyclyl), —N($C_{1-3}$ alkyl)S(O)$_2$N($C_{1-3}$ alkyl)(phenyl), —N($C_{1-3}$ alkyl)S(O)$_2$N($C_{1-3}$ alkyl)(heterocyclyl), —N($C_{1-3}$ alkyl)C(O)N($C_{1-3}$ alkyl)(phenyl), —N($C_{1-3}$ alkyl)C(O)N($C_{1-3}$ alkyl)(heterocyclyl), or —Si($C_{1-3}$ alkyl)$_3$; or two $R_a$ attached to the same carbon atom form =O; and A, B, D, $R_2$, $R_5$, $R_6$, $L_1$, $L_2$, X, and Z are defined in the first aspect. Included in this embodiment are compounds in which each $R_a$ is independently F, Cl, —CN, —OH, —NO$_2$, —NH$_2$, $C_{1-3}$ alkyl, $C_{1-3}$ fluoroalkyl, $C_{1-3}$ alkoxy, or $C_{1-3}$ fluoroalkoxy. Also included in this embodiment are compounds in which two $R_a$ attached to the same carbon atom form =O.

One embodiment provides a compound of Formula (I) or a salt thereof, wherein each $R_b$ is independently H, $C_{1-3}$ alkyl substituted with zero to 6 $R_f$, $C_{3-7}$ cycloalkyl substituted with zero to 6 $R_f$, 5- to 7-membered heterocyclyl substituted with zero to 6 $R_f$, phenyl substituted with zero to 3 $R_f$, or mono- or bicyclic heteroaryl substituted with zero to 3 $R_f$; and A, B, D, $R_2$, $R_5$, $R_6$, $R_f$, $L_1$, $L_2$, X, and Z are defined in the first aspect. Included in this embodiment are compounds in which each $R_b$ is independently H or $C_{1-3}$ alkyl substituted with zero to 6 $R_f$. Also included in this embodiment are compounds in which each $R_b$ is independently $C_{3-7}$ cycloalkyl substituted with zero to 6 $R_f$, 5- to 7-membered heterocyclyl substituted with zero to 6 $R_f$, phenyl substituted with zero to 3 $R_f$, or mono- or bicyclic heteroaryl substituted with zero to 3 $R_f$.

One embodiment provides a compound of Formula (I) or a salt thereof, wherein each $R_e$ is independently H, $C_{1-3}$ alkyl substituted with zero to 6 $R_f$, $C_{3-7}$ cycloalkyl substituted with zero to 6 $R_f$, 5- to 7-membered heterocyclyl substituted with zero to 6 $R_f$, phenyl substituted with zero to 3 $R_f$, or mono- or bicyclic heteroaryl substituted with zero to 3 $R_f$; or two $R_c$ attached to the same nitrogen atom form a 4- to 8-membered heterocyclic ring substituted with zero to 3 $R_g$; and A, B, D, $R_2$, $R_5$, $R_6$, $R_f$, $L_1$, $L_2$, X, and Z are defined in the first aspect. Included in this embodiment are compounds in which each $R_e$ is independently H, $C_{1-3}$ alkyl substituted with zero to 6 $R_f$, $C_{3-7}$ cycloalkyl substituted with zero to 6 $R_f$, 5- to 7-membered heterocyclyl substituted with zero to 6 $R_f$, phenyl substituted with zero to 3 $R_f$, or mono- or bicyclic heteroaryl substituted with zero to 3 $R_f$. Also included in this embodiment are compounds in which two $R_c$ attached to the same nitrogen atom form a 4- to 8-membered heterocyclic ring substituted with zero to 3 $R_g$.

One embodiment provides a compound of Formula (I) or a salt thereof, wherein each $R_d$ is independently H, $C_{1-4}$ alkyl substituted with zero to 6 $R_f$, $C_{3-7}$ cycloalkyl substituted with zero to 6 $R_f$, 5- to 7-membered heterocyclyl substituted with zero to 6 $R_f$, phenyl substituted with zero to 3 $R_f$, or mono- or bicyclic heteroaryl substituted with zero to 3 $R_f$; and A, B, D, $R_2$, $R_5$, $R_6$, $R_f$, $L_1$, $L_2$, X, and Z are defined in the first aspect. Included in this embodiment are compounds in which each $R_d$ is independently H or $C_{1-3}$ alkyl substituted with zero to 6 $R_f$. Also included in this embodiment are compounds in which each $R_d$ is independently $C_{3-7}$ cycloalkyl substituted with zero to 6 $R_f$, 5- to 7-membered heterocyclyl substituted with zero to 6 $R_f$, phenyl substituted with zero to 3 $R_f$, or mono- or bicyclic heteroaryl substituted with zero to 3 $R_f$.

One embodiment provides a compound of Formula (I) or a salt thereof, wherein each $R_e$ is independently H, $C_{1-4}$ alkyl substituted with zero to 7 $R_f$, $C_{3-7}$ cycloalkyl substituted with zero to 6 $R_f$, 5- to 7-member heterocyclyl substituted with zero to 6 $R_f$, phenyl substituted with zero to 3 $R_f$, or mono- or bicyclic heteroaryl substituted with zero to 3 $R_f$; and A, B, D, $R_2$, $R_5$, $R_6$, $R_f$, $L_1$, $L_2$, X, and Z are defined in the first aspect. Included in this embodiment are compounds in which each $R_e$ is independently H or $C_{1-3}$ alkyl substituted with zero to 7 $R_f$. Also included in this embodiment are compounds in which each $R_e$ is independently $C_{3-7}$ cycloalkyl substituted with zero to 6 $R_f$, 5- to 7-member heterocyclyl substituted with zero to 6 $R_f$, phenyl substituted with zero to 3 $R_f$, or mono- or bicyclic heteroaryl substituted with zero to 3 $R_f$.

One embodiment provides a compound of Formula (I) or a salt thereof, wherein each $R_f$ is independently H, F, Cl, Br, —OH, —CN, $C_{1-4}$ alkyl substituted with zero to 6 $R_a$, $C_{1-3}$ alkoxy substituted with zero to 7 $R_a$, $C_{3-7}$ cycloalkyl substituted with zero to 6 $R_a$, 5- to 7-membered heterocyclyl substituted with zero to 6 $R_a$, aryl substituted with zero to 3 $R_a$, or mono- or bicyclic heteroaryl substituted with zero to 3 $R_a$; and A, B, D, $R_2$, $R_5$, $R_6$, $R_a$, $L_1$, $L_2$, X, and Z are defined in the first aspect. Included in this embodiment are compounds in which each $R_f$ is independently H, F, Cl, —OH, —CN, $C_{1-3}$ alkyl substituted with zero to 6 $R_a$, or $C_{1-3}$ alkoxy substituted with zero to 7 $R_a$. Also included in this embodiment are compounds in which each $R_f$ is independently $C_{3-7}$ cycloalkyl substituted with zero to 6 $R_a$, 5- to 7-membered heterocyclyl substituted with zero to 6 $R_a$, aryl substituted with zero to 3 $R_a$, or mono- or bicyclic heteroaryl substituted with zero to 3 $R_a$.

One embodiment provides a compound of Formula (I) or a salt thereof, wherein each $R_g$ is independently H, F, —OH, —CN, $C_{1-2}$ alkyl, —$CF_3$, or phenyl; and A, B, D, $R_2$, $R_5$, $R_6$, $R_a$, $L_1$, $L_2$, X, and Z are defined in the first aspect. Included in this embodiment are compounds in which each $R_g$ is independently H, F, —OH, —CN, —$CH_3$, or —$CF_3$. Also included in this embodiment are compounds in which each $R_g$ is independently H or —$CH_3$.

One embodiment provides a compound of Formula (I) or a salt thereof, wherein each $R_h$ is independently H, $C_{1-3}$ alkyl substituted with zero to 2 $R_x$, $C_{3-7}$ cycloalkyl substituted with zero to 2 $R_x$, mono- or bicyclic heterocyclyl substituted with zero to 2 $R_x$, phenyl substituted with zero to 2 $R_x$, or mono- or bicyclic heteroaryl substituted with zero to 2 $R_x$; and A, B, D, $R_2$, $R_5$, $R_6$, $R_x$, $L_1$, $L_2$, X, and Z are defined in the first aspect. Included in this embodiment are compounds in which each $R_h$ is H or $C_{1-3}$ alkyl substituted with zero to 2 $R_x$. Also included in this embodiment are compounds in which each $R_h$ is independently $C_{3-7}$ cycloalkyl substituted with zero to 2 $R_x$, mono- or bicyclic heterocyclyl substituted with zero to 2 $R_x$, phenyl substituted with zero to 2 $R_x$, or mono- or bicyclic heteroaryl substituted with zero to 2 $R_x$.

One embodiment provides a compound of Formula (I) or a salt thereof, wherein each $R_x$ is independently H, F, Cl, Br, —CN, $C_{1-4}$ alkyl, $C_{1-6}$ fluoroalkyl, or $C_{1-3}$ alkoxy; and A, B, D, $R_2$, $R_5$, $R_6$, $L_1$, $L_2$, X, and Z are defined in the first aspect. Included in this embodiment are compounds in which each $R_x$ is independently H, F, Cl, —CN, $C_{1-2}$ alkyl, $C_{1-3}$ fluoroalkyl, or $C_{1-3}$ alkoxy. Also included in this embodiment are compounds in which each $R_x$ is independently H, F, Cl, —CN, —$CH_3$, —$CF_3$, or —$OCH_3$.

One embodiment provides a compound of Formula (I) or a salt thereof, wherein each $R_y$ is independently $C_{1-3}$ alkyl; and A, B, D, $R_2$, $R_5$, $R_6$, $L_1$, $L_2$, X, and Z are defined in the first aspect. Included in this embodiment are compounds in which each $R_y$ is independently $C_{1-2}$ alkyl. Also included are compounds in which each $R_y$ is —$CH_3$.

One embodiment provides a compound of Formula (I) or a salt thereof, wherein each p is independently 1 or 2; and A, B, D, $R_2$, $R_5$, $R_6$, $L_1$, $L_2$, X, and Z are defined in the first aspect. Included in this embodiment are compounds in which each p is 2.

One embodiment provides a compound of Formula (I) or a salt thereof, wherein each r is independently zero, 1, 2, or 3; and A, B, D, $R_2$, $R_5$, $R_6$, $L_1$, $L_2$, X, and Z are defined in the first aspect. Included in this embodiment are compounds in which p is zero, 1, or 2. Also included are compounds in which each p is zero or 1.

One embodiment provides a compound of Formula (I) or a salt thereof, wherein: A is $CR_1$; B is $CR_3$; D is $CR_4$; $R_2$ is —$(CR_gR_g)_r$(mono- or bicyclic heteroaryl substituted with zero to 3 $R_{1a}$); $R_5$ is $C_{1-3}$ alkyl substituted with zero to 6 $R_a$; $R_6$ is F, Cl, or —CN; m is zero or 1; n is zero or 1; X is —$NR_8$—; and Z is phenyl substituted with zero to 3 $R_a$; and $L_1$, $L_2$, r, $R_1$, $R_3$, $R_4$, $R_8$, $R_{1a}$, $R_a$, or $R_g$ are defined in the first aspect. Included in this embodiment are compounds in which each $R_a$ is independently —OH or —NH(phenyl substituted with zero to 2 $R_x$). Also included are compounds in which $R_1$ is H; $R_3$ is H; and $R_4$ is H.

One embodiment provides a compound of Formula (I) or a salt thereof, wherein: A is CH; B is CH; D is CH; $R_2$ is pyrazolyl, pyridinyl, or pyrimidinyl, each substituted with —CN, —$CH_3$, or —$C(CH_3)_2OH$; $R_5$ is —$CH_3$, —$CH_2OH$, or —$CH_2NH$(dimethyl phenyl); $R_6$ is Cl; $L_1$ is a bond; $L_2$ is a bond; X is —NH—; and Z is dimethyl phenyl.

One embodiment provides a compound of Formula (I) or a salt thereof, wherein $R_2$ is H, F, Cl, or Br; and A, B, D, $L_1$, $L_2$, X, Z, $R_5$, and $R_6$ are defined in the first aspect. Included in this embodiment are compounds in which $R_2$ is F, Cl, or Br. Also included in this embodiment are compounds in which $R_2$ is H.

One embodiment provides a compound of Formula (I) or a salt thereof, wherein $R_2$ is phenyl or pyrimidinyl substituted with zero to 3 $R_{1a}$; and A, B, D, $L_1$, $L_2$, X, Z, $R_5$, $R_6$, and $R_{1a}$ are defined in the first aspect. Included in this embodiment are compounds in which $R_2$ is phenyl or pyrimidinyl substituted with —$C(CH_3)_2OH$. Also included are compounds in which $R_2$ is pyrimidinyl substituted with —$C(CH_3)_2OH$.

One embodiment provides a compound of Formula (I) or a salt thereof, wherein $R_2$ is pyrimidinyl substituted with zero to 3 $R_{1a}$; and A, B, D, $L_1$, $L_2$, X, Z, $R_5$, $R_6$, and $R_{1a}$ are defined in the first aspect. Included in this embodiment are compounds in which $R_2$ is pyrimidinyl substituted with —$C(CH_3)_2OH$, —$CH(CH_3)(OH)CH_2OH$, piperazinyl substituted with —$CH_2C(O)OH$, piperazinonyl, or cyanopyridinyl.

One embodiment provides a compound of Formula (I) or a salt thereof, wherein Z is phenyl substituted with zero to 2 substituents independently selected from F, Cl, Br, —CN, —OH, —$CH_3$, —$NH_2$, —$CH_2OH$, —$OCH_3$, —$C(O)NH_2$, —$CH(OH)CH_2OH$, phenyl, and pyridinyl, pyrimidinyl, pyrazolyl; and A, B, D, $L_1$, $L_2$, X, $R_2$, $R_5$, and $R_6$ are defined in the first aspect. Included in this embodiment are compounds in which Z is dimethyl phenyl, fluorophenyl, difluorophenyl, bromo, fluorophenyl, and trifluoromethyl phenyl.

One embodiment provides a compound of Formula (I) or a salt thereof, wherein Z is pyridinyl substituted with zero to 2 substituents independently selected from F, Cl, Br, —$NH_2$, and —$C(O)NH_2$; and A, B, D, $L_1$, $L_2$, X, $R_2$, $R_5$, and $R_6$ are defined in the first aspect.

One embodiment provides a compound of Formula (I) or a salt thereof, wherein: X is a —C(OH)—, —C(O)—, —$C(NH_2)$—, or —$NR_8$—; Z is $C_{4-8}$ alkyl substituted with zero to 6 $R_q$; $R_8$ is H or $C_{1-2}$ alkyl; and A, B, D, $L_1$, $L_2$, $R_2$, $R_5$, $R_6$, $R_8$, and $R_q$ are defined in the third aspect. Included in this embodiment are compounds in which $L_1$ is a bond. Also included are compounds in which $L_2$ is a bond. Additionally, included in this embodiment are compounds in which $L_1$ is a bond and $L_2$ is a bond.

One embodiment provides a compound of Formula (I) or a salt thereof, wherein: X is a —C(OH)—, —C(O)—, —$C(NH_2)$—, or —NH—; Z is $C_{4-8}$ alkyl substituted with zero to 6 $R_q$; each $R_q$ is independently H, F, —CN, —OH, —$CF_3$, or —$OCH_3$; $L_1$ is a bond; $L_2$ is a bond; and A, B, D, $R_2$, $R_5$, and $R_6$ are defined in the third aspect. Included in this embodiment are compounds in which zero or one of A, B, and D is N. Also included are compounds in which A is $CR_1$, B is $CR_3$, and D is $CR_4$. Additionally, included in this embodiment are compounds in which Z is $C_{5-7}$ alkyl substituted with zero to 3 $R_q$.

One embodiment provides a compound according to the second embodiment or a salt thereof, wherein: X is a —O—, —S—, or —$NR_8$—.

One embodiment provides a compound according to the second embodiment or a salt thereof, wherein X is a —O—, —S—, or —NR$_8$—; R$_5$ and R$_6$ are independently H, halo, —OH, —CN, C$_{1-5}$ alkyl substituted with zero to 6 R$_a$, C$_{3-6}$ cycloalkyl substituted with zero to 6 R$_a$, C$_{1-5}$ alkylthio substituted with zero to 6 R$_a$, arylthio substituted with zero to 6 R$_a$, C$_{1-5}$ alkoxy substituted with zero to 6 R$_a$, aryloxy substituted with zero to 6 R$_a$, —NR$_h$R$_h$, —NR$_b$C(O)NR$_c$R$_c$, —NR$_h$C(O)R$_y$, —NR$_b$S(O)$_2$NR$_c$R$_c$, or —NR$_h$S(O)$_2$R$_y$; or R$_5$ and R$_6$ together with the carbons to which they are attached form a 5- to 7-membered carbocyclic or a heterocyclic ring; and one of m and n is zero, 1, or 2, and the other of m and n is 1 or 2.

One embodiment provides a compound according to the second embodiment or a salt thereof, wherein: A is CR$_1$; B is CR$_3$; and D is CR$_4$.

One embodiment provides a compound according to the second embodiment or a salt thereof, wherein: A is CR$_1$; B is CR$_3$; D is CR$_4$; X is —NR$_8$—; Z is phenyl substituted with zero to 3 R$_a$; R$_2$ is —(CR$_g$R$_g$)$_r$(mono- or bicyclic heteroaryl substituted with zero to 3 R$_{1a}$); R$_5$ is C$_{1-3}$ alkyl substituted with zero to 6 R$_a$; R$_6$ is F, Cl, or —CN; m is zero or 1; and n is zero or 1.

One embodiment provides a compound according to the second embodiment or a salt thereof, wherein: A is CH; B is CH; D is CH; R$_2$ is pyrazolyl, pyridinyl, or pyrimidinyl, each substituted with —CN, —CH$_3$, or —C(CH$_3$)$_2$OH; R$_5$ is —CH$_3$, —CH$_2$OH, or —CH$_2$NH(dimethyl phenyl); R$_6$ is Cl; L$_1$ is a bond; L$_2$ is a bond; X is —NH—; and Z is dimethyl phenyl.

One embodiment provides a compound of Formula (I) or a salt thereof, wherein said compound is: 2-(5-(3-chloro-4-((2,5-dimethylphenyl)amino)-2-methylquinolin-6-yl)pyrimidin-2-yl) propan-2-ol (1); 3-chloro-N-(2,5-dimethylphenyl)-2-(((2,5-dimethylphenyl)amino)methyl)-6-(1-methyl-1H-pyrazol-4-yl)quinolin-4-amine (2); 5-(3-chloro-4-((2,5-dimethylphenyl)amino)-2-(((2,5-dimethylphenyl)amino)methyl)quinolin-6-yl)picolinonitrile (3); 2-(5-(3-chloro-4-((2,5-dimethylphenyl)amino)-2-(hydroxymethyl)quinolin-6-yl)pyrimidin-2-yl)propan-2-ol (4); ethyl 3-chloro-6-(6-cyanopyridin-3-yl)-4-((2,5-dimethylphenyl)amino)quinoline-2-carboxylate (5); tert-butyl 4-(4-(3-chloro-4-((2,5-dimethylphenyl)amino)-2-methylquinolin-6-yl)benzyl)piperazine-1-carboxylate (6); 3-chloro-N-(2,5-dimethylphenyl)-2-methyl-6-(4-(piperazin-1-ylmethyl) phenyl)quinolin-4-amine (7); 5-(3-chloro-4-((2,5-dimethylphenyl)amino)-2-methylquinolin-6-yl)-N-methylpicolinamide (8); 5-(3-chloro-4-((2,5-dimethylphenyl)amino)-2-methylquinolin-6-yl)picolinic acid (9); 2-(5-(3-chloro-4-((2-fluoro-1-(2-fluorophenyl)ethyl)amino)quinolin-6-yl)pyrimidin-2-yl)propan-2-ol (10); 2-(5-(3-chloro-4-((phenylamino)methyl)quinolin-6-yl)pyrimidin-2-yl)propan-2-ol (11); 2-(5-(3-chloro-4-((2-(dimethylamino)-1-(2-fluorophenyl)ethyl)amino)quinolin-6-yl)pyrimidin-2-yl) propan-2-ol (12); (S)-(4-(3-chloro-4-((2,2-difluoro-1-(2-fluorophenyl)ethyl)amino) quinolin-6-yl)benzyl)glycine (13); methyl (S)-2-(4-(5-(3-chloro-4-((2,2-difluoro-1-(2-fluorophenyl)ethyl)amino)quinolin-6-yl) pyrimidin-2-yl)piperazin-1-yl)acetate (14); (S)-2-(4-(5-(3-chloro-4-((2,2-difluoro-1-(2-fluorophenyl)ethyl)amino) quinolin-6-yl)pyrin-2-yl)piperazin-1-yl)acetic acid (15); (S)-2-(4-(4-(3-chloro-4-((2,2-difluoro-1-(2-fluorophenyl)ethyl)amino)quinolin-6-yl)phenyl)piperazin-1-yl)acetic acid (16); (R)-3-chloro-N-(1-(2-fluorophenyl)ethyl)-6-(2-(methylamino)pyrimidin-5-yl)quinolin-4-amine (17); 4-(5-(3,8-dichloro-4-((1-(2-fluorophenyl)ethyl)amino)quinolin-6-yl)pyrimidin-2-yl)piperazin-2-one (18); 3,8-dichloro-N-(1-(2-fluorophenyl)ethyl)-6-(2-(methylamino)pyrimidin-5-yl)quinolin-4-amine (19); 3,8-dichloro-N-(1-(2-fluorophenyl)ethyl)-6-(1-methyl-1H-pyrazol-4-yl)quinolin-4-amine (20); 2-(4-(3,8-dichloro-4-((1-(2-fluorophenyl)ethyl)amino)quinolin-6-yl)phenyl)propan-2-ol (21); 4-(3,8-dichloro-4-((1-(2-fluorophenyl)ethyl)amino)quinolin-6-yl)-N-methylbenzenesulfonamide (22); 6-(1-((3-chloro-6-(2-(3-oxopiperazin-1-yl)pyrimidin-5-yl)quinolin-4-yl)amino)propyl)-5-fluoropicolinamide (23); 6-(1-((3-chloro-6-(4-(2-hydroxypropan-2-yl)phenyl)quinolin-4-yl)amino)propyl)-5-fluoropicolinamide (24); 6-(1-((3-chloro-6-(2-(3-oxopiperazin-1-yl)pyrimidin-5-yl)quinolin-4-yl)amino)ethyl)-5-fluoropicolinamide (25 and 26); 6-(1-((3-chloro-6-(4-(2-hydroxypropan-2-yl)phenyl)quinolin-4-yl)amino)ethyl)-5-fluoropicolinamide (27); 6-(1-((3-chloro-6-(2-(2-hydroxypropan-2-yl)pyrimidin-5-yl)quinolin-4-yl)amino)ethyl)-5-fluoropicolinamide (28); (R)-3-chloro-6-(4-((ethylamino)methyl)phenyl)-N-(1-(2-fluorophenyl)ethyl) quinolin-4-amine (29); (R)-6-(4-(azetidin-1-ylmethyl)phenyl)-3-chloro-N-(1-(2-fluorophenyl)ethyl)quinolin-4-amine (30); 3-chloro-6-(6-cyanopyridin-3-yl)-4-((2,5-dimethylphenyl)amino)quinoline-2-carboxylic acid (31); 3-chloro-6-(6-cyanopyridin-3-yl)-4-((2,5-dimethylphenyl)amino)-N-(pyridin-3-yl) quinoline-2-carboxamide (32); 3-chloro-6-(6-cyanopyridin-3-yl)-4-((2,5-dimethylphenyl)amino)-N-methylquinoline-2-carboxamide (33); 3-chloro-6-(6-cyanopyridin-3-yl)-4-((2,5-dimethylphenyl)amino)-N,N-dimethylquinoline-2-carboxamide (34); 3-chloro-6-(6-cyanopyridin-3-yl)-4-((2,5-dimethylphenyl)amino)-N-phenylquinoline-2-carboxamide (35); 3-chloro-6-(6-cyanopyridin-3-yl)-4-((2,5-dimethylphenyl)amino)-N-(pyridin-4-yl)quinoline-2-carboxamide (36); 6-(6-carbamoylpyridin-3-yl)-3-chloro-4-((2,5-dimethylphenyl)amino)-N-(pyridin-3-yl) quinoline-2-carboxamide (37); 6-(1-((3-chloro-6-(2-(3-oxopiperazin-1-yl)pyrimidin-5-yl)quinolin-4-yl)amino)ethyl)-5-fluoro-N-phenylpicolinamide (38); 6-(1-((3-chloro-6-(2-(3-oxopiperazin-1-yl)pyrimidin-5-yl)quinolin-4-yl)amino)ethyl)-N-ethyl-5-fluoropicolinamide (39); 5-(3-chloro-4-((2,5-dimethylphenyl)amino)-2-(hydroxymethyl) quinolin-6-yl) picolinonitrile (40); 5-(3-chloro-4-((2,5-dimethylphenyl)amino)-2-((pyridin-3-yloxy)methyl)quinolin-6-yl) picolinonitrile (41); 5-(2-(azidomethyl)-3-chloro-4-((2,5-dimethylphenyl)amino) quinolin-6-yl)picolinonitrile (42); 5-(2-(aminomethyl)-3-chloro-4-((2,5-dimethylphenyl)amino)quinolin-6-yl) picolinonitrile (43); 2-(5-(3-chloro-4-((2,5-dimethylphenyl)amino)-2-(hydroxymethyl)quinolin-6-yl)pyrimidin-2-yl) propan-2-ol (44); 2-(4-(5-(2-amino-3-chloro-4-((2,5-dimethylphenyl)amino)quinolin-6-yl)pyrimidin-2-yl) piperazin-1-yl)acetic acid (45); 2-(4-(5-(2-amino-3-chloro-4-((1-(2-fluorophenyl)ethyl)amino)quinolin-6-yl)pyrimidin-2-yl)piperazin-1-yl) acetic acid (46); 2-(5-(3-chloro-4-(indolin-1-ylamino)quinolin-6-yl)pyrimidin-2-yl) propan-2-ol (47); 2-(5-(3-chloro-4-((2-methylindolin-1-yl)amino) quinolin-6-yl)pyrimidin-2-yl)propan-2-ol (48); 1-((3-chloro-6-(2-(2-hydroxypropan-2-yl)pyrimidin-5-yl)quinolin-4-yl)amino)-1-(2-fluorophenyl)-2-methylpropan-2-ol (49); 2-(5-(3-chloro-4-((1-cyclobutylpropyl)amino) quinolin-6-yl)pyrimidin-2-yl)propan-2-ol (50); 2-(5-(3-chloro-4-((2-methyl-1-(pyridin-2-yl)propyl)amino) quinolin-6-yl)pyrimidin-2-yl)propan-2-ol (51); 2-(5-(3-chloro-4-((1-(pyridin-2-yl)propyl)amino)quinolin-6-yl) pyrimidin-2-yl)propan-2-ol (52); (R)-2-(5-(3-chloro-4-((1-(2-chloro-5-fluoropyridin-4-yl)ethyl)amino)quinolin-6-yl) pyrimidin-2-yl)propan-2-ol (53); 2-(5-(3-chloro-4-(2-methyl-2-phenylhydrazinyl)quinolin-6-yl)pyrimidin-2-yl) propan-2-ol (54); 2-(5-(3-chloro-4-((2,2-difluoro-1-(2- fluorophenyl)ethyl)amino)quinolin-6-yl)pyrimidin-2-yl) propan-2-ol (55); 2-(5-(4-((4-bromo-2-(1H-pyrazol-1-yl)benzyl)amino)-3-chloroquinolin-6-yl)pyrimidin-2-yl) propan-2-ol (56); 2-(5-(3-chloro-4-((2,2-difluoro-1-phenylethyl)amino)quinolin-6-yl)pyrimidin-2-yl)propan-2-ol (57); (R)-2-(5-(3-chloro-4-((1-cyclohexylethyl)amino)quinolin-6-yl)pyrimidin-2-yl)propan-2-ol (58); (S)-2-(5-(3-chloro-4-((1-cyclohexylethyl)amino)quinolin-6-yl)pyrimidin-2-yl)propan-2-ol (59); tert-butyl (S)-3-((S)-1-((3-chloro-6-(2-(2-hydroxypropan-2-yl)pyrimidin-5-yl)quinolin-4-yl)amino)ethyl)piperidine-1-carboxylate (60); tert-butyl (R)-3-((R)-1-((3-chloro-6-(2-(2-hydroxypropan-2-yl)pyrimidin-5-yl)quinolin-4-yl)amino)ethyl)piperidine-1-carboxylate (61); 2-(5-(3-chloro-4-((1-(4-chloropyridin-2-yl)ethyl)amino)quinolin-6-yl)pyrimidin-2-yl)propan-2-ol (62); (R)-2-(5-(3-chloro-4-((1-(4-chloropyridin-2-yl)but-3-en-1-yl)amino)quinolin-6-yl)pyrimidin-2-yl)propan-2-ol (63); 2-(5-(4-((1-(6-bromo-3-fluoropyridin-2-yl)propyl)amino)-3-chloroquinolin-6-yl)pyrimidin-2-yl)propan-2-ol (64); N-(4-aminobutyl)-5-(3-chloro-4-((2,5-dimethylphenyl)amino)-2-methylquinolin-6-yl) picolinamide (65); 2-(5-(3-chloro-4-((ethyl(phenyl)amino)methyl)quinolin-6-yl)pyrimidin-2-yl)propan-2-ol (66); 2-(5-(3-chloro-4-(((2-fluorophenyl)(methyl)amino)methyl)quinolin-6-yl)pyrimidin-2-yl)propan-2-ol (67); 2-(5-(3-chloro-4-((ethyl(2-fluorophenyl)amino)methyl)quinolin-6-yl)pyrimidin-2-yl)propan-2-ol (68); 1-((5-(2-amino-3-chloro-4-((2,5-dimethylphenyl)amino)quinolin-6-yl)pyrimidin-2-yl)amino)-2-methylpropan-2-ol (69); 2-((5-(2-amino-3-chloro-4-((2,5-dimethylphenyl)amino)quinolin-6-yl)pyrimidin-2-yl)amino)ethan-1-ol (70); 2-((5-(2-amino-3-chloro-4-((2,5-dimethylphenyl)amino)quinolin-6-yl)pyrimidin-2-yl)amino)propane-1,3-diol (71); 4-(5-(2-amino-3-chloro-4-((2,5-dimethylphenyl)amino) quinolin-6-yl)pyrimidin-2-yl)piperazin-2-one (72); 3-((5-(2-amino-3-chloro-4-((2,5-dimethylphenyl)amino)quinolin-6-yl)pyrimidin-2-yl)amino)propane-1,2-diol (73); (S)-4-(5-(3-chloro-4-(((S)-2,2-difluoro-1-(2-fluorophenyl)ethyl)amino)quinolin-6-yl)pyrimidin-2-yl)piperazine-2-carboxylic acid (74); (S)-4-amino-1-(5-(3-chloro-4-((2,2-difluoro-1-(2-fluorophenyl)ethyl)amino)quinolin-6-yl)pyrimidin-2-yl)piperidine-4-carboxylic acid (75); (S)-2-(4-(5-(3-chloro-4-((2,2-difluoro-1-(2-fluorophenyl)ethyl)amino)quinolin-6-yl) pyrimidin-2-yl)-2-oxopiperazin-1-yl)acetic acid (76); 2-(4-(5-(3-chloro-4-(((S)-2,2-difluoro-1-(2-fluorophenyl)ethyl)amino) quinolin-6-yl)pyrimidin-2-yl)piperazin-2-yl) acetic acid (77); (S)-2-(1-(5-(3-chloro-4-((2,2-difluoro-1-(2-fluorophenyl)ethyl)amino) quinolin-6-yl)pyrimidin-2-yl)piperidin-4-yl)acetic acid (78); (S)-4-(5-(3-chloro-4-((2,2-difluoro-1-(2-fluorophenyl)ethyl)amino)quinolin-6-yl)pyrimidin-2-yl)piperazin-2-one (79); (S)-1-((5-(3-chloro-4-((2,2-difluoro-1-(2-fluorophenyl)ethyl)amino)quinolin-6-yl)pyrimidin-2-yl)amino)-2-methylpropan-2-ol (80); (R)-2-(4-(5-(3-chloro-4-((1-(2-fluorophenyl)ethyl)amino)quinolin-6-yl)pyridin-2-yl)-2-oxopiperazin-1-yl)acetic acid (81); (R)-2-(1-(5-(3-chloro-4-((1-(2-fluorophenyl)ethyl)amino)quinolin-6-yl)pyridin-2-yl)piperidin-4-yl)acetic acid (82); ((R)-4-(5-(3-chloro-4-(((R)-1-(2-fluorophenyl)ethyl)amino)quinolin-6-yl)pyridin-2-yl)morpholin-2-yl)methanol (83); ((S)-4-(5-(3-chloro-4-(((R)-1-(2-fluorophenyl)ethyl)amino)quinolin-6-yl)pyridin-2-yl)piperazin-2-yl)methanol (84); ((R)-4-(5-(3-chloro-4-(((R)-1-(2-fluorophenyl)ethyl)amino)quinolin-6-yl)pyridin-2-yl)morpholin-3-yl)methanol (85); ((S)-4-(5-(3-chloro-4-(((S)-2,2-difluoro-1-(2-fluorophenyl)ethyl)amino)quinolin-6-yl)pyrimidin-2-yl)piperazin-2-yl)methanol (86); ((S)-4-(5-(3-chloro-4-(((S)-2,2-difluoro-1-(2-fluorophenyl)ethyl)amino)quinolin-6-yl)pyrimidin-2-yl)morpholin-2-yl)methanol (87); (R)-3-chloro-N-(1-(2-fluorophenyl)ethyl)-6-(6-(piperazin-1-yl)pyridin-3-yl)quinolin-4-amine (88); (R)-2-(4-(5-(3-chloro-4-((1-(2-fluorophenyl)ethyl)amino)quinolin-6-yl)pyrimidin-2-yl) piperazin-1-yl)-N-methylacetamide (89); (R)-2-(4-(5-(3-chloro-4-((1-(2-fluorophenyl)ethyl)amino)quinolin-6-yl)pyrimidin-2-yl)piperazin-1-yl)acetamide (90); (R)-2-(4-(5-(3-chloro-4-((1-(2-fluorophenyl)ethyl)amino)quinolin-6-yl)pyrimidin-2-yl)piperazin-1-yl)-N-(methyl sulfonyl)acetamide (91); (S)-2-(4-(5-(3-chloro-4-((2,2-difluoro-1-(2-fluorophenyl)ethyl)amino)quinolin-6-yl)pyrimidin-2-yl)piperazin-1-yl)acetic acid (92); (S)-3-((tert-butoxycarbonyl)amino)-2-(4-(5-(3-chloro-4-(((R)-1-(2-fluorophenyl)ethyl)amino)quinolin-6-yl)pyrimidin-2-yl)piperazin-1-yl)propanoic acid (93); (S)-3-amino-2-(4-(5-(3-chloro-4-(((R)-1-(2-fluorophenyl)ethyl)amino)quinolin-6-yl)pyrimidin-2-yl) piperazin-1-yl) propanoic acid (94); (S)-3-acetamido-2-(4-(5-(3-chloro-4-(((R)-1-(2-fluorophenyl)ethyl)amino)quinolin-6-yl)pyrimidin-2-yl)piperazin-1-yl)propanoic acid (95); 2-(5-(3-chloro-4-(((S)-1-((S)-piperidin-3-yl)ethyl)amino)quinolin-6-yl)pyrimidin-2-yl)propan-2-ol (96 and 97); (R)-2-(5-(3-chloro-4-((1-(piperidin-3-yl)ethyl)amino) quinolin-6-yl)pyrimidin-2-yl)propan-2-ol (98); methyl (S)-3-amino-2-(4-(5-(3-chloro-4-(((R)-1-(2-fluorophenyl)ethyl)amino) quinolin-6-yl)pyrimidin-2-yl)piperazin-1-yl) propanoate (99); 2-amino-2-(4-(3-chloro-4-(((R)-1-(2-fluorophenyl)ethyl)amino) quinolin-6-yl)phenyl)ethan-1-ol (100); (R)—N-(4-aminobutyl)-5-(3-chloro-4-((1-(2-fluorophenyl)ethyl)amino)quinolin-6-yl)picolinamide (101); (R)-6-(4-(1-aminocyclopropyl)phenyl)-3-chloro-N-(1-(2-fluorophenyl)ethyl)quinolin-4-amine (102); (S)-3-((S)-1-((3-chloro-6-(2-(2-hydroxypropan-2-yl)pyrimidin-5-yl)quinolin-4-yl)amino)ethyl)piperidine-1-carboxamide (103); (R)-3-((R)-1-((3-chloro-6-(2-(2-hydroxypropan-2-yl)pyrimidin-5-yl)quinolin-4-yl)amino)ethyl)piperidine-1-carboxamide (104); 2-(5-(3-chloro-4-(((S)-1-((S)-1-ethylpiperidin-3-yl)ethyl)amino)quinolin-6-yl)pyrimidin-2-yl) propan-2-ol (105); 3-((S)-3-((S)-1-((3-chloro-6-(2-(2-hydroxypropan-2-yl)pyrimidin-5-yl)quinolin-4-yl)amino)ethyl)piperidin-1-yl)propane-1,2-diol (106); 1-((S)-3-((S)-1-((3-chloro-6-(2-(2-hydroxypropan-2-yl)pyrimidin-5-yl)quinolin-4-yl)amino) ethyl)piperidin-1-yl)ethanone (107); 1-((R)-3-((R)-1-((3-chloro-6-(2-(2-hydroxypropan-2-yl)pyrimidin-5-yl)quinolin-4-yl)amino)ethyl)piperidin-1-yl)ethan-1-one (108); methyl (S)-3-acetamido-2-(4-(5-(3-chloro-4-(((R)-1-(2-fluorophenyl)ethyl)amino)quinolin-6-yl)pyrimidin-2-yl)piperazin-1-yl)propanoate (109); (R)—N-(4-(3-chloro-4-((1-(2-fluorophenyl)ethyl)amino)quinolin-6-yl)benzyl) acetamide (110); (R)—N-(1-(4-(3-chloro-4-((1-(2-fluorophenyl)ethyl)amino)quinolin-6-yl)phenyl)cyclobutyl) methanesulfonamide (111); 3-(4-(5-(3-chloro-4-(((R)-1-(2-fluorophenyl)ethyl)amino)quinolin-6-yl)pyrimidin-2-yl)piperazin-1-yl)pyrrolidin-2-one (112); (R)—N-(1-(4-(3-chloro-4-((1-(2-fluorophenyl)ethyl)amino)quinolin-6-yl) phenyl)cyclobutyl)acetamide (113); (R)-4-(5-(3-chloro-4-((1-(2-fluorophenyl)ethyl)amino)quinolin-6-yl)pyrimidin-2-yl)-4-hydroxycyclohexan-1-one (114); 3-amino-3-(4-(3-chloro-4-(((R)-1-(2-fluorophenyl)ethyl)amino)quinolin-6-yl)phenyl)propanoic acid (115); 2-amino-3-(4-(3-chloro-4-(((R)-1-(2-fluorophenyl)ethyl)amino)quinolin-6-yl)phenyl) propanoic acid (116); (R)-2-(4-(3-chloro-4-((1-(2-fluorophenyl)ethyl)amino)quinolin-6-yl)phenyl)-1,3-difluoropropan-2-ol (117); (R)-6-(4-(1-aminocyclobutyl)phenyl)-3-chloro-N-(1-(2-fluorophenyl)ethyl)quinolin-4-amine (118); (R)-3-amino-3-(4-(3-chloro-4-((1-(2-fluorophenyl)ethyl)amino)quinolin-6-yl)phenyl) cyclobutan-1-ol ((119); (R)-1-(5-(3-chloro-4-((1-(2- fluorophenyl)ethyl)amino) quinolin-6-yl)pyrimidin-2-yl) cyclopentan-1-ol (120); (1R,2R)-1-(5-(3-chloro-4-(((R)-1-(2-fluorophenyl)ethyl)amino)quinolin-6-yl)pyrimidin-2-yl) cyclopentane-1,2-diol (121); 6-bromo-3,8-dichloro-N-(1-(2-fluorophenyl)ethyl)quinolin-4-amine (122); (R)-1-(4-(5-(3-chloro-4-((1-(2-fluorophenyl)ethyl)amino)quinolin-6-yl) pyridin-2-yl)piperazin-1-yl)prop-2-en-1-one (123); (R)—N-(5-(3-chloro-4-((1-(2-fluorophenyl)ethyl)amino quinolin-6-yl)pyrimidin-2-yl)-N-methylacrylamide (124); (R)-1-(4-(5-(3-chloro-4-((1-(2-fluorophenyl)ethyl)amino)quinolin-6-yl)pyridin-2-yl)piperazin-1-yl)but-2-yn-1-one (125); 2-(5-(3-chloro-4-((1-(3-fluoro-6-vinylpyridin-2-yl)propyl) amino)quinolin-6-yl)pyrimidin-2-yl)propan-2-ol (126); 1-(6-(1-((3-chloro-6-(2-(2-hydroxypropan-2-yl)pyrimidin-5-yl)quinolin-4-yl)amino)propyl)-5-fluoropyridin-2-yl)ethane-1,2-diol (127); 6-(1-((3-chloro-6-(2-(2-hydroxypropan-2-yl)pyrimidin-5-yl)quinolin-4-yl)amino) propyl)-5-fluoropicolinic acid (128); 6-(1-((3-chloro-6-(2-(2-hydroxypropan-2-yl)pyrimidin-5-yl) quinolin-4-yl)amino) propyl)-5-fluoropicolinamide (129); 2-(5-(3-chloro-4-((1-(3-fluoro-6-(hydroxymethyl)pyridin-2-yl)propyl)amino) quinolin-6-yl)pyrimidin-2-yl)propan-2-ol (130); (R)—N-(4-(5-(3-chloro-4-((1-(2-fluorophenyl)ethyl)amino)quinolin-6-yl)pyrimidin-2-yl)-4-hydroxycyclohexyl)acetamide (131 and 132); 2-(5-(3-chloro-4-((1-(furan-2-yl) propan-2-yl) amino)quinolin-6-yl)pyrimidin-2-yl)propan-2-ol (133); 2-(5-(3-chloro-4-((1-(2,3,3-trimethylcyclopent-1-en-1-yl) propan-2-yl)amino)quinolin-6-yl)pyrimidin-2-yl) propan-2-ol (134); (R)-2-(5-(3-chloro-4-((1-(3-morpholinophenyl) ethyl)amino)quinolin-6-yl)pyrimidin-2-yl)propan-2-ol (136); 2-(5-(3-chloro-4-((1-(4-(trifluoromethoxy)phenyl) propan-2-yl)amino)quinolin-6-yl)pyrimidin-2-yl)propan-2-ol (137); 4-(2-((3-chloro-6-(2-(2-hydroxypropan-2-yl)pyrimidin-5-yl)quinolin-4-yl)amino)propyl)-2-methylisoquinolin-1(2H)-one (138); 2-(5-(3-chloro-4-(heptan-2-ylamino)quinolin-6-yl)pyrimidin-2-yl) propan-2-ol (139); 2-(5-(3-chloro-4-((1-cyclopentylpropan-2-yl)amino)quinolin-6-yl)pyrimidin-2-yl)propan-2-ol (140); 2-(5-(3-chloro-4-((4-(6-methyl-1H-indol-3-yl)butan-2-yl)amino)quinolin-6-yl)pyrimidin-2-yl)propan-2-ol (141); 2-(5-(3-chloro-4-((1-(1-(4-chlorophenyl)cyclopentyl)ethyl)amino)quinolin-6-yl) pyrimidin-2-yl)propan-2-ol (142); 3-((3-chloro-6-(2-(2-hydroxypropan-2-yl)pyrimidin-5-yl)quinolin-4-yl)amino)-1,1-diphenylbutan-1-ol (143); 2-(5-(4-((1-(1H-indol-4-yl) propan-2-yl)amino)-3-chloroquinolin-6-yl)pyrimidin-2-yl) propan-2-ol (144); 2-(5-(3-chloro-4-(4-(trifluoromethyl) benzylamino)quinolin-6-yl)pyrimidin-2-yl)propan-2-ol (145); 2-(5-(3-chloro-4-((2-(trifluoromethyl)benzyl)amino) quinolin-6-yl)pyrimidin-2-yl)propan-2-ol (146); 2-(5-(3-chloro-4-((1-(3-(trifluoromethyl)phenyl)ethyl)amino)quinolin-6-yl)pyrimidin-2-yl)propan-2-ol (147); 2-(5-(3-chloro-4-((4-(difluoromethoxy)benzyl)amino) quinolin-6-yl) pyrimidin-2-yl)propan-2-ol (148); 2-(5-(3-chloro-4-((1-(2,5-dimethylphenyl)ethyl)amino)quinolin-6-yl)pyrimidin-2-yl)propan-2-ol (149); 2-(5-(3-chloro-4-((1-(4-(trifluoromethyl)phenyl)ethyl)amino)quinolin-6-yl) pyrimidin-2-yl)propan-2-ol (150); 2-(5-(3-chloro-4-((1-(2-(trifluoromethyl)phenyl)ethyl)amino) quinolin-6-yl) pyrimidin-2-yl)propan-2-ol (151); 2-(5-(3-chloro-4-((1-(2-fluorophenyl)ethyl)amino)quinolin-6-yl)pyrimidin-2-yl) propan-2-ol (152); 2-(5-(3-chloro-4-((1-(2-chlorophenyl) ethyl)amino)quinolin-6-yl)pyrimidin-2-yl)propan-2-ol (153); (R)-2-(5-(3-chloro-4-((1-phenylethyl)amino)quinolin-6-yl)pyrimidin-2-yl)propan-2-ol (154); 2-(5-(3-chloro-4-((1-(3-fluorophenyl)ethyl)amino)quinolin-6-yl)pyrimidin-2-yl)propan-2-ol (155); 2-(5-(3-fluoro-4-((1-(2-fluorophenyl)ethyl)amino)quinolin-6-yl)pyrimidin-2-yl) propan-2-ol (156); 2-(5-(3-chloro-4-((1-(4-fluorophenyl) ethyl)amino)quinolin-6-yl)pyrimidin-2-yl)propan-2-ol (157); 2-(5-(3-chloro-4-((1-(2-fluorophenyl)cyclopropyl) amino)quinolin-6-yl)pyrimidin-2-yl)propan-2-ol (158); 2-(5-(3-fluoro-4-((1-(2-fluorophenyl)ethyl)amino)-2-methylquinolin-6-yl)pyrimidin-2-yl)propan-2-ol (159); 2-(5-(3-chloro-4-((1-(2,5-difluorophenyl)ethyl)amino)quinolin-6-yl)pyrimidin-2-yl)propan-2-ol (160); 2-(5-(3-chloro-4-((1-phenylcyclopropyl)amino)quinolin-6-yl)pyrimidin-2-yl) propan-2-ol (161); 2-(5-(3-chloro-4-((1-(3-fluoropyridin-4-yl)ethyl)amino)quinolin-6-yl)pyrimidin-2-yl)propan-2-ol (162); 2-(5-(3-chloro-4-((1-(2,4-difluorophenyl)ethyl) amino)quinolin-6-yl)pyrimidin-2-yl)propan-2-ol (163); 2-(5-(3-chloro-4-((2,2,2-trifluoro-1-(2-fluorophenyl)ethyl) amino)quinolin-6-yl)pyrimidin-2-yl)propan-2-ol (164); 2-(5-(3-chloro-4-((3,3,3-trifluoro-1-phenylpropyl)amino) quinolin-6-yl)pyrimidin-2-yl)propan-2-ol (165); 2-(4-(3-chloro-4-((1-(pyridin-3-yl)ethyl)amino)quinolin-6-yl)phenyl)propan-2-ol (166); 3-((3-chloro-6-(2-(2-hydroxypropan-2-yl)pyrimidin-5-yl)quinolin-4-yl)amino)-3-(2-fluorophenyl)propan-1-ol (167); 2-(5-(3-chloro-4-((3,3-difluoro-1-(2-fluorophenyl) propyl)amino)quinolin-6-yl) pyrimidin-2-yl)propan-2-ol (168); 2-(5-(3-chloro-4-((3,3,3-trifluoro-1-(2-fluorophenyl)propyl)amino)quinolin-6-yl) pyrimidin-2-yl)propan-2-ol (169); 2-(4-(3-chloro-4-((1-(3-fluoropyridin-2-yl)ethyl)amino)quinolin-6-yl)phenyl) propan-2-ol (170); 2-(5-(3-chloro-4-((1-(3-fluoropyridin-2-yl)ethyl)amino)quinolin-6-yl)pyrimidin-2-yl)propan-2-ol (171); 2-(4-(3-chloro-4-((1-(isothiazol-4-yl)ethyl)amino) quinolin-6-yl)phenyl)propan-2-ol (172); 2-(4-(3-chloro-4-((1-(pyridin-4-yl)ethyl)amino)quinolin-6-yl)phenyl)propan-2-ol (173); 2-(4-(3-chloro-4-((1-(isoxazol-3-yl)ethyl) amino)quinolin-6-yl)phenyl)propan-2-ol (174); 2-(4-(3-chloro-4-((1-(pyridin-2-yl)ethyl)amino)quinolin-6-yl) phenyl)propan-2-ol (175); 2-(4-(3-chloro-4-((1-(pyridin-4-yl)ethyl) amino)quinolin-6-yl)phenyl)propan-2-ol (176); 2-(4-(3-chloro-4-((1-(pyrimidin-2-yl)ethyl)amino)quinolin-6-yl)phenyl)propan-2-ol (177); 2-(4-(3-chloro-4-((1-(4-methylpyrimidin-2-yl)ethyl)amino)quinolin-6-yl)phenyl) propan-2-ol (178); 2-(4-(3-chloro-4-((1-(oxazol-2-yl)ethyl) amino)quinolin-6-yl)phenyl)propan-2-ol (179); 2-(5-(4-(2,5-dimethylphenylamino)-2-methoxy-3-methylquinolin-6-yl)pyrimidin-2-yl) propan-2-ol (180); 4-((2,5-dimethylphenyl)amino)-6-(2-(2-hydroxypropan-2-yl) pyrimidin-5-yl)-3-methylquinolin-2-ol (181); 2-(5-(3-chloro-4-((2-(3-(trifluoromethyl)phenyl)propan-2-yl) amino)quinolin-6-yl)pyrimidin-2-yl)propan-2-ol (182); 2-(5-(4-((2,5-dimethylphenyl)amino)-3-fluoro-2-methylquinolin-6-yl)pyrimidin-2-yl)propan-2-ol (183); 2-(5-(4-((2,5-dimethylphenyl)amino)-2,3-dimethylquinolin-6-yl) pyrimidin-2-yl)propan-2-ol (184); 2-(5-(3-chloro-4-((2-(4-(trifluoromethyl)phenyl)propan-2-yl)amino)quinolin-6-yl) pyrimidin-2-yl)propan-2-ol (185); 5-(4-((2,5-dimethylphenyl)amino)-3-fluoro-2-methylquinolin-6-yl)-N-methylpicolinamide (186); 2-(4-(5-(4-((2,5-dimethylphenyl)amino)-3-fluoro-2-methylquinolin-6-yl) pyrimidin-2-yl)piperazin-1-yl)acetic acid (187); (R)-2-(5-(7-chloro-3-fluoro-8-((1-(2-fluoro-5-vinylphenyl)ethyl) amino)-1,5-naphthyridin-2-yl)pyrimidin-2-yl)propan-2-ol (188); 2-(5-(3-chloro-4-((1-(2-fluorophenyl)-2-methylpropyl)amino)quinolin-6-yl)pyrimidin-2-yl)propan-2-ol (189); 2-(5-(3-chloro-4-((1-(2-fluorophenyl)propyl)amino)quinolin-6-yl)pyrimidin-2-yl)propan-2-ol (190); 2-(5-(3-chloro-4-((cyclopropyl(2-fluorophenyl)methyl)amino)quinolin-6-yl) pyrimidin-2-yl)propan-2-ol (191); 2-(4-(3-chloro-4-((1-(furan-2-yl)ethyl)amino)quinolin-6-yl)phenyl)propan-2-ol (192); (R)-2-(5-(7-chloro-3-fluoro-8-((1-phenylethyl)

amino)-1,5-naphthyridin-2-yl)pyrimidin-2-yl)propan-2-ol (193); 2-(4-(3-chloro-4-((1-(thiazol-2-yl)ethyl)amino)quinolin-6-yl)phenyl)propan-2-ol (194); 2-(4-(3-chloro-4-((1-(1-methyl-1H-pyrazol-5-yl)ethyl)amino)quinolin-6-yl)phenyl)propan-2-ol (195); 2-(4-(3-chloro-4-((1-(thiophen-3-yl)ethyl)amino)quinolin-6-yl)phenyl)propan-2-ol (196); 2-(4-(3-chloro-4-((1-(1-methyl-1H-pyrazol-4-yl)ethyl)amino)quinolin-6-yl)phenyl)propan-2-ol (197); 2-(4-(3-chloro-4-((1-(pyrazin-2-yl)ethyl)amino)quinolin-6-yl)phenyl)propan-2-ol (198); 2-(4-(3-chloro-4-((1-(thiophen-2-yl)ethyl)amino)quinolin-6-yl)phenyl)propan-2-ol (199); 2-(4-(3-chloro-4-((1-(1-methyl-1H-pyrazol-3-yl)ethyl)amino)quinolin-6-yl)phenyl)propan-2-ol (200); 2-(4-(3-chloro-4-((1-(1-methyl-1H-imidazol-2-yl)ethyl)amino)quinolin-6-yl)phenyl)propan-2-ol (201); 2-(4-(3-chloro-4-((1-(thiazol-4-yl)ethyl)amino)quinolin-6-yl)phenyl)propan-2-ol (202); 2-(4-(3-chloro-4-((1-(oxazol-5-yl)ethyl)amino)quinolin-6-yl) phenyl)propan-2-ol (203); 2-(4-(3-chloro-4-((1-(furan-3-yl)ethyl)amino)quinolin-6-yl)phenyl)propan-2-ol (204); 2-(4-(3-chloro-4-((1-(1-methyl-1H-imidazol-4-yl)ethyl) amino) quinolin-6-yl)phenyl)propan-2-ol (205); 2-(4-(3-chloro-4-((1-(oxazol-4-yl)ethyl)amino) quinolin-6-yl)phenyl)propan-2-ol (206); (S)-2-(5-(7-chloro-8-((2,2-difluoro-1-(2-fluorophenyl)ethyl)amino)-3-fluoro-1,5-naphthyridin-2-yl)pyrimidin-2-yl)propan-2-ol (207); (S)-2-(5-(7-chloro-3-fluoro-8-((1-phenylethyl)amino)-1,5-naphthyridin-2-yl)pyrimidin-2-yl)propan-2-ol (208); 2-(5-(7-chloro-3-fluoro-8-((1-(2-fluorophenyl)ethyl)amino)-1,5-naphthyridin-2-yl)pyrimidin-2-yl)propan-2-ol (209); 2-(4-(3-chloro-4-((1-(1-methyl-1H-imidazol-5-yl)ethyl)amino)quinolin-6-yl) phenyl)propan-2-ol (210); 2-(4-(3-chloro-4-((1-(thiazol-5-yl)ethyl)amino)quinolin-6-yl)phenyl)propan-2-ol (211); 2-(5-(7-chloro-8-((2,2-difluoro-1-phenyl ethyl)amino)-3-fluoro-1,5-naphthyridin-2-yl)pyrimidin-2-yl)propan-2-ol (212); (R)-2-(5-(7-chloro-3-fluoro-6-methyl-8-((1-phenylethyl)amino)-1,5-naphthyridin-2-yl)pyrimidin-2-yl)propan-2-ol (213); 2-(5-(7-chloro-8-((2,2-difluoro-1-phenylethyl)amino)-3-fluoro-6-methyl-1,5-naphthyridin-2-yl)pyrimidin-2-yl)propan-2-ol (214); (R)-2-(5-(7-chloro-8-((2,2-difluoro-1-(2-fluoro-5-vinylphenyl)ethyl)amino)-3-fluoro-1,5-naphthyridin-2-yl)pyrimidin-2-yl)propan-2-ol (215); 2-(5-(7-chloro-8-((2,2-difluoro-1-(3-vinylphenyl)ethyl)amino)-3-fluoro-1,5-naphthyridin-2-yl)pyrimidin-2-yl) propan-2-ol (216); (R)-2-(5-(3-chloro-4-(1-(2-fluorophenyl)ethylamino)quinolin-6-yl)pyrimidin-2-yl)propan-2-ol (217); 2-(5-(3-chloro-4-((1-(2-fluorophenyl)ethyl)amino)-2-methylquinolin-6-yl)pyrimidin-2-yl)propan-2-ol (218); (R)-3-chloro-N-(1-(2-fluorophenyl)ethyl)-6-(2-morpholinopyrimidin-5-yl) quinolin-4-amine (219); (R)-(4-(3-chloro-4-((1-(2-fluorophenyl)ethyl)amino)quinolin-6-yl)phenyl)methanol (220); (R)-3-chloro-N-(1-(2-fluorophenyl)ethyl)-6-(6-(methylsulfonyl)pyridin-3-yl)quinolin-4-amine (221); (R)-3-chloro-6-(2-ethoxypyrimidin-5-yl)-N-(1-(2-fluorophenyl)ethyl)quinolin-4-amine (222); (R)-3-chloro-6-(2-ethylpyrimidin-5-yl)-N-(1-(2-fluorophenyl)ethyl) quinolin-4-amine (223); methyl (R)-2-(4-(5-(3-chloro-4-((1-(2-fluorophenyl)ethyl)amino) quinolin-6-yl)pyrimidin-2-yl)piperazin-1-yl)acetate (224); (R)-4-(5-(3-chloro-4-((1-(2-fluorophenyl)ethyl)amino)quinolin-6-yl)pyrimidin-2-yl) thiomorpholine 1,1-dioxide (225); (R)-4-(5-(3-chloro-4-((1-(2-fluorophenyl)ethyl)amino)quinolin-6-yl)pyrimidin-2-yl) piperazin-2-one (226); (R)-3-(5-(3-chloro-4-((1-(2-fluorophenyl)ethyl)amino)quinolin-6-yl)pyrimidin-2-yl) oxetan-3-ol (227); (R)-2-(4-(3-chloro-4-((1-(2-fluorophenyl)ethyl)amino)quinolin-6-yl)phenyl)propan-2-ol (228); 2-(5-(3-chloro-4-((2-fluoro-1-(2-fluorophenyl)-2-methylpropyl)amino)quinolin-6-yl)pyrimidin-2-yl)propan-2-ol (229); 2-(5-(3-chloro-4-((3-fluoro-1-(2-fluorophenyl)propyl)amino)quinolin-6-yl)pyrimidin-2-yl) propan-2-ol (230); 2-(4-(3-chloro-4-((3-fluoro-1-(2-fluorophenyl)propyl)amino)quinolin-6-yl)phenyl)propan-2-ol (232); (R)-2-(4-(5-(3-chloro-4-((1-(2-fluorophenyl)ethyl)amino) quinolin-6-yl)pyrimidin-2-yl)piperazin-1-yl)acetonitrile (233); (R)-6-(2-(4-((2H-tetrazol-5-yl)methyl)piperazin-1-yl)pyrimidin-5-yl)-3-chloro-N-(1-(2-fluorophenyl)ethyl) quinolin-4-amine (237); (R)-2-(5-(3-chloro-4-((3-fluoro-1-(2-fluorophenyl)propyl)amino) quinolin-6-yl)pyrimidin-2-yl) propan-2-ol (238); ± 2-(5-(8-((1-(3-aminophenyl)ethyl)amino)-7-chloro-3-fluoro-1,5-naphthyridin-2-yl)pyrimidin-2-yl)propan-2-ol (239); (R)-2-(5-(4-((1-(2-fluorophenyl)ethyl)amino)-3-methylquinolin-6-yl)pyrimidin-2-yl) propan-2-ol (240); 2-(5-(3-chloro-7-fluoro-4-((1-(2-fluorophenyl)ethyl)amino)quinolin-6-yl)pyrimidin-2-yl) propan-2-ol (homochiral) (241); 2-(4-(5-(3-chloro-7-fluoro-4-((1-(2-fluorophenyl)ethyl)amino)quinolin-6-yl)pyrimidin-2-yl) piperazin-1-yl)acetic acid (242); ethyl-1-(5-(3-chloro-7-fluoro-4-((1-(2-fluorophenyl)ethyl)amino)quinolin-6-yl)pyrimidin-2-yl)piperidine-4-carboxylate (243); 1-(5-(3-chloro-7-fluoro-4-((1-(2-fluorophenyl)ethyl)amino) quinolin-6-yl)pyrimidin-2-yl) piperidine-4-carboxylic acid (244); 2-(1-(5-(3-chloro-7-fluoro-4-((1-(2-fluorophenyl) ethyl)amino)quinolin-6-yl)pyrimidin-2-yl)piperidin-4-yl) propan-2-ol (245); 2-(5-(3-chloro-7-fluoro-4-((1-(2-fluorophenyl)ethyl)amino)quinolin-6-yl)pyrimidin-2-yl)propan-2-ol (246); 2-(5-(3-chloro-8-fluoro-4-((1-(2-fluorophenyl)ethyl)amino)quinolin-6-yl)pyrimidin-2-yl)propan-2-ol (247); 2-(5-(3-chloro-7-fluoro-4-((1-(2-fluorophenyl)ethyl)amino)quinolin-6-yl)pyrimidin-2-yl)propan-2-ol (248); 2-(5-(3-chloro-7-fluoro-4-((1-(2-fluorophenyl)ethyl)amino) quinolin-6-yl)pyrimidin-2-yl)propan-2-ol (249); 2-(5-(3-chloro-7-fluoro-4-((1-(2-fluorophenyl)ethyl)amino)quinolin-6-yl)pyrimidin-2-yl)propan-2-ol (250); 4-(4-(3-chloro-7-fluoro-4-((1-(2-fluorophenyl)ethyl)amino)quinolin-6-yl) phenyl)-4-hydroxycyclohexane-1-carboxylic acid (251); 2-(5-(3-chloro-7-fluoro-4-((1-(2-fluorophenyl)ethyl)amino)quinolin-6-yl)pyrimidin-2-yl)propan-2-ol (252); 2-(5-(3-chloro-5-fluoro-4-((1-(2-fluorophenyl)ethyl)amino)quinolin-6-yl)pyrimidin-2-yl)propan-2-ol (253); 2-(5-(3-chloro-7-fluoro-4-((1-(2-fluorophenyl)ethyl)amino)quinolin-6-yl) pyrimidin-2-yl)propane-1,2-diol (254); 5-(3-chloro-7-fluoro-4-((1-(2-fluorophenyl)ethyl)amino)quinolin-6-yl) pyrimidine-2-carbonitrile (255); 1-(4-(3-chloro-7-fluoro-4-((1-(2-fluorophenyl)ethyl)amino)quinolin-6-yl)phenyl) ethane-1,2-diol (256); 2-(5-(3-chloro-7-fluoro-4-((1-(2-fluorophenyl)ethyl)amino)quinolin-6-yl)pyrimidin-2-yl) propane-1,2-diol (257); 2-(4-(3-chloro-7-fluoro-4-((1-(2-fluorophenyl)ethyl)amino)quinolin-6-yl)-2-fluorophenyl) propan-2-ol (258); 2-(5-(3-chloro-7-fluoro-4-((1-(2-fluorophenyl)ethyl)amino)quinolin-6-yl)pyrimidin-2-yl) propane-1,2-diol (259); (4-(3-chloro-7-fluoro-4-((1-(2-fluorophenyl)ethyl)amino)quinolin-6-yl)phenyl) (cyclopropyl)methanol (260); (4-(3-chloro-7-fluoro-4-((1-(2-fluorophenyl)ethyl)amino)quinolin-6-yl)phenyl) (cyclopropyl) methanol (261); (4-(3-chloro-7-fluoro-4-((1-(2-fluorophenyl)ethyl)amino)quinolin-6-yl)phenyl) (cyclopropyl)methanol (262); (4-(3-chloro-7-fluoro-4-((1-(2-fluorophenyl)ethyl)amino)quinolin-6-yl)phenyl) (cyclopropyl)methanol (263); (1-(4-(3-chloro-7-fluoro-4-((1-(2-fluorophenyl)ethyl)amino)quinolin-6-yl)phenyl) cyclopropyl)methanol (264); (1-(4-(3-chloro-7-fluoro-4-((1-(2-fluorophenyl)ethyl)amino)quinolin-6-yl)phenyl) cyclopropyl) methanol (265); 2-(1-(5-(3-chloro-7-fluoro-4-((1-(2-fluorophenyl)ethyl)amino)quinolin-6-yl)pyrimidin-2-yl)piperidin-4-yl)acetic acid (266); 2-(4-(3-chloro-7- fluoro-4-((1-(2-fluorophenyl)ethyl)amino)quinolin-6-yl)-2,6-difluorophenyl)propan-2-ol (267); 2-(4-(3-chloro-7-fluoro-4-((1-(2-fluorophenyl)ethyl)amino)quinolin-6-yl)-2,6-difluorophenyl) propan-2-ol (268); (S)-2-(5-(3-chloro-4-((2,2-difluoro-1-(2-fluorophenyl)ethyl)amino)-7-fluoroquinolin-6-yl)pyrimidin-2-yl)propan-2-ol (269); (S)-2-(5-(3-chloro-4-((2,2-difluoro-1-(2-fluorophenyl)ethyl)amino)-7-fluoroquinolin-6-yl)pyridin-2-yl)propan-2-ol (270); 2-(5-(3-chloro-7-fluoro-4-(((1S,2R)-2-phenylcyclopropyl)amino)quinolin-6-yl)pyrimidin-2-yl)propan-2-ol (271); 1-(4-(3-chloro-7-fluoro-4-((1-(2-fluorophenyl)ethyl)amino)quinolin-6-yl)phenyl)-2-morpholinoethan-1-ol (272); 1-(5-(3-chloro-7-fluoro-4-((1-(2-fluorophenyl)ethyl)amino)quinolin-6-yl)pyrazin-2-yl)-2-morpholinoethan-1-ol (273); 1-(5-(3-chloro-7-fluoro-4-((1-(2-fluorophenyl)ethyl)amino)quinolin-6-yl)pyrazin-2-yl)-2-morpholinoethan-1-ol (274); 1-(5-(3-chloro-7-fluoro-4-((1-(2-fluorophenyl)ethyl)amino)quinolin-6-yl)pyrazin-2-yl)-2-morpholinoethan-1-ol (275); 1-(5-(3-chloro-7-fluoro-4-((1-(2-fluorophenyl)ethyl)amino)quinolin-6-yl)pyrazin-2-yl)-2-morpholinoethan-1-ol (276); 1-(4-(3-chloro-7-fluoro-4-((1-(2-fluorophenyl)ethyl)amino) quinolin-6-yl)phenyl)-2-morpholinoethan-1-ol (277); 2-(5-(3-chloro-7-fluoro-4-((1-(2-fluorophenyl)cyclopropyl)amino)quinolin-6-yl)pyrimidin-2-yl)propan-2-ol (278); 2-(4-(3-chloro-7-fluoro-4-((1-(2-fluorophenyl)cyclopropyl)amino)quinolin-6-yl)phenyl) propan-2-ol (279); (R)-2-(4-(4-(3-chloro-7-fluoro-4-((1-(2-fluorophenyl)ethyl)amino) quinolin-6-yl)phenyl)piperazin-1-yl)acetic acid (280); methyl 1-(5-(3-chloro-7-fluoro-4-(((R)-1-(2-fluorophenyl)ethyl)amino)quinolin-6-yl)pyrimidin-2-yl)pyrrolidine-3-carboxylate (281); 1-(5-(3-chloro-7-fluoro-4-(((R)-1-(2-fluorophenyl)ethyl)amino) quinolin-6-yl)pyrimidin-2-yl)pyrrolidine-3-carboxylic acid (282); 2-(1-(5-(3-chloro-7-fluoro-4-(((R)-1-(2-fluorophenyl)ethyl)amino)quinolin-6-yl)pyrimidin-2-yl)pyrrolidin-3-yl)propan-2-ol (283); 1-(5-(3-chloro-7-fluoro-4-((1-(2-fluorophenyl)ethyl)amino) quinolin-6-yl)pyrazin-2-yl)pyrrolidin-3-ol (284); (R)-2-(4-(5-(3-chloro-4-((1-(2-fluorophenyl)ethyl)amino)quinolin-6-yl)pyrimidin-2-yl)piperazin-1-yl)acetic acid (285); 1-(4-(3-chloro-7-fluoro-4-((1-(2-fluorophenyl)ethyl)amino)quinolin-6-yl)phenyl)-2-morpholinoethan-1-ol (286); 4-(5-(7-fluoro-4-((1-(2-fluorophenyl)ethyl)amino)quinolin-6-yl)pyrimidin-2-yl)tetrahydro-2H-pyran-4-ol (287); 1-(4-(3-chloro-7-fluoro-4-((1-(2-fluorophenyl)ethyl)amino)quinolin-6-yl)phenyl)-2-morpholinoethan-1-ol (288); 4-(5-(3-chloro-7-fluoro-4-((1-(2-fluorophenyl)ethyl)amino)quinolin-6-yl)pyrimidin-2-yl)-4-hydroxytetrahydro-2H-thiopyran 1,1-dioxide (289); 1-(4-(3-chloro-7-fluoro-4-((1-(2-fluorophenyl)ethyl)amino)quinolin-6-yl)phenyl)ethane-1,2-diol (290); 1-(4-(3-chloro-7-fluoro-4-((1-(2-fluorophenyl)ethyl)amino)quinolin-6-yl)phenyl)ethane-1,2-diol (291); 2-(5-(3-chloro-7-fluoro-4-((1-(2-fluorophenyl)ethyl)amino)quinolin-6-yl)pyrimidin-2-yl)-1-methoxypropan-2-ol (292); 2-(5-(3-chloro-7-fluoro-4-((1-(2-fluorophenyl)ethyl)amino) quinolin-6-yl)pyrimidin-2-yl)-1-methoxypropan-2-ol (293); 2-(5-(3-chloro-7-fluoro-4-((1-(2-fluorophenyl)ethyl)amino)quinolin-6-yl)pyrazin-2-yl)propan-2-ol (294); 4-(5-(3-chloro-7-fluoro-4-((1-(2-fluorophenyl)ethyl)amino)quinolin-6-yl)pyrimidin-2-yl)-4-hydroxycyclohexane-1-carboxylic acid (295); 2-(5-(3,5-dichloro-4-((1-(2-fluorophenyl)ethyl)amino)quinolin-6-yl)pyrimidin-2-yl)propan-2-ol (296); (S)-2-(5-(3-chloro-4-((2,2-difluoro-1-(2-fluorophenyl)ethyl)amino)-8-fluoroquinolin-6-yl)pyrimidin-2-yl)propan-2-ol (297); 2-(5-(3-chloro-8-fluoro-4-((1-(2-fluorophenyl)ethyl)amino)-2-methylquinolin-6-yl)pyrimidin-2-yl)propan-2-ol (298); (S)-2-(5-(3-chloro-4-((2,2-difluoro-1-(2-fluorophenyl)ethyl) amino)-8-fluoro-2-methylquinolin-6-yl)pyrimidin-2-yl)propan-2-ol (299); 1-(5-(3-chloro-7-fluoro-4-((1-(2-fluorophenyl)ethyl)amino)quinolin-6-yl)pyrimidin-2-yl)ethane-1,2-diol (300); 2-(5-(3-chloro-8-fluoro-4-((1-(4-fluorophenyl)ethyl)amino)-2-methylquinolin-6-yl)pyrimidin-2-yl)propan-2-ol (301); (R)-3-(1-((3-chloro-8-fluoro-6-(2-(2-hydroxypropan-2-yl)pyrimidin-5-yl)-2-methylquinolin-4-yl)amino)ethyl)-4-fluorobenzonitrile (302); (R)-3-(1-((3-chloro-8-fluoro-6-(2-(2-hydroxypropan-2-yl)pyrimidin-5-yl)-2-methylquinolin-4-yl)amino)ethyl)-4-fluorobenzamide (303); (R)-(2-(4-(5-(3-chloro-7-fluoro-4-((1-(2-fluorophenyl)ethyl)amino)quinolin-6-yl)pyrimidin-2-yl)piperazin-1-yl)acetyl)glycine (304); (S)-2-(4-(3-chloro-4-((2,2-difluoro-1-(2-fluorophenyl)ethyl) amino)-8-fluoro-2-methylquinolin-6-yl)phenyl)propan-2-ol (305); 2-(5-(3-chloro-8-fluoro-2-methyl-4-((1-phenylethyl)amino) quinolin-6-yl)pyrimidin-2-yl)propan-2-ol (306); 2-(5-(3-chloro-8-fluoro-4-((1-(3-fluorophenyl)ethyl)amino)-2-methylquinolin-6-yl)pyrimidin-2-yl)propan-2-ol (307); ± 2-(4-(3-chloro-4-((1-(2-fluorophenyl)ethyl)amino)-2-methylquinolin-6-yl)phenyl) propan-2-ol (308); 2-(4-(5-(3-chloro-4-((1-(2-fluorophenyl)ethyl)amino)-2-methylquinolin-6-yl)pyrimidin-2-yl)piperazin-1-yl)acetic acid (309); 4-(5-(3-chloro-4-((1-(2-fluorophenyl)ethyl)amino)-2-methylquinolin-6-yl)pyrimidin-2-yl)thiomorpholine 1,1-dioxide (310); 3-chloro-N-(1-(2-fluorophenyl)ethyl)-2-methyl-6-(2-morpholinopyrimidin-5-yl)quinolin-4-amine (311); (R)-3-(1-((3-chloro-6-(4-(2-hydroxypropan-2-yl)phenyl)-2-methylquinolin-4-yl)amino)ethyl)-4-fluorobenzamide (312); (R)-3-(1-((3-chloro-2-methyl-6-(2-morpholinopyrimidin-5-yl)quinolin-4-yl)amino)ethyl)-4-fluorobenzamide (313); (R)-4-fluoro-3-(1-((6-(2-(2-hydroxypropan-2-yl)pyrimidin-5-yl)-2,3-dimethylquinolin-4-yl)amino)ethyl)benzonitrile (314); (R)-4-fluoro-3-(1-((6-(2-(2-hydroxypropan-2-yl)pyrimidin-5-yl)-2,3-dimethylquinolin-4-yl)amino)ethyl)benzamide (315); (R)-2-(5-(4-((1-(5-bromo-2-fluorophenyl)ethyl)amino)-3-chloro-2-methylquinolin-6-yl)pyrimidin-2-yl)propan-2-ol (316); 2-(5-(3-chloro-4-((1-(2,5-difluorophenyl)ethyl)amino)-2-methylquinolin-6-yl)pyrimidin-2-yl) propan-2-ol (317); (R)-2-(5-(4-((1-(5-bromo-2-fluorophenyl)ethyl)amino)-3-chloroquinolin-6-yl)pyrimidin-2-yl)propan-2-ol (318); (R)-2-(5-(4-((1-(3-bromophenyl)ethyl)amino)-3-chloroquinolin-6-yl)pyrimidin-2-yl)propan-2-ol (319); (S)-2-(5-(4-((1-(5-bromo-2-fluorophenyl)-2,2-difluoroethyl)amino)-3-chloro-2-methylquinolin-6-yl)pyrimidin-2-yl)propan-2-ol (320); (R)-2-(5-(4-((1-(5-bromo-2-fluorophenyl)-2,2-difluoroethyl)amino)-3-chloro-2-methylquinolin-6-yl)pyrimidin-2-yl) propan-2-ol (321); (R)-2-(5-(3-chloro-2-methyl-4-((1-phenylethyl)amino)quinolin-6-yl)pyrimidin-2-yl)propan-2-ol (322); (R)-2-(5-(3-chloro-4-((1-(2-fluoro-5-(2-hydroxyethyl)phenyl)ethyl)amino)-2-methylquinolin-6-yl)pyrimidin-2-yl)propan-2-ol (323); (R)-2-(5-(3-chloro-7-fluoro-4-((1-(2-fluoro-5-(2-hydroxyethoxy)phenyl)ethyl)amino)-2-methylquinolin-6-yl)pyrimidin-2-yl)propan-2-ol (324); (R)-2-(5-(3-chloro-7-fluoro-4-((1-(2-fluoro-5-(2-hydroxyethyl)phenyl)ethyl)amino)-2-methylquinolin-6-yl)pyrimidin-2-yl) propan-2-ol (325); (R)-2-(5-(3-chloro-4-((1-(2-fluoro-5-methoxyphenyl)ethyl)amino)-2-methylquinolin-6-yl)pyrimidin-2-yl)propan-2-ol (326); (R)-2-(5-(3-chloro-4-((1-(2-fluoro-5-methoxyphenyl)ethyl)amino)quinolin-6-yl)pyrimidin-2-yl)propan-2-ol (327); (R)-6-bromo-3-chloro-N-(1-(2-fluoro-5-methoxyphenyl)ethyl)-2-methylquinolin-4-amine (328); (R)-3-chloro-N-(1-(2-fluoro-5-methoxyphenyl)ethyl)-2-methylquinolin-4-amine (329); (R)-2-(5-(3-chloro-4-((1-(2-fluoro-5-vinylphenyl)ethyl)amino)-2-methylquinolin-6-yl)pyrimidin-2-yl)propan-2-ol (330); (R)-2-(5-(3-chloro-4-((1-(4-fluoro-[1,1'-biphenyl]—3-yl)ethyl)amino)-2-methylquinolin-6-yl)pyrimidin-2-yl)propan-2-ol (331); (R)-2-(5-(3-chloro-4-((1-(4-fluoro-2'-methyl-[1,1'-biphenyl]-3-yl)ethyl)amino)-2-methylquinolin-6-yl)pyrimidin-2-yl)propan-2-ol (332); (R)-2-(5-(3-chloro-4-((1-(5-(cyclopent-1-en-1-yl)-2-fluorophenyl)ethyl)amino)-2-methylquinolin-6-yl)pyrimidin-2-yl)propan-2-ol (333); (R)-2-(5-(3-chloro-4-((1-(2-fluoro-5-methylphenyl)ethyl)amino)-2-methylquinolin-6-yl)pyrimidin-2-yl)propan-2-ol (334); (R)-2-(5-(3-chloro-4-((1-(2-fluoro-5-(1H-pyrazol-4-yl)phenyl)ethyl)amino)-2-methylquinolin-6-yl)pyrimidin-2-yl) propan-2-ol (335); (R)-2-(5-(3-chloro-4-((1-(2-fluoro-5-(1H-pyrazol-3-yl)phenyl)ethyl)amino)-2-methylquinolin-6-yl)pyrimidin-2-yl)propan-2-ol (336); tert-butyl (R)-4-(3-(1-(((3-chloro-6-(2-(2-hydroxypropan-2-yl)pyrimidin-5-yl)quinolin-4-yl)amino)ethyl)-4-fluorophenyl)-3,6-dihydropyridine-1(2H)-carboxylate (337); (R)-2-(5-(3-chloro-4-((1-(2-fluoro-5-(1,2,3,6-tetrahydropyridin-4-yl)phenyl)ethyl)amino)quinolin-6-yl)pyrimidin-2-yl)propan-2-ol (338); (R)-2-(5-(3-chloro-4-((1-(2-fluoro-5-(1-methyl-1H-pyrazol-4-yl)phenyl)ethyl)amino)quinolin-6-yl)pyrimidin-2-yl)propan-2-ol (339); (R)-2-(5-(3-chloro-4-((1-(2-fluoro-5-(pyrimidin-5-yl)phenyl)ethyl)amino)quinolin-6-yl)pyrimidin-2-yl) propan-2-ol (340); (R)-2-(5-(3-chloro-4-((1-(2-fluoro-5-(pyrazin-2-yl)phenyl)ethyl)amino)quinolin-6-yl)pyrimidin-2-yl)propan-2-ol (341); (R)-2-(4-(5-(3-chloro-4-((1-(2-fluoro-5-(1H-pyrazol-4-yl)phenyl)ethyl)amino)-2-methylquinolin-6-yl)pyrimidin-2-yl) piperazin-1-yl)acetic acid (342); (R)-2-(5-(3-chloro-4-((1-(2-fluoro-5-(2-(2-hydroxypropan-2-yl)pyrimidin-5-yl)phenyl)ethyl)amino)-2-methylquinolin-6-yl)pyrimidin-2-yl)propan-2-ol (343); (R)-2-(5-(3-chloro-4-((1-(2-fluoro-5-(1-methyl-1H-pyrazol-4-yl)phenyl)ethyl)amino)-2-methylquinolin-6-yl)pyrimidin-2-yl)propan-2-ol (344); (R)-2-(5-(3-chloro-4-((1-(2-fluoro-5-(pyrimidin-2-yl)phenyl)ethyl)amino)quinolin-6-yl)pyrimidin-2-yl)propan-2-ol (345); (R)-2-(4-(3-(1-((3-chloro-6-(2-(2-hydroxypropan-2-yl)pyrimidin-5-yl)quinolin-4-yl)amino)ethyl)-4-fluorophenyl)-1H-pyrazol-1-yl)acetic acid (346); (R)-2-(5-(3-chloro-4-((1-(2-fluoro-5-(thiazol-5-yl)phenyl)ethyl)amino) quinolin-6-yl)pyrimidin-2-yl)propan-2-ol (347); (R)-2-(5-(4-((1-(5-(6-aminopyridin-3-yl)-2-fluorophenyl)ethyl)amino)-3-chloroquinolin-6-yl)pyrimidin-2-yl)propan-2-ol (348); (R)-1-(4-(3-(1-((3-chloro-6-(2-(2-hydroxypropan-2-yl)pyrimidin-5-yl)quinolin-4-yl)amino)ethyl)-4-fluorophenyl)-1H-pyrazol-1-yl)-2-methylpropan-2-ol (349); (R)-2-(5-(4-((1-(5-(2-aminopyridin-4-yl)-2-fluorophenyl)ethyl)amino)-3-chloroquinolin-6-yl)pyrimidin-2-yl)propan-2-ol (350); (S)-2-(5-(3-chloro-4-((2,2-difluoro-1-(2-fluoro-5-methylphenyl)ethyl)amino)-2-methylquinolin-6-yl)pyrimidin-2-yl)propan-2-ol (351); (S)-2-(5-(3-chloro-4-((2,2-difluoro-1-(2-fluoro-5-vinylphenyl)ethyl)amino)-2-methylquinolin-6-yl)pyrimidin-2-yl)propan-2-ol (352); 2-(5-(4-([1,1'-biphenyl]-2-yl)-3-chloro-2-methylquinolin-6-yl)pyrimidin-2-yl)propan-2-ol (353); (S)-methyl 3-((S)-1-((3-chloro-6-(2-(2-hydroxypropan-2-yl)pyrimidin-5-yl)quinolin-4-yl)amino)ethyl)piperidine-1-carboxylate (354); tert-Butyl (R)-(3-(1-((3-chloro-6-(2-(2-hydroxypropan-2-yl)pyrimidin-5-yl)-2-methylquinolin-4-yl)amino)ethyl)-4-fluorophenyl)carbamate (359); (R)-2-(5-(4-((1-(5-amino-2-fluorophenyl)ethyl)amino)-3-chloro-2-methylquinolin-6-yl)pyrimidin-2-yl)propan-2-ol (360); (R)-1-(3-(1-((3-chloro-6-(2-(2-hydroxypropan-2-yl)pyrimidin-5-yl)-2-methylquinolin-4-yl)amino)ethyl)-4-fluorophenyl)pyrrolidin-2-one (361); (R)-1-(3-(1-((3-chloro-6-(2-(2-hydroxypropan-2-yl)pyrimidin-5-yl)quinolin-4-yl)amino)ethyl)-4-fluorophenyl)pyrrolidin-2-one (362); (R)-1-(3-(1-((3-chloro-6-(2-(2-hydroxypropan-2-yl)pyrimidin-5-yl)quinolin-4-yl)amino)ethyl)phenyl)pyrrolidin-2-one (363); (R)-2-(5-(3-chloro-4-((1-(2-fluoro-5-(pyrrolidin-1-yl)phenyl)ethyl)amino) quinolin-6-yl)pyrimidin-2-yl)propan-2-ol (364); (R)-2-(5-(3-chloro-4-((1-(2-fluoro-5-(1H-pyrazol-1-yl)phenyl)ethyl)amino)-2-methylquinolin-6-yl)pyrimidin-2-yl)propan-2-ol (365); (R)-2-(5-(3-chloro-4-((1-(2-fluoro-5-(1H-pyrazol-1-yl)phenyl)ethyl)amino) quinolin-6-yl)pyrimidin-2-yl)propan-2-ol (366); (R)-3-(3-(1-((3-chloro-6-(2-(2-hydroxypropan-2-yl)pyrimidin-5-yl)quinolin-4-yl)amino)ethyl)-4-fluorophenyl) oxazolidin-2-one (367); (R)-2-(5-(4-((1-(3-(1H-pyrazol-1-yl)phenyl)ethyl)amino)-3-chloroquinolin-6-yl)pyrimidin-2-yl)propan-2-ol (368); (R)-4-(3-(1-((3-chloro-6-(2-(2-hydroxypropan-2-yl)pyrimidin-5-yl)quinolin-4-yl)amino)ethyl)-4-fluorophenyl) morpholin-3-one (369); (R)-1-(3-(1-((3-chloro-6-(2-(2-hydroxypropan-2-yl)pyrimidin-5-yl)quinolin-4-yl)amino) ethyl)-4-fluorophenyl)imidazolidin-2-one (370); (R)-2-(5-(3-chloro-4-((1-(2-fluoro-5-(4H-1,2,4-triazol-4-yl)phenyl)ethyl)amino)quinolin-6-yl)pyrimidin-2-yl)propan-2-ol (371); (S)-1-(3-(1-((3-chloro-6-(2-(2-hydroxypropan-2-yl)pyrimidin-5-yl)-2-methylquinolin-4-yl)amino)-2,2-difluoroethyl)-4-fluorophenyl) imidazolidin-2-one (372); (R)-1-(3-(1-((3-chloro-6-(2-(2-hydroxypropan-2-yl)pyrimidin-5-yl)-2-methylquinolin-4-yl)amino)ethyl)-4-fluorophenyl) imidazolidin-2-one (373); (R)-2-(5-(4-((1-(5-amino-2-fluorophenyl)ethyl)amino)-3-chloroquinolin-6-yl)pyrimidin-2-yl)propan-2-ol (374); (R)-3-(1-((3-chloro-6-(2-(2-hydroxypropan-2-yl)pyrimidin-5-yl)-2-methylquinolin-4-yl)amino)ethyl)-4-fluorobenzonitrile (375); (R)-3-(1-((3-chloro-6-(2-(2-hydroxypropan-2-yl)pyrimidin-5-yl)quinolin-4-yl)amino)ethyl)-4-fluorobenzonitrile (376); (R)-2-(4-(5-(3-chloro-4-((1-(5-cyano-2-fluorophenyl)ethyl)amino)-2-methylquinolin-6-yl)pyrimidin-2-yl)piperazin-1-yl)acetic acid (377); (R)-3-(1-((3-chloro-6-(2-(2-hydroxypropan-2-yl)pyrimidin-5-yl)-2-methylquinolin-4-yl)amino)-2,2-difluoroethyl)-4-fluorobenzonitrile (378); (R)-3-(1-((3-chloro-7-fluoro-6-(2-(2-hydroxypropan-2-yl)pyrimidin-5-yl)quinolin-4-yl)amino)ethyl)-4-fluorobenzonitrile (379); (S)-3-(1-((3-chloro-6-(2-(2-hydroxypropan-2-yl)pyrimidin-5-yl)-2-methylquinolin-4-yl)amino)-2,2-difluoroethyl)-4-fluorobenzonitrile (380); (S)-3-(1-((3-chloro-7-fluoro-6-(2-(2-hydroxypropan-2-yl)pyrimidin-5-yl)quinolin-4-yl)amino)-2,2-difluoroethyl)-4-fluorobenzonitrile (381); (R)-3-(1-((3-chloro-7-fluoro-6-(2-(2-hydroxypropan-2-yl)pyrimidin-5-yl)-2-methylquinolin-4-yl)amino)ethyl)-4-fluorobenzonitrile (382); (R)-3-(1-((3-chloro-7-fluoro-6-(2-(2-hydroxypropan-2-yl)pyrimidin-5-yl)-2-methylquinolin-4-yl)amino)ethyl)benzonitrile (383); ethyl (R)-3-chloro-4-((1-(5-cyano-2-fluorophenyl)ethyl)amino)-6-(2-(2-hydroxypropan-2-yl)pyrimidin-5-yl)quinoline-2-carboxylate (384); (R)-3-chloro-4-((1-(5-cyano-2-fluorophenyl)ethyl)amino)-6-(2-(2-hydroxypropan-2-yl)pyrimidin-5-yl)-N-(pyridin-3-yl)quinoline-2-carboxamide (385); (R)-3-(1-((3-chloro-6-(2-(2-hydroxypropan-2-yl)pyrimidin-5-yl)-2-methyl quinolin-4-yl)amino)ethyl)benzonitrile (386); (R)-3-(1-((3-chloro-6-(2-(2-hydroxypropan-2-yl)pyrimidin-5-yl)-2-methylquinolin-4-yl)amino)ethyl)-4-fluorobenzamide (387); (R)-3-(1-((3-chloro-6-(2-(2-hydroxypropan-2-yl)pyrimidin-5-yl)quinolin-4-yl)amino) ethyl)-4-fluorobenzamide (388); (R)-2-(4-(5-(4-((1-(5-carbamoyl-2-fluorophenyl)ethyl)amino)-3-chloro-2-methylquinolin-6-yl)pyrimidin-2-yl)piperazin-1-yl)acetic acid (389); (S)-3-(1-((3-chloro-6-(2-(2-hydroxypropan-2-yl)pyrimidin-5-yl)-2-methylquinolin-4-yl)amino)-2,2-difluoroethyl)-4-fluorobenzamide (390); (S)-3-(1-((3-chloro-7-fluoro-6-(2-(2-hydroxypropan-2-yl)pyrimidin-5-yl)

quinolin-4-yl)amino)-2,2-difluoroethyl)-4-fluorobenzamide (391); (R)-3-(1-((3-chloro-7-fluoro-6-(2-(2-hydroxypropan-2-yl)pyrimidin-5-yl)quinolin-4-yl)amino)ethyl)-4-fluorobenzamide (392); (R)-3-(1-((3-chloro-7-fluoro-6-(2-(2-hydroxypropan-2-yl)pyrimidin-5-yl)-2-methylquinolin-4-yl)amino)ethyl)-4-fluorobenzamide (393); (R)-3-(1-((3-chloro-7-fluoro-6-(2-(2-hydroxypropan-2-yl)pyrimidin-5-yl)-2-methylquinolin-4-yl)amino)ethyl)benzamide (394); (R)-4-((1-(5-carbamoyl-2-fluorophenyl)ethyl)amino)-3-chloro-6-(2-(2-hydroxypropan-2-yl)pyrimidin-5-yl)-N-(pyridin-3-yl)quinoline-2-carboxamide (395); (R)-2-(5-(4-((1-(5-benzyl-2-fluorophenyl)ethyl)amino)-3-chloro-2-methylquinolin-6-yl)pyrimidin-2-yl)propan-2-ol (396); 1-(3-((R)-1-((3-chloro-6-(2-(2-hydroxypropan-2-yl)pyrimidin-5-yl)-2-methylquinolin-4-yl)amino)ethyl)-4-fluorophenyl)ethane-1,2-diol (397); 1-(3-((R)-1-((3-chloro-6-(2-(2-hydroxypropan-2-yl)pyrimidin-5-yl)quinolin-4-yl)amino)ethyl)-4-fluorophenyl)ethane-1,2-diol (398); 3-((R)-1-((3-chloro-6-(2-(2-hydroxypropan-2-yl)pyrimidin-5-yl) quinolin-4-yl)amino)ethyl)-4-fluorophenyl)propane-1,2-diol (399); 1-(3-((R)-1-((3-chloro-6-(2-(2-hydroxypropan-2-yl)pyrimidin-5-yl) quinolin-4-yl)amino)ethyl)-4-fluorophenyl)ethane-1,2-diol (400); 1-(3-((R)-1-((3-chloro-6-(2-(2-hydroxypropan-2-yl)pyrimidin-5-yl)quinolin-4-yl)amino)ethyl)-4-fluorophenyl) ethane-1,2-diol (401); 1-(3-((S)-1-((3-chloro-6-(2-(2-hydroxypropan-2-yl)pyrimidin-5-yl)-2-methylquinolin-4-yl)amino)-2,2-difluoroethyl)-4-fluorophenyl)ethane-1,2-diol (402); 2-(3-((R)-1-((3-chloro-6-(2-(2-hydroxypropan-2-yl)pyrimidin-5-yl)-2-methylquinolin-4-yl)amino)ethyl)-4-fluorophenyl)propane-1,2-diol (403); (R)-3-(1-((3-chloro-6-(2-(2-hydroxypropan-2-yl)pyrimidin-5-yl)-2-methylquinolin-4-yl)amino)ethyl)-4-fluorophenol (404); (R)-3-(1-((3-chloro-6-(2-(2-hydroxypropan-2-yl)pyrimidin-5-yl) quinolin-4-yl)amino)ethyl)-4-fluorophenol (405); (R)-2-(5-(3-chloro-4-((1-(5-chloro-2-fluorophenyl)ethyl)amino)-2-methylquinolin-6-yl)pyrimidin-2-yl)propan-2-ol (406); (R)-3-(1-((3-chloro-6-(2-(2-hydroxypropan-2-yl)pyrimidin-5-yl)-2-methylquinolin-4-yl)amino)ethyl)-4-fluorobenzoic acid (407); (R)-2-(5-(3-chloro-4-((1-(2-fluoro-5-(2-hydroxypropan-2-yl)phenyl)ethyl)amino)-2-methylquinolin-6-yl)pyrimidin-2-yl)propan-2-ol, TFA salt (408); (R)-1-(3-(1-((3-chloro-6-(2-(2-hydroxypropan-2-yl)pyrimidin-5-yl) quinolin-4-yl)amino)ethyl)-4-fluorophenyl)ethan-1-one (409); (R)-2-(5-(3-chloro-4-((1-(2-fluoro-5-(2-hydroxypropan-2-yl)phenyl)ethyl)amino)quinolin-6-yl)pyrimidin-2-yl) propan-2-ol (410); (R)-2-(5-(3-chloro-4-((1-(2-fluoro-5-(phenylethynyl)phenyl)ethyl)amino)quinolin-6-yl)pyrimidin-2-yl)propan-2-ol (411); (R)-2-(5-(3-chloro-4-((1-(2-fluoro-5-(1H-tetrazol-5-yl)phenyl)ethyl)amino)-2-methylquinolin-6-yl)pyrimidin-2-yl) propan-2-ol (412); (R)-2-(5-(3-chloro-4-((1-(2-fluoro-5-(2-methyl-2H-tetrazol-5-yl)phenyl)ethyl)amino)quinolin-6-yl)pyrimidin-2-yl)propan-2-ol (413); (R)-2-(5-(3-chloro-4-((1-(2-fluoro-5-(1H-1,2,4-triazol-5-yl)phenyl)ethyl) amino)quinolin-6-yl)pyrimidin-2-yl)propan-2-ol (414); Methyl (R)-3-(1-((3-chloro-6-(2-(2-hydroxypropan-2-yl)pyrimidin-5-yl)quinolin-4-yl)amino)ethyl)-4-fluorobenzoate (415); (R)-3-(1-((3-chloro-6-(2-(2-hydroxypropan-2-yl)pyrimidin-5-yl)quinolin-4-yl)amino)ethyl)-4-fluoro-N-methylbenzamide (416); (R)-3-(1-((3-chloro-6-(2-(2-hydroxypropan-2-yl)pyrimidin-5-yl)quinolin-4-yl)amino)ethyl)-4-fluoro-N,N-dimethylbenzamide (417); (S)-2-(5-(3-chloro-4-((2,2-difluoro-1-(2-fluoro-5-(2-hydroxypropan-2-yl)phenyl)ethyl)amino)-2-methylquinolin-6-yl)pyrimidin-2-yl)propan-2-ol (418); (R)-2-(5-(3-chloro-4-((1-(2-fluoro-5-(1H-1,2,3-triazol-4-yl)phenyl)ethyl)amino)quinolin-6-yl) pyrimidin-2-yl)propan-2-ol (419); (R)-2-(5-(3-chloro-4-((1-(2-fluoro-5-(1-methyl-1H-1,2,3-triazol-4-yl)phenyl)ethyl) amino)quinolin-6-yl)pyrimidin-2-yl)propan-2-ol (420); (R)-2-(5-(3-chloro-4-((1-(2-fluoro-5-(1-methyl-1H-1,2,3-triazol-5-yl)phenyl)ethyl)amino)quinolin-6-yl)pyrimidin-2-yl)propan-2-ol (421); 5-(((R)-1-((3-chloro-6-(2-(2-hydroxypropan-2-yl)pyrimidin-5-yl) quinolin-4-yl)amino)ethyl)-4-fluorophenyl)imidazolidine-2,4-dione (422 and 423); (R)-3-(1-((3-chloro-6-(2-(2-hydroxypropan-2-yl)pyrimidin-5-yl)quinolin-4-yl)amino)ethyl)-4-fluorobenzaldehyde oxime (424); (R)-2-(5-(3-chloro-4-((1-(2-fluoro-5-(methylsulfonyl)phenyl)ethyl)amino)quinolin-6-yl) pyrimidin-2-yl)propan-2-ol (425); (R)-3-(1-((3-chloro-6-(2-(2-hydroxypropan-2-yl)pyrimidin-5-yl)quinolin-4-yl)amino)ethyl)-4-fluorobenzenesulfonamide (426); Methyl (R)-3-((3-(1-((3-chloro-6-(2-(2-hydroxypropan-2-yl)pyrimidin-5-yl)quinolin-4-yl)amino)ethyl)-4-fluorophenyl)sulfonyl)propanoate (427); (R)-3-(3-(1-((3-chloro-6-(2-(2-hydroxypropan-2-yl)pyrimidin-5-yl)quinolin-4-yl)amino) ethyl)-4-fluorophenyl)-1H-pyrazole-5-carboxylic acid (428); (R)-2-(5-(4-((1-(5-(aminomethyl)-2-fluorophenyl) ethyl)amino)-3-chloroquinolin-6-yl)pyrimidin-2-yl) propan-2-ol (429); (R)-2-(5-(3-chloro-4-((1-(2-fluoro-5-(hydroxymethyl)phenyl)ethyl)amino)quinolin-6-yl)pyrimidin-2-yl)propan-2-ol (430); (R)-2-(5-(3-chloro-4-((1-(2-fluoro-5-(hydroxymethyl)phenyl)ethyl)amino)-2-methylquinolin-6-yl)pyrimidin-2-yl) propan-2-ol (431); (R)-2-(5-(3-chloro-4-((1-(2-fluoro-5-(hydroxymethyl)phenyl)ethyl)amino)-2-methylquinolin-6-yl)-4,5-dihydropyrimidin-2-yl)propan-2-ol (432); 2-(5-(3-chloro-4-(((1R)-1-(2-fluoro-5-(1-hydroxyethyl)phenyl)ethyl)amino)-2-methylquinolin-6-yl) pyrimidin-2-yl)propan-2-ol (433); 2-(5-(4-(((1S)-1-(5-(1-amino-2-hydroxyethyl)-2-fluorophenyl)-2,2-difluoroethyl) amino)-3-chloro-2-methylquinolin-6-yl)pyrimidin-2-yl) propan-2-ol (434); (R)-2-(5-(3-chloro-4-((1-(2-fluoro-5-(2-hydroxyethoxy)phenyl)ethyl)amino)-2-methylquinolin-6-yl)pyrimidin-2-yl)propan-2-ol (435); (R)-2-(3-(1-((3-chloro-6-(2-(2-hydroxypropan-2-yl)pyrimidin-5-yl)-2-methylquinolin-4-yl)amino)ethyl)-4-fluorophenyl)acetic acid (436); (R)-2-(5-(3-chloro-4-((1-(3-(2-hydroxyethoxy) phenyl)ethyl)amino)-2-methylquinolin-6-yl)pyrimidin-2-yl) propan-2-ol (437); (R)-2-(3-(1-((3-chloro-6-(2-(2-hydroxypropan-2-yl)pyrimidin-5-yl)-2-methylquinolin-4-yl)amino) ethyl) phenoxy)acetic acid (438); (R)-2-(3-(1-((3-chloro-6-(2-(2-hydroxypropan-2-yl)pyrimidin-5-yl)-2-methylquinolin-4-yl)amino)ethyl)-4-fluorophenoxy)acetic acid (439); (R)-2-(5-(3-chloro-7-fluoro-4-((1-(2-fluoro-5-(2-hydroxyethoxy)phenyl)ethyl)amino)-2-methylquinolin-6-yl)pyrimidin-2-yl)propan-2-ol (440); (R)-2-(5-(3-chloro-4-((1-(2-fluorophenyl)ethyl)amino)-2-methylquinolin-6-yl) pyrimidin-2-yl)propan-2-ol (441); (R)-2-(5-(3-chloro-7-fluoro-4-((1-(2-fluoro-5-(2-hydroxyethyl)phenyl)ethyl) amino)-2-methylquinolin-6-yl)pyrimidin-2-yl)propan-2-ol (442); (R)-3-(3-(1-((3-chloro-7-fluoro-6-(2-(2-hydroxypropan-2-yl)pyrimidin-5-yl)-2-methylquinolin-4-yl)amino) ethyl)-4-fluorophenoxy)propan-1-ol (443); (R)-3-(3-(1-((3-chloro-6-(2-(2-hydroxypropan-2-yl)pyrimidin-5-yl)-2-methylquinolin-4-yl)amino)ethyl)-4-fluorophenoxy) propan-1-ol (444); (R)-3-(3-(1-((3-chloro-7-fluoro-6-(2-(2-hydroxypropan-2-yl)pyrimidin-5-yl)-2-methylquinolin-4-yl)amino)ethyl)-4-fluorophenyl)propanamide (445); (R)-3-(3-(1-((3-chloro-7-fluoro-6-(2-(2-hydroxypropan-2-yl) pyrimidin-5-yl)-2-methylquinolin-4-yl)amino)ethyl)-4-fluorophenyl)propanoic acid (446); (R)-3-(1-((3-chloro-2-methyl-6-(2-(3-oxopiperazin-1-yl)pyrimidin-5-yl)quinolin-4-yl)amino)ethyl)-4-fluorobenzamide (447); (R)-3-(1-((3-chloro-7-fluoro-2-methyl-6-(2-(3-oxopiperazin-1-yl) pyrimidin-5-yl) quinolin-4-yl)amino)ethyl)-4- fluorobenzamide (448); (R)-5-(4-((1-(5-bromo-2-fluorophenyl)ethyl)amino)-3-chloro-7-fluoro-2-methylquinolin-6-yl)pyridin-2(1H)-one (449); (R)-3-(1-((3-chloro-7-fluoro-2-methyl-6-(6-oxo-1,6-dihydropyridin-3-yl)quinolin-4-yl)amino)ethyl)-4-fluorobenzonitrile (450); (R)-3-chloro-N-(1-(2-fluoro-5-methoxyphenyl)ethyl)quinolin-4-amine (451); (R)—N-(1-(5-allyl-2-fluorophenyl)ethyl)-3-chloroquinolin-4-amine (452); 3-chloro-N-(1-(2-fluorophenyl)propyl)quinolin-4-amine (453); (R)-3-chloro-N-(1-(2-fluoro-5-(1-methyl-1H-pyrazol-4-yl)phenyl)ethyl)quinolin-4-amine (454); (R)-3-chloro-N-(1-(2-fluoro-5-(1H-pyrazol-4-yl)phenyl)ethyl)quinolin-4-amine (455); (R)-6-chloro-N-(1-(2-fluoro-5-methoxyphenyl)ethyl)quinolin-4-amine (456); (R)—N-(1-(5-(allyloxy)-2-fluorophenyl)ethyl)-3-chloroquinolin-4-amine (457); (R)-3-(3-(1-((3-chloroquinolin-4-yl)amino)ethyl)-4-fluorophenoxy)propan-1-ol (458); (R)-3-chloro-N-(1-(4-fluoro-[1,1'-biphenyl]-3-yl)ethyl)quinolin-4-amine (459); (R)-3-chloro-N-(1-(2-fluoro-5-(6-methoxypyridin-3-yl)phenyl)ethyl)quinolin-4-amine (460); (R)-3-chloro-N-(1-(2-fluoro-5-(pyridin-3-yl)phenyl)ethyl)quinolin-4-amine (461); (R)-3-chloro-N-(1-(3-methoxyphenyl)ethyl)quinolin-4-amine (462); 3-chloro-N-(1-(2-(trifluoromethyl)phenyl)ethyl)quinolin-4-amine (463); (R)-3-(3-(1-((3-chloroquinolin-4-yl)amino)ethyl)-4-fluorophenyl)propan-1-ol (464); (R)-1-(4-(3-(1-((3-chloroquinolin-4-yl)amino)ethyl)-4-fluorophenyl)-1H-pyrazol-1-yl)-2-methylpropan-2-ol (465); (R)—N-(1-(5-(1-benzyl-1H-pyrazol-4-yl)-2-fluorophenyl)ethyl)-3-chloroquinolin-4-amine (466); (R)-3-chloro-N-(1-(2-fluoro-5-(2-morpholinopyrimidin-5-yl)phenyl)ethyl)quinolin-4-amine (467); (R)-3-chloro-N-(1-(2-fluoro-5-(pyridin-4-yl)phenyl)ethyl)quinolin-4-amine (468); (R)-2-(5-(3-(1-((3-chloroquinolin-4-yl)amino)ethyl)-4-fluorophenyl)pyrimidin-2-yl)propan-2-ol (469); N-(5-bromo-2-methylphenyl)-3-chloro-2-methylquinolin-4-amine (470); (R)-3-chloro-N-(1-(5-(1-(difluoromethyl)-1H-pyrazol-4-yl)-2-fluorophenyl)ethyl)quinolin-4-amine (471); (R)-3-chloro-N-(1-(2-fluoro-5-(1-methyl-3-(trifluoromethyl)-1H-pyrazol-4-yl)phenyl)ethyl)quinolin-4-amine (472); (R)-3-chloro-N-(1-(5-(1-ethyl-1H-pyrazol-4-yl)-2-fluorophenyl)ethyl)quinolin-4-amine (473); (R)-3-chloro-N-(1-(5-(1,5-dimethyl-1H-pyrazol-4-yl)-2-fluorophenyl)ethyl)quinolin-4-amine (474); (R)-3-chloro-N-(1-(2-fluoro-5-(2-methylpyridin-3-yl)phenyl)ethyl)quinolin-4-amine (475); (S)-3-chloro-N-(1-(2-fluoro-5-methoxyphenyl)ethyl)quinolin-4-amine (476); (R)-3-chloro-N-(1-(2-fluoro-5-(6-methylpyridazin-4-yl)phenyl)ethyl)quinolin-4-amine (477); (R)—N-(1-(5-(6-aminopyridin-3-yl)-2-fluorophenyl)ethyl)-3-chloroquinolin-4-amine (478); (R)-3-chloro-N-(1-(2-fluoro-5-(pyrimidin-5-yl)phenyl)ethyl)quinolin-4-amine (479); (R)-3-chloro-N-(1-(2-fluoro-5-(1-(2-morpholinoethyl)-1H-pyrazol-4-yl)phenyl)ethyl)quinolin-4-amine (480); (R)—N-(1-(5-(2-aminopyrimidin-5-yl)-2-fluorophenyl)ethyl)-3-chloroquinolin-4-amine (481); N-(1-(4-(3-chloro-4-(((R)-1-(2-fluorophenyl)ethyl)amino) quinolin-6-yl)phenyl)-2-hydroxyethyl)acetamide (482); (R)-1-(1-(4-(3-chloro-4-((1-(2-fluorophenyl)ethyl)amino)quinolin-6-yl)phenyl)cyclobutyl)urea (483); 4-(5-(3-chloro-4-((1-(3-fluoro-6-methylpyridin-2-yl)ethyl)amino)quinolin-6-yl)pyrimidin-2-yl)piperazin-2-one (484); (R)-3-(1-((3-chloro-7-fluoro-6-(2-(2-hydroxypropan-2-yl)pyrimidin-5-yl)-1,5-naphthyridin-4-yl)amino)-2,2-difluoroethyl)-4-fluorobenzoic acid (485); (R)-2-(5-(7-chloro-8-((2,2-difluoro-1-(2-fluoro-5-(hydroxymethyl)phenyl)ethyl)amino)-3-fluoro-1,5-naphthyridin-2-yl)pyrimidin-2-yl)propan-2-ol (486); (R)-3-(1-((3-chloro-7-fluoro-6-(2-(2-hydroxypropan-2-yl)pyrimidin-5-yl)-1,5-naphthyridin-4-yl)amino)-2,2-difluoroethyl)-4-fluorobenzamide (487); 1-(3-((R)-1-((3-chloro-7-fluoro-6-(2-(2-hydroxypropan-2-yl)pyrimidin-5-yl)-1,5-naphthyridin-4-yl)amino)-2,2-difluoroethyl)-4-fluorophenyl)ethane-1,2-diol (488); (R)-3-(1-((3-chloro-7-fluoro-6-(2-(2-hydroxypropan-2-yl)pyrimidin-5-yl)-1,5-naphthyridin-4-yl)amino)-2,2-difluoroethyl)-4-fluorobenzonitrile (489); (R)-2-(4-(3-chloro-4-((1-(pyrazin-2-yl)ethyl)amino)quinolin-6-yl)phenyl)propan-2-ol (490); 1-(3-((S)-1-((3-chloro-7-fluoro-6-(2-(2-hydroxypropan-2-yl)pyrimidin-5-yl)-2-methyl-1,5-naphthyridin-4-yl)amino)-2,2-difluoroethyl)-4-fluorophenyl)ethane-1,2-diol (491); 1-(3-((S)-1-((3-chloro-7-fluoro-6-(2-(2-hydroxypropan-2-yl)pyrimidin-5-yl)-1,5-naphthyridin-4-yl)amino)-2,2-difluoroethyl)-4-fluorophenyl)ethane-1,2-diol (492); (S)-3-(1-((3-chloro-7-fluoro-6-(2-(2-hydroxypropan-2-yl)pyrimidin-5-yl)-1,5-naphthyridin-4-yl)amino)-2,2-difluoroethyl)-4-fluorobenzamide (493); (S)-2-(5-(7-chloro-8-((2,2-difluoro-1-(2-fluoro-5-vinylphenyl)ethyl)amino)-3-fluoro-6-methyl-1,5-naphthyridin-2-yl)pyrimidin-2-yl) propan-2-ol (494); (S)-2-(5-(7-chloro-8-((2,2-difluoro-1-(2-fluoro-5-vinylphenyl)ethyl)amino)-3-fluoro-1,5-naphthyridin-2-yl)pyrimidin-2-yl)propan-2-ol (495); (S)-2-(5-(7-chloro-8-((2,2-difluoro-1-(2-fluoro-5-(hydroxymethyl)phenyl)ethyl)amino)-3-fluoro-6-methyl-1,5-naphthyridin-2-yl)pyrimidin-2-yl) propan-2-ol (496); (S)-3-(1-((3-chloro-7-fluoro-6-(2-(2-hydroxypropan-2-yl)pyrimidin-5-yl)-2-methyl-1,5-naphthyridin-4-yl)amino)-2,2-difluoroethyl)-4-fluorobenzamide (497); (S)-3-(1-((3-chloro-7-fluoro-6-(2-(2-hydroxypropan-2-yl)pyrimidin-5-yl)-1,5-naphthyridin-4-yl)amino)-2,2-difluoroethyl)-4-fluorobenzonitrile (498); (S)-3-(1-((3-chloro-7-fluoro-6-(2-(2-hydroxypropan-2-yl)pyrimidin-5-yl)-2-methyl-1,5-naphthyridin-4-yl)amino)-2,2-difluoroethyl)-4-fluorobenzonitrile (499); (R)-2-(4-(3-chloro-4-((1-(2-fluorophenyl)ethyl)amino)-2-methylquinolin-6-yl)phenyl)propan-2-ol (500); (S)-2-(5-(7-chloro-8-((2,2-difluoro-1-(2-fluoro-5-(hydroxymethyl)phenyl)ethyl)amino)-3-fluoro-1,5-naphthyridin-2-yl)pyrimidin-2-yl)propan-2-ol (501); 2-(4-(3-chloro-2-methyl-4-((1-(thiophen-2-yl)ethyl)amino) quinolin-6-yl)phenyl) propan-2-ol (502); 2-(4-(3-chloro-2-methyl-4-((1-(thiophen-3-yl)ethyl)amino)quinolin-6-yl)phenyl)propan-2-ol (503); 1-(3-((R)-1-((3-chloro-7-fluoro-6-(2-(2-hydroxypropan-2-yl)pyrimidin-5-yl)-1,5-naphthyridin-4-yl)amino)ethyl)-4-fluorophenyl)ethane-1,2-diol (504); (R)-2-(5-(7-chloro-3-fluoro-8-((1-(2-fluoro-5-(hydroxymethyl)phenyl)ethyl)amino)-1,5-naphthyridin-2-yl)pyrimidin-2-yl) propan-2-ol (505); (R)-3-chloro-N-(1-(5-(6-(dimethylamino)pyridin-3-yl)-2-fluorophenyl)ethyl)quinolin-4-amine (506); (R)-3-chloro-N-(1-(2-fluoro-5-(5-methylpyridin-3-yl)phenyl)ethyl)quinolin-4-amine (507); (R)-3-chloro-N-(1-(5-(6-ethylpyridin-3-yl)-2-fluorophenyl)ethyl)quinolin-4-amine (508); (S)—N-(1-(5-bromo-2-fluorophenyl)-2,2-difluoroethyl)-3-chloroquinolin-4-amine (509); (R)—N-(1-(5-bromo-2-fluorophenyl)-2,2-difluoroethyl)-3-chloroquinolin-4-amine (510); (R)—N-(1-(5-(5-aminopyridin-3-yl)-2-fluorophenyl)ethyl)-3-chloroquinolin-4-amine (511); (R)—N-(1-(5-(2-aminopyridin-3-yl)-2-fluorophenyl)ethyl)-3-chloroquinolin-4-amine (512); (R)-3-chloro-N-(1-(5-(3,6-dimethoxypyridazin-4-yl)-2-fluorophenyl)ethyl)quinolin-4-amine (513); (R)-5-(3-(1-((3-chloroquinolin-4-yl)amino)ethyl)-4-fluorophenyl) picolinonitrile (514); (R)-3-chloro-N-(1-(2-fluoro-5-(pyridazin-4-yl)phenyl)ethyl)quinolin-4-amine (515); N-(5-bromo-2-fluorobenzyl)-3-chloroquinolin-4-amine (516); 3-chloro-N-(2-fluoro-5-methoxybenzyl)quinolin-4-amine (517); (R)-3-chloro-N-(1-(2-fluoro-5-(6-methylpyridin-3-yl)phenyl)ethyl)quinolin-4-amine (518); (R)-3-chloro-N-(1-

(5-(2-cyclopropylpyrimidin-5-yl)-2-fluorophenyl)ethyl) quinolin-4-amine (519); (R)-5-(3-(1-((3-chloroquinolin-4-yl)amino)ethyl)-4-fluorophenyl)-2-methoxynicotinonitrile (520); (R)—N-(1-(5-(5-amino-6-methoxypyridin-3-yl)-2-fluorophenyl)ethyl)-3-chloroquinolin-4-amine (521); (R)-3-chloro-N-(1-(2-fluoro-5-(5-methoxypyridin-3-yl)phenyl) ethyl)quinolin-4-amine (522); (R)-3-chloro-N-(1-(2-fluoro-5-(4-(methylamino)pyridin-3-yl)phenyl)ethyl)quinolin-4-amine (523); (R)-3-chloro-N-(1-(2-fluoro-5-(1-methyl-1H-imidazol-5-yl)phenyl)ethyl)quinolin-4-amine (524); (R)-3-chloro-N-(1-(2-fluoro-5-(1H-pyrrolo[2,3-b]pyridin-4-yl) phenyl)ethyl) quinolin-4-amine (525); (R)—N-(1-(3'-amino-4-fluoro-[1,1'-biphenyl]-3-yl)ethyl)-3-chloroquinolin-4-amine (526); (R)-3-chloro-N-(1-(2-fluoro-5-(5-fluoro-2-methoxypyridin-4-yl)phenyl)ethyl)quinolin-4-amine (527); (R)-3-chloro-N-(1-(2-fluoro-5-(1H-indol-2-yl)phenyl)ethyl)quinolin-4-amine (528); (R)-3-chloro-N-(1-(2-fluoro-5-(4-methylpyridin-3-yl)phenyl)ethyl)quinolin-4-amine (529); (R)-3-chloro-N-(1-(2-fluoro-5-(pyrimidin-5-yl)phenyl)ethyl)-2-methylquinolin-4-amine (530); (R)-3-chloro-N-(1-(2-fluoro-5-(pyridin-3-yl)phenyl)ethyl)-2-methylquinolin-4-amine (531); (R)-6-bromo-3-chloro-N-(1-(2-fluoro-5-(pyrimidin-5-yl)phenyl)ethyl)quinolin-4-amine (532); (R)-3-chloro-N-(1-(2-fluoro-5-(1H-pyrazol-4-yl)phenyl)ethyl)-2-methylquinolin-4-amine (533); (R)-3-chloro-N-(1-(2-fluoro-5-(2-methylpyrimidin-5-yl)phenyl)ethyl)-2-methylquinolin-4-amine (534); (R)-3-chloro-N-(1-(2-fluoro-5-(2-methylpyrimidin-5-yl)phenyl)ethyl)quinolin-4-amine (535); (R)-3-chloro-N-(1-(5-(2-(dimethylamino)pyrimidin-5-yl)-2-fluorophenyl)ethyl)quinolin-4-amine (536); (R)-3-chloro-N-(1-(2-fluoro-5-(1H-pyrrolo[2,3-b]pyridin-5-yl)phenyl)ethyl)quinolin-4-amine (537); (R)—N-(1-(5-bromo-2-fluorophenyl)ethyl)-3-chloro-2-methylquinolin-4-amine (538); (R)-3'-(1-((3-chloroquinolin-4-yl) amino)ethyl)-4'-fluoro-[1,1'-biphenyl]-3-carbonitrile (539); (R)-3-chloro-N-(1-(2-fluoro-5-(pyrimidin-5-yl)phenyl) ethyl)-6-(pyridin-4-yl)quinolin-4-amine (540); (R)-5-(3-(1-((3-chloroquinolin-4-yl)amino)ethyl)-4-fluorophenyl)nicotinonitrile (541); (R)-3-chloro-N-(1-(2-fluoro-5-(thiazol-5-yl)phenyl)ethyl)quinolin-4-amine (542); (R)-3-chloro-N-(1-(2-fluoro-5-(2-methoxypyrimidin-5-yl)phenyl)ethyl) quinolin-4-amine (543); (R)-3-chloro-6-fluoro-N-(1-(2-fluoro-5-(pyrimidin-5-yl)phenyl)ethyl)quinolin-4-amine (544); (R)-3,6-dichloro-N-(1-(2-fluoro-5-(pyrimidin-5-yl) phenyl)ethyl)quinolin-4-amine (545); (R)-6-bromo-N-(1-(2-fluoro-5-(pyrimidin-5-yl)phenyl)ethyl)quinolin-4-amine (546); (R)—N-(1-(2'-amino-4-fluoro-[1,1'-biphenyl]-3-yl) ethyl)-3-chloroquinolin-4-amine (547); (R)-3-chloro-N-(1-(2-fluoro-5-(4-methoxypyridin-3-yl)phenyl)ethyl) quinolin-4-amine (548); (R)-3-chloro-N-(1-(4-fluoro-2'-methoxy-[1,1'-biphenyl]-3-yl)ethyl)quinolin-4-amine (549); (R)-3-chloro-N-(1-(2-fluoro-5-(pyrimidin-5-yl)phenyl)ethyl)-6-(1-methyl-1H-pyrazol-4-yl)quinolin-4-amine (550); (R)-(5-(3-(1-((3-chloroquinolin-4-yl)amino)ethyl)-4-fluorophenyl) pyridin-3-yl)(morpholino)methanone (551); (R)-3'-(1-((3-chloroquinolin-4-yl)amino)ethyl)-4'-fluoro-[1,1'-biphenyl]-2-carbonitrile (552); (R)-2-(5-(3-chloro-4-((1-(2-fluoro-5-(pyridin-3-yl)phenyl)ethyl)amino)quinolin-6-yl)pyrimidin-2-yl)propan-2-ol (553); (R)-2-(3-(1-((3-chloro-7-fluoro-6-(2-(2-hydroxypropan-2-yl)pyrimidin-5-yl)-2-methylquinolin-4-yl)amino)ethyl)-4-fluorophenyl) acetamide (554); (R)-3-chloro-N-(1-(2-fluoro-5-(pyrimidin-5-yl)phenyl)ethyl)-1,5-naphthyridin-4-amine (555); (R)-3-chloro-N-(1-(2-fluoro-5-(pyrimidin-5-yl)phenyl)ethyl)-2-methyl-1,8-naphthyridin-4-amine (556); (S)-3-chloro-N-(1-(2-fluoro-5-(pyrimidin-5-yl)phenyl)propyl)quinolin-4-amine (557); (R)-3-chloro-N-(1-(2-fluoro-5-(pyrimidin-5-yl)phenyl)propyl)quinolin-4-amine (558); (S)-3-chloro-N-(2,2-difluoro-1-(2-fluoro-5-(pyrimidin-5-yl)phenyl)ethyl) quinolin-4-amine (559); (R)-4-(5-(4-((1-(5-bromo-2-fluorophenyl)ethyl)amino)-3-chloro-7-fluoro-2-methylquinolin-6-yl)pyrimidin-2-yl)piperazin-2-one (560); (R)-3-(1-((3-chloro-7-fluoro-2-methyl-6-(2-(3-oxopiperazin-1-yl)pyrimidin-5-yl)quinolin-4-yl)amino)ethyl)-4-fluorobenzonitrile (561); 4-(5-(4-((1-(6-amino-3-fluoropyridin-2-yl)ethyl)amino)-3-chloroquinolin-6-yl)pyrimidin-2-yl) piperazin-2-one (562); 2-(5-(3-chloro-4-(((S)-1-((S)-1-(methylsulfonyl)piperidin-3-yl)ethyl)amino)quinolin-6-yl) pyrimidin-2-yl)propan-2-ol (563); 2-(5-(3-chloro-4-(((S)-1-((S)-1-((1-methyl-1H-pyrazol-4-yl)sulfonyl)piperidin-3-yl) ethyl)amino)quinolin-6-yl)pyrimidin-2-yl)propan-2-ol (564); ((S)-3-((S)-1-((3-chloro-6-(2-(2-hydroxypropan-2-yl)pyrimidin-5-yl)quinolin-4-yl)amino)ethyl)piperidin-1-yl) (1H-pyrazol-4-yl)methanone (565); 2-(5-(3-chloro-4-(((S)-1-((S)-1-(pyrimidin-5-yl)piperidin-3-yl)ethyl)amino) quinolin-6-yl)pyrimidin-2-yl)propan-2-ol (567); (R)-2-((1-(4-(3-chloro-4-((1-(2-fluorophenyl)ethyl)amino)quinolin-6-yl)phenyl)cyclobutyl)amino)ethan-1-ol (568); (R)-1-(4-(3-chloro-4-((1-(2-fluorophenyl)ethyl)amino)quinolin-6-yl) benzyl)urea (569); 1-(3-((R)-1-((3-chloro-7-fluoro-6-(2-(2-hydroxypropan-2-yl)pyrimidin-5-yl)-2-methyl-1,5-naphthyridin-4-yl)amino)ethyl)-4-fluorophenyl)ethane-1,2-diol (570); (R)-2-(5-(7-chloro-3-fluoro-6-methyl-8-((1-(3-vinylphenyl)ethyl)amino)-1,5-naphthyridin-2-yl)pyrimidin-2-yl)propan-2-ol (571); (R)-2-(5-(7-chloro-3-fluoro-8-((1-(2-fluoro-5-vinylphenyl)ethyl)amino)-6-methyl-1,5-naphthyridin-2-yl)pyrimidin-2-yl)propan-2-ol (572); (R)-1-((5-(3-chloro-4-((1-(2-fluorophenyl)ethyl)amino)quinolin-6-yl)pyrimidin-2-yl)amino)cyclopropane-1-carboxamide (587); (R)-3-(1-((3-chloro-7-fluoro-6-(2-(2-hydroxypropan-2-yl)pyrimidin-5-yl)-1,5-naphthyridin-4-yl)amino)ethyl) benzonitrile (588); (R)-3-(1-((3-chloro-7-fluoro-6-(2-(2-hydroxypropan-2-yl)pyrimidin-5-yl)-2-methyl-1,5-naphthyridin-4-yl)amino)ethyl)benzonitrile (589); (R)-3-(1-((3-chloro-7-fluoro-6-(2-(2-hydroxypropan-2-yl)pyrimidin-5-yl)-1,5-naphthyridin-4-yl)amino)ethyl)-4-fluorobenzonitrile (590); 2-((5-(3-chloro-4-(((R)-1-(2-fluorophenyl)ethyl)amino) quinolin-6-yl)pyrimidin-2-yl) amino)propanamide (591); N-(2-(4-(3-chloro-4-((1-(2-fluorophenyl)ethyl)amino)quinolin-6-yl)phenyl)propan-2-yl)acetamide (592); (R)-2-(4-(5-(3-chloro-4-((1-(2-fluorophenyl)ethyl)amino)quinolin-6-yl)pyrimidin-2-yl) piperidin-1-yl)acetic acid (593); (R)-2-(4-(5-(3-chloro-7-fluoro-4-((1-(2-fluorophenyl)ethyl)amino) quinolin-6-yl) pyrimidin-2-yl)piperidin-1-yl)acetic acid (594); 2-(5-(3-chloro-7-fluoro-4-((1-(2-fluorophenyl)ethyl)amino) quinolin-6-yl)pyrazin-2-yl)propan-2-ol (595); 1-(5-(3-chloro-7-fluoro-4-((1-(2-fluorophenyl)ethyl)amino) quinolin-6-yl)pyrimidin-2-yl)ethane-1,2-diol (596); 1-(5-(3-chloro-7-fluoro-4-((1-(2-fluorophenyl)ethyl)amino) quinolin-6-yl)pyrimidin-2-yl)ethane-1,2-diol (597); 3-chloro-7-fluoro-N-(1-(2-fluorophenyl)ethyl)-6-(4-(morpholin-3-yl)phenyl)quinolin-4-amine (598); 3-(1-((3-chloro-6-(4-(1,2-dihydroxyethyl)phenyl)-7-fluoroquinolin-4-yl)amino)ethyl)-4-fluorobenzonitrile (599); 1-(4-(3-chloro-7-fluoro-4-((1-(2-fluorophenyl)ethyl)amino) quinolin-6-yl)phenyl)-2-(methylamino)ethan-1-ol (600); 3-(1-((3-chloro-6-(4-(1,2-dihydroxyethyl)phenyl)-7-fluoroquinolin-4-yl)amino)ethyl)-4-fluorobenzamide (601); 4-(4-(5-(3-chloro-7-fluoro-4-((1-(2-fluorophenyl)ethyl)amino) quinolin-6-yl)pyrimidin-2-yl)piperazin-1-yl)-4-oxobutanoic acid (602); 1-(4-(5-(3-chloro-7-fluoro-4-((1-(2-fluorophenyl)ethyl)amino) quinolin-6-yl)pyrimidin-2-yl)piperazin-1-yl)-2-hydroxypropan-1-one (603); (2S)-2-amino-1-(4-(5-(3- chloro-7-fluoro-4-((1-(2-fluorophenyl)ethyl)amino) quinolin-6-yl)pyrimidin-2-yl)piperazin-1-yl)-3-hydroxypropan-1-one (604); (3 S)-3-amino-4-(4-(5-(3-chloro-7-fluoro-4-((1-(2-fluorophenyl)ethyl)amino) quinolin-6-yl)pyrimidin-2-yl) piperazin-1-yl)-4-oxobutanoic acid (605); (2R)-2-amino-1-(4-(5-(3-chloro-7-fluoro-4-((1-(2-fluorophenyl)ethyl)amino)quinolin-6-yl) pyrimidin-2-yl)piperazin-1-yl)-3-hydroxypropan-1-one (606); (3R)-3-amino-4-(4-(5-(3-chloro-7-fluoro-4-((1-(2-fluorophenyl)ethyl)amino)quinolin-6-yl)pyrimidin-2-yl) piperazin-1-yl)-4-oxobutanoic acid (607); 3-chloro-7-fluoro-N-(1-(2-fluorophenyl)ethyl)-6-(2-(piperazin-1-yl) pyrimidin-5-yl)quinolin-4-amine (608); 2-(5-(3-chloro-7-fluoro-4-((1-(2-fluorophenyl)cyclobutyl)amino)quinolin-6-yl)pyrimidin-2-yl)propan-2-ol (609); 1-(2-(5-(3-chloro-7-fluoro-4-((1-(2-fluorophenyl)ethyl)amino)quinolin-6-yl) pyrimidin-2-yl)-2-hydroxyethyl) piperidine-4-carboxylic acid (610); (1R,5S,8r)-3-(5-(3-chloro-7-fluoro-4-((1-(2-fluorophenyl)ethyl)amino)quinolin-6-yl)pyrimidin-2-yl)-3-azabicyclo[3.2.1]octane-8-carboxylic acid (611); or 2-(5-(4-((1-(5-bromo-2-fluorophenyl)ethyl)amino)-3-chloro-8-fluoroquinolin-6-yl)pyrimidin-2-yl)propan-2-ol (612).

One embodiment provides a compound of Formula (I) or a salt thereof, wherein said compound is: 1-(3-((R)-1-((3-chloro-7-fluoro-6-(2-(2-hydroxypropan-2-yl)pyrimidin-5-yl)-1,5-naphthyridin-4-yl)amino)ethyl)phenyl)ethane-1,2-diol (573); (R)-2-(5-(7-chloro-3-fluoro-8-((1-(3-vinylphenyl)ethyl)amino)-1,5-naphthyridin-2-yl)pyrimidin-2-yl)propan-2-ol (574); 1-(3-((R)-1-((3-chloro-7-fluoro-6-(2-(2-hydroxypropan-2-yl)pyrimidin-5-yl)-2-methyl-1,5-naphthyridin-4-yl)amino)ethyl)phenyl)ethane-1,2-diol (575); (R)-2-(5-(7-chloro-3-fluoro-8-((1-(3-(hydroxymethyl)phenyl)ethyl)amino)-1,5-naphthyridin-2-yl)pyrimidin-2-yl)propan-2-ol (576); (R)-2-(5-(7-chloro-3-fluoro-8-((1-(2-fluoro-5-(hydroxymethyl)phenyl)ethyl)amino)-6-methyl-1,5-naphthyridin-2-yl)pyrimidin-2-yl)propan-2-ol (577); (R)-2-(5-(7-chloro-3-fluoro-8-((1-(3-(hydroxymethyl)phenyl)ethyl)amino)-6-methyl-1,5-naphthyridin-2-yl) pyrimidin-2-yl) propan-2-ol (578); (R)-3-(1-((3-chloro-7-fluoro-6-(2-(2-hydroxypropan-2-yl)pyrimidin-5-yl)-1,5-naphthyridin-4-yl)amino)ethyl)-4-fluorobenzoic acid (579); (R)-3-(1-((3-chloro-7-fluoro-6-(2-(2-hydroxypropan-2-yl) pyrimidin-5-yl)-2-methyl-1,5-naphthyridin-4-yl)amino) ethyl)benzamide (580); (R)-3-(1-((3-chloro-7-fluoro-6-(2-(2-hydroxypropan-2-yl)pyrimidin-5-yl)-1,5-naphthyridin-4-yl)amino)ethyl)benzamide(R)-3-(1-((3-chloro-7-fluoro-6-(2-(2-hydroxypropan-2-yl)pyrimidin-5-yl)-1,5-naphthyridin-4-yl)amino)ethyl)benzamide (581); (R)-3-(1-((3-chloro-7-fluoro-6-(2-(2-hydroxypropan-2-yl)pyrimidin-5-yl)-2-methyl-1,5-naphthyridin-4-yl)amino)ethyl)-4-fluorobenzoic acid (582); (R)-3-(1-((3-chloro-7-fluoro-6-(2-(2-hydroxypropan-2-yl)pyrimidin-5-yl)-1,5-naphthyridin-4-yl)amino)ethyl)-4-fluorobenzamide (583); (R)-3-(1-((3-chloro-7-fluoro-6-(2-(2-hydroxypropan-2-yl)pyrimidin-5-yl)-2-methyl-1,5-naphthyridin-4-yl)amino)ethyl)-4-fluorobenzamide (584); (R)-2-((5-(3-chloro-4-((1-(2-fluorophenyl)ethyl)amino)quinolin-6-yl)pyrimidin-2-yl) amino)acetamide (585); (R)-3-(1-((3-chloro-7-fluoro-6-(2-(2-hydroxypropan-2-yl)pyrimidin-5-yl)-2-methyl-1,5-naphthyridin-4-yl)amino)ethyl)-4-fluorobenzonitrile (586); or (R)-2-(5-(7-chloro-3-fluoro-8-((1-(2-fluoro-5-(pyridin-3-yl)phenyl)ethyl)amino)-6-methyl-1,5-naphthyridin-2-yl)pyrimidin-2-yl)propan-2-ol.

One embodiment provides a compound of Formula (I) or a salt thereof, wherein said compound is: (S)-2-(5-(3-chloro-4-(1-(2-fluorophenyl)ethylamino)-1,7-naphthyridin-6-yl) pyrimidin-2-yl)propan-2-ol (234); or (2-(4-(5-(3-chloro-4-((1-(2-fluorophenyl)ethyl)amino)-1,7-naphthyridin-6-yl) pyrimidin-2-yl)piperazin-1-yl)acetic acid (235 and 236).

One embodiment provides a compound of Formula (I) or a salt thereof, wherein said compound is: 2-(4-(6-chloro-5-((1-(2-fluorophenyl)ethyl)amino)-1,8-naphthyridin-3-yl) phenyl)propan-2-ol (231); or ((S)-3-((S)-1-((3-chloro-6-(2-(2-hydroxypropan-2-yl)pyrimidin-5-yl)quinolin-4-yl) amino)ethyl)piperidin-1-yl)(pyridin-3-yl)methanone (566).

One embodiment provides a compound of Formula (I) or a salt thereof, wherein said compound is: 2-(5-(3-chloro-4-((4-methylpentan-2-yl)amino)quinolin-6-yl)pyrimidin-2-yl) propan-2-ol (135); 1-(3-chloro-6-(2-(2-hydroxypropan-2-yl) pyrimidin-5-yl)-2-methylquinolin-4-yl)-2,4-dimethylpentan-1-ol (355); ± 1-(3-chloro-6-(2-(2-hydroxypropan-2-yl)pyrimidin-5-yl)-2-methylquinolin-4-yl)-2-methylpentan-1-one (356); or 2-(5-(4-(1-amino-2-methylpentyl)-3-chloro-2-methylquinolin-6-yl)pyrimidin-2-yl)propan-2-ol (357 and 358).

One embodiment provides a compound of Formula (I) or a salt thereof, wherein said compound is: 2-(5-(3-chloro-4-((2,5-dimethylphenyl)amino)-2-methylquinolin-6-yl)pyrimidin-2-yl)propan-2-ol (1); 3-chloro-N-(2,5-dimethylphenyl)-2-(((2,5-dimethylphenyl)amino)methyl)-6-(1-methyl-1H-pyrazol-4-yl)quinolin-4-amine (2); 5-(3-chloro-4-((2,5-dimethylphenyl)amino)-2-(((2,5-dimethylphenyl)amino) methyl)quinolin-6-yl)picolinonitrile (3); or 2-(5-(3-chloro-4-((2,5-dimethylphenyl)amino)-2-(hydroxymethyl) quinolin-6-yl)pyrimidin-2-yl)propan-2-ol (4).

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I); and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —NH$_2$.
The term "hydroxy" refers to the group —OH.
The term "nitro" refers to the group —NO$_2$.
The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "haloalkyl" as used herein is intended to include both branched and straight-chain saturated aliphatic hydrocarbon groups substituted with one or more halogen atoms. For example, "$C_{1-4}$ haloalkyl" is intended to include $C_1$, $C_2$, $C_3$, and $C_4$ alkyl groups substituted with one or more halogen atoms. Representative examples of haloalkyl groups include, but are not limited to, —CF$_3$, —CCl$_3$, —CFCl$_2$, and —CH$_2$CF$_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "aminoalkyl" includes both branched and straight-chain saturated alkyl groups substituted with one or more amine groups. For example, "aminoalkyl" includes —CH$_2$NH$_2$, —CH$_2$CH$_2$NH$_2$, and $C_{1-4}$ aminoalkyl.

The term "alkenyl" refers to a straight or branched chain hydrocarbon radical containing from 2 to 12 carbon atoms and at least one carbon-carbon double bond.

Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "cycloalkyl," as used herein, refers to a group derived from a saturated monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "cycloalkenyl," as used herein, refers to a group derived from a non-aromatic monocyclic or polycyclic hydrocarbon molecule having at least one carbon-carbon double bond, by removal of one hydrogen atom from a saturated ring carbon atom. Representative examples of cycloalkenyl groups include, but are not limited to, cyclobutenyl, cyclopentenyl, and cyclohexenyl. When numbers appear in a subscript after the symbol "C", the subscript defines with more specificity the number of carbon atoms that a particular cycloalkyl group may contain. For example, "$C_{4-6}$ cycloalkenyl" denotes cycloalkenyl groups with four to six carbon atoms.

The term "alkoxy," as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "haloalkoxy" and "—O(haloalkyl)" represent a haloalkyl group as defined above attached through an oxygen linkage (—O—). For example, "$C_{1-4}$ haloalkoxy" is intended to include $C_1$, $C_2$, $C_3$, and $C_4$ haloalkoxy groups.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The terms "hydroxyalkoxy" and "—O(hydroxyalkyl)" represent a hydroxyalkyl group as defined above attached through an oxygen linkage (—O—). For example, "$C_{1-4}$ hydroxyalkoxy" is intended to include $C_1$, $C_2$, $C_3$, and $C_4$ hydroxyalkoxy groups.

The term "alkylthio," as used herein, refers to an alkyl group attached to the parent molecular moiety through a sulfur atom, for example, methylthio group (—SCH$_3$). For example, "$C_{1-3}$ alkylthio" denotes alkylthio groups with one to three carbon atoms.

The term "arylthio," as used herein, refers to an aryl group attached to the parent molecular moiety through a sulfur atom, for example, phenylthio group (—S(phenyl)).

The terms "carbocyclo", "carbocyclic" or "carbocyclyl" may be used interchangeably and refer to cyclic groups having at least one saturated or partially saturated non-aromatic ring wherein all atoms of all rings are carbon. The carbocyclyl ring may be unsubstituted or may contain one or more substituents as valence allows. Thus, the term includes nonaromatic rings such as for example, cycloalkyl, cycloalkenyl, and cycloalkynyl rings. Exemplary bicyclic carbocyclyl groups include, indanyl, indenyl, dihydronaphthalenyl, tetrahydronaphthenyl, hexahydronaphthalenyl, octahydronaphthalenyl, decahydronaphthalenyl, bicycloheptanyl, bicyclooctanyl, and bicyclononanyl.

The term "aryl" as used herein, refers to a group of atoms derived from a molecule containing aromatic ring(s) by removing one hydrogen that is bonded to the aromatic ring(s). Heteroaryl groups that have two or more rings must include only aromatic rings. Representative examples of aryl groups include, but are not limited to, phenyl and naphthyl. The aryl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "aryloxy," as used herein, refers to an aryl group attached to the parent molecular moiety through an oxygen atom, for example, phenoxy group (—O(phenyl)).

The term "heteroatom" refers to oxygen (O), sulfur (S), and nitrogen (N).

The terms "heterocyclo", "heterocyclic", or "heterocyclyl" may be used interchangeably and refer to cyclic groups having at least saturated or partially saturated non-aromatic ring and wherein one or more of the rings have at least one heteroatom (0, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl The term "heteroaryl" refers to substituted and unsubstituted aromatic 5- or 6-membered monocyclic groups and 9- or 10-membered bicyclic groups that have at least one heteroatom (0, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain only carbon atoms. The nitrogen and sulfur atoms may optionally be oxidized and the nitrogen atoms may optionally be quaternized. Bicyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The term "spirocarbocyclo" "spirocarbocyclic", or "spirocarbocyclyl" refers to a carbocyclyl ring attached to the molecular moiety by a carbon atom in the carbocyclyl ring that is shared with the molecular moiety.

The term "spiroheterocyclo" "spiroheterocyclic", or "spiroheterocyclyl" refers to a heterocyclyl ring attached to the molecular moiety by a carbon atom in the heterocyclyl ring that is shared with the molecular moiety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TNFα, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutical compositions can be presented in a pack or dispenser device which can contain one or more unit dosage forms including the compound of Formula (I). The pack can, for example, comprise metal or plastic foil, such as a blister pack. The pack or dispenser device can be accompanied by instructions for administration.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The pharmaceutical compositions may contain other therapeutic agents and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The present invention also encompasses an article of manufacture. As used herein, article of manufacture is intended to include, but not be limited to, kits and packages.

The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Utility

The compounds of the invention modulate the activity of TNFα. Accordingly, compounds of Formula (I) have utility in treating conditions associated with the modulation of TNFα.

The compounds in accordance with the present invention are beneficial in the treatment and/or prevention of various human ailments. The compounds in accordance with the present invention can be beneficial either as a standalone therapy or in combination with other therapies that therapeutically could provide greater benefit. The ailments for which the compounds in the present invention could be of benefit include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus, psoriasis, psoriatic arthropathy, vasculitis, polymyositis, scleroderma, multiple sclerosis, systemic sclerosis, ankylosing spondylitis, rheumatoid arthritis, psoriatic arthritis, non-specific inflammatory arthritis, juvenile inflammatory arthritis, juvenile idiopathic arthritis (including oligoarticular and polyarticular forms thereof), anemia of chronic disease, Still's disease (juvenile and/or adult onset), Behcet's disease and Sjögren's syndrome. Autoimmune endocrine disorders include thyroiditis. Organ-specific autoimmune disorders include Addison's disease, hemolytic or pernicious anemia, acute kidney injury, diabetic nephropathy, obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis, minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease, respiratory distress syndrome, sepsis, fever, muscular dystrophy (including Duchenne muscular dystrophy), and organ transplant rejection (including kidney allograft rejection).

Neurological and neurodegenerative disorders include Alzheimer's disease, Parkinson's disease, Huntington's disease, ischemia, stroke, amyotrophic lateral sclerosis, spinal cord injury, head trauma, seizures, and epilepsy.

Cardiovascular disorders include thrombosis, cardiac hypertrophy, hypertension, irregular contractility of the heart (e.g. during heart failure), and myocardial infarction.

Metabolic disorders include diabetes (including insulin-dependent diabetes mellitus and juvenile diabetes), dyslipidemia, and metabolic syndrome.

Ocular disorders include retinopathy (including diabetic retinopathy, proliferative retinopathy, non-proliferative retinopathy and retinopathy of prematurity), macular edema (including diabetic macular edema), age-related macular degeneration, vascularization (including corneal vascularization and neovascularization), retinal vein occlusion, and various forms of uveitis and keratitis.

Oncological disorders, which may be acute or chronic, include proliferative disorders, especially cancer, and cancer-associated complications (including skeletal complications, cachexia and anemia). Particular categories of cancer include hematological malignancy (including leukemia and lymphoma) and non-hematological malignancy (including solid tumor cancer, sarcoma, meningioma, glioblastoma multiform, neuroblastoma, melanoma, gastric carcinoma and renal cell carcinoma). Chronic leukemia may be myeloid or lymphoid.

One embodiment provides a method of treating a disorder selected from autoimmune and inflammatory disorders; neurological and neurodegenerative disorders; pain and nociceptive disorders; cardiovascular disorders; metabolic disorders; ocular disorders; and oncological disorders, comprising administering to a mammalian patient in need of treatment, a compound according to claim 1 or a pharmaceutically acceptable salt thereof. Preferably, the patient is human. For example, a therapeutically effective amount for treating a disorder may be administered in the method of the present embodiment.

One embodiment provides a method of treating a disease or disorder associated with the activity of TNFα, comprising administering to a mammalian patient in need of treatment, a compound according to claim 1 or a pharmaceutically acceptable salt thereof. Preferably, the patient is human. For example, a therapeutically effective amount for treating a disorder may be administered in the method of the present embodiment.

One embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (I) for the treatment or prophylaxis of an allergic disorder and/or autoimmune and/or inflammatory disease.

The present invention also provides the use of the compounds of Formula (I) for the manufacture of a medicament for treatment of cancer. The present embodiment may include the use for the manufacture of a medicament includes the administration of a therapeutically-effective amount of a compound of Formula (I) for the treatment of cancer.

The present invention provides the use of compounds of Formula (I) as pharmacological tools in the search for new pharmacological agents or in the development of new biological assays. In one embodiment, the compounds of Formula (I) are useful as radioligands or can be coupled to a fluorophore and utilized in assays to identify pharmacologically active compounds.

In one embodiment, the compounds of Formula (I) inhibit TNFα functional activity with $IC_{50}$ values of less than 10 µM, for example, from 0.001 to less than 10 µM, as measured by the TNF induced HEK-Blue assay. Preferably, the compounds of Formula (I) inhibit TNFα functional activity with $IC_{50}$ values of less than 1 µM, for example, from 0.001 to less than 1 µM. Other preferred compounds inhibit TNFα functional activity with $IC_{50}$ values of 100 nM and less, for example, from 1 to 100 nM.

Examples of compounds of Formula (I) as specified in the "Examples" section below, have been tested in one or more of the assays described below.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Scheme 1 (FIG. 1) illustrates a general synthesis of compounds of Type I. Conrad-Limpach reaction of appropriately substituted anilines 1 with diethyl acetylenedicarboxylate under thermal conditions yields quinolones of type 2. Alternatively, this reaction can be done under mild conditions employing Eaton's reagent (*J. Org. Chem.*, 2007, 72, 4276). Halogenation at the 3-position, for example, using NCS provides the 3-haloquinolone which on reaction with POCl₃ provides the 3-halo-4-chloro quinoline intermediate 3. Displacement of the 4-choloro group in 3 with an appropriately substituted aniline under thermal or Buchwald-Hartwig conditions (*Aldrichimica Acta*, 2012, 45, 59 and *Synlett*, 2011, 268) gives the 4-anilino derivative which under Suzuki-Miyaura cross-coupling conditions (*Chem. Soc. Rev.* 2013, 42, 5270) yields intermediate 4. Reduction of the ester group in 4, for example using sodium borohydride yields 5 which on oxidation, for example with Dess-Martin periodane reagent followed by reaction with an organometallic compound, for example a Grignard reagent yields the secondary alcohol 6. Intermediate 4 can be hydrolyzed to the acid 7 for example using aqueous sodium hydroxide which on Curtius rearrangement (*Synthesis*, 2011, 1477) affords the amine 8. Diazotization of the amine followed by halogenation, for example with copper(II) bromide can afford the 2-bromoquinoline 9. The 2-bromo moiety in 9 can be displaced by a variety of nucleophiles, for example with alkoxides, thioalkoxides, nitrile, amines, substituted amines etc. or can be subjected to Suzuki-Miyaura cross-coupling conditions to yield analogs of type 12. Acid 7 can be reacted with a primary or secondary amines using coupling reagents for example T3P (n-propanephosphonic acid anhydride) to yields amides of the type 10. Amides and substituted amines of the type 11 may be synthesized using Buchwald-Hartwig conditions or coupling with acids using T3P.

Figure 2:
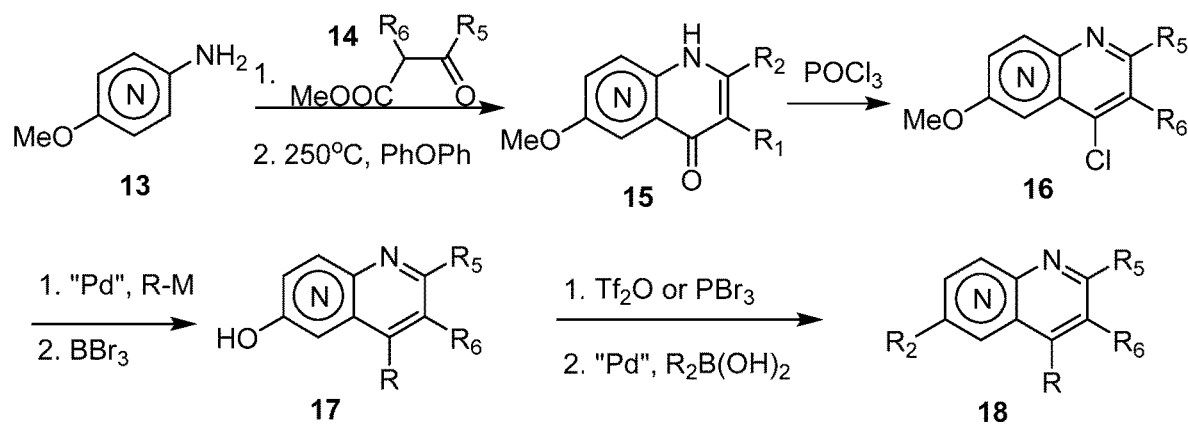
FIG. 2 shows the general synthesis of compounds of Formula (I) according to Scheme 2.

An alternative protocol for quinolines claimed in the invention is described in Scheme 2 (FIG. 2). Thermal reaction of anilines with β-keto esters (14) yields quinolones of the type 15 which of reaction with POCl₃ yields the 4-chloroquinoline 16. Palladium mediated coupling using Buchwald-Hartwig conditions (*Aldrichimica Acta*, 2012, 45, 59 and *Synlett*, 2011, 268) gives the 4-anilino derivative of 17. Alternatively, Suzuki-Miyaura cross-coupling conditions (*Chem. Soc. Rev.* 2013, 42, 5270) yields intermediate the carbon linked analog of 17. Boron tribromide mediated cleavage of the methoxy group yields the alcohol derivative which following triflation and Suzuki-Miyaura cross-coupling yields 18.

Figure 3:
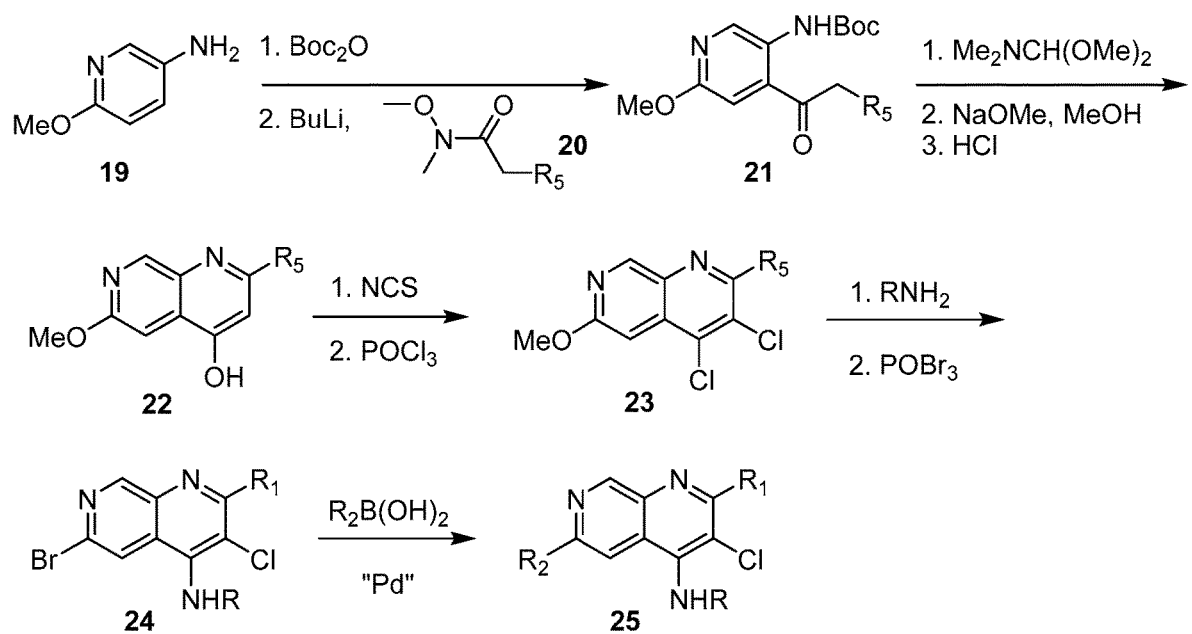
FIG. 3 shows the general synthesis of compounds of Formula (I) according to Scheme 3.
Figure 4:
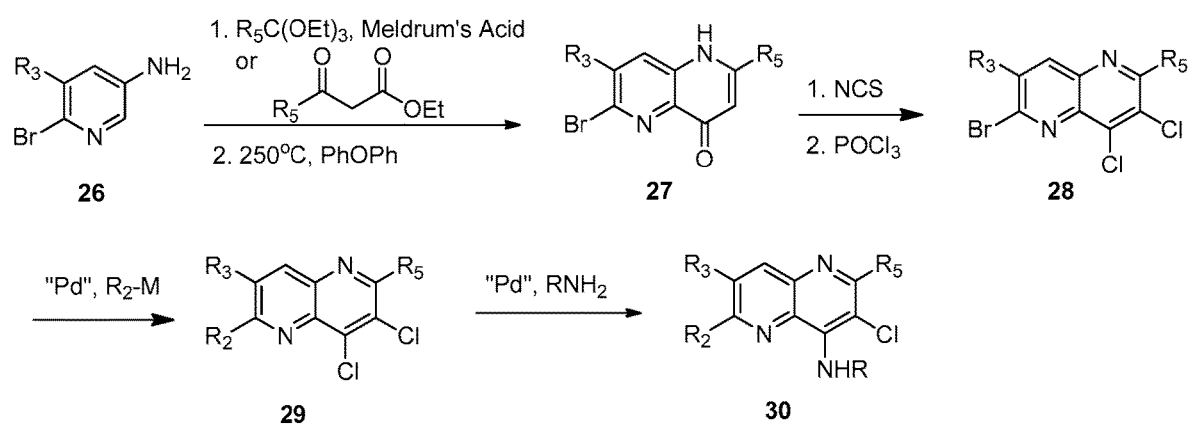
FIG. 4 shows the general synthesis of compounds of Formula (I).
Figure 5:
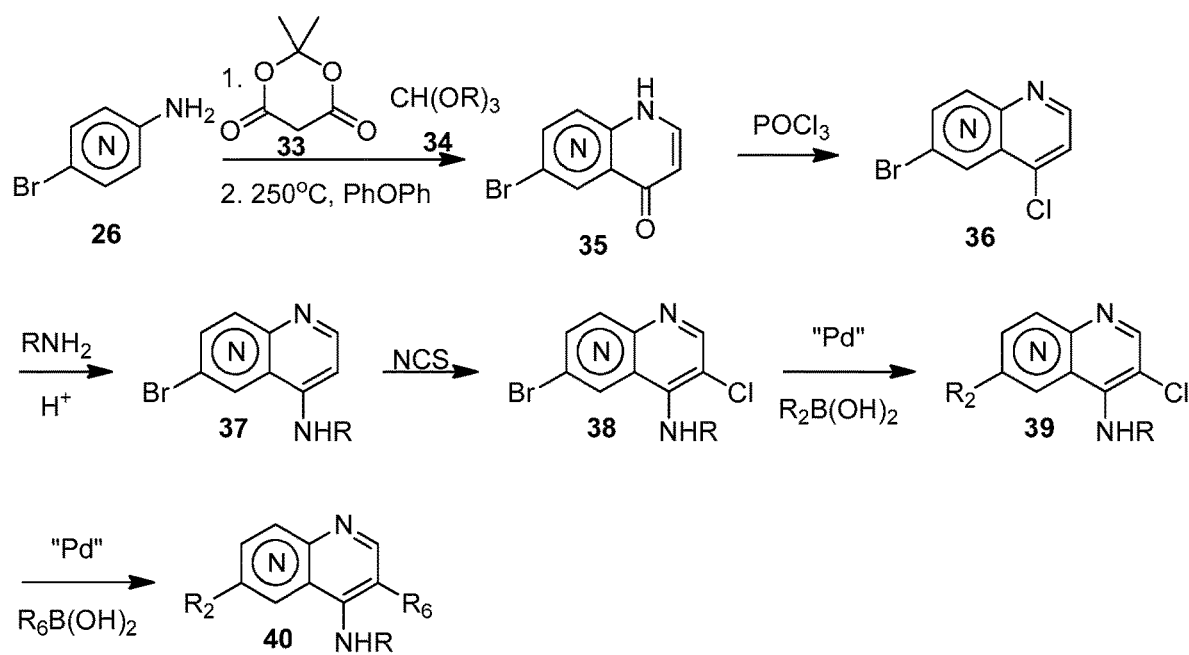
FIG. 5 shows the general synthesis of compounds of Formula (I).

Scheme 3 (FIG. 3) outlines an alternative approach to 1,7-naphthyridines claimed in this invention. Directed metalation of 5-amino-2-methoxypyridine with a strong base like n-BuLi followed by treatment with Weinreb amides of the type 20 can lead to intermediate 21. Cyclization using dimethylformamide dimethyl acetal affords the 4-hydroxyquinoline intermediate 22 which can be processed to products 24 and 25 as described in scheme 1.

Abbreviations

AcOH acetic acid
Ac₂O acetic anhydride
BINAP 2,2'-bis(diphenylphosphino)-1,1'-binaphthyl
BOC-BETA-ALA-OSU Boc-beta-alanine N-hydroxysuccinimide ester
Boc₂O di-teri-butyl dicarbonate
BOP benzotriazol-1-yloxytris-(dimethylamino)-phosphonium hexafluorophosphate
BuLi butyl lithium
DAST (diethylamino)sulfur trifluoride
DBU 1,8-diazabicyclo[5.4.0]undec-7-ene
DCE dichloroethane
DCM dichloromethane
DIAD diisopropyl azodicarboxylate
DIEA diisopropylethylamine
DMA N,N-dimethylacetamide
DMAP dimethylaminopyridine
DMF N,N-dimethylformamide
DMSO dimethyl sulfoxide
DPPA diphenylphosphoryl azide
EtOAc ethyl acetate
EtOH ethanol
Et₂O diethyl ether
h hour(s)
H-DAP(BOC)-OME HCl methyl (S)-2-amino-3-((tert-butoxycarbonyl)amino)propanoate hydrochloride
HOAc acetic acid
HPLC High Pressure Liquid Chromatography
LCMS Liquid Chromatography-Mass Spectroscopy
MeCN acetonitrile
MeOD deuterated methanol
MeOH methanol
min minute(s)
mmol millimole(s)
NCS N-chlorosuccinimide
NH₄Oac ammonium acetate NMO N-methylmorpholine-N-oxide
NMP N-methylpyrrolidinone
NMR nuclear magnetic resonance spectroscopy
PdCl$_2$(dppf) [1,1'-bis(diphenylphosphino)ferrocene]dichloropalladium(II)
Pd(OAc)$_2$ palladium acetate
Pd$_2$(dba)$_3$ tris-(dibenzylideneacetone)dipalladium
t-BuOH tertiary butanol
TEA triethylamine
TFA trifluoroacetic acid
THF tetrahydrofuran
TMS-Cl chlorotrimethylsilane

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined below. Common Intermediates are generally useful for the preparation of more than one Example and are identified sequentially by the Intermediate number and step in which they were prepared (e.g., Intermediate 1, Step A), or by the Intermediate number only where the compound is the title compound. Compounds of the Examples are identified by the Example number and step in which they were prepared (e.g., Example 1, Step A) if the compound is an intermediate, or by the Example number only where the compound is the title compound of the Example. In some instances alternative preparations of Intermediates or Examples are described. Frequently chemists skilled in the art of synthesis may devise alternative preparations which may be desirable based on one or more considerations such as shorter reaction time, less expensive starting materials, ease of operation or isolation, improved yield, suitability to catalysis, avoidance of toxic reagents, accessibility of specialized instrumentation, decreased number of linear steps, etc. The intent of describing alternative preparations is to further enable the preparation of the Examples of this invention. In some instances some functional groups in the outlined Examples and claims may be replaced by well known bioisosteric replacements known in the art, for example, replacement of a carboxylic acid group with a tetrazole or a phosphate moiety. Starting materials and intermediates for which no preparation is explicitly shown are available commercially, are known in the literature, or may be prepared by analogy to similar compounds which are known in the literature.

Heating of a reaction mixture via microwave irradiation was done in sealed vials using a Biotage® Initiator Microwave Synthesizer. Solvent removal was performed by concentration under reduced pressure. Column chromatography was generally performed using the flash chromatography technique (J. Org. Chem. 1978, 43, 2923), or with pre-packed silica gel cartridges using a CombiFlash® automated chromatography apparatus (Teledyne Isco), eluting with the solvent or solvent mixture indicated. Chiral super-critical fluid chromatographic (SFC) separation of enantiomers or diastereomers was performed using conditions described for the individual cases. Mass spectral data were obtained by liquid chromatography mass spectroscopy (LCMS) using electrospray ionization. Chemical names were determined using ChemBioDraw Ultra, version 14.0.0.126 (PerkinElmer Inc.).

Analytical HPLC Conditions

Condition A: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min.

Condition B: Column: Phenomenex Kinetex, C18 (2.1× 50) mm, 2.6 micron; Mobile Phase A: 10:90 acetonitrile:water with 0.1% TFA; Mobile Phase B: 90:10 acetonitrile:water with 0.1% TFA; Gradient: 0-100% B over 1.5 minutes, then a 0.5-minute hold at 100% B; Flow: 1 mL/min.

Condition C: Column: Waters Acquity UPLC BEH C18, 2.1×50 mm, 1.7 m particles; Mobile Phase A: 5:95 acetonitrile:water with 0.1% TFA; Mobile Phase B: 95:5 acetonitrile:water with 0.1% TFA; Temperature: 50° C.; Gradient: 2-98% B over 1 minutes, then a 0.5-minute hold at 98% B; Flow: 0.8 mL/min.

Condition D: Column: Supelco Ascentris Express 4.6×50 mm, 2.7 μm particles; Mobile Phase A: 5:95 acetonitrile:water with 10 mM NH$_4$OAc; Mobile Phase B: 95:5 acetonitrile:water with 10 mM NH$_4$OAc; Gradient: 0-100% B over 4 minutes, 4.0 mL/min; Detection: UV at 220 nm.

Condition E: Column: Supelco Ascentris Express 4.6×50 mm, 2.7 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-100% B over 4 minutes, Flow: 4 mL/min; Detection: UV at 220 nm.

Condition F: Column: Waters XBridge C18, 2.1 mm×50 mm, 1.7 m particles; Mobile Phase A: 5:95 acetonitrile:water with 10 mM NH$_4$OAc; Mobile Phase B: 95:5 acetonitrile:water with 10 mM NH$_4$OAc; Temperature: 50° C.; Gradient: 0-100% B over 3 min, then a 0.75 min hold at 100% B; Flow: 1 mL/min; Detection: MS and UV (220 nm).

Column G: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 1 minutes, then a 0.5-minute hold at 98% B; Flow: 0.8 mL/min.

Preparative LC/MS or HPLC Conditions

Condition A: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Flow: 20 mL/min.

Condition B: Column: XBridge C18, 19×200 mm, 5-μm particles; Mobile Phase A: 5:95 acetonitrile:water with 0.1% TFA; Mobile Phase B: 95:5 acetonitrile:water with 0.1% TFA; Flow: 20 mL/min.

Condition C: Column: Phenomenex Luna C18, 30×100 mm, 5-μm particles; Mobile Phase A: 10:90 MeOH:water with 0.1% TFA; Mobile Phase B: 95:5 MeOH:water with 0.1% TFA; Flow: 25 mL/min.

Intermediate I-1

Ethyl 6-bromo-3-chloro-4-((2,5-dimethylphenyl)amino)quinoline-2-carboxylate

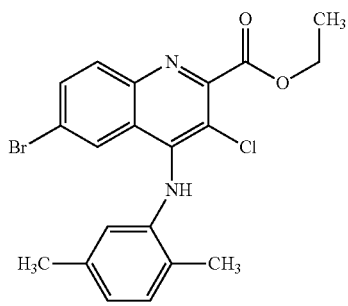

(I-1)

Intermediate I-1A: diethyl 2-((4-bromophenyl)amino)but-2-enedioate

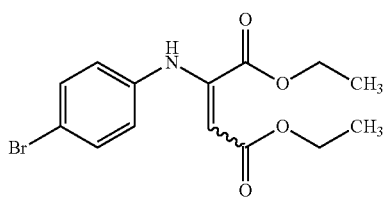

(I-1A)

A solution of 4-bromoaniline (20 g, 116 mmol) and diethyl but-2-ynedioate (21.76 g, 127.89 mmol) in ethanol (200 mL) was stirred at room temperature for 3 days and then concentrated under reduced pressure. The residue was used directly for the next step without further purification. LC/MS (M+H): 342.1, 344.1.

Intermediate I-1B: ethyl 6-bromo-4-oxo-1,4-dihydroquinoline-2-carboxylate

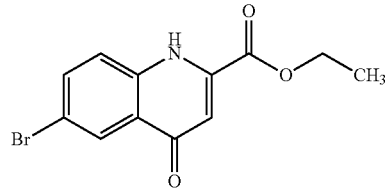

(I-1B)

Diphenyl ether (70 mL) was added to a three neck flask. The solvent was heated to 220~230° C. A solution of diethyl 2-((4-bromophenyl)amino)but-2-enedioate (35.3 g, 103 mmol) in diphenyl ether (40 mL) was added dropwise to the flask to keep the internal temperature between 220° C. and 225° C. The reaction mixture was then heated for 15 min at the same temperature and then cooled to ~70° C. Hexanes (100 mL) was added. The slurry was cooled to room temperature, filtered and washed with hexanes (60 mL) to yield ethyl 6-bromo-4-oxo-1,4-dihydroquinoline-2-carboxylate (9.7 g, 32.8 mmol, 31.8% yield). LC/MS (M+H): 298, $^1$H NMR (400 MHz, DMSO-$d_6$) δ 12.21 (br. s., 1H), 8.16 (s, 1H), 7.99-7.78 (m, 2H), 6.67 (s, 1H), 4.43 (q, J=7.1 Hz, 2H), 1.37 (t, J=7.1 Hz, 3H).

Intermediate I-1C: ethyl 6-bromo-3-chloro-4-oxo-1,4-dihydroquinoline-2-carboxylate

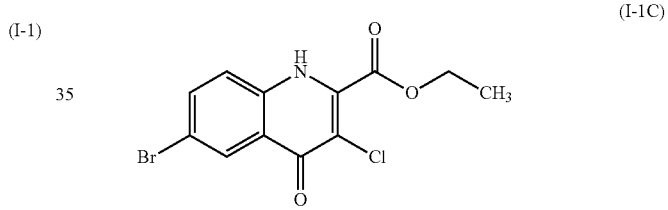

(I-1C)

A suspension of ethyl 6-bromo-4-oxo-1,4-dihydroquinoline-2-carboxylate (5 g, 16.89 mmol) and N-chlorosuccinimide (2.367 g, 17.73 mmol) in acetonitrile (120 mL) and acetic acid (6 mL) was stirred at 90° C. for 5 h. The solid was filtered and washed with MeCN to give ethyl 6-bromo-3-chloro-4-oxo-1,4-dihydroquinoline-2-carboxylate (5.23 g, 15.82 mmol, 94% yield) as a solid. LC/MS (M+H): 330, 332; LC retention time: 0.980 min (analytical HPLC Method B); $^1$H NMR (400 MHz, METHANOL-$d_4$) δ 8.40 (d, J=2.0 Hz, 1H), 7.84 (dd, J=9.0, 2.3 Hz, 1H), 7.67 (d, J=8.9 Hz, 1H), 4.53 (q, J=7.1 Hz, 2H), 1.46 (t, J=7.2 Hz, 3H).

Intermediate I-1D: ethyl 6-bromo-3,4-dichloroquinoline-2-carboxylate

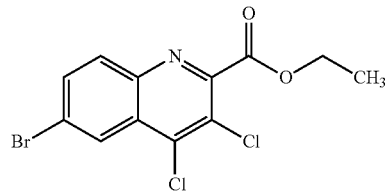

(I-1D)

Ethyl 6-bromo-3-chloro-4-oxo-1,4-dihydroquinoline-2-carboxylate (5.2 g, 15.73 mmol) was added to a 100 mL flask followed by POCl₃ (23 mL). The reaction mixture was stirred at 105° C. under nitrogen for 1.5 h. The mixture was concentrated at reduced pressure. The residue was mixed with EtOAc (10 mL). Ice (20 g) was added with ice-water bath cooling, followed by concentrated ammonium hydroxide (30 mL) and EtOAc (40 mL). The mixture was stirred at 0° C. for 30 min. The solid was filtered and washed with water and then EtOAc to give the first batch of the product (2.06 g) as a white solid. The filtrate was separated. The aqueous layer was extracted with ethyl acetate (2×10 mL). The combined organic solutions were dried over sodium sulfate, filtered, and concentrated under reduced pressure to give the second batch of the product (3.44 g) as a solid. Both batches of solid were identified as ethyl 6-bromo-3,4-dichloroquinoline-2-carboxylate (5.5 g, 15.76 mmol, 100% yield). LC/MS (M+H): 349.9; LC retention time: 1.463 min (analytical HPLC Method B); ¹H NMR (400 MHz, CHLOROFORM-d) δ 8.41 (d, J=1.8 Hz, 1H), 8.04 (d, J=8.9 Hz, 1H), 7.89 (dd, J=8.9, 2.1 Hz, 1H), 4.56 (q, J=7.1 Hz, 2H), 1.48 (t, J=7.2 Hz, 3H).

Intermediate I-1

A mixture of ethyl 6-bromo-3,4-dichloroquinoline-2-carboxylate (3.24 g, 9.28 mmol), (1R)-(−)-camphor-10-sulfonic acid (1.078 g, 4.64 mmol), and 2,5-dimethylaniline (4.5 mL, 36.0 mmol) was stirred at 140° C. under a nitrogen atmosphere for 2.5 h. The mixture was cooled. EtOAc (30 mL) was added, followed by saturated aqueous sodium bicarbonate solution (30 mL). The mixture was filtered through a pad of celite and the filter cake was washed with EtOAc. The filtrate was separated. The aqueous layer was extracted with ethyl acetate (2×5 mL). The combined organic solutions were dried over sodium sulfate, filtered, and concentrated under reduced pressure. Flash chromatography purification (80 g silica gel column, gradient elution from 0 to 30% of ethyl acetate in hexanes) afforded crude ethyl 6-bromo-3-chloro-4-((2,5-dimethylphenyl)amino)quinoline-2-carboxylate (7.5 g) (containing 2,5-dimethylaniline) as a liquid. The mixture was used as such in the next step without further purification. LC/MS (M+H): 433, 435; LC retention time: 1.457 min (analytical HPLC Method B);

Intermediate I-2

(6-bromo-3-chloro-4-((2,5-dimethylphenyl)amino)quinolin-2-yl)methanol

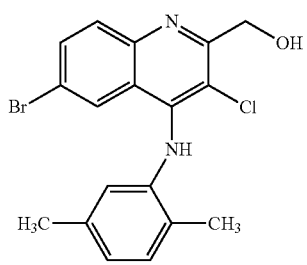

(I-2)

Intermediate I-2A:
6-bromo-4-hydroxyquinoline-2-carboxylate

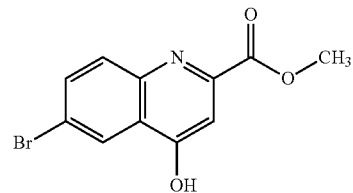

(I-2A)

To a stirred solution of 4-bromoaniline (6 g, 34.9 mmol) in anhydrous MeOH (10 mL) was added dimethyl acetylenedicarboxylate (4.49 mL, 36.6 mmol) dropwise at 0° C. under a nitrogen atmosphere. The mixture was stirred at room temperature overnight. More dimethyl acetylenedicarboxylate (1 mL) was added. The mixture was stirred at room temperature for 1 h and concentrated under reduced pressure to remove MeOH. To the residue was added diphenyl ether (10 mL, 63.0 mmol). The mixture was placed on a sand bath that was preheated to 220° C. The mixture was stirred at 180° C. (internal temperature) for 1 h, cooled and hexanes (10 mL) was added. The solid was filtered and washed with Et₂O to give methyl 6-bromo-4-hydroxyquinoline-2-carboxylate (0.7 g, 2.481 mmol, 7.11% yield) as a solid. LC/MS (M+H): 282, 284; LC retention time: 0.838 min (analytical HPLC Method B); ¹H NMR (400 MHz, METHANOL-d₄) δ 8.37 (d, J=2.2 Hz, 1H), 7.85 (dd, J=9.0, 2.2 Hz, 1H), 7.79 (d, J=8.8 Hz, 1H), 6.96 (s, 1H), 4.03 (s, 3H).

Intermediate I-2B: methyl
6-bromo-3-chloro-4-hydroxyquinoline-2-carboxylate

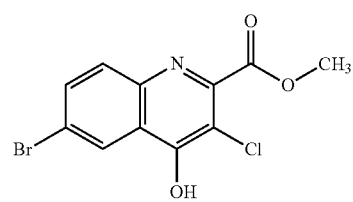

(I-2B)

A suspension of methyl 6-bromo-4-hydroxyquinoline-2-carboxylate (0.61 g, 2.162 mmol) and N-chlorosuccinimide (0.303 g, 2.271 mmol) in acetonitrile (17 mL) and acetic acid (0.85 mL) was stirred at 90° C. for 5 h. The solid was filtered and washed with Et₂O to give methyl 6-bromo-3-chloro-4-hydroxyquinoline-2-carboxylate (0.635 g, 2.006 mmol, 93% yield) as a solid. LC/MS (M+H): 316, 318; LC retention time: 0.915 min (analytical HPLC Method B); ¹H NMR (400 MHz, METHANOL-d₄) δ 8.43 (d, J=2.2 Hz, 1H), 7.82 (dd, J=9.0, 2.1 Hz, 1H), 7.65 (d, J=8.9 Hz, 1H), 4.08 (s, 3H).

Intermediate I-2C: Methyl 6-bromo-3,4-dichloroquinoline-2-carboxylate

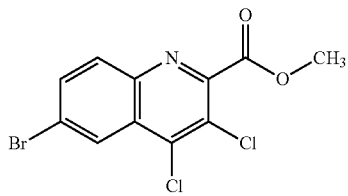
(I-2C)

Methyl 6-bromo-3-chloro-4-hydroxyquinoline-2-carboxylate (0.63 g, 1.990 mmol) was added to a 25 mL flask followed by $POCl_3$ (3 mL). The reaction mixture was stirred at 105° C. under nitrogen for 1.5 h. The mixture was concentrated under reduced pressure. The residue was quenched with ice (15 g) and then basified with concentrated ammonium hydroxide (5 mL). EtOAc (5 mL) and hexanes (5 mL) were added. The mixture was stirred at 0° C. for 30 min. The solid was filtered and washed with water and then a mixture of EtOAc and hexanes to give a white solid (339 mg). The filtrate was separated. The aqueous layer was extracted with ethyl acetate (3×3 mL). The combined organic solutions were dried over sodium sulfate, filtered, and concentrated under reduced pressure to give a white solid (330 mg). Both solids were identified as methyl 6-bromo-3,4-dichloroquinoline-2-carboxylate (0.669 g, 1.997 mmol, 100% yield). LC/MS (M+H): 334, 336, 338; LC retention time: 1.370 min (analytical HPLC Method B); $^1H$ NMR (400 MHz, CHLOROFORM-d) δ 8.41 (d, J=2.2 Hz, 1H), 8.03 (d, J=8.9 Hz, 1H), 7.89 (dd, J=9.0, 2.1 Hz, 1H), 4.08 (s, 3H).

Intermediate I-2

A mixture of 2,5-dimethylaniline (0.157 mL, 1.254 mmol), methyl 6-bromo-3,4-dichloroquinoline-2-carboxylate (140 mg, 0.418 mmol), (1R)-(−)-camphor-10-sulfonic acid (48.5 mg, 0.209 mmol) and anhydrous DMA (0.3 mL) was stirred at 140° C. for 2 h. Saturated aqueous sodium bicarbonate solution (3 mL) was added. The mixture was extracted with ethyl acetate (4×1 mL). The combined organic extracts were dried over sodium sulfate, filtered, and concentrated under reduced pressure. The residue was dissolved in DCM (2 mL) and MeOH (2 mL). $NaBH_4$ (31.6 mg, 0.836 mmol) was added. The mixture was stirred at room temperature for 2 h and then concentrated. Saturated aqueous sodium bicarbonate solution (5 mL) was added. The mixture was extracted with ethyl acetate (5 mL, 3×2 mL). The combined organic extracts were dried over sodium sulfate, filtered, and concentrated under reduced pressure. Flash chromatography purification afforded (6-bromo-3-chloro-4-((2,5-dimethylphenyl)amino) quinolin-2-yl)methanol (36 mg, 0.092 mmol, 21.99% yield). LC/MS (M+H): 391, 393; LC retention time: 0.943 min (analytical HPLC Method B); $^1H$ NMR of its TFA salt (400 MHz, METHANOL-$d_4$) δ 8.14 (d, J=9.0 Hz, 1H), 7.98 (dd, J=9.0, 2.1 Hz, 1H), 7.75 (d, J=2.0 Hz, 1H), 7.36-7.31 (m, 1H), 7.29-7.25 (m, 1H), 7.11 (s, 1H), 5.04 (s, 2H), 2.34 (s, 3H), 2.20 (s, 3H).

Intermediate I-3

6-bromo-3-chloro-4-((2,5-dimethylphenyl)amino) quinoline-2-carboxylic acid

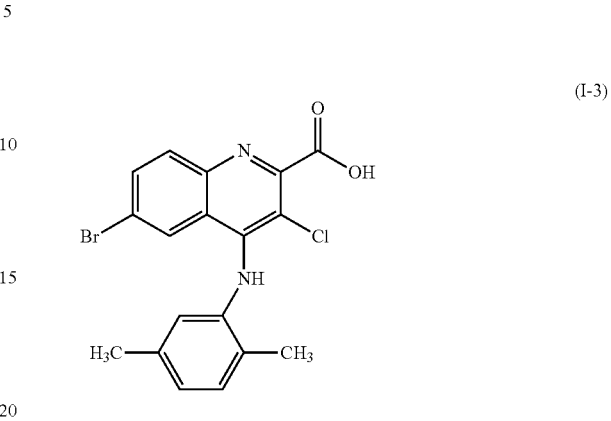
(I-3)

To a stirred solution of ethyl 6-bromo-3-chloro-4-((2,5-dimethylphenyl)amino) quinoline-2-carboxylate (Intermediate I-1, 1.3 mmol) in tetrahydrofuran (3 mL) was added 1 N aqueous solution of NaOH (3.90 mL, 3.90 mmol). The mixture was stirred at room temperature for 2 hr and 70° C. for 1.5 h. More 1 N aqueous solution of NaOH (1 mL) was added and the reaction mixture was stirred at 70° C. for 1 h. The solid-liquid mixture was cooled. Hexanes (3 mL) was added. The organic phase was decanted. The solid-liquid mixture that was left was neutralized with AcOH (0.447 mL, 7.80 mmol) at 0° C. After stirring for 1 h, the solid was filtered, washed with water (3×1 mL) and then a mixture of hexanes and EtOAc (3×1 mL) to give a solid. Trituration of the solid with $Et_2O$ gave 6-bromo-3-chloro-4-((2,5-dimethylphenyl)amino)quinoline-2-carboxylic acid (0.52 g, 1.282 mmol, 99% yield) as a yellow solid. LC/MS (M+H): 405, 407; LC retention time: 0.953 min (analytical HPLC Method B).

Intermediate I-4

6-bromo-3-chloro-N4-(2,5-dimethylphenyl)quinoline-2,4-diamine

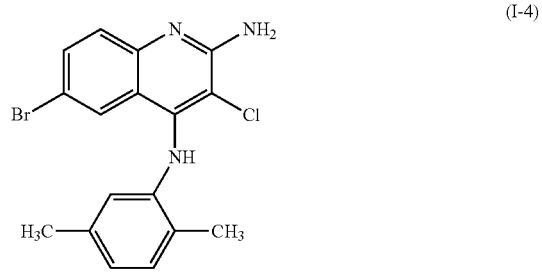 [SMILES: Cc1ccc(C)c(Nc2c(Cl)c(N)nc3ccc(Br)cc23)c1]
(I-4)

To a suspension of 6-bromo-3-chloro-4-((2,5-dimethylphenyl)amino)quinoline-2-carboxylic acid (Intermediate I-3, 0.2 g, 0.493 mmol) in anhydrous DMF (1.972 mL) was added DIEA (0.172 mL, 0.986 mmol) at room temperature under nitrogen, followed by DPPA (0.212 mL, 0.986 mmol). The suspension was stirred at room temperature for 2 h and at 60° C. for 1.5 h. The mixture was cooled and diluted with water (2 mL). The solid was separated by filtration and washed with water and $Et_2O$ give 6-bromo-3-chloro-N4-(2, 5-dimethylphenyl) quinoline-2,4-diamine (0.2 g, 108% yield). LC/MS (M+H): 376, 378; LC retention time: 0.978 min (analytical HPLC Method B);

Intermediate I-5

N-((6-bromo-3-chloroquinolin-4-yl)methyl)aniline

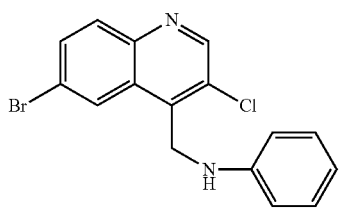

Intermediate I-5A:
(5-bromo-1H-indol-3-yl)methanol

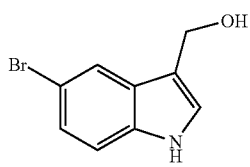

5-Bromoindole-3-carboxaldehyde (1 g, 4.46 mmol) was dissolved in DCM (6 mL), MeOH (6 mL), and THF (6 mL). NaBH$_4$ (0.169 g, 4.46 mmol) was added portion wise at room temperature. The mixture was stirred at room temperature for 3 h and concentrated. The residue was mixed with EtOAc (20 mL) and saturated aqueous NH$_4$Cl solution (6 mL). The aqueous layer was separated and extracted with ethyl acetate (3×2 mL). The combined organic solutions were dried over sodium sulfate and concentrated under reduced pressure. Flash chromatography purification afforded 5-bromo-1H-indol-3-yl)methanol (0.98 g, 4.33 mmol, 97% yield) as a solid. LC/MS (M+H—H$_2$O): 210.0; LC retention time: 0.855 min (analytical HPLC Method B);

Intermediate I-5B:
(6-bromo-3-chloroquinolin-4-yl)methanol

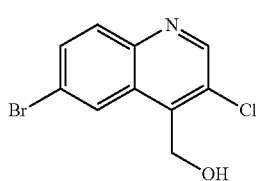

Sodium hydroxide (0.347 g, 8.67 mmol) was dissolved in water (0.4 mL, 22.20 mmol). The solution was added dropwise to a suspension of (5-bromo-1H-indol-3-yl) methanol (0.98 g, 4.33 mmol) and tetrabutylammonium chloride (0.181 g, 0.650 mmol) in CHCl$_3$ (20 mL, 248 mmol) at 0° C. The mixture was than stirred at room temperature for 1 day. Additional NaOH was added and the mixture was stirred at 60° C. for 1 h. The mixture was cooled. Water (10 mL) was added to quench the reaction. The aqueous layer was separated and extracted with ethyl acetate (3×5 mL). The combined organic solutions were dried over sodium sulfate and concentrated under reduced pressure. Flash chromatography purification (24 g silica gel column, gradient elution from 10 to 100% of ethyl acetate in hexanes) afforded (6-bromo-3-chloroquinolin-4-yl)methanol (0.28 g, 1.027 mmol, 23.70% yield) as a solid. LC/MS (M+H): 271.9, 273.9; LC retention time: 0.838 min (analytical HPLC Method B).

Intermediate I-5

To a stirred solution of (6-bromo-3-chloroquinolin-4-yl) methanol (167 mg, 0.613 mmol) and triphenylphosphine (193 mg, 0.735 mmol) in anhydrous CH$_2$Cl$_2$ (1 mL) was added N-bromosuccinimide (120 mg, 0.674 mmol) at −78° C. under nitrogen. The reaction mixture was stirred at the same temperature for 30 min and at 0° C. for 1.5 h. Aniline (0.224 mL, 2.451 mmol) was added at 0° C. The reaction mixture was stirred at 0° C. for 30 min and at room temperature for 3 days. The mixture was quenched with saturated aqueous sodium bicarbonate solution (3 mL). The aqueous layer was separated and extracted with ethyl acetate (3×1 mL). The combined organic solutions were dried over sodium sulfate, filtered, and concentrated under reduced pressure. Flash chromatography purification was followed by further purification using reverse phase HPLC (Phen Luna 5u 30×100 mm (Axia); gradient over 7 min from 30 to 100% of solvent B; solvent A: 10% MeOH: 90% H$_2$O: 0.1% TFA; solvent B: 90% MeOH, 10% H$_2$O, 0.1% TFA). The fraction containing the desired product was concentrated. The residue was basified with K$_2$CO$_3$ and extracted with EtOAc to give N-((6-bromo-3-chloroquinolin-4-yl)methyl) aniline (18 mg, 0.052 mmol, 8.45% yield) as a solid. LC/MS (M+H): 347.0, 349.0; LC retention time: 1.353 min (analytical HPLC Method B); $^1$H NMR (400 MHz, CHLOROFORM-d) δ 8.87 (s, 1H), 8.27 (d, J=2.1 Hz, 1H), 7.99 (d, J=8.9 Hz, 1H), 7.80 (dd, J=8.9, 2.1 Hz, 1H), 7.31-7.26 (m, 3H), 6.84 (t, J=7.4 Hz, 1H), 6.81-6.76 (m, 2H), 4.78 (s, 2H).

Intermediate I-6

2-(5-(3-chloro-4-(hydroxymethyl)quinolin-6-yl)pyrimidin-2-yl)propan-2-ol

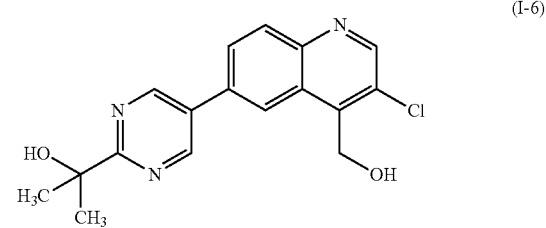 [SMILES: CC(C)(O)c1ncc(-c2ccc3ncc(Cl)c(CO)c3c2)cn1]

Intermediate I-6A: 2-(5-(3-chloro-4-vinylquinolin-6-yl)pyrimidin-2-yl)propan-2-ol

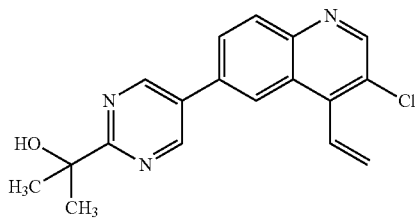

(I-6A)

A mixture of vinylboronic acid pinacol ester (0.264 mL, 1.556 mmol), 2-(5-(3,4-dichloroquinolin-6-yl)pyrimidin-2-yl)propan-2-ol (Intermediate I-45, 0.4 g, 1.197 mmol), K₂CO₃ (0.992 g, 7.18 mmol), and dioxane (4 mL) was bubbled with nitrogen for 2 min before tetrakis(triphenylphosphine)palladium(0) (0.277 g, 0.239 mmol) was added. Nitrogen gas was bubbled for an additional 2 min and the reaction mixture was stirred at 90° C. in a sealed pressure vial for 20 hr. Water (5 mL) was added and the mixture was extracted with EtOAc (5 mL, 3×3 mL). The combined organic solutions were dried over anhydrous sodium sulfate and concentrated. Flash chromatography purification (24 g silica gel column, gradient elution from 10 to 100% of ethyl acetate in hexanes) afforded 2-(5-(3-chloro-4-vinylquinolin-6-yl)pyrimidin-2-yl)propan-2-ol (0.39 g, 1.197 mmol, 100% yield) as a solid. LC/MS (M+H): 326.1; LC retention time: 1.083 min (analytical HPLC Method B);

Intermediate I-6B: 3-chloro-6-(2-(2-hydroxypropan-2-yl)pyrimidin-5-yl)quinoline-4-carbaldehyde

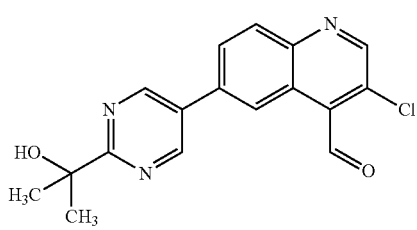

(I-6B)

To a stirred solution of 2-(5-(3-chloro-4-vinylquinolin-6-yl)pyrimidin-2-yl) propan-2-ol (0.39 g, 1.197 mmol) in 1,4-dioxane (9.58 mL) were added water (2.394 mL), 2,6-lutidine (0.279 mL, 2.394 mmol), osmium tetroxide (0.751 mL, 0.060 mmol) (2.5 wt % solution in t-BuOH), and sodium periodate (1.024 g, 4.79 mmol). The resulting thick suspension was stirred at room temperature for 3 h. Additional sodium periodate was added and the reaction mixture was at heated 50° C. for 1 h. Water (10 mL), EtOAc (5 mL) and hexanes (5 mL) were added. The aqueous layer was separated and extracted with ethyl acetate (3×10 mL). The combined organic solutions were dried over sodium sulfate, filtered, and concentrated under reduced pressure. Flash chromatography purification (12 g silica gel column, gradient elution from 10 to 100% of ethyl acetate in hexanes) afforded 3-chloro-6-(2-(2-hydroxypropan-2-yl)pyrimidin-5-yl)quinoline-4-carbaldehyde (0.3 g, 0.915 mmol, 76% yield) as a solid. LC/MS (M+H): 328.1; LC retention time: 0.993 min (analytical HPLC Method B).

Intermediate I-6

A mixture of 3-chloro-6-(2-(2-hydroxypropan-2-yl)pyrimidin-5-yl)quinoline-4-carbaldehyde (188 mg, 0.574 mmol) and sodium cyanoborohydride (108 mg, 1.721 mmol) and MeOH (2 mL) was stirred at room temperature for 3 h. The reaction mixture was concentrated and the residue was treated with 1 M aqueous NaOH. The mixture was extracted THF and EtOAc. The combined organic solutions were dried over sodium sulfate, filtered through a pad of silica gel, and concentrated under reduced pressure. The residue was triturated with a mixture of EtOAc and hexanes to afford 2-(5-(3-chloro-4-(hydroxymethyl)quinolin-6-yl)pyrimidin-2-yl)propan-2-ol (90 mg, 0.273 mmol, 47.6% yield) as a solid. LC/MS (M+H): 330.1; LC retention time: 0.815 min (analytical HPLC Method B); ¹H NMR (400 MHz, METHANOL-d₄) δ 9.23 (s, 2H), 8.88 (s, 1H), 8.66 (d, J=1.5 Hz, 1H), 8.26-8.20 (m, 1H), 8.17-8.12 (m, 1H), 5.31 (s, 2H), 1.65 (s, 6H).

Intermediate I-7

± 6-bromo-3-chloro-N-(2-fluoro-1-(2-fluorophenyl)ethyl)quinolin-4-amine

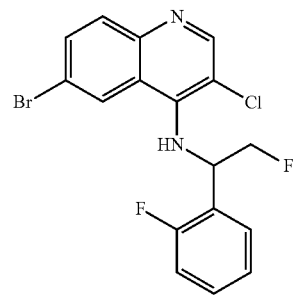

(I-7)

Intermediate I-7A: 2-((6-bromo-3-chloroquinolin-4-yl)amino)-2-(2-fluorophenyl)ethanol

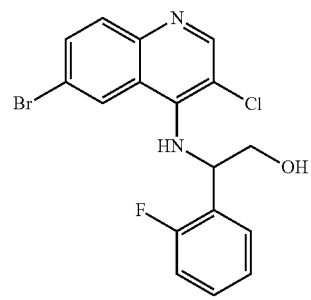

(I-7A)

2-((6-bromo-3-chloroquinolin-4-yl)amino)-2-(2-fluorophenyl)ethanol was prepared according to the general process used in the last synthesis step of Intermediate I-1.

LC/MS (M+H): 395.0, 397.0; LC retention time: 0.842 min (analytical HPLC Method B).

Intermediate I-7

To a stirred suspension of 2-((6-bromo-3-chloroquinolin-4-yl)amino)-2-(2-fluorophenyl)ethanol (43 mg, 0.109 mmol) in anhydrous $CH_2Cl_2$ (4 mL) was added DAST (0.072 mL, 0.543 mmol) dropwise at −78° C. The mixture was stirred at 0° C. for 3 h at room temperature for 17 h, and at 45° C. for 1 h. Saturated aqueous sodium bicarbonate solution (3 mL) was added at 0° C. to quench the reaction. The aqueous layer was separated and extracted with ethyl acetate (3×2 mL). The combined organic solutions were dried over sodium sulfate, filtered, and concentrated under reduced pressure. Flash chromatography purification (4 g silica gel column, gradient elution from 10 to 100% of ethyl acetate in hexanes) afforded 6-bromo-3-chloro-N-(2-fluoro-1-(2-fluorophenyl)ethyl)quinolin-4-amine (26 mg, 0.065 mmol, 60.2% yield). LC/MS (M+H): 397.0, 399.0; LC retention time: 0.980 min (analytical HPLC Method B); $^1$H NMR (400 MHz, CHLOROFORM-d) δ 8.61 (s, 1H), 8.03 (d, J=2.0 Hz, 1H), 7.85 (d, J=9.0 Hz, 1H), 7.68 (dd, J=8.9, 2.1 Hz, 1H), 7.46 (td, J=7.6, 1.6 Hz, 1H), 7.39-7.31 (m, 1H), 7.22-7.10 (m, 2H), 5.48-5.33 (m, 2H), 4.89-4.76 (m, 1H), 4.75-4.63 (m, 1H).

Intermediate I-8

3-chloro-6-(2-chloropyrimidin-5-yl)-N4-(2,5-dimethylphenyl)quinoline-2,4-diamine

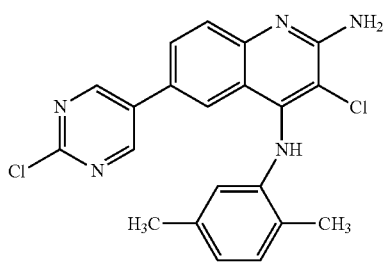

(I-8)

To a mixture of 6-bromo-3-chloro-N4-(2,5-dimethylphenyl)quinoline-2,4-diamine (Intermediate I-4, 0.46 g, 1.221 mmol), 4,4,4',4',5,5,5',5'-octamethyl-2,2'-bi(1,3,2-dioxaborolane) (0.465 g, 1.832 mmol), potassium acetate (0.180 g, 1.832 mmol), 1,4-dioxane (15 mL), and [1,1'-bis(diphenylphosphino)ferrocene]dichloropalladium(II) (0.089 g, 0.122 mmol) was bubbled nitrogen for 2 min. and then stirred at 90° C. for 2 h. 5-bromo-2-chloropyrimidine (0.472 g, 2.442 mmol) and potassium carbonate (2 M solution) (1.527 mL, 3.05 mmol) were added to the reaction. Nitrogen gas was bubbled for 2 min and the reaction mixture was stirred at 100° C. for 3 h. The reaction mixture was cooled and diluted with hexanes (5 mL) and EtOAc (10 mL). The aqueous layer was separated and extracted with ethyl acetate (3×1 mL). The combined organic solutions were dried over sodium sulfate, filtered, and concentrated under reduced pressure. The residue was purified by flash chromatography (24 g silica gel column, gradient elution from 10 to 100% of ethyl acetate in hexanes) to afford the desired product contaminated with minor impurities. Further crystallization using EtOAC/hexanes gave 3-chloro-6-(2-chloropyrimidin-5-yl)-N4-(2,5-dimethylphenyl)quinoline-2,4-diamine (0.11 g, 0.268 mmol, 21.95% yield) as a solid. LC/MS (M+H): 410.1; LC retention time: 0.943 min (analytical HPLC Method B).

Intermediate I-9

(±) N1-(6-bromo-3-chloroquinolin-4-yl)-1-(2-fluorophenyl)-N2,N2-dimethylethane-1,2-diamine

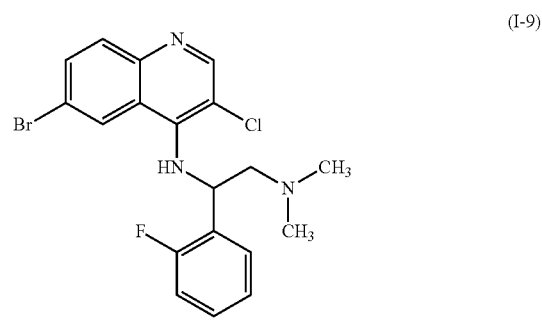 [SMILES: CN(C)CC(Nc1c(Cl)cnc2ccc(Br)cc12)c1ccccc1F]

(I-9)

To a stirred solution of 2-((6-bromo-3-chloroquinolin-4-yl)amino)-2-(2-fluorophenyl)ethanol (Intermediate I-7A, 20 mg, 0.051 mmol) in anhydrous THF (2 mL) was added methanesulfonyl chloride (5.88 μl, 0.076 mmol) at 0° C. under nitrogen. Triethylamine (0.021 mL, 0.152 mmol) was added dropwise at the same temperature. The reaction mixture was stirred at 0° C. for 1.5 h. Next, 2 M THF solution of dimethylamine (0.253 mL, 0.505 mmol) was added. The reaction mixture was stirred at 60° C. for 18 h. (reaction was not complete). The reaction mixture was concentrated and the residue was mixed with anhydrous THF (1 mL) and DMF (0.1 mL) in a sealed tube. The tube was cooled in a dry ice bath and 1 mL of dimethylamine was condensed. The tube was sealed and the clear solution was stirred at 80° C. for 3 h and 90° C. for 2 h. The reaction mixture was cooled, concentrated, the residue was made basic with saturated aqueous sodium bicarbonate solution (3 mL) and extracted with EtOAc (3×2 mL). The combined ethyl acetate extracts were dried over sodium sulfate and concentrated under reduced pressure. Flash chromatography purification (4 g silica gel column, gradient elution from 10 to 100% of ethyl acetate in hexanes) afforded N1-(6-bromo-3-chloroquinolin-4-yl)-1-(2-fluorophenyl)-N2,N2-dimethylethane-1,2-diamine (20 mg, 0.047 mmol, 94% yield, containing 20% of undesired regioisomer). LC/MS (M+H): 422.1, 424.1; LC retention time: 0.777 min (analytical HPLC Method B); $^1$H NMR (400 MHz, CHLOROFORM-d) δ 8.51 (s, 1H), 8.07 (d, J=2.1 Hz, 1H), 7.77 (d, J=8.9 Hz, 1H), 7.60 (dd, J=8.9, 2.1 Hz, 1H), 7.37-7.21 (m, 2H), 7.12-7.01 (m, 2H), 6.24 (d, J=6.0 Hz, 1H), 5.39 (dt, J=7.9, 5.7 Hz, 1H), 2.85-2.76 (m, 1H), 2.75-2.68 (m, 1H), 2.31 (s, 6H).

Intermediate I-10 tert-butyl 2-((4-(4,4,5,5-tetramethyl-1,3,2-dioxaborolan-2-yl)benzyl)amino)acetate

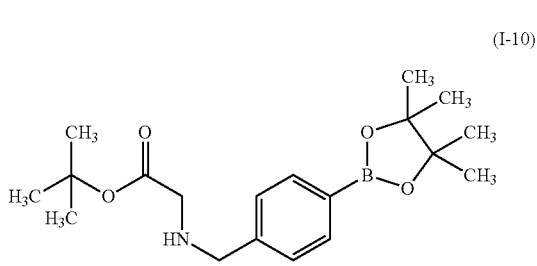 [SMILES: CC(C)(C)OC(=O)CNCc1ccc(B2OC(C)(C)C(C)(C)O2)cc1]

(I-10)

To a stirred mixture of tert-butyl glycinate (0.177 g, 1.347 mmol) and K$_2$CO$_3$ (0.186 g, 1.347 mmol) in acetonitrile (10 mL) was added 4-(bromomethyl)benzeneboronic acid pinacol ester (0.4 g, 1.347 mmol). The resulting reaction mixture was stirred at room temperature overnight. EtOAc (10 mL) was added. The solid was filtered through a pad of celite and concentrated. Flash chromatography purification (12 g silica gel column, gradient elution from 10 to 100% of ethyl acetate in hexanes) afforded tert-butyl 2-((4-(4,4,5,5-tetramethyl-1,3,2-dioxaborolan-2-yl)benzyl)amino)acetate (0.068 g, 0.196 mmol, 14.54% yield). LC/MS (M+H): 348.3; LC retention time: 0.948 min (analytical HPLC Method B).

Intermediates I-11 and I-12

± 3-(4-(5-bromopyrimidin-2-yl)piperazin-1-yl)pyrrolidin-2-one (I-11) and ± methyl 2-(4-(5-bromopyrimidin-2-yl)piperazin-1-yl)-4-(3-((tert-butoxycarbonyl)amino)propanamido)butanoate (I-12)

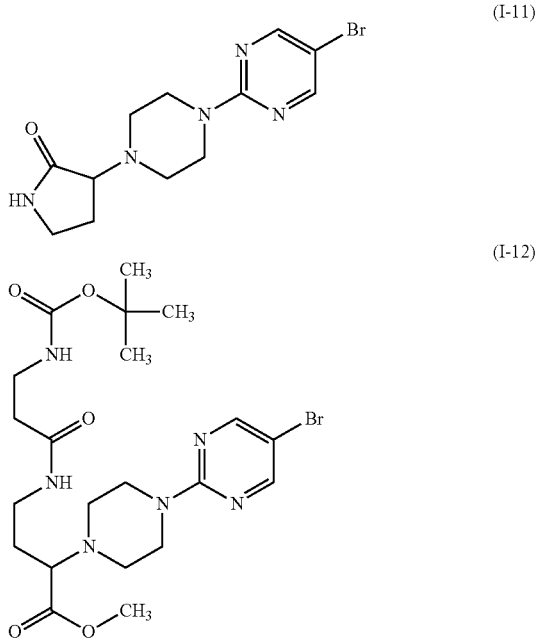

Intermediate I-12A: ± methyl 2-(4-(5-bromopyrimidin-2-yl)piperazin-1-yl)-4-(1,3-dioxoisoindolin-2-yl)butanoate

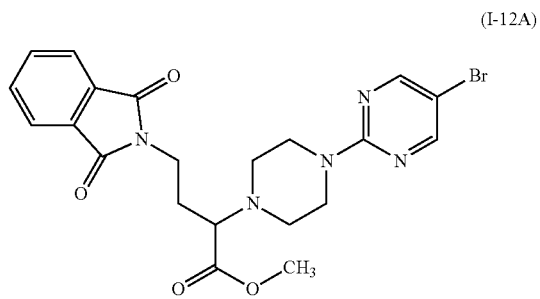 [SMILES: COC(=O)C(CCN1C(=O)c2ccccc2C1=O)N1CCN(c2ncc(Br)cn2)CC1]

(I-12A)

A mixture of methyl 2-bromo-4-(1,3-dioxoisoindolin-2-yl)butanoate (0.52 g, 1.594 mmol), 5-bromo-2-(piperazin-1-yl)pyrimidine (0.388 g, 1.594 mmol), DIEA (0.3 mL, 1.718 mmol), and anhydrous THF (7 mL) was stirred at 60° C. under a nitrogen atmosphere for 3 h and at 50° C. for 64 h. Saturated aqueous sodium bicarbonate solution (5 mL) and hexanes (4 mL) were added. The aqueous layer was separated and extracted with ethyl acetate (3×2 mL). The combined organic extracts were dried over sodium sulfate, filtered, and concentrated under reduced pressure. Flash chromatography purification using ISCO (12 g silica gel column, gradient elution from 5 to 100% of ethyl acetate in hexanes) afforded methyl 2-(4-(5-bromopyrimidin-2-yl)piperazin-1-yl)-4-(1,3-dioxoisoindolin-2-yl)butanoate (0.47 g, 0.962 mmol, 60.4% yield). LC/MS (M+H): 488.1, 490.0; LC retention time: 1.037 min (analytical HPLC Method B).

Intermediate I-11 and Intermediate I-12B: methyl 4-amino-2-(4-(5-bromopyrimidin-2-yl)piperazin-1-yl)butanoate

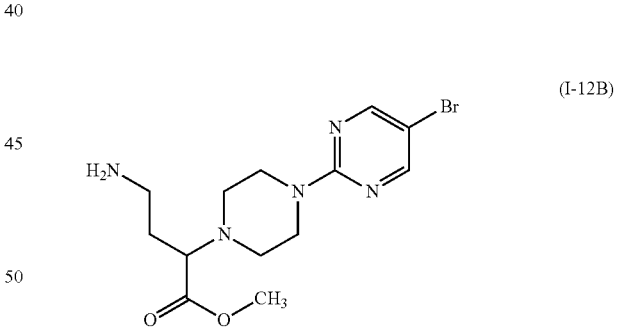

(I-12B)

To a clear solution of methyl 2-(4-(5-bromopyrimidin-2-yl)piperazin-1-yl)-4-(1,3-dioxoisoindolin-2-yl)butanoate (0.47 g, 0.962 mmol) in THF (3 mL) and 100% ethanol (6 mL) was added hydrazine hydrate (0.093 mL, 1.925 mmol). The solution was stirred at 70° C. for 2 h and concentrated under reduced pressure. The residue was mixed with MeOH-THF-DCM and the solid was filtered off. The filtrate was chromatographed (24 g silica gel column; eluted with 10-100% EtOAc and then 2-20% MeOH in DCM) to afford 3-(4-(5-bromopyrimidin-2-yl)piperazin-1-yl)pyrrolidin-2-one (Intermediate I-11, 0.19 g, 0.582 mmol, 60.5% yield), and methyl 4-amino-2-(4-(5-bromopyrimidin-2-yl)piperazin-1-yl)butanoate (Intermediate I-12B, 0.045 g, 0.126 mmol, 13.05% yield). Analytical data for 3-(4-(5-bromopyrimidin-2-yl)piperazin-1-yl)pyrrolidin-2-one (Intermediate I-11): LC/MS (M+H): 328.0; LC retention time: 0.710 min (analytical HPLC Method B). Analytical data for methyl 4-amino-2-(4-(5-bromopyrimidin-2-yl)piperazin-1-yl)butanoate (Intermediate I-12B): LC/MS (M+H): 358.0; LC retention time: 0.752 min (analytical HPLC Method B).

Intermediate I-12

To a stirred cloudy mixture of methyl 4-amino-2-(4-(5-bromopyrimidin-2-yl) piperazin-1-yl)butanoate (40 mg, 0.112 mmol) and anhydrous $CH_2Cl_2$ (5 mL) was added BOC-BETA-ALA-OSU (47.9 mg, 0.167 mmol) at room temperature under nitrogen, followed by DIEA (0.039 mL, 0.223 mmol). The mixture was stirred at room temperature for 1.5 h. Flash chromatography purification using ISCO (4 g silica gel column, gradient elution from 0 to 10% of MeOH in DCM) afforded methyl 2-(4-(5-bromopyrimidin-2-yl)piperazin-1-yl)-4-(3-((tert-butoxycarbonyl)amino)propanamido) butanoate (36 mg, 0.068 mmol, 60.9% yield) LC/MS (M+H): 531.1; LC retention time: 0.890 min (analytical HPLC Method B).

Intermediate I-13

(S)-methyl 2-(4-(5-bromopyrimidin-2-yl)piperazin-1-yl)-3-((tert-butoxycarbonyl)amino)propanoate

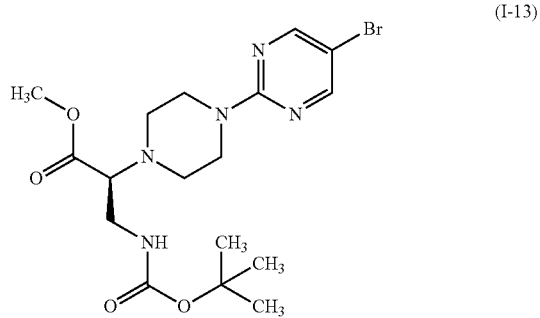 [SMILES: COC(=O)[C@H](CNC(=O)OC(C)(C)C)N1CCN(c2ncc(Br)cn2)CC1]

(I-13)

Intermediate I-13A: (S)-methyl 2-(4-benzylpiperazin-1-yl)-3-((tert-butoxycarbonyl)amino)propanoate

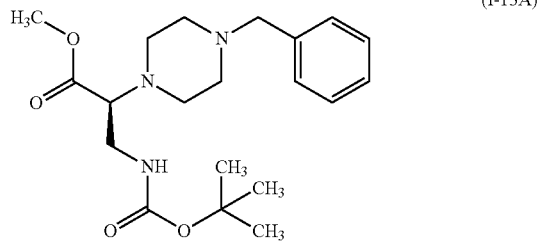

(I-13A)

To a stirred solution of N-benzyl-2-chloro-N-(2-chloroethyl)ethanamine (250 mg, 1.077 mmol) and H-DAP(BOC)-OME HCL (274 mg, 1.077 mmol) in ethanol (5 mL), DIPEA (1.881 mL, 10.77 mmol) was added at 0° C. and the resulting colorless solution was stirred at 120° C. for 12 h. After quenching with water (100 mL), the mixture was extracted with ethylacetate (2×100 mL). The organic layer was separated and washed with water (100 mL), brine (100 mL), dried over sodium sulfate, filtered and concentrated under reduced pressure. The crude compound was purified using silica gel chromatography, eluting with 20-30% ethyl acetate in hexanes. The desired fractions were concentrated to give a colorless oil. LC/MS (M+H): 378.4.

Intermediate I-13B: (S)-methyl 3-((tert-butoxycarbonyl)amino)-2-(piperazin-1-yl)propanoate

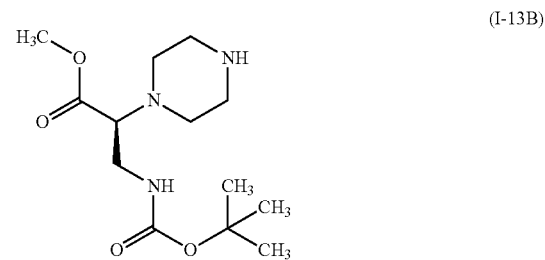 [SMILES: COC(=O)[C@H](CNC(=O)OC(C)(C)C)N1CCNCC1]

(I-13B)

To a stirred solution of (S)-methyl 2-(4-benzylpiperazin-1-yl)-3-((tert-butoxycarbonyl)amino)propanoate (2.5 g, 6.62 mmol) in trifluoroethanol (40 mL), Pd/C (0.141 g, 1.325 mmol) was added and the resulting dark solution was stirred under 1 $kg/cm^3$ of hydrogen pressure for 4 h. Pd/C was filtered off and the filtrate was concentrated under reduced pressure to give the compound as a colorless oil which was used as such for the subsequent step without further purification. LC/MS (M+H): 288.2.

Intermediate I-13C: (S)-methyl 2-(4-(5-bromopyrimidin-2-yl)piperazin-1-yl)-3-((tert-butoxycarbonyl)amino)propanoate

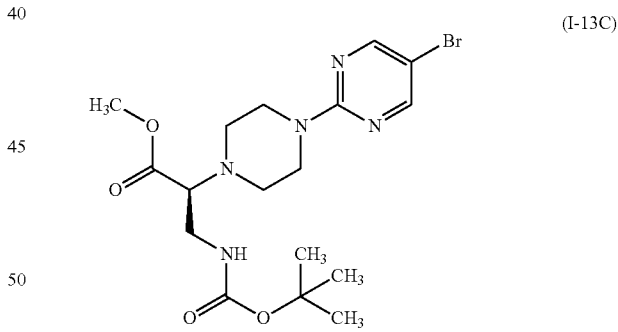

(I-13C)

To stirred solution of (S)-methyl 3-((tert-butoxycarbonyl)amino)-2-(piperazin-1-yl)propanoate (1.2 g, 4.18 mmol) in DIPEA (10 mL) and ethanol (10 mL), 5-bromo-2-chloropyrimidine (0.808 g, 4.18 mmol) was added at room temperature. The resulting yellow colored solution was stirred at 120° C. for 4 h in a microwave. The reaction mixture was cooled to room temperature, diluted with water (100 mL) and extracted with ethyl acetate (100 mL). The organic solution was washed with brine (100 mL), dried over sodium sulfate, filtered and concentrated under reduced pressure. The crude compound was purified using silica gel chromatography, eluting with 20-30% ethyl acetate in hexanes. The desired fractions were concentrated to yield a white solid. LC/MS (M+H): 444.2.

Intermediate I-14

2-(5-bromopyrimidin-2-yl)-3-difluoropropan-2-ol

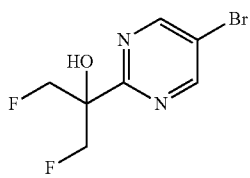

(I-14)

To a mixture of 2.5 M hexane solution of BuLi (0.702 mL, 1.755 mmol) and anhydrous toluene (4 mL) was added a solution of 5-bromo-2-iodopyrimidine (0.5 g, 1.755 mmol) in anhydrous toluene (2 mL) dropwise at −78° C. under nitrogen. The suspension obtained was stirred at the same temperature for 15 min. Next, 1,3-difluoroacetone (0.248 g, 2.63 mmol) was added dropwise over 2 min at −78° C. The mixture was stirred at −78° C. for 0.5 h and the temperature was raised slowly to 0° C. over 1 h. The reaction was quenched with saturated aqueous ammonium chloride (3 mL). The aqueous layer was separated and extracted with DCM (2×2 mL). The combined organic solutions were dried over sodium sulfate and filtered. Flash chromatography purification (12 g silica gel column, gradient elution from 5 to 100% of ethyl acetate in hexanes) afforded 2-(5-bromopyrimidin-2-yl)-1,3-difluoropropan-2-ol (0.228 g, 0.901 mmol, 51.3% yield) as a solid. LC/MS (M+H): 254.9; LC retention time: 0.782 min (analytical HPLC Method B), $^1$H NMR (400 MHz, CHLOROFORM-d) δ 8.94-8.77 (m, 2H), 4.86-4.71 (m, 4H).

Intermediate I-15

4-(5-bromopyrimidin-2-yl)-4-hydroxycyclohexanone

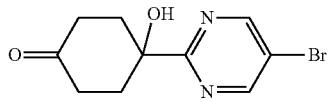

(I-15)

A mixture of 8-(5-bromopyrimidin-2-yl)-1,4-dioxaspiro[4.5]decan-8-ol (1 g, 1.586 mmol, prepared in a similar fashion as Intermediate I-14), THF (8 mL), 1 M aqueous HCl (8 mL, 8.00 mmol) was stirred at 60° C. for 1 h. The mixture was cooled and made basic with sodium bicarbonate (1 g, 11.90 mmol). The aqueous layer was separated and extracted with ethyl acetate (3×2 mL). The combined organic solutions were dried over sodium sulfate, filtered, and concentrated under reduced pressure. Flash chromatography purification (24 g silica gel column, gradient elution from 10 to 100% of ethyl acetate in hexanes) afforded 4-(5-bromopyrimidin-2-yl)-4-hydroxycyclohexanone (0.5 g, 1.844 mmol), as a solid. LC/MS (M+H): 273; LC retention time: 0.762 min (analytical HPLC Method B), $^1$H NMR (400 MHz, CHLOROFORM-d) δ 7.24 (s, 2H), 1.44-1.30 (m, 2H), 1.00-0.81 (m, 4H), 0.53-0.43 (m, 2H).

Intermediate I-16

± 6-(1-(((6-bromo-3-chloroquinolin-4-yl)amino)propyl)-5-fluoropicolinamide

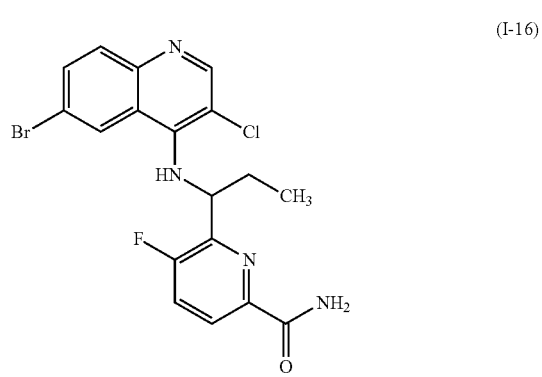 [SMILES: CCC(Nc1c(Cl)cnc2ccc(Br)cc12)c1nc(C(N)=O)ccc1F]

(I-16)

Intermediate I-16A: ± tert-butyl (1-(3-fluoro-6-vinylpyridin-2-yl)propyl)carbamate

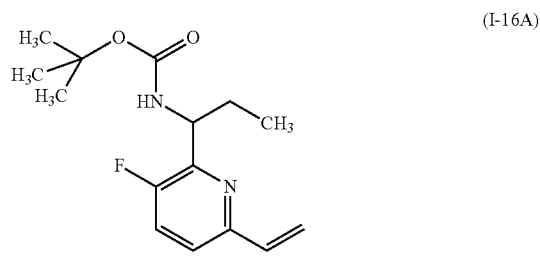 [SMILES: C=Cc1ccc(F)c(C(CC)NC(=O)OC(C)(C)C)n1]

(I-16A)

To a mixture of vinylboronic acid pinacol ester (0.291 mL, 1.716 mmol), 1-(6-bromo-3-fluoropyridin-2-yl)propan-1-amine (Intermediate I-75, 200 mg, 0.858 mmol), potassium carbonate (2M solution, 1.073 mL, 2.145 mmol), and 1,1'-bis(diphenylphosphino)ferrocene-palladium(ii)dichloride dichloromethane complex (70.1 mg, 0.086 mmol) in 1,4-dioxane (2 mL), was bubbled nitrogen gas for 2 min and the reaction mixture was stirred at 100° C. for 2 h. The mixture was extracted with EtOAc (3×1 mL) and the combined organic solutions were dried over sodium sulfate and filtered. Boc$_2$O (562 mg, 2.57 mmol) was added to the solution and the mixture was stirred at room temperature for 2.5 h. The reaction mixture was concentrated. Flash chromatography purification (12 g silica gel column, gradient elution from 2 to 100% of ethyl acetate in hexanes) afforded tert-butyl (1-(3-fluoro-6-vinylpyridin-2-yl)propyl) carbamate (170 mg, 0.606 mmol, 70.7% yield). LC/MS (M+H): 281.2; LC retention time: 1.273 min (analytical HPLC Method B).

Intermediate I-16B: ± tert-butyl (1-(3-fluoro-6-formylpyridin-2-yl)propyl)carbamate

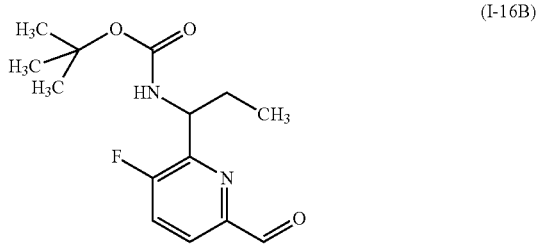 [SMILES: CCC(NC(=O)OC(C)(C)C)c1nc(C=O)ccc1F]

(I-16B)

To a solution of tert-butyl (1-(3-fluoro-6-vinylpyridin-2-yl)propyl)carbamate (170 mg, 0.606 mmol) and NMO in water (0.126 mL, 0.606 mmol) in tetrahydrofuran (5 mL) at room temperature was added 2.5% osmium tetroxide in tert-butanol (0.305 mL, 0.024 mmol). The reaction mixture was stirred at room temperature for 80 min. and treated with a solution of sodium periodate (195 mg, 0.910 mmol) in water (2 mL). The reaction mixture was stirred at room temperature under nitrogen for 60 min. The reaction mixture was extracted with ethyl acetate (3×4 mL). The combined organic solutions were dried over sodium sulfate, filtered, and concentrated under reduced pressure to give tert-butyl (1-(3-fluoro-6-formylpyridin-2-yl)propyl)carbamate which was used for the subsequent step without further purification. LC/MS (M+H): 282.9.

Intermediate I-16C: ± tert-butyl (1-(6-carbamoyl-3-fluoropyridin-2-yl)propyl)carbamate

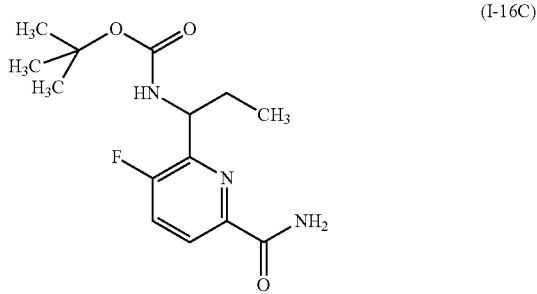 [SMILES: CCC(NC(=O)OC(C)(C)C)c1nc(C(N)=O)ccc1F]

(I-16C)

A solution of sodium chlorite (0.170 g, 1.500 mmol) and potassium dihydrogen phosphate (0.408 g, 3.00 mmol) in water (3 mL) was added to a stirred solution of tert-butyl (1-(3-fluoro-6-formylpyridin-2-yl)propyl)carbamate (0.169 g, 0.6 mmol) in THF (2.5 mL) and tert-butanol (2.5 mL) at room temperature. The mixture was stirred at room temperature for 1 hr and extracted with EtOAc (5 mL) and then DCM (3×2 mL). The combined organic fractions were dried over anhydrous sodium sulphate. Removal of organic solvents under reduced pressure furnished 6-(1-((tert-butoxycarbonyl)amino) propyl)-5-fluoropicolinic acid, which was directly used for the next step without further purification.

The acid from the step above was mixed with ammonium chloride (0.257 g, 4.80 mmol), $CH_2Cl_2$ (5 mL), and DIEA (0.6 mL, 3.44 mmol). BOP (0.398 g, 0.900 mmol) was added and the mixture was stirred at room temperature overnight. Saturated aqueous sodium bicarbonate solution (3 mL) was added to quench the reaction. The aqueous layer was separated and extracted with ethyl acetate (3×2 mL). The combined organic solutions were dried over sodium sulfate, filtered, and concentrated under reduced pressure. Flash chromatography purification (12 g silica gel column, gradient elution from 5 to 100% of ethyl acetate in hexanes) afforded tert-butyl (1-(6-carbamoyl-3-fluoropyridin-2-yl) propyl)carbamate (0.11 g, 0.370 mmol, 61.7% yield). LC/MS (M+Na): 320.1; LC retention time: 0.968 min (analytical HPLC Method B).

Intermediate I-16D: ± 6-(1-aminopropyl)-5-fluoropicolinamide

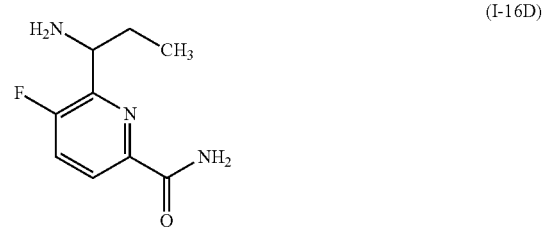

(I-16D)

A solution of tert-butyl (1-(6-carbamoyl-3-fluoropyridin-2-yl)propyl)carbamate (0.11 g, 0.370 mmol) in DCM (3 mL) and TFA (2 mL) was stirred at room temperature for 1 h. Dichloroethane (2 mL) was added and the mixture was concentrated. The residue was made basic with aq. $K_2CO_3$ and mixed with THF (5 mL). The mixture was dried over sodium sulfate, filtered, and concentrated under reduced pressure to give 6-(1-aminopropyl)-5-fluoropicolinamide (55 mg, 0.279 mmol, 75% yield). LC/MS (M+H): 198.0; LC retention time: 0.487 min (analytical HPLC Method B).

Intermediate I-16E: ± 6-(1-((6-bromoquinolin-4-yl)amino)propyl)-5-fluoropicolinamide

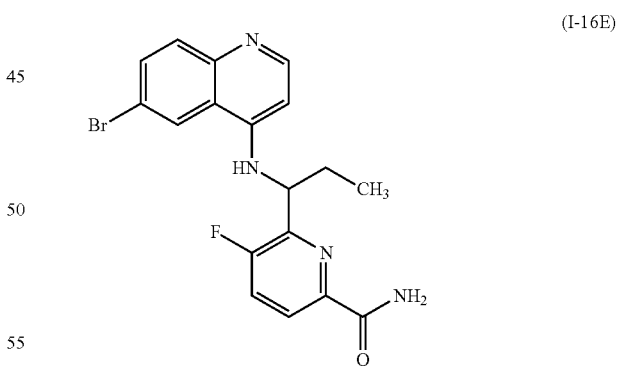

(I-16E)

A mixture of 6-bromo-4-chloroquinoline (133 mg, 0.548 mmol), 6-(1-aminopropyl)-5-fluoropicolinamide (54 mg, 0.274 mmol), (1R)-(−)-camphor-10-sulfonic acid (12.72 mg, 0.055 mmol), DIEA (0.019 mL, 0.110 mmol), and anhydrous NMP (0.1 mL) was stirred at 120° C. under a nitrogen atmosphere for 1 h. DCM, MeOH and DBU (0.050 mL, 0.329 mmol) were added. Flash chromatography purification (4 g silica gel column, gradient elution from 10 to 100% of ethyl acetate in hexanes) afforded 6-(1-((6-bromoquinolin-4-yl)amino)propyl)-5-fluoropicolinamide (50 mg).

LC/MS (M+H): 403, 405; $^1$H NMR (400 MHz, CHLOROFORM-d) δ 8.46 (d, J=5.4 Hz, 1H), 8.33 (d, J=2.1 Hz, 1H), 8.28 (d, J=2.2 Hz, 1H), 8.13 (dd, J=8.5, 4.0 Hz, 1H), 7.80 (d, J=8.9 Hz, 1H), 7.64 (dd, J=8.9, 2.1 Hz, 1H), 7.55 (t, J=8.9 Hz, 1H), 6.78 (d, J=8.7 Hz, 1H), 6.49 (d, J=5.4 Hz, 1H), 6.26 (d, J=2.3 Hz, 1H), 5.10-5.00 (m, 1H), 2.24-2.08 (m, 2H), 1.03 (t, J=7.5 Hz, 3H)

Intermediate I-16

To a solution of 6-(1-((6-bromoquinolin-4-yl)amino)propyl)-5-fluoropicolinamide (150 mg, 0.112 mmol) in CH$_2$Cl$_2$ (1 mL) was added N-chlorosuccinimide (14 mg, 0.105 mmol) at 0° C. The mixture was stirred at 0° C. for 30 min and at room temperature overnight. More N-chlorosuccinimide (14 mg, 0.105 mmol) was added at 0° C. The mixture was stirred at room temperature for 2 h. Additional N-chlorosuccinimide (7 mg, 0.05 mmol) was added at 0° C. The reaction mixture was stirred at room temperature for 90 min. Flash chromatography purification (4 g silica gel column, gradient elution from 10 to 100% of ethyl acetate in hexanes) afforded 6-(1-((6-bromo-3-chloroquinolin-4-yl)amino)propyl)-5-fluoropicolinamide (47 mg, 0.054 mmol, 48.1% yield). LC/MS (M+H): 437.0, 439.0; LC retention time: 0.850 min (analytical HPLC Method B), $^1$H NMR (400 MHz, METHANOL-d$_4$) δ 8.48 (d, J=1.2 Hz, 2H), 8.04 (dd, J=8.6, 3.9 Hz, 1H), 7.79-7.72 (m, 2H), 7.64 (t, J=8.9 Hz, 1H), 5.62 (t, J=7.0 Hz, 1H), 2.31-2.00 (m, 2H), 1.05 (t, J=7.4 Hz, 3H).

Intermediate I-17

(R)-tert-butyl (4-(5-(3-chloro-4-((1-(2-fluorophenyl)ethyl)amino)quinolin-6-yl)picolinamido)butyl)carbamate

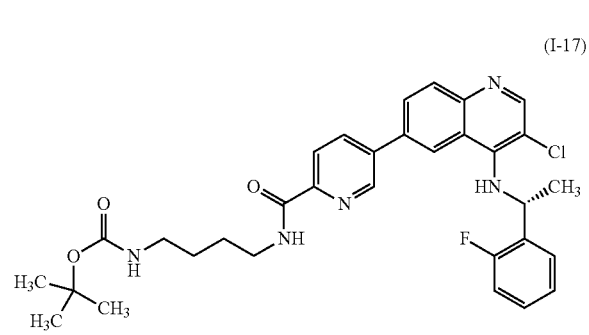 [SMILES: C[C@@H](Nc1c(Cl)cnc2ccc(-c3ccc(C(=O)NCCCCNC(=O)OC(C)(C)C)nc3)cc12)c1ccccc1F]

(I-17)

Intermediate I-17A: (R)-methyl 5-(3-chloro-4-((1-(2-fluorophenyl)ethyl)amino)quinolin-6-yl)picolinate

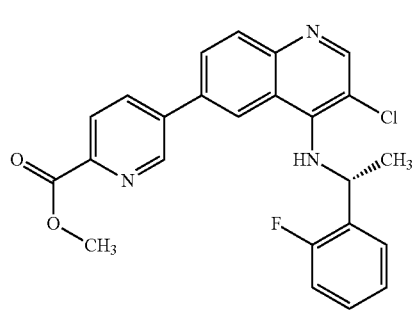

(I-17A)

Intermediate I-17A was prepared according to the general process disclosed in Intermediate I-1C using Intermediate I-58. LC/MS (M+H): 436.1; LC retention time: 0.885 min (analytical HPLC Method B).

Intermediate I-17

Intermediate I-17 was prepared according to the general process disclosed in Example 89 from the corresponding amine and ester. LC/MS (M+H): 592.3; LC retention time: 1.010 min (analytical HPLC Method B).

Intermediate I-18

1-(5-bromopyrimidin-2-yl)cyclopentanol

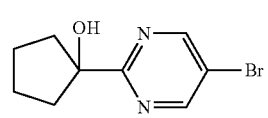

(I-18)

This compound was according to the general process disclosed in Intermediate I-14. LC/MS (M+H): 242.8; LC retention time: 0.902 min (analytical HPLC Method B).

Intermediate I-19

1-(5-bromopyrimidin-2-yl)cyclopentane-1,2-diol (single diastereomer

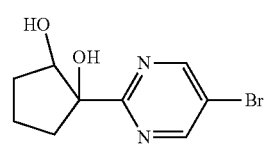

(I-19)

Intermediate I-19A:
5-bromo-2-(cyclopent-1-en-1-yl)pyrimidine

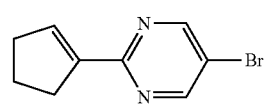

(I-19A)

To a stirred solution of 1-(5-bromopyrimidin-2-yl)cyclopentanol (Intermediate I-18, 280 mg, 1.152 mmol) in anhydrous pyridine (2000 μl, 24.73 mmol) was added phosphoryl chloride (161 μl, 1.728 mmol) at room temperature under nitrogen. The reaction mixture was stirred at room temperature for 3 h and 100° C. for 10 min. The reaction mixture was cooled to room temperature, water (3 mL) was added and the mixture extracted with diethyl ether (2×2 mL) and ethyl acetate (3×1 mL). The combined organic solutions were dried over sodium sulfate, filtered, and concentrated under reduced pressure. Flash chromatography purification (4 g silica gel column, gradient elution from 0 to 100% of ethyl acetate in hexanes) afforded 5-bromo-2-(cyclopent-1-en-1- yl)pyrimidine as a solid which was used for the subsequent step without further purification. LC/MS (M+H): 226.9; LC retention time: 1.160 min (analytical HPLC Method B).

Intermediate I-19

To a solution of 5-bromo-2-(cyclopent-1-en-1-yl)pyrimidine (160 mg, 0.711 mmol) and NMO in water (0.147 mL, 0.711 mmol) and tetrahydrofuran (5 mL) at room temperature was added osmium tetroxide in tert-butanol (0.357 mL, 0.028 mmol). The reaction mixture was stirred at room temperature for 3 h. The reaction mixture was concentrated. The residue was dissolved in DCM and chromatographed (4 g silica gel column, gradient elution from 0 to 20% of MeOH in DCM) to give the title compound which was used as such for the subsequent step without further purification. LC/MS (M+H): 259.0; LC retention time: 0.743 min (analytical HPLC Method B).

Intermediate I-20

± 6-(1-((6-bromo-3-chloroquinolin-4-yl)amino)ethyl)-5-fluoropicolinamide

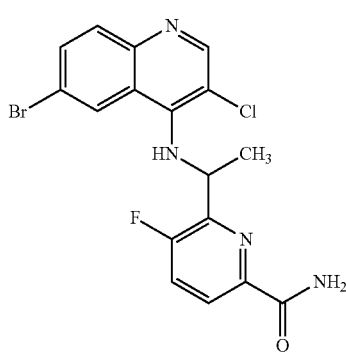

(I-20)

Intermediate I-20A: N-(1-(3-fluoro-6-vinylpyridin-2-yl)ethyl)-2-methylpropane-2-sulfinamide

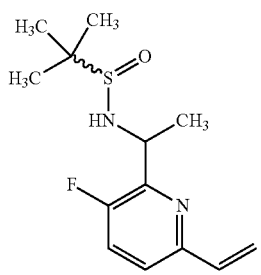

(I-20A)

N-(1-(3-fluoro-6-vinylpyridin-2-yl)ethyl)-2-methylpropane-2-sulfinamide was prepared according to the general process used in the synthesis of Intermediates I-65A and I-65B (with methyl Grignard) and B. LC/MS (M+H): 271.1; LC retention time: 0.985, 1.053 min (analytical HPLC Method B).

Intermediate I-20B: ± 6-bromo-N-(1-(3-fluoro-6-vinylpyridin-2-yl)ethyl)quinolin-4-amine

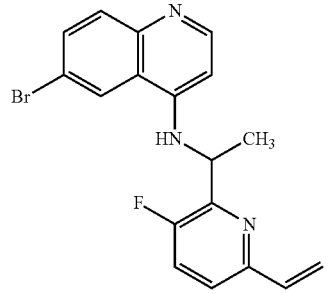

(I-20B)

To a solution of N-(1-(3-fluoro-6-vinylpyridin-2-yl)ethyl)-2-methylpropane-2-sulfinamide (500 mg, 1.849 mmol) in MeOH (10 mL) at 0° C. was added 4 M dioxane solution of HCl (1.387 mL, 5.55 mmol). The reaction mixture was stirred at room temperature for 45 min. DIEA (1.938 mL, 11.10 mmol) was added and the mixture was concentrated under reduced pressure. 6-bromo-4-chloroquinoline (1.35 g, 5.55 mmol) was added. The reaction mixture was heated at 120° C. for 2 h. The reaction mixture was cooled to room temperature and saturated aqueous sodium bicarbonate solution (15 mL), EtOAc (30 mL) and DCM (15 mL) were added and stirred at room temperature for 30 min. The solid was filtered and washed with EtOAc. The filtrate was separated. The aqueous layer was extracted with ethyl acetate (3×3 mL). The combined organic solutions were dried over sodium sulfate, filtered, and concentrated under reduced pressure. Flash chromatography purification (12 g silica gel column, gradient elution from 0 to 100% of ethyl acetate in hexanes) afforded 6-bromo-N-(1-(3-fluoro-6-vinylpyridin-2-yl)ethyl)quinolin-4-amine (210 mg, 0.564 mmol, 30.5% yield). LC/MS (M+H): 372.0; LC retention time: 0.918 min (analytical HPLC Method B), $^1$H NMR (400 MHz, CHLOROFORM-d) δ 8.54 (d, J=5.3 Hz, 1H), 8.07 (d, J=2.1 Hz, 1H), 7.83 (d, J=8.9 Hz, 1H), 7.67 (dd, J=8.9, 2.1 Hz, 1H), 7.41-7.33 (m, 1H), 7.30-7.23 (m, 1H), 6.92 (d, J=7.0 Hz, 1H), 6.82 (dd, J=17.4, 10.8 Hz, 1H), 6.52 (d, J=5.4 Hz, 1H), 6.25 (d, J=17.4 Hz, 1H), 5.55 (d, J=10.8 Hz, 1H), 5.12 (quin, J=6.5 Hz, 1H), 1.62 (d, J=6.5 Hz, 3H).

Intermediate I-20C: 1-(6-(1-((6-bromoquinolin-4-yl)amino)ethyl)-5-fluoropyridin-2-yl) ethane-1,2-diol

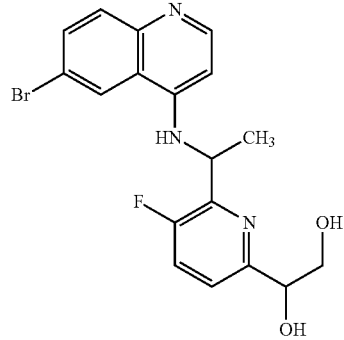

(I-20C)

To a solution of 6-bromo-N-(1-(3-fluoro-6-vinylpyridin-2-yl)ethyl)quinolin-4-amine (210 mg, 0.564 mmol) and 50% NMO in water (0.117 mL, 0.564 mmol) and tetrahydrofuran (5 mL) at room temperature was added 2.5% osmium tetroxide in tert-butanol (0.283 mL, 0.023 mmol). The reaction mixture was stirred at room temperature for 80 min. The reaction mixture was concentrated. The residue was dissolved in DCM and chromatographed (4 g silica gel column, gradient elution from 0 to 20% of MeOH in DCM) to afford 1-(6-(1-(((6-bromoquinolin-4-yl)amino)ethyl)-5-fluoropyridin-2-yl)ethane-1,2-diol (188 mg, 0.463 mmol, 82% yield). LC/MS (M+H): 406.0, 408.0; LC retention time: 0.758 min (analytical HPLC Method B).

Intermediate I-20D: 1-(6-(1-(((6-bromo-3-chloroquinolin-4-yl)amino)ethyl)-5-fluoropyridin-2-yl)ethane-1,2-diol

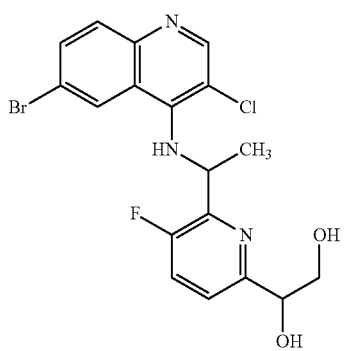

(I-20D)

To a solution of 1-(6-(1-(((6-bromoquinolin-4-yl)amino)ethyl)-5-fluoropyridin-2-yl)ethane-1,2-diol (188 mg, 0.463 mmol) in CH$_2$Cl$_2$ (5 mL) and MeOH (1 mL) was added N-chlorosuccinimide (68.0 mg, 0.509 mmol) at 0° C. The reaction mixture was stirred at 0° C. for 10 min and at room temperature for 2 h. The reaction mixture was concentrated to 0.5 mL volume and the resulting solid was filtered and washed with MeOH to give 1-(6-(1-(((6-bromo-3-chloroquinolin-4-yl)amino)ethyl)-5-fluoropyridin-2-yl)ethane-1,2-diol (132 mg, 0.294 mmol, 63.4% yield). LC/MS (M+H): 440.1, 442.0; LC retention time: 0.790 min (analytical HPLC Method B).

Intermediate I-20E: ± 6-(1-(((6-bromo-3-chloroquinolin-4-yl)amino)ethyl)-5-fluoropicolinaldehyde

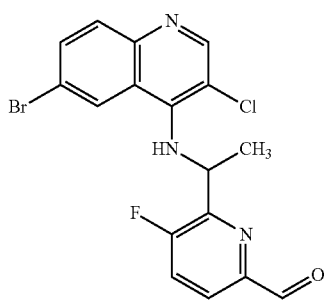

(I-20E)

To a solution of 1-(6-(1-(((6-bromo-3-chloroquinolin-4-yl)amino)ethyl)-5-fluoropyridin-2-yl)ethane-1,2-diol (74 mg, 0.168 mmol) in tetrahydrofuran (5 mL) at room temperature was added a solution of sodium periodate (71.8 mg, 0.336 mmol) in water (1 mL). The reaction mixture was stirred at room temperature under nitrogen for 3 h. The reaction mixture was extracted with extracted with ethyl acetate (4 mL, 3×1 mL). The combined organic solutions were dried over sodium sulfate, filtered, and concentrated under reduced pressure to give 6-(1-(((6-bromo-3-chloroquinolin-4-yl)amino)ethyl)-5-fluoropicolinaldehyde (70 mg, 0.171 mmol, 102% yield) that was used in the next step without further purification. LC/MS (M+H): 408.0, 410.0; LC retention time: 0.907 min (analytical HPLC Method B).

Intermediate I-20

A solution of potassium dihydrogen phosphate (117 mg, 0.856 mmol) in water (1 mL) was added to a stirred solution of 6-(1-(((6-bromo-3-chloroquinolin-4-yl)amino)ethyl)-5-fluoropicolinaldehyde (70 mg, 0.171 mmol) and 2M THF solution of 2-methyl-2-butene (0.856 mL, 1.713 mmol) in THF (2 mL) and tert-butanol (2.5 mL) at room temperature, followed by sodium chlorite (19.37 mg, 0.171 mmol). The mixture was stirred at room temperature for 1 hr. Additional sodium chlorite (10 mg) was added and the mixture was stirred at room temperature for 1 h. The mixture was extracted with EtOAc (5 mL) and then DCM (1 mL). The combined organic extracts were dried over anhydrous sodium sulphate. Removal of organic solvents under reduced pressure furnished the acid which was used for the next step without further purification.

The acid was mixed with ammonium chloride (73.3 mg, 1.370 mmol), anhydrous CH$_2$Cl$_2$ (5 mL), and DIEA (0.150 mL, 0.856 mmol). BOP (114 mg, 0.257 mmol) was added. The mixture was stirred at room temperature overnight. Saturated aqueous sodium bicarbonate solution (4 mL) was added to quench the reaction. The aqueous layer was separated and extracted with DCM (3×2 mL). The combined organic solutions were dried over sodium sulfate, filtered, and concentrated under reduced pressure. Flash chromatography purification (4 g silica gel column, gradient elution from 10 to 100% of EtOAc in hexanes) afforded 6-(1-((6-bromo-3-chloroquinolin-4-yl)amino)ethyl)-5-fluoropicolinamide (52 mg, 0.117 mmol, 68.1% yield) as a solid. LC/MS (M+H): 423, 425; LC retention time: 0.807 min (analytical HPLC Method B). $^1$H NMR (400 MHz, METHANOL-d$_4$) δ 8.47 (d, J=14.8 Hz, 2H), 8.04 (dd, J=8.5, 3.9 Hz, 1H), 7.73 (s, 2H), 7.63 (t, J=8.9 Hz, 1H), 5.78 (q, J=6.6 Hz, 1H), 1.72 (d, J=6.7 Hz, 3H).

Intermediate I-21

± 6-(1-(((6-bromo-3-chloroquinolin-4-yl)amino)ethyl)-5-fluoropicolinic acid

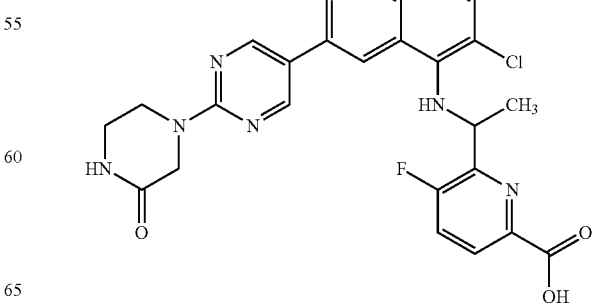

(I-21)

Intermediate I-21A: ±4-(5-(3-chloro-4-((1-(6-(1,2-dihydroxyethyl)-3-fluoropyridin-2-yl)ethyl)amino)quinolin-6-yl)pyrimidin-2-yl)piperazin-2-one

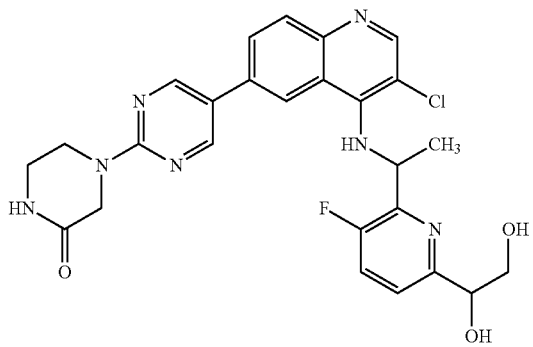

(I-21A)

1-(6-(1-((6-bromo-3-chloroquinolin-4-yl)amino)ethyl)-5-fluoropyridin-2-yl) ethane-1,2-diol (Intermediate I-20D) was converted to 4-(5-(3-chloro-4-((1-(6-(1,2-dihydroxyethyl)-3-fluoropyridin-2-yl)ethyl)amino)quinolin-6-yl)pyrimidin-2-yl)piperazin-2-one using the procedure outlined in Example 1C. LC/MS (M+H): 538.2; LC retention time: 0.752 min (analytical HPLC Method B).

Intermediate I-21B: 6-(1-((3-chloro-6-(2-(3-oxopiperazin-1-yl)pyrimidin-5-yl)quinolin-4-yl)amino)ethyl)-5-fluoropicolinaldehyde

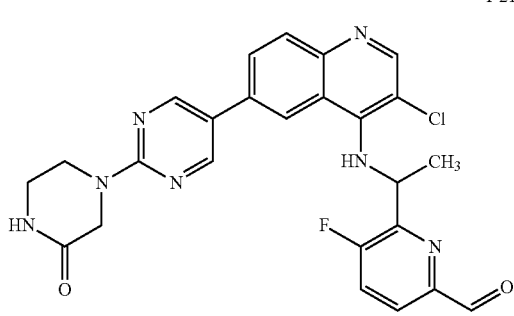

(I-21B)

4-(5-(3-chloro-4-((1-(6-(1,2-dihydroxyethyl)-3-fluoropyridin-2-yl)ethyl)amino) quinolin-6-yl)pyrimidin-2-yl)piperazin-2-one was converted to 6-(1-((3-chloro-6-(2-(3-oxopiperazin-1-yl)pyrimidin-5-yl)quinolin-4-yl)amino)ethyl)-5-fluoropicolinaldehyde using the general procedure of Intermediate I-20E. LC/MS (M+H): 506.1; LC retention time: 0.788 min (analytical HPLC Method B).

Intermediate I-21

To a solution of potassium dihydrogen phosphate (102 mg, 0.751 mmol) in water (1 mL) was added a stirred mixture of 6-(1-((3-chloro-6-(2-(3-oxopiperazin-1-yl)pyrimidin-5-yl)quinolin-4-yl)amino)ethyl)-5-fluoropicolinaldehyde (76 mg, 0.150 mmol), 2M THF solution of 2-methyl-2-butene (0.751 mL, 1.502 mmol), THF (10 mL), and tert-butanol (10 mL) at room temperature, followed by sodium chlorite (25.5 mg, 0.225 mmol). The mixture was stirred at room temperature for 2 hr. and concentrated under reduced pressure. The solid was filtered, washed with water, diethyl ether, and then methanol to afford 6-(1-((3-chloro-6-(2-(3-oxopiperazin-1-yl)pyrimidin-5-yl) quinolin-4-yl)amino)ethyl)-5-fluoropicolinic acid (70 mg, 0.127 mmol, 85% yield) which was directly used for the next step without further purification. LC/MS (M+H): 522.1; LC retention time: 0.765 min (analytical HPLC Method B).

The following intermediate was prepared according to the general procedure disclosed in the preparation of Intermediate I-1E from the corresponding quinoline and amine

| Int. No. | Structure | LCMS m/z observed | HPLC $t_R$ (min) | HPLC method |
|---|---|---|---|---|
| I-22 | 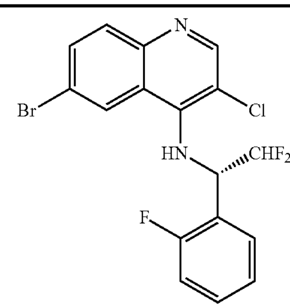 | 415.0, 417.0 | 1.113 | B |

The following intermediate was prepared from Intermediate I-22 according to the general procedure disclosed in the preparation of Intermediate I-8.

| Int. No. | Structure | LCMS m/z observed | HPLC $t_R$ (min) | HPLC method |
|---|---|---|---|---|
| I-23 | 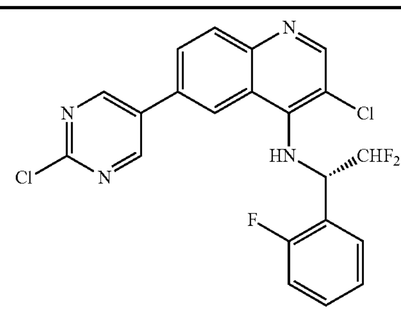 | 449.0 | 1.040 | B |

The following intermediates were prepared according to the general procedure used in the preparation of Intermediate I-1C from the corresponding Intermediate I-58.

| Int. No. | Structure | LCMS m/z observed | HPLC $t_R$ (min) | HPLC method |
|---|---|---|---|---|
| I-24 | 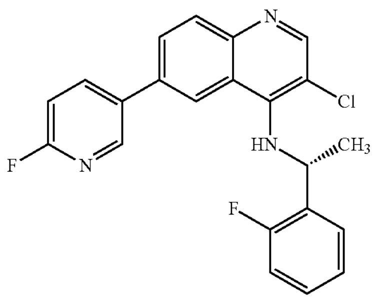 [SMILES: C[C@@H](Nc1c(Cl)cnc2ccc(-c3ccc(F)nc3)cc12)c1ccccc1F] | 396.1 | 0.940 | B |
| I-25 | 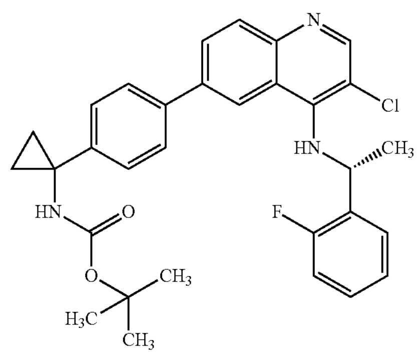 [SMILES: C[C@@H](Nc1c(Cl)cnc2ccc(-c3ccc(C4(NC(=O)OC(C)(C)C)CC4)cc3)cc12)c1ccccc1F] | 532.1 | 2.541 | A |
| I-26 | 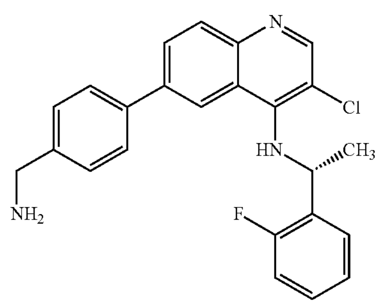 [SMILES: C[C@@H](Nc1c(Cl)cnc2ccc(-c3ccc(CN)cc3)cc12)c1ccccc1F] | 406.1 | 1.622 | A |

Intermediate I-27

(S)-6-bromo-3-chloro-N-(2,2-difluoro-1-(2-fluorophenyl)ethyl)-7-fluoroquinolin-4-amine

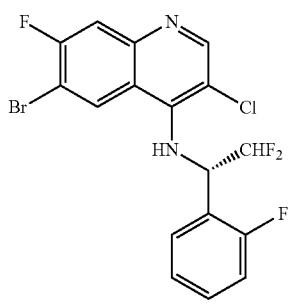

(I-27)

A mixture of ((1R,4S)-7,7-dimethyl-2-oxobicyclo[2.2.1]heptan-1-yl) methanesulfonic acid (19.69 mg, 0.085 mmol), (S)-2,2-difluoro-1-(2-fluorophenyl) ethanamine (Intermediate I-73, 44.5 mg, 0.254 mmol) and 6-bromo-3,4-dichloro-7-fluoroquinoline (Intermediate I-42C, 50 mg, 0.170 mmol) in DMA (0.200 mL) was stirred at 140° C. for 18 hours. The crude material was purified via preparative LC/MS using condition B to afford (S)-6-bromo-3-chloro-N-(2,2-difluoro-1-(2-fluorophenyl)ethyl)-7-fluoroquinolin-4-amine (35 mg, 0.077 mmol, 45.2% yield) as a brown gum. LC/MS (M+H): 433; LC retention time: 1.00 min (analytical HPLC Method C); $^1$H NMR (400 MHz, CHLOROFORM-d) δ 8.86 (s, 1H), 8.17 (d, J=6.6 Hz, 1H), 7.98 (d, J=8.6 Hz, 1H), 7.60-7.47 (m, 2H), 7.37-7.24 (m, 2H), 6.46-6.04 (m, 2H), 5.78-5.61 (m, 1H).

Intermediate I-28

6-bromo-3-chloro-7-fluoro-N-(1-(2-fluorophenyl)cyclopropyl)quinolin-4-amine

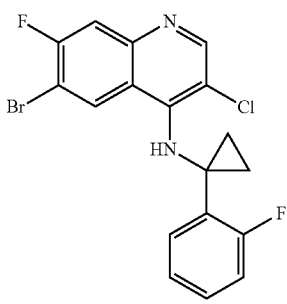

(I-28)

A mixture of 1-(2-fluorophenyl)cyclopropanamine (41.0 mg, 0.271 mmol), 6-bromo-3,4-dichloro-7-fluoroquinoline (Intermediate I-42C, 40 mg, 0.136 mmol) and (1R)-(−)-camphor-10-sulfonic acid (15.75 mg, 0.068 mmol) in NMP (0.10 mL) was stirred at 150° C. for 18 hours. The crude product was subjected to ISCO flash chromatography (silica gel/hexane-EtOAc 100:0 to 0:100 gradient) to afford 6-bromo-3-chloro-7-fluoro-N-(1-(2-fluorophenyl)cyclopropyl)quinolin-4-amine (17 mg, 0.039 mmol, 29.1% yield) as a brown gum. LC/MS (M+H): 109; LC retention time: 0.80 min (analytical HPLC Method C).

Intermediate I-29

± methyl 1-(5-(4,4,5,5-tetramethyl-1,3,2-dioxaborolan-2-yl)pyrimidin-2-yl)pyrrolidine-3-carboxylate

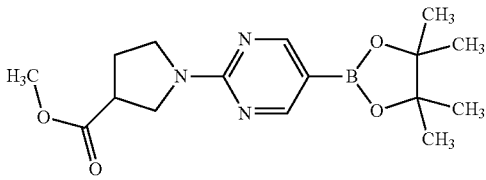

(I-29)

A mixture of 2-chloro-5-(4,4,5,5-tetramethyl-1,3,2-dioxaborolan-2-yl)pyrimidine (50 mg, 0.208 mmol), methyl 3-pyrrolidinecarboxylate HCl (34.4 mg, 0.208 mmol) and potassium carbonate (86 mg, 0.624 mmol) in DMF (1.0 mL) was stirred at 90° C. for 18 hours. The mixture was diluted with EtOAc (15 mL) and was washed with a solution of aqueous saturated sodium bicarbonate (2×15 mL). The ethyl acetate layer was dried over sodium sulfate and concentrated to afford methyl 1-(5-(4,4,5,5-tetramethyl-1,3,2-dioxaborolan-2-yl)pyrimidin-2-yl)pyrrolidine-3-carboxylate (19 mg, 0.051 mmol, 24.69% yield) as off-white solid. $^1$H NMR (400 MHz, CHLOROFORM-d) δ 8.63 (s, 2H), 4.00-3.78 (m, 3H), 3.75 (s, 3H), 3.71-3.61 (m, 1H), 3.24 (s, 1H), 2.31 (d, J=7.5 Hz, 2H), 1.34 (s, 12H).

Intermediate I-30

4-(5-bromopyrimidin-2-yl)tetrahydro-2H-pyran-4-ol

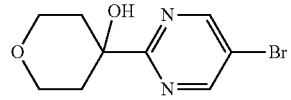

(I-30)

To a solution of 5-bromo-2-iodopyrimidine (500 mg, 1.755 mmol) in anhydrous ethyl ether (10 mL) at −78° C. under nitrogen atmosphere was added a solution of 2.5 M n-butyllithium in hexane (0.772 mL, 1.931 mmol). The mixture was stirred at −78° C. for 60 min. Dihydro-2H-pyran-4(3H)-one (176 mg, 1.755 mmol) was added to the mixture at −78° C. The reaction mixture was allowed to warm to room temperature and was stirred at room temperature for 3 hours. The reaction was quenched with a solution of 10% aqueous ammonium chloride (30 mL) and extracted with EtOAc (30 mL). The ethyl acetate layer was dried over sodium sulfate and concentrated. The crude product was subjected to ISCO flash chromatography (silica gel/hexane-EtOAc 100:0 to 0:100 gradient) to afford 4-(5-bromopyrimidin-2-yl)tetrahydro-2H-pyran-4-ol (129 mg, 0.473 mmol, 26.9% yield) white solid. LC/MS (M+H): 259; LC retention time: 0.61 min (analytical HPLC Method C); $^1$H NMR (400 MHz, CHLOROFORM-d) δ 8.81 (s, 2H), 4.26 (s, 1H), 4.06-3.87 (m, 4H), 2.52 (t, J=6.2 Hz, 2H), 2.38 (ddd, J=13.0, 11.2, 6.4 Hz, 2H).

Intermediate I-31

± 2-(5-bromopyrimidin-2-yl)-1-((tert-butyldimethylsilyl)oxy)propan-2-ol

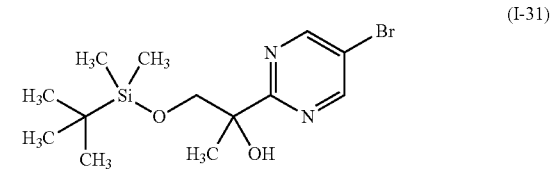 [SMILES: CC(O)(CO[Si](C)(C)C(C)(C)C)c1ncc(Br)cn1]

(I-31)

Intermediate I-31 was prepared according to the general procedure described in Intermediate I-30. LC/MS (M+H): 347; LC retention time: 1.12 min (analytical HPLC Method C); $^1$H NMR (400 MHz, CHLOROFORM-d) δ 8.79 (s, 2H), 4.27 (d, J=0.4 Hz, 1H), 4.00 (d, J=9.7 Hz, 1H), 3.76 (d, J=9.7 Hz, 1H), 1.55 (s, 3H), 0.81-0.73 (m, 9H), −0.02 (s, 3H), −0.11 (s, 3H).

Intermediate I-32

± 2-(5-bromopyrimidin-2-yl)-1-methoxypropan-2-ol

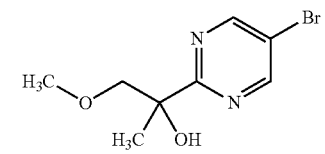

(I-32)

Intermediate I-32 was prepared according to the general procedure described in Example 30. LC/MS (M+H): 247;

LC retention time: 0.62 min (analytical HPLC Method C); $^1$H NMR (400 MHz, CHLOROFORM-d) δ 8.80 (s, 2H), 4.46 (s, 1H), 3.86 (d, J=9.5 Hz, 1H), 3.62 (d, J=9.2 Hz, 1H), 3.32 (s, 3H), 1.55 (s, 3H).

Intermediate I-33

4-(5-bromopyrimidin-2-yl)-4-hydroxytetrahydro-2H-thiopyran 1,1-dioxide

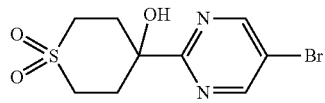

(I-33)

Intermediate I-33A: 4-(5-bromopyrimidin-2-yl)tetrahydro-2H-thiopyran-4-ol

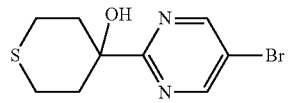

(I-33A)

To a solution of 5-bromo-2-iodopyrimidine (500 mg, 1.755 mmol) in anhydrous toluene (20 mL) at −78° C. under nitrogen was added a solution of 2.5 M n-butyllithium in hexane (0.772 mL, 1.931 mmol). The mixture was stirred at −78° C. for 60 min. Dihydro-2H-thiopyran-4(3H)-one (204 mg, 1.755 mmol) was added to the mixture at −78° C. The reaction mixture was allowed to warm to room temperature and was stirred at room temperature for 3 hours. The reaction was quenched with a solution of 10% aqueous ammonium chloride (30 mL). The reaction mixture was extracted with EtOAc (30 mL).

The ethyl acetate layer was dried over sodium sulfate and concentrated. The crude product was subjected to ISCO flash chromatography (silica gel/hexane-EtOAc 100:0 to 0:100 gradient) to afford 4-(5-bromopyrimidin-2-yl)tetrahydro-2H-thiopyran-4-ol (293 mg, 1.012 mmol, 57.6% yield) white solid. LC/MS (M+H): 245; LC retention time: 0.76 min (analytical HPLC Method C); $^1$H NMR (400 MHz, CHLOROFORM-d) δ 8.81 (s, 2H), 3.33-3.20 (m, 2H), 2.59-2.49 (m, 2H), 2.38 (td, J=13.1, 3.5 Hz, 2H), 1.97-1.87 (m, 2H).

Intermediate I-33

To a solution of 4-(5-bromopyrimidin-2-yl)tetrahydro-2H-thiopyran-4-ol (150 mg, 0.545 mmol) in acetone (2.0 mL) and water (0.200 mL) was added potassium peroxymonosulfate (1340 mg, 2.181 mmol). The reaction mixture was stirred at room temperature for 2 hours, diluted with EtOAc (25 mL) and washed with water (35 mL). The ethyl acetate layer was dried over sodium sulfate and concentrated. The crude product was subjected to ISCO flash chromatography (silica gel/hexane-EtOAc 100:0 to 0:100 gradient) to afford 4-(5-bromopyrimidin-2-yl)-4-hydroxytetrahydro-2H-thiopyran 1,1-dioxide (112 mg, 0.346 mmol, 63.5% yield) as white solid. LC/MS (M+H): 307; LC retention time: 0.57 min (analytical HPLC Method C); $^1$H NMR (400 MHz, CHLOROFORM-d) δ 8.84 (s, 2H), 4.49 (s, 1H), 3.62 (td, J=13.7, 3.6 Hz, 2H), 3.10-2.99 (m, 2H), 2.91 (td, J=13.9, 3.5 Hz, 2H), 2.11-2.01 (m, 2H).

Intermediate I-34 methyl 2-(4-(5-(4,4,5,5-tetramethyl-1,3,2-dioxaborolan-2-yl)pyrimidin-2-yl)piperazin-1-yl)acetate

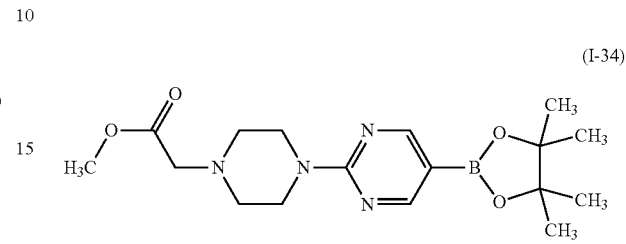

(I-34)

Intermediate I-34A; methyl 2-(4-(5-bromopyrimidin-2-yl)piperazin-1-yl)acetate

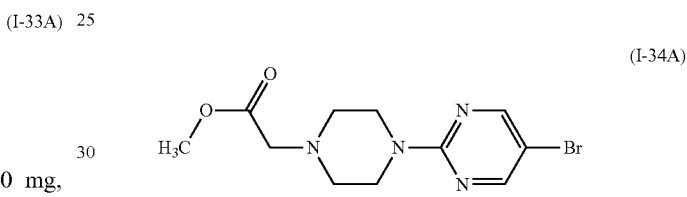

(I-34A)

To a solution of 5-bromo-2-(piperazin-1-yl)pyrimidine (1.0 g, 4.11 mmol) and potassium carbonate (1.137 g, 8.23 mmol) in DMF (10 mL) was added methyl 2-bromoacetate (0.629 g, 4.11 mmol). The mixture was stirred at 80° C. for 2 hours. The mixture was diluted with EtOAc (65 mL) and was washed with a solution of aqueous saturated sodium bicarbonate (2×65 mL). The ethyl acetate layer was dried over sodium sulfate and concentrated. The crude product was subjected to ISCO flash chromatography (silica gel/hexane-EtOAc 100:0 to 0:100 gradient) to afford methyl 2-(4-(5-bromopyrimidin-2-yl)piperazin-1-yl)acetate (1.15 g, 3.47 mmol, 84% yield) as white solid. LC/MS (M+H): 315; LC retention time: 0.55 min (analytical HPLC Method C).

Intermediate I-34

A mixture of methyl 2-(4-(5-bromopyrimidin-2-yl)piperazin-1-yl)acetate (600 mg, 1.904 mmol), 4,4,4',4',5,5,5',5'-octamethyl-2,2'-bi(1,3,2-dioxaborolane) (483 mg, 1.904 mmol), potassium acetate (374 mg, 3.81 mmol), and PdCl$_2$(dppf)-CH$_2$Cl$_2$ adduct (78 mg, 0.095 mmol) in dioxane (6.0 mL) was purged with nitrogen and stirred at 80° C. for 18 hours. The mixture was diluted with EtOAc (15 mL) and was washed with water (15 mL). The ethyl acetate layer was dried over sodium sulfate and concentrated. The crude product was subjected to ISCO flash chromatography (silica gel/hexane-EtOAc 100:0 to 0:100 gradient) to afford methyl 2-(4-(5-(4,4,5,5-tetramethyl-1,3,2-dioxaborolan-2-yl)pyrimidin-2-yl)piperazin-1-yl)acetate (267 mg, 0.700 mmol, 36.8% yield) as a white solid. LC/MS (M+H): 363; LC retention time: 0.66 min (analytical HPLC Method C). $^1$H NMR (400 MHz, CHLOROFORM-d) δ 8.60 (s, 2H), 4.03-3.90 (m, 4H), 3.76 (s, 3H), 3.29 (s, 2H), 2.70-2.57 (m, 4H), 1.34 (s, 12H).

Intermediate I-35 was prepared according to the general procedure used in the preparation of Intermediate I-34.

| Int. No. | Structure | LCMS m/z observed | HPLC $t_R$ (min) | HPLC method |
|---|---|---|---|---|
| I-35 | 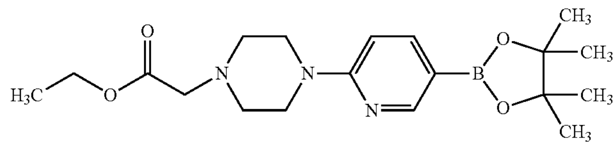 [SMILES: CCOC(=O)CN1CCN(c2ccc(B3OC(C)(C)C(C)(C)O3)cn2)CC1] | 294.1 (hydrolyzed product) | 0.422 | B |

Intermediate I-36 ethyl 1-(5-(4,4,5,5-tetramethyl-1,3,2-dioxaborolan-2-yl)pyrimidin-2-yl)piperidine-4-carboxylate

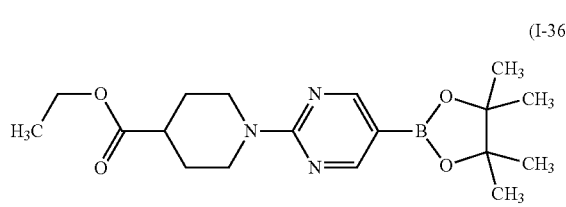

(I-36)

A mixture of ethyl piperidine-4-carboxylate (163 mg, 1.040 mmol), 2-chloro-5-(4,4,5,5-tetramethyl-1,3,2-dioxaborolan-2-yl)pyrimidine (250 mg, 1.040 mmol), and triethylamine (0.435 mL, 3.12 mmol) in EtOH (6.0 mL) was stirred at 80° C. for 18 hours. The reaction mixture was concentrated and the crude product was subjected to ISCO flash chromatography (silica gel/hexane-EtOAc 100:0 to 0:100 gradient) to yield ethyl 1-(5-(4,4,5,5-tetramethyl-1,3,2-dioxaborolan-2-yl)pyrimidin-2-yl)piperidine-4-carboxylate (169 mg, 0.444 mmol, 42.8% yield) as a white solid. $^1$H NMR (400 MHz, CHLOROFORM-d) δ 8.60 (s, 2H), 4.74 (d, J=13.6 Hz, 2H), 4.17 (q, J=7.0 Hz, 2H), 3.11 (d, J=2.6 Hz, 2H), 2.68-2.53 (m, 1H), 1.98 (d, J=3.3 Hz, 2H), 1.73 (br. s., 2H), 1.34 (s, 12H), 1.28 (t, J=7.2 Hz, 3H).

Intermediate I-37

6-bromo-3,4-dichloro-8-fluoro-2-methylquinoline

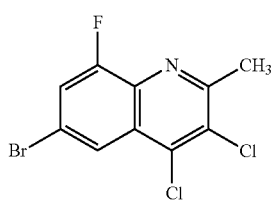

(I-37)

Intermediate I-37A: 5-(1-((4-bromo-2-fluorophenyl)amino)ethylidene)-2,2-dimethyl-1,3-dioxane-4,6-dione

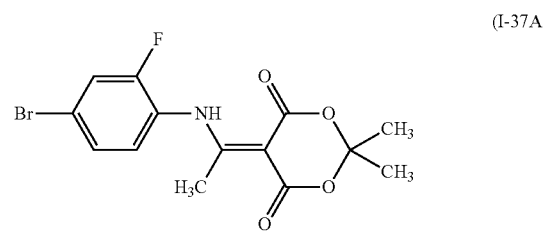 [SMILES: CC(Nc1ccc(Br)cc1F)=C1C(=O)OC(C)(C)OC1=O]

(I-37A)

A mixture of 2,2-dimethyl-1,3-dioxane-4,6-dione (8.19 g, 56.8 mmol) in 1,1,1-trimethoxyethane (17.07 g, 142 mmol) was stirred at 100° C. for 2 hours. The mixture was cooled to 80° C. 4-bromo-2-fluoroaniline (9.0 g, 47.4 mmol) in acetonitrile (25 mL) was added to the reaction mixture and the reaction mixture was heated at 100° C. for 18 hours, cooled to room temperature and ethyl ether (100 mL) was added. The solid was collected by filtration and dried under high vacuum to afford 5-(1-((4-bromo-2-fluorophenyl)amino)ethylidene)-2,2-dimethyl-1,3-dioxane-4,6-dione (4.30 g, 12.01 mmol, 25.3% yield) as yellow solid. $^1$H NMR (400 MHz, CHLOROFORM-d) δ 12.59 (br. s., 1H), 7.42 (t, J=9.9 Hz, 2H), 7.13 (t, J=8.0 Hz, 1H), 2.54 (s, 3H), 1.74 (s, 6H).

Intermediate I-37B:
6-bromo-8-fluoro-2-methylquinolin-4-ol (I-37B)

5-(((4-bromo-3-fluorophenyl)amino)methylene)-2,2-dimethyl-1,3-dioxane-4,6-dione was added portion-wise to Dowtherm A (30 mL) at 245° C. The mixture was stirred at 245° C. for 5 min. The mixture was cooled to room temperature, diluted with hexane (300 mL) and the precipitate was collected by filtration. The solid was dried under high vacuum to afford crude 6-bromo-8-fluoro-2-methylquinolin-4-ol (2.88 g, 10.68 mmol, 22.56% yield) as a brown solid. LC/MS (M+H): 256; LC retention time: 0.63 min (analytical HPLC Method C); $^1$H NMR (400 MHz, METHANOL-d$_4$) δ 8.15 (s, 1H), 7.72 (dd, J=10.3, 2.0 Hz, 1H), 6.25 (s, 1H), 2.50 (s, 3H).

Intermediate I-37C:
6-bromo-3-chloro-8-fluoro-2-methylquinolin-4-ol

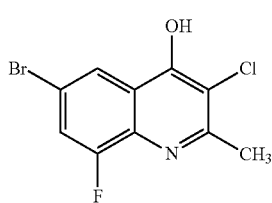

(I-37C)

A mixture of 6-bromo-8-fluoro-2-methylquinolin-4-ol (2.80 g, 10.93 mmol) and NCS (1.460 g, 10.93 mmol) in acetic acid (5.00 mL) and acetonitrile (35 mL) was stirred at 90° C. for 18 hours. The solid was collected by filtration, washed with acetonitrile and dried under high vacuum to afford crude 6-bromo-3-chloro-8-fluoro-2-methylquinolin-4-ol. LC/MS (M+H): 290; LC retention time: 0.75 min (analytical HPLC Method C).

Intermediate I-37

A mixture of 6-bromo-3-chloro-8-fluoro-2-methylquinolin-4-ol and phosphorous oxychloride (5.10 mL, 54.7 mmol) was stirred at 90° C. for 60 min. The mixture was cooled to room temperature and concentrated. The mixture was diluted with DCM (35 mL) and was washed with a solution of aqueous saturated sodium bicarbonate (35 mL). The DCM layer was dried over sodium sulfate and concentrated. The crude product was subjected to ISCO flash chromatography (silica gel/hexane-EtOAc 100:0 to 50:50 gradient) to afford 6-bromo-3,4-dichloro-8-fluoro-2-methylquinoline (2.54 g, 7.81 mmol, 71.4% yield). LC/MS (M+H): 309; LC retention time: 1.07 min (analytical HPLC Method C); $^1$H NMR (400 MHz, CHLOROFORM-d) δ 8.18-8.09 (m, 1H), 7.58 (dd, J=9.5, 2.0 Hz, 1H), 2.89 (s, 3H).

Intermediate I-38

(S)-6-bromo-3-chloro-N-(2,2-difluoro-1-(2-fluorophenyl)ethyl)-8-fluoroquinolin-4-amine

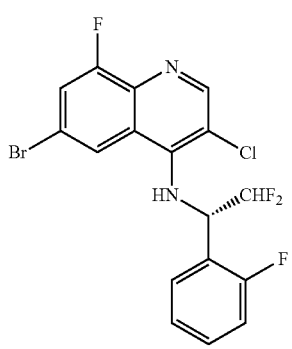

(I-38)

A mixture of (S)-2,2-difluoro-1-(2-fluorophenyl)ethanamine (Intermediate I-73, 44.50 mg, 0.254 mmol), ((1R,4S)-7,7-dimethyl-2-oxobicyclo[2.2.1]heptan-1-yl)methanesulfonic acid (19.69 mg, 0.085 mmol) and 6-bromo-3,4-dichloro-8-fluoroquinoline (Intermediate I-44, 50 mg, 0.170 mmol) in DMA (0.200 mL) was stirred at 140° C. for 18 hours. Another portion of (S)-2,2-difluoro-1-(2-fluorophenyl) ethanamine (44.5 mg, 0.254 mmol) was added and the mixture was stirred at 140° C. for 18 hours. The crude product was subjected to ISCO flash chromatography (silica gel/hexane-EtOAc 100:0 to 0:100 gradient) to afford (S)-6-bromo-3-chloro-N-(2,2-difluoro-1-(2-fluorophenyl)ethyl)-8-fluoroquinolin-4-amine as a clear gum. LC/MS (M+H): 433; LC retention time: 1.03 min (analytical HPLC Method C).

Intermediate I-39

± 6-bromo-3-chloro-8-fluoro-N-(1-(2-fluorophenyl)ethyl)-2-methylquinolin-4-amine

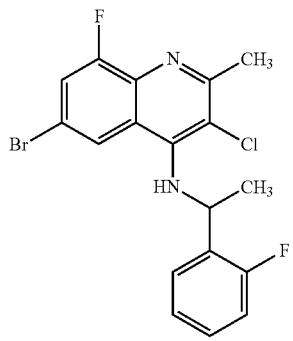

(I-39)

Intermediate I-39 was prepared according to the general procedure disclosed for the preparation of Intermediate I-38 using Intermediate I-37 as the starting material. LC/MS (M+H): 411; LC retention time: 0.85 min (analytical HPLC Method C); $^1$H NMR (400 MHz, CHLOROFORM-d) δ 7.87 (t, J=1.8 Hz, 1H), 7.46-7.33 (m, 2H), 7.20-7.05 (m, 2H), 5.30-5.12 (m, 2H), 2.77 (s, 3H), 1.70 (d, J=6.2 Hz, 3H).

Intermediate I-40

(S)-6-bromo-3-chloro-N-(2,2-difluoro-1-(2-fluorophenyl)ethyl)-8-fluoro-2-methylquinolin-4-amine

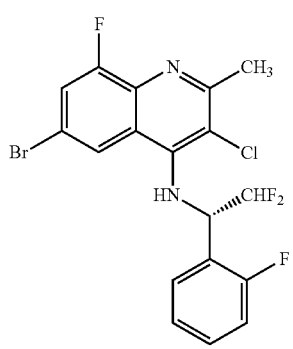

(I-40)

Intermediate I-40 was prepared according to the general procedure disclosed for the preparation of Intermediate I-38 using Intermediate I-37 as the starting material. LC/MS (M+H): 447; LC retention time: 1.01 min (analytical HPLC Method C); $^1$H NMR (400 MHz, CHLOROFORM-d) δ 7.71 (t, J=1.7 Hz, 1H), 7.57 (td, J=7.5, 1.3 Hz, 1H), 7.51-7.41 (m, 2H), 7.35-7.16 (m, 2H), 6.33-5.97 (m, 1H), 5.52 (d, J=10.1 Hz, 1H), 5.40-5.24 (m, 1H), 2.81 (s, 3H).

Intermediate I-41

2-(5-(3,4-dichloro-8-fluoro-2-methylquinolin-6-yl)pyrimidin-2-yl)propan-2-ol

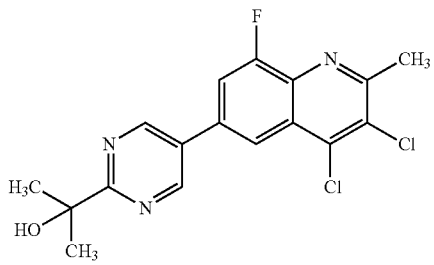
(I-38)

A mixture of 2-(5-bromopyrimidin-2-yl)propan-2-ol (309 mg, 1.424 mmol), 4,4,4',4',5,5,5',5'-octamethyl-2,2'-bi(1,3,2-dioxaborolane) (345 mg, 1.359 mmol), potassium acetate (254 mg, 2.59 mmol) and PdCl$_2$(dppf)-CH$_2$Cl$_2$ adduct (52.9 mg, 0.065 mmol) in dioxane (3.0 mL) under nitrogen in a seal vial was stirred at 80° C. for 3 hours. The mixture was cooled to room temperature. Next, 6-bromo-3,4-dichloro-8-fluoro-2-methylquinoline (Intermediate I-37, 400 mg, 1.295 mmol), 2.0 M aqueous potassium phosphate (1.295 mL, 2.59 mmol), and 1,1'-bis(di-tert-butylphosphino)ferrocene palladium dichloride (42.2 mg, 0.065 mmol) were added to the mixture. The reaction mixture was stirred at room temperature for 18 hours. The reaction mixture was diluted with EtOAc (15 mL) and was washed with a solution of aqueous saturated sodium bicarbonate (2×15 mL). The ethyl acetate layer was dried over sodium sulfate and concentrated. The crude product was subjected to ISCO flash chromatography (silica gel/hexane-EtOAc 100:0 to 0:100 gradient) to afford 2-(5-(3,4-dichloro-8-fluoro-2-methylquinolin-6-yl)pyrimidin-2-yl)propan-2-ol (252 mg, 0.654 mmol, 50.5% yield) as white solid. LC/MS (M+H): 366; LC retention time: 0.95 min (analytical HPLC Method C).

Intermediate I-42

Mixture of 6-bromo-3,4-dichloro-7-fluoroquinoline and 6-bromo-3,4-dichloro-5-fluoroquinoline

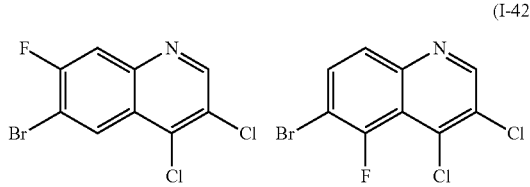
(I-42)

Intermediate I-42A: 5-(((4-bromo-3-fluorophenyl)amino)methylene)-2,2-dimethyl-1,3-dioxane-4,6-dione

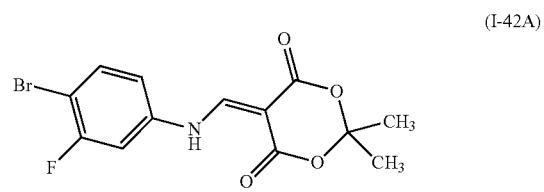 [SMILES: CC1(C)OC(=O)C(=CNc2ccc(Br)c(F)c2)C(=O)O1]
(I-42A)

A mixture of 2,2-dimethyl-1,3-dioxane-4,6-dione (0.910 g, 6.32 mmol) in trimethyl orthoformate (1.745 mL, 15.79 mmol) was stirred at 100° C. for 90 min. The mixture was cooled to 80° C. and 4-bromo-3-fluoroaniline (1.0 g, 5.26 mmol) was added to the mixture. The reaction mixture was stirred at 100° C. for 3.5 hours, cooled to room temperature and ethyl ether (100 mL) was added. The solid was collected by filtration and dried under high vacuum to afford 5-(((4-bromo-3-fluorophenyl)amino)methylene)-2,2-dimethyl-1,3-dioxane-4,6-dione (1.36 g, 3.75 mmol, 71.3% yield) as light yellow solid. LC/MS (M+H): 344; LC retention time: 0.96 min (analytical HPLC Method C). $^1$H NMR (400 MHz, DMSO-d$_6$) δ 11.31-11.18 (m, 1H), 8.59 (s, 1H), 7.85-7.70 (m, 2H), 7.43 (dt, J=8.7, 1.4 Hz, 1H), 1.69 (s, 6H).

Intermediate I-42B: Mixture of 6-bromo-7-fluoroquinolin-4-ol and 6-bromo-5-fluoroquinolin-4-ol

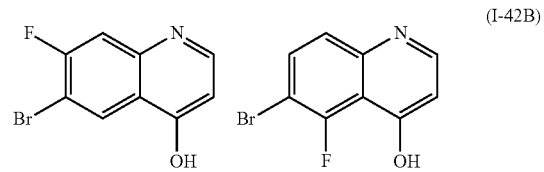
(I-42B)

To Dowtherm A (7.0 mL) at 245° C. was added 5-(((4-bromo-3-fluorophenyl)amino)methylene)-2,2-dimethyl-1,3-dioxane-4,6-dione (1.36 g, 3.95 mmol) and the mixture was stirred at 245° C. for 10 min. The mixture was cooled to room temperature. Hexanes (35 mL) was added and the solid was collected by filtration to yield a mixture of 6-bromo-5-fluoroquinolin-4-ol and 6-bromo-7-fluoroquinolin-4-ol (1:1) (850 mg, 1.492 mmol, 37.8% yield) (45:55, by LCMS) as a brown solid. LC/MS (M+H): 242; LC retention time: 0.60 min and 0.62 min (analytical HPLC Method C).

Intermediate I-42C: Mixture of 6-bromo-3,4-dichloro-7-fluoroquinoline and 6-bromo-3,4-dichloro-5-fluoroquinoline

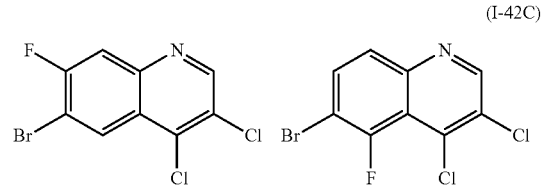
(I-42C)

A mixture of 6-bromo-5-fluoroquinolin-4-ol, 6-bromo-7-fluoroquinolin-4-ol (796 mg, 1.644 mmol) and NCS (220 mg, 1.644 mmol) in acetonitrile (20 mL) and acetic acid (2 mL) was stirred at 90° C. for 18 hours. The mixture was cooled to room temperature. The solid separated from solution and was collected by filtration, washed with acetonitrile, and dried under high vacuum to yield a mixture of 6-bromo-3-chloro-5-fluoroquinolin-4-ol and 6-bromo-3-chloro-7-fluoroquinolin-4-ol (1:1) (942 mg, 1.363 mmol, 83% yield) as a white solid. LC/MS (M+H): 277; LC retention time: 0.69 min and 0.74 min (analytical HPLC Method C).

Intermediate I-42

A mixture of 6-bromo-3-chloro-5-fluoroquinolin-4-ol and 6-bromo-3-chloro-7-fluoroquinolin-4-ol (942 mg, 1.363 mmol) and POCl$_3$ (3.07 mL, 32.9 mmol) was stirred at 90° C. for 60 min. The mixture was cooled to room temperature and concentrated. The crude product was dissolved in DCM (25 mL) and was slowly added to a solution of saturated sodium bicarbonate (30 mL). The DCM layer was dried over sodium sulfate and concentrated. The crude product was subjected to ISCO flash chromatography (silica gel/hexane-EtOAc 100:0 to 0:100 gradient) to yield a mixture of 6-bromo-3,4-dichloro-5-fluoroquinoline compound and 6-bromo-3,4-dichloro-7-fluoroquinoline (45:55, by LCMS) (642 mg, 1.034 mmol, 62.9% yield) as a white solid. LC/MS (M+H): 296; LC retention time: 1.18 min and 1.20 min (analytical HPLC Method C).

Intermediate I-43

Mixture of 6-bromo-3-chloro-5-fluoro-N-(1-(2-fluorophenyl)ethyl)quinolin-4-amine Isomers and 6-bromo-3-chloro-7-fluoro-N-(1-(2-fluorophenyl)ethyl)quinolin-4-amine Isomers

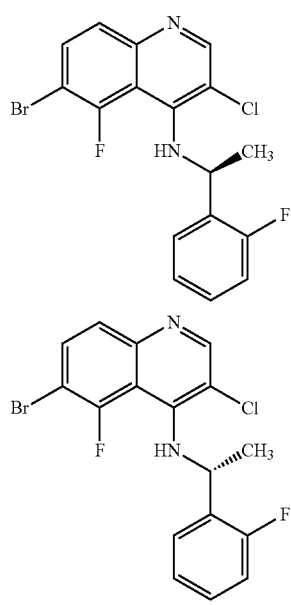

(I-43)

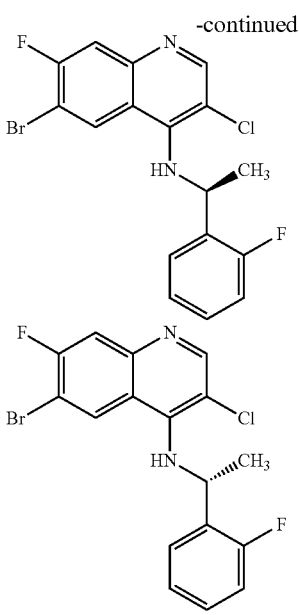

A mixture of 6-bromo-3,4-dichloro-5-fluoroquinoline, 6-bromo-3,4-dichloro-7-fluoroquinoline (640 mg, 1.085 mmol), 1-(2-fluorophenyl)ethanamine (906 mg, 6.51 mmol) and ((1R,4S)-7,7-dimethyl-2-oxobicyclo[2.2.1]heptan-1-yl)methanesulfonic acid (126 mg, 0.542 mmol) in DMA (700 µL) was stirred at 140° C. for 6 hour. The mixture was cooled to room temperature. The mixture was diluted with DCM (25 mL) and was washed with a solution of aqueous saturated sodium bicarbonate (25 mL). The DCM layer was dried over sodium sulfate and concentrated. The crude product was subjected to ISCO flash chromatography (silica gel/hexane-EtOAc 100:0 to 50:50 gradient) followed by chiral separation (ASH column, 5% MEOH in CO$_2$, 3 mL/min, 40 C, 140 bars, 220 nm).

Four peaks were isolated. The absolute stereochemistry of the peaks were not assigned.

Peak 1 (retention time 3.04 min), yielded 6-bromo-3-chloro-5-fluoro-N-(1-(2-fluorophenyl)ethyl)quinolin-4-amine (115 mg, 0.275 mmol, 25.3% yield);

Peak 2 (retention time 3.38 min), yielded 6-bromo-3-chloro-5-fluoro-N-(1-(2-fluorophenyl)ethyl)quinolin-4-amine (116 mg, 0.277 mmol, 25.5% yield);

Peak 3 (retention time 3.74 min), yielded 6-bromo-3-chloro-7-fluoro-N-(1-(2-fluorophenyl)ethyl)quinolin-4-amine (167 mg, 0.399 mmol, 36.8% yield);

Peak 4 (retention time 4.70 min), yielded 6-bromo-3-chloro-7-fluoro-N-(1-(2-fluorophenyl)ethyl)quinolin-4-amine (168 mg, 0.401 mmol, 37.0% yield).

LC/MS (M+H): 398; LC retention time: 0.90 min (analytical HPLC Method B), $^1$H NMR (400 MHz, CHLOROFORM-d) δ 8.44 (s, 1H), 7.78-7.58 (m, 2H), 7.36-7.17 (m, 2H), 7.14-6.96 (m, 2H), 6.38-6.16 (m, 1H), 5.84-5.67 (m, 1H), 1.75-1.59 (m, 3H) for (R)-6-bromo-3-chloro-5-fluoro-N-(1-(2-fluorophenyl)ethyl)quinolin-4-amine and (S)-6-bromo-3-chloro-5-fluoro-N-(1-(2-fluorophenyl)ethyl)quinolin-4-amine.

LC/MS (M+H): 398; LC retention time: 0.98 min (analytical HPLC Method C), $^1$H NMR (400 MHz, CHLOROFORM-d) δ 8.58 (s, 1H), 8.17 (d, J=7.3 Hz, 1H), 7.63 (d, J=9.5 Hz, 1H), 7.36 (td, J=7.6, 1.8 Hz, 1H), 7.32-7.24 (m, 1H), 7.18-7.03 (m, 2H), 5.36-5.23 (m, 1H), 5.14 (d, J=8.8 Hz, 1H), 1.71 (d, J=6.6 Hz, 3H) for (S)-6-bromo-3-chloro-7-fluoro-N-(1-(2-fluorophenyl)ethyl)quinolin-4-amine and (R)-6-bromo-3-chloro-7-fluoro-N-(1-(2-fluorophenyl)ethyl)quinolin-4-amine.

Intermediate I-44

6-bromo-3,4-dichloro-8-fluoroquinoline

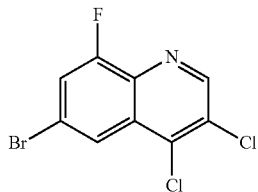
(I-44)

Intermediate I-44 was prepared according to the general procedure described in Intermediate I-42 by using 4-bromo-2-fluoroaniline. LC/MS (M+H): 294; LC retention time: 1.03 min (analytical HPLC Method C); $^1$H NMR (400 MHz, CHLOROFORM-d) δ 8.91 (s, 1H), 8.25-8.18 (m, 1H), 7.63 (dd, J=9.2, 2.0 Hz, 1H).

Intermediate I-45

2-(5-(3,4-dichloroquinolin-6-yl)pyrimidin-2-yl)propan-2-ol

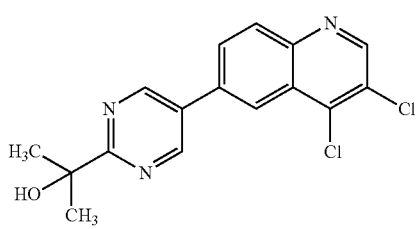
(I-45)

To 2-(5-bromopyrimidin-2-yl)propan-2-ol (1.60 g, 7.37 mmol, 1.0 eq.) in a sealed tube was added bis(pinacolato)diboron (2.25 g, 8.85 mmol, 1.2 eq.), potassium acetate (1.09 g, 11.1 mmol, 1.5 eq.), PdCl$_2$(dppf)-CH$_2$Cl$_2$ adduct (0.377 g, 0.737 mmol, 0.10 eq.), and 1,4-dioxane (32 mL). N$_2$ gas was bubbled through the reaction mixture for 5 min. The reaction mixture was at 80° C. for 2 hours in a sealed tube. After cooling to room temperature, 6-bromo-3,4-dichloroquinoline (2.04 g, 7.37 mmol) and 2M potassium carbonate solution (9.21 mL, 18.4 mmol, 2.5 eq.) were added to the reaction. N$_2$ gas was bubbled for 5 min and the reaction mixture was heated at 100° C. for 3 hours. After cooling to room temperature, the reaction mixture was diluted with EtOAc (20 mL) and water (20 mL). The organic layer was dried over sodium sulfate, filtered, and concentrated under reduced pressure. The residue was purified by column chromatography on silica gel (40 g), eluting with EtOAc-hexanes (gradient from 0-50%) to afford 2-(5-(3,4-dichloroquinolin-6-yl)pyrimidin-2-yl)propan-2-ol (1.50 g, 4.49 mmol, 60.9% yield) as a tan solid. LCMS m/z 334.0 (M+H)$^+$, HPLC t$_R$ 0.94 min (method C). $^1$H NMR (400 MHz, CDCl$_3$) δ 9.10 (s, 1H), 8.93 (s, 1H), 8.43 (d, J=1.7 Hz, 1H), 8.30 (d, J=8.7 Hz, 1H), 8.00 (dd, J=8.7, 2.0 Hz, 1H), 4.66 (s, 1H), 1.70 (s, 6H).

The Intermediates in Table 1 were prepared according to the general method used to prepare Intermediate I-45.

TABLE 1

| Int. No. | Structure | LCMS m/z observed | HPLC t$_R$ (min) | HPLC method |
|---|---|---|---|---|
| I-46 | 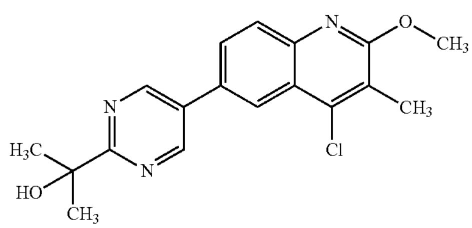 [SMILES: COc1nc2ccc(-c3cnc(C(C)(C)O)nc3)cc2c(Cl)c1C] | 344.1 (M + H)$^+$ | 1.11 | C |
| I-47 | 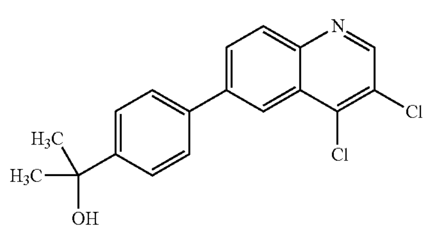 [SMILES: CC(C)(O)c1ccc(-c2ccc3ncc(Cl)c(Cl)c3c2)cc1] | 332.1 (M + H)$^+$ | 1.08 | C |

TABLE 1-continued

| Int. No. | Structure | LCMS m/z observed | HPLC $t_R$ (min) | HPLC method |
|---|---|---|---|---|
| I-48 | 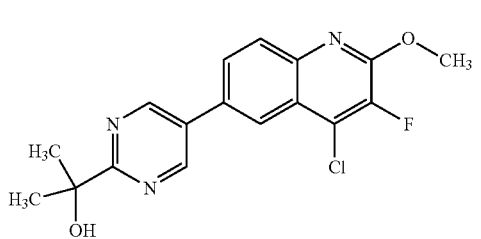 | 328.1 (M + H)⁺ | 0.67 | C |
| I-49 | 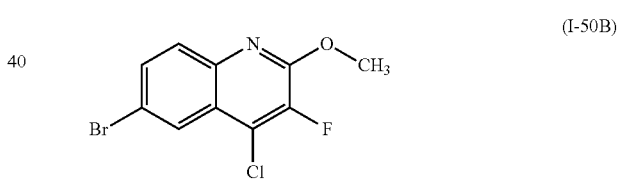 | 335.1 (M + H)⁺ | 0.93 | C |

Intermediate I-50

2-(5-(4-chloro-3-fluoro-2-methoxyquinolin-6-yl)pyrimidin-2-yl)propan-2-ol (I-50)

Intermediate I-50A:
6-bromo-2,4-dichloro-3-fluoroquinoline

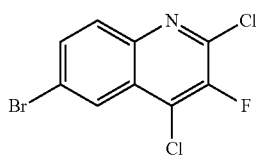

(I-50A)

A suspension of 2-fluoromalonic acid (1.20 g, 9.83 mmol) in POCl₃ (10 mL, 107 mmol, 10.9 eq.) was heated to 100° C. for 1 hour. The mixture was then cooled to room temperature. 4-bromoaniline (1.69 g, 9.83 mmol, 1.0 eq.) was added portion wise. After completion of addition, the reaction mixture was warmed to 110° C. and stirred at that temperature for 4 hours. The reaction mixture was cooled to room temperature and concentrated under reduced pressure. The resulting residue was carefully poured onto crushed ice and extracted with dichloromethane (30 mL×2). The combined extracts were washed with 10% sodium hydroxide solution (20 mL), water (30 mL), brine solution (30 mL), dried over sodium sulfate, filtered and concentrated to afford a yellow solid. The crude product was purified by column chromatography on silica gel (40 g), eluting with EtOAc-hexanes (gradient from 0~5%) to yield 6-bromo-2,4-dichloro-3-fluoroquinoline (0.70 g, 2.37 mmol, 24.1% yield) as an off-white solid. LCMS m/z 293.9 (M+H)⁺, HPLC $t_R$ 1.18 min (method C). ¹H NMR (400 MHz, CDCl₃) δ 8.33 (d, J=2.1 Hz, 1H), 7.97-7.90 (m, 1H), 7.89-7.83 (m, 1H).

Intermediate I-50B:
6-bromo-4-chloro-3-fluoro-2-methoxyquinoline (I-50B)

To a suspension of 6-bromo-2,4-dichloro-3-fluoroquinoline (200 mg, 0.68 mmol) in methanol (2 mL) was added 0.5M sodium methoxide solution in methanol (1.68 mL, 0.81 mmol, 1.2 eq.). The reaction mixture was heated to 85° C. for 2 hours and cooled to room temperature. The solvent was removed under reduced pressure. The resulting residue was added to ice water (10 mL) and extracted with DCM (20 mL×2). The combined organic layers were washed with brine solution (10 mL), dried over sodium sulfate, filtered and concentrated to afford a yellow solid. The crude product was purified by column chromatography on silica gel (24 g), eluting with EtOAc-hexanes (gradient from 0~10%) to give a 6-bromo-4-chloro-3-fluoro-2-methoxyquinoline (120 mg, 0.413 mmol, 60.9% yield) as a white solid. LCMS m/z 289.9 (M+H)⁺, HPLC $t_R$ 1.20 min (method C).

Intermediate I-50

2-(5-(4-chloro-3-fluoro-2-methoxyquinolin-6-yl)pyrimidin-2-yl)propan-2-ol was prepared using the same method used to prepare Intermediate I-45, by employing 6-bromo- 4-chloro-3-fluoro-2-methoxyquinoline. LCMS m/z 348.1 (M+H)+, HPLC t_R 1.01 min (method C).

Intermediate I-51

2-(5-(4-chloro-3-fluoro-2-methylquinolin-6-yl)pyrimidin-2-yl)propan-2-ol (I-51)

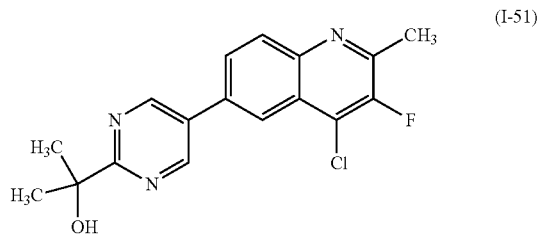 [SMILES: Cc1nc2ccc(-c3cnc(C(C)(C)O)nc3)cc2c(Cl)c1F]

Intermediate I-51A: 2-(5-(2,4-dichloro-3-fluoroquinolin-6-yl)pyrimidin-2-yl)propan-2-ol (I-51A)

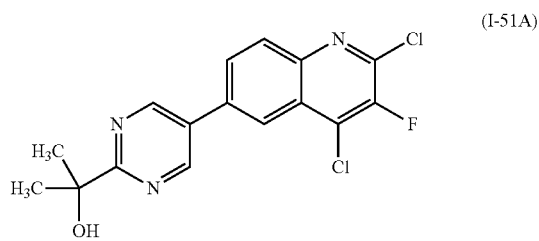 [SMILES: CC(C)(O)c1ncc(-c2ccc3nc(Cl)c(F)c(Cl)c3c2)cn1]

2-(5-(2,4-dichloro-3-fluoroquinolin-6-yl)pyrimidin-2-yl)propan-2-ol was prepared according to the general process described in Intermediate I-45, by using Intermediate I-50A. LCMS m/z 352.0 (M+H)+, HPLC t_R 1.00 min (method C).

Intermediate I-51

Methylboronic acid (7.5 mg, 0.13 mmol, 1.1 eq.), 2-(5-(2,4-dichloro-3-fluoroquinolin-6-yl)pyrimidin-2-yl)propan-2-ol (40 mg, 0.11 mmol) and 2 M potassium carbonate solution (0.14 mL, 0.28 mmol, 0.25 eq.) were mixed with 1,4-dioxane (0.4 mL). $N_2$ gas was bubbled through the reaction mixture for 2 min. $PdCl_2$(dppf)-$CH_2Cl_2$ adduct (13.9 mg, 0.017 mmol, 0.15 eq.) was then added. $N_2$ gas was bubbled for an additional 2 min. The vessel was sealed. The mixture was vigorously stirred at 100° C. for 1 hour. After cooling to room temperature, the reaction mixture was diluted with EtOAc (10 mL) and water (10 mL). Organic layer was washed with brine solution (5 mL), dried over sodium sulfate, filtered and concentrated. The residue was purified by column chromatography on silica gel (12 g), eluting with EtOAc-hexanes (gradient from 0~20%) to give a 2-(5-(4-chloro-3-fluoro-2-methylquinolin-6-yl)pyrimidin-2-yl)propan-2-ol (11 mg, 0.033 mmol, 29% yield). LCMS m/z 332.1 (M+H)+, HPLC t_R 0.92 min (method C).

The Intermediates in Table 2 were prepared according to the general method used to prepare Intermediate I-51.

TABLE 2

| Int. No. | Structure | LCMS m/z observed | HPLC t_R (min) | HPLC method |
|---|---|---|---|---|
| I-52 | ![structure] | 330.2 (M + H)+ | 0.91 | C |
| I-53 | ![structure] | 444.1 (M + H)+ | 0.79 | C |

Intermediate I-54

2-(5-(4-chloro-3-fluoroquinolin-6-yl)pyrimidin-2-yl)propan-2-ol

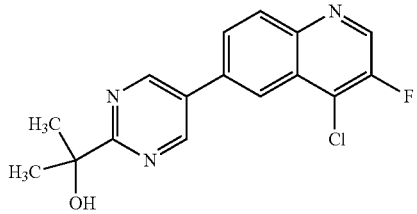
(I-54)

2-(5-(2,4-dichloro-3-fluoroquinolin-6-yl)pyrimidin-2-yl)propan-2-ol (Intermediate I-51A, 50 mg, 0.14 mmol) was mixed with triethylamine (260 mg, 2.6 mmol, 18 eq.) and solvent mixture of 1,4-dioxane/water (2:1, 0.5 mL). Nitrogen gas was bubbled through the solution for 5 min and then 10% Pd/C (5.0 mg, 10 wt %) was added. After bubbling $N_2$ for 2 min, formic acid (26 mg, 0.57 mmol, 4.0 eq.) was added. The reaction mixture was heated at 80° C. for 1 hour. After cooling to room temperature, the reaction mixture was diluted with EtOAc (10 mL) and water (10 mL). The organic layer was collected, dried over sodium sulfate, filtered, and concentrated under reduced pressure. The residue was purified by column chromatography on silica gel (12 g), eluting with EtOAc-hexanes (gradient from 0~50%) to give a 2-(5-(4-chloro-3-fluoro-2-methylquinolin-6-yl)pyrimidin-2-yl)propan-2-ol (14 mg, 0.044 mmol, 31% yield). LCMS m/z 318.1 (M+H)$^+$, HPLC $t_R$ 0.87 min (method C). $^1$H NMR (400 MHz, CDCl$_3$) δ 9.11 (s, 2H), 8.91 (d, J=0.6 Hz, 1H), 8.40 (d, J=1.7 Hz, 1H), 8.32 (d, J=8.7 Hz, 1H), 7.98 (dd, J=8.7, 2.0 Hz, 1H), 4.67 (s, 1H), 1.41-1.13 (m, 6H).

Intermediate I-55

2-(5-(7,8-dichloro-3-fluoro-1,5-naphthyridin-2-yl)pyrimidin-2-yl)propan-2-ol

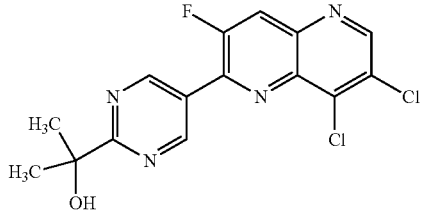
(I-55)

Intermediate I-55A: 5-(((6-bromo-5-fluoropyridin-3-ylamino)methylene)-2,2-dimethyl-1,3-dioxane-4,6-dione

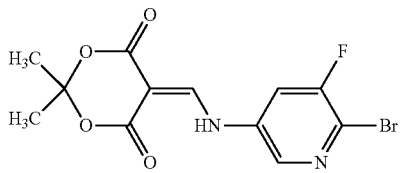
(I-55A)

To a solution of 6-bromo-5-fluoropyridin-3-amine (12.0 g, 62.8 mmol) in ethanol (120 mL) was added 2,2-dimethyl-1,3-dioxane-4,6-dione (11.3 g, 79.0 mmol, 1.25 eq.) and triethoxymethane (10.6 mL, 63.5 mmol, 1.01 eq.). The reaction mixture was heated at reflux for 2 hours. Upon cooling to room temperature, a precipitate was formed. After filtration, 5-(((6-bromo-5-fluoropyridin-3-yl)amino)methylene)-2,2-dimethyl-1,3-dioxane-4,6-dione (18.5 g, 53.6 mmol, 85.0% yield) was obtained as a yellow solid. LCMS m/z 346.9 (M+H)$^+$, HPLC $t_R$ 0.82 min (method C). $^1$H NMR (400 MHz, DMSO-d$_6$) δ 11.31 (br. s., 1H), 8.64 (s, 1H), 8.59 (d, J=2.2 Hz, 1H), 8.31 (dd, J=9.7, 2.4 Hz, 1H), 1.69 (s, 6H).

Intermediate I-55B:
6-bromo-7-fluoro-1,5-naphthyridin-4-ol

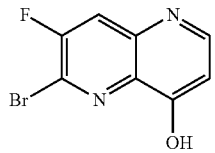
(I-55B)

5-(((6-bromo-5-fluoropyridin-3-yl)amino)methylene)-2,2-dimethyl-1,3-dioxane-4,6-dione (18.0 g, 52.2 mmol) was added portion-wise to refluxing diphenyl ether (180 mL) in 1 hour. The reaction mixture was then stirred for 30 min and cooled to room temperature in 2 hours. After filtration, 6-bromo-7-fluoro-1,5-naphthyridin-4-ol (10.5 g, 43.2 mmol, 83.0% yield) was obtained as a brown solid. LCMS m/z 242.8 (M+H)$^+$, HPLC $t_R$ 0.50 min (method C). $^1$H NMR (400 MHz, DMSO-d$_6$) δ 12.01 (br. s., 1H), 8.16-7.85 (m, 2H), 6.27 (br. s., 1H).

Intermediate I-55C:
6-bromo-3-chloro-7-fluoro-1,5-naphthyridin-4-ol

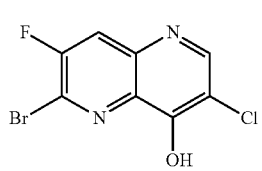
(I-55C)

To a mixture of 6-bromo-7-fluoro-1,5-naphthyridin-4-ol (5.0 g, 20.6 mmol) and NCS (3.02 g, 22.6 mmol, 1.10 eq.) was added acetic acid (60 mL). The reaction mixture was stirred at 65° C. for 2 hours and cooled to room temperature. After filtration, 6-bromo-3-chloro-7-fluoro-1,5-naphthyridin-4-ol (5.0 g, 18.0 mmol, 88.0% yield) was obtained as a grey solid. LCMS m/z 278.6 (M+H)$^+$, HPLC $t_R$ 0.56 min (method C). $^1$H NMR (400 MHz, DMSO-d$_6$) δ 12.59 (br. s., 1H), 8.54 (s, 1H), 7.98 (d, J=8.2 Hz, 1H)

Intermediate I-55D: 2-bromo-7,8-dichloro-3-fluoro-1,5-naphthyridine

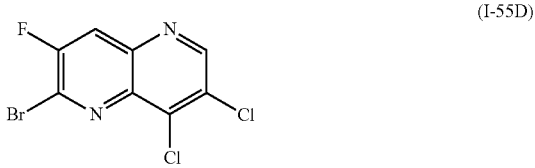 [SMILES: Fc1cc2ncc(Cl)c(Cl)c2nc1Br]

(I-55D)

6-bromo-3-chloro-7-fluoro-1,5-naphthyridin-4-ol (5.0 g, 18.0 mmol) was added to a 250 mL flask followed by POCl$_3$ (30 mL). The reaction mixture was stirred at 105° C. for 2 hours and then cooled to room temperature. POCl$_3$ was removed under vacuo. The residue was diluted with water (20 mL) at 0° C. 1N sodium hydroxide solution was added to adjust the pH to ~6. The slurry was stirred for 1 hour at room temperature and was then filtered to give 2-bromo-7,8-dichloro-3-fluoro-1,5-naphthyridine (4.6 g, 14.0 mmol, 78.0% yield) as a grey solid. LCMS m/z 293.9 (M+H)$^+$, HPLC t$_R$ 1.01 min (method C). $^1$H NMR (400 MHz, DMSO-d$_6$) δ 9.20-9.18 (m, 1H), 8.72 (d, J=8.7 Hz, 1H).

Intermediate I-55

2-(5-(7,8-dichloro-3-fluoro-1,5-naphthyridin-2-yl)pyrimidin-2-yl)propan-2-ol was prepared using the same method used to prepare Intermediate I-45, by employing 2-bromo-7,8-dichloro-3-fluoro-1,5-naphthyridine. LCMS m/z 352.9 (M+H)$^+$, HPLC t$_R$ 0.97 min (method C). $^1$H NMR (400 MHz, CDCl$_3$) δ 9.59 (d, J=1.3 Hz, 2H), 8.99 (s, 1H), 8.27 (d, J=10.9 Hz, 1H), 4.68 (s, 1H), 1.71 (s, 6H).

Intermediate I-56

2-(5-(7,8-dichloro-3-fluoro-6-methyl-1,5-naphthyridin-2-yl)pyrimidin-2-yl)propan-2-ol

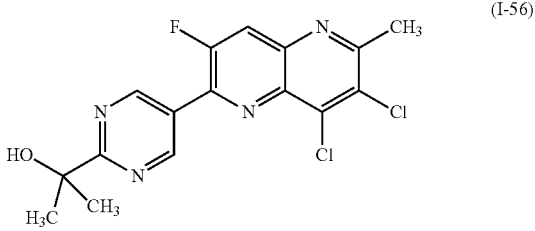 [SMILES: Cc1nc2cc(F)c(-c3cnc(C(C)(C)O)nc3)nc2c(Cl)c1Cl]

(I-56)

Intermediate I-56A: 3-(6-bromo-5-fluoropyridin-3-ylimino)-1-ethoxybut-1-en-1-ol

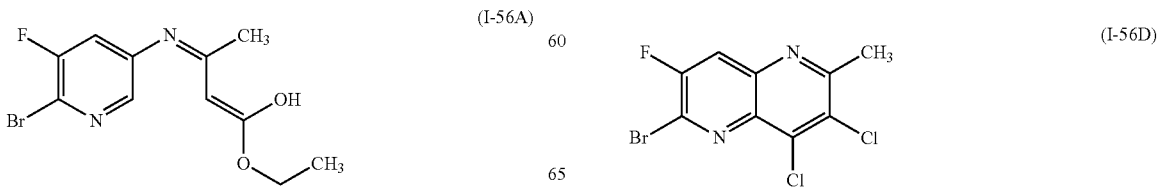

(I-56A)

A mixture of 6-bromo-5-fluoropyridin-3-amine (3.30 g, 17.3 mmol), ethyl 3-oxobutanoate (2.47 g, 19.0 mmol, 1.10 eq.), magnesium sulfate (4.16 g, 34.6 mmol, 2.0 eq.), and acetic acid (0.073 mL, 1.28 mmol, 0.074 eq.) in ethanol (30 mL) was heated to reflux for 3 days. After cooling to room temperature, the crude reaction mixture was filtered through a pad of celite. The celite pad was washed with EtOAc (50 mL). The filtrate was dried under vacuo and the residue was purified by column chromatography on silica gel (40 g), eluting with EtOAc-hexanes (gradient from 0~20%) to give 3-((6-bromo-5-fluoropyridin-3-yl)imino)-1-ethoxybut-1-en-1-ol (1.80 g, 5.94 mmol, 34.4% yield) as a white solid. LCMS m/z 303.0 (M+H)$^+$, HPLC t$_R$ 1.03 min (method G)

Intermediate I-56B: 6-bromo-7-fluoro-2-methyl-1,5-naphthyridin-4-ol

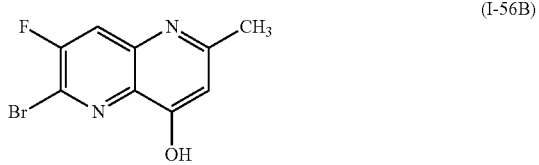

(I-56B)

6-bromo-7-fluoro-2-methyl-1,5-naphthyridin-4-ol (1.0 g, 3.30 mmol) was dissolved in diphenyl ether (10 mL) at room temperature and was heated to 250° C. for 0.5 h until a thick suspension formed. After cooling to room temperature, the suspension was filtered. The solid was washed with ether (2×10 mL) then dried under vacuo to obtain 6-bromo-7-fluoro-2-methyl-1,5-naphthyridin-4-ol (0.50 g, 1.94 mmol, 59.0% yield). LCMS m/z 257.0 (M+H)$^+$, HPLC t$_R$ 0.45 min (method C). $^1$H NMR (400 MHz, DMSO-d$_6$) δ 11.91 (br. s., 1H), 7.82 (d, J=8.3 Hz, 1H), 6.14 (s, 1H), 2.36 (s, 3H).

Intermediate I-56C: 6-bromo-3-chloro-7-fluoro-2-methyl-1,5-naphthyridin-4-ol

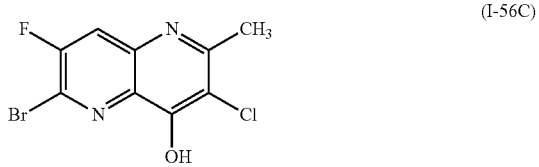

(I-56C)

Intermediate I-56C was prepared according to the process described in Intermediate I-55C. LCMS m/z 292.9 (M+H)$^+$, HPLC t$_R$ 0.56 min (method C). $^1$H NMR (400 MHz, DMSO-d$_6$) δ 12.49 (br. s., 1H), 7.89 (d, J=8.2 Hz, 1H), 2.54 (s, 3H).

Intermediate I-56D: 6-bromo-3,4-dichloro-7-fluoro-2-methyl-1,5-naphthyridine

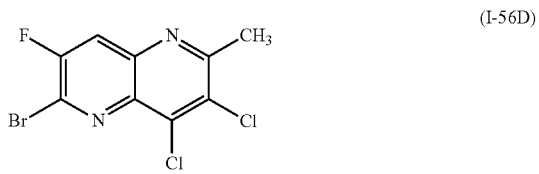

(I-56D)

Intermediate I-56D was prepared according to the general method described in Intermediate I-55D. LCMS m/z 307.9 (M+H)+, HPLC $t_R$ 1.05 min (method C). $^1$H NMR (400 MHz, CDCl$_3$) δ 8.04 (d, J=7.8 Hz, 1H), 2.89 (s, 3H).

Intermediate I-56

2-(5-(7,8-dichloro-3-fluoro-6-methyl-1,5-naphthyridin-2-yl)pyrimidin-2-yl) propan-2-ol was prepared according to the general method used to prepare Intermediate I-45, by employing 6-bromo-3,4-dichloro-7-fluoro-2-methyl-1,5-naphthyridine. LCMS m/z 352.9 (M+H)+, HPLC $t_R$ 0.97 min (method C). $^1$H NMR (400 MHz, CDCl$_3$) δ 9.59 (d, J=1.3 Hz, 2H), 8.99 (s, 1H), 8.27 (d, J=10.9 Hz, 1H), 4.68 (s, 1H), 1.71 (s, 6H).

Intermediate I-57

± 6-bromo-3-chloro-N-(1-(2-fluorophenyl)ethyl) quinolin-4-amine

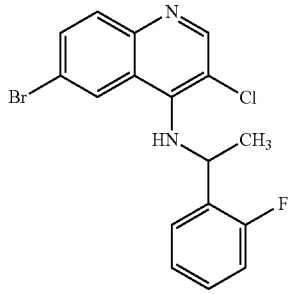

(I-57)

6-bromo-3-chloro-N-(1-(2-fluorophenyl)ethyl)quinolin-4-amine was synthesized from 6-bromo-3,4-dichloroquinoline and 1-(2-fluorophenyl)ethanamine, using the general process described in the last synthesis step of Intermediate I-1. LCMS m/z 380.9 (M+H)+, HPLC $t_R$ 0.80 min (method C). $^1$H NMR (400 MHz, CDCl$_3$) δ 8.61 (s, 1H), 8.12 (d, J=2.1 Hz, 1H), 7.85 (d, J=8.9 Hz, 1H), 7.69 (dd, J=9.0, 2.1 Hz, 1H), 7.38 (td, J=7.6, 1.7 Hz, 1H), 7.32-7.23 (m, 1H), 7.19-7.04 (m, 2H), 5.42-5.26 (m, 1H), 5.10 (d, J=8.9 Hz, 1H), 1.71 (d, J=6.7 Hz, 3H).

Intermediate I-58

(R)-6-bromo-3-chloro-N-(1-(2-fluorophenyl)ethyl) quinolin-4-amine

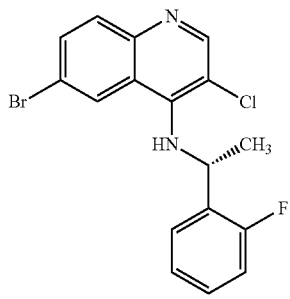

(I-58)

Racemic 6-bromo-3-chloro-N-(1-(2-fluorophenyl)ethyl) quinolin-4-amine (1.80 g, 4.74 mmol) was separated by preparative chiral SFC (50×250 mm 10 m AD column, 10/90 MeOH/CO$_2$ with 0.1% NH$_4$OH mobile phase, 250 mL/min flow rate, 35° C., 100 bars, UV 220 nm). (R)-6-bromo-3-chloro-N-(1-(2-fluorophenyl)ethyl)quinolin-4-amine was the first eluding enantiomer (0.60 g, 1.58 mmol, 33% yield). Chiral analytical SFC (4.6×250 mm, 5 m AD-H column, 20/80 MeOH/CO$_2$ with 0.1% NH$_4$OH mobile phase, 3 mL/min flow rate, 40° C., 140 bars, UV 200-400 nm) retention time: 3.25 min (>99% ee). The absolute configuration of Intermediate I-58 was established from the single crystal X-ray of Example 217.

Intermediate I-59

± 6-bromo-3-chloro-N-(1-(2-fluorophenyl)ethyl)-2-methylquinolin-4-amine

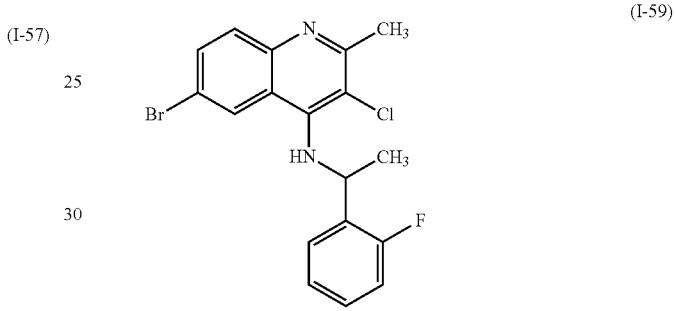

(I-59)

6-bromo-3-chloro-N-(1-(2-fluorophenyl)ethyl)-2-methylquinolin-4-amine was synthesized from 6-bromo-3,4-dichloro-2-methylquinoline and 1-(2-fluorophenyl)ethanamine (Intermediate I-68), using the general process described in the last synthesis step of Intermediate I-1. LCMS m/z 394.8 (M+H)+, HPLC $t_R$ 0.81 min (method C). $^1$H NMR (400 MHz, CDCl$_3$) δ 8.07 (d, J=2.1 Hz, 1H), 7.78 (d, J=9.0 Hz, 1H), 7.65 (dd, J=9.0, 2.1 Hz, 1H), 7.39 (td, J=7.6, 1.6 Hz, 1H), 7.32-7.24 (m, 1H), 7.18-7.03 (m, 2H), 5.29-5.19 (m, 1H), 5.15 (br. s., 1H), 2.73 (s, 3H), 1.69 (d, J=6.6 Hz, 3H).

Intermediate I-60

± 3-chloro-4-(1-(2-fluorophenyl)ethylamino)-1,7-naphthyridin-6-yl trifluoromethanesulfonate

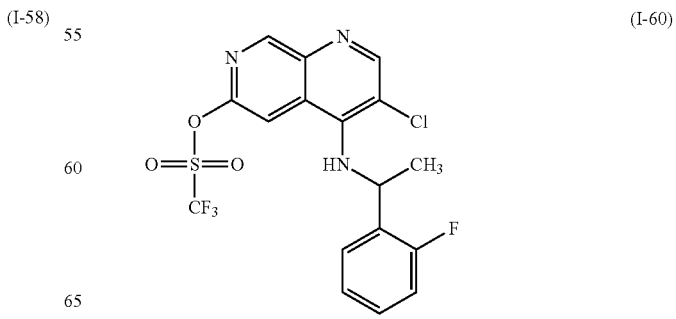

(I-60)

Intermediate I-60A:
3-chloro-6-methoxy-1,7-naphthyridin-4-ol

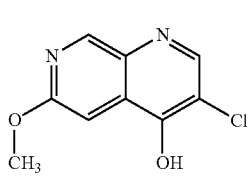

(I-60A)

3-chloro-6-methoxy-1,7-naphthyridin-4-ol was prepared from 6-methoxy-1,7-naphthyridin-4(1H)-one (*Tetrahedron* 2008, 64, 2772), as in Intermediate I-55C. LCMS m/z 211.0 (M+H)$^+$, HPLC $t_R$ 0.52 min (method C). $^1$H NMR (400 MHz, DMSO-d$_6$) δ 12.61 (br. s., 1H), 8.78 (s, 1H), 8.48 (s, 1H), 7.29 (d, J=0.4 Hz, 1H), 3.93 (s, 3H).

Intermediate I-60B:
3,4-dichloro-6-methoxy-1,7-naphthyridine

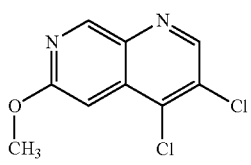

(I-60B)

3,4-dichloro-6-methoxy-1,7-naphthyridine was prepared from 3-chloro-6-methoxy-1,7-naphthyridin-4-ol, using the same method as in Intermediate I-55D. LCMS m/z 230.9 (M+H)$^+$, HPLC $t_R$ 0.97 min (method C). $^1$H NMR (400 MHz, CDCl$_3$) δ 9.22 (d, J=0.6 Hz, 1H), 8.73 (s, 1H), 7.31 (d, J=0.6 Hz, 1H), 4.12 (s, 3H)

Intermediate I-60C: ± 3-chloro-N-(1-(2-fluorophenyl)ethyl)-6-methoxy-1,7-naphthyridin-4-amine

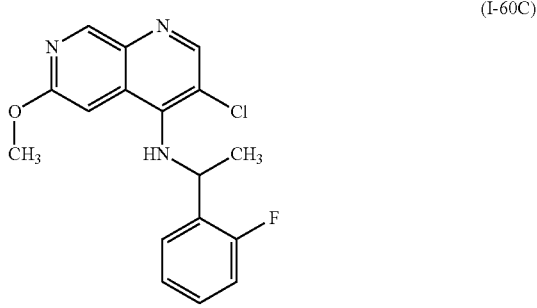 [SMILES: COc1cc2c(NC(C)c3ccccc3F)c(Cl)cnc2cn1]

(I-60C)

3-chloro-N-(1-(2-fluorophenyl)ethyl)-6-methoxy-1,7-naphthyridin-4-amine was synthesized from 3,4-dichloro-6-methoxy-1,7-naphthyridine and 1-(2-fluorophenyl)ethanamine, using the general process described in the last synthesis step of Intermediate I-1. LCMS m/z 332.1 (M+H)$^+$, HPLC $t_R$ 0.83 min (method C).

Intermediate I-60D: ± 3-chloro-4-(1-(2-fluorophenyl)ethylamino)-1,7-naphthyridin-6-ol

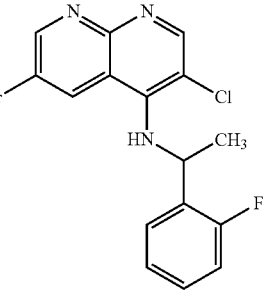

(I-60D)

3-chloro-N-(1-(2-fluorophenyl)ethyl)-6-methoxy-1,7-naphthyridin-4-amine (200 mg, 0.603 mmol) was dissolved in DMF (2 mL). PBr$_3$ (0.10 mL) was added at room temperature. The mixture was stirred at 80° C. for 2 hours. After cooling to 0° C., water (5 mL) was added to quench the reaction. DCM (5 mL×3) was used to extract the product. The combined organic layer was dried over sodium sulfate, filtered, and evaporated. The residue was purified by column chromatography on silica gel (12 g), eluting with EtOAc-hexanes (gradient from 0~50%) to give 3-chloro-4-(1-(2-fluorophenyl)ethylamino)-1,7-naphthyridin-6-ol (100 mg, 0.315 mmol, 52.2% yield) as a yellow solid. LCMS m/z 318.1 (M+H)$^+$, HPLC $t_R$ 0.73 min (method C). $^1$H NMR (400 MHz, CDCl$_3$) δ 8.86 (s, 1H), 8.43 (s, 1H), 7.40-7.22 (m, 2H), 7.16-7.02 (m, 4H), 5.57-5.41 (m, 1H), 5.06 (d, J=9.5 Hz, 1H), 1.73 (d, J=6.7 Hz, 3H).

Intermediate I-60

To a solution of 3-chloro-4-((1-(2-fluorophenyl)ethyl)amino)-1,7-naphthyridin-6-ol (90 mg, 0.283 mmol) in CH$_2$Cl$_2$ (5 mL) at 0° C. were added triethylamine (0.20 mL, 1.42 mmol, 5.0 eq.) and trifluoromethanesulfonic anhydride (0.048 mL, 0.283 mmol, 1.0 eq.). The reaction mixture was stirred for 30 min. The reaction was quenched with saturated NH$_4$Cl solution (2 mL). The organic layer was collected, dried over sodium sulfate, and evaporated. The residue was purified by column chromatography on silica gel (24 g), eluting with EtOAc-hexanes (gradient from 0~20%) to give 3-chloro-4-((1-(2-fluorophenyl)ethyl)amino)-1,7-naphthyridin-6-yl trifluoromethanesulfonate (110 mg, 0.245 mmol, 86.0% yield) as colorless oil. LCMS m/z 450.1 (M+H)$^+$, HPLC $t_R$ 1.11 min (method C). $^1$H NMR (400 MHz, CDCl$_3$) δ 9.16 (s, 1H), 8.75 (s, 1H), 7.63 (s, 1H), 7.44-7.30 (m, 2H), 7.22-7.05 (m, 2H), 5.46-5.33 (m, 2H), 1.77 (d, J=6.1 Hz, 3H).

Intermediate I-61

± 6-bromo-3-chloro-N-(1-(2-fluorophenyl)ethyl)-1,8-naphthyridin-4-amine

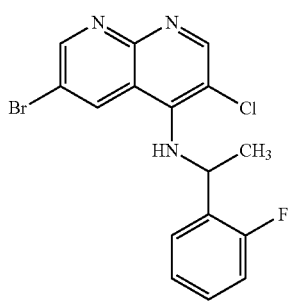

(I-61)

Intermediate I-61A:
6-bromo-3-chloro-1,8-naphthyridin-4-ol

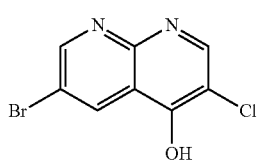

(I-61A)

3-chloro-6-bromo-1,7-naphthyridin-4-ol was prepared from 6-bromo-1,7-naphthyridin-4(1H)-one (*ACS Medicinal Chemistry Letters*, 2015, 434), using the general process described in the synthesis of Intermediate I-55C. LCMS m/z 260.9 (M+H)$^+$, HPLC $t_R$ 0.61 min (method C). $^1$H NMR (400 MHz, DMSO-d$_6$) δ 12.95 (br. s., 1H), 8.92 (d, J=2.6 Hz, 1H), 8.63 (d, J=2.4 Hz, 1H), 8.48 (s, 1H).

Intermediate I-61B:
6-bromo-3,4-dichloro-1,8-naphthyridine

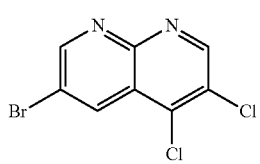

(I-61B)

6-bromo-3,4-dichloro-1,8-naphthyridine was prepared from 6-bromo-3-chloro-1,8-naphthyridin-4-ol), using the general process described in the synthesis of Intermediate I-55D. LCMS m/z 278.9 (M+H)$^+$, HPLC $t_R$ 0.88 min (method C). $^1$H NMR (400 MHz, CDCl$_3$) δ 9.17 (d, J=2.3 Hz, 1H), 9.11 (s, 1H), 8.77 (d, J=2.4 Hz, 1H).

Intermediate I-61

6-bromo-3-chloro-N-(1-(2-fluorophenyl)ethyl)-1,8-naphthyridin-4-amine was synthesized from 6-bromo-3,4-dichloro-1,8-naphthyridine and 1-(2-fluorophenyl) ethanamine, using the general process described in the last synthesis step of Intermediate I-1. LCMS m/z 381.9 (M+H)$^+$, HPLC $t_R$ 0.74 min (method C). $^1$H NMR (400 MHz, CDCl$_3$) δ 8.97 (d, J=2.3 Hz, 1H), 8.80 (s, 1H), 8.47 (d, J=2.3 Hz, 1H), 7.41-7.25 (m, 2H), 7.18-7.04 (m, 2H), 5.38-5.20 (m, 2H), 1.74 (d, J=6.4 Hz, 3H).

Intermediate I-62

± 6-bromo-3-chloro-N-(2-fluoro-1-(2-fluorophenyl)-2-methylpropyl)quinolin-4-amine

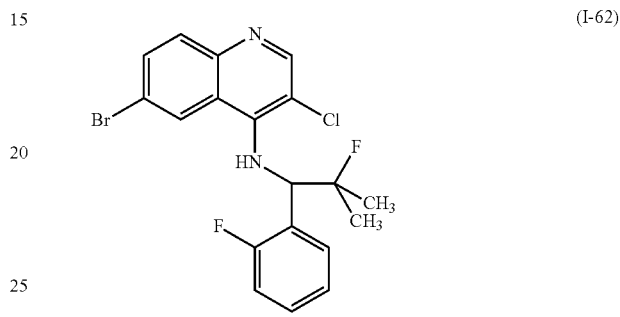

(I-62)

Intermediate I-62A: ± 1-(6-bromo-3-chloroquinolin-4-ylamino)-1-(2-fluorophenyl)-2-methylpropan-2-ol

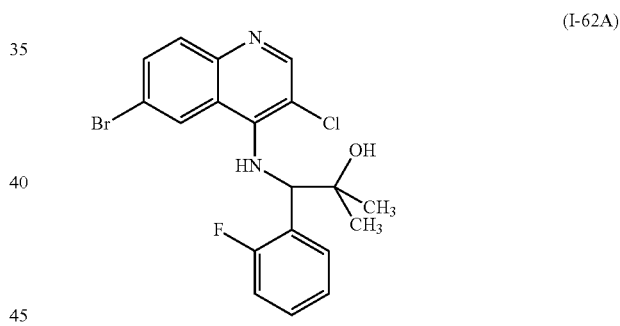

(I-62A)

A mixture of 1-amino-1-(2-fluorophenyl)-2-methylpropan-2-ol, HCl salt (476 mg, 2.17 mmol, 3.0 eq.), 6-bromo-3,4-dichloroquinoline (200 mg, 0.722 mmol, 1.0 eq.), DBU (0.272 mL, 1.80 mmol, 2.5 eq.), and anhydrous DMA (0.6 mL) was stirred at 140° C. for 18 hours. After cooling to room temperature, the reaction mixture was diluted with DCM (5 mL) and purified by column chromatography on silica gel (24 g), eluting with EtOAc-hexanes (gradient from 0~50%) to give 1-((6-bromo-3-chloroquinolin-4-yl)amino)-1-(2-fluorophenyl)-2-methylpropan-2-ol (220 mg, 0.519 mmol, 71.9% yield). LCMS m/z 423.0 (M+H)$^+$, HPLC $t_R$ 0.77 min (method C).

Intermediate I-62

To a stirred suspension of 1-((6-bromo-3-chloroquinolin-4-yl)amino)-1-(2-fluorophenyl)-2-methylpropan-2-ol (180 mg, 0.425 mmol) in anhydrous DCM (9 mL) was added DAST (0.281 mL, 2.12 mmol, 5.0 eq.) dropwise at −78° C. The mixture was stirred at −78° C. for 1 hour and then at room temperature for 2 hours. Saturated sodium bicarbonate solution (5 mL) was added at 0° C. to quench the reaction. The aqueous layer was separated and extracted with ethyl acetate (3 mL×2). The combined organic solutions were dried over sodium sulfate, filtered, and concentrated under reduced pressure. The residue was purified by column chromatography on silica gel (12 g), eluting with EtOAc-hexanes (gradient from 0~10%) to give 6-bromo-3-chloro-N-(2-fluoro-1-(2-fluorophenyl)-2-methylpropyl)quinolin-4-amine (26 mg, 0.061 mmol, 14% yield). LCMS m/z 425.1 (M+H)$^+$, HPLC $t_R$ 0.90 min (method C).

Intermediate I-63

± 6-bromo-3-chloro-N-(3-fluoro-1-(2-fluorophenyl)propyl)quinolin-4-amine

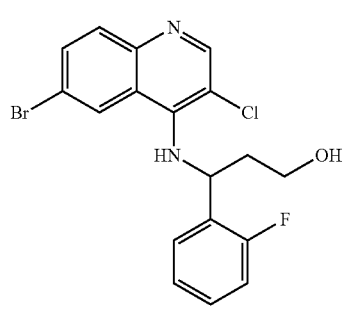

(I-63)

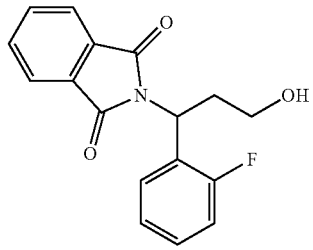

Intermediate I-63A: ± 3-(6-bromo-3-chloroquinolin-4-ylamino)-3-(2-fluorophenyl)propan-1-ol (I-63A)

3-(6-bromo-3-chloroquinolin-4-ylamino)-3-(2-fluorophenyl)propan-1-ol was synthesized from 6-bromo-3,4-dichloroquinoline and 3-amino-3-(2-fluorophenyl)propan-1-ol, using the general process described in the last synthesis step of Intermediate I-1. LCMS m/z 409.0 (M+H)$^+$, HPLC $t_R$ 0.73 min (method C).

Intermediate I-63

To a stirred suspension of 3-((6-bromo-3-chloroquinolin-4-yl)amino)-3-(2-fluorophenyl)propan-1-ol (130 mg, 0.317 mmol) in anhydrous DCM (9 mL) was added DAST (0.210 mL, 1.59 mmol, 5.0 eq.) dropwise at −78° C. The mixture was stirred at −78° C. for 1 hour and then room temperature for 2 hours. Saturated aqueous sodium bicarbonate solution (3 mL) was added at 0° C. to quench the reaction. The aqueous layer was separated and extracted with ethyl acetate (3 mL×2). The combined organic solutions were dried over sodium sulfate, filtered, and concentrated under reduced pressure. The residue was purified by column chromatography on silica gel (12 g), eluting with EtOAc-hexanes (gradient from 0~10%) to give 6-bromo-3-chloro-N-(3-fluoro-1-(2-fluorophenyl)propyl)quinolin-4-amine (80 mg, 0.19 mmol, 61% yield). LCMS m/z 411.0 (M+H)$^+$, HPLC $t_R$ 0.81 min (method C). $^1$H NMR (400 MHz, CDCl$_3$) δ 8.58 (s, 1H), 8.13 (d, J=2.1 Hz, 1H), 7.86 (d, J=8.9 Hz, 1H), 7.70 (dd, J=8.9, 2.1 Hz, 1H), 7.36-7.29 (m, 2H), 7.16-7.07 (m, 2H), 5.44-5.34 (m, 2H), 4.82-4.45 (m, 2H), 2.55-2.33 (m, 2H).

Intermediate I-64

± 3,3-difluoro-1-(2-fluorophenyl)propan-1-amine

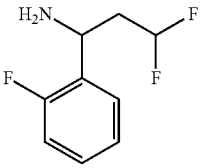

(I-64)

Intermediate I-64A: ± 2-(1-(2-fluorophenyl)-3-hydroxypropyl)isoindoline-1,3-dione (I-64A)

Ethyl 1,3-dioxoisoindoline-2-carboxylate (2.64 g, 12.0 mmol, 1.2 eq.) was added to a mixture of 3-amino-3-(2-fluorophenyl)propan-1-ol (1.70 g, 10.0 mmol, 1.0 eq.) and sodium carbonate (1.60 g, 15.1 mmol, 1.5 eq.) in a 1:1 mixture of THF—H$_2$O (34 mL). The reaction mixture was stirred at room temperature for 18 hours and then diluted with ethyl acetate (30 mL). The aqueous phase was extracted with ethyl acetate (20 mL×2) and the combined organic phase was dried over magnesium sulfate, filtered, and concentrated. The residue was purified by column chromatography on silica gel (40 g), eluting with EtOAc-hexanes (gradient from 0~40%) to give 2-(1-(2-fluorophenyl)-3-hydroxypropyl) isoindoline-1,3-dione (1.80 g, 6.01 mmol, 59.9% yield). LCMS m/z 300.1 (M+H)$^+$, HPLC $t_R$ 0.82 min (method C). $^1$H NMR (400 MHz, CDCl$_3$) δ 7.90-7.80 (m, 2H), 7.78-7.67 (m, 3H), 7.33-7.25 (m, 1H), 7.18 (td, J=7.6, 1.1 Hz, 1H), 7.08-6.99 (m, 1H), 5.95 (dd, J=10.7, 5.1 Hz, 1H), 3.90-3.63 (m, 2H), 2.87-2.72 (m, 1H), 2.45 (ddt, J=14.0, 8.6, 5.3 Hz, 1H).

Intermediate I-64B: ± 3-(1,3-dioxoisoindolin-2-yl)-3-(2-fluorophenyl)propanal

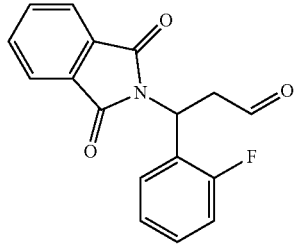

(I-64B)

To a solution of 2-(1-(2-fluorophenyl)-3-hydroxypropyl)isoindoline-1,3-dione (1.20 g, 4.01 mmol) in anhydrous DMSO (12 mL) and triethylamine (1.74 mL, 12.0 mmol, 3.0 eq.) was added pyridine sulfur trioxide (1.91 g, 12.0 mmol, 3.0 eq.) in DMSO (12 mL) at 0° C. under nitrogen. The mixture was stirred at room temperature for 1 hour. The reaction was then quenched with ice-water (40 mL) and extracted with EtOAc (60 mL). The organic layer was washed with 10% acetic acid solution (15 mL), water (15 mL) and saturated sodium bicarbonate solution (10 mL). The organic layer was then dried over sodium sulfate, filtered, and concentrated under reduced pressure. The residue was purified by column chromatography on silica gel (40 g), eluting with EtOAc-hexanes (gradient from 0~20%) to give 3-(1,3-dioxoisoindolin-2-yl)-3-(2-fluorophenyl)propanal (0.70 g, 2.4 mmol, 58% yield) as an oily solid. LCMS m/z 298.1 (M+H)$^+$, HPLC $t_R$ 0.85 min (method C).

Intermediate I-64C: ± 2-(3,3-difluoro-1-(2-fluorophenyl)propyl)isoindoline-1,3-dione

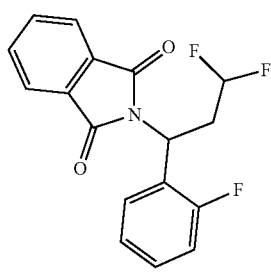

(I-64C)

To a stirred solution of 3-(1,3-dioxoisoindolin-2-yl)-3-(2-fluorophenyl)propanal (200 mg, 0.673 mmol) in anhydrous CH$_2$Cl$_2$ (9 mL) was added DAST (0.444 mL, 3.36 mmol, 5.0 eq.) dropwise at −78° C. The mixture was stirred at −78° C. for 1 hour and then at room temperature for 1 hour. Saturated sodium bicarbonate solution (10 mL) was added at 0° C. to quench the reaction. The aqueous layer was separated and extracted with ethyl acetate (10 mL). The combined organic solutions were dried over sodium sulfate, filtered, and concentrated under reduced pressure. The residue was purified by column chromatography on silica gel (12 g), eluting with EtOAc-hexanes (gradient from 0~20%) to give 2-(3,3-difluoro-1-(2-fluorophenyl)propyl)isoindoline-1,3-dione (50 mg, 0.157 mmol, 23.28% yield). LCMS m/z 320.1 (M+H)$^+$, HPLC $t_R$ 0.97 min (method C). $^1$H NMR (400 MHz, CDCl$_3$) δ 7.86 (dd, J=5.5, 3.1 Hz, 2H), 7.78-7.63 (m, 3H), 7.38-7.27 (m, 1H), 7.19 (td, J=7.6, 1.2 Hz, 1H), 7.07 (ddd, J=10.3, 8.3, 1.1 Hz, 1H), 6.12-5.71 (m, 2H), 3.42-3.21 (m, 1H), 2.84-2.62 (m, 1H).

Intermediate I-64

A mixture of 2-(3,3-difluoro-1-(2-fluorophenyl)propyl)isoindoline-1,3-dione (40 mg, 0.12 mmol), hydrazine hydrate (6.1 μl, 0.12 mmol, 1.0 eq.) and 100% EtOH (0.2 mL) was stirred at 85° C. for 3 hours. After cooling to room temperature, the reaction mixture was diluted with DCM (2 mL) and purified by column chromatography on silica gel (12 g), eluting with EtOAc-hexanes (gradient from 0~50%) to give 3,3-difluoro-1-(2-fluorophenyl)propan-1-amine (15 mg, 0.079 mmol, 63% yield). $^1$H NMR (400 MHz, CDCl$_3$) δ 7.38 (td, J=7.5, 1.7 Hz, 1H), 7.32-7.24 (m, 1H), 7.21-7.13 (m, 1H), 7.08 (ddd, J=10.9, 8.2, 1.1 Hz, 1H), 6.14-5.78 (m, 1H), 4.41 (dd, J=8.1, 6.1 Hz, 1H), 2.39-2.21 (m, 2H), 1.63 (br. s., 2H).

Intermediate I-65

± 2,2-difluoro-1-(3-vinylphenyl)ethanamine

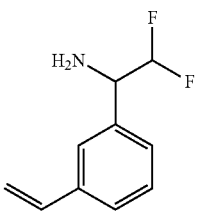

(I-65)

Intermediate I-65A: ± N-(1-(3-bromophenyl)-2,2-difluoroethyl)-2-methylpropane-2-sulfinamide

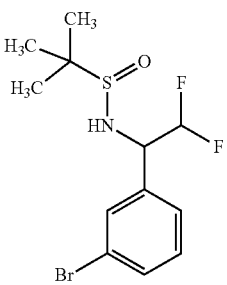

(I-65A)

To a stirred solution of N-(3-bromobenzylidene)-2-methylpropane-2-sulfinamide (PCT Int. Appl., 2007145571, 21 Dec. 2007) (3.20 g, 11.1 mmol) and difluoromethyltrimethylsilane (4.00 g, 32.2 mmol, 2.9 eq.) in anhydrous THF (30 mL) was added 1M THF solution of potassium tert-butoxide (32.2 mL, 32.2 mmol, 2.9 eq.) dropwise at −78° C. under N$_2$. The mixture was stirred at −78° C. for 1 hour. The temperature was raised to room temperature over 1 hour. Saturated NH$_4$Cl solution (30 mL) and water (10 mL) were added to quench the reaction. The mixture was extracted with hexanes (40 mL) and then ethyl acetate (30 mL×2). The combined organic solutions were dried over sodium sulfate, filtered, and concentrated under reduced pressure. The residue was purified by column chromatography on silica gel (80 g), eluting with EtOAc-hexanes (gradient from 0~100%) to give an impure product. Trituration of the crude product with MeOH (10 mL) gave N-(1-(3-bromophenyl)-2,2-difluoroethyl)-2-methylpropane-2-sulfinamide (0.48 g, 1.41 mmol, 12.7% yield) as a grey solid. LCMS m/z 340.0 (M+H)$^+$, HPLC $t_R$ 0.90 min (method C). $^1$H NMR (400 MHz, CDCl$_3$) δ 7.59-7.50 (m, 2H), 7.40-7.29 (m, 2H), 6.17-5.82 (m, 1H), 4.65 (tdd, J=12.9, 6.5, 3.1 Hz, 1H), 3.67 (d, J=6.4 Hz, 1H), 1.27 (s, 9H), J=10.3, 8.3, 1.1 Hz, 1H), 6.12-5.71 (m, 2H), 3.42-3.21 (m, 1H), 2.84-2.62 (m, 1H).

Intermediate I-65B: ± N-(2,2-difluoro-1-(3-vinylphenyl)ethyl)-2-methylpropane-2-sulfinamide

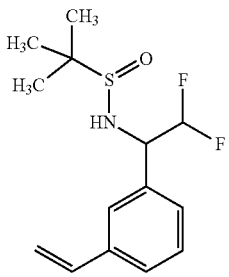

(I-65B)

To a mixture of vinylboronic acid pinacol ester (0.479 mL, 2.82 mmol, 2.0 eq.), N-(1-(3-bromophenyl)-2,2-difluoroethyl)-2-methylpropane-2-sulfinamide (480 mg, 1.41 mmol), 2M potassium carbonate solution (1.76 mL, 3.53 mmol), and PdCl$_2$(dppf)-CH$_2$Cl$_2$ adduct (115 mg, 0.141 mmol, 0.1 eq.) in 1,4-dioxane (8 mL), was bubbled N$_2$ gas for 2 min. The reaction mixture was then stirred at 100° C. for 2 hours. After cooling to room temperature, the solvent was removed under vacuo. The residue was purified by column chromatography on silica gel (24 g), eluting with EtOAc-hexanes (gradient from 0~50%) to give N-(2,2-difluoro-1-(3-vinylphenyl)ethyl)-2-methylpropane-2-sulfinamide (260 mg, 0.905 mmol, 64.1% yield) as a yellow oil. LCMS m/z 288.1 (M+H)$^+$, HPLC $t_R$ 0.89 min (method C). $^1$H NMR (400 MHz, CDCl$_3$) δ 7.48-7.35 (m, 3H), 7.31 (s, 1H), 6.74 (dd, J=17.6, 10.9 Hz, 1H), 6.18-5.84 (m, 1H), 5.80 (dd, J=17.5, 0.6 Hz, 1H), 5.33 (d, J=11.2 Hz, 1H), 4.67 (tdd, J=12.8, 5.8, 3.5 Hz, 1H), 3.65 (d, J=5.7 Hz, 1H), 1.28 (s, 9H).

Intermediate I-65

N-(2,2-difluoro-1-(3-vinylphenyl)ethyl)-2-methylpropane-2-sulfinamide (260 mg, 0.905 mmol) was dissolved in anhydrous MeOH (15 mL). 4N dioxane solution of HCl (0.565 mL, 2.26 mmol, 2.5 eq.) was added at 0° C. under N$_2$. The reaction mixture was stirred at room temperature for 1 hour. After the solvent was evaporated, the residue was triturated with ether (20 mL). 2,2-difluoro-1-(3-vinylphenyl)ethanamine HCl salt was collected by filtration as a white solid. The HCl salt was dissolved in EtOAc (4 mL) and washed with 2 M K$_2$CO$_3$ (4 mL). The aqueous K$_2$CO$_3$ was back-washed with EtOAc (4 mL). The combined EtOAc phase was dried over Na$_2$SO$_4$ and filtered. The filtrate was concentrated to give 2,2-difluoro-1-(3-vinylphenyl) ethanamine (100 mg, 0.546 mmol, 60.3% yield) as a yellow oil. $^1$H NMR (400 MHz, CDCl$_3$) δ 7.49-7.29 (m, 4H), 6.75 (dd, J=17.6, 11.0 Hz, 1H), 5.95-5.62 (m, 2H), 5.31 (dd, J=11.1, 0.7 Hz, 1H), 4.22 (ddd, J=13.5, 9.4, 4.5 Hz, 1H), 1.66 (br. s., 2H).

Intermediate I-66

(R)-2,2-difluoro-1-(2-fluoro-5-vinylphenyl)ethan-1-amine

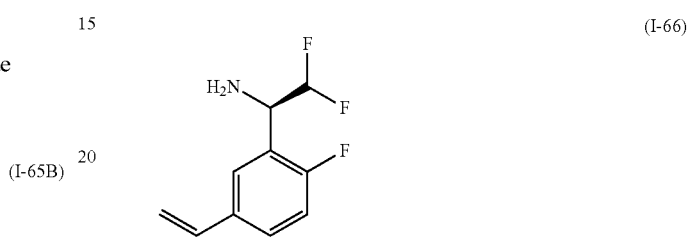

(I-66)

To a mixture of vinylboronic acid pinacol ester (0.668 mL, 3.94 mmol, 2.0 eq.), (R)-1-(5-bromo-2-fluorophenyl)-2,2-difluoroethanamine (Enantiomer 2 from Intermediate I-76, 500 mg, 1.97 mmol), 2M potassium carbonate solution (2.46 mL, 4.92 mmol, 2.5 eq.), and PdCl$_2$(dppf)-CH$_2$Cl$_2$ adduct (161 mg, 0.197 mmol, 0.1 eq.) in 1,4-dioxane (10 mL), was bubbled N$_2$ for 2 min. The reaction mixture was stirred at 100° C. for 2 hours. After cooling to room temperature, the solvent was removed under vacuo. The residue was purified by column chromatography on silica gel (24 g), eluting with EtOAc-hexanes (gradient from 0~50%) to give (R)-2,2-difluoro-1-(2-fluoro-5-vinylphenyl) ethanamine (190 mg, 0.944 mmol, 48.0% yield) as a yellow oil. LCMS m/z 202.0 (M+H)$^+$, HPLC $t_R$ 0.56 min (method C). $^1$H NMR (400 MHz, CDCl$_3$) δ 7.61 (dd, J=6.8, 2.2 Hz, 1H), 7.47 (ddd, J=8.5, 5.1, 2.3 Hz, 1H), 7.10 (dd, J=9.9, 8.6 Hz, 1H), 7.03 (s, 1H), 6.13-5.72 (m, 1H), 4.54 (ddd, J=15.1, 9.0, 3.8 Hz, 1H), 1.75 (br. s., 2H).

Intermediate I-67

(R)-3-(1-(((6-bromo-3-chloro-2-methylquinolin-4-yl) amino)ethyl)-4-fluorobenzamide

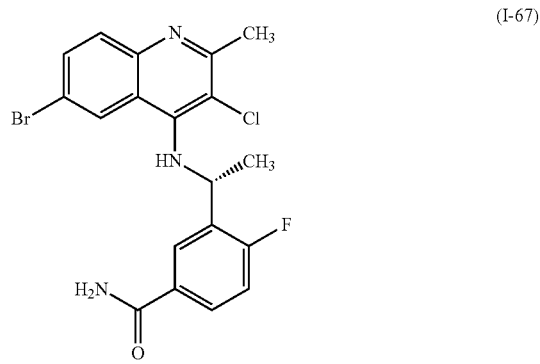 [SMILES: Cc1nc2ccc(Br)cc2c(N[C@H](C)c2cc(C(N)=O)ccc2F)c1Cl]

(I-67)

Intermediate I-67A:
(R)-3-(1-aminoethyl)-4-fluorobenzonitrile

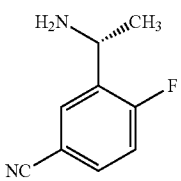

(I-67A)

A mixture of (R)-1-(5-bromo-2-fluorophenyl)ethanamine hydrochloride (1.1 g, 4.32 mmol, Intermediate I-70), dicyanozinc (1.015 g, 8.64 mmol), di-tert-butyl(2',4',6'-triisopropyl-[1,1'-biphenyl]-2-yl)phosphine (0.367 g, 0.864 mmol), $Pd_2(dba)_3$ (396 mg, 0.432 mmol) and zinc (565 mg, 8.64 mmol) in DMF (7 mL) was heated at 95° C. under nitrogen in a sealed tube for 1 h. The mixture was cooled to room temperature, filtered through a celite pad and washed with MeOH (20 mL). The filtrate was concentrated under reduced pressure to give a crude mixture containing (R)-3-(1-aminoethyl)-4-fluorobenzonitrile (710 mg) which was used as such for the subsequent step. LC/MS (M+H): 165; LC retention time: 0.44 min (analytical HPLC Method C).

Intermediate I-67B:
(R)-3-(1-aminoethyl)-4-fluorobenzamide

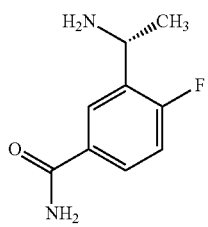

(I-67B)

A 1 N aqueous sodium hydroxide (13.0 mL, 13.0 mmol) and 30% aqueous hydrogen peroxide (441 mg, 13.0 mmol) were added to a mixture of (R)-3-(1-aminoethyl)-4-fluorobenzonitrile (Intermediate I-67A, 710 mg) in methanol (20 mL). After stirring at room temperature for 1 h, the mixture was quenched with 1 N aqueous HCl (13 mL). Most of the solvents were removed under reduced pressure. The residue was purified by reverse phase chromatography (100 g C18 column, gradient elution from 0 to 30% of methanol in water) to afford (R)-3-(1-aminoethyl)-4-fluorobenzamide (380 mg, 48% yield for 2 steps). LC/MS (M+H): 474; LC retention time: 0.40 min (analytical HPLC Method C).

Intermediate I-67C: (R)-3-(1-((6-bromo-2-methylquinolin-4-yl)amino)ethyl)-4-fluorobenzamide

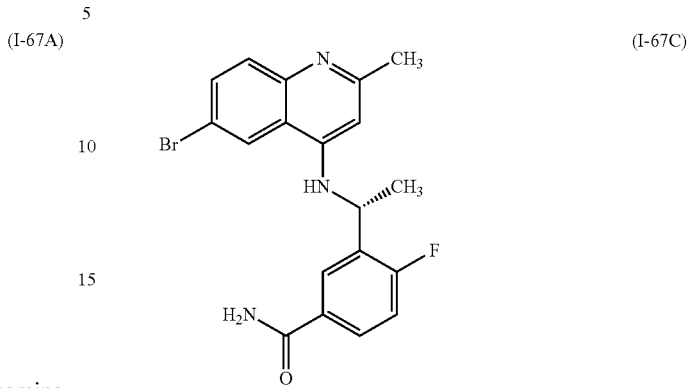

(I-67C)

A mixture of 6-bromo-4-chloro-2-methylquinoline (56.3 mg, 0.220 mmol), (R)-3-(1-aminoethyl)-4-fluorobenzamide (40 mg, 0.220 mmol) and ((1R,4S)-7,7-dimethyl-2-oxobicyclo[2.2.1]heptan-1-yl)methanesulfonic acid (25.5 mg, 0.110 mmol) in NMP (0.5 mL) was heated in a sealed tube at 125° C. for 6 h. The mixture was cooled to room temperature, diluted with ethyl acetate (60 mL), washed with water, brine, dried over sodium sulfate and concentrated under reduced pressure. Flash chromatography purification (12 g silica gel column, gradient elution from 0 to 10% of methanol in dichloromethane) afforded (R)-3-(1-((6-bromo-2-methylquinolin-4-yl)amino)ethyl)-4-fluorobenzamide (13.0 mg, 15% yield). LC/MS (M+H): 402, 404; LC retention time: 0.64 min (analytical HPLC Method C); $^1$H NMR (400 MHz, methanol-$d_4$) δ 9.04 (d, J=6.6 Hz, 1H), 8.95 (d, J=1.8 Hz, 1H), 8.13-7.97 (m, 2H), 7.90 (ddd, J=8.6, 4.9, 2.3 Hz, 1H), 7.75 (d, J=8.9 Hz, 1H), 7.30 (dd, J=10.1, 8.7 Hz, 1H), 6.56 (s, 1H), 5.42 (t, J=6.8 Hz, 1H), 2.62 (s, 3H), 1.87-1.77 (m, 3H).

Intermediate I-67

N-chlorosuccinimide (5.18 mg, 0.039 mmol) was added to a mixture of (R)-3-(1-((6-bromo-2-methylquinolin-4-yl)amino)ethyl)-4-fluorobenzamide (13 mg, 0.032 mmol) in acetonitrile (2 mL). After stirring at ambient temperature for 1 h, the mixture was quenched with saturated sodium bicarbonate (2 mL), diluted with ethyl acetate (60 mL), washed with water, brine, dried over sodium sulfate and concentrated under reduced pressure. Flash chromatography purification (4 g silica gel column, gradient elution from 0 to 10% of methanol in dichloromethane) afforded (R)-3-(1-((6-bromo-3-chloro-2-methylquinolin-4-yl)amino)ethyl)-4-fluorobenzamide (12.0 mg, 85% yield). LC/MS (M+H): 436, 438; LC retention time: 0.67 min (analytical HPLC Method C); $^1$H NMR (400 MHz, methanol-$d_4$) δ 8.22-8.11 (m, 2H), 7.84 (ddd, J=8.6, 4.9, 2.4 Hz, 1H), 7.76-7.67 (m, 2H), 7.18 (dd, J=10.1, 8.6 Hz, 1H), 5.58-5.32 (m, 1H), 2.68 (s, 3H), 1.74 (d, J=6.7 Hz, 3H).

Intermediate I-68

6-Bromo-3,4-dichloro-2-methylquinoline

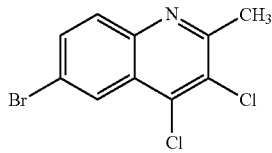
(I-68)

Intermediate I-68A:
6-bromo-3-chloro-2-methylquinolin-4-ol

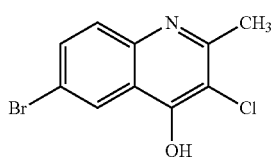
(I-68A)

N-chlorosuccinimide (1.7 g, 12.9 mmol) was added to an acetonitrile (120 mL)-acetic acid (6.00 mL) suspension of 6-bromo-2-methylquinolin-4-ol (3 g, 12.6 mmol) at 80° C. in small portions under $N_2$ over 1 h. The resulting mixture was heated at 80° C. for additional 3 h. After cooling to room temperature, the suspension was filtered. The solid was washed with MeCN (2×50 mL) and dried under vacuum to give 6-bromo-3-chloro-2-methylquinolin-4-ol as white solid (3.13 g, 91% yield). LC/MS (M+H): 274; LC retention time: 0.67 min (analytical HPLC Method C); $^1$H NMR (400 MHz, DMSO-$d_6$) δ 12.29 (br. s., 1H), 8.18 (d, J=2.3 Hz, 1H), 7.82 (dd, J=8.9, 2.4 Hz, 1H), 7.53 (d, J=8.8 Hz, 1H), 2.52 (s, 3H).

Intermediate I-68

A stirred $POCl_3$ (10.7 mL, 115 mmol) suspension of 6-bromo-3-chloro-2-methylquinolin-4-ol (3.13 g, 11.5 mmol) was heated to 100° C. for 3 h. After cooling to room temperature, the resulting suspension was added dropwise to ice-cold water (200 mL). Additional ice was added to the aqueous suspension to prevent overheating. Solid $K_2CO_3$ (20 g, 145 mmol) was added in small portions. The resulting suspension was filtered. The solid was washed with water (20 mL) then dried under vacuum to give 6-bromo-3,4-dichloro-2-methylquinoline as white solid (3.04 g, 91% yield). LC/MS (M+H): 292; LC retention time: 1.18 min (Method C); $^1$H NMR (400 MHz, chloroform-d) δ 8.32 (d, J=2.1 Hz, 1H), 7.93-7.87 (m, 1H), 7.83-7.77 (m, 1H), 2.84 (s, 3H).

Intermediate I-69

6-Bromo-3,4-dichloro-7-fluoro-2-methylquinoline

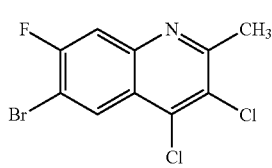
(I-69)

Intermediate I-69A: (1E,3Z)-3-((4-bromo-3-fluorophenyl)imino)-1-ethoxybut-1-en-1-ol

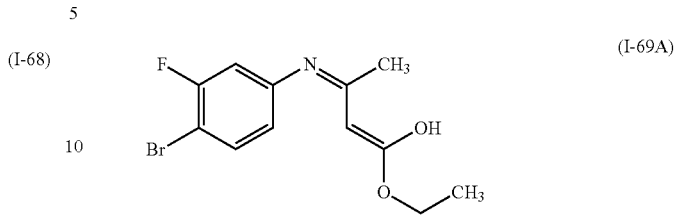
(I-69A)

An EtOH (20 mL) suspension of 4-bromo-3-fluoroaniline (5 g, 26.3 mmol), ethyl 3-oxobutanoate (3.77 g, 28.9 mmol), magnesium sulfate (6.33 g, 52.6 mmol) and acetic acid (0.077 mL, 1.345 mmol) was heated to reflux for 20 h. Additional ethyl 3-oxobutanoate (1 g) and acetic acid (0.1 mL) were added. Heating was continued for additional 24 h. After cooling to room temperature, the crude mixture was filtered through a short bed of celite. The filter cake was washed with EtOAc (20 mL). The combined filtrate was concentrated and stored at room temperature overnight. (1E,3Z)-3-((4-bromo-3-fluorophenyl)imino)-1-ethoxybut-1-en-1-ol was obtained as needle crystals (4.72 g, 59% yield). LC/MS (M+H): 304; LC retention time: 1.16 min (Method G); $^1$H NMR (400 MHz, chloroform-d) δ 10.46 (br. s., 1H), 7.46 (t, J=8.2 Hz, 1H), 6.87 (dd, J=9.9, 2.4 Hz, 1H), 6.76 (dd, J=8.6, 2.2 Hz, 1H), 4.76 (d, J=0.4 Hz, 1H), 4.15 (q, J=7.1 Hz, 2H), 2.05 (s, 3H), 1.29 (t, J=7.2 Hz, 3H).

Intermediate I-69B: Mixture of 6-bromo-7-fluoro-2-methylquinolin-4-ol and 6-bromo-5-fluoro-2-methylquinolin-4-ol

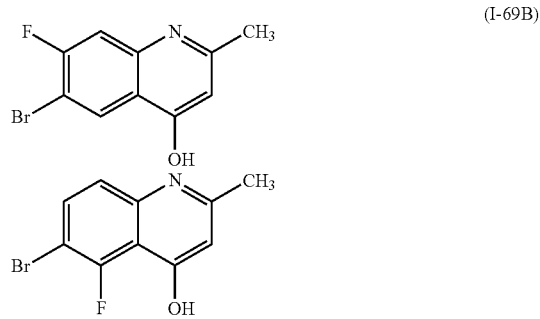
(I-69B)

Solid (1E,3Z)-3-((4-bromo-3-fluorophenyl)imino)-1-ethoxybut-1-en-1-ol (7.7 g, 25.5 mmol) was added to a pre-heated Dowtherm A (16 mL) at 250° C. The resulting solution was heated at 250° C. for 10 min. An off-white solid precipitated out. The mixture was cooled to room temperature and diluted with hexanes (20 mL). The resulting suspension was filtered. The solid was washed with hexanes (10 mL) and dried under vacuum to give a 3:1 mixture of 6-bromo-7-fluoro-2-methylquinolin-4-ol and 6-bromo-5-fluoro-2-methylquinolin-4-ol (4.01 g, 62% yield). LC/MS (M+H): 256, 258; LC retention time: 0.59 and 0.63 min (Method C).

Intermediate I-69C: Mixture of 6-bromo-3-chloro-7-fluoro-2-methylquinolin-4-ol and 6-bromo-3-chloro-5-fluoro-2-methylquinolin-4-ol

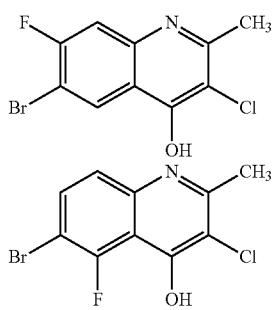
(I-69C)

1-Chloropyrrolidine-2,5-dione (1.05 g, 7.8 mmol) was added to an acetonitrile (55.5 mL)-acetic acid (2.9 mL) solution of 6-bromo-7-fluoro-2-methylquinolin-4-ol and 6-bromo-5-fluoro-2-methylquinolin-4-ol mixture (Intermediate I-69B, 2 g, 7.8 mmol). The suspension was stirred at 90° C. for 18 h. After cooling to room temperature, the resulting suspension was filtered. The solid was washed with acetonitrile (20 mL) and dried in vacuo to give a mixture of 6-bromo-3-chloro-7-fluoro-2-methylquinolin-4-ol and 6-bromo-3-chloro-5-fluoro-2-methylquinolin-4-ol (1.94 g, 86% yield). LC/MS (M+H): 290, 292; LC retention time: 0.67 and 0.72 min (Method C).

Intermediate I-69

To a mixture of 6-bromo-3-chloro-7-fluoro-2-methylquinolin-4-ol and 6-bromo-3-chloro-5-fluoro-2-methylquinolin-4-ol (Intermediate I-69C, 1.94 g, 6.7 mmol) was added $POCl_3$ (10 mL, 107 mmol). The suspension was heated to 105° C. for 1 h then cooled to room temperature. The crude mixture was added dropwise to a saturated $NaHCO_3$ (100 mL) solution at 0° C. Solid $K_2CO_3$ was added to adjust pH 7-10. The resulting suspension was filtered. The solid was washed with water (20 mL) and dried in vacuo. Further purification by silica gel chromatography (0-100% EtOAc-hexanes) gave pure 6-bromo-3,4-dichloro-7-fluoro-2-methylquinoline (0.14 g plus 0.76 g from the insoluble solid). The mixed fraction was further purified by SFC (IC 3×25 cm, 5 m column, 35° C., 100 bars, 85:15 $CO_2$/MeOH mobile phase, flow rate 180 mL/min) to give additional 6-bromo-3,4-dichloro-7-fluoro-2-methylquinoline (first eluding isomer, 0.14 g) and 6-bromo-3,4-dichloro-5-fluoro-2-methylquinoline (second eluding isomer, 0.32 g, 1.03 mmol, 13%). Total combined yield for 6-bromo-3,4-dichloro-7-fluoro-2-methylquinoline was 1.04 g (3.34 mmol, 43% yield). Analytical data for 6-bromo-3,4-dichloro-7-fluoro-2-methylquinoline: LC/MS (M+H): 310; LC retention time: 1.20 min (Method C); $^1H$ NMR (400 MHz, chloroform-d) δ 8.40 (d, $J_{FH}$=7.2 Hz, 1H), 7.71 (d, $J_{FH}$=9.2 Hz, 1H), 2.83 (s, 3H). Analytical data for 6-bromo-3,4-dichloro-5-fluoro-2-methylquinoline: LC/MS (M+H): 310; LC retention time: 1.18 min (Method C); $^1H$ NMR (400 MHz, chloroform-d) δ 7.81-7.74 (m, 1H), 7.70-7.64 (m, 1H), 2.80 (s, 3H).

Intermediate I-70

(R)-1-(5-bromo-2-fluorophenyl)ethan-1-amine

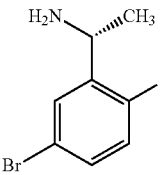
(I-70)

Intermediate I-70A: (R)—N—((R)-1-(5-bromo-2-fluorophenyl)ethyl)-2-methylpropane-2-sulfinamide

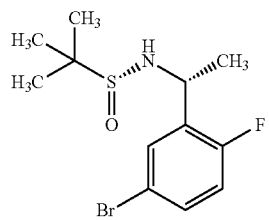
(I-70A)

(R)-(+)-2-Methyl-2-propanesulfinamide (2.5 g, 20.6 mmol) and titanium isopropoxide (12.2 mL, 41.3 mmol) were added to a stirred THF (20.6 mL) solution of 1-(5-bromo-2-fluorophenyl)ethanone (5.37 g, 24.8 mmol) at room temperature. The mixture was heated at 90° C. under $N_2$ for 24 h and then cooled to −35° C. $NaBH_4$ (2 g, 52.8 mmol) was added. The mixture was stirred at −35 to 0° C. for 3 h and quenched with MeOH (10 mL) and brine (100 mL). The resulting slurry was stirred at 0° C. for 1 h and filtered through a short bed of Celite. The bed was washed with EtOAc (4×30 mL). The two phases of the combined filtrate were separated. The aqueous phase was extracted with EtOAc (1×50 mL). The combined organic phase was dried over $Na_2SO_4$, filtered and concentrated. The crude mixture was purified by silica gel column chromatography (80 g ISCO cartridge, 0-100% EtOAc-hexanes) to give (R)—N—((R)-1-(5-bromo-2-fluorophenyl)ethyl)-2-methylpropane-2-sulfinamide (3.51 g, 53% yield). LC/MS (M+H): 322, 324; LC retention time: 0.92 min (Method C); $^1H$ NMR (400 MHz, chloroform-d) δ 7.49 (dd, J=6.4, 2.5 Hz, 1H), 7.38 (ddd, J=8.7, 4.5, 2.6 Hz, 1H), 6.95 (dd, J=9.9, 8.7 Hz, 1H), 4.79-4.71 (m, 1H), 3.51 (d, J=5.1 Hz, 1H), 1.54 (d, J=6.6 Hz, 3H), 1.24 (s, 9H).

Intermediate I-70B: (R)-1-(5-bromo-2-fluorophenyl)ethan-1-amine HCl Salt

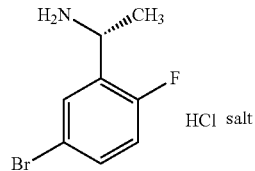
(I-70B)

A 4 N dioxane solution of HCl (10 mL, 40 mmol) was added to a MeOH (25 mL) solution of (R)—N—((R)-1-(5-bromo-2-fluorophenyl)ethyl)-2-methylpropane-2-sulfinamide (3.51 g, 10.9 mmol). The mixture was stirred at room temperature for 30 min. After the solvent was evaporated, the residue was triturated with ether (20 mL). (R)-1-(5-bromo-2-fluorophenyl)ethan-1-amine HCl salt (2.23 g, 81% yield) was collected by filtration as white solid. Chiral SFC analysis (4.6×250 mm 5 m AD-H column, 10/90 MeOH/CO$_2$ with 0.1% NH$_4$OH mobile phase, flow rate 3.0 mL/min, 40° C., 140 bars, UV 220 nm): retention time=2.89 min (>99% ee); LC/MS (M+H): 218, 220; LC retention time: 0.58 min (Method C); $^1$H NMR (400 MHz, chloroform-d) δ 8.94 (br. s., 3H), 7.85 (d, J=4.3 Hz, 1H), 7.50-7.43 (m, 1H), 7.01 (t, J=9.2 Hz, 1H), 4.73 (d, J=6.4 Hz, 1H), 1.74 (d, J=6.5 Hz, 3H).

Intermediate I-70

(R)-1-(5-bromo-2-fluorophenyl)ethan-1-amine HCl salt (200 mg, 0.79 mmol) was dissolved in EtOAc (3.9 mL) and washed with 2 M K$_2$CO$_3$ (3.9 mL). The aqueous K$_2$CO$_3$ was back-washed with EtOAc (3.9 mL). The combined EtOAc phase was dried over Na$_2$SO$_4$ and filtered. The filtrate was concentrated to give (R)-1-(5-bromo-2-fluorophenyl)ethan-1-amine (134 mg, 78% yield). LC/MS (M+H): 218, 220; LC retention time: 0.53 min (Method C); $^1$H NMR (400 MHz, chloroform-d) δ 7.58 (dd, J=6.6, 2.4 Hz, 1H), 7.32 (ddd, J=8.6, 4.5, 2.5 Hz, 1H), 6.91 (dd, J=10.0, 8.7 Hz, 1H), 4.37 (q, J=6.7 Hz, 1H), 1.40 (d, J=6.6 Hz, 3H)

Intermediate I-71

(R)-1-(2-fluoro-5-methoxyphenyl)ethan-1-amine HCl Salt

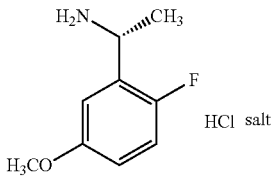
(I-71)

Using conditions analogous to the synthesis of Intermediate I-70, 1-(2-fluoro-5-methoxyphenyl)ethanone (1 g, 5.94 mmol) and (R)-(+)-2-methyl-2-propanesulfinamide (0.6 g, 4.95 mmol) were converted to (R)-1-(2-fluoro-5-methoxyphenyl)ethanamine HCl salt (0.226 g, 22% yield). Analytical chiral SFC (4.6×250 mm 5 m AD-H column, 15/85 MeOH/CO$_2$ with 0.1% NH$_4$OH mobile phase, flow rate 3.0 mL/min, 40° C., 140 bars, UV 220 nm): retention time=1.90 min (97% ee); LC/MS (M+H): 170; LC retention time: 0.50 min (Method C); $^1$H NMR (400 MHz, chloroform-d) δ 7.22 (dd, J=5.9, 3.1 Hz, 1H), 7.01 (t, J=9.3 Hz, 1H), 6.87-6.80 (m, 1H), 4.77 (q, J=6.6 Hz, 1H), 3.69 (s, 3H), 1.71 (d, J=6.8 Hz, 3H).

The following intermediates were synthesized employing the general procedure described for the preparation of Intermediates I-70 and I-76.

| Int. No. | Structure | LCMS m/z observed | HPLC t$_R$ (min) | HPLC method |
|---|---|---|---|---|
| I-72 | H$_2$N—CH(CHF$_2$)—Ph (±) | 158.0 | 0.463 | B |
| I-73 | H$_2$N—CH(CHF$_2$)—(2-F-C$_6$H$_4$) | 176 | 0.542 | B |
| I-74 | H$_2$N—CH(CH$_3$)—(5-F-2-Cl-pyridin-4-yl) | 175.0 | 0.358 | B |
| I-75 | H$_2$N—CH(CH$_3$)—(3-F-6-Br-pyridin-2-yl) | 234.9 | 0.697 | B |

Intermediate I-76

(S)-1-(5-bromo-2-fluorophenyl)-2,2-difluoroethan-1-amine

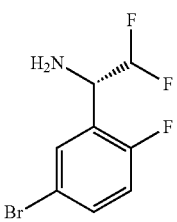
(I-76)

Intermediate I-76A:
1-(5-bromo-2-fluorophenyl)-2,2-difluoroethanone

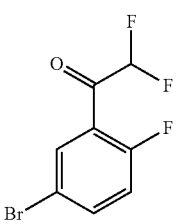
(I-76A)

A 2.5 M hexane solution of BuLi (25.1 mL, 62.9 mmol) was added to a stirred THF (190 mL) solution of diisopropylamine (8.96 mL, 62.9 mmol) at −78° C. The resulting solution was stirred at 0° C. for 10 min then cooled to −78° C. 1-bromo-4-fluorobenzene (10 g, 57.1 mmol) was added dropwise in 10 min. The resulting solution was stirred at −78° C. for 2.5 h. Ethyl 2,2-difluoroacetate (8.51 g, 68.6 mmol) was added dropwise over 5 min. The resulting mixture was stirred at −50° C. for 10 min and quenched by adding 1 M HCl (100 mL). After separation of the two phases, the aqueous layer was extracted with EtOAc (2×100 mL). The combined organic phase was dried over $Na_2SO_4$, filtered and evaporated to give a yellow oil. The crude mixture was purified by silica gel column chromatography (120 g ISCO cartridge, 0-50% EtOAc/Hexanes) to give 1-(5-bromo-2-fluorophenyl)-2,2-difluoroethanone (11 g, 73% yield). $^1$H NMR (400 MHz, chloroform-d) δ 8.06 (dd, J=6.0, 2.6 Hz, 1H), 7.76 (ddd, J=8.8, 4.5, 2.6 Hz, 1H), 7.13 (dd, J=10.2, 8.9 Hz, 1H), 6.58-6.24 (m, 1H).

Intermediate I-76B: Mixture of (S)-1-(5-bromo-2-fluorophenyl)-2,2-difluoroethan-1-amine and (R)-1-(5-bromo-2-fluorophenyl)-2,2-difluoroethan-1-amine

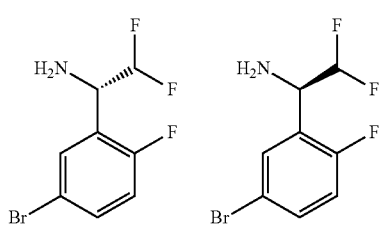

(I-76B)

Using conditions analogous to the synthesis of Intermediate I-70, 1-(5-bromo-2-fluorophenyl)-2,2-difluoroethanone (5.7 g, 22.5 mmol) and (S)-2-methylpropane-2-sulfinamide (2.3 g, 18.8 mmol) were converted to a 3:1 mixture of(S)-1-(5-bromo-2-fluorophenyl)-2,2-difluoroethan-1-amine and (R)-1-(5-bromo-2-fluorophenyl)-2,2-difluoroethan-1-amine (4 g, 84% yield). LC/MS (M+H): 254, 256; LC retention time: 0.54 min (Method C).

Intermediate I-76B: (S)-1-(5-bromo-2-fluorophenyl)-2,2-difluoroethan-1-amine

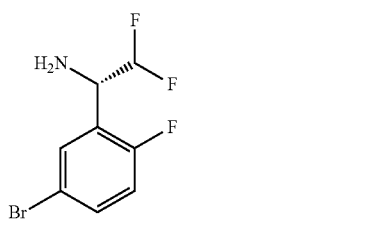

(I-76B)

The mixture of (S)-1-(5-bromo-2-fluorophenyl)-2,2-difluoroethan-1-amine and (R)-1-(5-bromo-2-fluorophenyl)-2,2-difluoroethan-1-amine (Intermediate I-76A, 4 g, 15.8 mmol) was separated by preparative SFC (30×250 mm 5 μm OJ-H column, 10/90 MeOH/$CO_2$ with 0.1% $NH_4OH$ mobile phase, 180 mL/min flow rate, 35° C., 100 bars, UV 220 nm).

(S)-1-(5-bromo-2-fluorophenyl)-2,2-difluoroethan-1-amine was the first eluting enantiomer (2.25 g, 56% yield) and (R)-1-(5-bromo-2-fluorophenyl)-2,2-difluoroethan-1-amine was the second eluting enantiomer (0.48 g, 11% yield). Analytical data for (S)-1-(5-bromo-2-fluorophenyl)-2,2-difluoroethan-1-amine: Chiral analytical SFC (4.6×250 mm 5 μm OJ-H column, 10/90 MeOH/$CO_2$ with 0.1% $NH_4OH$ mobile phase, 3 mL/min flow rate, 40° C., 140 bars, UV 200-400 nm) retention time: 1.791 min (>99% ee); LC/MS (M+H): 254, 256; LC retention time: 0.54 min (Method C); $^1$H NMR (400 MHz, chloroform-d δ 7.62 (dd, J=6.3, 2.5 Hz, 1H), 7.44 (ddd, J=8.7, 4.6, 2.6 Hz, 1H), 7.02-6.95 (m, 1H), 6.03-5.70 (m, 1H), 4.48 (ddd, J=14.6, 9.4, 3.7 Hz, 1H), 1.68 (br. s., 2H). Analytical data for (R)-1-(5-bromo-2-fluorophenyl)-2,2-difluoroethan-1-amine: Chiral analytical SFC (4.6×250 mm 5 μm OJ-H column, 10/90 MeOH/$CO_2$ with 0.1% $NH_4OH$ mobile phase, 3 mL/min flow rate, 40° C., 140 bars, UV 200-400 nm) retention time: 2.249 min (86% ee); LC/MS (M+H): 254, 256; LC retention time: 0.54 min (Method C).

Intermediate I-77

2-(5-(3,4-Dichloro-2-methylquinolin-6-yl)pyrimidin-2-yl)propan-2-ol

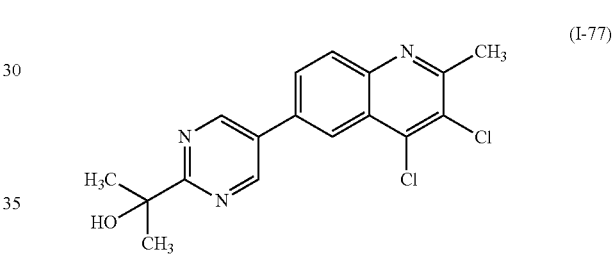

(I-77)

A stirred dioxane (34.4 mL) solution of 2-(5-bromopyrimidin-2-yl)propan-2-ol (1.67 g, 7.70 mmol), 4,4,4',4',5,5,5',5'-octamethyl-2,2'-bi(1,3,2-dioxaborolane) (2.35 g, 9.24 mmol), $PdCl_2$(dppf)-$CH_2Cl_2$ adduct (0.56 g, 0.69 mmol) and potassium acetate (1.133 g, 11.55 mmol) was pumped under vacuum and backfilled with nitrogen twice. The sealed tube was heated at 80° C. for 4 h and stirred at room temperature for 16 h. Intermediate I-68 (2 g, 6.87 mmol) and aqueous 2 M $K_2CO_3$ (8.59 mL, 17.2 mmol) were added. The degas cycle was repeated and the sealed vial was heated to 90° C. for 1 h. The crude mixture was diluted with EtOAc (100 mL) and washed with 2 M $K_2CO_3$ (50 mL). The resulting suspension was filtered. The solid was washed with water (2×20 mL) and dried in vacuo to give 2-(5-(3,4-dichloro-2-methylquinolin-6-yl)pyrimidin-2-yl) propan-2-ol (1.27 g). The two layers of the filtrate was separated. The EtOAc layer was washed with brine (10 mL), dried over $Na_2SO_4$ and filtered. The filtrate was concentrated and purified by silica gel column chromatography (40 g ISCO silica gel cartridge, 0-100% EtOAc/Hexanes) to give additional 2-(5-(3,4-dichloro-2-methylquinolin-6-yl)pyrimidin-2-yl)propan-2-ol (0.73 g). Total yield was 2 g (5.73 mmol, 83% yield). LC/MS (M+H): 348; LC retention time: 0.98 min (Method C); $^1$H NMR (400 MHz, chloroform-d) δ 9.08 (s, 2H), 8.36 (d, J=1.8 Hz, 1H), 8.19 (d, J=8.7 Hz, 1H), 7.95 (dd, J=8.7, 2.1 Hz, 1H), 4.66 (s, 1H), 2.90 (s, 3H), 1.68 (s, 6H).

The intermediates in Table 3 were prepared according to the general procedure used for the preparation of Intermediate I-77.

TABLE 3

| Int. No. | Structure | MS observed (M + 1) | HPLC ret. Time (min.) | HPLC method |
|---|---|---|---|---|
| I-78 | 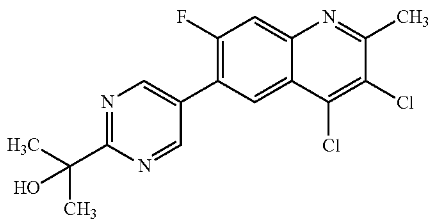 [SMILES: Cc1nc2cc(F)c(-c3cnc(C(C)(C)O)nc3)cc2c(Cl)c1Cl] | 366 | 1.01 | C |
| I-79 | 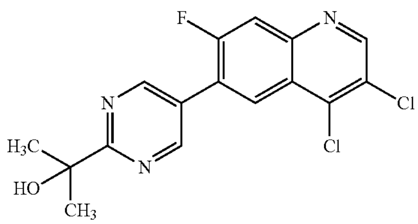 [SMILES: CC(C)(O)c1ncc(-c2cc3c(Cl)c(Cl)cnc3cc2F)cn1] | 352 | 0.96 | C |
| I-80 | 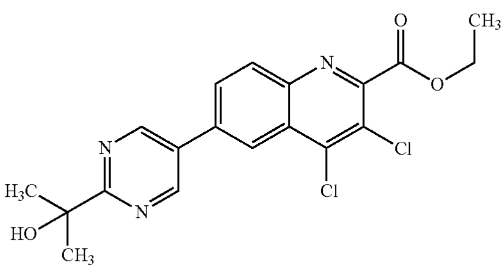 [SMILES: CCOC(=O)c1nc2ccc(-c3cnc(C(C)(C)O)nc3)cc2c(Cl)c1Cl] | 406 | 0.98 | C |

Intermediate I-81

2-(5-(3,4-Dichloro-2-methylquinolin-6-yl)pyrimidin-2-yl)propan-2-ol (I-81)

Intermediate I-81A: 3,4-dichloro-6-(2-(2-hydroxy-propan-2-yl)pyrimidin-5-yl)quinoline-2-carboxylic acid (I-81A)

Aqueous 1 M NaOH solution (0.25 mL, 0.25 mmol) was added to a MeOH (0.25 mL) solution of Intermediate I-80 (20 mg, 49 μmol). The mixture was stirred at room temperature for 1 h, was neutralized with aqueous 1 M HCl solution (0.25 mL) and filtered. The solid was washed with water (2 mL) and dried in vacuo to give 3,4-dichloro-6-(2-(2-hydroxypropan-2-yl)pyrimidin-5-yl)quinoline-2-carboxylic acid (12.4 mg, 67% yield). LC/MS (M+H): 378; LC retention time: 0.75 min (Method C).

Intermediate I-80B: 3,4-dichloro-6-(2-(2-hydroxypropan-2-yl)pyrimidin-5-yl)-N-(pyridin-3-yl)quinoline-2-carboxamide

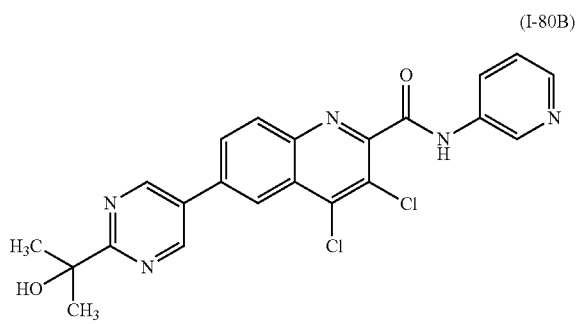 [SMILES: CC(C)(O)c1ncc(-c2ccc3nc(C(=O)Nc4cccnc4)c(Cl)c(Cl)c3c2)cn1]

(I-80B)

DIPEA (25 µL, 0.143 mmol) was added to an acetonitrile (0.5 mL) suspension of 3,4-dichloro-6-(2-(2-hydroxypropan-2-yl)pyrimidin-5-yl)quinoline-2-carboxylic acid (12.4 mg, 33 µmol), pyridin-3-amine (7 mg, 74 µmol) and BOP (21 mg, 47 µmol). After stirring at room temperature for 18 h, the mixture was purified by silica gel column chromatography (40 g ISCO cartridge, 0-100% EtOAc/Hexanes) to give 3,4-dichloro-6-(2-(2-hydroxypropan-2-yl)pyrimidin-5-yl)-N-(pyridin-3-yl)quinoline-2-carboxamide (17.8 mg, 96% yield). LC/MS (M+H): 454; LC retention time: 0.69 min (Method C); $^1$H NMR (400 MHz, chloroform-d) δ 9.84 (s, 1H), 9.12 (s, 2H), 8.37 (d, J=8.7 Hz, 1H), 8.13-8.07 (m, 2H), 8.03 (dd, J=4.6, 1.3 Hz, 1H), 7.39 (dd, J=8.3, 4.8 Hz, 1H), 7.11-7.06 (m, 1H), 7.02-6.97 (m, 1H), 1.70 (s, 6H).

Intermediate I-82

(R)-2-(3-(1-aminoethyl)-4-fluorophenyl)ethan-1-ol

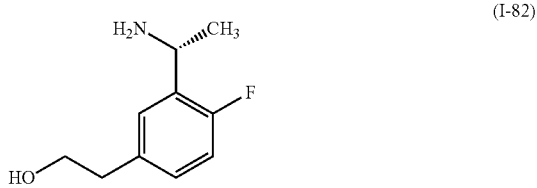

(I-82)

Intermediate I-82A: tert-butyl (R)-(1-(2-fluoro-5-vinylphenyl)ethyl)carbamate

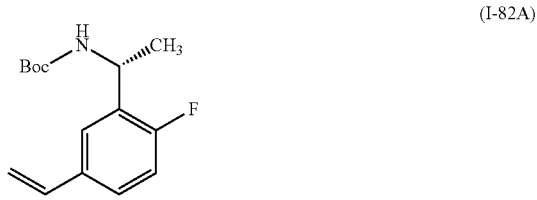 [SMILES: C=Cc1ccc(F)c([C@@H](C)NC(=O)OC(C)(C)C)c1]

(I-82A)

A dioxane (6 mL) solution of HCl salt of Intermediate I-70 (600 mg, 2.357 mmol), 2,4,6-trivinyl-1,3,5,2,4,6-trioxatriborinane pyridinium salt (285 mg, 1.179 mmol), PdCl$_2$(dppf)-CH$_2$Cl$_2$ adduct (193 mg, 0.236 mmol), solid potassium phosphate tribasic (1 g, 4.71 mmol) and aqueous 2 M potassium phosphate tribasic (1 mL, 2 mmol) was pumped under vacuum and backfilled with nitrogen twice. The sealed tube was then heated at 90° C. for 1 h. After cooling to room temperature, Boc$_2$O (550 mg, 2.52 mmol) was added. After stirring at room temperature for 1 h, the mixture was purified by ISCO (80 g silica gel cartridge, 0-50% EtOAc/hexanes) to give (R)-tert-butyl (1-(2-fluoro-5-vinylphenyl)ethyl)carbamate (450.3 mg, 72% yield). LC/MS (M-55): 210; LC retention time: 1.01 min (Method C); $^1$H NMR (400 MHz, chloroform-d) δ 7.30 (dd, J=7.2, 2.1 Hz, 1H), 7.25 (td, J=5.4, 2.4 Hz, 1H), 6.97 (dd, J=10.4, 8.6 Hz, 1H), 6.64 (dd, J=17.6, 10.9 Hz, 1H), 5.65 (d, J=17.6 Hz, 1H), 5.20 (d, J=10.9 Hz, 1H), 5.12-4.88 (m, 2H), 3.69 (s, 2H), 1.48-1.34 (m, 12H).

Intermediate I-82B: tert-butyl (R)-(1-(2-fluoro-5-(2-hydroxyethyl)phenyl)ethyl)carbamate

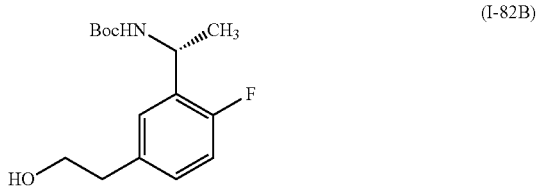 [SMILES: C[C@@H](NC(=O)OC(C)(C)C)c1cc(CCO)ccc1F]

(I-82B)

A 1 M THF solution of BH$_3$-THF complex (1.6 mL, 1.6 mmol) was added to a THF (5 mL) solution of (R)-tert-butyl (1-(2-fluoro-5-vinylphenyl)ethyl)carbamate (0.4054 g, 1.528 mmol) at 0° C. After stirring at 0° C. for 4 h, 35 wt % H$_2$O$_2$ (0.268 mL, 3.06 mmol) and aqueous 1 M NaOH (6 mL, 6 mmol) were added. The resulting mixture was allowed to warm to room temperature overnight. After concentration under reduced pressure, the residue was purified by ISCO (2×12 g silica gel cartridge, 0-100% EtOAc/hexanes) to give tert-butyl (R)-(1-(2-fluoro-5-(2-hydroxyethyl)phenyl)ethyl) carbamate (0.24 g, 55% yield). LC/MS (M-55): 228; LC retention time: 0.84 min (Method C).

Intermediate I-82

TFA (0.5 mL) was added to a solution of tert-butyl (R)-(1-(2-fluoro-5-(2-hydroxyethyl)phenyl)ethyl)carbamate (0.24 g, 0.847 mmol) in CH$_2$Cl$_2$ (1 mL). After stirring at room temperature for 30 min, the mixture was concentrated under vacuum. The resulting TFA salt was dissolved in MeOH (0.5 mL) and free-based by an ion-exchange cartridge (Phenomenex, strata-X-C 33u polymeric strong cation 1 g/12 mL Giga Tubes) to give (R)-2-(3-(1-aminoethyl)-4-fluorophenyl)ethan-1-ol (0.116 g, 75% yield). LC/MS (M+H): 184; LC retention time: 0.47 min (Method C); $^1$H NMR (400 MHz, chloroform-d) δ 7.29-7.25 (m, 1H), 7.10-7.04 (m, 1H), 6.96 (dd, J=10.4, 8.3 Hz, 1H), 4.37 (q, J=6.7 Hz, 1H), 3.86 (t, J=6.5 Hz, 2H), 2.85 (t, J=6.5 Hz, 2H), 1.42 (d, J=6.6 Hz, 3H).

Intermediate I-83

(R)-2-(3-(1-aminoethyl)-4-fluorophenoxy)ethan-1-ol

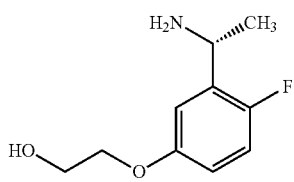
(I-83)

An ethylene glycol (0.786 mL, 14.09 mmol) solution of HCl salt of Intermediate I-70 (0.2 g, 0.786 mmol), copper(II) chloride (5.28 mg, 0.039 mmol) and K$_2$CO$_3$ (0.326 g, 2.357 mmol) was heated at 130° C. in a sealed vial for 20 h. The crude was diluted with MeOH (9 mL) and filtered. The filtrate was purified by preparative reverse-phase HPLC (Condition C, 0-100% solvent B in 10 min then a 2-min hold at 100% B) and free-based with an ion-exchange cartridge (Phenomenex, strata-X-C 33μ polymeric strong cation 1 g/12 mL Giga Tubes) to give (R)-2-(3-(1-aminoethyl)-4-fluorophenoxy)ethan-1-ol (81.2 mg, 52% yield). LC/MS (M+H): 200; LC retention time: 0.46 min (Method C); $^1$H NMR (400 MHz, chloroform-d) δ 7.00 (dd, J=6.0, 3.2 Hz, 1H), 6.98-6.91 (m, 1H), 6.73 (dt, J=8.9, 3.5 Hz, 1H), 4.37 (q, J=6.6 Hz, 1H), 4.09-4.05 (m, 2H), 3.98-3.93 (m, 2H), 1.41 (d, J=6.7 Hz, 3H).

Intermediate I-84

6-bromo-3-chloro-8-fluoro-N-(1-(2-fluorophenyl)ethyl)quinolin-4-amine

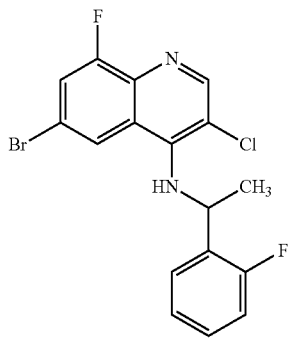
(I-84)

Intermediate I-84 was prepared following the procedure described in Intermediate I-38 by using the corresponding benzylamine. LC/MS (M+H): 397; LC retention time: 0.92 min (analytical HPLC Method C).

Intermediate I-85

Mixture 6-bromo-3,7-dichloro-N-(1-(2-fluorophenyl)ethyl)quinolin-4-amine and 6-bromo-3,5-dichloro-N-(1-(2-fluorophenyl)ethyl)quinolin-4-amine

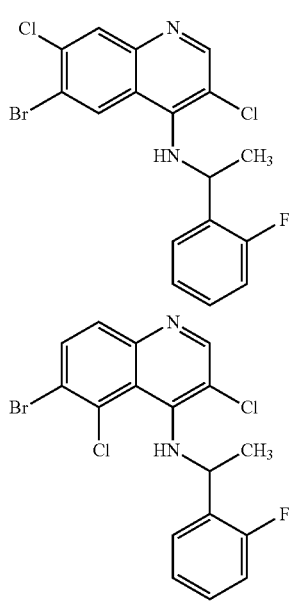
(I-85)

Intermediate I-85A: 5-(((4-bromo-3-chlorophenyl)amino)methylene)-2,2-dimethyl-1,3-dioxane-4,6-dione

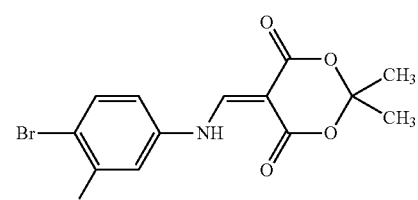
(I-85A)

A mixture of 2,2-dimethyl-1,3-dioxane-4,6-dione (4.19 g, 29.1 mmol) and trimethyl orthoformate (13.38 mL, 121 mmol) was stirred at 100° C. for 90 min. The mixture was cooled to 80° C. 4-bromo-3-chloroaniline (5.0 g, 24.22 mmol) and acetonitrile (60 mL) was added to the mixture and the reaction mixture was stirred at 100° C. for 3.5 hour. The mixture was poured into ethyl ether (300 mL). The solid was collected by filtration and dried under high vacuum to afford 5-(((4-bromo-3-chlorophenyl)amino)methylene)-2,2-dimethyl-1,3-dioxane-4,6-dione (6.01 g, 15.83 mmol, 65.4%, off-white solid). LC/MS (M+H): 360; LC retention time: 1.00 min (analytical HPLC Method C); $^1$H NMR (400 MHz, DMSO-d$_6$) δ 11.22 (br. s., 1H), 8.58 (s, 1H), 7.99 (d, J=2.6 Hz, 1H), 7.80 (d, J=8.8 Hz, 1H), 7.53 (dd, J=8.8, 2.6 Hz, 1H), 1.68 (s, 6H).

Intermediate I-85B: Mixture of 6-bromo-7-chloroquinolin-4-ol and 6-bromo-5-chloroquinolin-4-ol

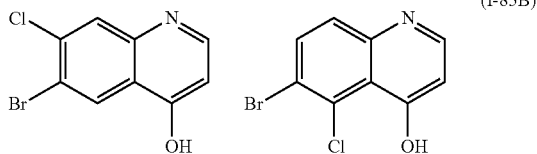

(I-85B)

A mixture of 5-(((4-bromo-3-chlorophenyl)amino)methylene)-2,2-dimethyl-1,3-dioxane-4,6-dione (6.0 g, 16.64 mmol) and Dowtherm A (50 mL) was stirred at 245° C. for 20 min. The mixture was cooled to room temperature. Hexane (35 mL) was added and the solid was collected by filtration. The solid was a mixture of 6-bromo-5-chloroquinolin-4-ol compound and 6-bromo-7-chloroquinolin-4-ol (3.10 g, 5.70 mmol, 34.2% yield) (45:55, by LCMS) as brown solid. LC/MS (M+H): 260; LC retention time: 0.67 and 0.71 min (analytical HPLC Method C).

Intermediate I-85C: Mixture of 6-bromo-3,4,7-trichloroquinoline and 6-bromo-3,4,5-trichloroquinoline

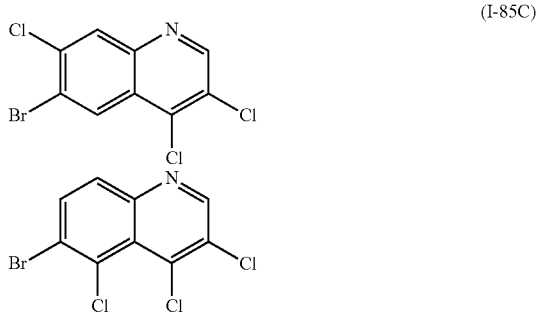

(I-85C)

A mixture of 6-bromo-5-chloroquinolin-4-ol compound and 6-bromo-7-chloroquinolin-4-ol (1:1) (200 mg, 0.387 mmol) and NCS (62.0 mg, 0.464 mmol) in acetonitrile (10 mL) and acetic acid (2.000 mL) was stirred at 90° C. for 18 hour. The solid was collected by filtration, washed with acetonitrile and dried under high vacuum to give crude a mixture of 6-bromo-3,5-dichloroquinolin-4-ol compound and 6-bromo-3,7-dichloroquinolin-4-ol (1:1) as light brown solid. LC/MS (M+H): 292; LC retention time: 0.76 and 0.79 min (analytical HPLC Method C).

A mixture of 6-bromo-3,5-dichloroquinolin-4-ol and 6-bromo-3,7-dichloroquinolin-4-ol (1:1) and POCl$_3$ (0.721 mL, 7.74 mmol) was stirred at 90° C. for 60 min. The mixture was cooled to room temperature and was then concentrated. The mixture was diluted with DCM (15 mL) and was washed with a solution of aqueous saturated sodium bicarbonate (15 mL). The DCM layer was dried over sodium sulfate and concentrated. The crude product was subjected to ISCO flash chromatography (silica gel/hexane-EtOAc 100:0 to 0:100 gradient). The white solid was a mixture of 6-bromo-3,4,5-trichloroquinoline compound and 6-bromo-3,4,7-trichloroquinoline (1:1) (146 mg, 0.211 mmol, 54.5% yield. LC/MS (M+H): 310; LC retention time: 1.13 and 1.27 min (analytical HPLC Method C).

Intermediate I-85

A mixture of 6-bromo-3,4,5-trichloroquinoline compound and 6-bromo-3,4,7-trichloroquinoline (1:1) (70 mg, 0.112 mmol), 1-(2-fluorophenyl)ethanamine (46.9 mg, 0.337 mmol) and (1R)-(−)-camphor-10-sulfonic acid (13.05 mg, 0.056 mmol) in DMA (0.100 mL) was stirred at 130° C. for 2.5 hour. The mixture was cooled to room temperature. LCMS indicated the reaction was not complete. The mixture was stirred for another 2 hours at 140° C. Another portion of 1-(2-fluorophenyl)ethanamine (46.9 mg, 0.337 mmol) and (1R)-(−)-camphor-10-sulfonic acid (13.05 mg, 0.056 mmol) was added and the mixture was stirred at 140° C. for 2 hours. The mixture was cooled to room temperature. The crude product was purified by prep-HPLC (condition A). Two peaks were isolated. $^1$H NMR indicated the first eluted peak was 6-bromo-3,7-dichloro-N-(1-(2-fluorophenyl)ethyl)quinolin-4-amine (12 mg, 0.028 mmol, 24.49% yield), LC/MS (M+H): 413; LC retention time: 0.97 min (analytical HPLC Method C); $^1$H NMR (400 MHz, CHLOROFORM-d) δ 8.80 (s, 1H), 8.40 (s, 1H), 8.30 (s, 1H), 7.43-7.32 (m, 2H), 7.25-7.14 (m, 2H), 5.72 (q, J=6.6 Hz, 1H), 1.87 (d, J=6.6 Hz, 3H). The second eluted peak was 6-bromo-3,5-dichloro-N-(1-(2-fluorophenyl)ethyl)quinolin-4-amine (29 mg, 0.067 mmol, 59.2% yield), LC/MS (M+H): 413; LC retention time: 1.03 min (analytical HPLC Method C); $^1$H NMR (400 MHz, CHLOROFORM-d) δ 8.64 (s, 1H), 8.04-7.99 (m, 1H), 7.98-7.91 (m, 1H), 7.33-7.21 (m, 2H), 7.16-7.00 (m, 2H), 5.83 (q, J=6.6 Hz, 1H), 1.76 (d, J=6.8 Hz, 3H).

Example 1

2-(5-(3-chloro-4-((2,5-dimethylphenyl)amino)-2-methylquinolin-6-yl)pyrimidin-2-yl)propan-2-ol

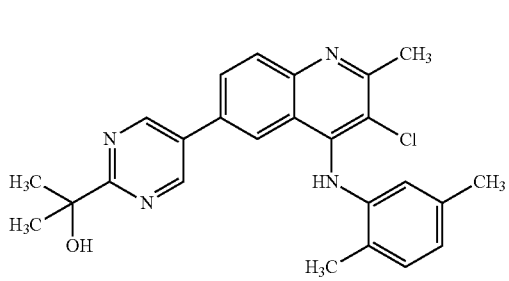

(1)

Intermediate 1A: 6-bromo-N-(2,5-dimethylphenyl)-2-methylquinolin-4-amine

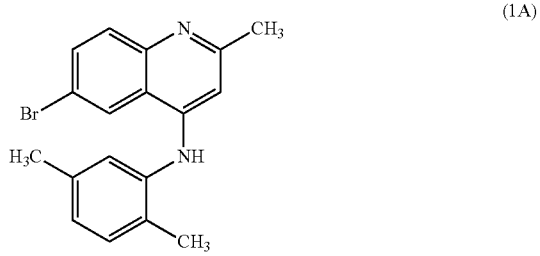 [SMILES: Cc1ccc(C)c(Nc2cc(C)nc3ccc(Br)cc23)c1]

(1A)

A mixture of 6-bromo-4-chloro-2-methylquinoline (0.1 g, 0.390 mmol), (1R)-(−)-camphor-10-sulfonic acid (0.045 g, 0.195 mmol), and 2,5-dimethylaniline (0.2 mL, 1.601 mmol) was stirred at 140° C. under nitrogen for 2 h. The mixture was partitioned between EtOAc (3 mL) and saturated aqueous sodium bicarbonate solution (3 mL). The aqueous layer was separated and extracted with ethyl acetate (3×1 mL). The combined organic solutions were dried over sodium sulfate and concentrated under reduced pressure. Flash chromatography purification (12 g silica gel column, gradient elution from 15 to 100% of ethyl acetate in hexanes) afforded 6-bromo-N-(2,5-dimethylphenyl)-2-methylquinolin-4-amine (0.13 g, 0.381 mmol, 98% yield). LC/MS (M+H): 341, 343; LC retention time: 0.95 min (analytical HPLC Method B); $^1$H NMR (400 MHz, METHANOL-$d_4$) δ 8.50 (d, J=2.0 Hz, 1H), 7.75 (dd, J=9.0, 2.0 Hz, 1H), 7.71 (d, J=8.9 Hz, 1H), 7.24 (d, J=7.7 Hz, 1H), 7.10 (d, J=8.1 Hz, 1H), 7.07 (s, 1H), 6.04 (s, 1H), 2.39 (s, 3H), 2.34 (s, 3H), 2.16 (s, 3H).

Intermediate 1B: 6-bromo-3-chloro-N-(2,5-dimethylphenyl)-2-methylquinolin-4-amine

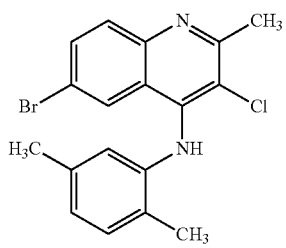

(1B)

A solution of 6-bromo-N-(2,5-dimethylphenyl)-2-methylquinolin-4-amine (106 mg, 0.311 mmol) and N-chlorosuccinimide (41.5 mg, 0.311 mmol) in anhydrous DMF (1 mL) was stirred at room temperature overnight. The mixture was concentrated. Flash chromatography (4 g silica gel column, gradient elution from 5 to 100% of ethyl acetate in hexanes) gave a crude mixture containing 6-bromo-3-chloro-N-(2,5-dimethylphenyl)-2-methylquinolin-4-amine (20 mg) which was used as such for the subsequent step. LC/MS (M+H): 375, 377; LC retention time: 0.98 min (analytical HPLC Method B).

Example 1

The above mixture (20 mg), 2-(1-hydroxy-1-methylethyl)pyrimidine-5-boronic acid pinacol ester (16.87 mg, 0.064 mmol), and 2 M aqueous $K_2CO_3$ (66.5 µl, 0.133 mmol) were mixed with dioxane (177 µl). Nitrogen gas was bubbled for 2 min before $PdCl_2$(dppf)-$CH_2Cl_2$ adduct (6.52 mg, 7.99 µmol) was added. Nitrogen gas was bubbled for an additional 2 min. The vessel was sealed and the mixture was stirred at 100° C. under nitrogen for 3 hr. The crude material was purified via preparative LC/MS using the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 19 minutes, then a 5-minute hold at 100% B; Flow: 20 mL/min. Fractions containing the desired product were combined and dried via centrifugal evaporation to give 2-(5-(3-chloro-4-((2,5-dimethylphenyl)amino)-2-methylquinolin-6-yl)pyrimidin-2-yl)propan-2-ol, TFA (8.6 mg). LC/MS (M+H): 433; LC retention time: 2.13 min (analytical HPLC Method A); $^1$H NMR (500 MHz, DMSO-$d_6$) δ 9.96 (br. s., 1H), 8.91 (s, 2H), 8.33 (d, J=8.7 Hz, 1H), 8.26 (s, 1H), 8.05 (d, J=8.8 Hz, 1H), 7.34-7.24 (m, 1H), 7.17 (m, 1H), 7.09-7.00 (m, 1H), 2.76 (s, 3H), 2.25 (s, 3H), 2.18 (s, 3H), 1.51 (s, 6H).

Example 2

3-chloro-N-(2,5-dimethylphenyl)-2-(((2,5-dimethylphenyl)amino)methyl)-6-(1-methyl-1H-pyrazol-4-yl)quinolin-4-amine

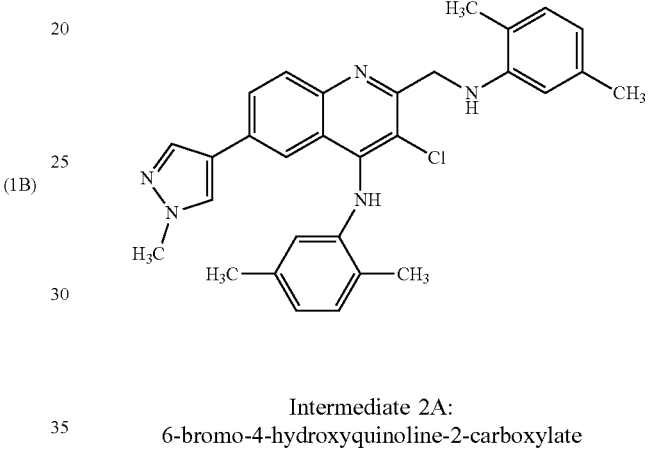

(2)

Intermediate 2A:
6-bromo-4-hydroxyquinoline-2-carboxylate

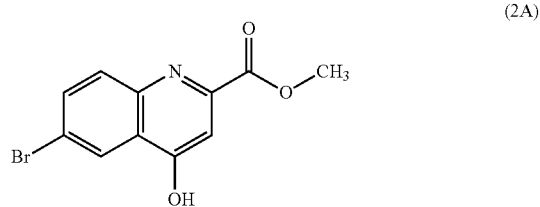 [SMILES: COC(=O)c1cc(O)c2cc(Br)ccc2n1]

(2A)

To a stirred solution of 4-bromoaniline (6 g, 34.9 mmol) in anhydrous MeOH (10 mL) was added dimethyl acetylenedicarboxylate (4.49 mL, 36.6 mmol) dropwise at 0° C. under nitrogen. The mixture was stirred at room temperature overnight. More dimethyl acetylenedicarboxylate (1 mL) was added. The mixture was stirred at room temperature for 1 h and concentrated under reduced pressure to remove MeOH. To the residue was added diphenyl ether (10 mL, 63.0 mmol). The mixture was placed on a sand bath that was preheated to 220° C. The mixture was stirred at 180° C. internal temperature for 1 h, cooled and hexanes (10 mL) was added. The solid was filtered and washed with $Et_2O$ to give methyl 6-bromo-4-hydroxyquinoline-2-carboxylate (0.7 g, 2.481 mmol, 7.11% yield) as a solid. LC/MS (M+H): 282, 284; LC retention time: 0.838 min (analytical HPLC Method B); $^1$H NMR (400 MHz, METHANOL-$d_4$) δ 8.37 (d, J=2.2 Hz, 1H), 7.85 (dd, J=9.0, 2.2 Hz, 1H), 7.79 (d, J=8.8 Hz, 1H), 6.96 (s, 1H), 4.03 (s, 3H).

Intermediate 2B: methyl 6-bromo-3-chloro-4-hydroxyquinoline-2-carboxylate

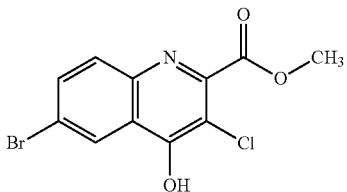

(2B)

A suspension of methyl 6-bromo-4-hydroxyquinoline-2-carboxylate (0.61 g, 2.162 mmol) and N-chlorosuccinimide (0.303 g, 2.271 mmol) in acetonitrile (17 mL) and acetic acid (0.85 mL) was stirred at 90° C. for 5 h. The solid was filtered and washed with Et$_2$O to give methyl 6-bromo-3-chloro-4-hydroxyquinoline-2-carboxylate (0.635 g, 2.006 mmol, 93% yield) as a solid. LC/MS (M+H): 316, 318; LC retention time: 0.915 min (analytical HPLC Method B); $^1$H NMR (400 MHz, METHANOL-d$_4$) δ 8.43 (d, J=2.2 Hz, 1H), 7.82 (dd, J=9.0, 2.1 Hz, 1H), 7.65 (d, J=8.9 Hz, 1H), 4.08 (s, 3H).

Intermediate 2C: Methyl 6-bromo-3,4-dichloroquinoline-2-carboxylate

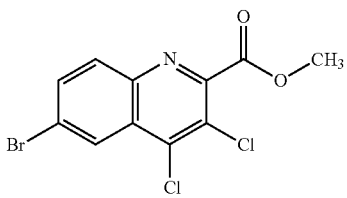

(2C)

Methyl 6-bromo-3-chloro-4-hydroxyquinoline-2-carboxylate (0.63 g, 1.990 mmol) was added to a 25 mL flask followed by POCl$_3$ (3 mL). The reaction mixture was stirred at 105° C. under nitrogen for 1.5 h. The mixture was concentrated under reduced pressure. The residue was quenched with ice (15 g) and then basified with concentrated ammonium hydroxide (5 mL). EtOAc (5 mL) and hexanes (5 mL) were added. The mixture was stirred at 0° C. for 30 min. The solid was filtered and washed with water and then a mixture of EtOAc and hexanes to give a white solid (339 mg). The filtrate was separated. The aqueous layer was extracted with ethyl acetate (3×3 mL). The combined organic solutions were dried over sodium sulfate, filtered, and concentrated under reduced pressure to give a white solid (330 mg). Both solids were methyl 6-bromo-3,4-dichloroquinoline-2-carboxylate (0.669 g, 1.997 mmol, 100% yield). LC/MS (M+H): 334, 336, 338; LC retention time: 1.370 min (analytical HPLC Method B); $^1$H NMR (400 MHz, CHLOROFORM-d) δ 8.41 (d, J=2.2 Hz, 1H), 8.03 (d, J=8.9 Hz, 1H), 7.89 (dd, J=9.0, 2.1 Hz, 1H), 4.08 (s, 3H).

Intermediate 2D: (6-Bromo-3,4-dichloroquinolin-2-yl)methanol

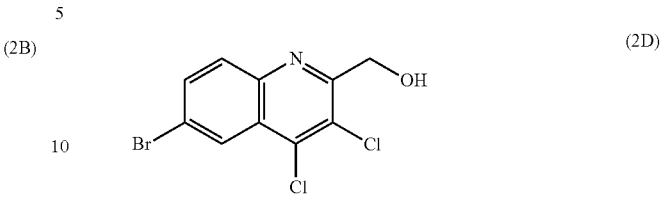

(2D)

Methyl 6-bromo-3,4-dichloroquinoline-2-carboxylate (150 mg, 0.448 mmol) was dissolved in MeOH (0.5 mL) and DCM (0.5 mL). NaBH$_4$ (33.9 mg, 0.896 mmol) was added at 0° C. The mixture was stirred at 0° C. for 1.5 h and at room temperature for 1 h. The reaction was quenched with acetone. Water (1 mL), saturated aqueous sodium bicarbonate solution (2 mL), and EtOAc (2 mL) were added. The solid was filtered and washed with water (2×1 mL) and EtOAc (2×1 mL) to give a white solid (84 mg). The filtrate was extracted with EtOAc. The combined organic solutions were dried over sodium sulfate, filtered, and concentrated under reduced pressure. The solid residue was triturated with methanol to give an off white solid (39 mg). Both solids were (6-bromo-3,4-dichloroquinolin-2-yl)methanol (123 mg, 0.401 mmol, 89% yield). LC/MS (M+H): 306, 308, 310; LC retention time: 1.227 min (analytical HPLC Method B); $^1$H NMR (400 MHz, CHLOROFORM-d) δ 8.39 (d, J=2.1 Hz, 1H), 7.98 (d, J=8.9 Hz, 1H), 7.87 (dd, J=8.9, 2.2 Hz, 1H), 4.93 (d, J=4.6 Hz, 2H), 4.46 (t, J=4.6 Hz, 1H).

Example 2

A mixture of 2,5-dimethylaniline (36.6 µl, 0.293 mmol), (6-bromo-3,4-dichloroquinolin-2-yl)methanol (30 mg, 0.098 mmol), (1R)-(−)-camphor-10-sulfonic acid (11.35 mg, 0.049 mmol), and DMA (0.03 mL) was stirred at 140° C. under nitrogen for 2 h. 1-Methyl-4-(4,4,5,5-tetramethyl-1,3,2-dioxaborolan-2-yl)-1H-pyrazole (24.40 mg, 0.117 mmol), 2M aq. K$_2$CO$_3$ (244 µl, 0.489 mmol), and dioxane (326 µl) were then added at room temperature. Nitrogen was bubbled through the reaction mixture for 2 min. PdCl$_2$(dppf)-CH$_2$Cl$_2$ adduct (11.97 mg, 0.015 mmol) was added. Nitrogen was bubbled through the reaction for an additional 2 min. The vessel was sealed. The mixture was vigorously stirred at 100° C. for 3 h. The crude material was purified via preparative LC/MS using the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-90% B over 19 minutes, then a 5-minute hold at 100% B; Flow: 20 mL/min. Fractions containing the desired product were combined and dried via centrifugal evaporation. The material was further purified via preparative LC/MS with the following conditions: Column: XBridge Phenyl, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-65% B over 25 minutes, then a 2-minute hold at 65% B; Flow: 20 mL/min. Fractions containing the desired product were combined and dried via centrifugal evaporation to yield 3-chloro-N-(2,5-dimethylphenyl)-2-(((2,5-dimethylphenyl)amino)methyl)-6-(1-methyl-1H-pyrazol-4-yl)quinolin-4-amine (7.5 mg, 0.015 mmol, 15% yield. LC/MS (M+H): 496; LC retention time: 2.227 min (analytical HPLC Method A); ¹H NMR (500 MHz, DMSO-d₆) δ 8.02 (s, 1H), 7.96 (s, 2H), 7.89-7.79 (m, 2H), 7.62 (s, 1H), 7.11 (d, J=7.6 Hz, 1H), 6.83 (d, J=7.6 Hz, 1H), 6.49 (s, 1H), 6.43 (s, 1H), 6.33 (s, 1H), 4.09 (s, 2H), 3.74 (br. s., 3H), 2.17 (s, 3H), 2.15 (s, 3H), 2.09 (s, 3H), 1.84 (s, 3H).

Example 3

5-(3-chloro-4-((2,5-dimethylphenyl)amino)-2-(((2,5-dimethylphenyl)amino)methyl)quinolin-6-yl)picolinonitrile

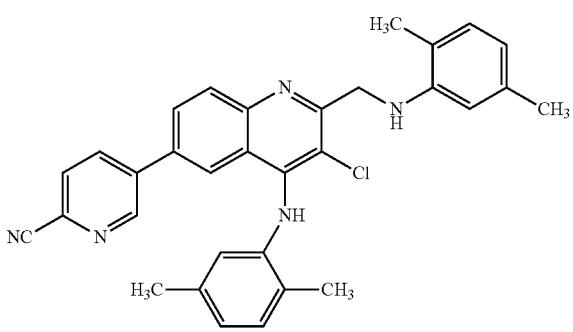

(3)

Example 3 was prepared employing reaction conditions used in the final step for Example 2. LC/MS (M+H): 518; HPLC retention time: 2.439 min (analytical HPLC Method A).

Example 4

2-(5-(3-chloro-4-((2,5-dimethylphenyl)amino)-2-(hydroxymethyl)quinolin-6-yl)pyrimidin-2-yl)propan-2-ol

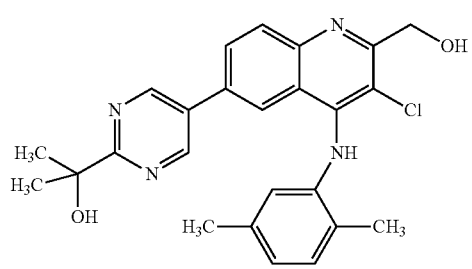

(4)

To a mixture of 2-(1-hydroxy-1-methylethyl)pyrimidine-5-boronic acid pinacol ester (15.37 mg, 0.058 mmol), (6-bromo-3-chloro-4-((2,5-dimethylphenyl)amino) quinolin-2-yl)methanol (19 mg, 0.049 mmol), 2 M aqueous K₂CO₃ (60.6 μl, 0.121 mmol), in dioxane (162 μl), was added [1,1'-bis(diphenylphosphino)ferrocene] dichloropalladium(II) (5.32 mg, 7.28 μmol). Nitrogen gas was bubbled for 2 min. The vessel was sealed. The mixture was stirred at 100° C. under nitrogen for 3 hr. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 5-minute hold at 100% B; Flow: 20 mL/min. Fractions containing the desired product were combined and dried via centrifugal evaporation to yield 2-(5-(3-chloro-4-((2,5-dimethylphenyl)amino)-2-(hydroxymethyl)quinolin-6-yl)pyrimidin-2-yl)propan-2-ol (8.3 mg, 0.018 mmol, 37.7% yield). LC/MS (M+H): 449; LC retention time: 1.993 min (analytical HPLC Method A); ¹H NMR (500 MHz, DMSO-d₆) δ 8.95 (s, 2H), 8.22 (d, J=9.7 Hz, 2H), 8.14-8.06 (m, 2H), 7.16 (d, J=7.8 Hz, 1H), 6.90 (d, J=7.9 Hz, 1H), 6.61 (s, 1H), 5.35 (br. s., 1H), 5.25 (d, J=2.1 Hz, 1H), 4.74 (d, J=5.3 Hz, 2H), 2.19 (s, 3H), 2.13 (s, 3H), 1.50 (s, 6H).

Example 5 ethyl 3-chloro-6-(6-cyanopyridin-3-yl)-4-((2,5-dimethylphenyl)amino)quinoline-2-carboxylate

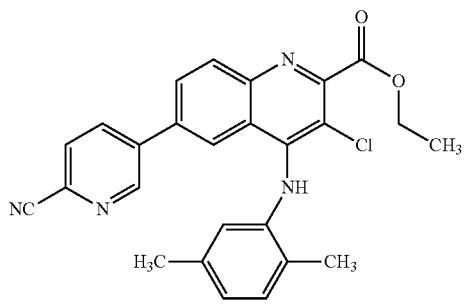

(5)

2-cyanopyridine-5-boronic acid pinacol ester (0.856 g, 3.72 mmol), ethyl 6-bromo-3-chloro-4-((2,5-dimethylphenyl)amino)quinoline-2-carboxylate (Intermediate I-1, 3.1 mmol), PdCl₂(dppf)-CH₂Cl₂ adduct (0.380 g, 0.465 mmol) and 2M aq. K₂CO₃ (3.88 mL, 7.75 mmol) were mixed with dioxane (10.33 mL). The mixture was bubbled with N₂ gas for 2 min. The vessel was sealed. The mixture was stirred at 100° C. under nitrogen for 3 hr. EtOAc (10 mL) was added. The organic solution was dried (Na₂SO₄), filtered, and concentrated. Flash chromatography gave ethyl 3-chloro-6-(6-cyanopyridin-3-yl)-4-((2,5-dimethylphenyl)amino)quinoline-2-carboxylate (1.24 g, 2.71 mmol, 88% yield). LC/MS (M+H): 457.2; LC retention time: 2.292 min (analytical HPLC Method A); ¹H NMR (500 MHz, DMSO-d₆) δ 9.02 (s, 1H), 8.84 (s, 1H), 8.48 (s, 1H), 8.34 (dd, J=8.2, 2.2 Hz, 1H), 8.26-8.20 (m, 1H), 8.17 (d, J=8.2 Hz, 1H), 8.08 (d, J=8.8 Hz, 1H), 7.20 (d, J=7.8 Hz, 1H), 7.01 (d, J=8.0 Hz, 1H), 6.85 (s, 1H), 4.40 (q, J=7.1 Hz, 2H), 2.21 (s, 3H), 2.17 (s, 3H), 1.33 (t, J=7.1 Hz, 3H).

The following compounds were prepared in a similar fashion as Example 5 from the corresponding bromo-intermediates and boronic acids/ester

| Ex. No. | Structure | LCMS m/z observed | HPLC $t_R$ (min) | HPLC method |
|---|---|---|---|---|
| 6 | 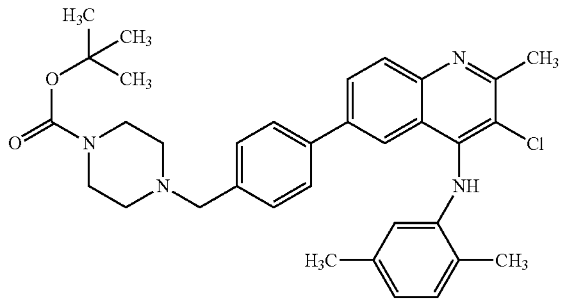 [SMILES: Cc1ccc(C)c(Nc2c(Cl)c(C)nc3ccc(-c4ccc(CN5CCN(C(=O)OC(C)(C)C)CC5)cc4)cc23)c1] | 571 | 2.85 | A |
| 7 | 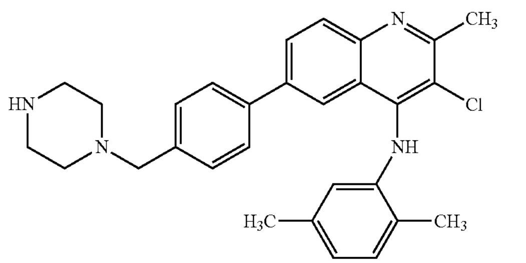 [SMILES: Cc1ccc(C)c(Nc2c(Cl)c(C)nc3ccc(-c4ccc(CN5CCNCC5)cc4)cc23)c1] | 471 | 1.84 | A |
| 8 | 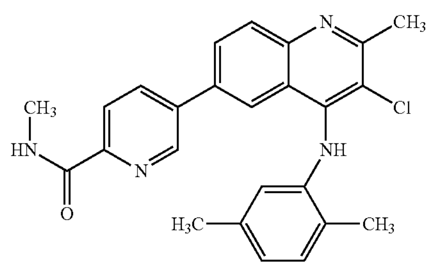 [SMILES: CNC(=O)c1ccc(-c2ccc3nc(C)c(Cl)c(Nc4cc(C)ccc4C)c3c2)cn1] | 431 | 2.111 | A |
| 9 | 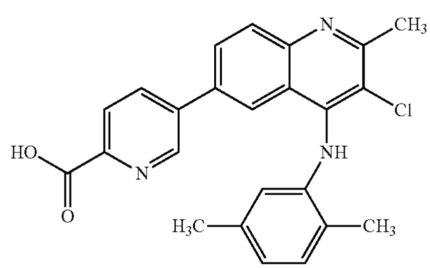 [SMILES: Cc1ccc(C)c(Nc2c(Cl)c(C)nc3ccc(-c4ccc(C(=O)O)nc4)cc23)c1] | 418 | 0.823 | B |
| 10 (±) | 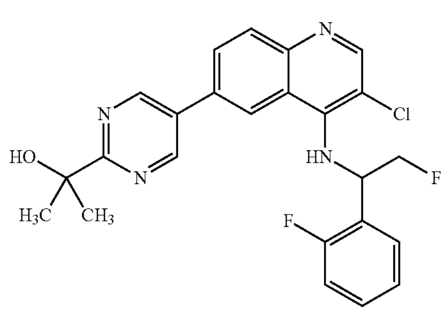 [SMILES: CC(C)(O)c1ncc(-c2ccc3ncc(Cl)c(NC(CF)c4ccccc4F)c3c2)cn1] | 454.9 | 1.884 | A |

-continued

| Ex. No. | Structure | LCMS m/z observed | HPLC $t_R$ (min) | HPLC method |
|---|---|---|---|---|
| 11 | 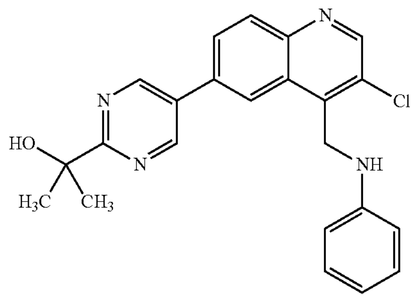 [SMILES: CC(C)(O)c1ncc(-c2ccc3ncc(Cl)c(CNc4ccccc4)c3c2)cn1] | 405.2 | 1.900 | A |
| 12 (±) | 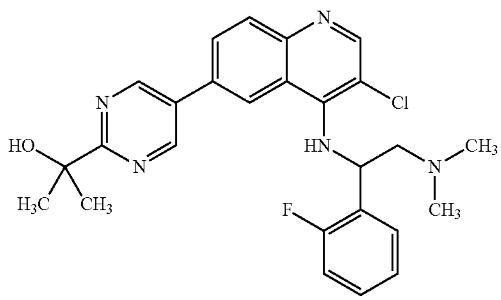 [SMILES: CN(C)CC(Nc1c(Cl)cnc2ccc(-c3cnc(C(C)(C)O)nc3)cc12)c1ccccc1F] | 478.1 | 2.068 | A |
| 13 | 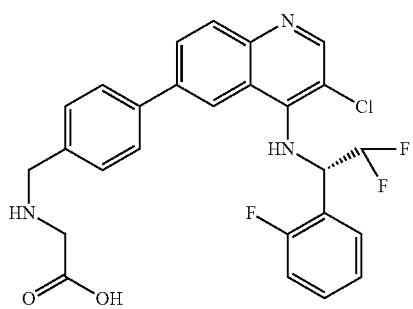 [SMILES: O=C(O)CNCc1ccc(-c2ccc3ncc(Cl)c(N[C@@H](c4ccccc4F)C(F)F)c3c2)cc1] | 500.0 | 1.587 | A |
| 14 | 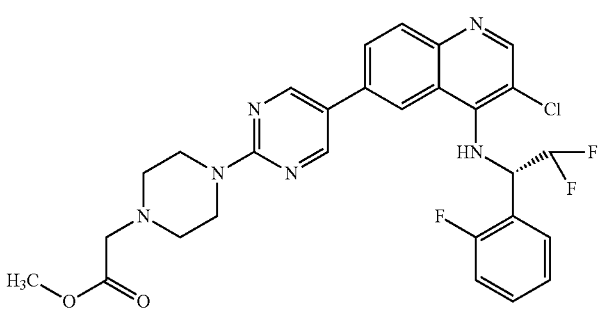 [SMILES: COC(=O)CN1CCN(c2ncc(-c3ccc4ncc(Cl)c(N[C@@H](c5ccccc5F)C(F)F)c4c3)cn2)CC1] | 571.2 | 0.827 | B |
| 15 | 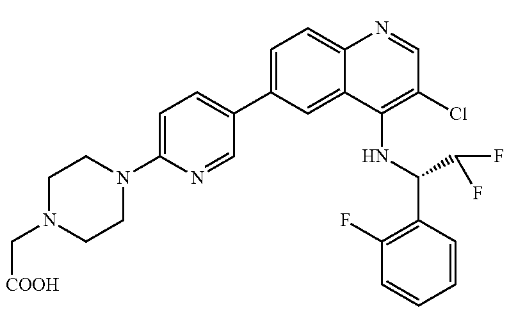 [SMILES: O=C(O)CN1CCN(c2ccc(-c3ccc4ncc(Cl)c(N[C@@H](c5ccccc5F)C(F)F)c4c3)cn2)CC1] | 556.2 | 1.666 | A |

-continued

| Ex. No. | Structure | LCMS m/z observed | HPLC $t_R$ (min) | HPLC method |
|---|---|---|---|---|
| 16 | 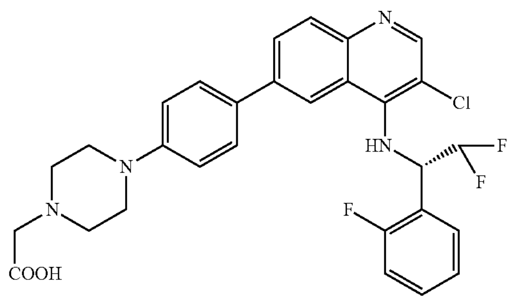 [SMILES: O=C(O)CN1CCN(c2ccc(-c3ccc4ncc(Cl)c(N[C@@H](c5ccccc5F)C(F)F)c4c3)cc2)CC1] | 555.3 | 1.538 | A |
| 17 | 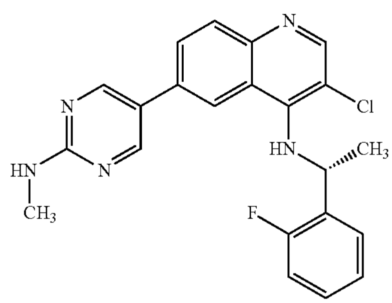 [SMILES: CNc1ncc(-c2ccc3ncc(Cl)c(N[C@H](C)c4ccccc4F)c3c2)cn1] | 408.1 | 1.902 | A |
| 18 (±) | 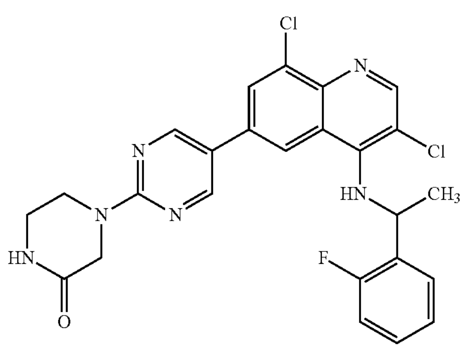 [SMILES: CC(Nc1c(Cl)cnc2c(Cl)cc(-c3cnc(N4CCNC(=O)C4)nc3)cc12)c1ccccc1F] | 511.2 | 1.993 | A |
| 19 (±) | 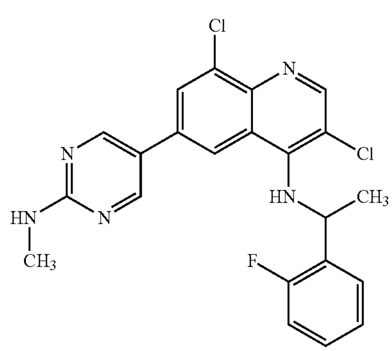 [SMILES: CNc1ncc(-c2cc(Cl)c3ncc(Cl)c(NC(C)c4ccccc4F)c3c2)cn1] | 442.3 | 2.097 | A |

-continued

| Ex. No. | Structure | LCMS m/z observed | HPLC $t_R$ (min) | HPLC method |
|---|---|---|---|---|
| 20 (±) | 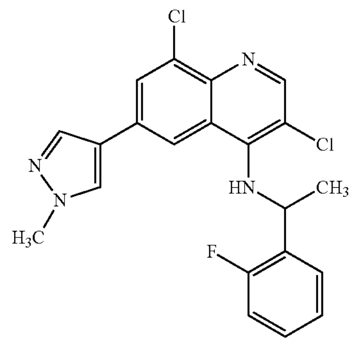 [SMILES: CC(Nc1c(Cl)cnc2c(Cl)cc(-c3cnn(C)c3)cc12)c1ccccc1F] | 415.2 | 2.116 | A |
| 21 (±) | 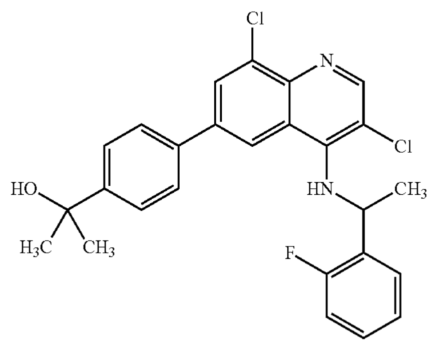 [SMILES: CC(Nc1c(Cl)cnc2c(Cl)cc(-c3ccc(C(C)(C)O)cc3)cc12)c1ccccc1F] | 469.2 | 2.386 | A |
| 22 (±) | 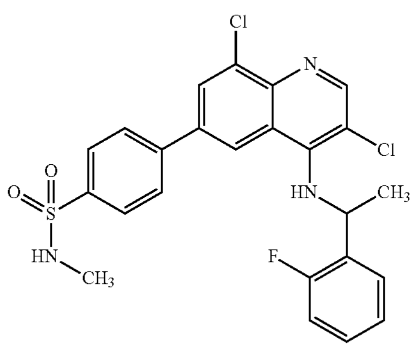 [SMILES: CNS(=O)(=O)c1ccc(-c2cc(Cl)c3ncc(Cl)c(NC(C)c4ccccc4F)c3c2)cc1] | 504.2 | 2.221 | A |
| 23 (±) | 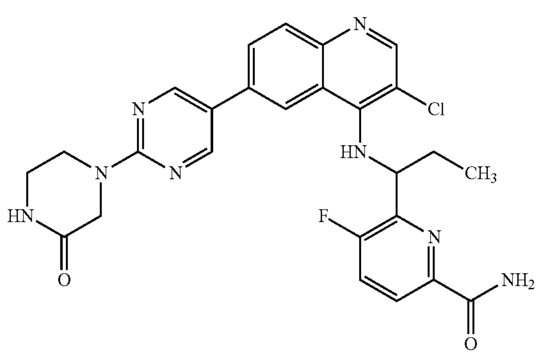 [SMILES: CCC(Nc1c(Cl)cnc2ccc(-c3cnc(N4CCNC(=O)C4)nc3)cc12)c1nc(C(N)=O)ccc1F] | 535.0 | 1.519 | A |

-continued
| Ex. No. | Structure | LCMS m/z observed | HPLC $t_R$ (min) | HPLC method |
|---|---|---|---|---|
| 24 (±) | 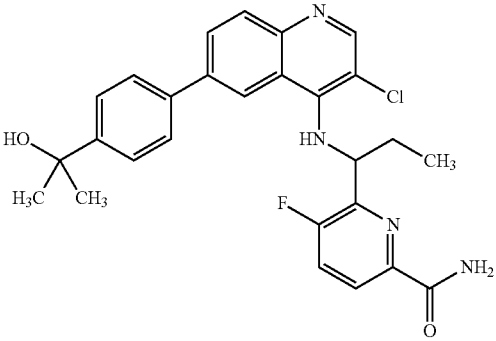 [SMILES: CCC(Nc1c(Cl)cnc2ccc(-c3ccc(C(C)(C)O)cc3)cc12)c1nc(C(N)=O)ccc1F] | 493.0 | 1.843 | A |
| 25 Isomer 1 | 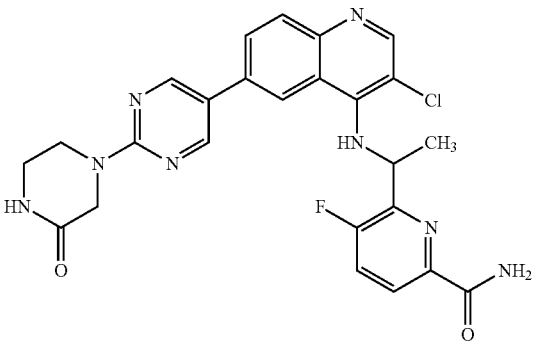 [SMILES: CC(Nc1c(Cl)cnc2ccc(-c3cnc(N4CCNC(=O)C4)nc3)cc12)c1nc(C(N)=O)ccc1F] | 521.2 | 0.747 | B |
| 26 Isomer 2 | | 521.2 | 0.758 | B |
| 27 (±) | 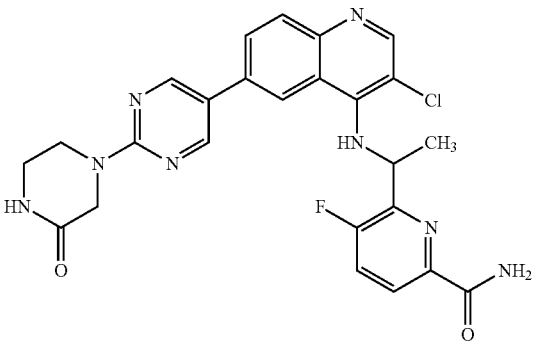 [SMILES: CC(Nc1c(Cl)cnc2ccc(-c3cnc(N4CCNC(=O)C4)nc3)cc12)c1nc(C(N)=O)ccc1F] | 479.2 | 1.795 | A |
| 28 (±) | 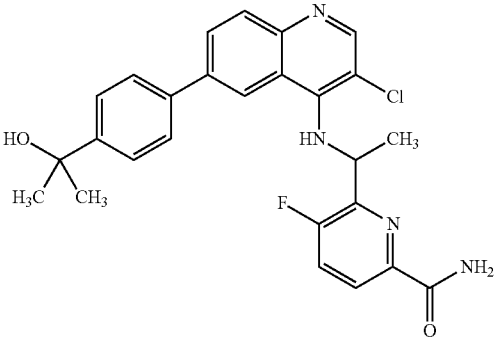 [SMILES: CC(Nc1c(Cl)cnc2ccc(-c3ccc(C(C)(C)O)cc3)cc12)c1nc(C(N)=O)ccc1F] | 481.1 | 1.547 | A |

-continued

| Ex. No. | Structure | LCMS m/z observed | HPLC $t_R$ (min) | HPLC method |
|---|---|---|---|---|
| 29 | 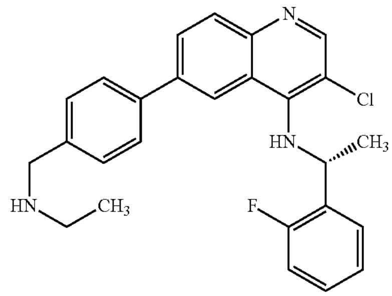 [SMILES: CCNCc1ccc(-c2ccc3ncc(Cl)c(N[C@H](C)c4ccccc4F)c3c2)cc1] | 434.3 | 1.676 | A |
| 30 | 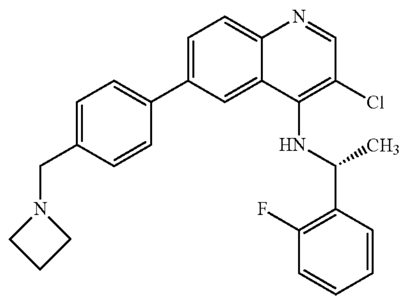 [SMILES: C[C@@H](Nc1c(Cl)cnc2ccc(-c3ccc(CN4CCC4)cc3)cc12)c1ccccc1F] | 446.1 | 1.843 | A |

* column for chiral separation and conditions: OJH (3 × 25 cm, repacked, OJ324), 30% MEOH in CO$_2$, 140 mL/min, 40° C., 100 bars BPR, 220 nm.

Example 31

3-chloro-6-(6-cyanopyridin-3-yl)-4-((2,5-dimethylphenyl)amino)quinoline-2-carboxylic acid

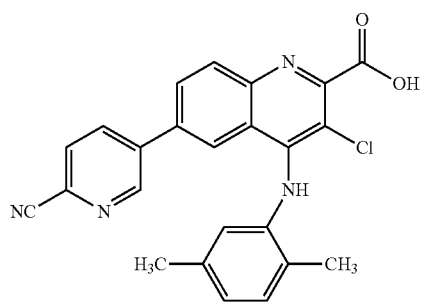

(31)

To a stirred solution of ethyl 3-chloro-6-(6-cyanopyridin-3-yl)-4-((2,5-dimethylphenyl)amino)quinoline-2-carboxylate (Example 5, 100 mg, 0.219 mmol) in tetrahydrofuran (1 mL) was added 30% aq. NaOH (88 mg, 0.657 mmol). The mixture was vigorously stirred at room temperature for 2 h. Water (2 mL) and hexanes (1 mL) were added. The aqueous layer was separated and extracted with hexanes (1 mL). The aqueous layer was acidified with HOAc. The solid was filtered, washed with water, and dried to give 3-chloro-6-(6-cyanopyridin-3-yl)-4-((2,5-dimethylphenyl)amino)quinoline-2-carboxylic acid (45 mg, 0.105 mmol, 47.9% yield) as a yellow solid. The material (7 mg) was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 4-minute hold at 100% B; Flow: 20 mL/min. Fractions containing the desired product were combined and dried via centrifugal evaporation. The yield of the product was 6.0 mg. LC/MS (M+H): 429.0; LC retention time: 1.299 min (analytical HPLC Method A); $^1$H NMR (500 MHz, DMSO-d$_6$) δ 9.00 (s, 1H), 8.78 (s, 1H), 8.44 (br. s., 1H), 8.32 (d, J=8.3 Hz, 1H), 8.21 (d, J=9.0 Hz, 1H), 8.15 (d, J=8.1 Hz, 1H), 8.06 (d, J=8.6 Hz, 1H), 7.19 (d, J=7.7 Hz, 1H), 6.99 (d, J=7.6 Hz, 1H), 6.81 (s, 1H), 2.20 (s, 3H), 2.17 (s, 3H).

Example 32

3-chloro-6-(6-cyanopyridin-3-yl)-4-((2,5-dimethylphenyl)amino)-N-(pyridin-3-yl)quinoline-2-carboxamide

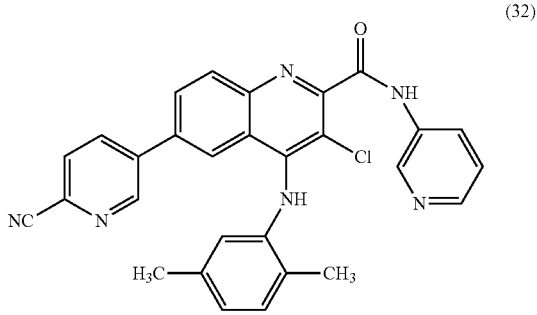 [SMILES: Cc1ccc(C)c(Nc2c(Cl)c(C(=O)Nc3cccnc3)nc3ccc(-c4ccc(C#N)nc4)cc23)c1]

(32)

To a stirred cloudy mixture of 3-chloro-6-(6-cyanopyridin-3-yl)-4-((2,5-dimethylphenyl)amino)quinoline-2-carboxylic acid (Example 31, 10 mg, 0.023 mmol), 3-aminopyridine (8.78 mg, 0.093 mmol), and anhydrous THF (3 mL) was added BOP (41.3 mg, 0.093 mmol) at room temperature under nitrogen. The mixture was stirred at room temperature for 2 hr. And concentrated. The crude material was purified via preparative LC/MS using the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 20 minutes, then a 4-minute hold at 100% B; Flow: 20 mL/min. Fractions containing the desired product were combined and dried via centrifugal evaporation. The yield of the product was 7.5 mg. LC/MS (M+H): 505.2; LC retention time: 2.004 min (analytical HPLC Method A); $^1$H NMR (500 MHz, DMSO-d$_6$) δ 11.33 (s, 1H), 9.06 (br. s., 1H), 8.98 (s, 1H), 8.82 (s, 1H), 8.47 (br. s., 1H), 8.44 (s, 1H), 8.36 (d, J=8.2 Hz, 1H), 8.31 (d, J=8.2 Hz, 1H), 8.24 (d, J=7.8 Hz, 1H), 8.15 (t, J=8.0 Hz, 2H), 7.69-7.65 (m, 1H), 7.29-7.14 (m, 2H), 7.06 (s, 1H), 7.01 (d, J=7.7 Hz, 1H), 6.84 (s, 1H), 2.22 (s, 3H), 2.19 (s, 3H).

The following compounds were prepared in a similar fashion as in Example 32 from the corresponding intermediates.

| Ex. No. | Structure | LCMS m/z observed | HPLC t$_R$ (min) | HPLC method |
|---|---|---|---|---|
| 33 | 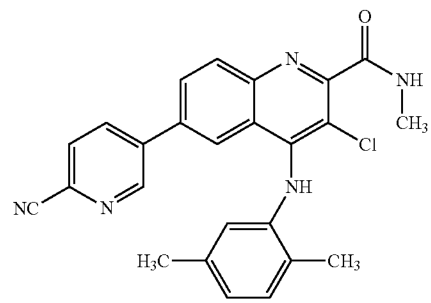 [SMILES: CNC(=O)c1nc2ccc(-c3ccc(C#N)nc3)cc2c(Nc2cc(C)ccc2C)c1Cl] | 442.3 | 1.804 | A |
| 34 | 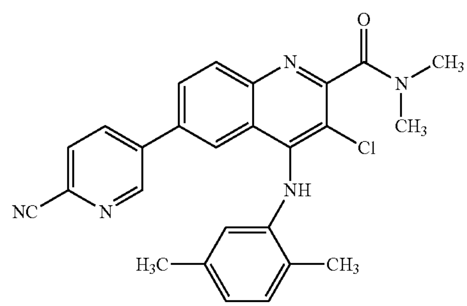 [SMILES: Cc1ccc(C)c(Nc2c(Cl)c(C(=O)N(C)C)nc3ccc(-c4ccc(C#N)nc4)cc23)c1] | 455.9 | 1.815 | A |
| 35 | 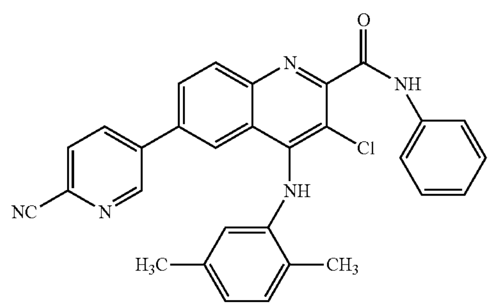 [SMILES: Cc1ccc(C)c(Nc2c(Cl)c(C(=O)Nc3ccccc3)nc3ccc(-c4ccc(C#N)nc4)cc23)c1] | 504.3 | 2.316 | A |
| 36 | 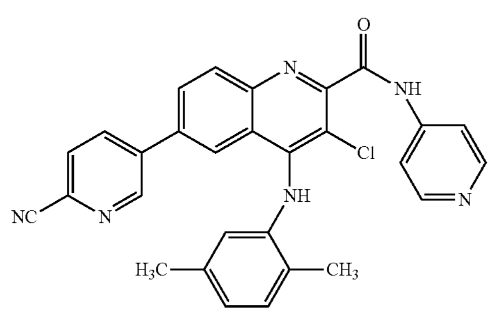 | 505.0 | 1.986 | A |

| Ex. No. | Structure | LCMS m/z observed | HPLC $t_R$ (min) | HPLC method |
|---|---|---|---|---|
| 37 | 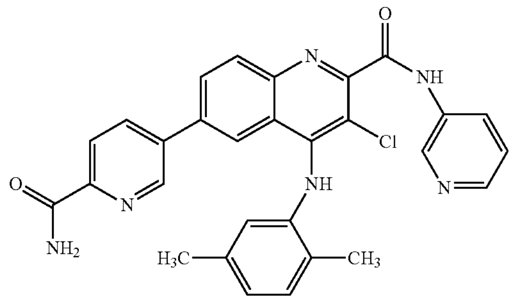 [SMILES: Cc1ccc(C)c(Nc2c(Cl)c(C(=O)Nc3cccnc3)nc3ccc(-c4ccc(C(N)=O)nc4)cc23)c1] | 523.0 | 1.649 | A |
| 38 (±) | 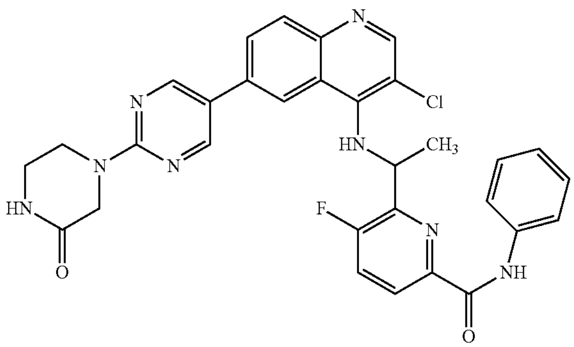 [SMILES: CC(Nc1c(Cl)cnc2ccc(-c3cnc(N4CCNC(=O)C4)nc3)cc12)c1nc(C(=O)Nc2ccccc2)ccc1F] | 597.3 | 1.884 | A |
| 39 (±) | 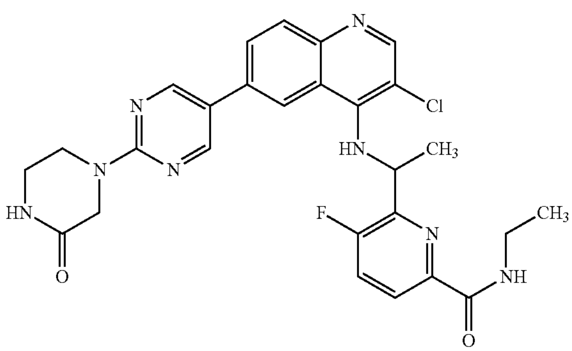 [SMILES: CCNC(=O)c1ccc(F)c(C(C)Nc2c(Cl)cnc3ccc(-c4cnc(N5CCNC(=O)C5)nc4)cc23)n1] | 549.3 | 1.653 | A |

Example 40

5-(3-chloro-4-((2,5-dimethylphenyl)amino)-2-(hydroxymethyl)quinolin-6-yl)picolinonitrile

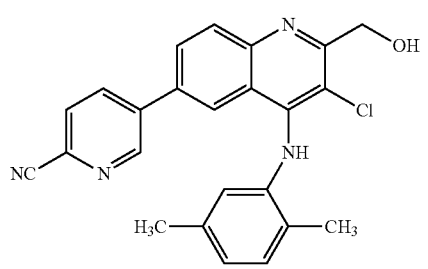

(40)

Ethyl 3-chloro-6-(6-cyanopyridin-3-yl)-4-((2,5-dimethylphenyl)amino)quinoline-2-carboxylate (Example 5, 0.51 g, 1.116 mmol) was dissolved in MeOH (3 mL) and DCM (3 mL). NaBH$_4$ (0.084 g, 2.232 mmol) was added at room temperature. The mixture was stirred at room temperature for 2 h. More NaBH$_4$ (0.084 g, 2.232 mmol) was added at 0° C. The mixture was stirred at 0° C. for 5 h and at room temperature overnight. Acetone (1 mL) was added at 0° C. to quench the reaction. The mixture was concentrated to remove solvents. The residue was mixed with water (10 mL), EtOAc (20 mL), and potassium carbonate (0.5 g). The aqueous layer was separated and extracted with ethyl acetate (3×3 mL). The combined organic solutions were washed with water (5 mL), dried over sodium sulfate, filtered, and concentrated under reduced pressure. The residue was triturated with methanol to give 5-(3-chloro-4-((2,5-dimethylphenyl)amino)-2-(hydroxymethyl)quinolin-6-yl)picolinonitrile (0.17 g, 0.410 mmol, 36.7% yield) as a yellow solid. LC/MS (M+H): 415.2; LC retention time: 0.893 min (analytical HPLC Method B); $^1$H NMR (400 MHz, DMSO-d$_6$) δ 9.00 (dd, J=2.3, 0.7 Hz, 1H), 8.40 (d, J=2.0 Hz, 1H), 8.38 (s, 1H), 8.34-8.29 (m, 1H), 8.21-8.14 (m, 2H), 8.09 (d, J=8.7

Hz, 1H), 7.18 (d, J=7.7 Hz, 1H), 6.93 (d, J=7.6 Hz, 1H), 6.70 (s, 1H), 5.20 (t, J=5.6 Hz, 1H), 4.74 (d, J=5.6 Hz, 2H), 2.20 (s, 3H), 2.17 (s, 3H).

Example 41

5-(3-chloro-4-((2,5-dimethylphenyl)amino)-2-((pyridin-3-yloxy)methyl)quinolin-6-yl)picolinonitrile

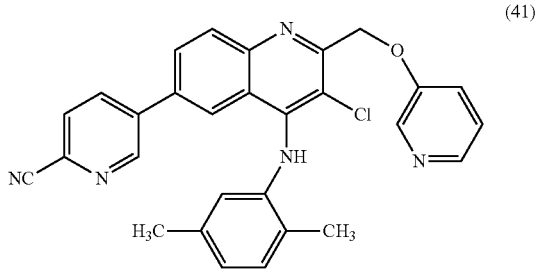 [SMILES: Cc1ccc(C)c(Nc2c(Cl)c(COc3cccnc3)nc3ccc(-c4ccc(C#N)nc4)cc23)c1]

(41)

Diisopropyl azodicarboxylate (0.019 mL, 0.096 mmol) was added dropwise to a solution of 5-(3-chloro-4-((2,5-dimethylphenyl)amino)-2-(hydroxymethyl)quinolin-6-yl) picolinonitrile (Example 40, 20 mg, 0.048 mmol), 3-hydroxypyridine (5.50 mg, 0.058 mmol) and triphenylphosphine (25.3 mg, 0.096 mmol) in dry THF (1 mL) at 0° C. Resultant solution was allowed to warm up to room temperature and stirred for 3 h. The solvent was removed in vacuo. The crude material was purified via preparative LC/MS using the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 4-minute hold at 100% B; Flow: 20 mL/min. Fractions containing the desired product were combined and dried via centrifugal evaporation. The yield of the product was 11.9 mg. LC/MS (M+H): 491.9; LC retention time: 2.167 min (analytical HPLC Method A); $^1$H NMR (500 MHz, DMSO-$d_6$) δ 8.95 (s, 1H), 8.66 (br. s., 1H), 8.50 (br. s., 1H), 8.37 (s, 1H), 8.31-8.24 (m, 2H), 8.21-8.10 (m, 2H), 8.04 (d, J=8.7 Hz, 1H), 7.72 (d, J=8.5 Hz, 1H), 7.55-7.45 (m, 1H), 7.27-7.11 (m, 2H), 7.04 (s, 1H), 6.97 (d, J=7.7 Hz, 1H), 6.75 (s, 1H), 5.51 (s, 2H), 2.18 (s, 6H).

Example 42

5-(2-(azidomethyl)-3-chloro-4-((2,5-dimethylphenyl)amino)quinolin-6-yl)picolinonitrile

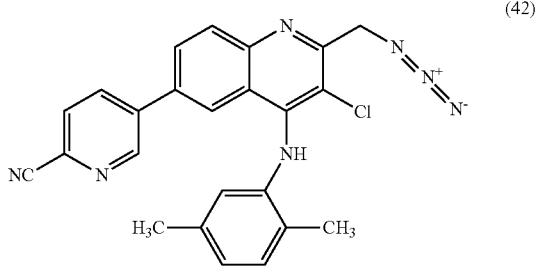 [SMILES: Cc1ccc(C)c(Nc2c(Cl)c(CN=[N+]=[N-])nc3ccc(-c4ccc(C#N)nc4)cc23)c1]

(42)

To a stirred solution of 5-(3-chloro-4-((2,5-dimethylphenyl)amino)-2-(hydroxymethyl)quinolin-6-yl)picolinonitrile (Example 40, 73 mg, 0.176 mmol) in anhydrous THF (2 mL) was added 1,8-diazabicyclo[5.4.0]undec-7-ene (0.037 mL, 0.246 mmol) and diphenylphosphoryl azide (0.053 mL, 0.246 mmol) at room temperature under nitrogen. The mixture was stirred at room temperature for 3 h. Concentration and flash chromatography gave 5-(2-(azidomethyl)-3-chloro-4-((2,5-dimethylphenyl)amino) quinolin-6-yl)picolinonitrile (30 mg, 0.065 mmol, 36.8% yield) as a solid. LC/MS (M+H): 440.2; LC retention time: 1.107 min (analytical HPLC Method B); $^1$H NMR (400 MHz, METHANOL-$d_4$) δ 8.51 (dd, J=2.2, 0.9 Hz, 1H), 8.10 (d, J=8.8 Hz, 1H), 7.96 (dd, J=8.9, 2.1 Hz, 1H), 7.92-7.87 (m, 1H), 7.87-7.83 (m, 1H), 7.80 (d, J=1.8 Hz, 1H), 7.76 (s, 1H), 7.26 (d, J=7.7 Hz, 1H), 7.11 (d, J=6.8 Hz, 1H), 6.88 (s, 1H), 4.78 (br. s., 2H), 2.25 (s, 3H), 2.24 (s, 3H).

Example 43

5-(2-(aminomethyl)-3-chloro-4-((2,5-dimethylphenyl)amino)quinolin-6-yl)picolinonitrile

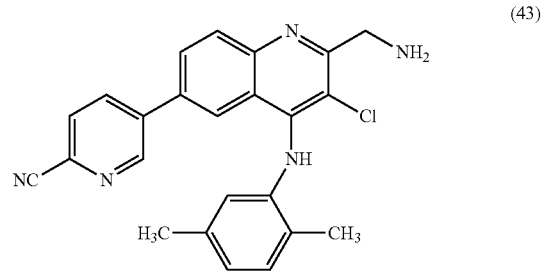 [SMILES: Cc1ccc(C)c(Nc2c(Cl)c(CN)nc3ccc(-c4ccc(C#N)nc4)cc23)c1]

(43)

A solution of 5-(2-(azidomethyl)-3-chloro-4-((2,5-dimethylphenyl)amino) quinolin-6-yl)picolinonitrile (Example 42, 30 mg, 0.068 mmol) and triphenylphosphine (Example 42, 26.8 mg, 0.102 mmol) in THF (2 mL) and water (0.2 mL) was stirred at room temperature overnight. The mixture was concentrated in vacuo to remove THF and water. The residue was triturated with some methanol to give 5-(2-(aminomethyl)-3-chloro-4-((2,5-dimethylphenyl)amino) quinolin-6-yl)picolinonitrile (18 mg, 0.043 mmol, 63.8% yield). Some of the product was further purified via preparative LC/MS using the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 4-minute hold at 100% B; Flow: 20 mL/min. Fractions containing the desired product were combined and dried via centrifugal evaporation. LC/MS (M+H): 414.2; LC retention time: 1.65 min (analytical HPLC Method A); $^1$H NMR (500 MHz, DMSO-$d_6$) δ 9.02 (s, 1H), 8.70 (s, 1H), 8.49 (s, 1H), 8.33 (d, J=8.2 Hz, 1H), 8.24 (d, J=8.8 Hz, 1H), 8.17 (d, J=8.2 Hz, 1H), 8.10 (d, J=8.9 Hz, 1H), 7.29-7.14 (m, 2H), 7.00 (d, J=7.6 Hz, 1H), 6.77 (s, 1H), 4.39 (br. s., 2H), 2.20 (s, 3H), 2.17 (s, 3H).

Example 44

2-(5-(3-chloro-4-((2,5-dimethylphenyl)amino)-2-(hydroxymethyl)quinolin-6-yl)pyrimidin-2-yl)propan-2-ol

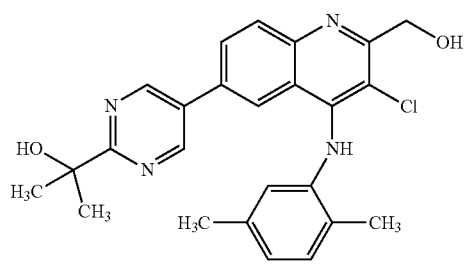

(44)

To a mixture of 2-(1-hydroxy-1-methylethyl)pyrimidine-5-boronic acid pinacol ester (15.37 mg, 0.058 mmol), (6-bromo-3-chloro-4-((2,5-dimethylphenyl)amino) quinolin-2-yl)methanol (Intermediate I-2, 19 mg, 0.049 mmol), 2 M aq. $K_2CO_3$ (60.6 µl, 0.121 mmol), dioxane (162 µl), and [1,1'-bis(diphenylphosphino)ferrocene] dichloropalladium (II) (5.32 mg, 7.28 µmol) was bubbled with $N_2$ gas for 2 min. The vessel was sealed. The mixture was stirred at 100° C. under nitrogen for 3 hr. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 5-minute hold at 100% B; Flow: 20 mL/min. Fractions containing the desired product were combined and dried via centrifugal evaporation to give 2-(5-(3-chloro-4-((2,5-dimethylphenyl)amino)-2-(hydroxymethyl)quinolin-6-yl)pyrimidin-2-yl)propan-2-ol (8.3 mg, 0.018 mmol, 37.7% yield, 99% purity). LC/MS (M+H): 449; LC retention time: 1.99 min (analytical HPLC Method A); $^1$H NMR (500 MHz, DMSO-$d_6$) δ 8.95 (s, 2H), 8.22 (d, J=9.7 Hz, 2H), 8.14-8.06 (m, 2H), 7.16 (d, J=7.8 Hz, 1H), 6.90 (d, J=7.9 Hz, 1H), 6.61 (s, 1H), 5.35 (br. s., 1H), 5.25 (d, J=2.1 Hz, 1H), 4.74 (d, J=5.3 Hz, 2H), 2.19 (s, 3H), 2.13 (s, 3H), 1.50 (s, 6H).

Example 45

2-(4-(5-(2-amino-3-chloro-4-((2,5-dimethylphenyl)amino)quinolin-6-yl)pyrimidin-2-yl)piperazin-1-yl) acetic acid

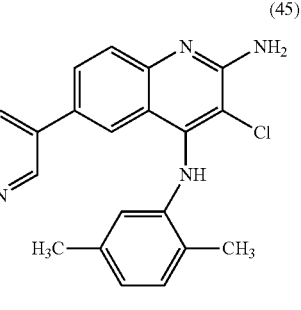

(45)

6-bromo-3-chloro-N4-(2,5-dimethylphenyl)quinoline-2,4-diamine (Intermediate I-4, 40 mg, 0.106 mmol), (2-(4-(2-ethoxy-2-oxoethyl)piperazin-1-yl)pyrimidin-5-yl)boronic acid (156 mg, 0.265 mmol), $PdCl_2(dppf)\text{-}CH_2Cl_2$ adduct (17.34 mg, 0.021 mmol), and 2M aq. $K_2CO_3$ (186 µl, 0.372 mmol) were mixed with dioxane (354 µl). The reaction mixture was purged with nitrogen gas for 2 min. The vessel was sealed. The mixture was vigorously stirred at 100° C. for 3 h. Saturated aqueous sodium bicarbonate solution (2 mL) was added. The mixture was extracted with ethyl acetate (3×1 mL). The combined organic solutions were concentrated under reduced pressure. The residue was mixed with methanol (1 mL) and 30% aqueous NaOH (150 mg, 1.125 mmol) was added and the mixture was heated to 70° C. for 1 h. The crude material was purified via preparative LC/MS using the following conditions: Column: XBridge Phenyl, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 minutes, then a 5-minute hold at 100% B; Flow: 20 mL/min. Fractions containing the desired product were combined and dried via centrifugal evaporation. The yield of the product was 21.2 mg. LC/MS (M+H): 518.3; LC retention time: 1.318 min (analytical HPLC Method A);

The following compound was prepared in a similar fashion

| Ex. No. | Structure | LCMS m/z observed | HPLC $t_R$ (min) | HPLC method |
|---|---|---|---|---|
| 46 (±) | (structure shown) | 536.3 | 1.312 | A |

Example 47

2-(5-(3-chloro-4-(indolin-1-ylamino)quinolin-6-yl)pyrimidin-2-yl)propan-2-ol

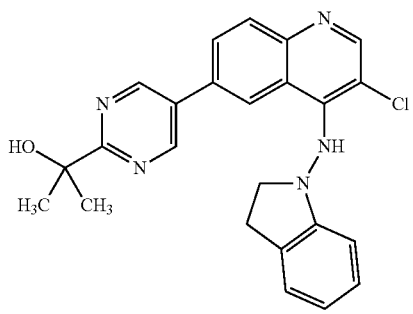

(47)

A mixture of indolin-1-amine, HCl (22.98 mg, 0.135 mmol), 2-(5-(3,4-dichloroquinolin-6-yl)pyrimidin-2-yl)propan-2-ol (Intermediate I-45, 15 mg, 0.045 mmol), DBU (0.014 mL, 0.090 mmol), and anhydrous DMA (0.05 mL) was stirred under nitrogen at 90° C. for 1 h and at 100° C. for 1 h. The crude material was purified via preparative LC/MS using the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to give 2-(5-(3-chloro-4-(indolin-1-ylamino)quinolin-6-yl)pyrimidin-2-yl)propan-2-ol (6.9 mg, 0.015 mmol; 34.5% yield, 97% purity) LC/MS (M+H): 432; LC retention time: 2.01 min (analytical HPLC Method A); $^1$H NMR (500 MHz, DMSO-$d_6$) δ 9.11 (s, 2H), 9.08 (br. s., 1H), 8.72 (br. s., 1H), 8.60 (s, 1H), 8.16 (d, J=8.9 Hz, 1H), 8.04 (d, J=8.8 Hz, 1H), 7.20 (d, J=7.2 Hz, 1H), 7.10 (t, J=7.6 Hz, 1H), 6.85 (t, J=7.4 Hz, 1H), 6.75 (d, J=7.7 Hz, 1H), 5.14 (s, 1H), 3.73 (br. s., 2H), 3.00 (d, J=13.4 Hz, 2H), 1.51 (s, 6H).

The following compounds were prepared in a similar fashion as outlined for Example 47

| Ex. No. | Structure | LCMS m/z observed | HPLC $t_R$ (min) | HPLC method |
|---|---|---|---|---|
| 48 (±) | 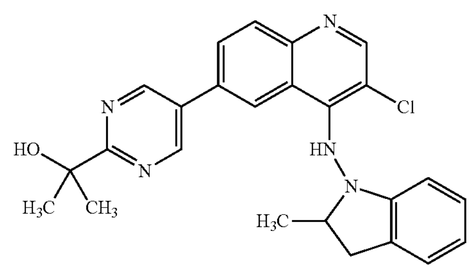 [SMILES: CC1Cc2ccccc2N1Nc1c(Cl)cnc2ccc(-c3cnc(C(C)(C)O)nc3)cc12] | 446.3 | 2.069 | A |
| 49 (±) | 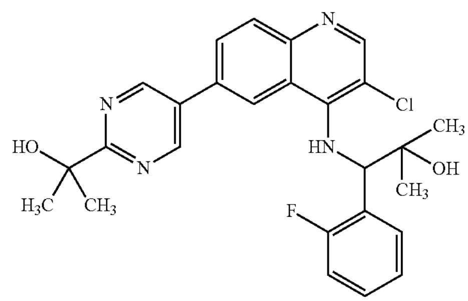 [SMILES: CC(C)(O)c1ncc(-c2ccc3ncc(Cl)c(NC(c4ccccc4F)C(C)(C)O)c3c2)cn1] | 481.3 | 1.890 | A |
| 50 (±) | 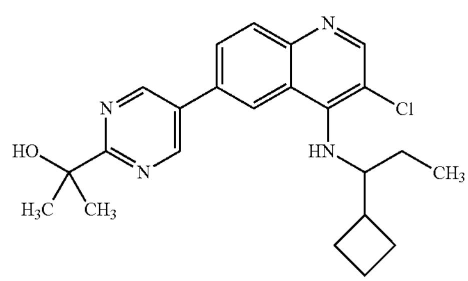 [SMILES: CCC(Nc1c(Cl)cnc2ccc(-c3cnc(C(C)(C)O)nc3)cc12)C1CCC1] | 410.9 | 2.314 | A |

-continued

| Ex. No. | Structure | LCMS m/z observed | HPLC $t_R$ (min) | HPLC method |
|---|---|---|---|---|
| 51 (±) | 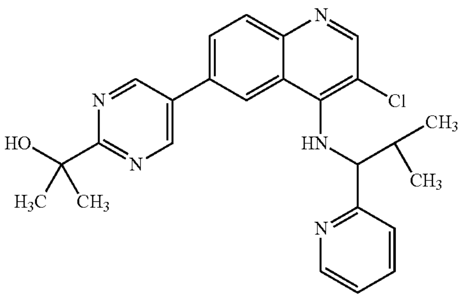 [SMILES: CC(C)C(Nc1c(Cl)cnc2ccc(-c3cnc(C(C)(C)O)nc3)cc12)c1ccccn1] | 447.9 | 2.087 | A |
| 52 (±) | 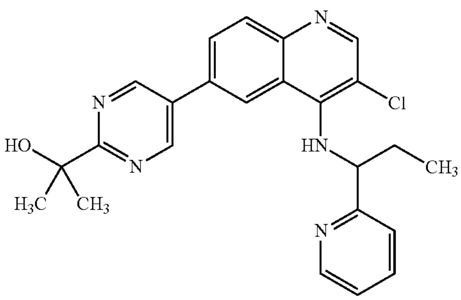 [SMILES: CCC(Nc1c(Cl)cnc2ccc(-c3cnc(C(C)(C)O)nc3)cc12)c1ccccn1] | 434.2 | 1.892 | A |
| 53 | 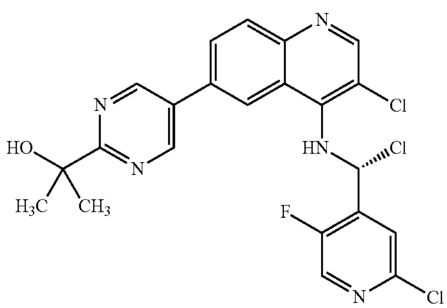 [SMILES: CC(C)(O)c1ncc(-c2ccc3ncc(Cl)c(N[C@H](Cl)c4cc(Cl)ncc4F)c3c2)cn1] | 471.9 | 1.852 | A |

The following analogs were prepared according to the general process described in Intermediate 1A or Intermediate 126A starting from Intermediate I-45.

| Ex. No. | Structure | LCMS m/z observed | HPLC $t_R$ (min) | HPLC method |
|---|---|---|---|---|
| 54 | 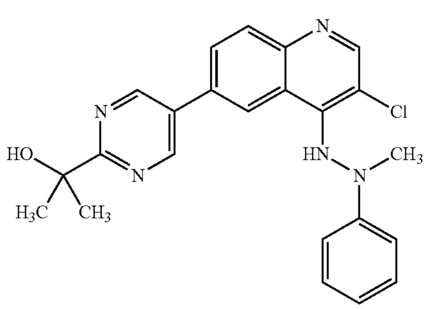 [SMILES: CN(Nc1c(Cl)cnc2ccc(-c3cnc(C(C)(C)O)nc3)cc12)c1ccccc1] | 420.3 | 1.889 | A |

-continued

| Ex. No. | Structure | LCMS m/z observed | HPLC $t_R$ (min) | HPLC method |
|---|---|---|---|---|
| 55 (±) 55a Isomer 2 | 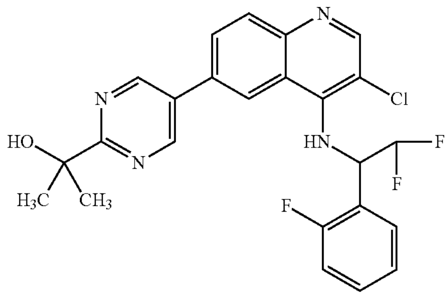 [SMILES: CC(C)(O)c1ncc(-c2ccc3ncc(Cl)c(NC(c4ccccc4F)C(F)F)c3c2)cn1] | 472.9 473.2 | 1.930 0.953 | A B |
| 56 | 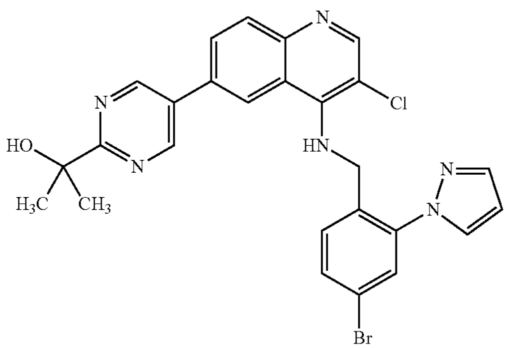 [SMILES: CC(C)(O)c1ncc(-c2ccc3ncc(Cl)c(NCc4ccc(Br)cc4-n4cccn4)c3c2)cn1] | 548.9 | 2.104 | A |
| 57 (±) | 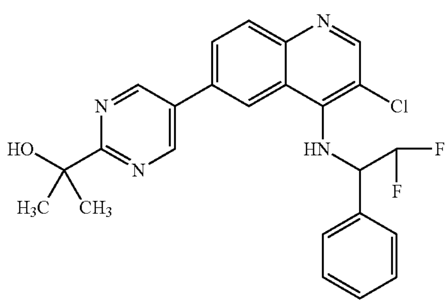 [SMILES: CC(C)(O)c1ncc(-c2ccc3ncc(Cl)c(NC(c4ccccc4)C(F)F)c3c2)cn1] | 455.2 | 2.014 | A |
| 58 | 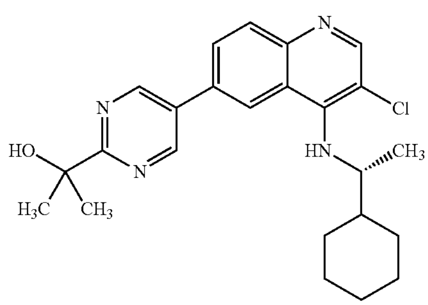 [SMILES: C[C@@H](Nc1c(Cl)cnc2ccc(-c3cnc(C(C)(C)O)nc3)cc12)C1CCCCC1] | 425.3 | 2.457 | A |
| 59 | 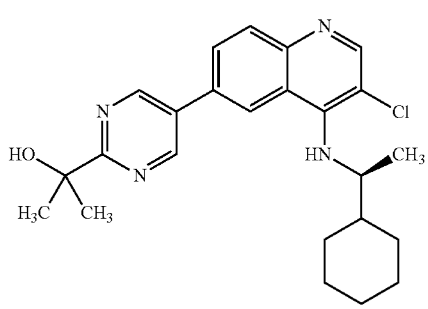 [SMILES: C[C@H](Nc1c(Cl)cnc2ccc(-c3cnc(C(C)(C)O)nc3)cc12)C1CCCCC1] | 425.0 | 2.456 | A |

-continued

| Ex. No. | Structure | LCMS m/z observed | HPLC $t_R$ (min) | HPLC method |
|---|---|---|---|---|
| 60 (diastereomeric mixture) | 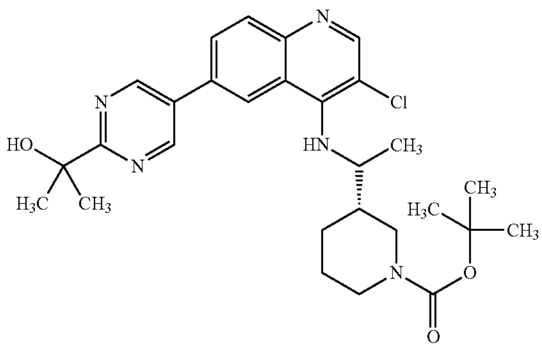 [SMILES: CC(Nc1c(Cl)cnc2ccc(-c3cnc(C(C)(C)O)nc3)cc12)[C@H]1CCCN(C(=O)OC(C)(C)C)C1] | 526.3 | 2.184 | A |
| 61 (diastereomeric mixture) | 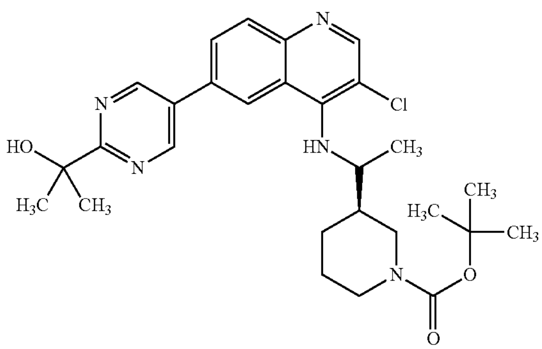 [SMILES: CC(Nc1c(Cl)cnc2ccc(-c3cnc(C(C)(C)O)nc3)cc12)[C@@H]1CCCN(C(=O)OC(C)(C)C)C1] | 526.1 | 0.958 | B |
| 62 (±) | 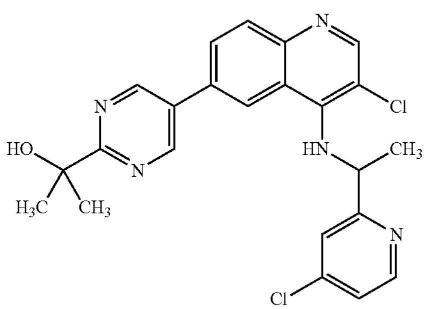 [SMILES: CC(Nc1c(Cl)cnc2ccc(-c3cnc(C(C)(C)O)nc3)cc12)c1cc(Cl)ccn1] | 454.2 | 1.994 | A |
| 63 | 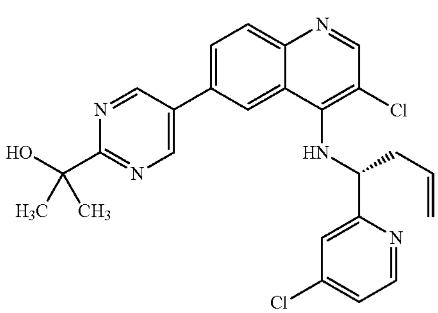 [SMILES: C=CC[C@@H](Nc1c(Cl)cnc2ccc(-c3cnc(C(C)(C)O)nc3)cc12)c1cc(Cl)ccn1] | 479.9 | 2.154 | A |

| Ex. No. | Structure | LCMS m/z observed | HPLC $t_R$ (min) | HPLC method |
|---|---|---|---|---|
| 64 (±) | 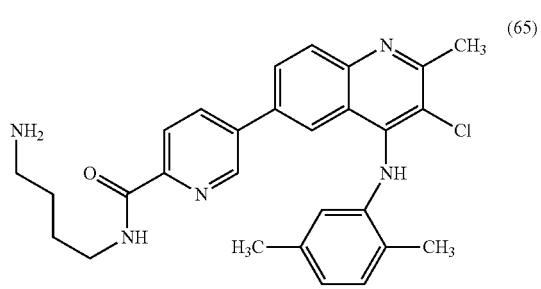 [SMILES: Cc1ccc(C)c(Nc2c(Cl)c(C)nc3ccc(-c4ccc(C(=O)NCCCCN)nc4)cc23)c1] | 530.0 | 2.307 | A |

Example 65

N-(4-aminobutyl)-5-(3-chloro-4-((2,5-dimethylphenyl)amino)-2-methylquinolin-6-yl) picolinamide

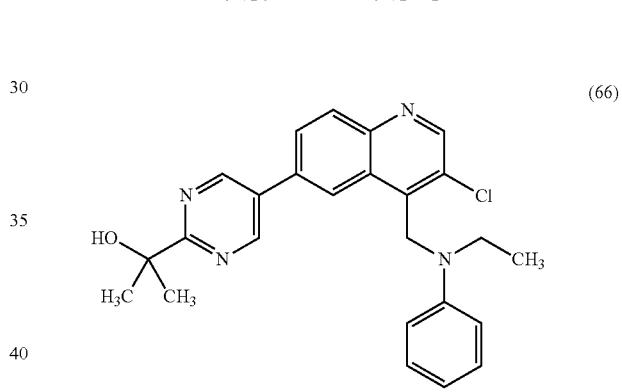

(65)

To a stirred solution of 5-(3-chloro-4-((2,5-dimethylphenyl)amino)-2-methylquinolin-6-yl)picolinic acid (Example 9, 70 mg, 0.168 mmol), tert-butyl n-(4-aminobutyl)carbamate (0.064 mL, 0.335 mmol), DIEA (0.117 mL, 0.670 mmol) in anhydrous dichloromethane (2 mL) was added BOP (148 mg, 0.335 mmol) at room temperature under nitrogen. The mixture was stirred at room temperature for 3 hr. Saturated aqueous sodium bicarbonate solution (2 mL) was added to quench the reaction. The aqueous layer was separated and extracted with ethyl acetate (3×1 mL). The combined organic solutions were dried over sodium sulfate, filtered, and concentrated under reduced pressure. Flash chromatography gave tert-butyl (4-(5-(3-chloro-4-((2,5-dimethylphenyl)amino)-2-methylquinolin-6-yl)picolinamido)butyl)carbamate (75 mg, 0.128 mmol, 76% yield) as a solid.

A mixture of tert-butyl (4-(5-(3-chloro-4-((2,5-dimethylphenyl)amino)-2-methylquinolin-6-yl)picolinamido)butyl)carbamate (72 mg, 0.122 mmol) and TFA (1 mL) was stirred at room temperature for 1 h. DCE (1 mL) was added and the solvents were removed in vacuo. The residue was dissolved in MeOH. 1 N aqueous solution of HCl (0.245 mL, 0.245 mmol) was added. Lyophilization gave N-(4-aminobutyl)-5-(3-chloro-4-((2,5-dimethylphenyl)amino)-2-methylquinolin-6-yl)picolinamide, 2 HCl (88 mg, 0.124 mmol), as a solid. LC/MS (M+H): 488.2; LC retention time: 0.757 min (analytical HPLC Method B); $^1$H NMR (400 MHz, METHANOL-$d_4$) δ 8.48 (d, J=2.2 Hz, 1H), 8.25 (dd, J=8.9, 1.8 Hz, 1H), 8.13-8.07 (m, 1H), 8.01 (d, J=8.8 Hz, 1H), 7.79 (td, J=4.0, 2.3 Hz, 2H), 7.42-7.37 (m, 1H), 7.37-7.31 (m, 1H), 7.23 (s, 1H), 3.54-3.45 (m, 2H), 3.00 (br. s., 2H), 2.91 (s, 3H), 2.36 (s, 3H), 2.23 (s, 3H), 1.79-1.70 (m, 4H).

Example 66

2-(5-(3-chloro-4-((ethyl(phenyl)amino)methyl)quinolin-6-yl)pyrimidin-2-yl)propan-2-ol (66)

To a stirred mixture of 2-(5-(3-chloro-4-(hydroxymethyl)quinolin-6-yl)pyrimidin-2-yl)propan-2-ol (Intermediate I-6, 20 mg, 0.061 mmol) and Ph$_3$P (22.27 mg, 0.085 mmol) and NBS (14.03 mg, 0.079 mmol) was added anhydrous CH$_2$Cl$_2$ (1 mL) at −78° C. under nitrogen. The mixture was stirred at the same temperature for 30 min and 0° C. for 1.5 h. N-ethyl aniline (0.076 mL, 0.606 mmol) was added at 0° C. The reaction mixture was stirred at room temperature for 19 h and concentrated. The crude material was purified via preparative LC/MS using the following conditions: Column: XBridge C18, 19×200 mm, 5-Lm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-100% B over 15 minutes, then a 4-minute hold at 100% B; Flow: 20 mL/min. Fractions containing the desired product were combined and dried via centrifugal evaporation. The yield of the product was 10.6 mg. LC/MS (M+H): 432.9; LC retention time: 2.274 min (analytical HPLC Method A); $^1$H NMR (500 MHz, DMSO-$d_6$) δ 8.99 (s, 2H), 8.94 (s, 1H), 8.40 (s, 1H), 8.19 (s, 2H), 7.22 (d, J=7.4 Hz, 2H), 7.02 (d, J=7.7 Hz, 2H), 6.73 (s, 1H), 5.26 (br. s., 1H), 5.07 (s, 2H), 3.24-3.18 (m, 2H), 1.51 (s, 6H), 0.93 (t, J=6.3 Hz, 3H).

The following analogs were prepared using a similar experimental procedure as outlined for Example 66

| Ex. No. | Structure | LCMS m/z observed | HPLC $t_R$ (min) | HPLC method |
|---|---|---|---|---|
| 67 | 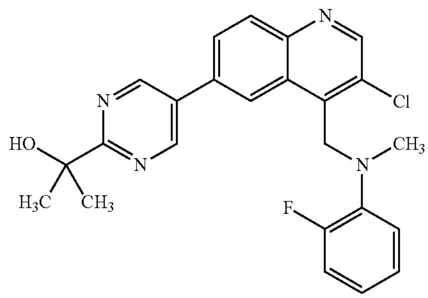 [SMILES: CN(Cc1c(Cl)cnc2ccc(-c3cnc(C(C)(C)O)nc3)cc12)c1ccccc1F] | 437.0 | 2.184 | A |
| 68 | 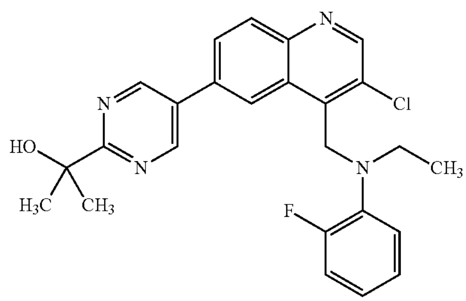 [SMILES: CCN(Cc1c(Cl)cnc2ccc(-c3cnc(C(C)(C)O)nc3)cc12)c1ccccc1F] | 451.1 | 2.374 | A |

Example 69

1-((5-(2-amino-3-chloro-4-((2,5-dimethylphenyl)amino)quinolin-6-yl)pyrimidin-2-yl)amino)-2-methylpropan-2-ol (69)

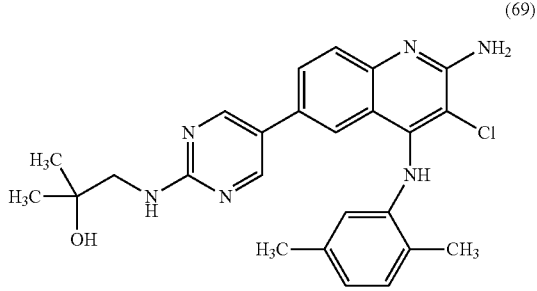 [SMILES: Cc1ccc(C)c(Nc2c(Cl)c(N)nc3ccc(-c4cnc(NCC(C)(C)O)nc4)cc23)c1]

A mixture of 3-chloro-6-(2-chloropyrimidin-5-yl)-N4-(2,5-dimethylphenyl) quinoline-2,4-diamine (Intermediate I-8, 12 mg, 0.029 mmol), 1-amino-2-methylpropan-2-ol (26.1 mg, 0.292 mmol) and anhydrous DMA (0.05 mL) was stirred at 100° C. under nitrogen for 1 h. The crude material was purified via preparative LC/MS employing the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 4-minute hold at 100% B; Flow: 20 mL/min. Fractions containing the desired product were combined and dried via centrifugal evaporation. The yield of the product was 15.9 mg. LC/MS (M+H): 462.9; LC retention time: 1.692 min (analytical HPLC Method A); $^1$H NMR (500 MHz, DMSO-$d_6$) δ 9.27 (br. s., 1H), 8.45 (br. s., 2H), 8.09 (s, 1H), 8.00 (d, J=6.9 Hz, 2H), 7.65 (d, J=8.7 Hz, 1H), 7.22 (d, J=7.7 Hz, 1H), 7.07 (d, J=7.9 Hz, 1H), 7.01 (t, J=6.1 Hz, 1H), 6.96 (s, 1H), 3.32 (d, J=6.1 Hz, 2H), 2.23 (s, 3H), 2.15 (s, 3H), 1.10 (s, 6H).

The following analogs were synthesized in a similar fashion as outlined for Example 69.

TABLE 4

| Ex. No. | Structure | LCMS m/z observed | HPLC $t_R$ (min) | HPLC method |
|---|---|---|---|---|
| 70 | 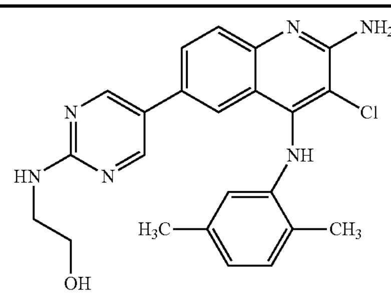 | 435.0 | 1.489 | A |

TABLE 4-continued

| Ex. No. | Structure | LCMS m/z observed | HPLC $t_R$ (min) | HPLC method |
|---|---|---|---|---|
| 71 | 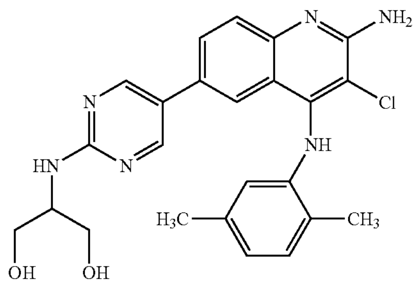 [SMILES: Cc1ccc(C)c(Nc2c(Cl)c(N)nc3ccc(-c4cnc(NC(CO)CO)nc4)cc23)c1] | 465.1 | 1.371 | A |
| 72 | 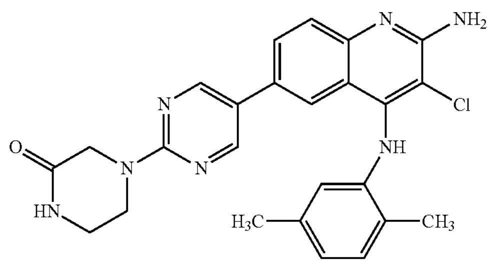 [SMILES: Cc1ccc(C)c(Nc2c(Cl)c(N)nc3ccc(-c4cnc(N5CCNC(=O)C5)nc4)cc23)c1] | 473.8 | 1.565 | A |
| 73 (±) | 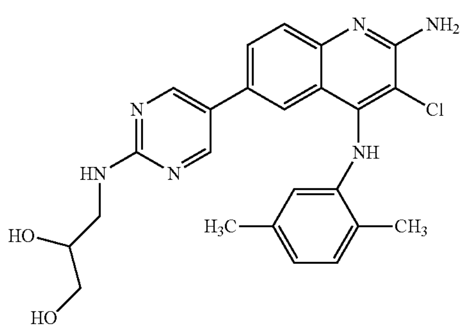 [SMILES: Cc1ccc(C)c(Nc2c(Cl)c(N)nc3ccc(-c4cnc(NCC(O)CO)nc4)cc23)c1] | 435.3 | 1.456 | A |
| 74 | 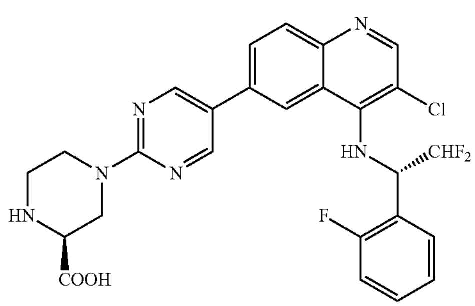 [SMILES: O=C(O)[C@@H]1CN(c2ncc(-c3ccc4ncc(Cl)c(N[C@@H](c5ccccc5F)C(F)F)c4c3)cn2)CCN1] | 542.8 | 1.486 | A |
| 75 | 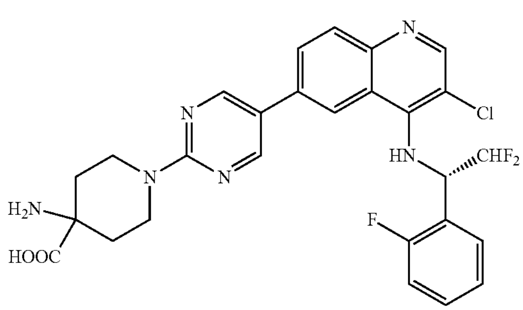 [SMILES: NC1(C(=O)O)CCN(c2ncc(-c3ccc4ncc(Cl)c(N[C@@H](c5ccccc5F)C(F)F)c4c3)cn2)CC1] | 557.1 | 1.499 | A |

TABLE 4-continued

| Ex. No. | Structure | LCMS m/z observed | HPLC t_R (min) | HPLC method |
|---|---|---|---|---|
| 76 | 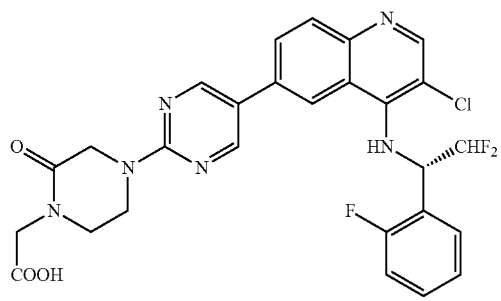 [SMILES: O=C(O)CN1CCN(c2ncc(-c3ccc4ncc(Cl)c(N[C@@H](c5ccccc5F)C(F)F)c4c3)cn2)CC1=O] | 571.3 | 1.427 | A |
| 77 (diastereomeric mixture) | 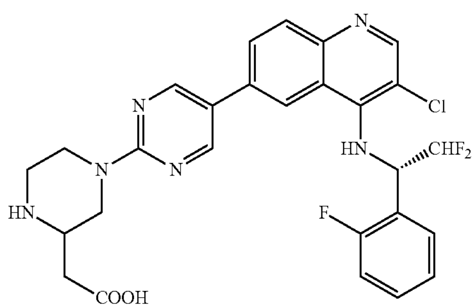 [SMILES: O=C(O)CC1CN(c2ncc(-c3ccc4ncc(Cl)c(N[C@@H](c5ccccc5F)C(F)F)c4c3)cn2)CCN1] | 557.4 | 1.457 | A |
| 78 | 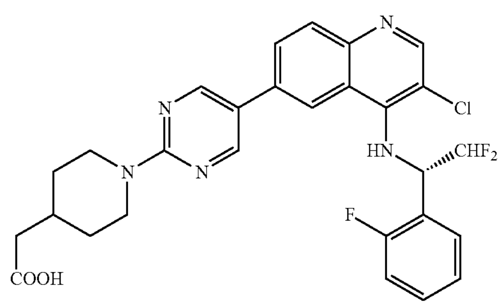 [SMILES: O=C(O)CC1CCN(c2ncc(-c3ccc4ncc(Cl)c(N[C@@H](c5ccccc5F)C(F)F)c4c3)cn2)CC1] | 556.2 | 1.814 | A |
| 79 | 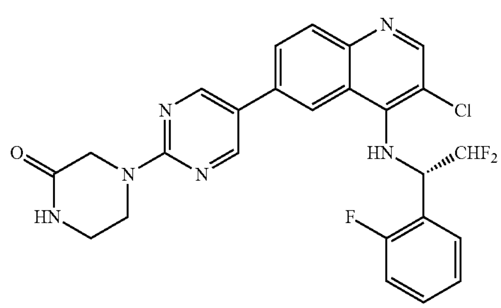 [SMILES: O=C1CN(c2ncc(-c3ccc4ncc(Cl)c(N[C@@H](c5ccccc5F)C(F)F)c4c3)cn2)CCN1] | 513.3 | 1.744 | A |
| 80 | 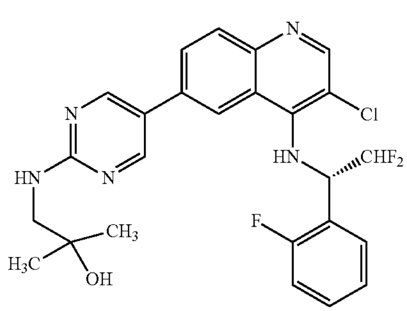 [SMILES: CC(C)(O)CNc1ncc(-c2ccc3ncc(Cl)c(N[C@@H](c4ccccc4F)C(F)F)c3c2)cn1] | 501.9 | 1.858 | A |

TABLE 4-continued

| Ex. No. | Structure | LCMS m/z observed | HPLC $t_R$ (min) | HPLC method |
|---|---|---|---|---|
| 81 | 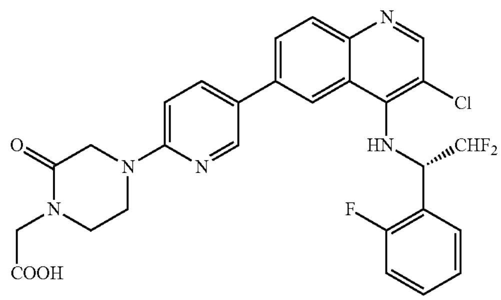 [SMILES: O=C(O)CN1CCN(c2ccc(-c3ccc4ncc(Cl)c(N[C@@H](c5ccccc5F)C(F)F)c4c3)cn2)CC1=O] | 534.4 | 1.454 | A |
| 82 | 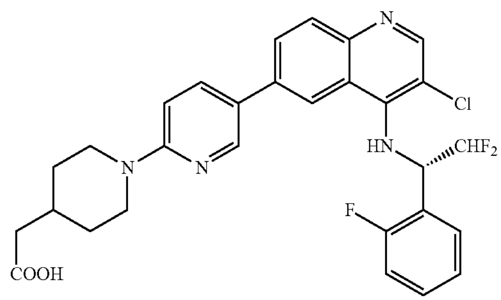 [SMILES: O=C(O)CC1CCN(c2ccc(-c3ccc4ncc(Cl)c(N[C@@H](c5ccccc5F)C(F)F)c4c3)cn2)CC1] | 519.2 | 1.738 | A |
| 83 | 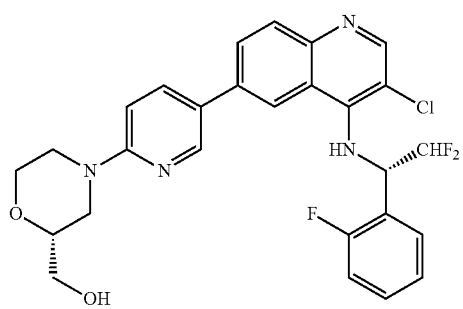 [SMILES: OC[C@H]1CN(c2ccc(-c3ccc4ncc(Cl)c(N[C@@H](c5ccccc5F)C(F)F)c4c3)cn2)CCO1] | 492.9 | 2.057 | A |
| 84 | 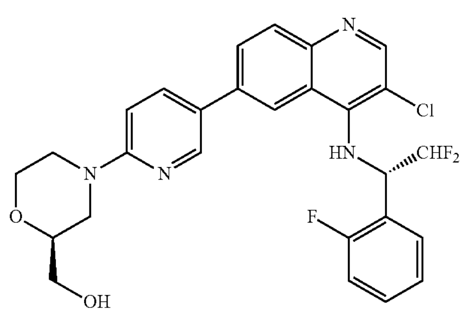 [SMILES: OC[C@@H]1CN(c2ccc(-c3ccc4ncc(Cl)c(N[C@@H](c5ccccc5F)C(F)F)c4c3)cn2)CCO1] | 492.2 | 1.681 | A |
| 85 | 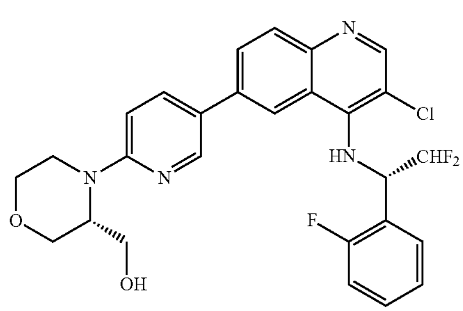 [SMILES: OC[C@@H]1COCCN1c1ccc(-c2ccc3ncc(Cl)c(N[C@@H](c4ccccc4F)C(F)F)c3c2)cn1] | 493.1 | 2.011 | A |

TABLE 4-continued

| Ex. No. | Structure | LCMS m/z observed | HPLC $t_R$ (min) | HPLC method |
|---|---|---|---|---|
| 86 | 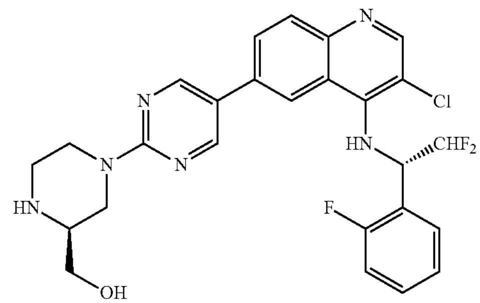 [SMILES: OC[C@@H]1CN(c2ncc(-c3ccc4ncc(Cl)c(N[C@@H](c5ccccc5F)C(F)F)c4c3)cn2)CCN1] | 529.2 | 1.770 | A |
| 87 | 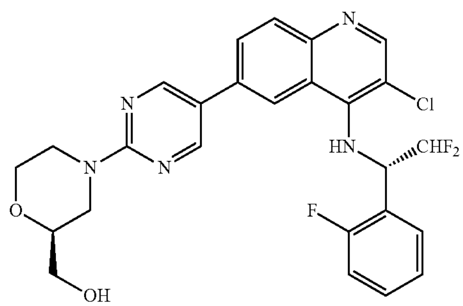 [SMILES: OC[C@@H]1CN(c2ncc(-c3ccc4ncc(Cl)c(N[C@@H](c5ccccc5F)C(F)F)c4c3)cn2)CCO1] | 529.9 | 1.895 | A |
| 88 | 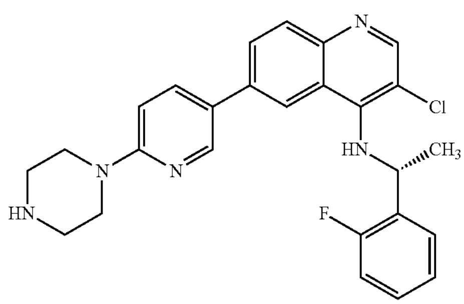 [SMILES: C[C@@H](Nc1c(Cl)cnc2ccc(-c3ccc(N4CCNCC4)nc3)cc12)c1ccccc1F] | 462.3 | 1.587 | A |

Example 89

(R)-2-(4-(5-(3-chloro-4-((1-(2-fluorophenyl)ethyl) amino)quinolin-6-yl)pyrimidin-2-yl)piperazin-1-yl)-N-methylacetamide (89)

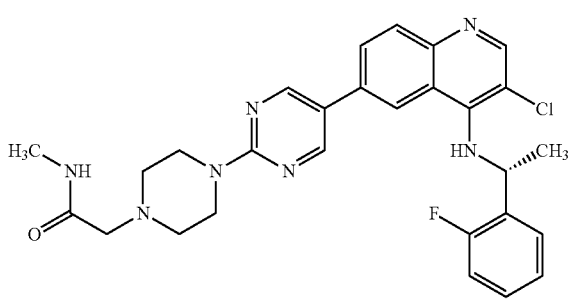

A mixture of (R)-ethyl 2-(4-(5-(3-chloro-4-((1-(2-fluorophenyl)ethyl)amino) quinolin-6-yl)pyrimidin-2-yl)piperazin-1-yl)acetate (Example 224, 20 mg, 0.036 mmol), 1 M aqueous NaOH (0.109 mL, 0.109 mmol) and MeOH (3 mL) was stirred at room temperature overnight. The mixture was neutralized with dry ice, concentrated in vacuo, and lyophilized to give a solid (for analytical data, see Example 285). The solid was mixed with methylamine hydrochloride (24.59 mg, 0.364 mmol) and $CH_2Cl_2$ (1 mL). BOP (32.2 mg, 0.073 mmol) was added at room temperature. The mixture was stirred at room temperature for 2 h. The crude material was purified via preparative LC/MS using the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 9.7 mg. LC/MS (M+H): 534.0; LC retention time: 2.087 min (analytical HPLC Method A); $^1$H NMR (500 MHz, DMSO-$d_6$) δ 8.87 (s, 2H), 8.52 (s, 1H), 8.41 (s, 1H), 7.99 (d, J=8.8 Hz, 1H), 7.90 (d, J=8.6 Hz, 1H), 7.55 (t, J=7.8 Hz, 1H), 7.23 (q, J=6.7 Hz, 1H), 7.16-7.05 (m, 2H), 6.65 (d, J=8.8 Hz, 1H), 5.82-5.72 (m, 1H), 3.87 (br. s., 4H), 2.99 (br. s., 2H), 2.64 (d, J=4.6 Hz, 3H), 1.66 (d, J=6.7 Hz, 3H). 4 protons are buried under solvent peaks.

The following analog can be prepared in a similar fashion

| Ex. No. | Structure | LCMS m/z observed | HPLC $t_R$ (min) | HPLC method |
|---|---|---|---|---|
| 90 | 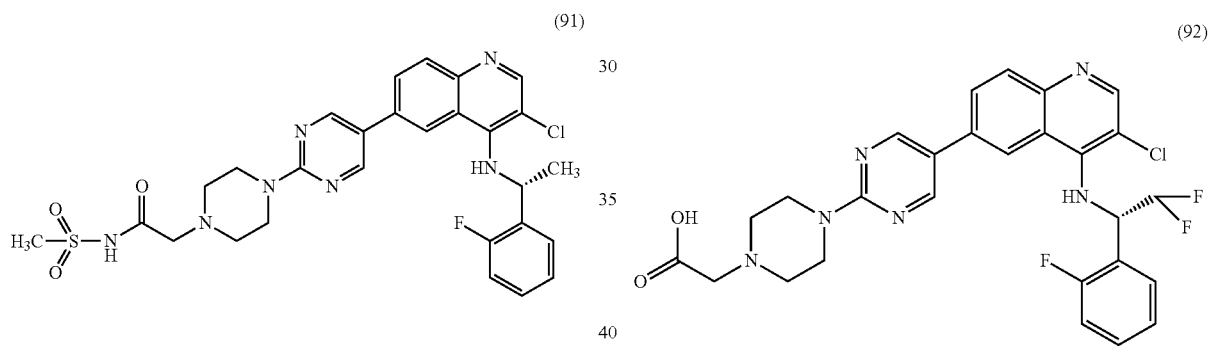 | 519.9 | 1.880 | A |

Example 91

(R)-2-(4-(5-(3-chloro-4-((1-(2-fluorophenyl)ethyl)amino)quinolin-6-yl)pyrimidin-2-yl)piperazin-1-yl)-N-(methylsulfonyl)acetamide (91)

Example 92

(S)-2-(4-(5-(3-chloro-4-((2,2-difluoro-1-(2-fluorophenyl)ethyl)amino)quinolin-6-yl)pyrimidin-2-yl)piperazin-1-yl)acetic acid (92)

1-(3-dimethylaminopropyl)-3-ethylcarbodiimide hydrochloride (8.28 mg, 0.043 mmol) was added to a stirred solution of methanesulfonamide (5.48 mg, 0.058 mmol), (R)-2-(4-(5-(3-chloro-4-((1-(2-fluorophenyl)ethyl)amino)quinolin-6-yl)pyrimidin-2-yl)piperazin-1-yl)acetic acid (Example 285, 15 mg, 0.029 mmol), and DMAP (10.55 mg, 0.086 mmol) in anhydrous DMF (0.3 mL) and the resulting mixture was stirred at room temperature overnight. The crude material was purified via preparative LC/MS using the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation. The yield of the product was 11.3 mg. LC/MS (M+H): 598.2; LC retention time: 1.575 min (analytical HPLC Method A)

To a stirred solution of (S)-methyl 2-(4-(5-(3-chloro-4-((2,2-difluoro-1-(2-fluorophenyl)ethyl)amino)quinolin-6-yl)pyrimidin-2-yl)piperazin-1-yl)acetate (Example 14, 89 mg, 0.156 mmol) in MeOH (3 mL) and THF (1.5 mL) was added 1 M aqueous NaOH (468 μl, 0.468 mmol). The mixture was stirred at room temperature overnight. The organic solvents were removed in vacuo. The residue was mixed with water (3 mL), AcOH (200 μl, 3.49 mmol), methanol (0.5 mL), and Et2O (2 mL). The solid was filtered, washed with water (3×0.5 mL), ether (3×0.5 mL), and dried to give (S)-2-(4-(5-(3-chloro-4-((2,2-difluoro-1-(2-fluorophenyl)ethyl)amino)quinolin-6-yl)pyrimidin-2-yl)piperazin-1-yl)acetic acid (82 mg, 0.143 mmol, 92% yield). LC/MS (M+H): 557.1; LC retention time: 0.798 min (analytical HPLC Method B);

The following analogs were prepared using a similar protocol as outlined for Example 92

| Ex. No. | Structure | LCMS m/z observed | HPLC $t_R$ (min) | HPLC method |
|---|---|---|---|---|
| 93 | 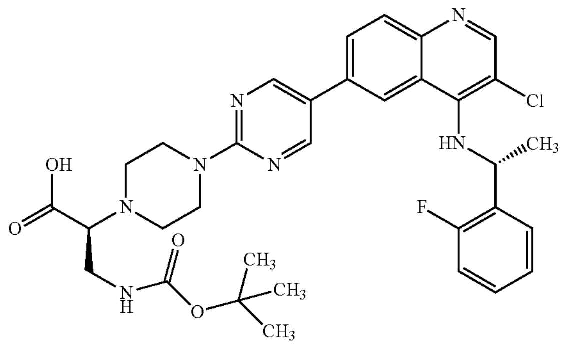 [SMILES: C[C@@H](Nc1c(Cl)cnc2ccc(-c3cnc(N4CCN([C@@H](CNC(=O)OC(C)(C)C)C(=O)O)CC4)nc3)cc12)c1ccccc1F] | 650.1 | 1.820 | A |
| 94 | 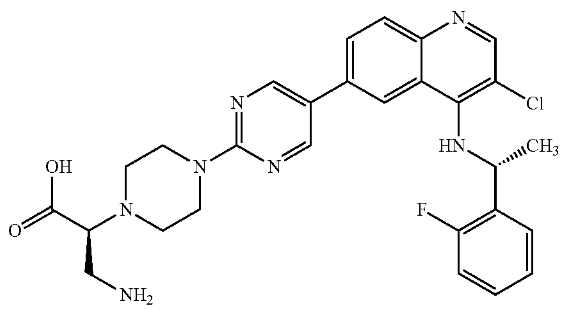 [SMILES: C[C@@H](Nc1c(Cl)cnc2ccc(-c3cnc(N4CCN([C@@H](CN)C(=O)O)CC4)nc3)cc12)c1ccccc1F] | 550.3 | 1.602 | A |
| 95 | 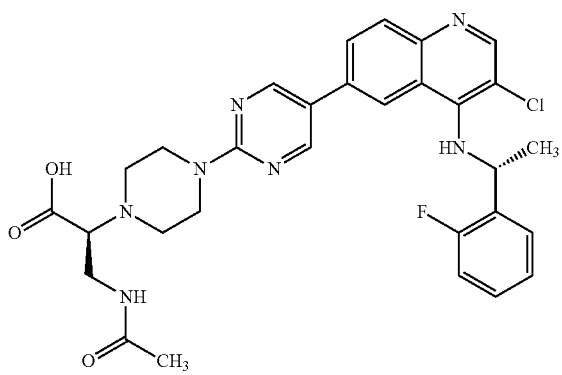 [SMILES: CC(=O)NC[C@@H](C(=O)O)N1CCN(c2ncc(-c3ccc4ncc(Cl)c(N[C@H](C)c5ccccc5F)c4c3)cn2)CC1] | 592.2 | 1.549 | A |

Examples 96 and 97

2-(5-(3-chloro-4-(((S)-1-((S)-piperidin-3-yl)ethyl)amino)quinolin-6-yl)pyrimidin-2-yl)propan-2-ol

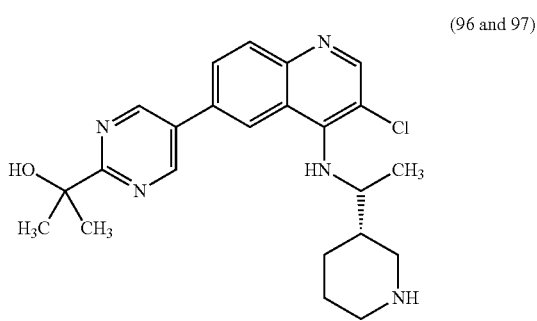 [SMILES: CC(Nc1c(Cl)cnc2ccc(-c3cnc(C(C)(C)O)nc3)cc12)[C@H]1CCCNC1]

(96 and 97)

To a solution of (S)-tert-butyl 3-(1-((3-chloro-6-(2-(2-hydroxypropan-2-yl)pyrimidin-5-yl)quinolin-4-yl)amino)ethyl)piperidine-1-carboxylate (Example 60, 260 mg, 0.494 mmol) in CH$_2$Cl$_2$ (2 mL) was added TFA (2 mL). The solution was stirred at room temperature for 1 h. DCE (4 mL) was added and the mixture was concentrated under reduced pressure. Preparative HPLC (Luna 5u 30×100 mm (AXIA) column; gradient from 5% to 100 of solvent B over 10 min; flow rate 40 mL/min; Solvent A: 10% MeOH-90% H$_2$O-0.1% TFA; Solvent B: 90% MeOH-10% H$_2$O-0.1% TFA); gave peak 1 (63 mg; Example 96) and peak 2 (138 mg; Example 97) after concentration, basifying with K$_2$CO$_3$, extraction with EtOAc and concentration under reduced pressure.

Analytical data for Example 96: LC/MS (M+H): 426.2; LC retention time: 0.710 min (analytical HPLC Method B); $^1$H NMR (400 MHz, MeOD) δ 9.19 (s, 2H), 8.51 (d, J=1.0 Hz, 1H), 8.49 (s, 1H), 8.07-8.01 (m, 2H), 4.35 (quin, J=6.7 Hz, 1H), 3.10 (d, J=11.4 Hz, 1H), 2.95 (d, J=11.9 Hz, 1H), 2.53-2.38 (m, 2H), 2.04 (br. s., 1H), 1.89-1.77 (m, 1H), 1.74-1.66 (m, 1H), 1.65 (s, 6H), 1.54-1.41 (m, 1H), 1.36 (d, J=6.6 Hz, 3H), 1.31-1.19 (m, 1H).

Analytical data for Example 97: LC/MS (M+H): 426.1; LC retention time: 0.708 min (analytical HPLC Method B); ¹H NMR (400 MHz, MeOD) δ 9.23-9.15 (m, 2H), 8.52 (d, J=1.1 Hz, 1H), 8.51-8.48 (m, 1H), 8.12-7.99 (m, 2H), 4.30 (quin, J=6.8 Hz, 1H), 3.29-3.22 (m, 1H), 2.99 (d, J=12.0 Hz, 1H), 2.52 (td, J=12.3, 2.8 Hz, 1H), 2.42 (t, J=11.6 Hz, 1H), 1.95 (d, J=13.0 Hz, 1H), 1.90-1.70 (m, 2H), 1.65 (s, 6H), 1.58-1.44 (m, 1H), 1.36 (d, J=6.6 Hz, 3H), 1.30-1.19 (m, 1H).

The following analogs were prepared from the corresponding Boc protected compounds using conditions outlined for Examples 96/97

| Ex. No. | Structure | LCMS m/z observed | HPLC $t_R$ (min) | HPLC method |
|---|---|---|---|---|
| 98 (diastereomeric mixture) | 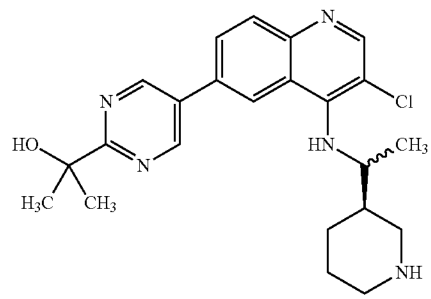 [SMILES: CC(Nc1c(Cl)cnc2ccc(-c3cnc(C(C)(C)O)nc3)cc12)[C@@H]1CCCNC1] | 426.1 | 0.682 | B |
| 99 | 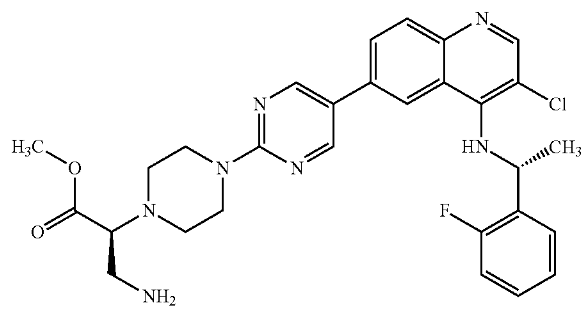 [SMILES: COC(=O)[C@H](CN)N1CCN(c2ncc(-c3ccc4ncc(Cl)c(N[C@H](C)c5ccccc5F)c4c3)cn2)CC1] | 564.1 | 1.821 | A |
| 100 | 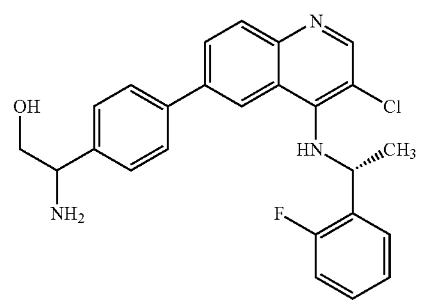 [SMILES: C[C@@H](Nc1c(Cl)cnc2ccc(-c3ccc(C(N)CO)cc3)cc12)c1ccccc1F] | 436.2 | 1.562 | A |
| 101 | 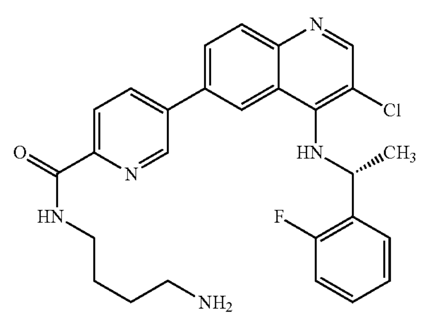 [SMILES: C[C@@H](Nc1c(Cl)cnc2ccc(-c3ccc(C(=O)NCCCCN)nc3)cc12)c1ccccc1F] | 492.3 | 0.758 | B |

| Ex. No. | Structure | LCMS m/z observed | HPLC $t_R$ (min) | HPLC method |
|---|---|---|---|---|
| 102 | 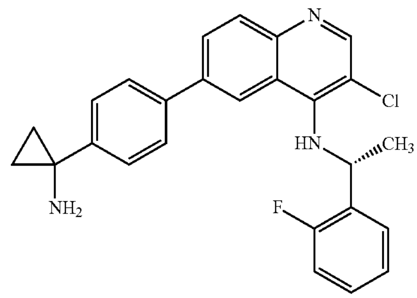 [SMILES: C[C@@H](Nc1c(Cl)cnc2ccc(-c3ccc(C4(N)CC4)cc3)cc12)c1ccccc1F] | 432.3 | 2.126 | A |

Example 103

(S)-3-((S)-1-((3-chloro-6-(2-(2-hydroxypropan-2-yl)pyrimidin-5-yl)quinolin-4-yl)amino)ethyl)piperidine-1-carboxamide (103)

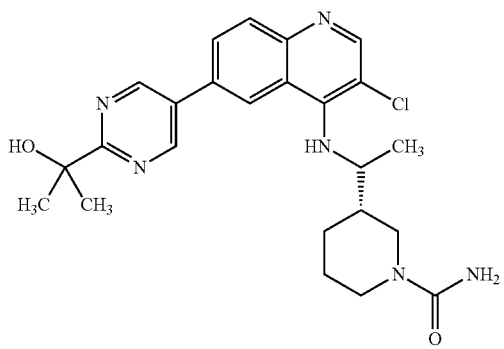

To a stirred solution of 2-(5-(3-chloro-4-(((S)-1-((S)-piperidin-3-yl)ethyl)amino) quinolin-6-yl)pyrimidin-2-yl)propan-2-ol (Example 97, 8 mg, 0.019 mmol) and AcOH (6.45 µl, 0.113 mmol) in anhydrous DMF (0.2 mL) was added sodium cyanate (7.33 mg, 0.113 mmol) at room temperature under nitrogen. The mixture was stirred at room temperature for 4 h in a sealed vial. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 19 minutes, then a 5-minute hold at 100% B; Flow: 20 mL/min. Fractions containing the desired product were combined and dried via centrifugal evaporation. The yield of the product was 6.7 mg. LC/MS (M+H): 469; LC retention time: 1.397 min (analytical HPLC Method A); $^1$H NMR (500 MHz, DMSO-d$_6$) δ 9.30 (s, 2H), 8.70 (s, 1H), 8.49 (s, 1H), 8.14-8.09 (m, 1H), 7.99 (d, J=8.6 Hz, 1H), 6.30 (d, J=10.2 Hz, 1H), 5.83 (s, 2H), 5.19 (s, 1H), 4.32-4.20 (m, 2H), 3.79 (d, J=12.7 Hz, 1H), 2.67-2.56 (m, 1H), 2.37 (t, J=12.2 Hz, 1H), 1.85 (br. s., 1H), 1.79-1.68 (m, 1H), 1.62 (d, J=12.9 Hz, 1H), 1.56 (s, 6H), 1.34-1.09 (m, 5H).

Example 104

(R)-3-((R)-1-((3-chloro-6-(2-(2-hydroxypropan-2-yl)pyrimidin-5-yl)quinolin-4-yl)amino)ethyl)piperidine-1-carboxamide (104)

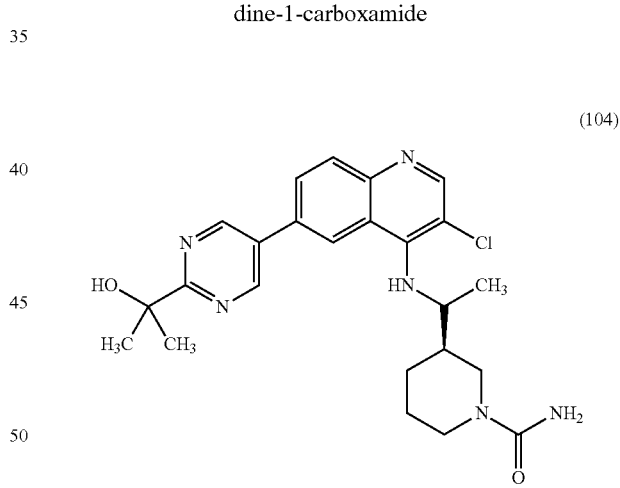

Example 104 was synthesized in a similar manner to Example 103 starting from Example 98. This compound was homochiral. The absolute stereochemistry of the methyl group on the carbon linked to NH) was not determined. LC/MS (M+H): 469.0; LC retention time: 1.116 min (analytical HPLC Method A);

Example 105

2-(5-(3-chloro-4-(((S)-1-((S)-1-ethylpiperidin-3-yl)ethyl)amino)quinolin-6-yl)pyrimidin-2-yl)propan-2-ol

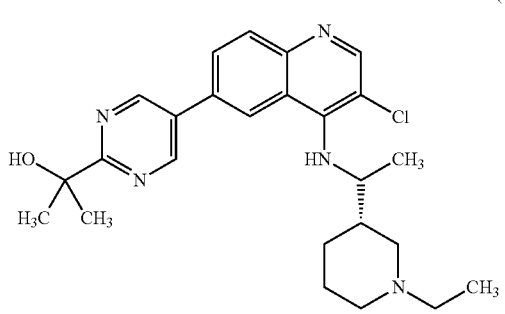

(105)

To a stirred mixture of 2-(5-(3-chloro-4-(((S)-1-((S)-piperidin-3-yl)ethyl)amino) quinolin-6-yl)pyrimidin-2-yl)propan-2-ol (Example 97, 9 mg, 0.021 mmol) and acetaldehyde (2.387 μl, 0.042 mmol) in DCE (1 mL) was added sodium triacetoxyborohydride (8.96 mg, 0.042 mmol) at room temperature under nitrogen. The mixture was stirred at room temperature for 3 h. The crude material was purified via preparative LC/MS using the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 20 minutes, then a 2-minute hold at 100% B; Flow: 20 mL/min. Fractions containing the desired product were combined and dried via centrifugal evaporation. The yield of the product was 4.6 mg. LC/MS (M+H): 453.9; LC retention time: 1.163 min (analytical HPLC Method A);

Example 106

3-((S)-3-((S)-1-((3-chloro-6-(2-(2-hydroxypropan-2-yl)pyrimidin-5-yl)quinolin-4-yl)amino)ethyl)piperidin-1-yl)propane-1,2-diol

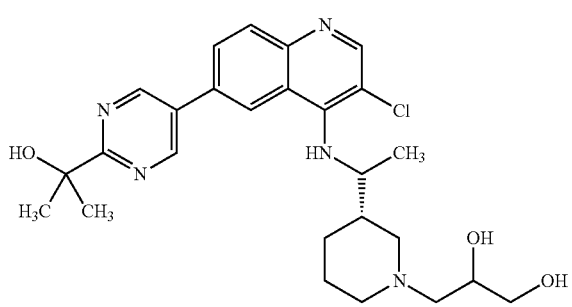

(106)

A mixture of 2-(5-(3-chloro-4-(((S)-1-((S)-piperidin-3-yl)ethyl)amino)quinolin-6-yl)pyrimidin-2-yl)propan-2-ol (Example 97, 9 mg, 0.021 mmol), 3-chloro-1,2-propanediol (2.65 μl, 0.032 mmol), 100% ethanol (0.5 mL), and DIEA (0.011 mL, 0.063 mmol) was stirred at 80° C. overnight. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 19 minutes, then a 5-minute hold at 100% B; Flow: 20 mL/min. Fractions containing the desired product were combined and dried via centrifugal evaporation. The yield of the product was 6.5 mg. LC/MS (M+H): 500.3; LC retention time: 1.077 min (analytical HPLC Method A). This compound was a diastereomeric mixture.

Example 107

1-((S)-3-((S)-1-((3-chloro-6-(2-(2-hydroxypropan-2-yl)pyrimidin-5-yl)quinolin-4-yl)amino)ethyl)piperidin-1-yl)ethanone

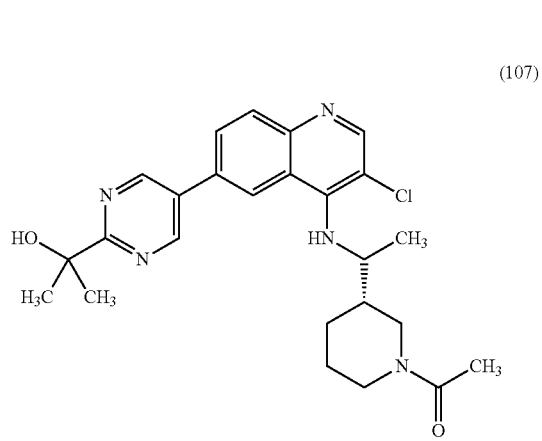 [SMILES: CC(=O)N1CCC[C@H](C(C)Nc2c(Cl)cnc3ccc(-c4cnc(C(C)(C)O)nc4)cc23)C1]

(107)

A mixture of 2-(5-(3-chloro-4-(((S)-1-((S)-piperidin-3-yl)ethyl)amino)quinolin-6-yl)pyrimidin-2-yl)propan-2-ol (Example 97, 9 mg, 0.021 mmol), Ac₂O (2.99 μl, 0.032 mmol), anhydrous CH₂Cl₂ (0.5 mL), and DIEA (0.011 mL, 0.063 mmol) was stirred at room temperature for 1.5 h. The mixture was concentrated. The crude material was purified via preparative LC/MS using the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 18-58% B over 20 minutes, then a 5-minute hold at 100% B; Flow: 20 mL/min. Fractions containing the desired product were combined and dried via centrifugal evaporation. The yield of the product was 7.8 mg. LC/MS (M+H): 468; LC retention time: 1.521 min (analytical HPLC Method A);

The following N-acetyl analogs were prepared according to the general procedure disclosed in Example 107.

| Ex. No. | Structure | LCMS m/z observed | HPLC $t_R$ (min) | HPLC method |
|---|---|---|---|---|
| 108 (homochiral) | 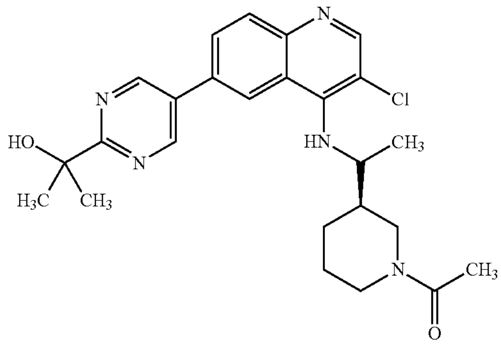 [SMILES: CC(=O)N1CCC[C@@H](C(C)Nc2c(Cl)cnc3ccc(-c4cnc(C(C)(C)O)nc4)cc23)C1] | 468.0 | 1.591 | A |
| 109 | 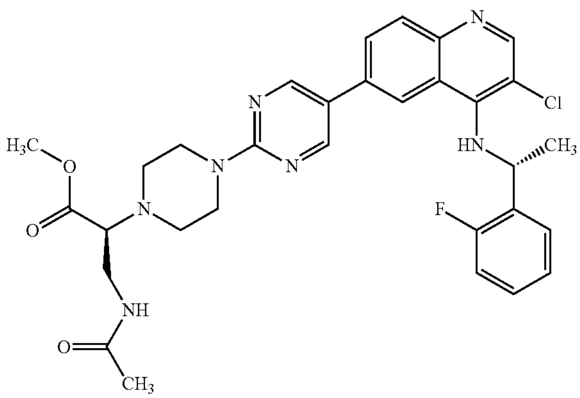 [SMILES: COC(=O)[C@H](CNC(C)=O)N1CCN(c2ncc(-c3ccc4ncc(Cl)c(N[C@H](C)c5ccccc5F)c4c3)cn2)CC1] | 606.0 | 2.056 | A |
| 110 | 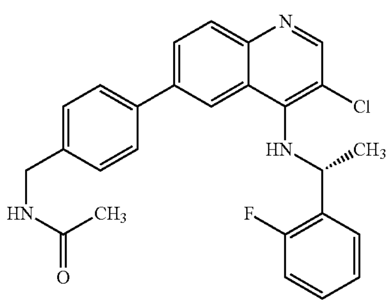 [SMILES: CC(=O)NCc1ccc(-c2ccc3ncc(Cl)c(N[C@H](C)c4ccccc4F)c3c2)cc1] | 448.2 | 1.952 | A |

The following compounds were prepared according to the general procedure used in the preparation of Intermediate I-8 using aryl or heteroaryl bromide intermediates.

| Ex. No. | Structure | LCMS m/z observed | HPLC $t_R$ (min) | HPLC method |
|---|---|---|---|---|
| 111 | 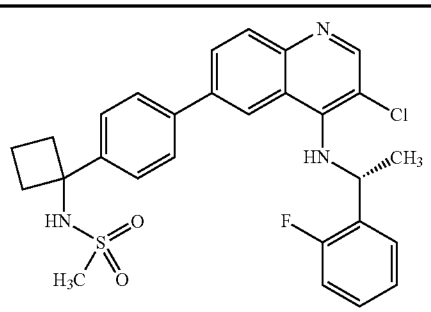 | 524.3 | 2.310 | A |

-continued

| Ex. No. | Structure | LCMS m/z observed | HPLC $t_R$ (min) | HPLC method |
|---|---|---|---|---|
| 112 (diastereomeric mixture) | 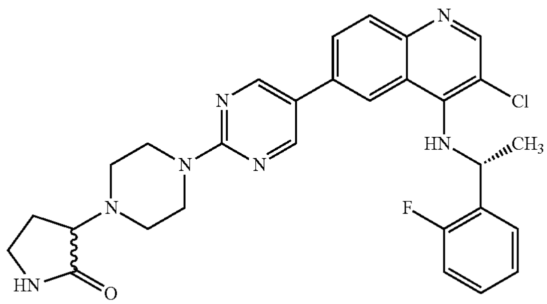 [SMILES: C[C@@H](Nc1c(Cl)cnc2ccc(-c3cnc(N4CCN(C5CCNC5=O)CC4)nc3)cc12)c1ccccc1F] | 546.1 | 0.775 | B |
| 113 | 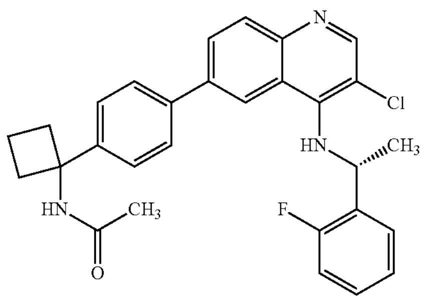 [SMILES: CC(=O)NC1(c2ccc(-c3ccc4ncc(Cl)c(N[C@H](C)c5ccccc5F)c4c3)cc2)CCC1] | 488.1 | 2.191 | A |
| 114 | 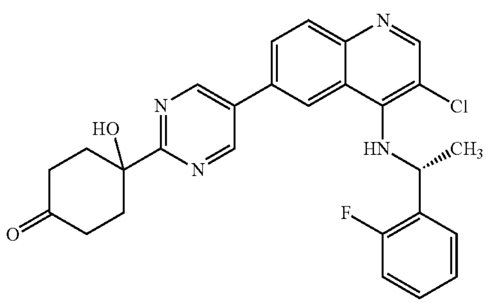 [SMILES: C[C@@H](Nc1c(Cl)cnc2ccc(-c3cnc(C4(O)CCC(=O)CC4)nc3)cc12)c1ccccc1F] | 491.1 | 1.947 | A |
| 115 (diastereomeric mixture) | 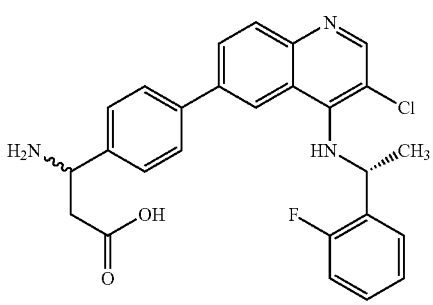 [SMILES: C[C@@H](Nc1c(Cl)cnc2ccc(-c3ccc(C(N)CC(=O)O)cc3)cc12)c1ccccc1F] | 464.2 | 1.493 | A |
| 116 (diastereomeric mixture) | 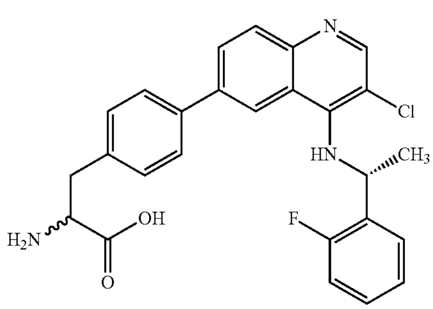 [SMILES: C[C@@H](Nc1c(Cl)cnc2ccc(-c3ccc(CC(N)C(=O)O)cc3)cc12)c1ccccc1F] | 464.1 | 1.516 | A |

| Ex. No. | Structure | LCMS m/z observed | HPLC $t_R$ (min) | HPLC method |
|---|---|---|---|---|
| 117 | 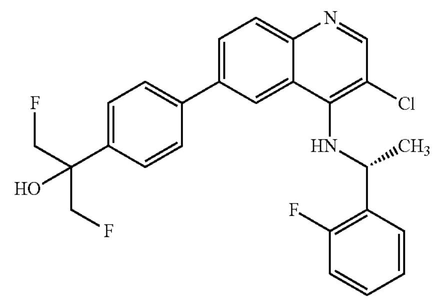 [SMILES: C[C@@H](Nc1c(Cl)cnc2ccc(-c3ccc(C(O)(CF)CF)cc3)cc12)c1ccccc1F] | 473.1 | 2.030 | A |
| 118 | 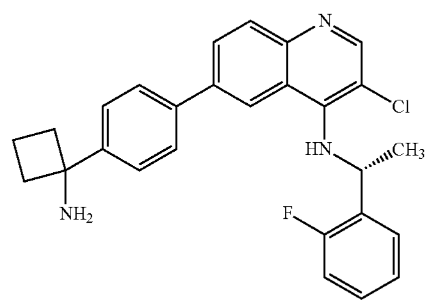 [SMILES: C[C@@H](Nc1c(Cl)cnc2ccc(-c3ccc(C4(N)CCC4)cc3)cc12)c1ccccc1F] | 446.1 | 2.322 | A |
| 119 (diastereomeric mixture) | 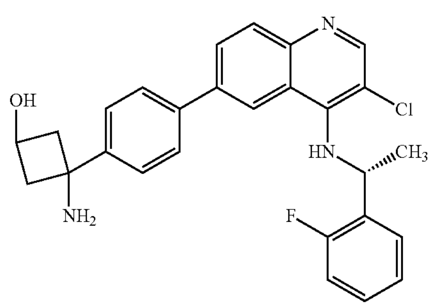 [SMILES: C[C@@H](Nc1c(Cl)cnc2ccc(-c3ccc(C4(N)CC(O)C4)cc3)cc12)c1ccccc1F] | 462.0 | 1.656 | A |
| 120 | 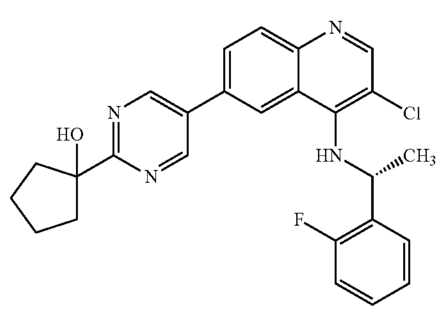 [SMILES: C[C@@H](Nc1c(Cl)cnc2ccc(-c3cnc(C4(O)CCCC4)nc3)cc12)c1ccccc1F] | 463.3 | 2.233 | A |
| 121 (diastereomeric mixture) | 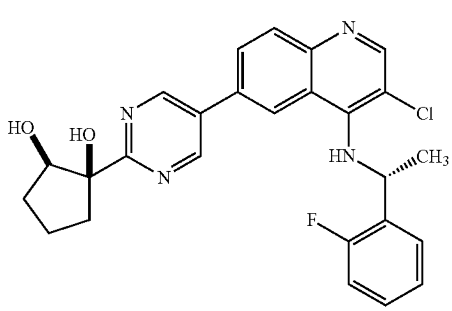 [SMILES: C[C@@H](Nc1c(Cl)cnc2ccc(-c3cnc([C@]4(O)CCC[C@H]4O)nc3)cc12)c1ccccc1F] | 479.1 | 1.911 | A |

Example 122

± 6-bromo-3,8-dichloro-N-(1-(2-fluorophenyl)ethyl) quinolin-4-amine

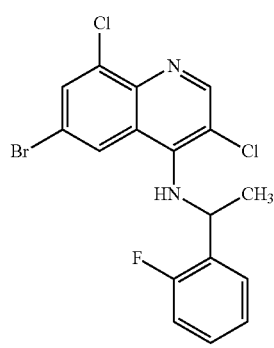
(122)

To a stirred solution of 6-bromo-N-(1-(2-fluorophenyl) ethyl)quinolin-4-amine (Intermediate I-57, 3 g, 8.69 mmol) in anhydrous DMF (10 mL) was added N-chlorosuccinimide (1.160 g, 8.69 mmol) portionwise at 0° C. The mixture was stirred at room temperature overnight. More of N-chlorosuccinimide (1.160 g, 8.69 mmol) was added and the mixture was stirred at room temperature overnight. Additional N-chlorosuccinimide (1.160 g, 8.69 mmol) was added and the mixture was stirred at room temperature for 1 day and concentrated to remove some DMF. 1 M NaOH was added and the mixture was extracted with Et₂O. The combined Et₂O extracts were dried over anhydrous sodium sulfate and concentrated. Flash chromatography purification and trituration of the solid with Et₂O gave 6-bromo-3,8-dichloro-N-(1-(2-fluorophenyl)ethyl) quinolin-4-amine (0.8 g, 1.546 mmol, 17.78% yield). LC/MS (M+H): 414.9; LC retention time: 1.325 min (analytical HPLC Method B); $^1$H NMR (400 MHz, CHLOROFORM-d) δ 8.69 (s, 1H), 8.03 (d, J=2.1 Hz, 1H), 7.84 (d, J=2.1 Hz, 1H), 7.36-7.23 (m, 2H), 7.16-7.03 (m, 2H), 5.34-5.20 (m, 1H), 5.12 (d, J=9.0 Hz, 1H), 1.69 (d, J=6.7 Hz, 3H).

Example 123

(R)-1-(4-(5-(3-chloro-4-((1-(2-fluorophenyl)ethyl) amino)quinolin-6-yl)pyridin-2-yl)piperazin-1-yl) prop-2-en-1-one

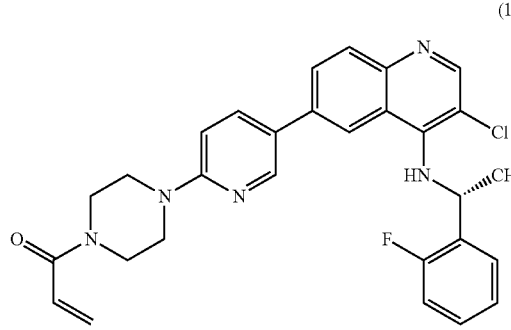
(123)

To a stirred solution of (R)-3-chloro-N-(1-(2-fluorophenyl)ethyl)-6-(6-(piperazin-1-yl)pyridin-3-yl)quinolin-4-amine (Example 88, 10 mg, 0.022 mmol) and DIEA (10 μl, 0.057 mmol) in anhydrous THF (0.5 mL) was added acryloyl chloride (1.924 μl, 0.024 mmol) at 0° C. The mixture was stirred at room temperature for 30 min. and then concentrated. The residue was mixed with DCM, made basic with the addition of saturated aqueous sodium bicarbonate solution, and dried (Na₂SO₄). Flash chromatography purification (4 g silica gel column, gradient elution from 10 to 100% of ethyl acetate in hexanes) afforded (R)-1-(4-(5-(3-chloro-4-((1-(2-fluorophenyl)ethyl)amino)quinolin-6-yl) pyridin-2-yl)piperazin-1-yl)prop-2-en-1-one (10 mg, 0.019 mmol, 87% yield) as a white solid. LC/MS (M+H): 516.0; LC retention time: 0.807 min (analytical HPLC Method B); $^1$H NMR (400 MHz, CHLOROFORM-d) δ 8.59 (s, 1H), 8.44 (d, J=2.0 Hz, 1H), 8.04-7.98 (m, 2H), 7.83-7.77 (m, 1H), 7.61 (dd, J=8.8, 2.6 Hz, 1H), 7.46 (td, J=7.6, 1.6 Hz, 1H), 7.32-7.26 (m, 1H), 7.17-7.02 (m, 2H), 6.73-6.58 (m, 2H), 6.36 (dd, J=16.8, 1.9 Hz, 1H), 5.80-5.73 (m, 1H), 5.46-5.35 (m, 1H), 5.08 (d, J=9.0 Hz, 1H), 3.94-3.60 (m, 8H), 1.70 (d, J=6.7 Hz, 3H).

Example 124

(R)—N-(5-(3-chloro-4-((1-(2-fluorophenyl)ethyl) amino)quinolin-6-yl)pyrimidin-2-yl)-N-methylacrylamide

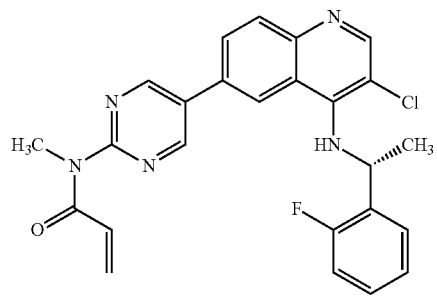
(124)

The compound was synthesized in a manner similar to Example 123 starting from Example 17. LC/MS (M+H): 462.1; LC retention time: 0.93 min (analytical HPLC Method B).

Example 125

(R)-1-(4-(5-(3-chloro-4-((1-(2-fluorophenyl)ethyl) amino)quinolin-6-yl)pyridin-2-yl)piperazin-1-yl)but-2-yn-1-one

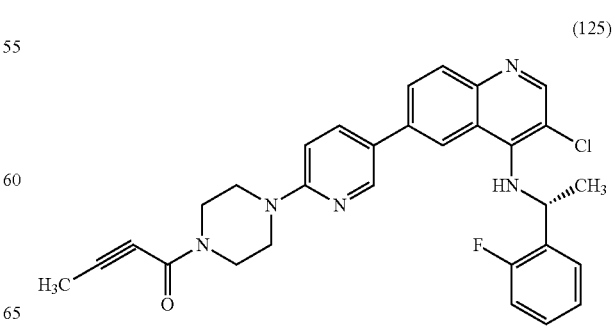
(125)

A mixture of (R)-3-chloro-N-(1-(2-fluorophenyl)ethyl)-6-(6-(piperazin-1-yl)pyridin-3-yl)quinolin-4-amine (Example 88, 10 mg, 0.022 mmol), but-2-ynoic acid (2.184 mg, 0.026 mmol), BOP (11.49 mg, 0.026 mmol), DIEA (0.019 mL, 0.108 mmol) and DMF (0.5 mL) was stirred at room temperature for 1 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-90% B over 22 minutes, then a 5-minute hold at 100% B; Flow: 20 mL/min. Fractions containing the desired product were combined and dried via centrifugal evaporation. The yield of the product was 8.4 mg. LC/MS (M+H): 528.3; LC retention time: 2.23 min (analytical HPLC Method A); ¹H NMR (500 MHz, DMSO-d₆) δ 8.64 (d, J=2.5 Hz, 1H), 8.45 (s, 1H), 8.41 (s, 1H), 8.02-7.95 (m, 2H), 7.89 (d, J=8.8 Hz, 1H), 7.63-7.56 (m, 1H), 7.28-7.21 (m, 1H), 7.17-7.08 (m, 2H), 7.01 (d, J=8.8 Hz, 1H), 6.65 (d, J=8.5 Hz, 1H), 5.75-5.66 (m, 1H), 3.80 (d, J=5.2 Hz, 2H), 3.68 (d, J=5.2 Hz, 2H), 3.61 (s, 4H), 2.05 (s, 3H), 1.67 (d, J=6.9 Hz, 3H).

Example 126

± 2-(5-(3-chloro-4-((1-(3-fluoro-6-vinylpyridin-2-yl)propyl)amino)quinolin-6-yl)pyrimidin-2-yl)propan-2-ol

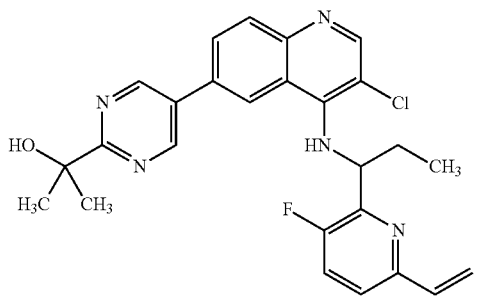

(126)

Intermediate 126A: 2-(5-(4-((1-(6-bromo-3-fluoropyridin-2-yl)propyl)amino)-3-chloroquinolin-6-yl)pyrimidin-2-yl)propan-2-ol

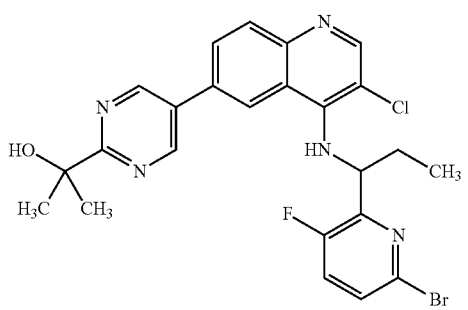

(126A)

A mixture of 1-(6-bromo-3-fluoropyridin-2-yl)propan-1-amine (Intermediate I-75, 201 mg, 0.862 mmol), 2-(5-(3,4-dichloroquinolin-6-yl)pyrimidin-2-yl)propan-2-ol (Intermediate I-45, 96 mg, 0.287 mmol), anhydrous NMP (0.2 mL) and (1R)-(−)-camphor-10-sulfonic acid (33.4 mg, 0.144 mmol) was stirred at 140° C. under nitrogen for 70 min. The mixture was cooled and dissolved in DCM and a little MeOH and DBU (0.065 mL, 0.431 mmol) was added. Flash chromatography purification (12 g silica gel column, gradient elution from 10 to 100% of ethyl acetate in hexanes) afforded 2-(5-(4-((1-(6-bromo-3-fluoropyridin-2-yl)propyl)amino)-3-chloroquinolin-6-yl)pyrimidin-2-yl)propan-2-ol (137 mg, 0.258 mmol, 90% yield). LC/MS (M+H): 530.0; LC retention time: 2.307 min (analytical HPLC Method A); ¹H NMR (500 MHz, DMSO-d₆) δ 9.33 (s, 2H), 8.84 (s, 1H), 8.54 (s, 1H), 8.13 (d, J=8.5 Hz, 1H), 7.98 (d, J=8.9 Hz, 1H), 7.63-7.55 (m, 1H), 7.48 (d, J=7.0 Hz, 1H), 6.78 (d, J=10.0 Hz, 1H), 5.57 (d, J=8.9 Hz, 1H), 2.21-2.09 (m, 1H), 2.02-1.92 (m, 1H), 1.55 (s, 6H), 1.02 (t, J=7.2 Hz, 3H).

Intermediate 126B: 2-(5-(3-chloro-4-((1-(3-fluoro-6-vinylpyridin-2-yl)propyl)amino)quinolin-6-yl)pyrimidin-2-yl)propan-2-ol

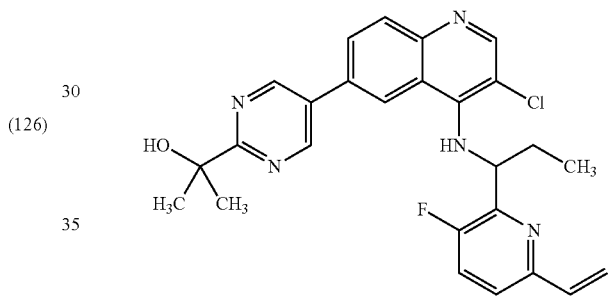

(126B)

To a mixture of vinylboronic acid pinacol ester (0.083 mL, 0.490 mmol), 2-(5-(4-((1-(6-bromo-3-fluoropyridin-2-yl)propyl)amino)-3-chloroquinolin-6-yl)pyrimidin-2-yl)propan-2-ol (0.13 g, 0.245 mmol), potassium carbonate (2 M, 0.306 mL, 0.612 mmol), and 1,1'-bis(diphenylphosphino)ferrocene-palladium(ii)dichloride dichloromethane complex (0.020 g, 0.024 mmol) in 1,4-dioxane (1 mL), was bubbled N₂ gas for 2 min. And the contents were heated at 100° C. for 2 h. Purification using reverse phase HPLC (Phen Luna 5u 30×100 mm (Axia); gradient over 9 min from 20 to 100% of solvent B; solvent A: 10% MeOH: 90% H₂O: 0.1% TFA; solvent B: 90% MeOH, 10% H₂O, 0.1% TFA), concentration, neutralization with K₂CO₃, and extraction with EtOAc gave 2-(5-(3-chloro-4-((1-(3-fluoro-6-vinylpyridin-2-yl)propyl)amino)quinolin-6-yl)pyrimidin-2-yl)propan-2-ol (33 mg, 0.067 mmol, 27.3% yield). LC/MS (M+H): 478.1; LC retention time: 0.963 min (analytical HPLC Method B); ¹H NMR (400 MHz, CHLOROFORM-d) δ 9.04 (s, 2H), 8.64 (s, 1H), 8.31 (d, J=1.8 Hz, 1H), 8.13 (d, J=8.7 Hz, 1H), 7.84 (dd, J=8.7, 2.0 Hz, 1H), 7.38-7.32 (m, 1H), 7.30-7.24 (m, 1H), 6.81 (dd, J=17.4, 10.8 Hz, 1H), 6.49 (d, J=9.4 Hz, 1H), 6.24-6.16 (m, 1H), 5.66-5.56 (m, 1H), 5.46 (d, J=10.9 Hz, 1H), 4.72 (s, 1H), 2.18-1.98 (m, 2H), 1.69 (s, 6H), 0.92-0.83 (m, 3H).

Starting from Example 126, Example 127 was prepared according to the general procedure used in the preparation of Example 397.

| Ex. No. | Structure | LCMS m/z observed | HPLC $t_R$ (min) | HPLC method |
|---|---|---|---|---|
| 127 (±) | 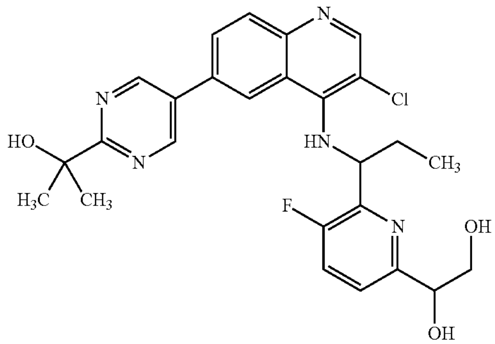 [SMILES: CCC(Nc1c(Cl)cnc2ccc(-c3cnc(C(C)(C)O)nc3)cc12)c1nc(C(O)CO)ccc1F] | 511.9 | 1.638 | A |

Starting with Example 127, the following compound was prepared according to the general procedure used in the preparation of Example 407.

| Ex. No. | Structure | LCMS m/z observed | HPLC $t_R$ (min) | HPLC method |
|---|---|---|---|---|
| 128 (±) | 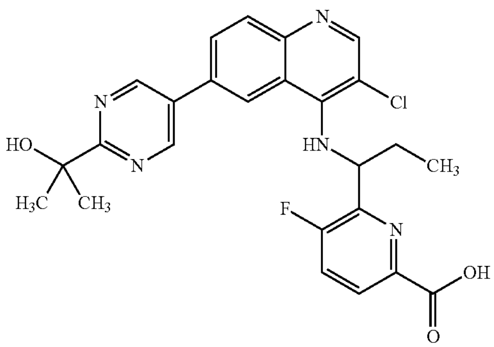 [SMILES: CCC(Nc1c(Cl)cnc2ccc(-c3cnc(C(C)(C)O)nc3)cc12)c1nc(C(=O)O)ccc1F] | 496.1 | 0.823 | B |

Starting from Example 128, the following example was prepared according to the general procedure used in the preparation of Example 416.

| Ex. No. | Structure | LCMS m/z observed | HPLC $t_R$ (min) | HPLC method |
|---|---|---|---|---|
| 129 (±) | 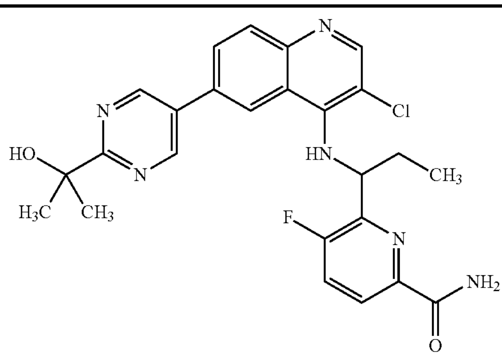 | 495.1 | 0.795 | B |

Starting from Example 127, the following example was prepared according to the general procedures used in the preparation of Intermediate 407A and Example 431.

| Ex. No. | Structure | LCMS m/z observed | HPLC $t_R$ (min) | HPLC method |
|---|---|---|---|---|
| 130 (±) | 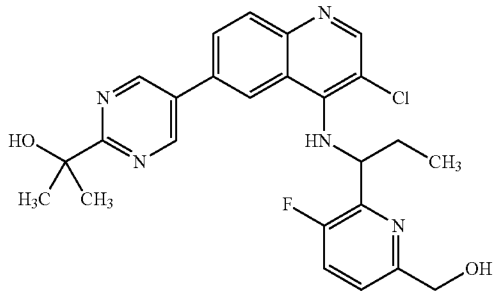 [SMILES: CCC(Nc1c(Cl)cnc2ccc(-c3cnc(C(C)(C)O)nc3)cc12)c1nc(CO)ccc1F] | 482.1 | 1.766 | A |

Examples 131 and 132

(R)—N-(4-(5-(3-chloro-4-((1-(2-fluorophenyl)ethyl)amino)quinolin-6-yl)pyrimidin-2-yl)-4-hydroxycyclohexyl)acetamide

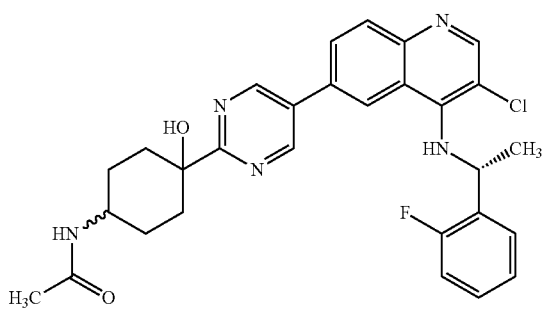

(131 and 132)

Intermediate 131A: (R)-4-amino-1-(5-(3-chloro-4-((1-(2-fluorophenyl)ethyl)amino)quinolin-6-yl)-1,6-dihydropyrimidin-2-yl)cyclohexanol

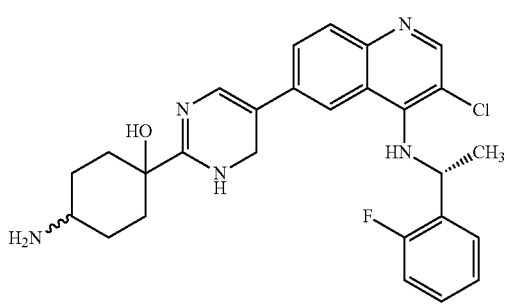

(131A)

To stirred solution of ammonium acetate (204 mg, 2.65 mmol) and (R)-4-(5-(3-chloro-4-((1-(2-fluorophenyl)ethyl)amino)quinolin-6-yl)pyrimidin-2-yl)-4-hydroxycyclohexanone (Example 114, 65 mg, 0.132 mmol) in methanol (5 mL) and $CH_2Cl_2$ (1 mL) was added sodium cyanoborohydride (41.6 mg, 0.662 mmol) at room temperature. After stirring for 1.5 h. The mixture was concentrated in vacuo and the residue was mixed with EtOAc (2 mL) and water (4 mL). The aqueous layer was separated and extracted with ethyl acetate (3×1 mL). The combined organic solutions were concentrated. The residue was mixed with EtOAc (1 mL) and THF (1 mL) and acidified with 1 M aqueous HCl solution. $K_2CO_3$ was then added to make the mixture basic. The mixture was then dried ($Na_2SO_4$) and concentrated under reduced pressure to give (R)-4-amino-1-(5-(3-chloro-4-((1-(2-fluorophenyl)ethyl)amino)quinolin-6-yl)-1,6-dihydropyrimidin-2-yl)cyclohexanol (70 mg, 0.142 mmol), as a solid. LC/MS (M+H): 493.9; LC retention time: 0.727 min (analytical HPLC Method B)

Examples 131 and 132

(R)-4-amino-1-(5-(3-chloro-4-((1-(2-fluorophenyl)ethyl)amino)quinolin-6-yl)-1,6-dihydropyrimidin-2-yl)cyclohexanol (10 mg, 0.020 mmol) was mixed with anhydrous $CH_2Cl_2$ (0.5 mL) and DIEA (0.053 mL, 0.304 mmol). Acetic anhydride (2.87 µl, 0.030 mmol) was added at room temperature. The solution was stirred at room temperature for 1.5 h. 2,3-dichloro-5,6-dicyano-1,4-benzoquinone (4.60 mg, 0.020 mmol) and acetonitrile (1 mL) was added. The mixture was stirred at room temperature overnight. The crude material was purified via preparative LC/MS using the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 5-minute hold at 100% B; Flow: 20 mL/min. Fractions containing the desired product were combined and dried via centrifugal evaporation. Two products were isolated. The yield of the products were 2.0 mg (Example 131) and 1.5 mg (Example 132). Analytical data for Example 131: LC/MS (M+H): 534.4; LC retention time: 1.789 min (analytical HPLC Method A). Analytical data for Example 132: LC/MS (M+H): 534.4; LC retention time: 1.762 min (analytical HPLC Method A).

The compounds in Table 5 were synthesized using the general procedure outlined below.

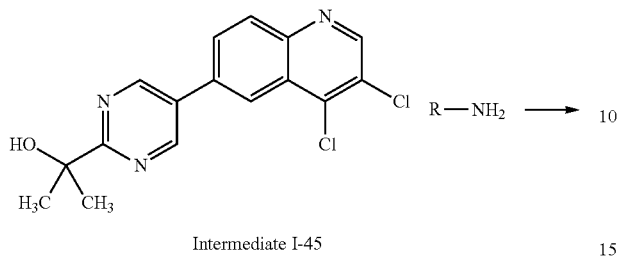

Intermediate I-45

R—NH₂ ⟶

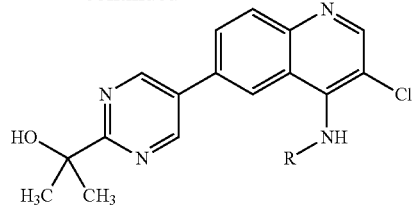

Into a reaction vessel was added the amine (0.090 mmol) followed by cesium carbonate (0.045 mmol) and 2-(5-(3,4-dichloroquinolin-6-yl)pyrimidin-2-yl)propan-2-ol (Intermediate I-45, 15 mg, 0.045 mmol) in DMA (200 μL). The reaction mixture was degassed, purged with N₂ and stirred at 140° C. for 2 h. Upon complete conversion as monitored by LC-MS the reaction mixture was diluted with DMF (1.8 mL), filtered and purified via preparative HPLC (condition A) to afford the desired product.

TABLE 5

| Ex. No. | Structure | MS observed ($M^{+1}$) | HPLC ret. Time (min.) | HPLC method |
|---|---|---|---|---|
| 133 (±) | 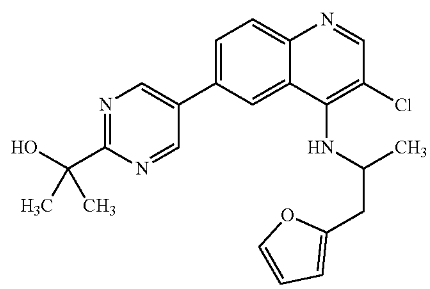 [SMILES: CC(Cc1ccco1)Nc1c(Cl)cnc2ccc(-c3cnc(C(C)(C)O)nc3)cc12] | 422.9 | 2.02 | D |
| 134 (±) | 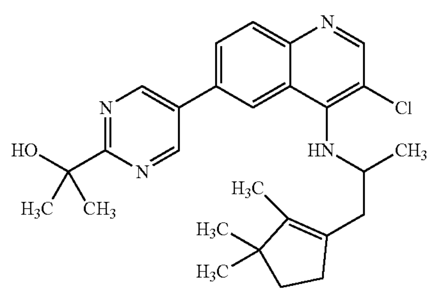 [SMILES: CC1=C(CC(C)Nc2c(Cl)cnc3ccc(-c4cnc(C(C)(C)O)nc4)cc23)CCC1(C)C] | 464.9 | 1.82 | E |
| 135 (±) | 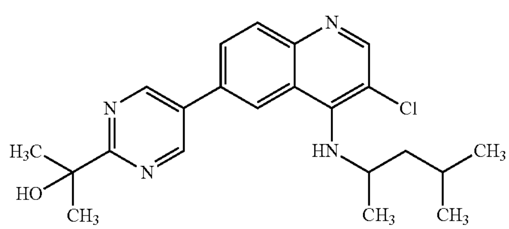 [SMILES: CC(C)CC(C)Nc1c(Cl)cnc2ccc(-c3cnc(C(C)(C)O)nc3)cc12] | 399.1 | 1.45 | E |

TABLE 5-continued

| Ex. No. | Structure | MS observed (M+1) | HPLC ret. Time (min.) | HPLC method |
|---|---|---|---|---|
| 136 | 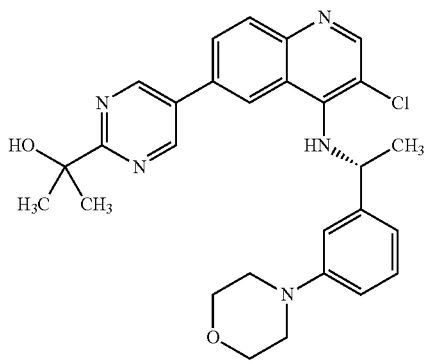 [SMILES: C[C@@H](Nc1c(Cl)cnc2ccc(-c3cnc(C(C)(C)O)nc3)cc12)c1cccc(N2CCOCC2)c1] | 504.0 | 1.35 | E |
| 137 (±) | 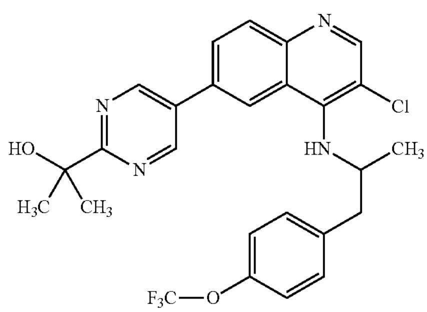 [SMILES: CC(Cc1ccc(OC(F)(F)F)cc1)Nc1c(Cl)cnc2ccc(-c3cnc(C(C)(C)O)nc3)cc12] | 517.0 | 1.64 | E |
| 138 (±) | 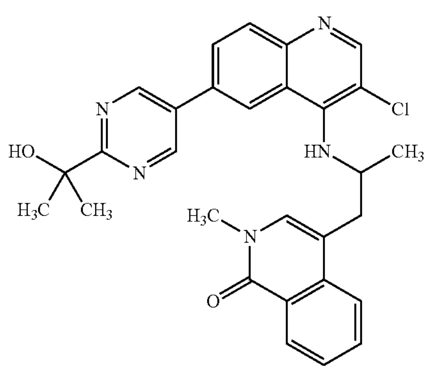 [SMILES: CC(Cc1cn(C)c(=O)c2ccccc12)Nc1c(Cl)cnc2ccc(-c3cnc(C(C)(C)O)nc3)cc12] | 514.0 | 1.68 | D |
| 139 (±) | 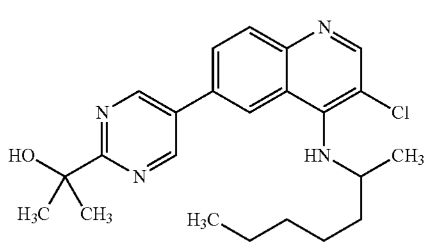 [SMILES: CCCCCC(C)Nc1c(Cl)cnc2ccc(-c3cnc(C(C)(C)O)nc3)cc12] | 413.9 | 2.42 | D |

TABLE 5-continued

| Ex. No. | Structure | MS observed (M$^{+1}$) | HPLC ret. Time (min.) | HPLC method |
|---|---|---|---|---|
| 140 (±) | 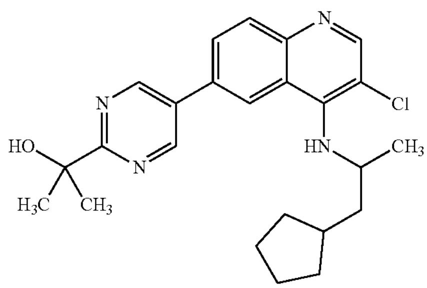 [SMILES: CC(CC1CCCC1)Nc1c(Cl)cnc2ccc(-c3cnc(C(C)(C)O)nc3)cc12] | 425.0 | 1.68 | E |
| 141 (±) | 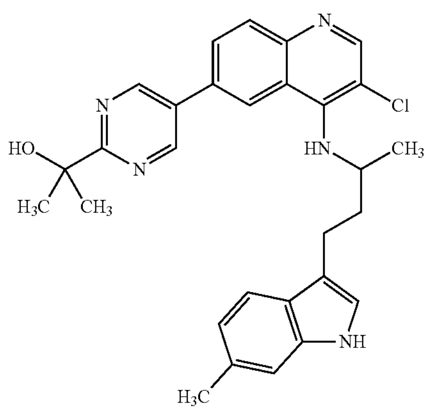 [SMILES: Cc1ccc2c(CCC(C)Nc3c(Cl)cnc4ccc(-c5cnc(C(C)(C)O)nc5)cc34)c[nH]c2c1] | 500.1 | | E |
| 142 (±) | 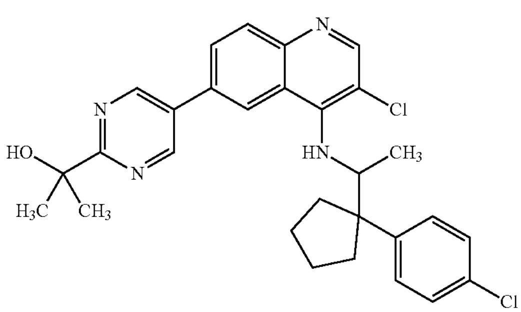 [SMILES: CC(Nc1c(Cl)cnc2ccc(-c3cnc(C(C)(C)O)nc3)cc12)C1(c2ccc(Cl)cc2)CCCC1] | 521.0 | 1.92 | E |
| 143 (±) | 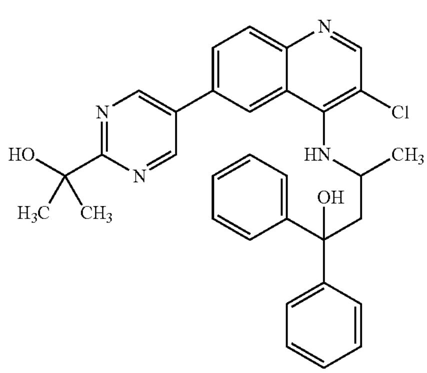 [SMILES: CC(CC(O)(c1ccccc1)c1ccccc1)Nc1c(Cl)cnc2ccc(-c3cnc(C(C)(C)O)nc3)cc12] | 525.1 | 2.03 | D |

TABLE 5-continued

| Ex. No. | Structure | MS observed (M+1) | HPLC ret. Time (min.) | HPLC method |
|---|---|---|---|---|
| 144 (±) | 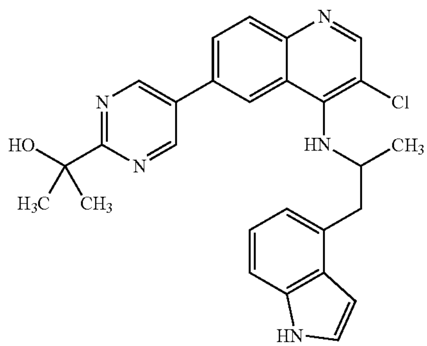 [SMILES: CC(Cc1cccc2[nH]ccc12)Nc1c(Cl)cnc2ccc(-c3cnc(C(C)(C)O)nc3)cc12] | 472.3 | 1.31 | D |

Example 145

2-(5-(3-chloro-4-(4-(trifluoromethyl)benzylamino)quinolin-6-yl)pyrimidin-2-yl)propan-2-ol

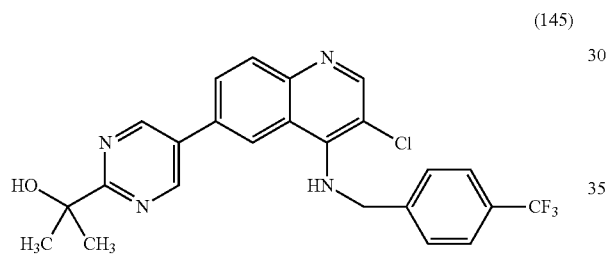

(145)

2-(5-(3-chloro-4-(4-(trifluoromethyl)benzylamino)quinolin-6-yl)pyrimidin-2-yl) propan-2-ol was prepared from Intermediate I-45 and (4-(trifluoromethyl)phenyl) methanamine using the procedure outlined for Example 316. LCMS m/z 473.2 (M+H)+, HPLC $t_R$ 0.77 min (method C).

The examples in Table 6 were prepared according to the general procedure used in the preparation of Example 145.

TABLE 6

| Ex. No. | Structure | LCMS m/z observed | HPLC $t_R$ (min) | HPLC method |
|---|---|---|---|---|
| 146 | 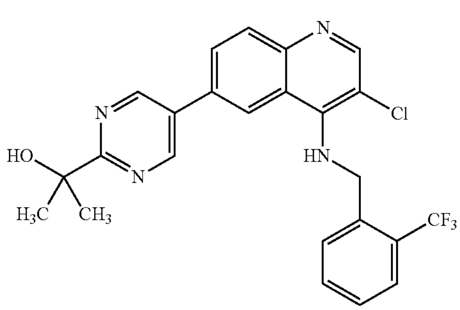 [SMILES: CC(C)(O)c1ncc(-c2ccc3ncc(Cl)c(NCc4ccccc4C(F)(F)F)c3c2)cn1] | 473.2 (M + H)+ | 0.76 | C |

TABLE 6-continued

| Ex. No. | Structure | LCMS m/z observed | HPLC t_R (min) | HPLC method |
|---|---|---|---|---|
| 147 (±) | 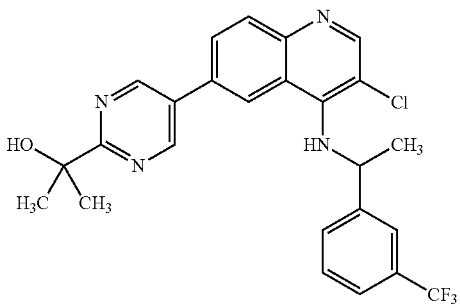 [SMILES: CC(Nc1c(Cl)cnc2ccc(-c3cnc(C(C)(C)O)nc3)cc12)c1cccc(C(F)(F)F)c1] | 487.2 (M + H)+ | 0.79 | C |
| 148 | 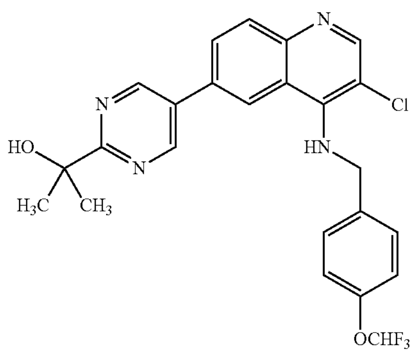 | 471.2 (M + H)+ | 0.73 | C |
| 149 (±) | 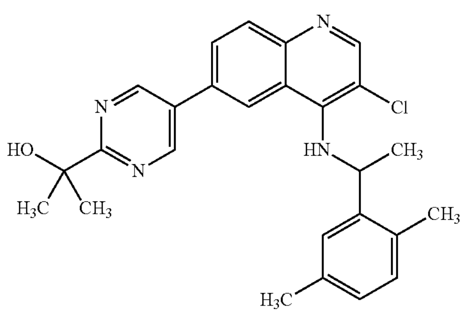 [SMILES: Cc1ccc(C)c(C(C)Nc2c(Cl)cnc3ccc(-c4cnc(C(C)(C)O)nc4)cc23)c1] | 447.3 (M + H)+ | 0.79 | C |
| 150 (±) | 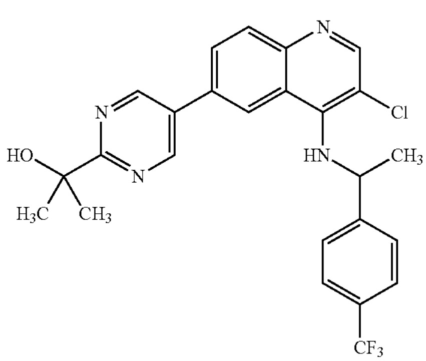 [SMILES: CC(Nc1c(Cl)cnc2ccc(-c3cnc(C(C)(C)O)nc3)cc12)c1ccc(C(F)(F)F)cc1] | 487.2 (M + H)+ | 0.80 | C |

TABLE 6-continued

| Ex. No. | Structure | LCMS m/z observed | HPLC t_R (min) | HPLC method |
|---|---|---|---|---|
| 151 (±) | 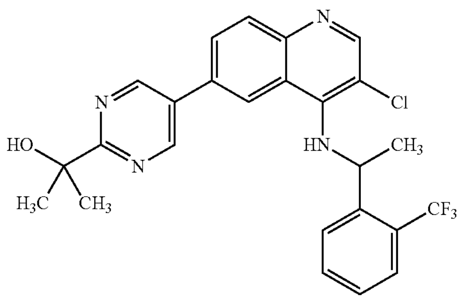 [SMILES: CC(Nc1c(Cl)cnc2ccc(-c3cnc(C(C)(C)O)nc3)cc12)c1ccccc1C(F)(F)F] | 487.2 (M + H)+ | 0.79 | C |
| 152 (±) | 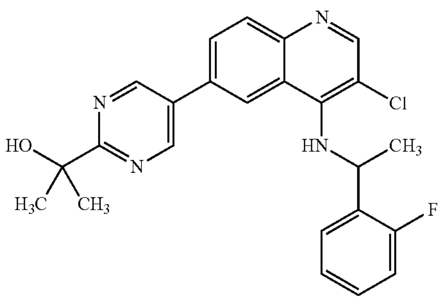 [SMILES: CC(Nc1c(Cl)cnc2ccc(-c3cnc(C(C)(C)O)nc3)cc12)c1ccccc1F] | 437.2 (M + H)+ | 0.74 | C |
| 153 (±) | 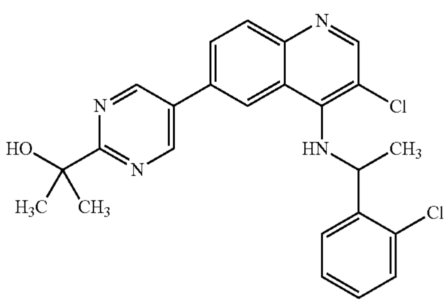 [SMILES: CC(Nc1c(Cl)cnc2ccc(-c3cnc(C(C)(C)O)nc3)cc12)c1ccccc1Cl] | 453.1 (M + H)+ | 0.76 | C |
| 154 | 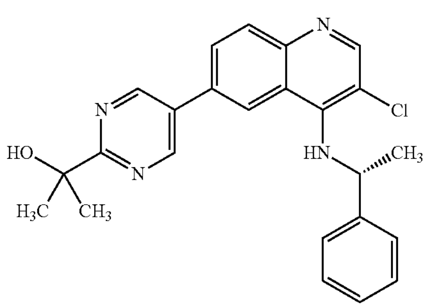 [SMILES: C[C@@H](Nc1c(Cl)cnc2ccc(-c3cnc(C(C)(C)O)nc3)cc12)c1ccccc1] | 419.2 (M + H)+ | 0.72 | C |
| 155 (±) | 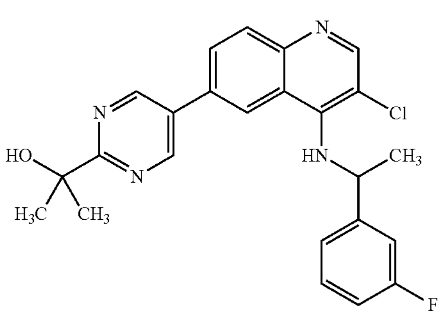 [SMILES: CC(Nc1c(Cl)cnc2ccc(-c3cnc(C(C)(C)O)nc3)cc12)c1cccc(F)c1] | 437.2 (M + H)+ | 0.73 | C |

TABLE 6-continued

| Ex. No. | Structure | LCMS m/z observed | HPLC $t_R$ (min) | HPLC method |
|---|---|---|---|---|
| 156 (±) | 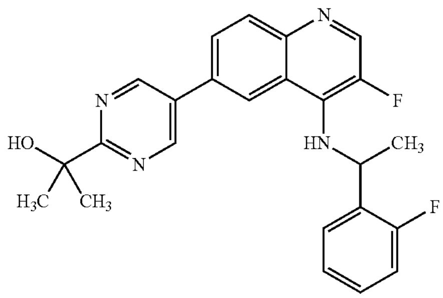 [SMILES: CC(Nc1c(F)cnc2ccc(-c3cnc(C(C)(C)O)nc3)cc12)c1ccccc1F] | 421.2 (M + H)+ | 0.72 | C |
| 157 (±) | 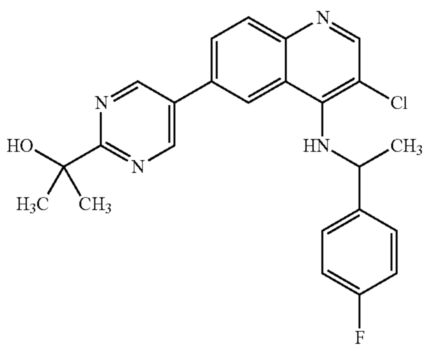 [SMILES: CC(Nc1c(Cl)cnc2ccc(-c3cnc(C(C)(C)O)nc3)cc12)c1ccc(F)cc1] | 437.2 (M + H)+ | 0.73 | C |
| 158 | 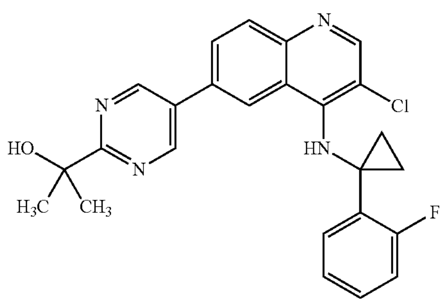 [SMILES: CC(C)(O)c1ncc(-c2ccc3ncc(Cl)c(NC4(c5ccccc5F)CC4)c3c2)cn1] | 449.2 (M + H)+ | 0.72 | C |
| 159 (±) | 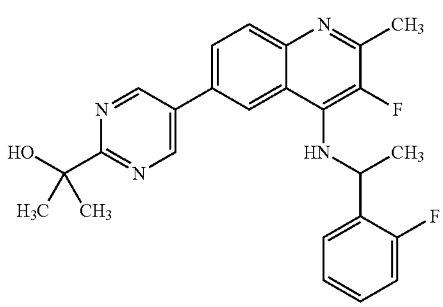 [SMILES: Cc1nc2ccc(-c3cnc(C(C)(C)O)nc3)cc2c(NC(C)c2ccccc2F)c1F] | 435.2 (M + H)+ | 0.75 | C |
| 160 (±) | 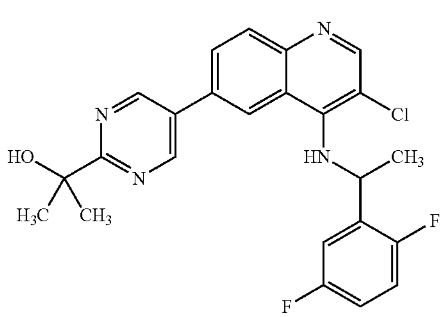 [SMILES: CC(Nc1c(Cl)cnc2ccc(-c3cnc(C(C)(C)O)nc3)cc12)c1cc(F)ccc1F] | 455.1 (M + H)+ | 0.75 | C |

TABLE 6-continued

| Ex. No. | Structure | LCMS m/z observed | HPLC $t_R$ (min) | HPLC method |
|---|---|---|---|---|
| 161 | 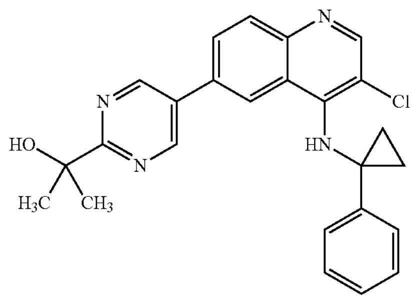 [SMILES: CC(C)(O)c1ncc(-c2ccc3ncc(Cl)c(NC4(c5ccccc5)CC4)c3c2)cn1] | 431.1 (M + H)⁺ | 0.70 | C |
| 162 (±) | 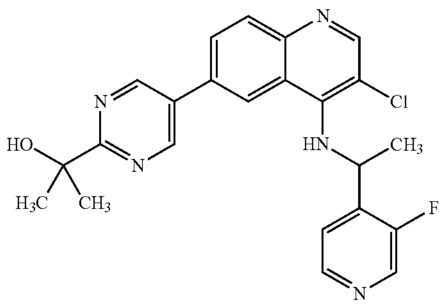 [SMILES: CC(Nc1c(Cl)cnc2ccc(-c3cnc(C(C)(C)O)nc3)cc12)c1ccncc1F] | 438.2 (M + H)⁺ | 0.62 | C |
| 163 (±) | 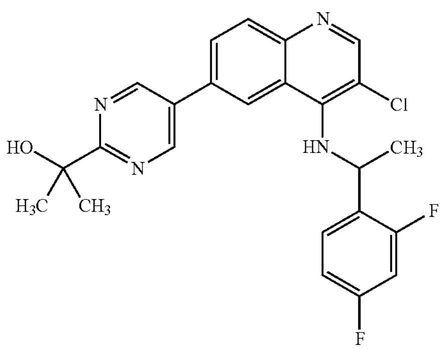 [SMILES: CC(Nc1c(Cl)cnc2ccc(-c3cnc(C(C)(C)O)nc3)cc12)c1ccc(F)cc1F] | 455.2 (M + H)⁺ | 0.75 | C |
| 164 (±) | 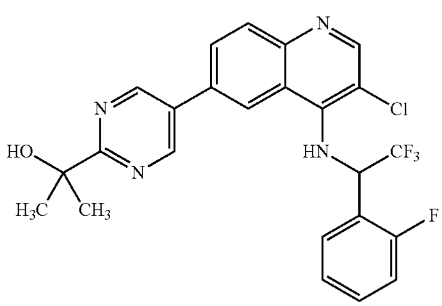 [SMILES: CC(C)(O)c1ncc(-c2ccc3ncc(Cl)c(NC(c4ccccc4F)C(F)(F)F)c3c2)cn1] | 491.2 (M + H)⁺ | 0.92 | C |
| 165 (±) | 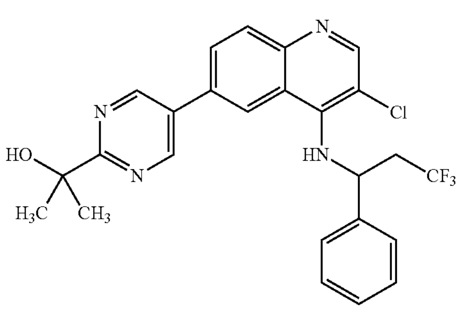 [SMILES: CC(C)(O)c1ncc(-c2ccc3ncc(Cl)c(NC(CC(F)(F)F)c4ccccc4)c3c2)cn1] | 487.2 (M + H)⁺ | 0.77 | C |

TABLE 6-continued
| Ex. No. | Structure | LCMS m/z observed | HPLC $t_R$ (min) | HPLC method |
|---|---|---|---|---|
| 166 (±) | 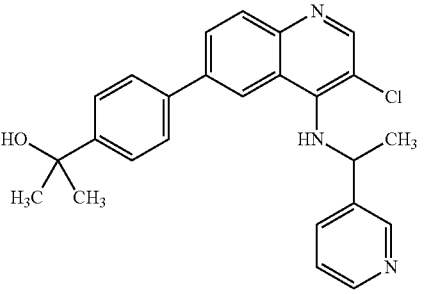 [SMILES: CC(Nc1c(Cl)cnc2ccc(-c3ccc(C(C)(C)O)cc3)cc12)c1cccnc1] | 418.2 (M + H)+ | 0.57 | C |
| 167 (±) | 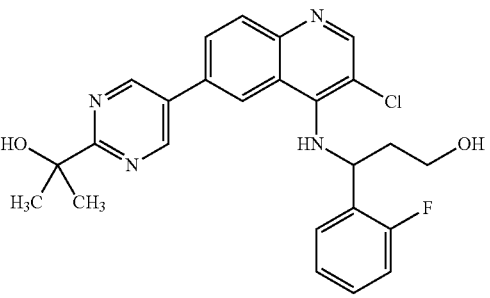 [SMILES: CC(C)(O)c1ncc(-c2ccc3ncc(Cl)c(NC(CCO)c4ccccc4F)c3c2)cn1] | 467.2 (M + H)+ | 0.67 | C |
| 168 (±) | 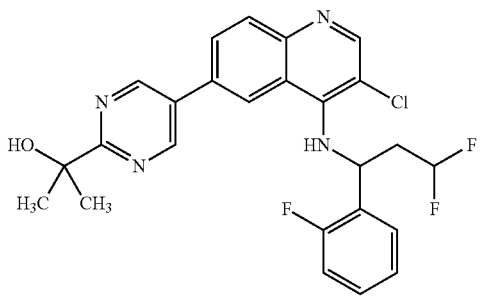 [SMILES: CC(C)(O)c1ncc(-c2ccc3ncc(Cl)c(NC(CC(F)F)c4ccccc4F)c3c2)cn1] | 487.1 (M + H)+ | 0.77 | C |
| 169 (±) | 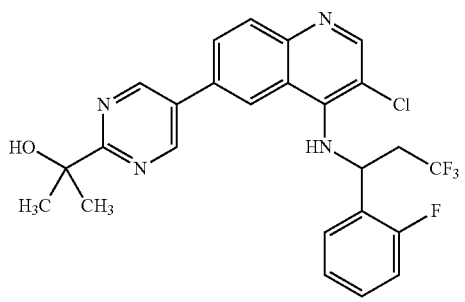 [SMILES: CC(C)(O)c1ncc(-c2ccc3ncc(Cl)c(NC(CC(F)(F)F)c4ccccc4F)c3c2)cn1] | 505.2 (M + H)+ | 0.81 | C |
| 170 (±) | 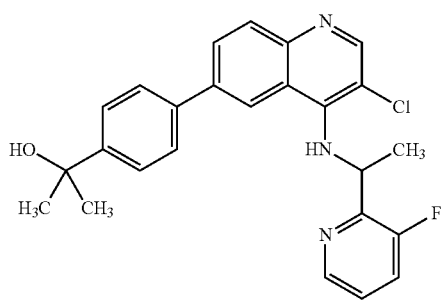 [SMILES: CC(Nc1c(Cl)cnc2ccc(-c3ccc(C(C)(C)O)cc3)cc12)c1ncccc1F] | 436.1 (M + H)+ | 0.76 | C |

TABLE 6-continued

| Ex. No. | Structure | LCMS m/z observed | HPLC $t_R$ (min) | HPLC method |
|---|---|---|---|---|
| 171 (±) | 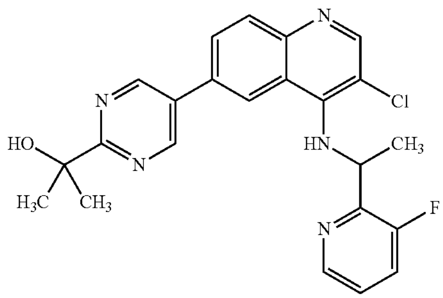 [SMILES: CC(Nc1c(Cl)cnc2ccc(-c3cnc(C(C)(C)O)nc3)cc12)c1ncccc1F] | 438.1 (M + H)+ | 0.69 | C |
| 172 (±) | 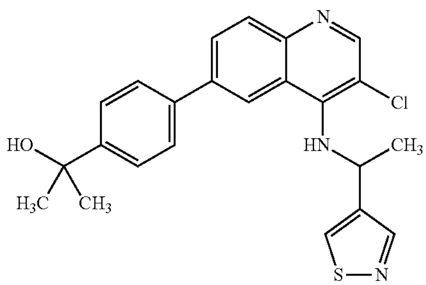 [SMILES: CC(Nc1c(Cl)cnc2ccc(-c3ccc(C(C)(C)O)cc3)cc12)c1cnsc1] | 424.0 (M + H)+ | 0.70 | C |
| 173 (±) | 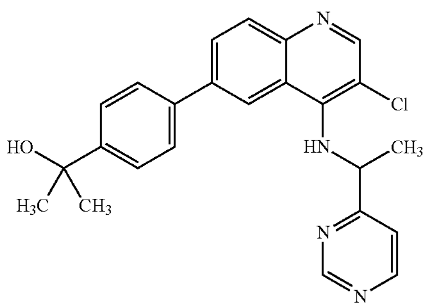 [SMILES: CC(Nc1c(Cl)cnc2ccc(-c3ccc(C(C)(C)O)cc3)cc12)c1ccncn1] | 418.9 (M + H)+ | 0.65 | C |
| 174 (±) | 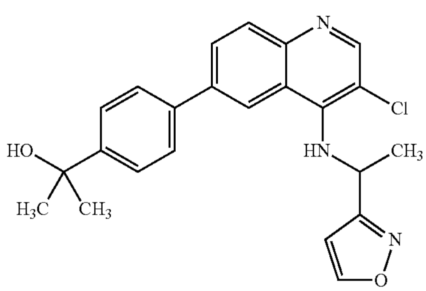 [SMILES: CC(Nc1c(Cl)cnc2ccc(-c3ccc(C(C)(C)O)cc3)cc12)c1ccon1] | 408.1 (M + H)+ | 0.69 | C |
| 175 (±) | 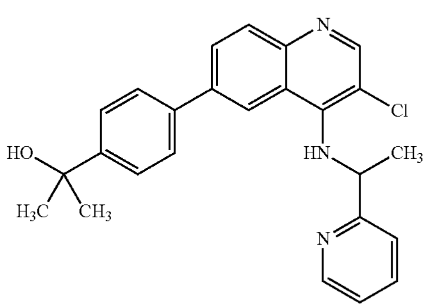 [SMILES: CC(Nc1c(Cl)cnc2ccc(-c3ccc(C(C)(C)O)cc3)cc12)c1ccccn1] | 418.1 (M + H)+ | 0.70 | C |

TABLE 6-continued

| Ex. No. | Structure | LCMS m/z observed | HPLC t$_R$ (min) | HPLC method |
|---|---|---|---|---|
| 176 (±) | 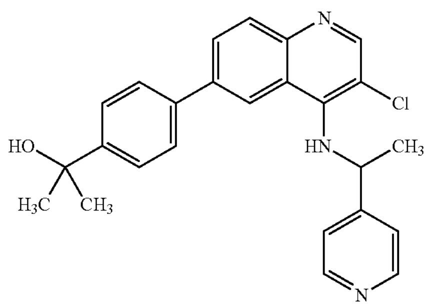 [SMILES: CC(Nc1c(Cl)cnc2ccc(-c3ccc(C(C)(C)O)cc3)cc12)c1ccncc1] | 418.1 (M + H)⁺ | 0.57 | C |
| 177 (±) | 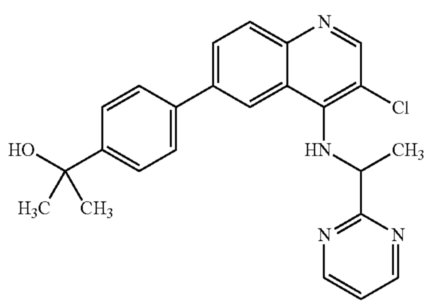 [SMILES: CC(Nc1c(Cl)cnc2ccc(-c3ccc(C(C)(C)O)cc3)cc12)c1ncccn1] | 419.1 (M + H)⁺ | 0.69 | C |
| 178 (±) | 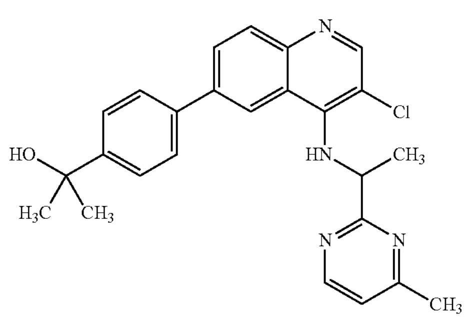 [SMILES: Cc1ccnc(C(C)Nc2c(Cl)cnc3ccc(-c4ccc(C(C)(C)O)cc4)cc23)n1] | 433.1 (M + H)⁺ | 0.72 | C |
| 179 (±) | 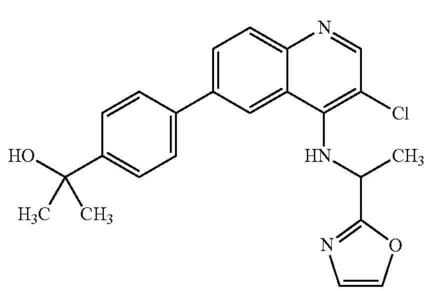 [SMILES: CC(Nc1c(Cl)cnc2ccc(-c3ccc(C(C)(C)O)cc3)cc12)c1ncco1] | 408.1 (M + H)⁺ | 0.68 | C |

Examples 180 and 181

2-(5-(4-(2,5-dimethylphenylamino)-2-methoxy-3-methylquinolin-6-yl)pyrimidin-2-yl)propan-2-ol (180) and 4-((2,5-dimethylphenyl)amino)-6-(2-(2-hydroxypropan-2-yl)pyrimidin-5-yl)-3-methylquinolin-2-ol (181)

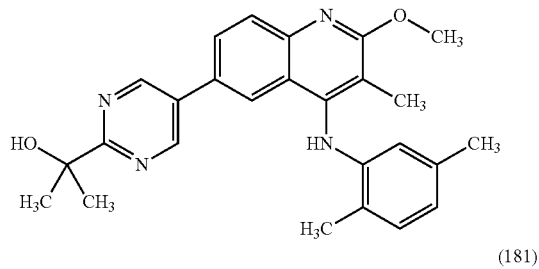
(180)

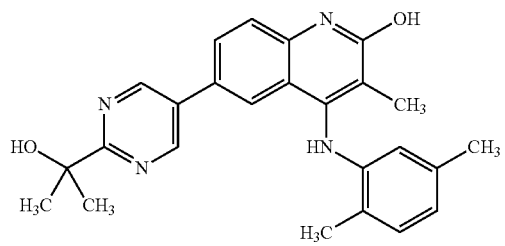
(181)

To a mixture of 2,5-dimethylaniline (7.8 mg, 0.064 mmol, 1.1 eq.), Intermediate I-46 (20 mg, 0.058 mmol), and sodium tert-butoxide (14.0 mg, 0.145 mmol, 2.5 eq.) in anhydrous dioxane (0.2 mL) was bubbled $N_2$ gas for 2 min. Bis(tri-tert-butylphosphine) palladium(0) (3.0 mg, 5.8 µmol, 0.1 eq.) was added to the mixture. $N_2$ gas was bubbled through the reaction mixture for 2 min and stirred at 130° C. under $N_2$ for 20 hours. After cooling to room temperature, the reaction mixture was purified via preparative LC/MS (Condition A: Gradient: 30-100% B over 20 minutes, then a 5-minute hold at 100% B). Analytical data for major product (Example 180): 2-(5-(4-((2,5-dimethylphenyl)amino)-2-methoxy-3-methylquinolin-6-yl)pyrimidin-2-yl)propan-2-ol (8.8 mg, 0.020 mmol, 35% yield) was isolated. LCMS m/z 429.3 (M+H)$^+$, HPLC $t_R$ 0.99 min (method C). $^1$H NMR (500 MHz, DMSO-d$_6$) δ 9.07 (s, 2H), 8.29 (s, 1H), 8.00 (d, J=8.6 Hz, 1H), 7.87 (d, J=8.6 Hz, 1H), 7.54 (s, 1H), 7.09 (d, J=7.5 Hz, 1H), 6.67 (d, J=7.5 Hz, 1H), 6.21 (s, 1H), 4.02 (s, 3H), 2.31 (s, 3H), 2.05 (s, 3H), 1.90 (s, 3H), 1.51 (s, 6H) Analytical data for minor product (Example 181) 4-((2,5-dimethylphenyl)amino)-6-(2-(2-hydroxypropan-2-yl)pyrimidin-5-yl)-3-methylquinolin-2-ol. Yield: (1.5 mg, 3.6 µmol, 6.2% yield). LCMS m/z 415.2 (M+H)$^+$, HPLC $t_R$ 0.86 min (method C). $^1$H NMR (500 MHz, DMSO-d$_6$) δ 8.99 (s, 2H), 8.11 (s, 1H), 7.89 (d, J=8.2 Hz, 1H), 7.55-7.32 (m, 2H), 7.09 (d, J=7.6 Hz, 1H), 6.71 (d, J=7.6 Hz, 1H), 6.37 (s, 1H), 2.99 (s, 1H), 2.27 (s, 3H), 2.11 (s, 3H), 1.72 (s, 3H), 1.50 (s, 6H).

The Examples in Table 7 were prepared according to the general procedures used in the preparation of Example 180.

TABLE 7

| Ex. No. | Structure | LCMS m/z observed | HPLC $t_R$ (min) | HPLC method |
|---|---|---|---|---|
| 182 | 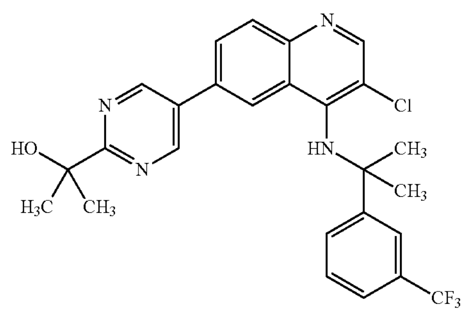 [SMILES: CC(C)(O)c1ncc(-c2ccc3ncc(Cl)c(NC(C)(C)c4cccc(C(F)(F)F)c4)c3c2)cn1] | 501.2 (M + H)$^+$ | 0.82 | C |
| 183 | 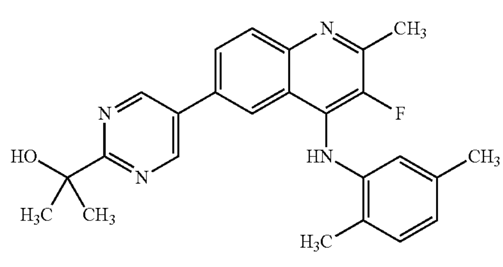 [SMILES: Cc1ccc(C)c(Nc2c(F)c(C)nc3ccc(-c4cnc(C(C)(C)O)nc4)cc23)c1] | 417.3 (M + H)$^+$ | 0.74 | C |

TABLE 7-continued

| Ex. No. | Structure | LCMS m/z observed | HPLC $t_R$ (min) | HPLC method |
|---|---|---|---|---|
| 184 | 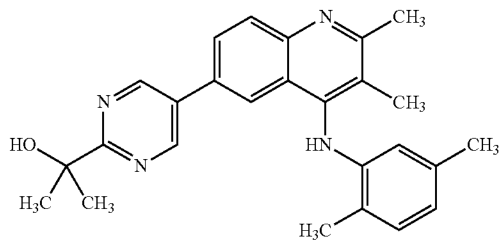 [SMILES: Cc1ccc(C)c(Nc2c(C)c(C)nc3ccc(-c4cnc(C(C)(C)O)nc4)cc23)c1] | 413.3 (M + H)+ | 0.75 | C |
| 185 | 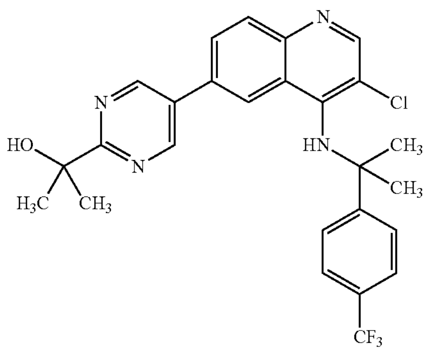 [SMILES: CC(C)(O)c1ncc(-c2ccc3ncc(Cl)c(NC(C)(C)c4ccc(C(F)(F)F)cc4)c3c2)cn1] | 501.3 (M + H)+ | 0.83 | C |
| 186 | 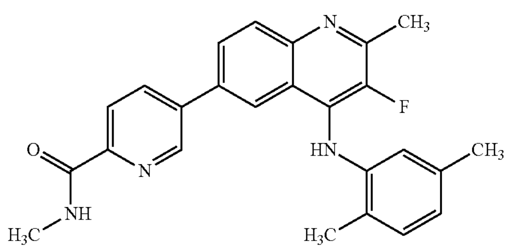 [SMILES: CNC(=O)c1ccc(-c2ccc3nc(C)c(F)c(Nc4cc(C)ccc4C)c3c2)cn1] | 415.2 (M + H)+ | 0.74 | C |
| 187 | 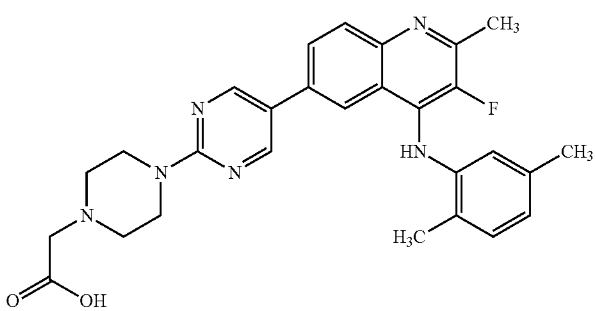 [SMILES: Cc1ccc(C)c(Nc2c(F)c(C)nc3ccc(-c4cnc(N5CCN(CC(=O)O)CC5)nc4)cc23)c1] | 501.3 (M + H)+ | 0.66 | C |
| 188 | homochiral | 482.3 (M + H)+ | 0.93 | C |

TABLE 7-continued

| Ex. No. | Structure | LCMS m/z observed | HPLC $t_R$ (min) | HPLC method |
|---|---|---|---|---|
| 189 | 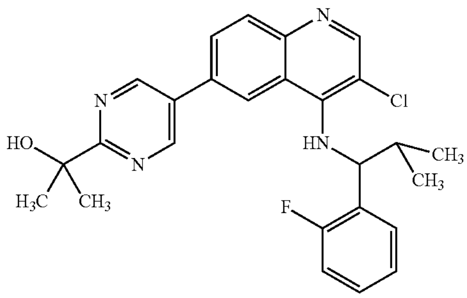 [SMILES: CC(C)C(Nc1c(Cl)cnc2ccc(-c3cnc(C(C)(C)O)nc3)cc12)c1ccccc1F] | 465.2 (M + H)+ | 0.81 | C |
| 190 (±) | 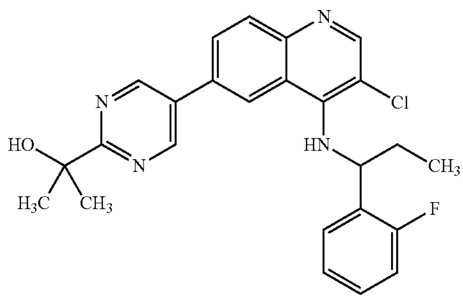 [SMILES: CCC(Nc1c(Cl)cnc2ccc(-c3cnc(C(C)(C)O)nc3)cc12)c1ccccc1F] | 451.2 (M + H)+ | 0.77 | C |
| 191 (±) | 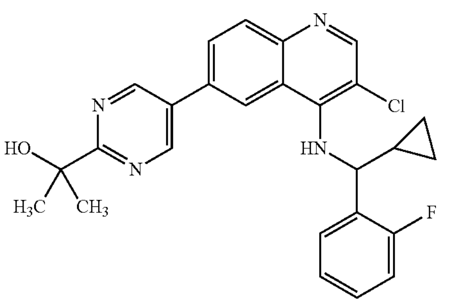 [SMILES: CC(C)(O)c1ncc(-c2ccc3ncc(Cl)c(NC(c4ccccc4F)C4CC4)c3c2)cn1] | 462.9 (M + H)+ | 0.77 | C |

Example 192

± 2-(4-(3-chloro-4-((1-(furan-2-yl)ethyl)amino)qui-nolin-6-yl)phenyl)propan-2-ol (192)

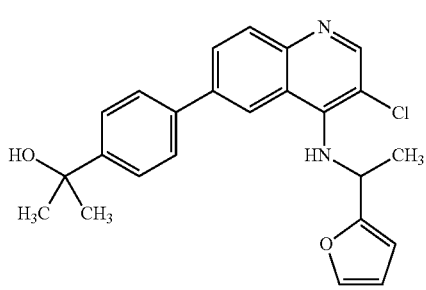

A mixture of 1-(furan-2-yl)ethanamine (10 mg, 0.090 mmol, 1.0 eq.), Intermediate I-47 (30 mg, 0.090 mmol, 1.0 eq.), sodium tert-butoxide (17.4 mg, 0.181 mmol, 2.0 eq.), Pd$_2$(dba)$_3$ (8.3 mg, 9.0 µmol, 0.1 eq.), racemic BINAP (11.2 mg, 0.018 mmol, 0.2 eq.), and anhydrous 1,4-dioxane (1.0 mL) was bubbled with N$_2$ gas for 2 min. The reaction mixture was stirred at 100° C. under N$_2$ for 1 hour. After cooling to room temperature, the reaction mixture was purified via preparative LC/MS (Condition A: Gradient: 40-80% B over 25 minutes, then a 5-minute hold at 100% B). 2-(5-(3-chloro-4-(4-(trifluoromethyl)benzylamino)qui-nolin-6-yl)pyrimidin-2-yl)propan-2-ol (11.2 mg, 0.027 mmol, 29.9% yield) was isolated. LCMS m/z 407.2 (M+H)+, HPLC t$_R$ 0.76 min (method C). $^1$H NMR (500 MHz, DMSO-d$_6$) δ 8.64-8.45 (m, 2H), 8.11-7.98 (m, 1H), 7.97-7.91 (m, 1H), 7.74 (d, J=8.2 Hz, 2H), 7.60 (d, J=8.3 Hz, 2H), 7.53 (s, 1H), 6.53 (d, J=9.5 Hz, 1H), 6.41-6.32 (m, 1H), 6.28 (d, J=3.0 Hz, 1H), 5.50-5.32 (m, 1H), 1.68 (d, J=6.7 Hz, 3H), 1.48 (s, 6H).

The Examples in Table 8 were prepared according to the general procedures used in the preparation of Example 47 or similar procedures.

TABLE 8

| Ex. No. | Structure | LCMS m/z observed | HPLC t$_R$ (min) | HPLC method |
|---|---|---|---|---|
| 193 | 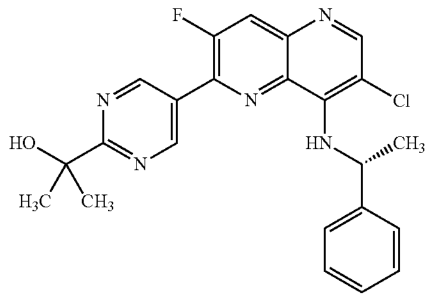 [SMILES: C[C@@H](Nc1c(Cl)cnc2cc(F)c(-c3cnc(C(C)(C)O)nc3)nc12)c1ccccc1] | 438.1 (M + H)$^+$ | 0.83 | C |
| 194 (±) | 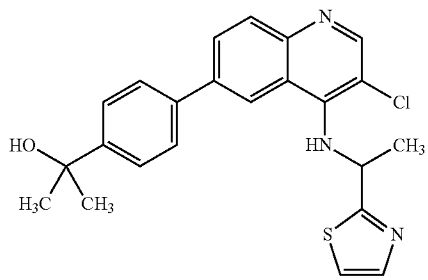 [SMILES: CC(Nc1c(Cl)cnc2ccc(-c3ccc(C(C)(C)O)cc3)cc12)c1nccs1] | 424.0 (M + H)$^+$ | 0.71 | C |
| 195 (±) | 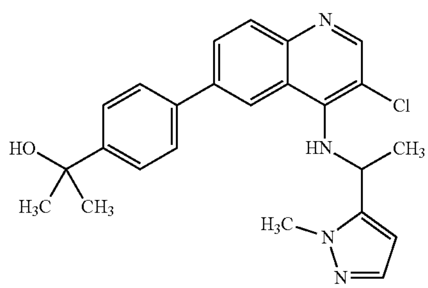 [SMILES: CC(Nc1c(Cl)cnc2ccc(-c3ccc(C(C)(C)O)cc3)cc12)c1ccnn1C] | 421.1 (M + H)$^+$ | 0.67 | C |
| 196 (±) | 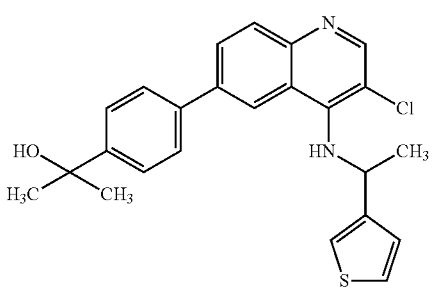 [SMILES: CC(Nc1c(Cl)cnc2ccc(-c3ccc(C(C)(C)O)cc3)cc12)c1ccsc1] | 423.1 (M + H)$^+$ | 0.78 | C |
| 197 (±) | 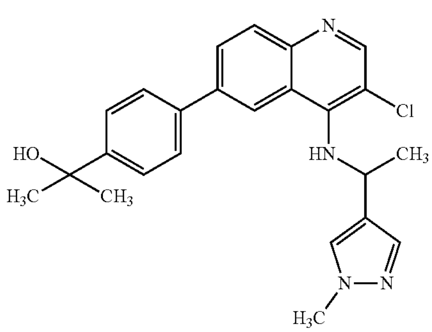 [SMILES: CC(Nc1c(Cl)cnc2ccc(-c3ccc(C(C)(C)O)cc3)cc12)c1cnn(C)c1] | 421.1 (M + H)$^+$ | 0.66 | C |

TABLE 8-continued

| Ex. No. | Structure | LCMS m/z observed | HPLC $t_R$ (min) | HPLC method |
|---|---|---|---|---|
| 198 (±) | 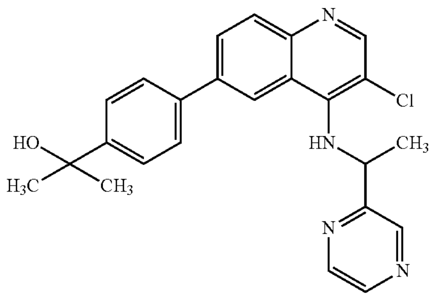 [SMILES: CC(Nc1c(Cl)cnc2ccc(-c3ccc(C(C)(C)O)cc3)cc12)c1cnccn1] | 419.1 (M + H)+ | 0.68 | C |
| 199 (±) | 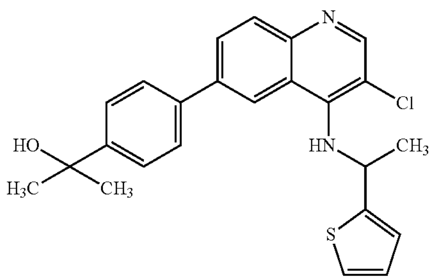 [SMILES: CC(Nc1c(Cl)cnc2ccc(-c3ccc(C(C)(C)O)cc3)cc12)c1cccs1] | 423.0 (M + H)+ | 0.78 | C |
| 200 (±) | 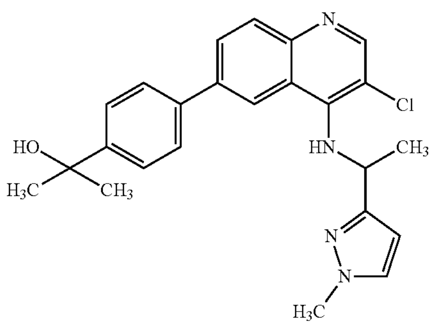 [SMILES: CC(Nc1c(Cl)cnc2ccc(-c3ccc(C(C)(C)O)cc3)cc12)c1ccn(C)n1] | 421.1 (M + H)+ | 0.69 | C |
| 201 (±) | 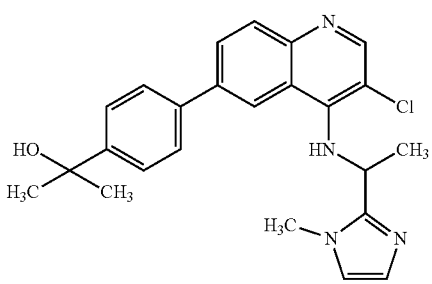 [SMILES: CC(Nc1c(Cl)cnc2ccc(-c3ccc(C(C)(C)O)cc3)cc12)c1nccn1C] | 421.1 (M + H)+ | 0.60 | C |
| 202 (±) | 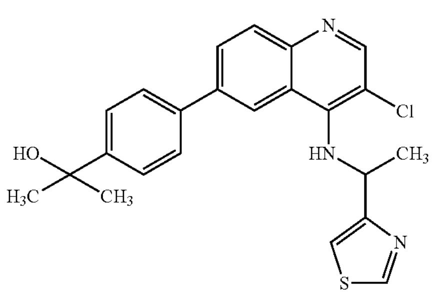 [SMILES: CC(Nc1c(Cl)cnc2ccc(-c3ccc(C(C)(C)O)cc3)cc12)c1cscn1] | 424.0 (M + H)+ | 0.71 | C |

TABLE 8-continued

| Ex. No. | Structure | LCMS m/z observed | HPLC $t_R$ (min) | HPLC method |
|---|---|---|---|---|
| 203 (±) | 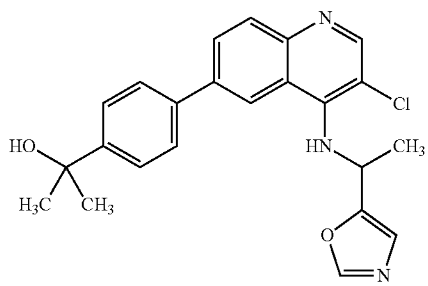 [SMILES: CC(Nc1c(Cl)cnc2ccc(-c3ccc(C(C)(C)O)cc3)cc12)c1cnco1] | 408.0 (M + H)+ | 0.67 | C |
| 204 (±) | 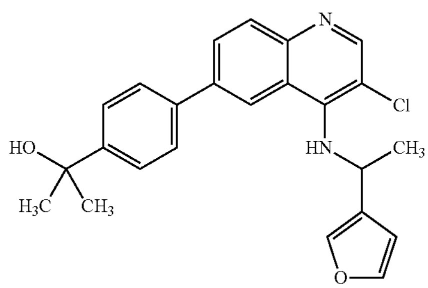 [SMILES: CC(Nc1c(Cl)cnc2ccc(-c3ccc(C(C)(C)O)cc3)cc12)c1ccoc1] | 406.9 (M + H)+ | 0.73 | C |
| 205 (±) | 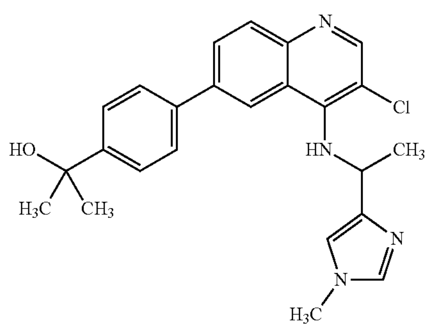 [SMILES: CC(Nc1c(Cl)cnc2ccc(-c3ccc(C(C)(C)O)cc3)cc12)c1cn(C)cn1] | 421.1 (M + H)+ | 0.57 | C |
| 206 (±) | 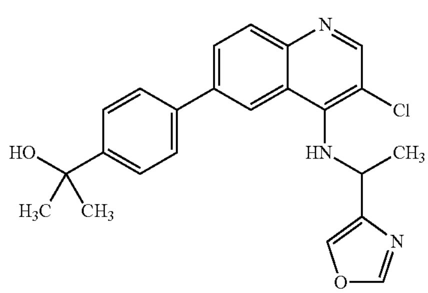 [SMILES: CC(Nc1c(Cl)cnc2ccc(-c3ccc(C(C)(C)O)cc3)cc12)c1cocn1] | 408.0 (M + H)+ | 0.67 | C |
| 207 | 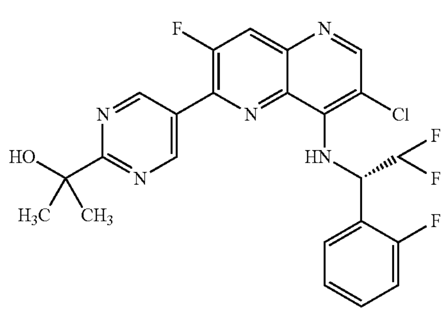 [SMILES: CC(C)(O)c1ncc(-c2nc3c(N[C@@H](c4ccccc4F)C(F)F)c(Cl)cnc3cc2F)cn1] | 492.1 (M + H)+ | 0.96 | C |

TABLE 8-continued

| Ex. No. | Structure | LCMS m/z observed | HPLC $t_R$ (min) | HPLC method |
|---|---|---|---|---|
| 208 | 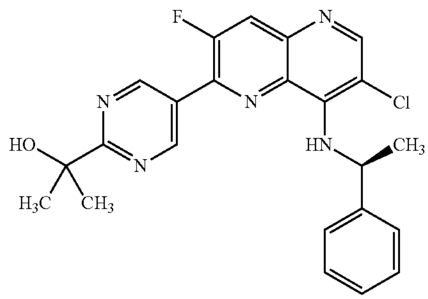 [SMILES: C[C@H](Nc1c(Cl)cnc2cc(F)c(-c3cnc(C(C)(C)O)nc3)nc12)c1ccccc1] | 438.1 (M + H)⁺ | 0.83 | C |
| 209 (±) | 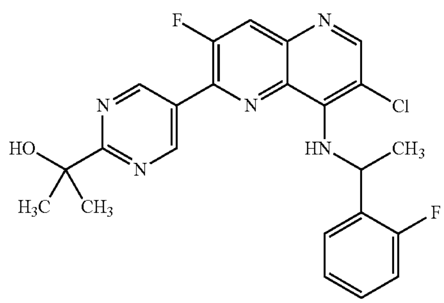 [SMILES: CC(Nc1c(Cl)cnc2cc(F)c(-c3cnc(C(C)(C)O)nc3)nc12)c1ccccc1F] | 456.1 (M + H)⁺ | 0.86 | C |
| 210 (±) | 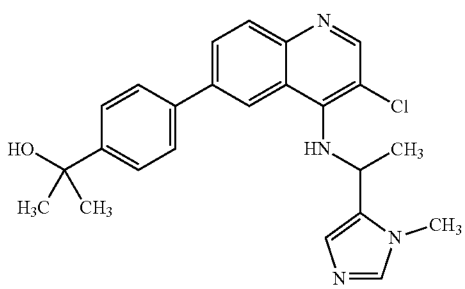 [SMILES: CC(Nc1c(Cl)cnc2ccc(-c3ccc(C(C)(C)O)cc3)cc12)c1cncn1C] | 421.1 (M + H)⁺ | 0.57 | C |
| 211 (±) | 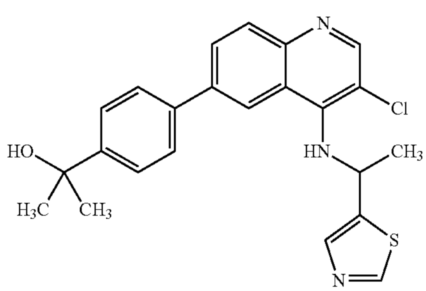 [SMILES: CC(Nc1c(Cl)cnc2ccc(-c3ccc(C(C)(C)O)cc3)cc12)c1cncs1] | 424.0 (M + H)⁺ | 0.67 | C |
| 212 (±) | 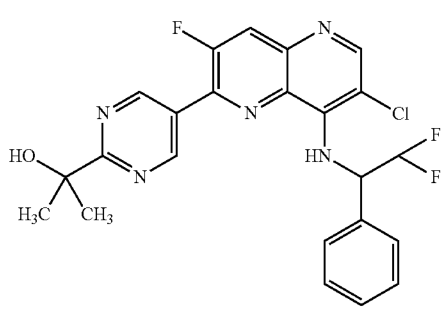 [SMILES: CC(C)(O)c1ncc(-c2nc3c(NC(c4ccccc4)C(F)F)c(Cl)cnc3cc2F)cn1] | 474.1 (M + H)⁺ | 0.92 | C |

TABLE 8-continued

| Ex. No. | Structure | LCMS m/z observed | HPLC $t_R$ (min) | HPLC method |
|---|---|---|---|---|
| 213 | 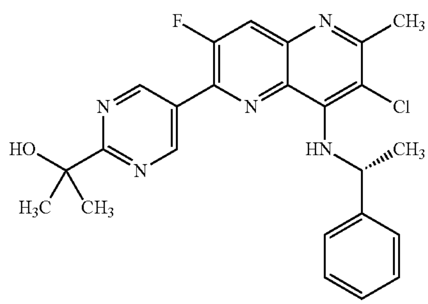 [SMILES: Cc1nc2cc(F)c(-c3cnc(C(C)(C)O)nc3)nc2c(N[C@H](C)c2ccccc2)c1Cl] | 452.1 (M + H)+ | 0.77 | C |
| 214 (±) | 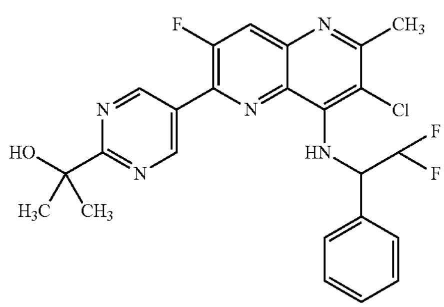 [SMILES: Cc1nc2cc(F)c(-c3cnc(C(C)(C)O)nc3)nc2c(NC(c2ccccc2)C(F)F)c1Cl] | 488.1 (M + H)+ | 0.83 | C |
| 215 | 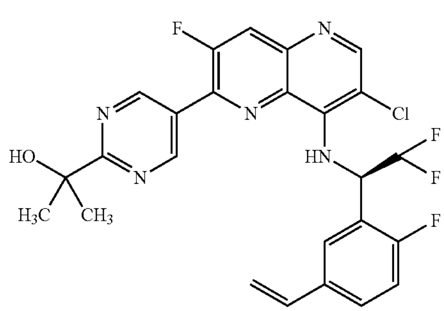 [SMILES: C=Cc1ccc(F)c([C@@H](Nc2c(Cl)cnc3cc(F)c(-c4cnc(C(C)(C)O)nc4)nc23)C(F)F)c1] | 518.1 (M + H)+ | 1.01 | C |
| 216 (±) | 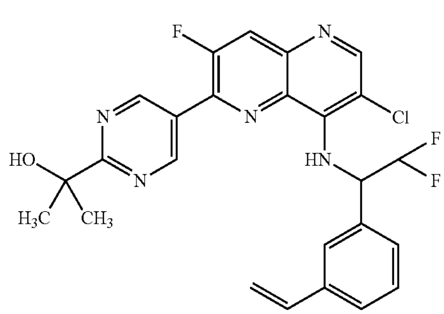 [SMILES: C=Cc1cccc(C(Nc2c(Cl)cnc3cc(F)c(-c4cnc(C(C)(C)O)nc4)nc23)C(F)F)c1] | 500.1 (M + H)+ | 0.98 | C |

Example 217

(R)-2-(5-(3-chloro-4-(1-(2-fluorophenyl)ethylamino)
quinolin-6-yl)pyrimidin-2-yl)propan-2-ol

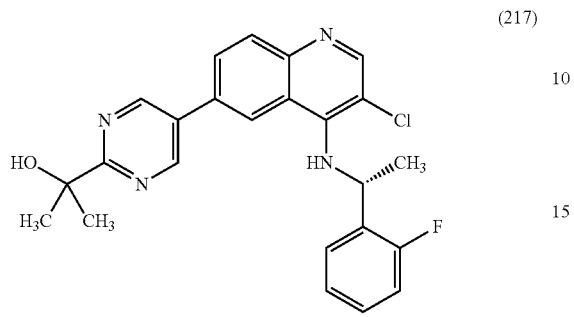

(217)

(R)-2-(5-(3-chloro-4-(1-(2-fluorophenyl)ethylamino)qui-nolin-6-yl)pyrimidin-2-yl)propan-2-ol was prepared from Intermediate I-58, using an analogous procedure to the synthesis of Intermediate I-45. LCMS m/z 437.1 (M+H)$^+$, HPLC $t_R$ 0.73 min (method C).

The Examples in Table 9 were prepared according to the general procedure used in the preparation of Example 217.

TABLE 9

| Ex. No. | Structure | LCMS m/z observed | HPLC $t_R$ (min) | HPLC method |
|---|---|---|---|---|
| 218 (±) | 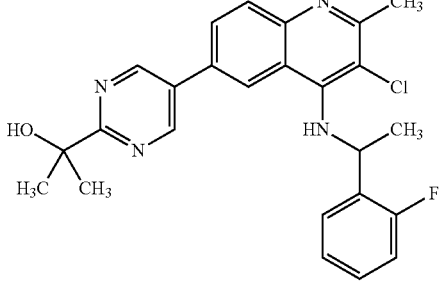 | 451.2 (M + H)$^+$ | 0.75 | C |
| 219 | 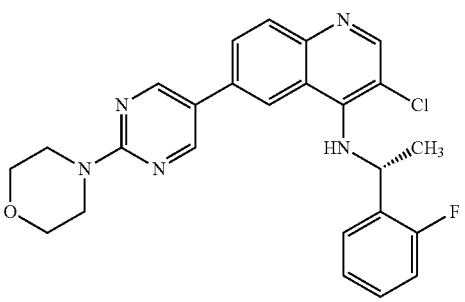 [SMILES: C[C@@H](Nc1c(Cl)cnc2ccc(-c3cnc(N4CCOCC4)nc3)cc12)c1ccccc1F] | 464.2 (M + H)$^+$ | 0.78 | C |

TABLE 9-continued

| Ex. No. | Structure | LCMS m/z observed | HPLC $t_R$ (min) | HPLC method |
|---|---|---|---|---|
| 220 | 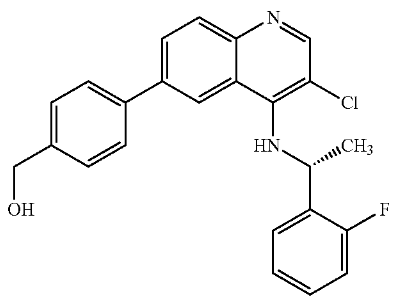 [SMILES: C[C@@H](Nc1c(Cl)cnc2ccc(-c3ccc(CO)cc3)cc12)c1ccccc1F] | 407.2 (M + H)+ | 0.73 | C |
| 221 | 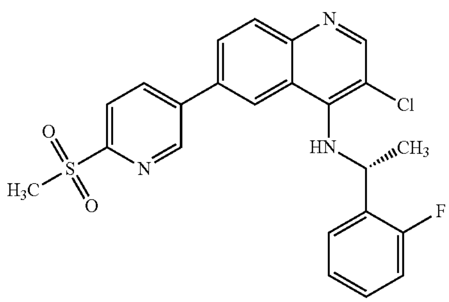 [SMILES: C[C@@H](Nc1c(Cl)cnc2ccc(-c3ccc(S(C)(=O)=O)nc3)cc12)c1ccccc1F] | 456.2 (M + H)+ | 0.72 | C |
| 222 | 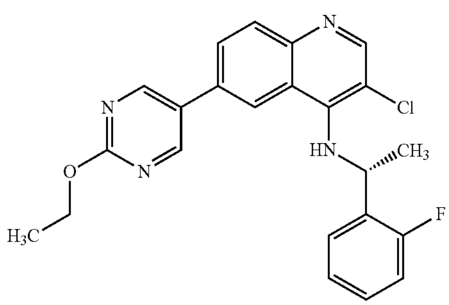 [SMILES: CCOc1ncc(-c2ccc3ncc(Cl)c(N[C@H](C)c4ccccc4F)c3c2)cn1] | 423.2 (M + H)+ | 0.79 | C |
| 223 | 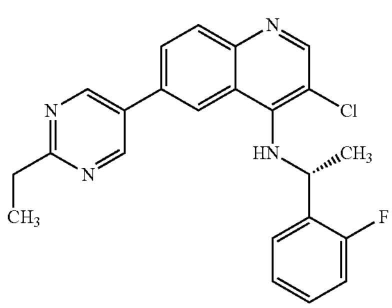 [SMILES: CCc1ncc(-c2ccc3ncc(Cl)c(N[C@H](C)c4ccccc4F)c3c2)cn1] | 407.2 (M + H)+ | 0.76 | C |
| 224 | 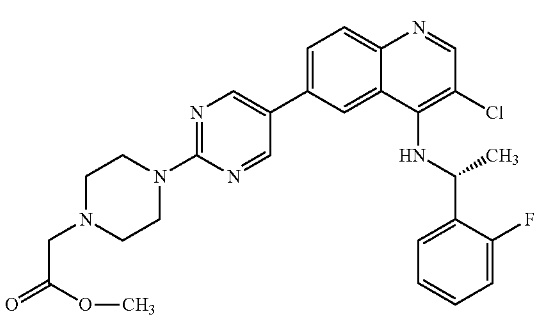 [SMILES: COC(=O)CN1CCN(c2ncc(-c3ccc4ncc(Cl)c(N[C@H](C)c5ccccc5F)c4c3)cn2)CC1] | 535.2 (M + H)+ | 0.67 | C |

TABLE 9-continued

| Ex. No. | Structure | LCMS m/z observed | HPLC $t_R$ (min) | HPLC method |
|---|---|---|---|---|
| 225 | 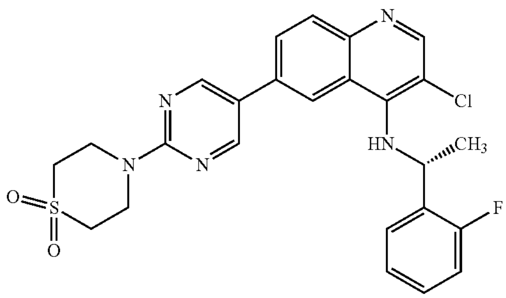 [SMILES: C[C@@H](Nc1c(Cl)cnc2ccc(-c3cnc(N4CCS(=O)(=O)CC4)nc3)cc12)c1ccccc1F] | 512.2 (M + H)+ | 0.74 | C |
| 226 | 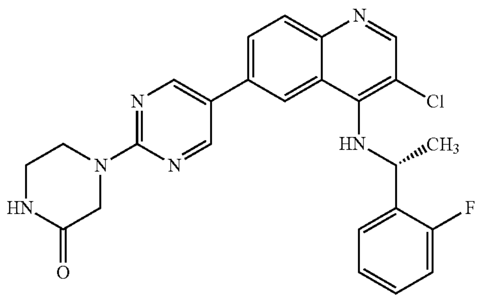 [SMILES: C[C@@H](Nc1c(Cl)cnc2ccc(-c3cnc(N4CCNC(=O)C4)nc3)cc12)c1ccccc1F] | 477.2 (M + H)+ | 0.68 | C |
| 227 | 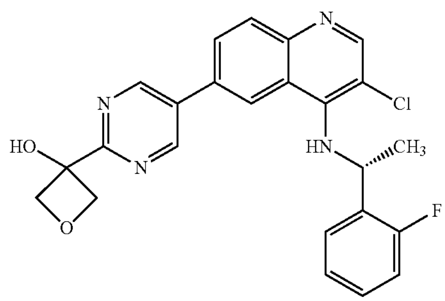 [SMILES: C[C@@H](Nc1c(Cl)cnc2ccc(-c3cnc(C4(O)COC4)nc3)cc12)c1ccccc1F] | 451.2 (M + H)+ | 0.67 | C |
| 228 | 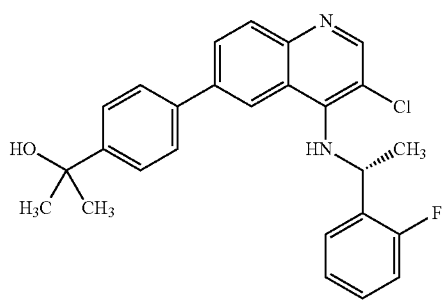 [SMILES: C[C@@H](Nc1c(Cl)cnc2ccc(-c3ccc(C(C)(C)O)cc3)cc12)c1ccccc1F] | 435.2 (M + H)+ | 0.79 | C |
| 229 (±) | 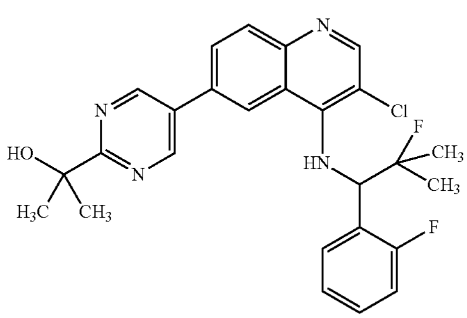 [SMILES: CC(C)(O)c1ncc(-c2ccc3ncc(Cl)c(NC(c4ccccc4F)C(C)(C)F)c3c2)cn1] | 483.2 (M + H)+ | 0.80 | C |

TABLE 9-continued

| Ex. No. | Structure | LCMS m/z observed | HPLC t$_R$ (min) | HPLC method |
|---|---|---|---|---|
| 230 (±) | 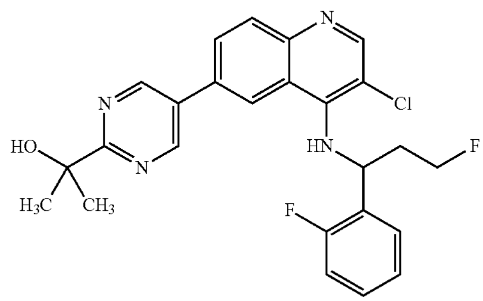 [SMILES: CC(C)(O)c1ncc(-c2ccc3ncc(Cl)c(NC(CCF)c4ccccc4F)c3c2)cn1] | 469.2 (M + H)$^+$ | 0.74 | C |
| 231 (±) | 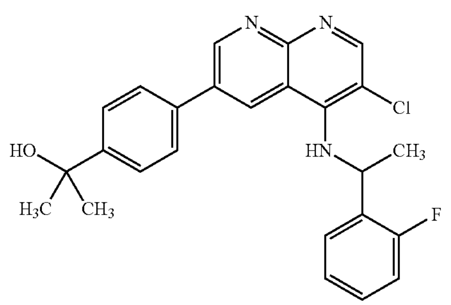 [SMILES: CC(Nc1c(Cl)cnc2ncc(-c3ccc(C(C)(C)O)cc3)cc12)c1ccccc1F] | 436.2 (M + H)$^+$ | 0.76 | C |
| 232 (±) | 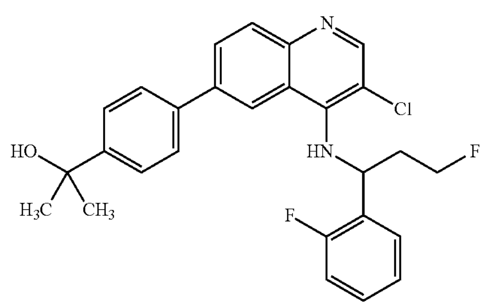 [SMILES: CC(C)(O)c1ccc(-c2ccc3ncc(Cl)c(NC(CCF)c4ccccc4F)c3c2)cc1] | 467.1 (M + H)$^+$ | 0.79 | C |
| 233 | 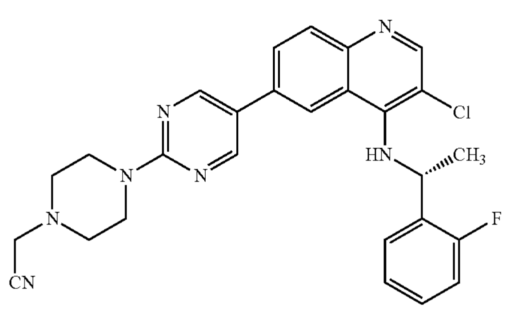 [SMILES: C[C@@H](Nc1c(Cl)cnc2ccc(-c3cnc(N4CCN(CC#N)CC4)nc3)cc12)c1ccccc1F] | 502.1 (M + H)$^+$ | 0.75 | C |

Example 234

(S)-2-(5-(3-chloro-4-(1-(2-fluorophenyl)ethyl-amino)-1,7-naphthyridin-6-yl)pyrimidin-2-yl)propan-2-ol

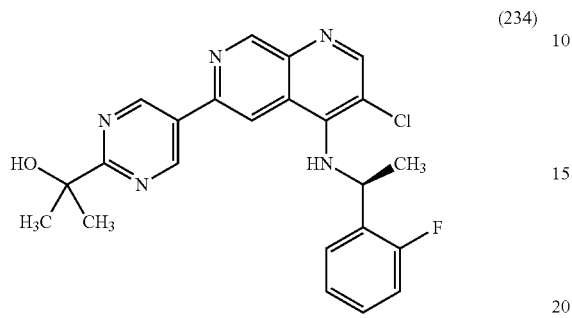
(234)

Intermediate 234A: ± 2-(5-(3-chloro-4-((1-(2-fluorophenyl)ethyl)amino)-1,7-naphthyridin-6-yl)pyrimidin-2-yl)propan-2-ol

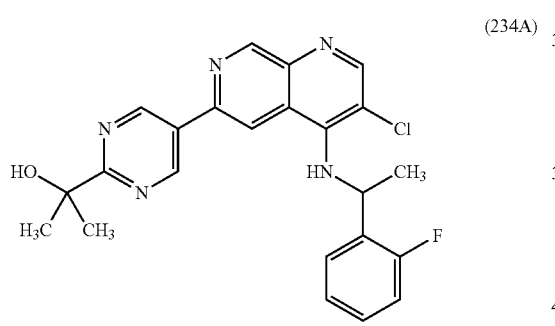
(234A)

Intermediate I-60 (30 mg, 0.067 mmol), 2-(5-(4,4,5,5-tetramethyl-1,3,2-dioxaborolan-2-yl)pyrimidin-2-yl)propan-2-ol (19 mg, 0.073 mmol, 1.1 eq.), and PdCl$_2$(dppf)-CH$_2$Cl$_2$ adduct (3.3 mg, 4.0 µmol, 0.15 eq.) were dissolved in DMF (1 mL). next, 2M sodium carbonate solution (0.033 mL, 0.067 mmol, 1.0 eq.) was added. Nitrogen gas was bubbled for 5 min and the reaction mixture was heated at 90° C. for 30 min. After cooling to room temperature, the reaction mixture was diluted with DCM (3 mL) and purified by column chromatography on silica gel (12 g), eluting with EtOAc-hexanes (gradient from 0~50%) to give 2-(5-(3-chloro-4-((1-(2-fluorophenyl)ethyl)amino)-1,7-naphthyridin-6-yl)pyrimidin-2-yl)propan-2-ol (19 mg, 43 mmol, 65% yield). LCMS m/z 438.2 (M+H)$^+$, HPLC t$_R$ 0.90 min (method C).

Example 234

Racemic 2-(5-(3-chloro-4-((1-(2-fluorophenyl)ethyl)amino)-1,7-naphthyridin-6-yl)pyrimidin-2-yl)propan-2-ol (19 mg, 0.067 mmol) was subjected to preparative SFC (30×250 mm 5 µm OJ-H column, 20/80 MeOH/CO$_2$ with 0.1% NH$_4$OH mobile phase, 150 mL/min flow rate, 35° C., 100 bars, UV 254 nm). (S)-2-(5-(3-chloro-4-(1-(2-fluorophenyl)ethylamino)-1,7-naphthyridin-6-yl)pyrimidin-2-yl)propan-2-ol was the first eluting enantiomer (7.0 mg, 0.015 mmol, 37% yield). The absolute stereochemistry was assigned tentatively as shown. LCMS m/z 438.2 (M+H)$^+$, HPLC t$_R$ 0.90 min (method C). $^1$H NMR (500 MHz, DMSO-d$_6$) δ 9.51 (s, 2H), 9.31 (s, 1H), 8.91 (s, 1H), 8.55 (s, 1H), 7.49 (t, J=7.6 Hz, 1H), 7.33-7.20 (m, 1H), 7.16-7.08 (m, 2H), 7.02 (d, J=8.4 Hz, 1H), 6.00-5.79 (m, 1H), 5.25 (s, 1H), 1.70 (d, J=6.6 Hz, 3H), 1.57 (s, 6H).

Examples 235 and 236

(R)-2-(4-(5-(3-chloro-4-((1-(2-fluorophenyl)ethyl)amino)-1,7-naphthyridin-6-yl)pyrimidin-2-yl)piperazin-1-yl)acetic acid and (S)-2-(4-(5-(3-chloro-4-((1-(2-fluorophenyl)ethyl)amino)-1,7-naphthyridin-6-yl)pyrimidin-2-yl)piperazin-1-yl)acetic acid
(Enantiomers)

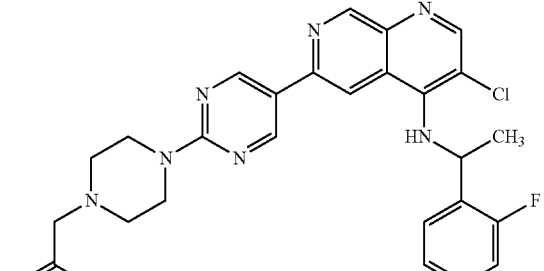
(235 and 236)

Intermediate 235A: methyl 2-(4-(5-(3-chloro-4-((1-(2-fluorophenyl)ethyl)amino)-1,7-naphthyridin-6-yl)pyrimidin-2-yl)piperazin-1-yl)acetate

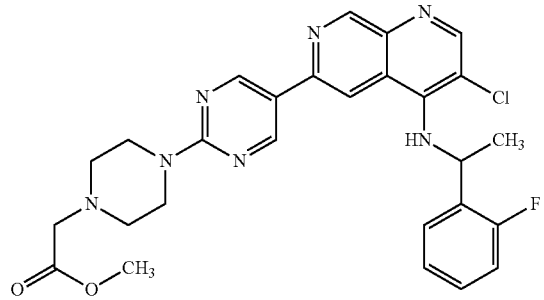
(235A)

Methyl 2-(4-(5-(3-chloro-4-((1-(2-fluorophenyl)ethyl)amino)-1,7-naphthyridin-6-yl)pyrimidin-2-yl)piperazin-1-yl)acetate was prepared from Intermediate I-60 and Intermediate I-34 by using same method as for Intermediate 234A. LCMS m/z 536.2 (M+H)$^+$, HPLC t$_R$ 0.76 min (method C).

Intermediates 235B and 235C: Methyl-2-(4-(5-(3-chloro-4-((1-(2-fluorophenyl)ethyl)amino)-1,7-naphthyridin-6-yl)pyrimidin-2-yl)piperazin-1-yl)acetate (Enantiomers)

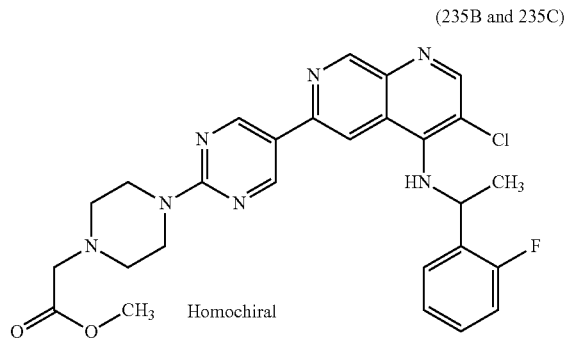 [SMILES: COC(=O)CN1CCN(c2ncc(-c3cc4c(NC(C)c5ccccc5F)c(Cl)cnc4cn3)cn2)CC1]

(235B and 235C)

Racemic methyl 2-(4-(5-(3-chloro-4-((1-(2-fluorophenyl)ethyl)amino)-1,7-naphthyridin-6-yl)pyrimidin-2-yl)piperazin-1-yl)acetate (30 mg, 0.056 mmol) was separated into its homochiral components by preparative SFC (30×250 mm 5 μm OJ-H column, 30/70 MeOH/CO$_2$ with 0.1% NH$_4$OH mobile phase, 150 mL/min flow rate, 35° C., 100 bars, UV 300 nm). Analytical data for peaks 1 and 2 are as follows. Peak 1: (11 mg, 0.020 mmol, 37% yield). LCMS m/z 536.2 (M+H)$^+$, HPLC t$_R$ 0.76 min (method C). Peak 2: (11 mg, 0.020 mmol, 37% yield). LCMS m/z 536.2 (M+H)$^+$, HPLC t$_R$ 0.76 min (method C). The absolute stereochemistry of peaks 1 and 2 was not determined.

Examples 235 and 236

To a solution of Peak 2 (Intermediate 235C) (10 mg, 0.019 mmol) in MeOH (0.1 mL) and THF (0.2 mL) was added 1M sodium hydroxide solution (0.037 mL, 0.037 mmol, 2.0 eq.). The reaction mixture was allowed to stir at room temperature for 16 hours. The reaction mixture was diluted with MeOH (2 mL) and purified via preparative LC/MS (Condition A: Gradient: 15-100% B over 20 minutes, then a 2-minute hold at 100% B). (8 mg, 0.015 mmol, 81% yield). LCMS m/z 522.2 (M+H)+; HPLC t$_R$ 0.73 min (method C). $^1$H NMR (500 MHz, DMSO-d$_6$) δ 9.21 (s, 1H), 9.16 (s, 2H), 8.66 (s, 1H), 8.47 (s, 1H), 7.49 (t, J=7.4 Hz, 1H), 7.31-7.20 (m, 1H), 7.13 (t, J=8.0 Hz, 2H), 6.91 (d, J=8.5 Hz, 1H), 6.00-5.80 (m, 1H), 3.90 (br. s., 4H), 3.26 (s, 2H), 2.71 (br. s., 4H), 1.69 (d, J=6.6 Hz, 3H). Peak 1 was subjected to the same reaction conditions as peak 2 above. LCMS m/z 522.2 (M+H)$^+$, HPLC t$_R$ 0.73 min (method C). The absolute stereochemistries of Examples 235 and 236 were not determined.

Example 237

(R)-6-(2-(4-((2H-tetrazol-5-yl)methyl)piperazin-1-yl)pyrimidin-5-yl)-3-chloro-N-(1-(2-fluorophenyl)ethyl)quinolin-4-amine

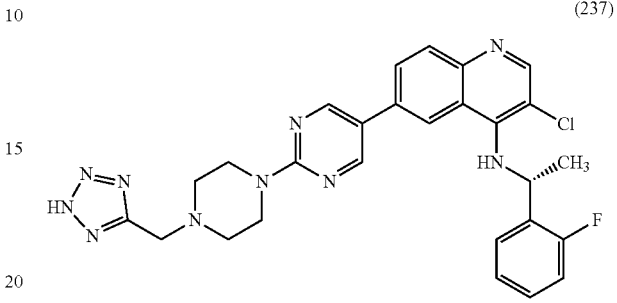

(237)

(R)-6-(2-(4-((2H-tetrazol-5-yl)methyl)piperazin-1-yl)pyrimidin-5-yl)-3-chloro-N-(1-(2-fluorophenyl)ethyl)quinolin-4-amine was prepared according to the general method used in the preparation of Example 412. LCMS m/z 545.1 (M+H)+; HPLC t$_R$ 0.64 min (method A).

Example 238

(R)-2-(5-(3-chloro-4-((3-fluoro-1-(2-fluorophenyl)propyl)amino)quinolin-6-yl)pyrimidin-2-yl)propan-2-ol

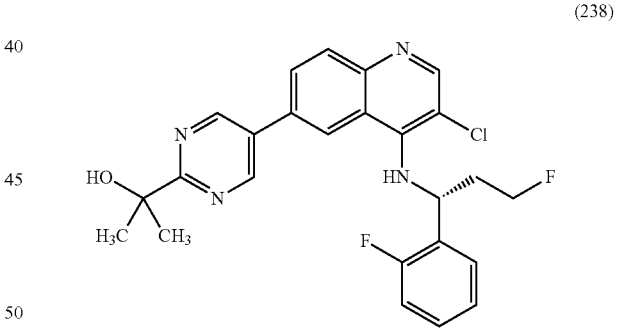

(238)

Example 230 (100 mg, 0.213 mmol) was separated by preparative SFC (30×250 mm 5 μm OJ-H column, 15/85 MeOH/CO$_2$ with 0.1% NH$_4$OH mobile phase, 160 mL/min flow rate, 35° C., 100 bars, UV 254 nm). (R)-2-(5-(3-chloro-4-((3-fluoro-1-(2-fluorophenyl)propyl)amino)quinolin-6-yl)pyrimidin-2-yl)propan-2-ol was the second eluting enantiomer (40.0 mg, 0.092 mmol, 40% yield). LCMS m/z 469.2 (M+H)$^+$, HPLC t$_R$ 0.74 min (method C). $^1$H NMR (500 MHz, DMSO-d$_6$) δ 9.23 (s, 2H), 8.68 (s, 1H), 8.50 (s, 1H), 8.13 (d, J=8.5 Hz, 1H), 8.00 (d, J=8.5 Hz, 1H), 7.64 (t, J=7.3 Hz, 1H), 7.30-7.22 (m, 1H), 7.20-7.14 (m, 1H), 7.09 (t, J=9.5 Hz, 1H), 6.77 (d, J=9.8 Hz, 1H), 5.91-5.74 (m, 1H), 5.20 (s, 1H), 4.91-4.44 (m, 2H), 2.58 (d, J=5.8 Hz, 1H), 2.34-2.10 (m, 1H), 1.58 (s, 6H). The absolute stereochemistry was assigned tentatively as shown.

Example 239

±2-(5-(8-((1-(3-aminophenyl)ethyl)amino)-7-chloro-3-fluoro-1,5-naphthyridin-2-yl)pyrimidin-2-yl)propan-2-ol

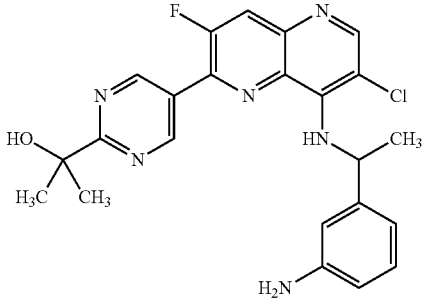

(239)

To a mixture of tert-butyl (3-(1-aminoethyl)phenyl)carbamate (22 mg, 0.093 mmol, 1.1 eq.), 2-(5-(7,8-dichloro-3-fluoro-1,5-naphthyridin-2-yl)pyrimidin-2-yl)propan-2-ol (Intermediate I-55, 30 mg, 0.085 mmol), sodium tert-butoxide (16.3 mg, 0.170 mmol, 2.0 eq.), Pd$_2$(dba)$_3$ (7.78 mg, 8.49 µmol, 0.1 eq.), racemic BINAP (10.58 mg, 0.017 mmol, 0.2 eq.), in anhydrous 1,4-dioxane (1 mL) was bubbled with N$_2$ for 2 min. The reaction mixture was stirred at 100° C. under N$_2$ for 2 hours. After cooling to room temperature, the reaction mixture was diluted with DCM (3 mL) and purified by column chromatography on silica gel (12 g), eluting with EtOAc-hexanes (gradient from 0~100%) to yield tert-butyl (3-(1-((3-chloro-7-fluoro-6-(2-(2-hydroxypropan-2-yl)pyrimidin-5-yl)-1,5-naphthyridin-4-yl)amino)ethyl)phenyl)carbamate. LCMS m/z 553.1 (M+H)$^+$, HPLC t$_R$ 0.90 min (method C).

To tert-butyl (3-(1-((3-chloro-7-fluoro-6-(2-(2-hydroxypropan-2-yl)pyrimidin-5-yl)-1,5-naphthyridin-4-yl)amino)ethyl)phenyl)carbamate in DCM (2 mL) was added TFA (0.5 mL). The mixture was stirred at room temperature for 1 h and concentrated in vacuo. The residue was purified by column chromatography on silica gel (12 g), eluting with MeOH-DCM (gradient from 0~10%) to give 2-(5-(8-((1-(3-aminophenyl)ethyl)amino)-7-chloro-3-fluoro-1,5-naphthyridin-2-yl)pyrimidin-2-yl)propan-2-ol (12 mg, 0.026 mmol, 31% yield). LCMS m/z 453.0 (M+H)$^+$, HPLC t$_R$ 0.61 min (method C). $^1$H NMR (500 MHz, DMSO-d$_6$) δ 9.38 (s, 2H), 8.52 (s, 1H), 8.27 (d, J=11.5 Hz, 1H), 7.09 (br. s., 1H), 6.91 (t, J=7.7 Hz, 1H), 6.57-6.46 (m, 2H), 6.38 (d, J=7.7 Hz, 1H), 5.88 (br. s., 1H), 1.61 (d, J=6.7 Hz, 3H), 1.58 (s, 6H).

Example 240

(R)-2-(5-(4-((1-(2-fluorophenyl)ethyl)amino)-3-methylquinolin-6-yl)pyrimidin-2-yl)propan-2-ol

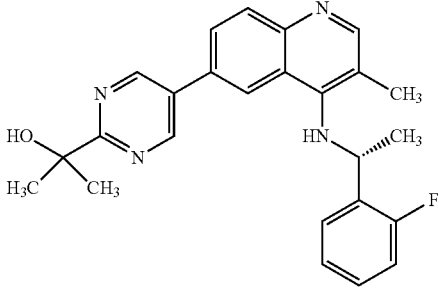

(240)

To a solution of Example 217 (20 mg, 0.046 mmol) in toluene (2 mL) and water (0.1 mL) solvent mixture under nitrogen was added methylboronic acid (6.9 mg, 0.11 mmol, 2.5 eq.), tricyclohexylphosphine in toluene solution (25.7 mg, 20 wt %, 0.018 mmol, 0.4 eq.), potassium phosphate tribasic (29.2 mg, 0.137 mmol, 3.0 eq.) and palladium (II) acetate (2.0 mg, 9.2 µmol, 0.2 eq.). The reaction mixture was heated at 100° C. for 16 hours. After cooling to room temperature, the reaction mixture was filtered to remove solids. The filtrate was concentrated under vacuo. The residue was purified via preparative LC/MS (Condition A: Gradient: 30-70% B over 20 minutes, then a 5-minute hold at 100% B) to yield (R)-2-(5-(4-((1-(2-fluorophenyl)ethyl)amino)-3-methylquinolin-6-yl)pyrimidin-2-yl)propan-2-ol (7.1 mg, 0.016 mmol, 36% yield). LCMS m/z 417.2 (M+H)$^+$, HPLC t$_R$ 0.73 min (method C). $^1$H NMR (500 MHz, DMSO-d$_6$) δ 9.20 (s, 2H), 8.60 (s, 1H), 8.41 (s, 1H), 8.02 (d, J=8.9 Hz, 1H), 7.94 (d, J=8.9 Hz, 1H), 7.65 (t, J=7.8 Hz, 1H), 7.23 (br. s., 1H), 7.18-7.12 (m, 1H), 7.11-7.01 (m, 1H), 6.22 (d, J=8.9 Hz, 1H), 5.27 (br. s., 1H), 2.35 (s, 3H), 1.65 (d, J=6.7 Hz, 3H), 1.57 (s, 6H).

Example 241

2-(5-(3-chloro-7-fluoro-4-((1-(2-fluorophenyl)amino)quinolin-6-yl)pyrimidin-2-yl)propan-2-ol (Homochiral)

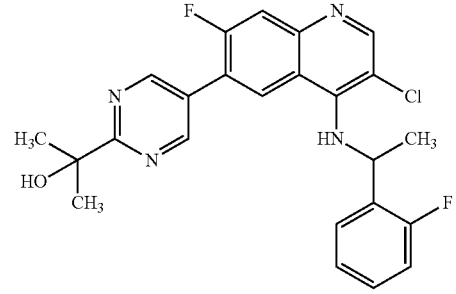

(241)

A mixture of 2-(5-(4,4,5,5-tetramethyl-1,3,2-dioxaborolan-2-yl)pyrimidin-2-yl) propan-2-ol (5.31 mg, 0.020 mmol), 6-bromo-3-chloro-7-fluoro-N-(1-(2-fluorophenyl)ethyl)quinolin-4-amine (peak 4 from Intermediate I-43, 8.0 mg, 0.020 mmol), and 2.0 M potassium phosphate tribasic (0.030 mL, 0.060 mmol) and 1,1'-bis(di-tert-butylphosphino)ferrocene palladium dichloride (0.656 mg, 1.006 µmol) in dioxane (1.0 mL) was stirred at 60° C. in a sealed vial under nitrogen for 3 hour. The mixture was diluted with EtOAc (2 mL) and was washed with a solution of aqueous saturated sodium bicarbonate (2 mL). The ethyl acetate layer was dried over sodium sulfate and concentrated. The crude material was purified via preparative LC/MS using the condition B. Yield 2-(5-(3-chloro-7-fluoro-4-((1-(2-fluorophenyl)ethyl)amino)quinolin-6-yl)pyrimidin-2-yl)propan-2-ol (6.60 mg, 0.014 mmol, 68.5% yield). LC/MS (M+H): 455; LC retention time: 0.80 min (analytical HPLC Method C); $^1$H NMR (500 MHz, DMSO-d$_6$) δ 9.11 (s, 2H), 8.68 (d, J=7.9 Hz, 1H), 8.48 (s, 1H), 7.78 (d, J=11.6 Hz, 1H), 7.51 (t, J=7.3 Hz, 1H), 7.29-7.22 (m, 1H), 7.17-7.06 (m, 2H), 6.86 (d, J=8.5 Hz, 1H), 5.90-5.79 (m, 1H), 1.66 (d, J=6.7 Hz, 3H), 1.58 (s, 6H).

Example 242

2-(4-(5-(3-chloro-7-fluoro-4-((1-(2-fluorophenyl)ethyl)amino)quinolin-6-yl)pyrimidin-2-yl)piperazin-1-yl)acetic acid (Homochiral)

(242)

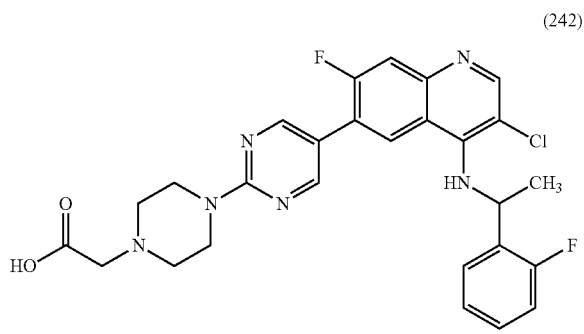 [SMILES: CC(Nc1c(Cl)cnc2cc(F)c(-c3cnc(N4CCN(CC(=O)O)CC4)nc3)cc12)c1ccccc1F]

A mixture of methyl 2-(4-(5-(4,4,5,5-tetramethyl-1,3,2-dioxaborolan-2-yl)pyrimidin-2-yl)piperazin-1-yl)acetate (30.1 mg, 0.083 mmol), 6-bromo-3-chloro-7-fluoro-N-(1-(2-fluorophenyl)ethyl)quinolin-4-amine (peak 4 from Intermediate I-43, 33 mg, 0.083 mmol), and 2.0 M potassium phosphate tribasic (0.124 mL, 0.249 mmol) and 1,1'-bis(di-tert-butylphosphino)ferrocene palladium dichloride (2.70 mg, 4.15 µmol) in dioxane (1.0 mL) was stirred at room temperature in a sealed vial under nitrogen for 18 hour. The mixture was diluted with EtOAc (2 mL) and was washed with a solution of aqueous saturated sodium bicarbonate (2 mL). The ethyl acetate layer was dried over sodium sulfate and concentrated to give crude methyl 2-(4-(5-(3-chloro-7-fluoro-4-((1-(2-fluorophenyl)ethyl)amino)quinolin-6-yl)pyrimidin-2-yl)piperazin-1-yl)acetate (42 mg, 0.072 mmol, 87% yield) as white foam.

To a solution of methyl 2-(4-(5-(3-chloro-7-fluoro-4-((1-(2-fluorophenyl)ethyl)amino)quinolin-6-yl)pyrimidin-2-yl)piperazin-1-yl)acetate and a solution of 2.0 M aqueous lithium hydroxide (0.207 mL, 0.415 mmol) in MeOH (1.0 mL) was stirred at 50° C. for 2 hour. A solution of 1.0 M aqueous HCl (0.498 mL, 0.498 mmol) was added to the mixture and it was then concentrated. The crude material was purified via preparative LC/MS using the condition B. The pure product was lyophilized with acetonitrile/H$_2$O (1:1, 10 mL) to yield 2-(4-(5-(3-chloro-7-fluoro-4-((1-(2-fluorophenyl)ethyl)amino) quinolin-6-yl)pyrimidin-2-yl)piperazin-1-yl)acetic acid (35 mg, 0.062 mmol, 74.3% yield) as white powder. LC/MS (M+H): 539; LC retention time: 0.63 min (analytical HPLC Method C). $^1$H NMR (400 MHz, METHANOL-d$_4$) δ 8.70 (s, 1H), 8.58 (d, J=1.8 Hz, 2H), 8.37-8.29 (m, 1H), 7.74-7.66 (m, 1H), 7.62-7.53 (m, 1H), 7.40-7.30 (m, 1H), 7.26-7.09 (m, 2H), 6.01-5.91 (m, 1H), 4.39-4.16 (m, 4H), 4.07 (s, 2H), 3.52 (br. s., 4H), 1.81 (d, J=6.6 Hz, 3H).

Example 243 ethyl-1-(5-(3-chloro-7-fluoro-4-((1-(2-fluorophenyl)ethyl)amino)quinolin-6-yl)pyrimidin-2-yl)piperidine-4-carboxylate (Homochiral)

(243)

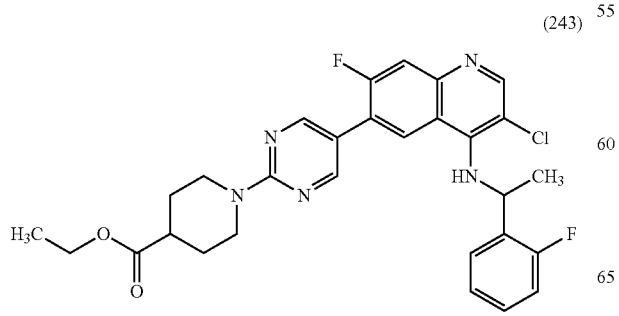

Example 243 was prepared following the procedure described in Intermediate 242A employing Intermediate I-36 and Intermediate I-43, peak 4. LC/MS (M+H): 552; LC retention time: 0.87 min (analytical HPLC Method C); $^1$H NMR (400 MHz, CHLOROFORM-d) δ 8.60 (s, 1H), 8.45 (d, J=1.8 Hz, 2H), 7.91 (d, J=8.1 Hz, 1H), 7.69 (d, J=11.7 Hz, 1H), 7.41 (td, J=7.6, 1.8 Hz, 1H), 7.33-7.24 (m, 2H), 7.18-7.03 (m, 2H), 5.46-5.34 (m, 1H), 5.15 (d, J=9.0 Hz, 1H), 4.76 (dt, J=13.5, 3.5 Hz, 2H), 4.20 (q, J=7.0 Hz, 2H), 3.18 (ddd, J=13.6, 11.3, 2.9 Hz, 2H), 2.65 (tt, J=11.0, 3.9 Hz, 1H), 2.12-2.00 (m, 2H), 1.87-1.76 (m, 2H), 1.72 (d, J=6.6 Hz, 3H), 1.34-1.28 (m, 3H).

Example 244

1-(5-(3-chloro-7-fluoro-4-((1-(2-fluorophenyl)ethyl)amino)quinolin-6-yl)pyrimidin-2-yl)piperidine-4-carboxylic acid (Homochiral)

(244)

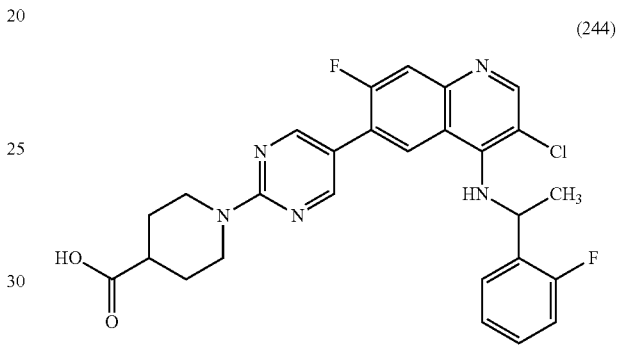

Example 244 was prepared following the procedure described in Example 242, by using ethyl 1-(5-(3-chloro-7-fluoro-4-((1-(2-fluorophenyl)ethyl)amino)quinolin-6-yl)pyrimidin-2-yl)piperidine-4-carboxylate (Example 243). LC/MS (M+H): 524; LC retention time: 0.75 min (analytical HPLC Method C); $^1$H NMR (500 MHz, DMSO-d$_6$) δ 8.69 (s, 2H), 8.52 (d, J=8.2 Hz, 1H), 8.43 (s, 1H), 7.70 (d, J=11.6 Hz, 1H), 7.52 (t, J=7.6 Hz, 1H), 7.29-7.19 (m, 1H), 7.18-7.07 (m, 2H), 6.78 (d, J=8.7 Hz, 1H), 5.80 (t, J=7.6 Hz, 1H), 4.62 (d, J=13.0 Hz, 2H), 3.23-3.10 (m, 2H), 2.60 (d, J=11.6 Hz, 1H), 1.93 (d, J=11.3 Hz, 2H), 1.65 (d, J=6.7 Hz, 3H), 1.59-1.45 (m, 2H).

Example 245

2-(1-(5-(3-chloro-7-fluoro-4-((1-(2-fluorophenyl)ethyl)amino)quinolin-6-yl)pyrimidin-2-yl)piperidin-4-yl)propan-2-ol (Homochiral)

(245)

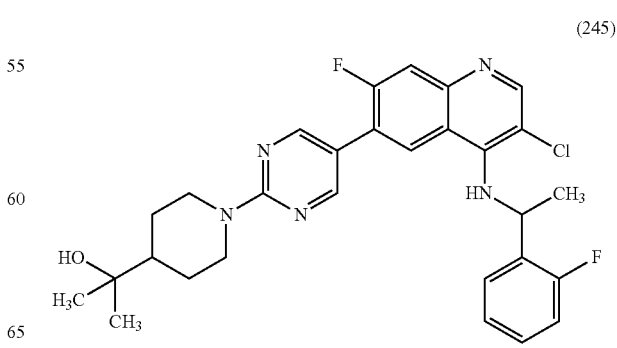

To a solution of ethyl 1-(5-(3-chloro-7-fluoro-4-((1-(2-fluorophenyl)ethyl)amino) quinolin-6-yl)pyrimidin-2-yl)piperidine-4-carboxylate (Example 243, 10 mg, 0.018 mmol) in THF (1.0 mL) was added a solution of 1.0 M methylmagnesium bromide in THF (0.091 mL, 0.091 mmol) and the mixture was stirred at room temperature for 3 hours. A solution of 10% ammonium chloride solution (5.0 mL) was added and the reaction mixture was extracted with EtOAc (2×5.0 mL). The ethyl acetate layer was dried over sodium sulfate and concentrated. The crude material was purified via preparative LC/MS using the condition B to afford 2-(1-(5-(3-chloro-7-fluoro-4-((1-(2-fluorophenyl)ethyl)amino)quinolin-6-yl)pyrimidin-2-yl)piperidin-4-yl)propan-2-ol (7.70 mg, 0.014 mmol, 75% yield). LC/MS (M+H): 538; LC retention time: 0.80 min (analytical HPLC Method C); $^1$H NMR (500 MHz, DMSO-$d_6$) δ 8.65 (s, 2H), 8.49 (d, J=8.2 Hz, 1H), 8.43 (s, 1H), 7.68 (d, J=11.6 Hz, 1H), 7.52 (t, J=7.6 Hz, 1H), 7.30-7.20 (m, 1H), 7.18-7.06 (m, 2H), 6.76 (d, J=8.9 Hz, 1H), 5.85-5.73 (m, 1H), 4.86 (d, J=12.8 Hz, 2H), 2.85 (t, J=12.4 Hz, 2H), 1.82 (d, J=12.8 Hz, 2H), 1.65 (d, J=6.7 Hz, 3H), 1.58-1.47 (m, 1H), 1.26-1.11 (m, 2H), 1.06 (s, 6H).

Example 246

(±) 2-(5-(3-chloro-7-fluoro-4-((1-(2-fluorophenyl)ethyl)amino)quinolin-6-yl)pyrimidin-2-yl)propan-2-ol

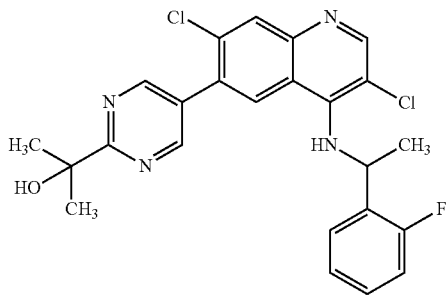

(246)

Example 246 was prepared following the procedure described in Example 241 starting from Intermediate I-85, peak 1. LC/MS (M+H): 471; LC retention time: 0.83 min (analytical HPLC Method C); $^1$H NMR (500 MHz, DMSO-$d_6$) δ 9.01 (s, 2H), 8.58 (s, 1H), 8.48 (s, 1H), 8.08 (s, 1H), 7.47 (t, J=7.4 Hz, 1H), 7.29-7.19 (m, 1H), 7.17-7.04 (m, 2H), 6.88 (d, J=8.4 Hz, 1H), 5.83 (t, J=7.3 Hz, 1H), 5.28 (s, 1H), 1.66-1.51 (m, 9H).

Example 247

(±) 2-(5-(3-chloro-8-fluoro-4-((1-(2-fluorophenyl)ethyl)amino)quinolin-6-yl)pyrimidin-2-yl)propan-2-ol

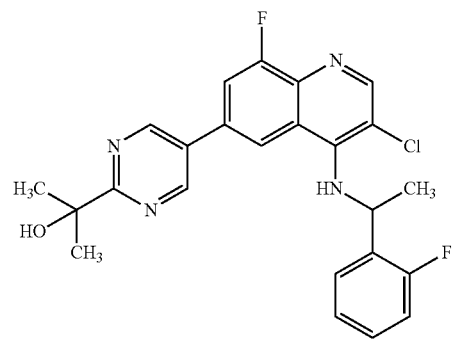

(247)

Example 247 was prepared following the procedure described in Example 241 starting from Intermediate I-84. LC/MS (M+H): 455; LC retention time: 0.81 min (analytical HPLC Method C); $^1$H NMR (500 MHz, DMSO-$d_6$) δ 9.25 (s, 2H), 8.60-8.43 (m, 2H), 8.07 (d, J=11.4 Hz, 1H), 7.52 (t, J=7.4 Hz, 1H), 7.29-7.20 (m, 1H), 7.18-7.05 (m, 2H), 6.90 (d, J=8.6 Hz, 1H), 5.89-5.78 (m, 1H), 1.67 (d, J=6.7 Hz, 3H), 1.56 (s, 6H).

The examples in Table 10 were prepared according to the general procedure used in the preparation of Example 241.

TABLE 10

| Ex. No. | Structure | MS observed ($M^{+1}$) | HPLC ret. Time (min.) | HPLC method |
|---|---|---|---|---|
| 248 | ![structure] | 455 | 0.80 | C |

Homochiral from peak 3 of Intermediate I-43

TABLE 10-continued

| Ex. No. | Structure | MS observed (M+1) | HPLC ret. Time (min.) | HPLC method |
|---|---|---|---|---|
| 249 | Homochiral from peak 2 of Intermediate I-43 | 453 | 0.90 | C |
| 250 | Homochiral from peak 1 of Intermediate I-43 | 453 | 0.90 | C |
| 251 (±) | 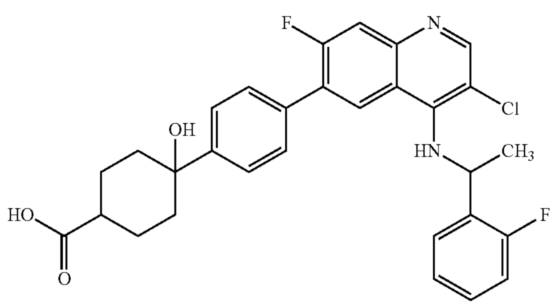 [SMILES: CC(Nc1c(Cl)cnc2cc(F)c(-c3ccc(C4(O)CCC(C(=O)O)CC4)cc3)cc12)c1ccccc1F] | 539 | 0.74 | C |
| 252 | Homochiral from peak 4 of Intermediate I-43 | 454 | 0.70 | C |

TABLE 10-continued

| Ex. No. | Structure | MS observed (M$^{+1}$) | HPLC ret. Time (min.) | HPLC method |
|---|---|---|---|---|
| 253 (±) | | 455 | 0.85 | C |
| 254 homochiral | | 472 | 0.67 | C |
| 255 Homochiral from peak 4 of Intermediate I-43 | | 422 | 0.80 | C |
| 256 Diastereomeric mixture | | 455 | 0.71 | C |

TABLE 10-continued
| Ex. No. | Structure | MS observed ($M^{+1}$) | HPLC ret. Time (min.) | HPLC method |
|---|---|---|---|---|
| 257 | 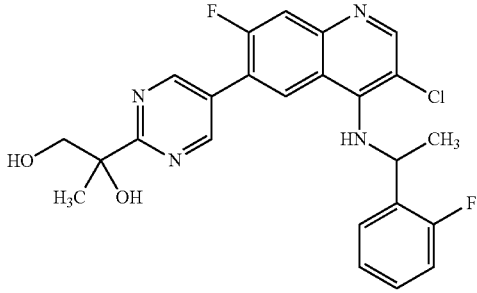 homochiral | 472 | 0.67 | C |
| 258 | 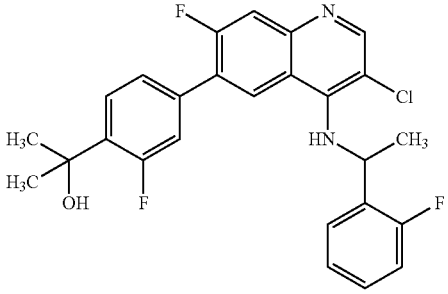 Homochiral from peak 3 of Intermediate I-43 | 471 | 0.82 | C |
| 259 | 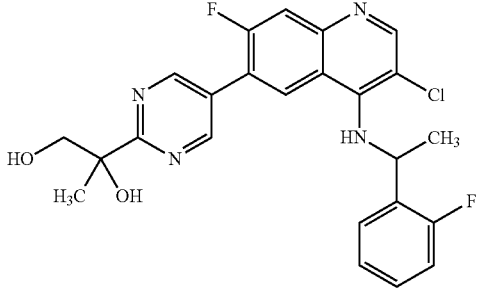 homochiral | 472 | 0.67 | C |
| 260 | 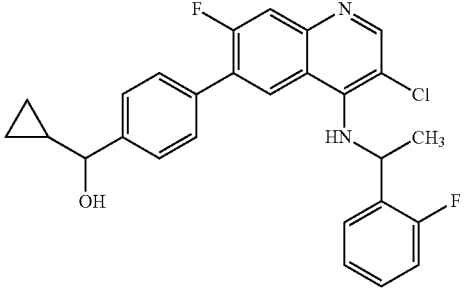 homochiral | 465 | 0.79 | C |

TABLE 10-continued

| Ex. No. | Structure | MS observed (M+1) | HPLC ret. Time (min.) | HPLC method |
|---|---|---|---|---|
| 261 | homochiral | 465 | 0.79 | C |
| 262 | Homochiral | 465 | 0.79 | C |
| 263 | homochiral | 465 | 0.79 | C |
| 264 (±) | 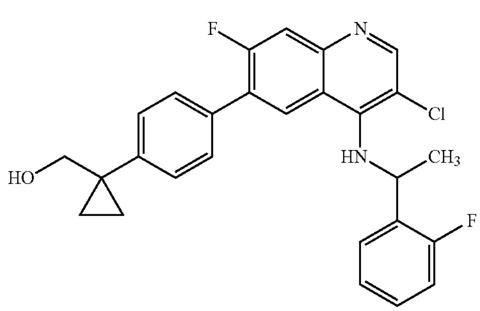 [SMILES: CC(Nc1c(Cl)cnc2cc(F)c(-c3ccc(C4(CO)CC4)cc3)cc12)c1ccccc1F] | 465 | 0.80 | C |

TABLE 10-continued

| Ex. No. | Structure | MS observed (M$^{+1}$) | HPLC ret. Time (min.) | HPLC method |
|---|---|---|---|---|
| 265 | Homochiral from peak 4 of Intermediate I-43 | 465 | 0.80 | C |
| 266 (±) | 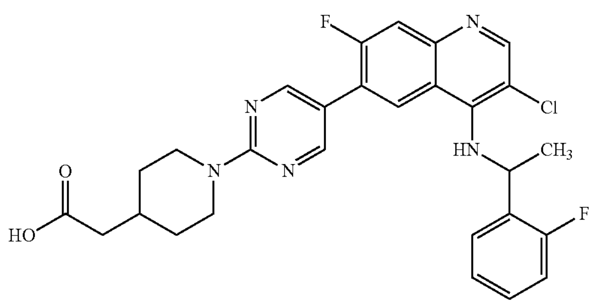 [SMILES: CC(Nc1c(Cl)cnc2cc(F)c(-c3cnc(N4CCC(CC(=O)O)CC4)nc3)cc12)c1ccccc1F] | 538 | 0.80 | C |
| 267 (±) | 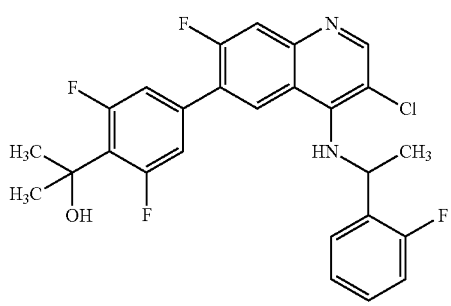 [SMILES: CC(Nc1c(Cl)cnc2cc(F)c(-c3cc(F)c(C(C)(C)O)c(F)c3)cc12)c1ccccc1F] | 489 | 0.82 | C |
| 268 | Homochiral from peak 4 of Intermediate I-43 | 489 | 0.82 | C |

TABLE 10-continued

| Ex. No. | Structure | MS observed (M$^{+1}$) | HPLC ret. Time (min.) | HPLC method |
|---|---|---|---|---|
| 269 | 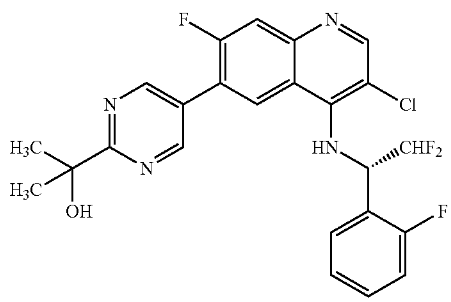 | 491 | 0.89 | C |
| 270 | 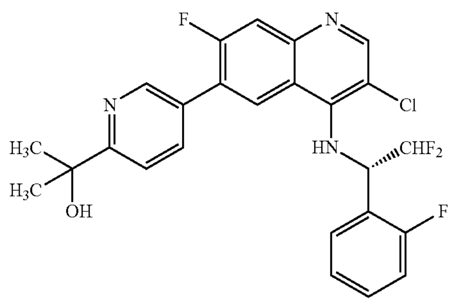 [SMILES: CC(C)(O)c1ccc(-c2cc3c(N[C@@H](c4ccccc4F)C(F)F)c(Cl)cnc3cc2F)cn1] | 490 | 0.77 | C |
| 271 | Diastereomeric mixture | 449 | 0.70 | C |
| 272 | homochiral | 524 | 0.65 | C |

TABLE 10-continued

| Ex. No. | Structure | MS observed (M$^{+1}$) | HPLC ret. Time (min.) | HPLC method |
|---|---|---|---|---|
| 273 | homochiral | 526 | 0.63 | C |
| 274 | homochiral | 526 | 0.63 | C |
| 275 | homochiral | 526 | 0.63 | C |
| 276 | homochiral | 526 | 0.63 | C |

TABLE 10-continued
| Ex. No. | Structure | MS observed ($M^{+1}$) | HPLC ret. Time (min.) | HPLC method |
|---|---|---|---|---|
| 277 | 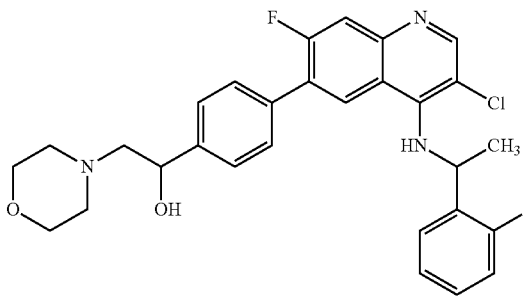 homochiral | 524 | 0.65 | C |
| 278 | 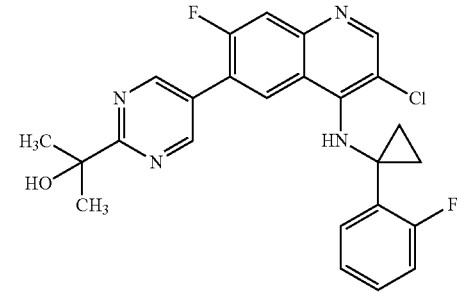 [SMILES: CC(C)(O)c1ncc(-c2cc3c(NC4(c5ccccc5F)CC4)c(Cl)cnc3cc2F)cn1] | 467 | 0.74 | C |
| 279 | 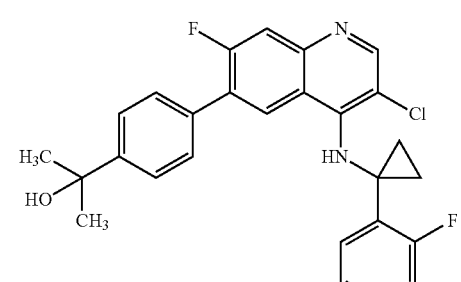 | 465 | 0.79 | C |
| 280 | 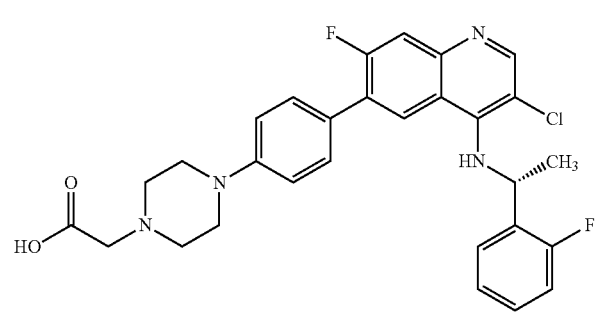 [SMILES: C[C@@H](Nc1c(Cl)cnc2cc(F)c(-c3ccc(N4CCN(CC(=O)O)CC4)cc3)cc12)c1ccccc1F] | 537 | 0.71 | C |

TABLE 10-continued
| Ex. No. | Structure | MS observed (M+1) | HPLC ret. Time (min.) | HPLC method |
|---|---|---|---|---|
| 281 | 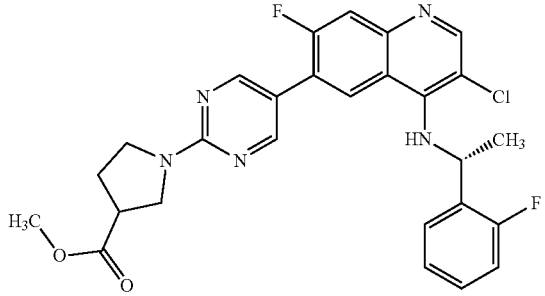<br>Diastereomeric mixture | 524 | 0.78 | C |
| 282 | 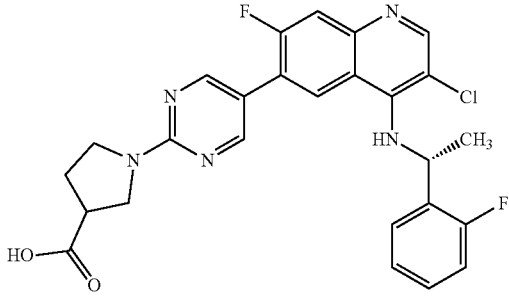<br>Diastereomeric mixture | 510 | 0.73 | C |
| 283 | 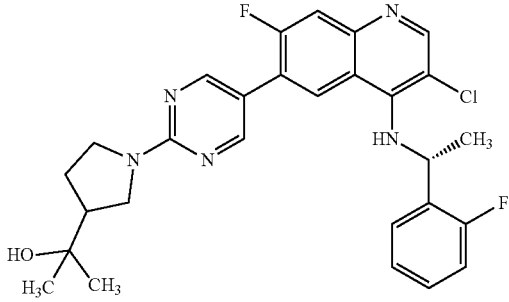<br>Diastereomeric mixture | 524 | 0.75 | C |
| 284 | 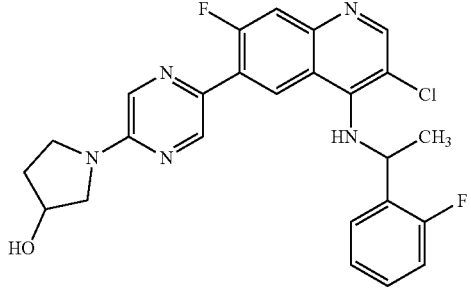<br>Diastereomeric mixture | 482 | 0.72 | C |

TABLE 10-continued

| Ex. No. | Structure | MS observed (M+1) | HPLC ret. Time (min.) | HPLC method |
|---|---|---|---|---|
| 285 | 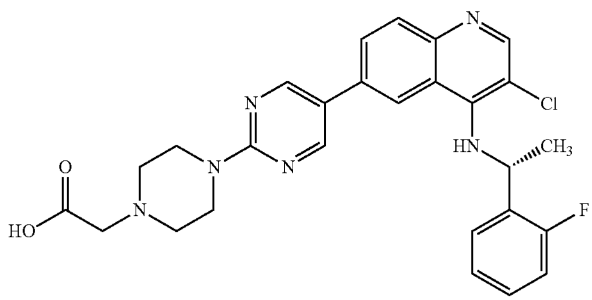 [SMILES: C[C@@H](Nc1c(Cl)cnc2ccc(-c3cnc(N4CCN(CC(=O)O)CC4)nc3)cc12)c1ccccc1F] | 521 | 0.63 | C |
| 286 | homochiral | 524 | 0.65 | C |
| 287 (±) | 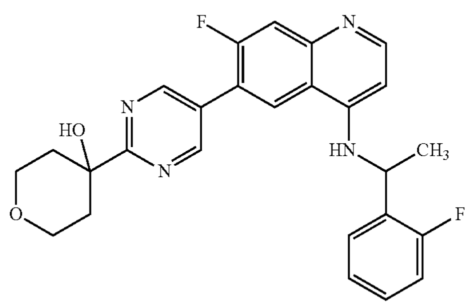 [SMILES: CC(Nc1ccnc2cc(F)c(-c3cnc(C4(O)CCOCC4)nc3)cc12)c1ccccc1F] | 462 | 0.72 | C |
| 288 | homochiral | 524 | 0.65 | C |

TABLE 10-continued
| Ex. No. | Structure | MS observed (M$^{+1}$) | HPLC ret. Time (min.) | HPLC method |
|---|---|---|---|---|
| 289 | 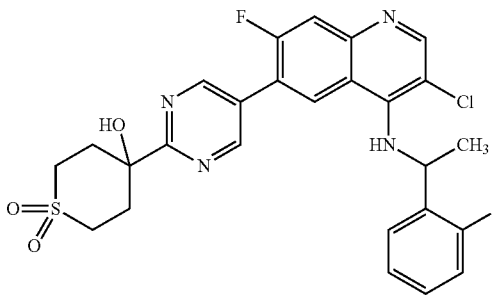 homochiral | 545 | 0.70 | C |
| 290 | 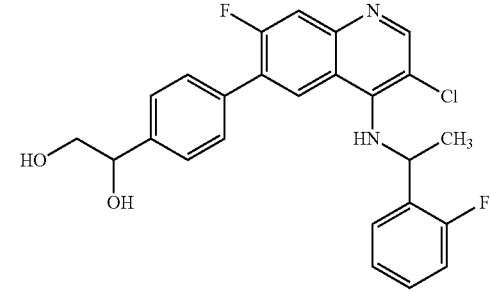 homochiral | 455 | 0.71 | C |
| 291 | 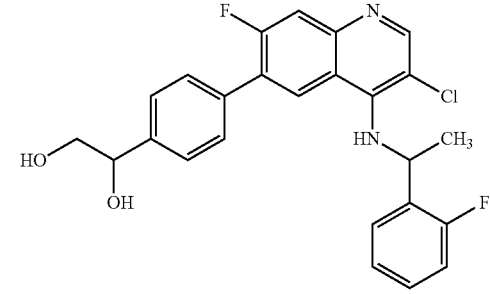 homochiral | 455 | 0.71 | C |
| 292 | 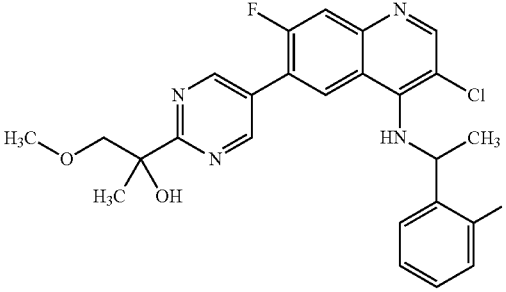 homochiral | 485 | 0.73 | C |

TABLE 10-continued

| Ex. No. | Structure | MS observed (M$^{+1}$) | HPLC ret. Time (min.) | HPLC method |
|---|---|---|---|---|
| 293 | homochiral | 485 | 0.73 | C |
| 294 (±) | 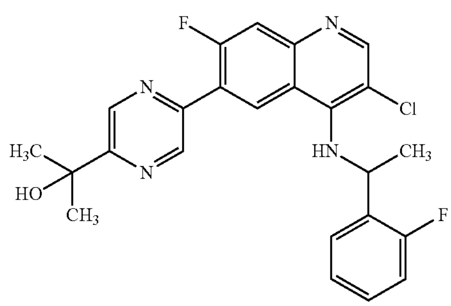 [SMILES: CC(Nc1c(Cl)cnc2cc(F)c(-c3cnc(C(C)(C)O)cn3)cc12)c1ccccc1F] | 455 | 0.74 | C |
| 295 | homochiral | 539 | 0.74 | C |
| 296 (±) | 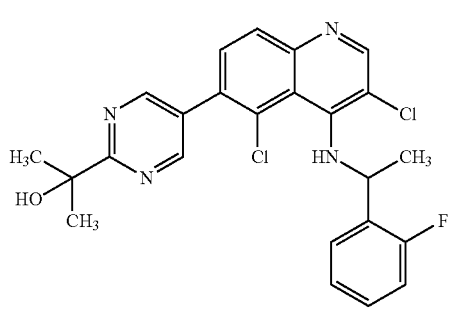 [SMILES: CC(Nc1c(Cl)cnc2ccc(-c3cnc(C(C)(C)O)nc3)c(Cl)c12)c1ccccc1F] | 471 | 0.87 | C |

TABLE 10-continued

| Ex. No. | Structure | MS observed ($M^{+1}$) | HPLC ret. Time (min.) | HPLC method |
|---|---|---|---|---|
| 297 | 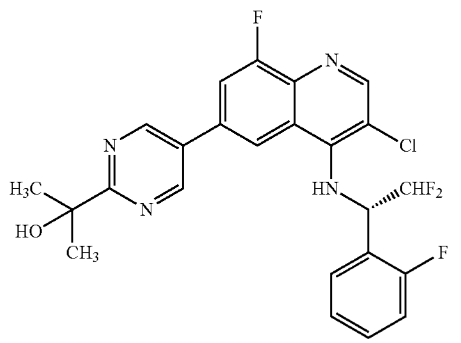 [SMILES: CC(C)(O)c1ncc(-c2cc(F)c3ncc(Cl)c(N[C@@H](c4ccccc4F)C(F)F)c3c2)cn1] | 491 | 0.92 | C |
| 298 (±) | 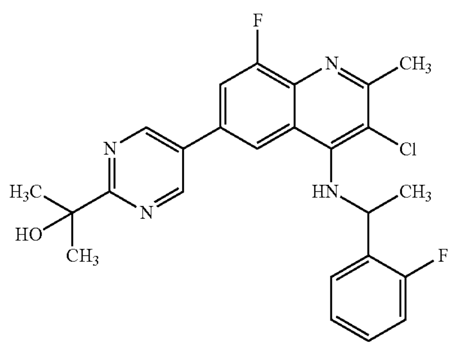 [SMILES: Cc1nc2c(F)cc(-c3cnc(C(C)(C)O)nc3)cc2c(NC(C)c2ccccc2F)c1Cl] | 469 | 0.81 | C |
| 299 | 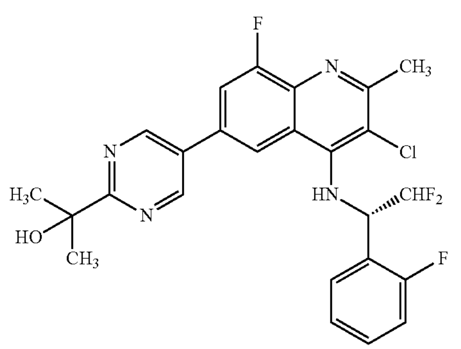 [SMILES: Cc1nc2c(F)cc(-c3cnc(C(C)(C)O)nc3)cc2c(N[C@@H](c2ccccc2F)C(F)F)c1Cl] | 505 | 0.91 | C |
| 300 (±) | 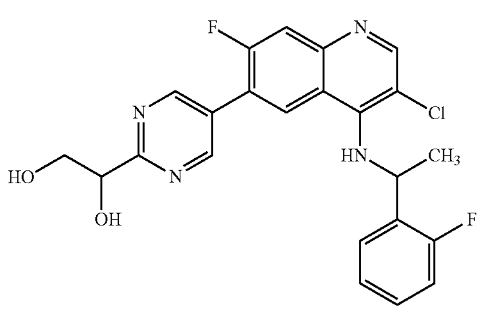 [SMILES: CC(Nc1c(Cl)cnc2cc(F)c(-c3cnc(C(O)CO)nc3)cc12)c1ccccc1F] | 457 | 0.64 | C |

TABLE 10-continued

| Ex. No. | Structure | MS observed (M$^{+1}$) | HPLC ret. Time (min.) | HPLC method |
|---|---|---|---|---|
| 301 (±) | 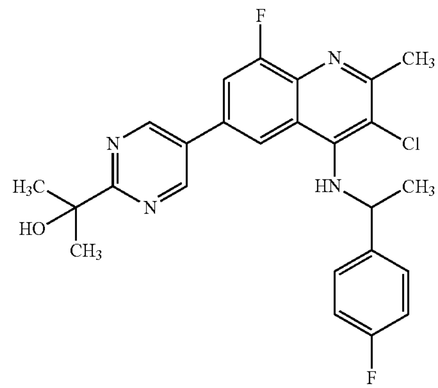 [SMILES: Cc1nc2c(F)cc(-c3cnc(C(C)(C)O)nc3)cc2c(NC(C)c2ccc(F)cc2)c1Cl] | 469 | 0.75 | C |
| 302 | 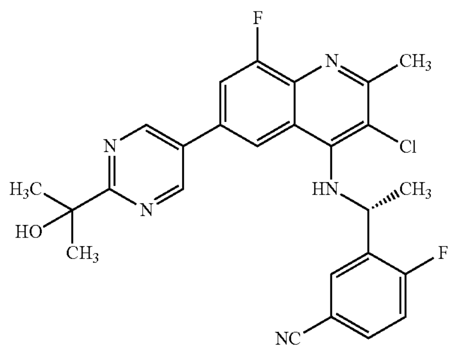 [SMILES: Cc1nc2c(F)cc(-c3cnc(C(C)(C)O)nc3)cc2c(N[C@H](C)c2cc(C#N)ccc2F)c1Cl] | 494 | 0.78 | C |
| 303 | 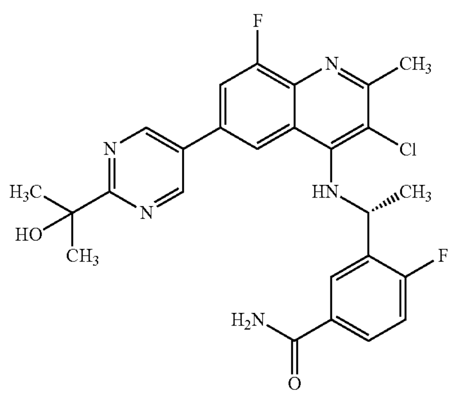 [SMILES: Cc1nc2c(F)cc(-c3cnc(C(C)(C)O)nc3)cc2c(N[C@H](C)c2cc(C(N)=O)ccc2F)c1Cl] | 512 | 0.66 | C |
| 304 | homochiral | 596 | 0.63 | C |

TABLE 10-continued

| Ex. No. | Structure | MS observed ($M^{+1}$) | HPLC ret. Time (min.) | HPLC method |
|---|---|---|---|---|
| 305 | 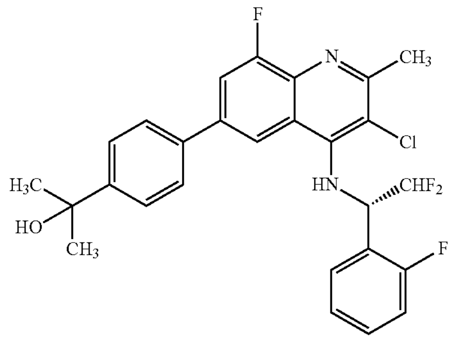 [SMILES: Cc1nc2c(F)cc(-c3ccc(C(C)(C)O)cc3)cc2c(N[C@@H](c2ccccc2F)C(F)F)c1Cl] | 503 | 0.89 | C |
| 306 | 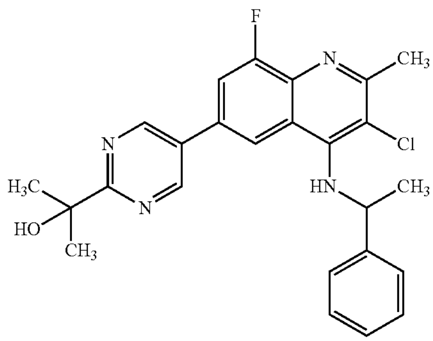 [SMILES: Cc1nc2c(F)cc(-c3cnc(C(C)(C)O)nc3)cc2c(NC(C)c2ccccc2)c1Cl] | 451 | 0.73 | C |
| 307 | homochiral | 469 | 0.75 | C |

Example 308

± 2-(4-(3-chloro-4-((1-(2-fluorophenyl)ethyl)amino)-2-methylquinolin-6-yl)phenyl) propan-2-ol (308)

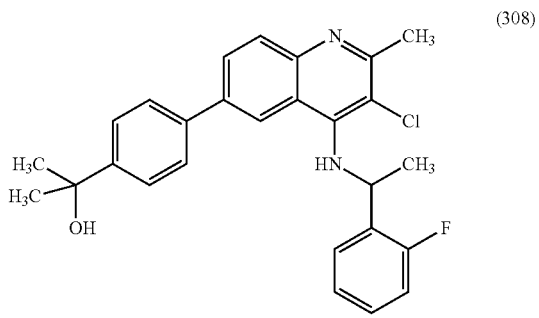 [SMILES: Cc1nc2ccc(-c3ccc(C(C)(C)O)cc3)cc2c(NC(C)c2ccccc2F)c1Cl]

A mixture of 6-bromo-3-chloro-N-(1-(2-fluorophenyl)ethyl)-2-methylquinolin-4-amine (10 mg, 0.025 mmol, Intermediate I-59), (4-(2-hydroxypropan-2-yl)phenyl) boronic acid (5.49 mg, 0.030 mmol)), PdCl$_2$(dppf)-CH$_2$Cl$_2$ adduct (4.15 mg, 5.08 µmol) and 2.0 M aqueous potassium phosphate (0.025 mL, 0.051 mmol) in N,N-dimethylformamide (0.5 mL) was degassed with nitrogen in a sealed vial and heated to 90° C. for 2 h. The mixture was cooled to room temperature and purified via preparative LC/MS using the following conditions: Column: Waters XBridge C18, 19×200 mm, 5-m particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 308 (5.5 mg, 48% yield). LC/MS (M+H): 449.1; LC retention time: 2.26 min (analytical HPLC Method A); $^1$H NMR (500 MHz, DMSO-d$_6$) δ 8.24 (s, 1H), 7.96 (d, J=8.6 Hz, 1H), 7.86 (d, J=8.8 Hz, 1H), 7.72 (t, J=7.3 Hz, 1H), 7.55 (m, 4H), 7.38-7.25 (m, 1H), 7.25-7.09 (m, 2H), 5.61-5.39 (m, 1H), 2.62 (s, 3H), 1.65 (d, J=6.6 Hz, 3H), 1.47 (s, 6H).

The examples in Table 11 were prepared according to the general method described in Example 308.

TABLE 11

| Ex. No. | Structure | MS (M$^{+1}$) | HPLC ret. Time (min.) | HPLC method |
|---|---|---|---|---|
| 309 (±) | 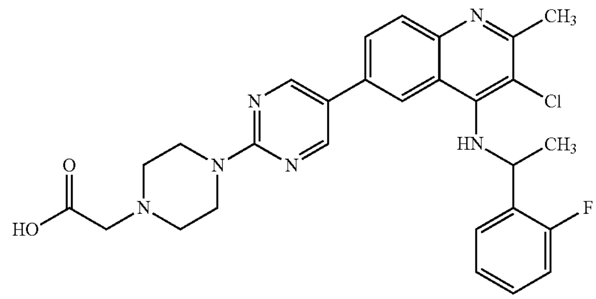 | 535.2 | 1.71 | A |
| 310 (±) | 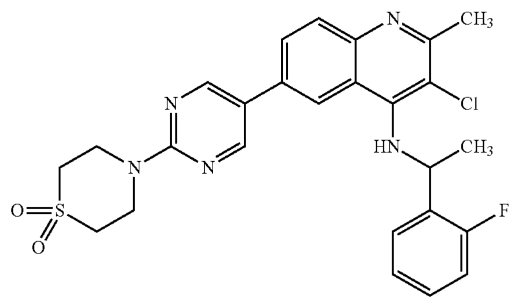 [SMILES: Cc1nc2ccc(-c3cnc(N4CCS(=O)(=O)CC4)nc3)cc2c(NC(C)c2ccccc2F)c1Cl] | 526.0 | 2.10 | A |
| 311 (±) | 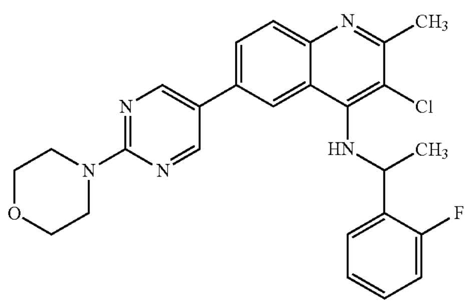 [SMILES: Cc1nc2ccc(-c3cnc(N4CCOCC4)nc3)cc2c(NC(C)c2ccccc2F)c1Cl] | 478.1 | 1.64 | A |
| 312 | 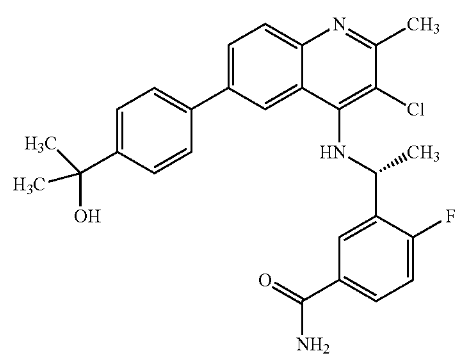 [SMILES: Cc1nc2ccc(-c3ccc(C(C)(C)O)cc3)cc2c(N[C@H](C)c2cc(C(N)=O)ccc2F)c1Cl] | 492.0 | 0.70 | C |

TABLE 11-continued

| Ex. No. | Structure | MS (M+1) | HPLC ret. Time (min.) | HPLC method |
|---|---|---|---|---|
| 313 | 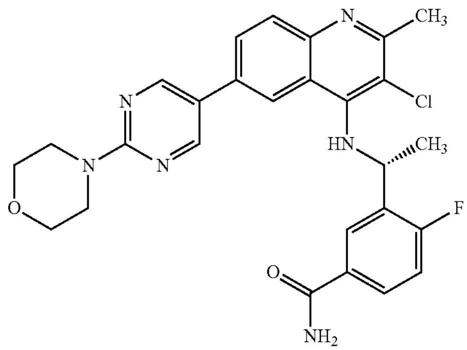 [SMILES: Cc1nc2ccc(-c3cnc(N4CCOCC4)nc3)cc2c(N[C@H](C)c2cc(C(N)=O)ccc2F)c1Cl] | 520.9 | 0.69 | C |

Example 314

(R)-4-fluoro-3-(1-((6-(2-(2-hydroxypropan-2-yl)pyrimidin-5-yl)-2,3-dimethylquinolin-4-yl)amino)ethyl)benzonitrile

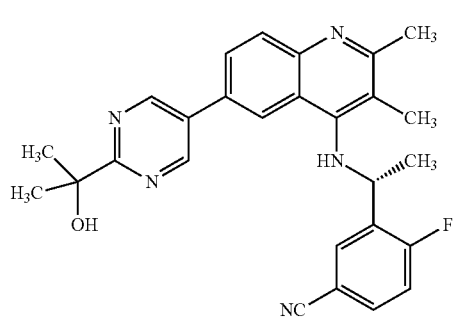

(314)

Intermediate 314A: (R)-2-(5-(4-((1-(5-bromo-2-fluorophenyl)ethyl)amino)-2,3-dimethylquinolin-6-yl)pyrimidin-2-yl)propan-2-ol

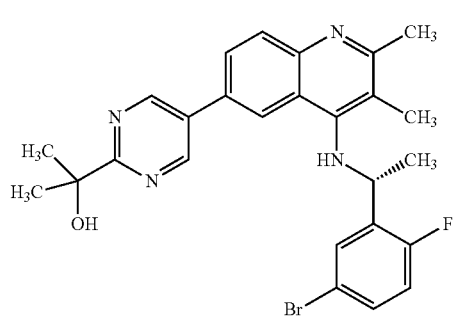

(314A)

A mixture of 2-(5-(4-chloro-2,3-dimethylquinolin-6-yl)pyrimidin-2-yl)propan-2-ol (9.0 mg, 0.027 mmol, Intermediate I-48), (R)-1-(5-bromo-2-fluorophenyl)ethanamine (6.59 mg, 0.030 mmol, Intermediate I-70), and ((1R,4S)-7,7-dimethyl-2-oxobicyclo[2.2.1]heptan-1-yl)methanesulfonic acid (3.19 mg, 0.014 mmol) in NMP (0.5 mL) was heated in a sealed tube at 140° C. for 24 h. The mixture was cooled to room temperature, diluted with ethyl acetate (60 mL), washed with water, brine, dried over sodium sulfate and concentrated under reduced pressure. Flash chromatography purification (4 g silica gel column, gradient elution from 0 to 10% of methanol in dichloromethane) afforded (R)-2-(5-(4-((1-(5-bromo-2-fluorophenyl)ethyl)amino)-2,3-dimethylquinolin-6-yl)pyrimidin-2-yl)propan-2-ol (9.8 mg, 70% yield). LC/MS (M+H): 509, 511; LC retention time: 0.77 min (analytical HPLC Method C); $^1$H NMR (400 MHz, methanol-$d_4$) δ 9.06 (br. s., 2H), 8.29 (s, 1H), 7.90 (m, 1H), 7.70 (d, J=8.7 Hz, 1H), 7.37 (m, 1H), 6.95 (m, 1H), 5.14-4.97 (m, 1H), 2.65 (s, 3H), 2.40 (s, 3H), 1.76-1.69 (m, 3H), 1.67 (s., 6H).

Example 314

A mixture of (R)-2-(5-(4-((1-(5-bromo-2-fluorophenyl)ethyl)amino)-2,3-dimethylquinolin-6-yl)pyrimidin-2-yl)propan-2-ol (9.8 mg, 0.019 mmol), dicyanozinc (5.99 mg, 0.051 mmol), di-tert-butyl(2',4',6'-triisopropyl-[1,1'-biphenyl]-2-yl)phosphine (2.17 mg, 5.10 μmol), Pd$_2$(dba)$_3$ (2.34 mg, 2.55 μmol) and zinc (3.34 mg, 0.051 mmol) in DMF (1 mL) was heated at 95° C. under nitrogen in a sealed tube for 1 h. The mixture was cooled to room temperature, diluted with ethyl acetate (60 mL), washed with water, brine, dried over sodium sulfate and concentrated under reduced pressure. Flash chromatography purification (4 g silica gel column, gradient elution from 0 to 10% of methanol in dichloromethane) afforded (R)-4-fluoro-3-(1-((6-(2-(2-hydroxypropan-2-yl)pyrimidin-5-yl)-2,3-dimethylquinolin-4-yl)amino)ethyl)benzonitrile (5.0 mg, 47% yield). LC/MS (M+H): 456; LC retention time: 0.71 min (analytical HPLC Method C); $^1$H NMR (400 MHz, methanol-$d_4$) δ 9.11-9.03 (m, 2H), 8.27 (d, J=1.6 Hz, 1H), 8.16 (dd, J=6.9, 2.1 Hz, 1H), 8.03-7.91 (m, 2H), 7.71-7.63 (m, 1H), 7.22 (dd, J=10.0, 8.6 Hz, 1H), 2.66 (s, 3H), 2.41 (s, 3H), 1.71 (d, J=6.8 Hz, 3H), 1.70-1.63 (m, 6H).

Example 315

(R)-4-fluoro-3-(1-((6-(2-(2-hydroxypropan-2-yl)pyrimidin-5-yl)-2,3-dimethylquinolin-4-yl)amino)ethyl)benzamide

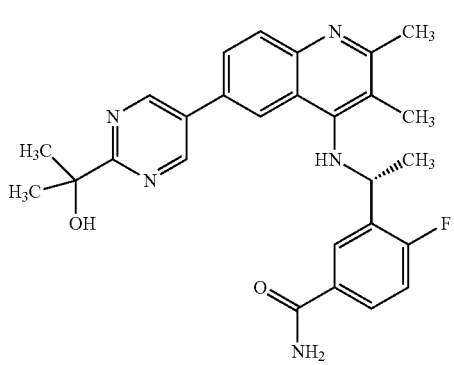
(315)

A 1 N aqueous sodium hydroxide (0.03 mL, 0.030 mmol) and 30% aqueous hydrogen peroxide (1.01 mg, 0.030 mmol) were added to a mixture of (R)-4-fluoro-3-(1-((6-(2-(2-hydroxypropan-2-yl)pyrimidin-5-yl)-2,3-dimethylquinolin-4-yl)amino)ethyl)benzonitrile (4.5 mg, 9.88 μmol) from Example 314 in methanol (0.3 mL). After stirring at room temperature for 1 h, the mixture was quenched with 1 N aqueous HCl (0.05 mL). The crude material was purified via preparative HPLC using the following conditions: Column: Luna C18, 30×100 mm, 5-μm particles; Mobile Phase A: 10:90 methanol:water with 0.1% trifluoroacetic acid; Mobile Phase B: 90:10 methanol: water with 0.1% trifluoroacetic acid; Gradient: 20-100% B over 10 minutes, then a 2-minute hold at 100% B; Flow: 20 mL/min. Fractions containing the desired product were combined and dried via centrifugal evaporation to give (R)-4-fluoro-3-(1-((6-(2-(2-hydroxypropan-2-yl)pyrimidin-5-yl)-2,3-dimethylquinolin-4-yl)amino)ethyl)benzamide, TFA salt (1.4 mg, 22% yield). LC/MS (M+H): 474; LC retention time: 0.62 min (analytical HPLC Method C); $^1$H NMR (400 MHz, methanol-$d_4$) δ 8.97 (s, 2H), 8.45 (d, J=1.6 Hz, 1H), 8.36-8.16 (m, 2H), 8.00 (d, J=8.8 Hz, 1H), 7.91 (ddd, J=8.5, 4.9, 2.4 Hz, 1H), 7.26 (dd, J=10.1, 8.7 Hz, 1H), 5.78 (q, J=6.7 Hz, 1H), 2.79 (s, 3H), 2.48 (s, 3H), 1.84 (d, J=6.6 Hz, 3H), 1.67 (s, 6H).

Example 316

(R)-2-(5-(4-((1-(5-bromo-2-fluorophenyl)ethyl)amino)-3-chloro-2-methylquinolin-6-yl)pyrimidin-2-yl)propan-2-ol

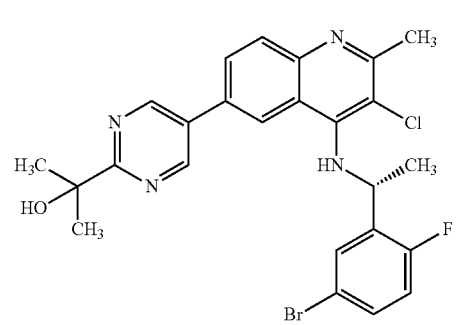
(316)

A stirred NMP (5 mL) solution of Intermediate I-77 (200 mg, 0.57 mmol), Intermediate I-70 (150 mg, 0.69 mmol) and ((1R,4S)-7,7-dimethyl-2-oxobicyclo[2.2.1] heptan-1-yl)methanesulfonic acid (67 mg, 0.29 mmol) was heated in a sealed vial at 130° C. for 16 h. Additional Intermediate I-70 (125 mg) was added. Heating was continued for additional 24 h. After cooling to room temperature, the mixture was treated with 10% aqueous LiCl solution (50 mL) and extracted with EtOAc (70 mL). The EtOAc phase was washed with 10% aqueous LiCl solution (10 mL) and brine (10 mL), dried over $Na_2SO_4$ and filtered. The filtrate was concentrated. The residue was purified by silica gel column chromatography (40 g ISCO cartridge, 0-100% EtOAc/hexanes) to give Example 316 (228 mg, 75% yield). LC/MS (M+H): 529, 531; LC retention time: 0.79 min (Method C); $^1$H NMR (400 MHz, chloroform-d) δ 8.82 (s, 2H), 8.06 (d, J=8.9 Hz, 1H), 7.97 (d, J=2.0 Hz, 1H), 7.81 (dd, J=8.7, 2.0 Hz, 1H), 7.65 (dd, J=6.7, 2.4 Hz, 1H), 7.42 (ddd, J=8.7, 4.6, 2.4 Hz, 1H), 7.02-6.96 (m, 1H), 5.29-5.21 (m, 1H), 5.10 (d, J=9.0 Hz, 1H), 4.70 (s, 1H), 2.80 (s, 3H), 1.69 (d, J=6.6 Hz, 3H), 1.67 (s, 6H).

The examples in Table 12 below were prepared according to the general process used in the preparation of Example 316.

TABLE 12

| Ex. No. | Structure | MS observed ($M^{+1}$) | HPLC ret. Time (min.) | HPLC method |
|---|---|---|---|---|
| 317 (±) | 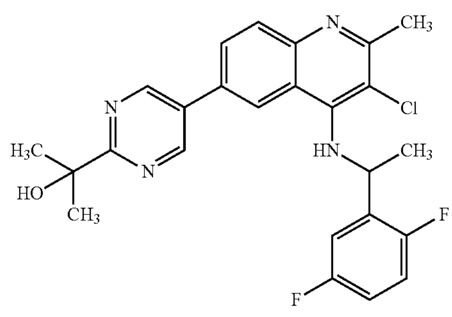 [SMILES: Cc1nc2ccc(-c3cnc(C(C)(C)O)nc3)cc2c(NC(C)c2cc(F)ccc2F)c1Cl] | 469 | 2.12 | A |

TABLE 12-continued

| Ex. No. | Structure | MS observed (M+1) | HPLC ret. Time (min.) | HPLC method |
|---|---|---|---|---|
| 318 | 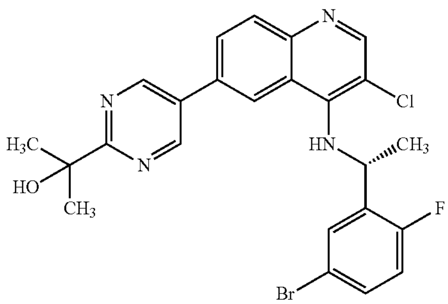 [SMILES: C[C@@H](Nc1c(Cl)cnc2ccc(-c3cnc(C(C)(C)O)nc3)cc12)c1cc(Br)ccc1F] | 513, 515 | 2.28 | A |
| 319 | 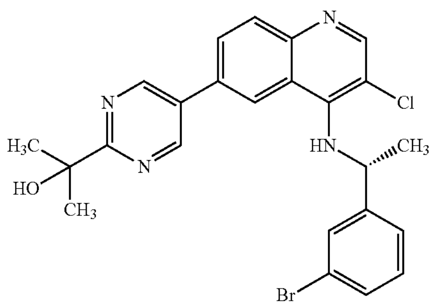 [SMILES: C[C@@H](Nc1c(Cl)cnc2ccc(-c3cnc(C(C)(C)O)nc3)cc12)c1cccc(Br)c1] | 497, 499 | 2.13 | A |
| 320 | 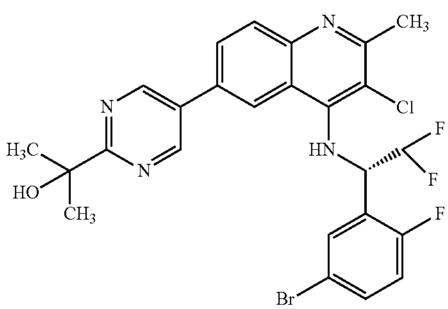 [SMILES: Cc1nc2ccc(-c3cnc(C(C)(C)O)nc3)cc2c(N[C@@H](c2cc(Br)ccc2F)C(F)F)c1Cl] | 565, 567 | 2.22 | A |
| 321 | 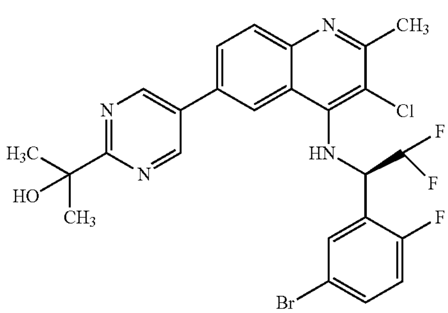 [SMILES: Cc1nc2ccc(-c3cnc(C(C)(C)O)nc3)cc2c(N[C@H](c2cc(Br)ccc2F)C(F)F)c1Cl] | 565, 567 | 2.30 | A |
| 322 | 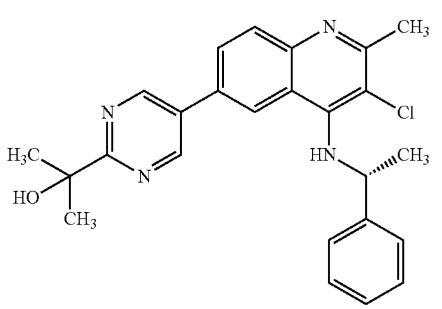 [SMILES: Cc1nc2ccc(-c3cnc(C(C)(C)O)nc3)cc2c(N[C@H](C)c2ccccc2)c1Cl] | 433 | 2.12 | A |

TABLE 12-continued

| Ex. No. | Structure | MS observed (M+1) | HPLC ret. Time (min.) | HPLC method |
|---|---|---|---|---|
| 323 | 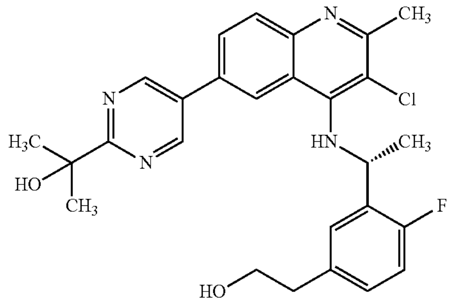 [SMILES: Cc1nc2ccc(-c3cnc(C(C)(C)O)nc3)cc2c(N[C@H](C)c2cc(CCO)ccc2F)c1Cl] | 495 | 0.69 | C |
| 324 | 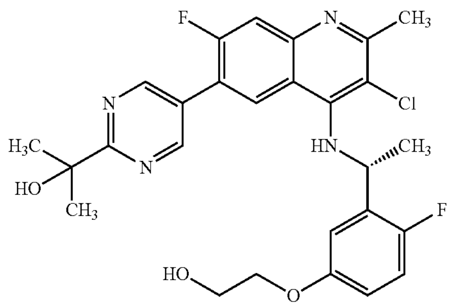 [SMILES: Cc1nc2cc(F)c(-c3cnc(C(C)(C)O)nc3)cc2c(N[C@H](C)c2cc(OCCO)ccc2F)c1Cl] | 529 | 0.69 | C |
| 325 | 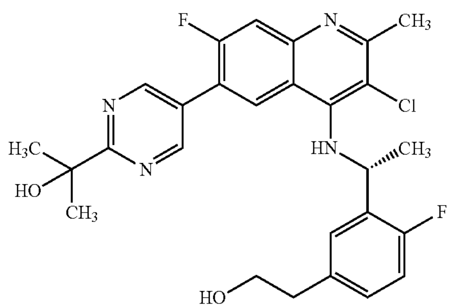 [SMILES: Cc1nc2cc(F)c(-c3cnc(C(C)(C)O)nc3)cc2c(N[C@H](C)c2cc(CCO)ccc2F)c1Cl] | 513 | 1.93 | A |

Example 326

(R)-2-(5-(3-chloro-4-((1-(2-fluoro-5-methoxyphenyl)ethyl)amino)-2-methylquinolin-6-yl)pyrimidin-2-yl)propan-2-ol

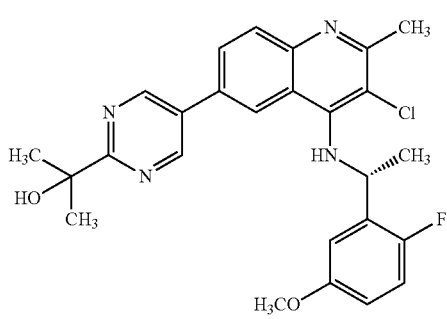

(326)

A DMA (0.5 mL) solution of Intermediate I-77 (20 mg, 0.057 mmol), HCl salt of Intermediate I-71 (23.62 mg, 0.115 mmol) and DBU (0.013 mL, 0.086 mmol) in a sealed safety vial was heated at 90° C. for 16 h and at 140° C. for 5 h. The crude material was purified via preparative LC/MS (Condition A: Gradient: 50-100% B over 20 minutes, then a 5-minute hold at 100% B) to give (R)-2-(5-(3-chloro-4-((1-(2-fluoro-5-methoxyphenyl)ethyl)amino)-2-methylquinolin-6-yl)pyrimidin-2-yl)propan-2-ol (3.5 mg, 13% yield). LC/MS (M+H): 481; LC retention time: 2.20 min (Method A); $^1$H NMR (500 MHz, DMSO-$d_6$) δ 9.15 (s, 2H), 8.49 (s, 1H), 8.06 (d, J=8.7 Hz, 1H), 7.91 (d, J=8.7 Hz, 1H), 7.19 (d, J=2.5 Hz, 1H), 6.97 (t, J=9.4 Hz, 1H), 6.76-6.70 (m, 1H), 6.39 (d, J=9.3 Hz, 1H), 5.59-5.50 (m, 1H), 3.16 (d, J=5.1 Hz, 3H), 2.62 (s, 3H), 1.64 (d, J=6.6 Hz, 3H), 1.55 (s, 6H).

Example 327

(R)-2-(5-(3-chloro-4-((1-(2-fluoro-5-methoxyphenyl)ethyl)amino)quinolin-6-yl)pyrimidin-2-yl)propan-2-ol

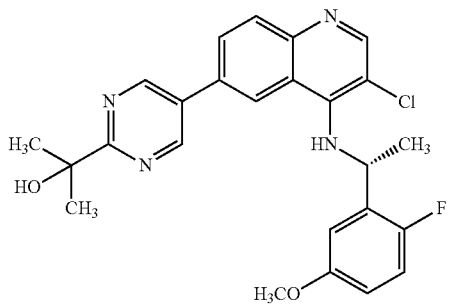

(327)

Using an analogous procedure to the synthesis of Example 326, 2-(5-(3,4-dichloroquinolin-6-yl)pyrimidin-2-yl)propan-2-ol from Intermediate I-45 (20 mg, 0.060 mmol) was converted to (R)-2-(5-(3-chloro-4-((1-(2-fluoro-5-methoxyphenyl)ethyl)amino)quinolin-6-yl)pyrimidin-2-yl)propan-2-ol (4.3 mg, 14% yield). LC/MS (M+H): 467; LC retention time: 2.04 min (Method A); $^1$H NMR (500 MHz, DMSO-$d_6$) δ 9.23 (s, 2H), 8.68 (s, 1H), 8.49 (s, 1H), 8.12 (d, J=8.5 Hz, 1H), 7.99 (d, J=8.8 Hz, 1H), 7.11 (dd, J=5.8, 3.1 Hz, 1H), 7.00 (t, J=9.5 Hz, 1H), 6.77-6.72 (m, 1H), 6.69 (d, J=9.2 Hz, 1H), 5.77-5.67 (m, 1H), 3.59 (s, 3H), 1.66 (d, J=6.7 Hz, 3H), 1.57 (s, 6H).

Example 328

(R)-6-bromo-3-chloro-N-(1-(2-fluoro-5-methoxyphenyl)ethyl)-2-methylquinolin-4-amine

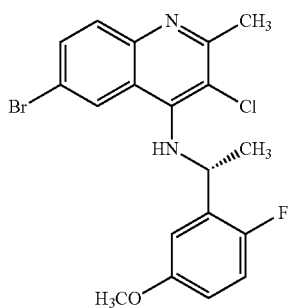

(328)

An NMP (0.5 mL) solution of Intermediate I-68 (30 mg, 0.1 mmol), HCl salt of Intermediate I-71 (32 mg, 0.16 mmol) and Cs$_2$CO$_3$ (34 mg, 0.1 mmol) in a sealed safety vial was heated at 140° C. for 16 h. Additional HCl salt of Intermediate I-71 (10 mg) was added. Heating was continued for additional 24 h. The crude material was purified via preparative LC/MS (Condition A: Gradient: 30-100% B over 19 minutes, then a 5-minute hold at 100% B) to give (R)-6-bromo-3-chloro-N-(1-(2-fluoro-5-methoxyphenyl)ethyl)-2-methylquinolin-4-amine (3.6 mg, 8% yield). LC/MS (M+H): 423, 425; LC retention time: 2.42 min (Method A); $^1$H NMR (500 MHz, DMSO-$d_6$) δ 8.42 (s, 1H), 7.77-7.69 (m, 2H), 7.22 (dd, J=5.8, 3.0 Hz, 1H), 7.02 (t, J=9.4 Hz, 1H), 6.81-6.72 (m, 1H), 6.38 (d, J=9.3 Hz, 1H), 5.50-5.38 (m, 1H), 3.70 (s, 3H), 2.58 (s, 3H), 1.60 (d, J=6.7 Hz, 3H).

Example 329

(R)-3-chloro-N-(1-(2-fluoro-5-methoxyphenyl)ethyl)-2-methylquinolin-4-amine

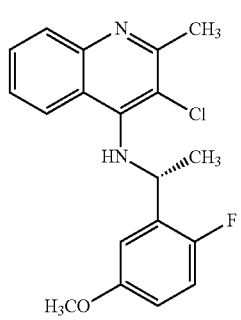

(329)

A MeOH (1.5 mL) solution of Example 328 (10 mg, 0.024 mmol) and 10% Pd on carbon (2.5 mg, 2.4 µmol) was hydrogenated at 25 psi H$_2$ at room temperature for 1 h. The crude mixture was filtered and the filtrate purified via preparative LC/MS (Condition A: Gradient: 25-100% B over 19 minutes, then a 5-minute hold at 100% B) to give (R)-3-chloro-N-(1-(2-fluoro-5-methoxyphenyl)ethyl)-2-methylquinolin-4-amine (4.2 mg, 52% yield). LC/MS (M+H): 345; LC retention time: 2.13 min (Method A); $^1$H NMR (500 MHz, DMSO-$d_6$) δ 8.11 (d, J=8.2 Hz, 1H), 7.77 (d, J=8.5 Hz, 1H), 7.63 (t, J=7.5 Hz, 1H), 7.45 (t, J=7.5 Hz, 1H), 7.06 (dd, J=5.8, 3.1 Hz, 1H), 6.95 (t, J=9.5 Hz, 1H), 6.75-6.67 (m, 1H), 6.08 (d, J=9.5 Hz, 1H), 5.49-5.39 (m, 1H), 3.62 (s, 3H), 2.55 (s, 3H), 1.59 (d, J=6.7 Hz, 3H).

Example 330

(R)-2-(5-(3-chloro-4-((1-(2-fluoro-5-vinylphenyl)ethyl)amino)-2-methylquinolin-6-yl)pyrimidin-2-yl)propan-2-ol

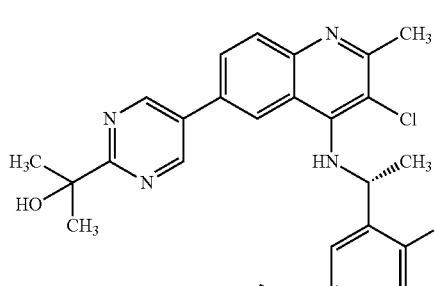

(330)

A dioxane (0.5 mL) solution of Example 316 (27 mg, 0.05 mmol), 2,4,6-trivinyl-1,3,5,2,4,6-trioxatriborinane, pyridinium salt (6.2 mg, 0.025 mmol), PdCl$_2$(dppf)-CH$_2$Cl$_2$ adduct (4.2 mg, 5 µmol) and aqueous 2 M K$_3$PO$_4$ (0.076 mL, 0.15 mmol) was pumped under vacuum and backfilled with nitrogen twice. The sealed tube was then heated at 90° C. for 40 min. The mixture was diluted with MeOH (1 mL) and filtered. The filtrate was purified via preparative LC/MS (Condition A: Gradient: 45-100% B over 20 minutes, then a 10-minute hold at 100% B) to give (R)-2-(5-(3-chloro-4-((1-(2-fluoro-5-vinylphenyl)ethyl)amino)-2-methylquinolin-6-yl)pyrimidin-2-yl)propan-2-ol (1.3 mg, 5% yield). LC/MS (M+H): 477; LC retention time: 2.30 min (Method A); $^1$H NMR (500 MHz, DMSO-$d_6$) δ 9.17 (s, 2H), 8.53 (s, 1H), 8.07 (d, J=8.6 Hz, 1H), 7.91 (d, J=8.7 Hz, 1H), 7.80 (d, J=6.3 Hz, 1H), 7.29 (br. s., 1H), 7.03 (t, J=9.3 Hz, 1H), 6.61 (dd, J=17.5, 11.0 Hz, 1H), 6.44 (d, J=9.3 Hz, 1H), 5.66-5.53 (m, 2H), 5.13 (d, J=10.9 Hz, 1H), 2.62 (s, 3H), 1.66 (d, J=6.6 Hz, 3H), 1.56 (s, 6H).

Examples 331-350 in Table 13 were prepared according to the general procedure used in the preparation of Example 330. Examples 351 and 352 were prepared according to the general procedure used in the preparation of Example 330 using Example 320 as the starting material.

TABLE 13

| Ex. No. | Structure | MS observed ($M^{+1}$) | HPLC ret. Time (min.) | HPLC method |
|---|---|---|---|---|
| 331 | 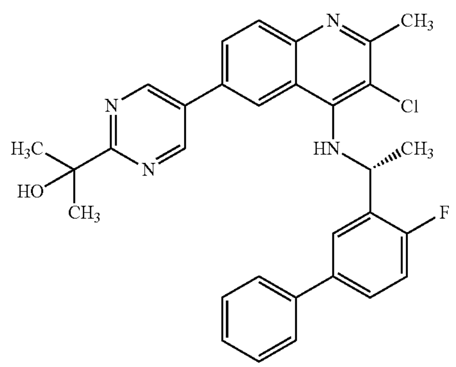 [SMILES: Cc1nc2ccc(-c3cnc(C(C)(C)O)nc3)cc2c(N[C@H](C)c2cc(-c3ccccc3)ccc2F)c1Cl] | 527 | 2.50 | A |
| 332 | 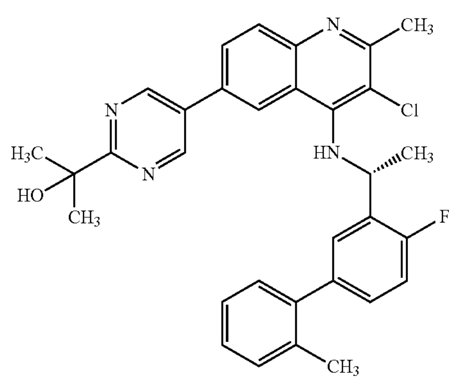 [SMILES: Cc1ccccc1-c1ccc(F)c([C@@H](C)Nc2c(Cl)c(C)nc3ccc(-c4cnc(C(C)(C)O)nc4)cc23)c1] | 541 | 3.62 | A |
| 333 | 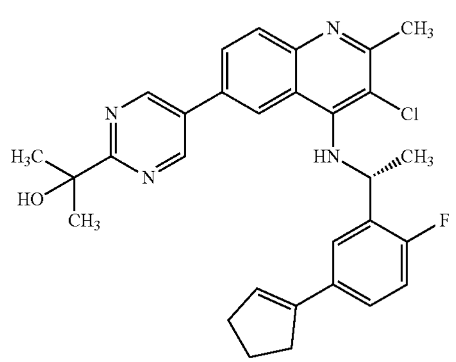 [SMILES: Cc1nc2ccc(-c3cnc(C(C)(C)O)nc3)cc2c(N[C@H](C)c2cc(C3=CCCC3)ccc2F)c1Cl] | 517 | 2.75 | A |

TABLE 13-continued

| Ex. No. | Structure | MS observed (M+1) | HPLC ret. Time (min.) | HPLC method |
|---|---|---|---|---|
| 334 | 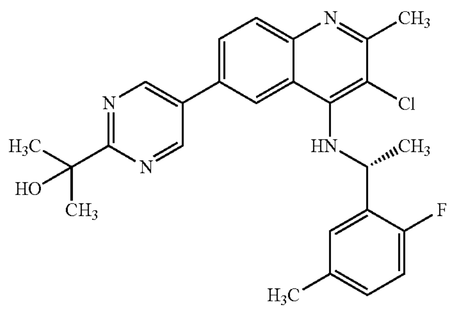 [SMILES: Cc1ccc(F)c([C@@H](C)Nc2c(Cl)c(C)nc3ccc(-c4cnc(C(C)(C)O)nc4)cc23)c1] | 465 | 2.32 | A |
| 335 | 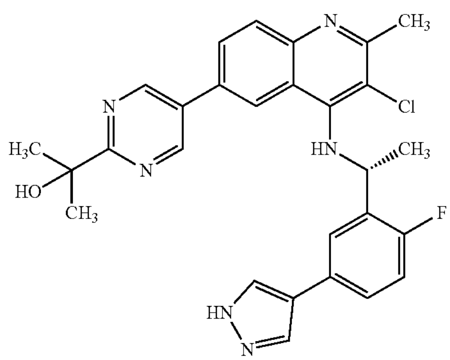 [SMILES: Cc1nc2ccc(-c3cnc(C(C)(C)O)nc3)cc2c(N[C@H](C)c2cc(-c3cn[nH]c3)ccc2F)c1Cl] | 517 | 1.89 | A |
| 336 | 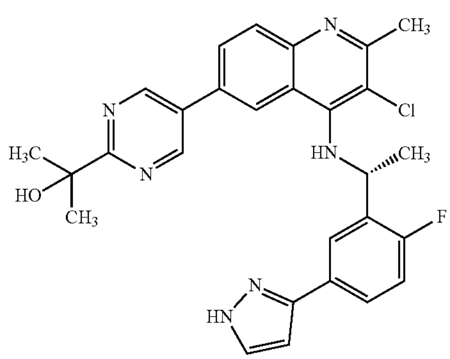 [SMILES: Cc1nc2ccc(-c3cnc(C(C)(C)O)nc3)cc2c(N[C@H](C)c2cc(-c3cc[nH]n3)ccc2F)c1Cl] | 517 | 1.82 | A |
| 337 | 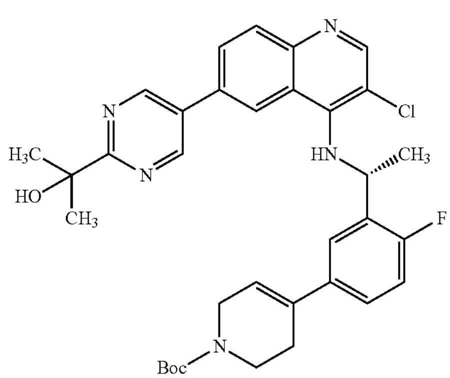 [SMILES: C[C@@H](Nc1c(Cl)cnc2ccc(-c3cnc(C(C)(C)O)nc3)cc12)c1cc(C2=CCN(C(=O)OC(C)(C)C)CC2)ccc1F] | 618 | 2.45 | A |

TABLE 13-continued

| Ex. No. | Structure | MS observed (M$^{+1}$) | HPLC ret. Time (min.) | HPLC method |
|---|---|---|---|---|
| 338 | 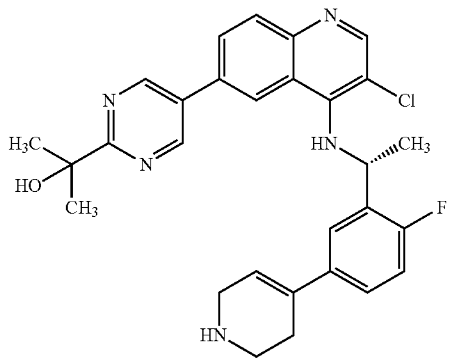 [SMILES: C[C@@H](Nc1c(Cl)cnc2ccc(-c3cnc(C(C)(C)O)nc3)cc12)c1cc(C2=CCNCC2)ccc1F] | 518 | 1.52 | A |
| 339 | 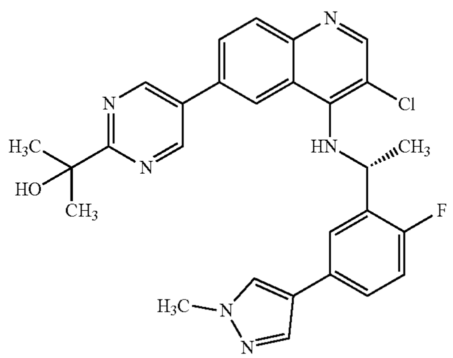 [SMILES: C[C@@H](Nc1c(Cl)cnc2ccc(-c3cnc(C(C)(C)O)nc3)cc12)c1cc(-c2cnn(C)c2)ccc1F] | 517 | 1.84 | A |
| 340 | 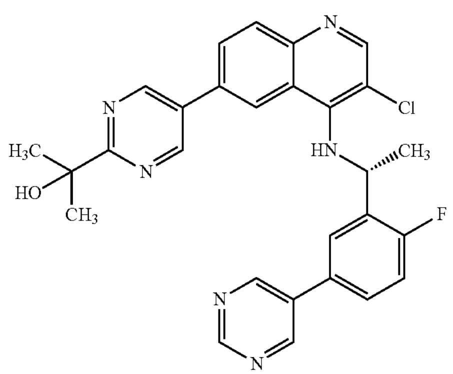 [SMILES: C[C@@H](Nc1c(Cl)cnc2ccc(-c3cnc(C(C)(C)O)nc3)cc12)c1cc(-c2cncnc2)ccc1F] | 515 | 1.74 | A |
| 341 | 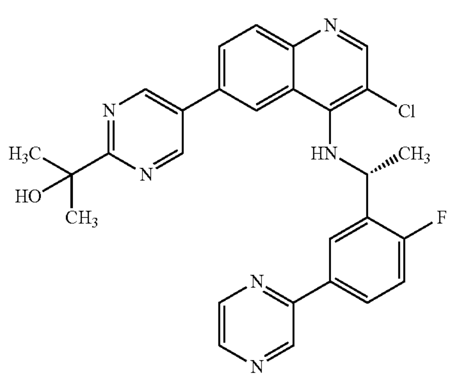 [SMILES: C[C@@H](Nc1c(Cl)cnc2ccc(-c3cnc(C(C)(C)O)nc3)cc12)c1cc(-c2cnccn2)ccc1F] | 515 | 2.01 | A |

TABLE 13-continued

| Ex. No. | Structure | MS observed ($M^{+1}$) | HPLC ret. Time (min.) | HPLC method |
|---|---|---|---|---|
| 342 | 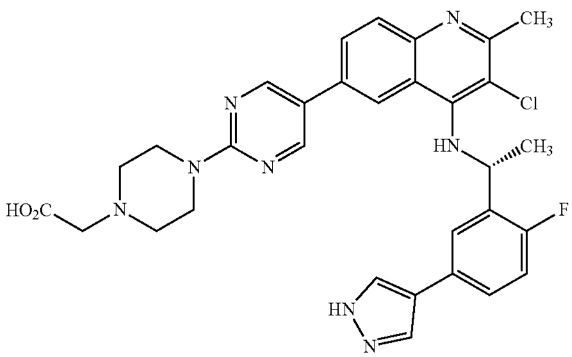 [SMILES: Cc1nc2ccc(-c3cnc(N4CCN(CC(=O)O)CC4)nc3)cc2c(N[C@H](C)c2cc(-c3cn[nH]c3)ccc2F)c1Cl] | 601 | 1.51 | A |
| 343 | 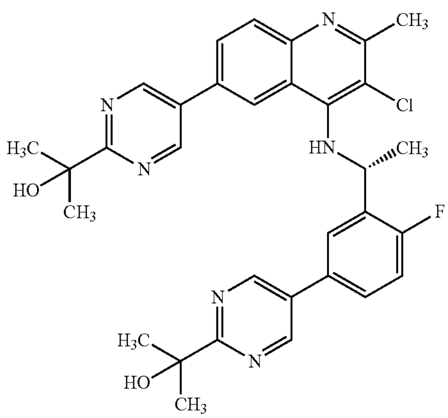 [SMILES: Cc1nc2ccc(-c3cnc(C(C)(C)O)nc3)cc2c(N[C@H](C)c2cc(-c3cnc(C(C)(C)O)nc3)ccc2F)c1Cl] | 587 | 1.45 | A |
| 344 | 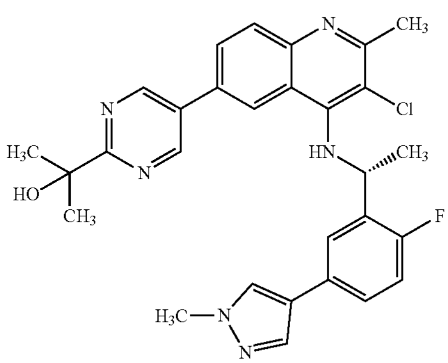 [SMILES: Cc1nc2ccc(-c3cnc(C(C)(C)O)nc3)cc2c(N[C@H](C)c2cc(-c3cnn(C)c3)ccc2F)c1Cl] | 531 | 1.94 | A |
| 345 | 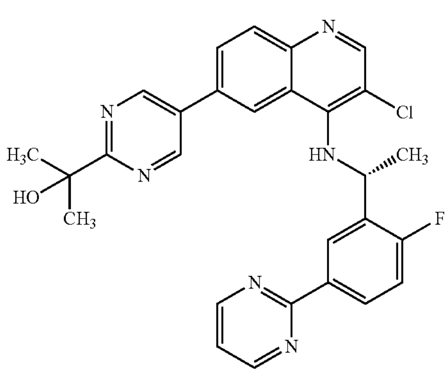 [SMILES: C[C@@H](Nc1c(Cl)cnc2ccc(-c3cnc(C(C)(C)O)nc3)cc12)c1cc(-c2ncccn2)ccc1F] | 515 | 2.02 | A |

TABLE 13-continued

| Ex. No. | Structure | MS observed (M$^{+1}$) | HPLC ret. Time (min.) | HPLC method |
|---|---|---|---|---|
| 346 | 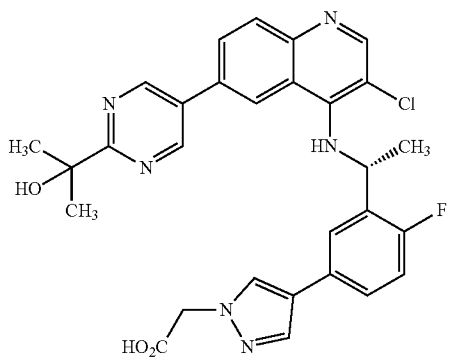 [SMILES: C[C@@H](Nc1c(Cl)cnc2ccc(-c3cnc(C(C)(C)O)nc3)cc12)c1cc(-c2cnn(CC(=O)O)c2)ccc1F] | 561 | 1.33 | A |
| 347 | 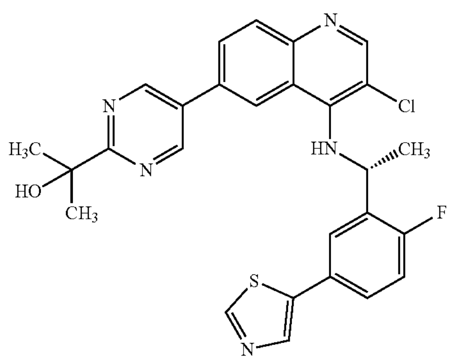 [SMILES: C[C@@H](Nc1c(Cl)cnc2ccc(-c3cnc(C(C)(C)O)nc3)cc12)c1cc(-c2cncs2)ccc1F] | 520 | 1.88 | A |
| 348 | 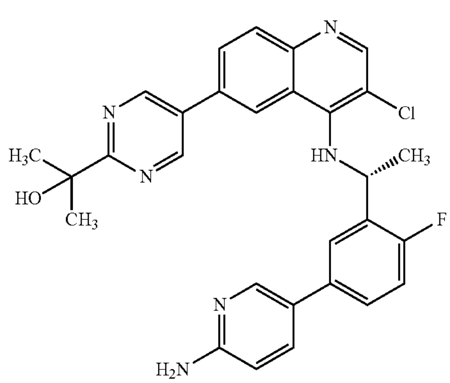 [SMILES: C[C@@H](Nc1c(Cl)cnc2ccc(-c3cnc(C(C)(C)O)nc3)cc12)c1cc(-c2ccc(N)nc2)ccc1F] | 529 | 1.87 | A |

TABLE 13-continued

| Ex. No. | Structure | MS observed (M$^{+1}$) | HPLC ret. Time (min.) | HPLC method |
|---|---|---|---|---|
| 349 | 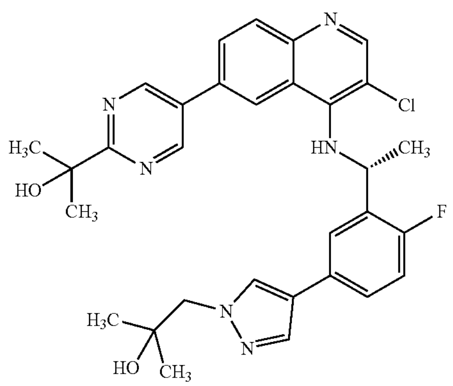 [SMILES: C[C@@H](Nc1c(Cl)cnc2ccc(-c3cnc(C(C)(C)O)nc3)cc12)c1cc(-c2cnn(CC(C)(C)O)c2)ccc1F] | 575 | 1.86 | A |
| 350 | 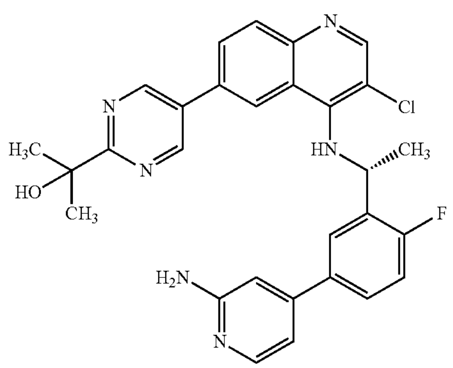 [SMILES: C[C@@H](Nc1c(Cl)cnc2ccc(-c3cnc(C(C)(C)O)nc3)cc12)c1cc(-c2ccnc(N)c2)ccc1F] | 529 | 1.84 | A |
| 351 | 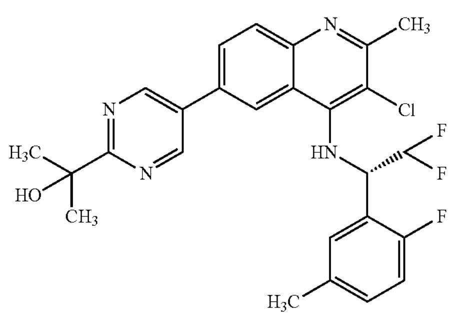 [SMILES: Cc1ccc(F)c([C@H](Nc2c(Cl)c(C)nc3ccc(-c4cnc(C(C)(C)O)nc4)cc23)C(F)F)c1] | 501 | 2.23 | A |
| 352 | 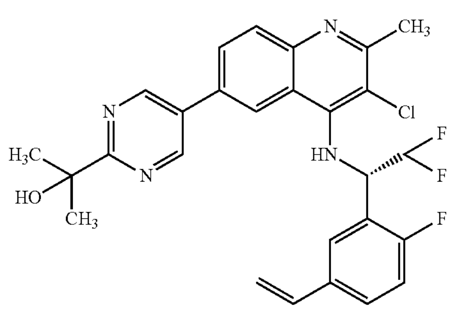 [SMILES: C=Cc1ccc(F)c([C@H](Nc2c(Cl)c(C)nc3ccc(-c4cnc(C(C)(C)O)nc4)cc23)C(F)F)c1] | 513 | 2.25 | A |

Example 353

2-(5-(4-([1,1'-biphenyl]-2-yl)-3-chloro-2-methylquinolin-6-yl)pyrimidin-2-yl)propan-2-ol

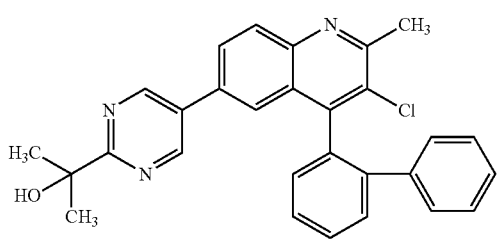

(353)

Using an analogous procedure to the synthesis of Example 330, Intermediate I-77 (20 mg, 0.028 mmol) was converted to 2-(5-(4-([1,1'-biphenyl]-2-yl)-3-chloro-2-methylquinolin-6-yl)pyrimidin-2-yl)propan-2-ol, TFA salt (11.7 mg, 72% yield). LC/MS (M+H): 466; LC retention time: 2.41 min (Method A); $^1$H NMR (500 MHz, DMSO-d$_6$) δ 8.93 (s, 2H), 8.05 (s, 2H), 7.70-7.65 (m, 1H), 7.63-7.56 (m, 2H), 7.43-7.36 (m, 2H), 7.24 (br. s., 2H), 7.09 (d, J=7.0 Hz, 4H), 2.74 (s, 3H), 1.51 (s, 6H).

Example 354

(S)-methyl 3-((S)-1-((3-chloro-6-(2-(2-hydroxypropan-2-yl)pyrimidin-5-yl)quinolin-4-yl)amino)ethyl)piperidine-1-carboxylate

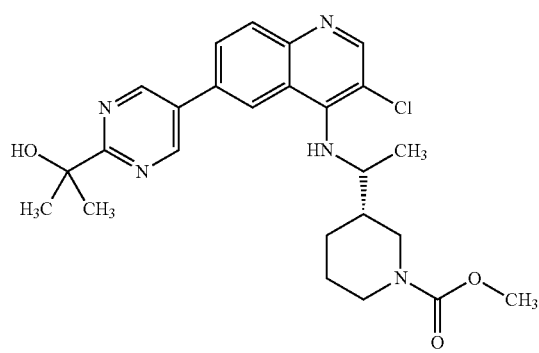

(354)

To a stirred solution of 2-(5-(3-chloro-4-(((S)-1-((S)-piperidin-3-yl)ethyl)amino) quinolin-6-yl)pyrimidin-2-yl)propan-2-ol (Example 97, 9 mg, 0.021 mmol) and DIEA (0.011 mL, 0.063 mmol) in anhydrous CH$_2$Cl$_2$ (0.5 mL) was added methyl chloroformate (2.449 μl, 0.032 mmol) at −40° C. The mixture was stirred at room temperature for 1 h and then MeOH was added. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-70% B over 19 minutes, then a 5-minute hold at 100% B; Flow: 20 mL/min. Fractions containing the desired product were combined and dried via centrifugal evaporation. The yield of the product was 8.4 mg. LC/MS (M+H): 484.0; LC retention time: 1.790 min (analytical HPLC Method A).

Example 355

1-(3-Chloro-6-(2-(2-hydroxypropan-2-yl)pyrimidin-5-yl)-2-methylquinolin-4-yl)-2,4-dimethylpentan-1-ol (Single Diastereomer)

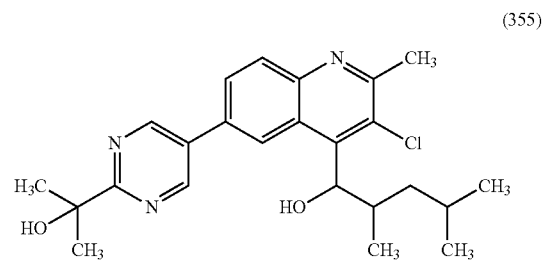 [SMILES: Cc1nc2ccc(-c3cnc(C(C)(C)O)nc3)cc2c(C(O)C(C)CC(C)C)c1Cl]

(355)

Intermediate 355A: 2-(5-(3-Chloro-2-methyl-4-vinylquinolin-6-yl)pyrimidin-2-yl)propan-2-ol

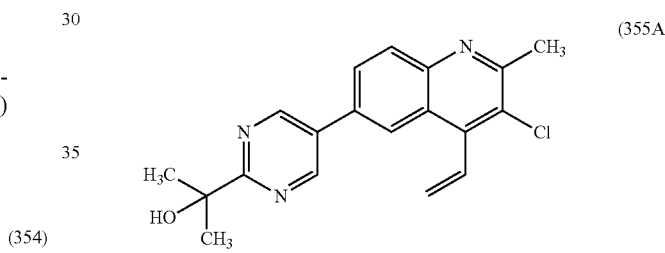

(355A)

In an analogous procedure to the synthesis of Example 330, Intermediate I-77 (395 mg, 1.13 mmol) was converted to 2-(5-(3-chloro-2-methyl-4-vinylquinolin-6-yl)pyrimidin-2-yl)propan-2-ol (179 mg, 46% yield). LC/MS (M+H): 340; LC retention time: 1.91 min (Method A); $^1$H NMR (500 MHz, DMSO-d$_6$) δ 9.22 (s, 2H), 8.37 (br. s., 1H), 8.21-8.15 (m, 1H), 8.14-8.09 (m, 1H), 7.12 (dd, J=18.0, 11.7 Hz, 1H), 6.06 (d, J=11.8 Hz, 1H), 5.88 (d, J=18.1 Hz, 1H), 2.77 (s, 3H), 1.55 (br. s., 6H).

Intermediate 355B: 3-chloro-6-(2-(2-hydroxypropan-2-yl)pyrimidin-5-yl)-2-methylquinoline-4-carbaldehyde

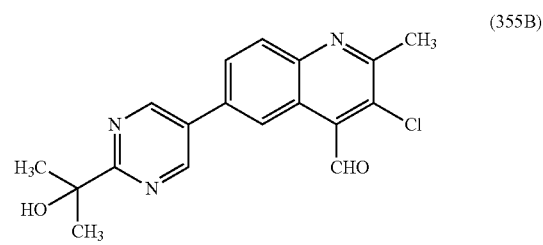 [SMILES: Cc1nc2ccc(-c3cnc(C(C)(C)O)nc3)cc2c(C=O)c1Cl]

(355B)

A THF (5 mL) suspension of Intermediate 355A (178 mg, 0.53 mmol), 50 wt % NMO in water (0.22 mL, 1.05 mmol) and 2.5 wt % osmium tetroxide in t-BuOH (0.16 mL, 0.016 mmol) was stirred at room temperature for 16 h. Sodium periodate (449 mg, 2.1 mmol) and water (0.2 mL) were added. The mixture was stirred at room temperature for additional 1 h and purified by silica gel column chromatography (24 g ISCO cartridge, 0-100% EtOAc/hexanes) to give 3-chloro-6-(2-(2-hydroxypropan-2-yl)pyrimidin-5-yl)-2-methylquinoline-4-carbaldehyde (179 mg, 100% yield). $^1$H NMR (400 MHz, chloroform-d) δ 10.92 (s, 1H), 9.10-9.05 (m, 3H), 8.20 (d, J=8.7 Hz, 1H), 7.96 (dd, J=8.7, 2.0 Hz, 1H), 2.94 (s, 3H), 1.68 (s, 6H).

Example 355

2-bromo-4-methylpentane (100 mg, 0.61 mmol) was added to a THF (0.5 mL) suspension of magnesium turning (14.6 mg, 0.6 mmol) and the mixture was stirred at room temperature for 3 h. A THF (0.25 mL) solution of 3-chloro-6-(2-(2-hydroxypropan-2-yl)pyrimidin-5-yl)-2-methylquinoline-4-carbaldehyde (Intermediate 355B, 10 mg, 0.029 mmol) was added to the freshly prepared Grignard reagent. The resulting mixture was stirred at room temperature for 10 min and quenched with saturated NH$_4$Cl (0.5 mL). After separation of the two layers, the bottom aqueous layer was extracted with EtOAc (1 mL). The combined organic phase was concentrated, dissolved in MeOH (1.5 mL) then filtered. The filtrate was purified via preparative LC/MS (Condition A: Gradient: 15-55% B over 19 minutes, then a 5-minute hold at 100% B) to give 1-(3-chloro-6-(2-(2-hydroxypropan-2-yl)pyrimidin-5-yl)-2-methylquinolin-4-yl)-2,4-dimethylpentan-1-ol (2 mg, 16% yield) as the first eluting isomer. LC/MS (M+H): 428; LC retention time: 2.24 min (Method A); $^1$H NMR (500 MHz, DMSO-d$_6$) δ 9.17-9.09 (m, 3H), 8.17-8.04 (m, 2H), 5.32 (br. s., 1H), 2.77 (br. s., 3H), 2.31 (br. s., 1H), 1.56 (br. s., 6H), 1.16 (br. s., 1H), 1.09 (d, J=6.4 Hz, 3H), 1.00 (d, J=6.4 Hz, 1H), 0.81 (br. s., 1H), 0.74 (d, J=6.1 Hz, 3H), 0.57 (d, J=6.1 Hz, 3H).

Example 356

± 1-(3-Chloro-6-(2-(2-hydroxypropan-2-yl)pyrimidin-5-yl)-2-methyl quinolin-4-yl)-2-methylpentan-1-one

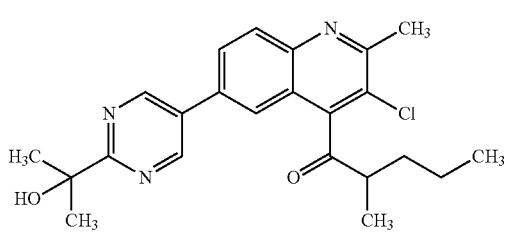

(356)

Intermediate 356A: 1-(3-chloro-6-(2-(2-hydroxypropan-2-yl)pyrimidin-5-yl)-2-methylquinolin-4-yl)-2-methylpentan-1-ol

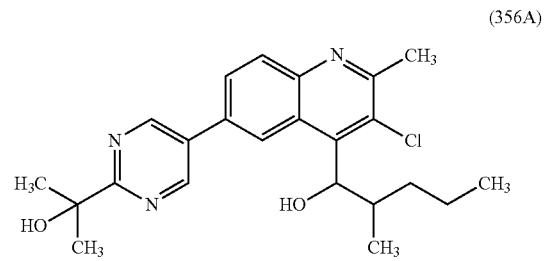 [SMILES: CCCC(C)C(O)c1c(Cl)c(C)nc2ccc(-c3cnc(C(C)(C)O)nc3)cc12]

(356A)

Using an analogous procedure to the synthesis of Example 355, 2-bromopentane (0.11 mL, 0.9 mmol), magnesium turning (32.5 mg, 1.34 mmol) and 3-chloro-6-(2-(2-hydroxypropan-2-yl)pyrimidin-5-yl)-2-methylquinoline-4-carbaldehyde (Intermediate 355B, 20 mg, 0.059 mmol) were converted to 1-(3-chloro-6-(2-(2-hydroxypropan-2-yl)pyrimidin-5-yl)-2-methylquinolin-4-yl)-2-methylpentan-1-ol (18 mg, 74% yield). LC/MS (M+H): 414; LC retention time: 0.98 min (Method C).

Example 356

Dess-Martin periodinane (4 mg, 9.4 μmol) was added to a CH$_2$Cl$_2$ (0.3 mL) solution of 1-(3-chloro-6-(2-(2-hydroxypropan-2-yl)pyrimidin-5-yl)-2-methylquinolin-4-yl)-2-methylpentan-1-ol (Intermediate 356A, 3.7 mg, 8.9 μmol). The mixture was stirred at room temperature for 1 h and quenched by adding sat. NaHCO$_3$ (1 mL). The CH$_2$Cl$_2$ phase was separated and concentrated. The residue was dissolved in MeOH (1.5 mL) and filtered. The filtrate was purified via preparative LC/MS (Condition A: Gradient: 40-80% B over 20 minutes, then a 5-minute hold at 100% B) to give 1-(3-chloro-6-(2-(2-hydroxypropan-2-yl)pyrimidin-5-yl)-2-methylquinolin-4-yl)-2-methylpentan-1-one (1.9 mg, 52% yield). LC/MS (M+H): 412; LC retention time: 2.32 min (Method A); $^1$H NMR (500 MHz, DMSO-d$_6$) δ 9.15 (br. s., 2H), 8.26-8.20 (m, 1H), 8.20-8.16 (m, 1H), 7.78 (s, 1H), 5.17 (br. s., 1H), 3.30-3.21 (m, 1H), 2.79 (s, 3H), 1.77 (br. s., 1H), 1.59-1.39 (m, 8H), 1.37-1.28 (m, 1H), 1.19 (d, J=7.0 Hz, 3H), 0.85 (t, J=7.2 Hz, 3H).

Examples 357 and 358

2-(5-(4-(1-amino-2-methylpentyl)-3-chloro-2-methylquinolin-6-yl)pyrimidin-2-yl)propan-2-ol (Diastereomers 1 and 2)

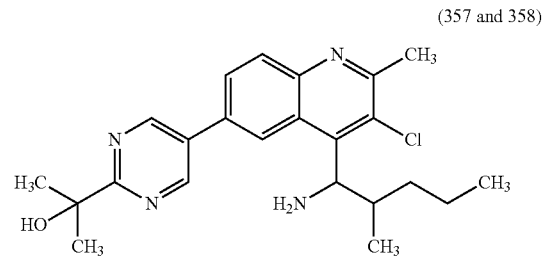 [SMILES: CCCC(C)C(N)c1c(Cl)c(C)nc2ccc(-c3cnc(C(C)(C)O)nc3)cc12]

(357 and 358)

Intermediate 357A: 2-(5-(4-(1-azido-2-methylpentyl)-3-chloro-2-methylquinolin-6-yl)pyrimidin-2-yl)propan-2-ol

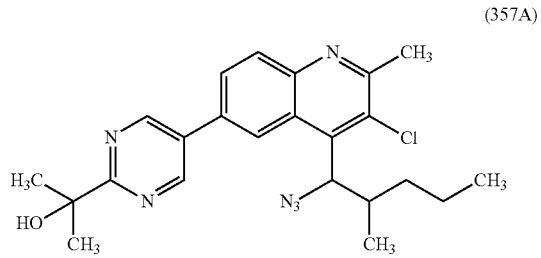 [SMILES: CCCC(C)C(N=[N+]=[N-])c1c(Cl)c(C)nc2ccc(-c3cnc(C(C)(C)O)nc3)cc12]

(357A)

DIAD (0.032 mL, 0.167 mmol) was added to a THF (0.5 mL) solution of 1-(3-chloro-6-(2-(2-hydroxypropan-2-yl)pyrimidin-5-yl)-2-methylquinolin-4-yl)-2-methylpentan-1-ol (Intermediate 356A, 23 mg, 0.056 mmol) and triphenylphosphine (44 mg, 0.167 mmol) at 0° C. After stirring for 15 min, diphenylphosphoryl azide (0.036 mL, 0.167 mmol) was added. The resulting mixture was stirred at 0° C. for additional 30 min and at room temperature for 3 h. The crude material was purified by silica gel column chromatography (4 g ISCO cartridge, 0-100% EtOAc/hexanes) to give impure 2-(5-(4-(1-azido-2-methylpentyl)-3-chloro-2-methylquinolin-6-yl)pyrimidin-2-yl)propan-2-ol. LC/MS (M+H): 439; LC retention time: 1.18 and 1.19 min (Method A).

Example 357 (Diastereomer 1)

Zinc powder (12.5 mg, 0.19 mmol) was added to an EtOH (1 mL)-water (0.1 mL) solution of 2-(5-(4-(1-azido-2-methylpentyl)-3-chloro-2-methylquinolin-6-yl)pyrimidin-2-yl)propan-2-ol (Intermediate 357A, 24 mg, 0.055 mmol) and ammonium chloride (11 mg, 0.21 mmol). The mixture was stirred at room temperature for 10 min, diluted with MeOH (0.9 mL) and filtered. The filtrate was purified via preparative LC/MS (Condition A: Gradient: 30-70% B over 19 minutes, then a 5-minute hold at 100% B) to give the first eluting isomer as diastereomer of 1-(3-chloro-6-(2-(2-hydroxypropan-2-yl)pyrimidin-5-yl)-2-methylquinolin-4-yl)-2-methylpentan-1-one (4.2 mg, 18% yield) and the impure second eluting isomer. Analytical data for diastereomer 1: LC/MS (M+H): 413; LC retention time: 1.99 min (Method A); $^1$H NMR (500 MHz, DMSO-$d_6$) δ 9.20 (br. s., 2H), 9.11 (br. s., 1H), 8.18-8.12 (m, 1H), 8.11-8.06 (m, 1H), 4.74 (br. s., 1H), 2.77 (s, 3H), 1.56 (s, 6H), 1.32-1.13 (m, 5H), 1.07-0.90 (m, 2H), 0.83 (br. s., 1H), 0.59 (t, J=7.0 Hz, 3H).

Example 358 (Diastereomer 2)

The impure second eluding isomer was further purified via preparative LC/MS (Condition B: Gradient: 10-50% B over 20 minutes, then a 5-minute hold at 100% B) to give Diastereomer 2 of 1-(3-chloro-6-(2-(2-hydroxypropan-2-yl)pyrimidin-5-yl)-2-methylquinolin-4-yl)-2-methylpentan-1-one bis-TFA salt (6 mg, 16% yield). LC/MS (M+H): 413; LC retention time: 2.02 min (Method A); $^1$H NMR (500 MHz, DMSO-$d_6$) δ 9.32-9.25 (m, 2H), 8.72-8.40 (m, 1H), 8.28-8.15 (m, 2H), 5.37-5.01 (m, 1H), 2.84-2.79 (m, 3H), 1.57 (s, 7H), 1.41-1.11 (m, 3H), 1.03-0.93 (m, 4H), 0.62-0.57 (m, 3H).

Example 359 tert-Butyl (R)-(3-(1-((3-chloro-6-(2-(2-hydroxypropan-2-yl)pyrimidin-5-yl)-2-methylquinolin-4-yl)amino)ethyl)-4-fluorophenyl)carbamate

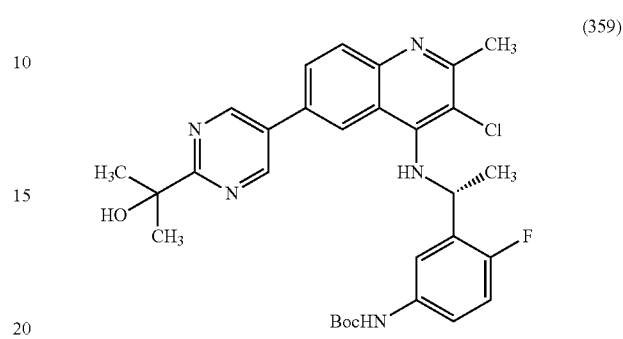

(359)

A stirred dioxane (0.5 mL) solution of Example 316 (39 mg, 0.074 mmol), tert-butyl carbamate (10.4 mg, 0.088 mmol), 2-di-tert-butylphosphino-2',4',6'-triisopropylbiphenyl (7.8 mg, 0.018 mmol), Pd$_2$(dba)$_3$ (6.7 mg, 7.36 μmol) and sodium tert-butoxide (8.8 mg, 0.092 mmol) was pumped under vacuum and backfilled with nitrogen twice. The sealed tube was then heated at 90° C. for 1 h. Additional tert-butyl carbamate (31 mg), di-tert-butylphosphino-2',4',6'-triisopropylbiphenyl (7.8 mg), Pd$_2$(dba)$_3$ (6.8 mg) and sodium tert-butoxide (9 mg) were added. The degas cycle was repeated and the heating continued for additional 4 h. The crude mixture was diluted with MeOH (1.5 mL) and filtered. One quarter of the filtrate (approximately 18.5 μmol) was purified via preparative LC/MS (Condition A: Gradient: 40-80% B over 20 minutes, then a 5-minute hold at 100% B) to give (R)-tert-butyl (3-(1-((3-chloro-6-(2-(2-hydroxypropan-2-yl)pyrimidin-5-yl)-2-methylquinolin-4-yl)amino)ethyl)-4-fluorophenyl) carbamate (1.9 mg, 18% yield). LC/MS (M+H): 566; LC retention time: 2.27 min (Method A); $^1$H NMR (500 MHz, DMSO-$d_6$) δ 9.27-9.19 (m, 3H), 8.61 (s, 1H), 8.07 (d, J=8.5 Hz, 1H), 7.89 (d, J=8.7 Hz, 1H), 7.79 (br. s., 1H), 7.08 (br. s., 1H), 6.97 (t, J=9.4 Hz, 1H), 6.48 (d, J=8.8 Hz, 1H), 5.72-5.61 (m, 1H), 2.60 (s, 3H), 1.64 (d, J=6.6 Hz, 3H), 1.55 (s, 6H), 1.33 (s, 9H).

Example 360

(R)-2-(5-(4-((1-(5-amino-2-fluorophenyl)ethyl)amino)-3-chloro-2-methylquinolin-6-yl)pyrimidin-2-yl)propan-2-ol

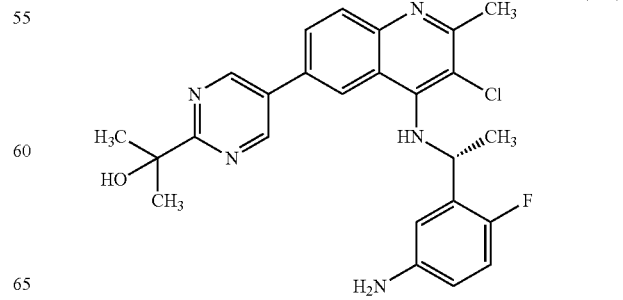

(360)

Three quarters of the filtrate from Example 359 (approximately 55.5 µmol) was concentrated. To the residue was added 4 M HCl in dioxane (0.5 mL) and the mixture was stirred at room temperature for 1 h. The crude mixture was diluted with MeOH (1.5 mL) and filtered. The filtrate was purified via preparative LC/MS (Condition A: Gradient: 20-60% B over 20 minutes, then a 5-minute hold at 100% B) to give (R)-2-(5-(4-((1-(5-amino-2-fluorophenyl)ethyl)amino)-3-chloro-2-methylquinolin-6-yl)pyrimidin-2-yl)propan-2-ol (2.2 mg, 8% yield). LC/MS (M+H): 466; LC retention time: 1.84 min (Method A); $^1$H NMR (500 MHz, DMSO-d$_6$) δ 9.11 (s, 2H), 8.43 (s, 1H), 8.05 (d, J=8.6 Hz, 1H), 7.90 (d, J=8.7 Hz, 1H), 6.78-6.70 (m, 2H), 6.41-6.35 (m, 1H), 6.27 (d, J=8.8 Hz, 1H), 5.49-5.41 (m, 1H), 2.61 (s, 3H), 1.60 (d, J=6.6 Hz, 3H), 1.54 (s, 6H).

The examples in Table 14 below were prepared according to the general procedure used in the preparation of Example 359.

Example 364

(R)-2-(5-(3-chloro-4-((1-(2-fluoro-5-(pyrrolidin-1-yl)phenyl)ethyl)amino)quinolin-6-yl)pyrimidin-2-yl)propan-2-ol (364)

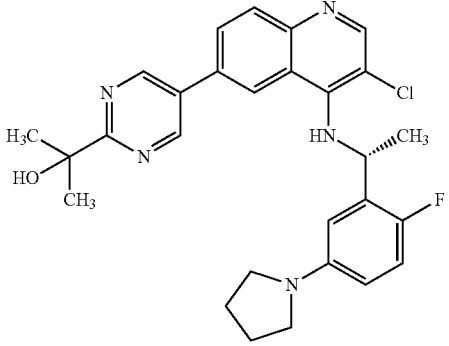

TABLE 14

| Ex. No. | Structure | MS observed (M$^{+1}$) | HPLC ret. time (min.) | HPLC method |
|---|---|---|---|---|
| 361 | 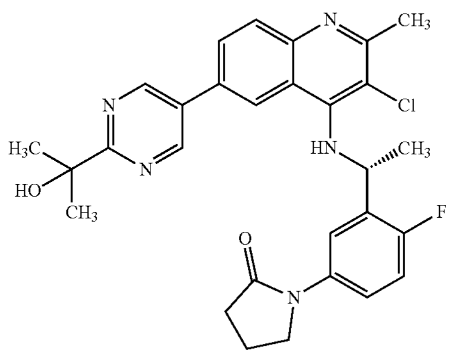 [SMILES: Cc1nc2ccc(-c3cnc(C(C)(C)O)nc3)cc2c(N[C@H](C)c2cc(N3CCCC3=O)ccc2F)c1Cl] | 534 | 1.88 | A |
| 362 | 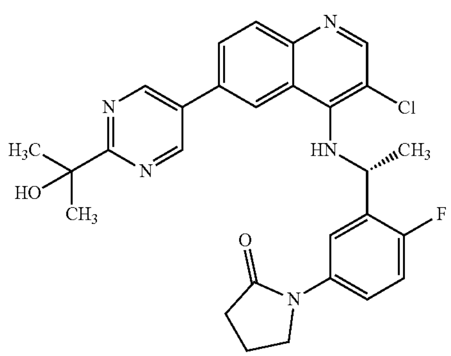 | 520 | 1.75 | A |
| 363 | 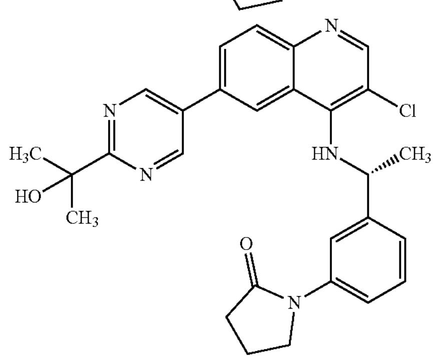 | 502 | 1.70 | A |

A DMF (0.5 mL) solution of Example 318 (10 mg, 19 µmol), pyrrolidine (14 mg, 0.19 mmol), Pd(OAc)$_2$ (0.3 mg, 1.2 µmol), dicyclohexyl-(2',4',6'-triisopropyl-biphenyl-3-yl)-phosphane (Xphos, 0.9 mg, 1.9 µmol) and Cs$_2$CO$_3$ (16 mg, 0.048 mmol) was pumped under vacuum and backfilled with nitrogen twice. The sealed tube was then heated at 100° C. for 1 h. The mixture was diluted with MeOH (1 mL) and filtered. The filtrate was purified via preparative LC/MS (Condition A: Gradient: 10-60% B over 18 minutes, then a 5-minute hold at 100% B) to give (R)-2-(5-(3-chloro-4-((1-(2-fluoro-5-(pyrrolidin-1-yl)phenyl)ethyl)amino)quinolin-6-yl)pyrimidin-2-yl)propan-2-ol (1.5 mg, 15% yield). LC/MS (M+H): 506; LC retention time: 1.58 min (Method A); $^1$H NMR (500 MHz, DMSO-d$_6$) δ 9.25 (s, 2H), 8.76 (s, 1H), 8.52 (s, 1H), 8.11 (d, J=8.8 Hz, 1H), 7.98 (d, J=8.5 Hz, 1H), 6.82 (t, J=9.6 Hz, 1H), 6.74-6.65 (m, 2H), 6.28-6.20 (m, 1H), 5.80-5.69 (m, 1H), 3.02 (d, J=5.8 Hz, 2H), 2.93-2.88 (m, 2H), 1.76 (br. s., 4H), 1.67 (d, J=6.7 Hz, 3H), 1.57 (s, 6H).

Example 365

(R)-2-(5-(3-chloro-4-((1-(2-fluoro-5-(1H-pyrazol-1-yl)phenyl)ethyl)amino)-2-methylquinolin-6-yl)pyrimidin-2-yl)propan-2-ol

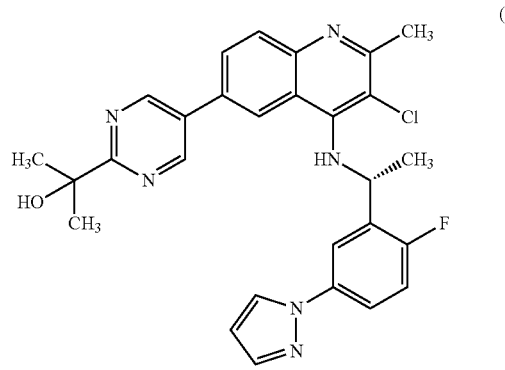

(365)

A dioxane (0.5 mL) solution of Example 316 (20 mg, 38 µmol), 1H-pyrazole (25 mg, 0.37 mmol), copper(I) iodide (1.4 mg, 7.6 µmol), N1,N2-dimethylethane-1,2-diamine (20 µL, 0.2 mmol) and potassium carbonate (26 mg, 0.2 mmol) was pumped under vacuum and backfilled with nitrogen twice. The mixture was heated in a sealed safety tube at 110° C. for 20 h, cooled to room temperature and diluted with concentrated NH$_4$OH (0.1 mL) and MeOH (1 mL). The suspension was filtered and the filtrate purified via preparative LC/MS (Condition A: Gradient: 25-100% B over 19 minutes, then a 5-minute hold at 100% B) to give (R)-2-(5-(3-chloro-4-((1-(2-fluoro-5-(1H-pyrazol-1-yl)phenyl)ethyl)amino)-2-methylquinolin-6-yl)pyrimidin-2-yl)propan-2-ol (5.4 mg, 27% yield). LC/MS (M+H): 517; LC retention time: 2.03 min (Method A); $^1$H NMR (500 MHz, DMSO-d$_6$) δ 9.19 (s, 2H), 8.59 (s, 1H), 8.28 (d, J=2.1 Hz, 1H), 8.22 (d, J=3.7 Hz, 1H), 8.05 (d, J=8.5 Hz, 1H), 7.91 (d, J=8.5 Hz, 1H), 7.66-7.59 (m, 2H), 7.20 (t, J=9.3 Hz, 1H), 6.57 (d, J=9.5 Hz, 1H), 6.45 (s, 1H), 5.70-5.59 (m, 1H), 2.62 (s, 3H), 1.70 (d, J=6.7 Hz, 3H), 1.56 (s, 6H).

The examples in Table 15 below were prepared according to the general procedure used in the synthesis of Example 365.

TABLE 15

| Ex. No. | Structure | MS observed (M$^{+1}$) | HPLC ret. Time (min.) | HPLC method |
|---|---|---|---|---|
| 366 | 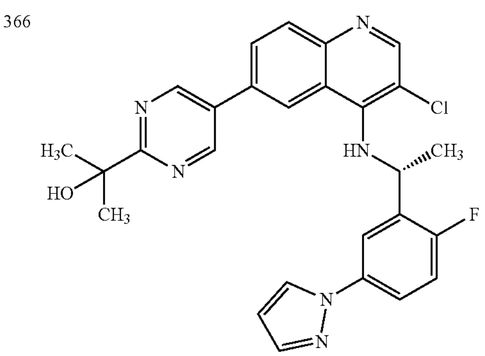 | 503 | 1.91 | A |

TABLE 15-continued

| Ex. No. | Structure | MS observed (M+1) | HPLC ret. Time (min.) | HPLC method |
|---|---|---|---|---|
| 367 | 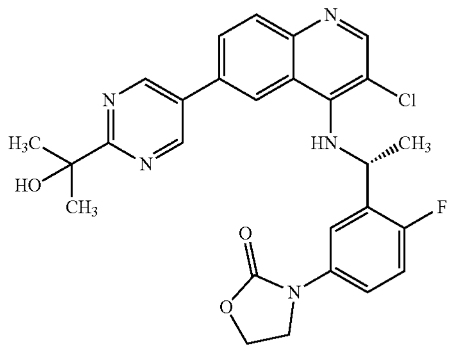 [SMILES: C[C@@H](Nc1c(Cl)cnc2ccc(-c3cnc(C(C)(C)O)nc3)cc12)c1cc(N2CCOC2=O)ccc1F] | 522 | 1.71 | A |
| 368 | 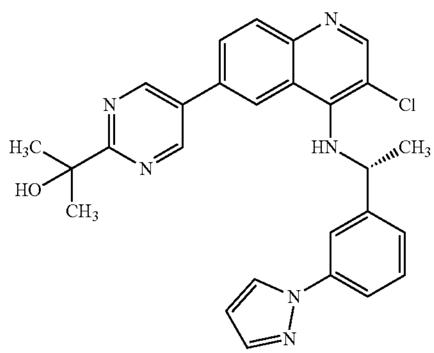 [SMILES: C[C@@H](Nc1c(Cl)cnc2ccc(-c3cnc(C(C)(C)O)nc3)cc12)c1cccc(-n2cccn2)c1] | 485 | 1.87 | A |
| 369 | 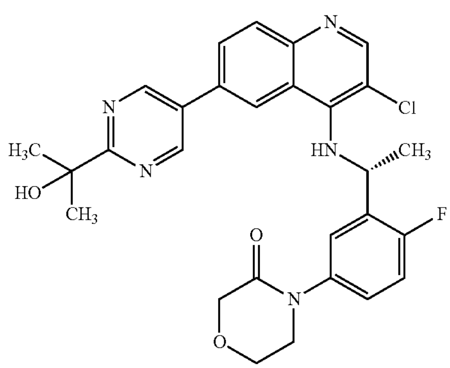 [SMILES: C[C@@H](Nc1c(Cl)cnc2ccc(-c3cnc(C(C)(C)O)nc3)cc12)c1cc(N2CCOCC2=O)ccc1F] | 536 | 1.57 | A |
| 370 | 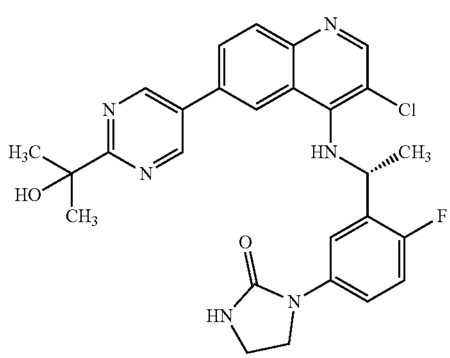 [SMILES: C[C@@H](Nc1c(Cl)cnc2ccc(-c3cnc(C(C)(C)O)nc3)cc12)c1cc(N2CCNC2=O)ccc1F] | 521 | 1.62 | A |

TABLE 15-continued

| Ex. No. | Structure | MS observed (M$^{+1}$) | HPLC ret. Time (min.) | HPLC method |
|---|---|---|---|---|
| 371 | 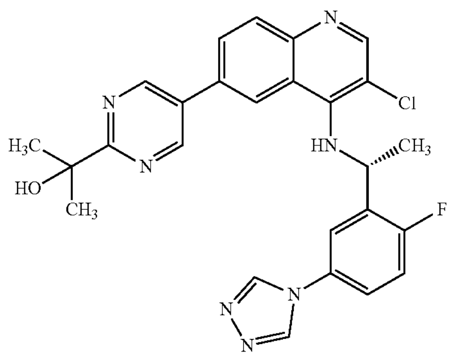 [SMILES: C[C@@H](Nc1c(Cl)cnc2ccc(-c3cnc(C(C)(C)O)nc3)cc12)c1cc(-n2cnnc2)ccc1F] | 504 | 1.82 | A |
| 372 | 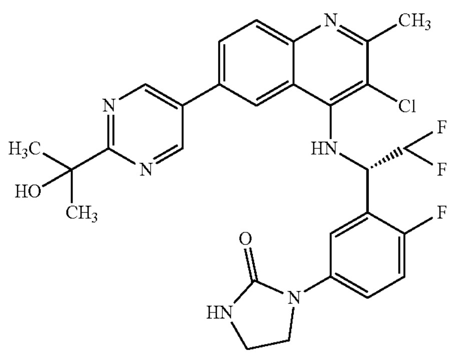 [SMILES: Cc1nc2ccc(-c3cnc(C(C)(C)O)nc3)cc2c(N[C@@H](c2cc(N3CCNC3=O)ccc2F)C(F)F)c1Cl] | 571 | 1.72 | A |
| 373 | 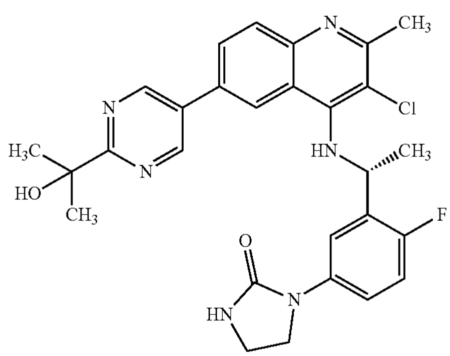 [SMILES: Cc1nc2ccc(-c3cnc(C(C)(C)O)nc3)cc2c(N[C@H](C)c2cc(N3CCNC3=O)ccc2F)c1Cl] | 535 | 1.72 | A |
| 374 | 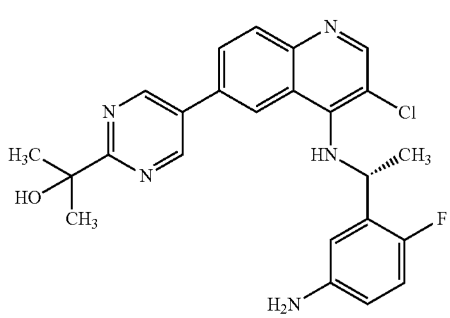 [SMILES: C[C@@H](Nc1c(Cl)cnc2ccc(-c3cnc(C(C)(C)O)nc3)cc12)c1cc(N)ccc1F] | 452 | 1.77 | A |

Example 375

(R)-3-(1-((3-chloro-6-(2-(2-hydroxypropan-2-yl)pyrimidin-5-yl)-2-methylquinolin-4-yl)amino)ethyl)-4-fluorobenzonitrile

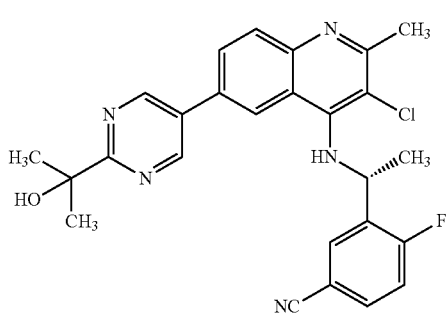

(375)

A stirred DMF (0.5 mL) solution of Example 316 (15 mg, 28 μmol), dicyanozinc (7 mg, 57 μmol), $Pd_2(dba)_3$ (3 mg, 2.8 μmol), 2-di-tert-butylphosphino-2',4',6'-triisopropylbiphenyl (2.4 mg, 5.7 μmol) and zinc (4 mg, 57 μmol) was pumped under vacuum and backfilled with nitrogen twice. The sealed tube was then heated at 95° C. for 1 h. The mixture was diluted with MeOH (1 mL) and filtered. The filtrate was purified via preparative LC/MS (Condition A: Gradient: 10-50% B over 25 minutes, then a 5-minute hold at 100% B) to give (R)-3-(1-((3-chloro-6-(2-(2-hydroxypropan-2-yl)pyrimidin-5-yl)-2-methylquinolin-4-yl)amino)ethyl)-4-fluorobenzonitrile (7.9 mg, 59% yield). LC/MS (M+H): 476; LC retention time: 1.99 min (Method A); $^1$H NMR (500 MHz, DMSO-$d_6$) δ 9.21 (s, 2H), 8.59 (br. s., 1H), 8.24-8.17 (m, 2H), 7.99 (d, J=8.6 Hz, 1H), 7.85 (br. s., 1H), 7.41 (t, J=9.1 Hz, 1H), 5.78 (br. s., 1H), 2.66 (s, 3H), 1.69 (d, J=6.5 Hz, 3H), 1.56 (s, 6H).

The examples in Table 16 below were prepared by in same manner as outlined for Example 375.

TABLE 16

| Ex. No. | Structure | MS observed ($M^{+1}$) | HPLC ret. Time (min.) | HPLC method |
|---|---|---|---|---|
| 376 | 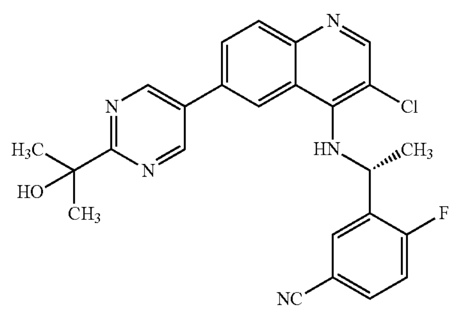 [SMILES: C[C@@H](Nc1c(Cl)cnc2ccc(-c3cnc(C(C)(C)O)nc3)cc12)c1cc(C#N)ccc1F] | 462 | 1.94 | A |
| 377 | 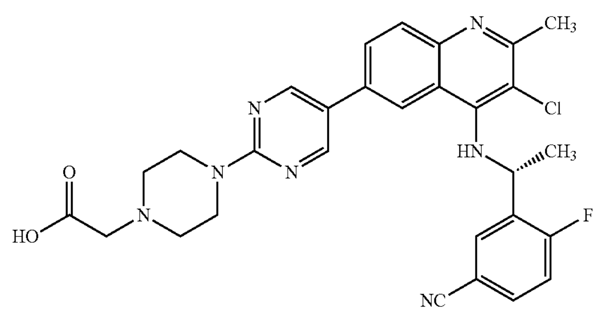 [SMILES: Cc1nc2ccc(-c3cnc(N4CCN(CC(=O)O)CC4)nc3)cc2c(N[C@H](C)c2cc(C#N)ccc2F)c1Cl] | 560 | 1.61 | A |
| 378 | 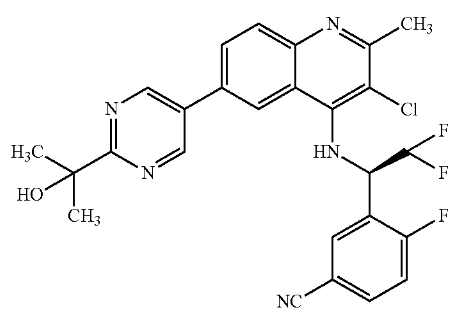 [SMILES: Cc1nc2ccc(-c3cnc(C(C)(C)O)nc3)cc2c(N[C@H](c2cc(C#N)ccc2F)C(F)F)c1Cl] | 512 | 1.94 | A |

TABLE 16-continued

| Ex. No. | Structure | MS observed (M⁺¹) | HPLC ret. Time (min.) | HPLC method |
|---|---|---|---|---|
| 379 | 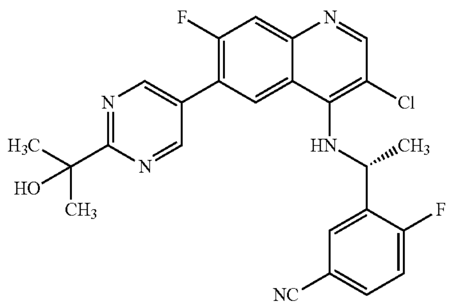 [SMILES: C[C@@H](Nc1c(Cl)cnc2cc(F)c(-c3cnc(C(C)(C)O)nc3)cc12)c1cc(C#N)ccc1F] | 480 | 2.00 | A |
| 380 | 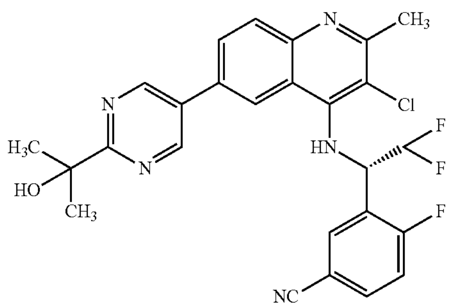 [SMILES: Cc1nc2ccc(-c3cnc(C(C)(C)O)nc3)cc2c(N[C@@H](c2cc(C#N)ccc2F)C(F)F)c1Cl] | 512 | 1.92 | A |
| 381 | 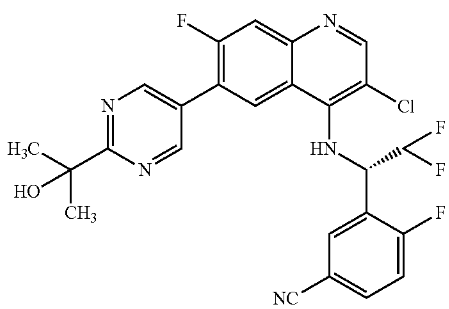 [SMILES: CC(C)(O)c1ncc(-c2cc3c(N[C@@H](c4cc(C#N)ccc4F)C(F)F)c(Cl)cnc3cc2F)cn1] | 516 | 1.95 | A |
| 382 | 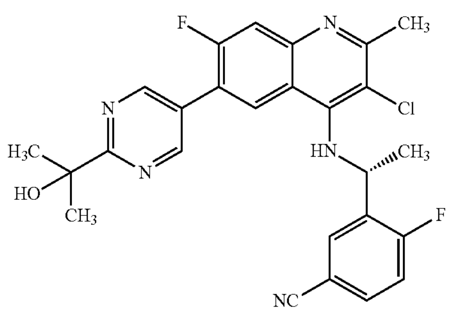 [SMILES: Cc1nc2cc(F)c(-c3cnc(C(C)(C)O)nc3)cc2c(N[C@H](C)c2cc(C#N)ccc2F)c1Cl] | 494 | 2.10 | A |
| 383 | 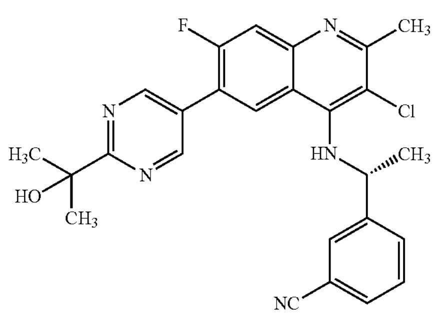 [SMILES: Cc1nc2cc(F)c(-c3cnc(C(C)(C)O)nc3)cc2c(N[C@H](C)c2cccc(C#N)c2)c1Cl] | 476 | 2.02 | A |

TABLE 16-continued

| Ex. No. | Structure | MS observed ($M^{+1}$) | HPLC ret. Time (min.) | HPLC method |
|---|---|---|---|---|
| 384 | 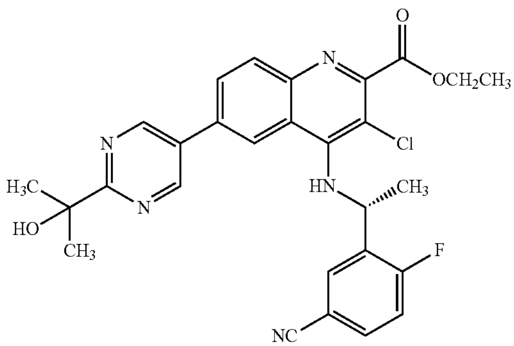 [SMILES: CCOC(=O)c1nc2ccc(-c3cnc(C(C)(C)O)nc3)cc2c(N[C@H](C)c2cc(C#N)ccc2F)c1Cl] | 534 | 0.96 | C |
| 385 | 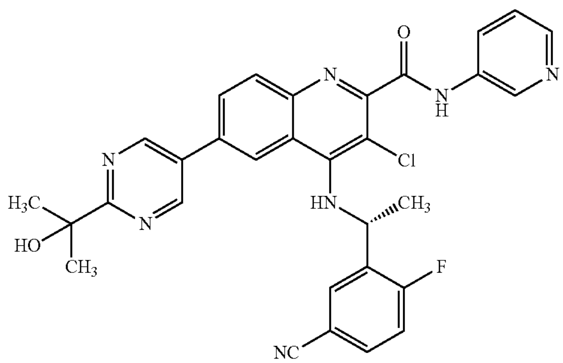 [SMILES: C[C@@H](Nc1c(Cl)c(C(=O)Nc2cccnc2)nc2ccc(-c3cnc(C(C)(C)O)nc3)cc12)c1cc(C#N)ccc1F] | 582 | 0.76 | C |
| 386 | 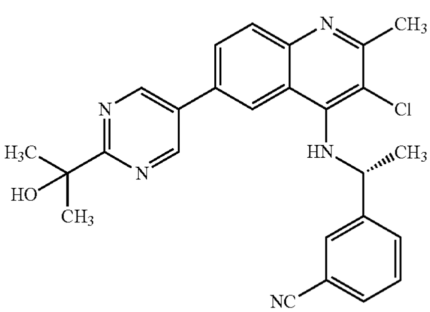 [SMILES: Cc1nc2ccc(-c3cnc(C(C)(C)O)nc3)cc2c(N[C@H](C)c2cccc(C#N)c2)c1Cl] | 458 | 1.91 | A |

Example 387

(R)-3-(1-((3-chloro-6-(2-(2-hydroxypropan-2-yl)pyrimidin-5-yl)-2-methylquinolin-4-yl)amino)ethyl)-4-fluorobenzamide

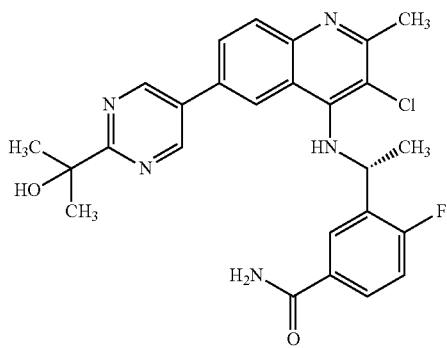

(387)

To a MeOH (1 mL) solution of Example 375 (89 mg, 0.19 mmol) was added 1 M NaOH (0.38 mL, 0.38 mmol) and 30 wt % $H_2O_2$ (0.35 mL, 3.43 mmol). The resulting suspension was stirred at room temperature for 1 h. After evaporation of the MeOH, the resulting suspension was neutralized with 1 M HCl (0.38 mL). The mixture was extracted with EtOAc (2×5 mL). The combined EtOAc layer was dried over $Na_2SO_4$ and filtered. The filtrate was concentrated and purified by silica gel column chromatography (12 g ISCO cartridge, 0-10% MeOH/$CH_2Cl_2$) to give (R)-3-(1-((3-chloro-6-(2-(2-hydroxypropan-2-yl)pyrimidin-5-yl)-2-methylquinolin-4-yl)amino)ethyl)-4-fluorobenzamide (79 mg, 84% yield). LC/MS (M+H): 494; LC retention time: 0.63 min (Method C); $^1$H NMR (400 MHz, chloroform-d) δ 8.79 (s, 2H), 8.11 (dd, J=7.2, 2.2 Hz, 1H), 8.05 (d, J=8.7 Hz, 1H), 7.95 (d, J=1.8 Hz, 1H), 7.80 (dd, J=8.7, 2.0 Hz, 1H), 7.72 (ddd, J=8.5, 4.9, 2.4 Hz, 1H), 7.16 (dd, J=9.8, 8.6 Hz, 1H), 5.35-5.26 (m, 1H), 5.15 (d, J=8.9 Hz, 1H), 4.67 (s, 1H), 3.50 (d, J=2.9 Hz, 2H), 2.79 (s, 3H), 1.72 (d, J=6.6 Hz, 3H), 1.67 (s, 6H).

The examples in Table 17 below were prepared following a procedure similar to synthesis of Example 387.

TABLE 17

| Ex. No. | Structure | MS observed ($M^{+1}$) | HPLC ret. Time (min.) | HPLC method |
|---|---|---|---|---|
| 388 | 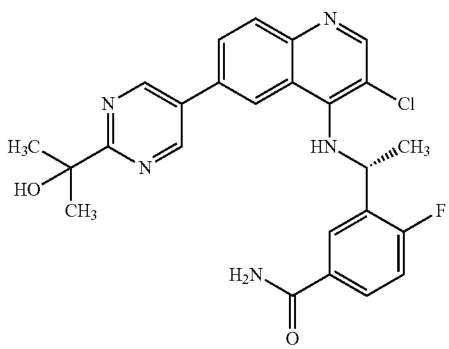 [SMILES: C[C@@H](Nc1c(Cl)cnc2ccc(-c3cnc(C(C)(C)O)nc3)cc12)c1cc(C(N)=O)ccc1F] | 480 | 1.58 | A |
| 389 | 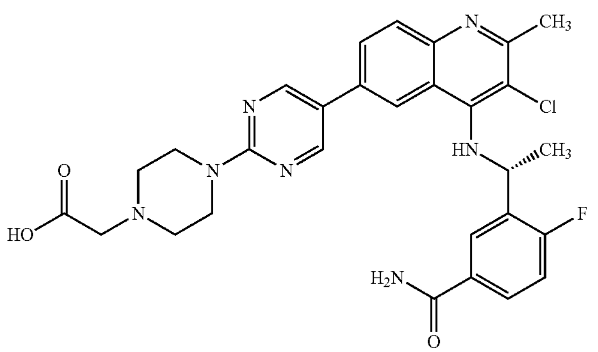 [SMILES: Cc1nc2ccc(-c3cnc(N4CCN(CC(=O)O)CC4)nc3)cc2c(N[C@H](C)c2cc(C(N)=O)ccc2F)c1Cl] | 578 | 1.38 | A |
| 390 | 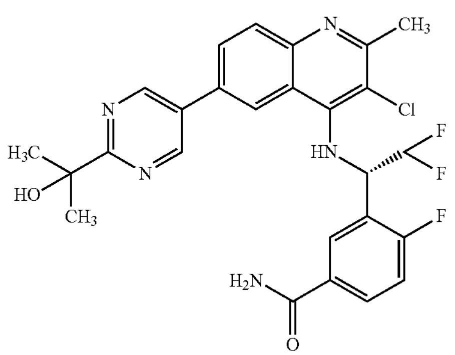 [SMILES: Cc1nc2ccc(-c3cnc(C(C)(C)O)nc3)cc2c(N[C@@H](c2cc(C(N)=O)ccc2F)C(F)F)c1Cl] | 530 | 1.63 | A |
| 391 | 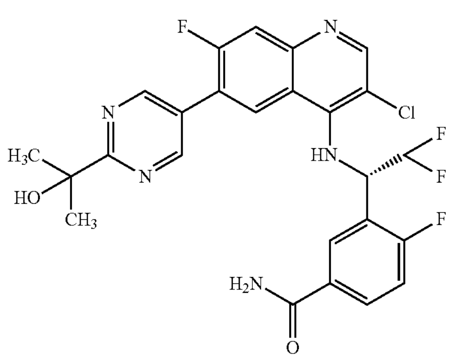 [SMILES: CC(C)(O)c1ncc(-c2cc3c(N[C@@H](c4cc(C(N)=O)ccc4F)C(F)F)c(Cl)cnc3cc2F)cn1] | 534 | 1.66 | A |

TABLE 17-continued

| Ex. No. | Structure | MS observed (M+1) | HPLC ret. Time (min.) | HPLC method |
|---|---|---|---|---|
| 392 | 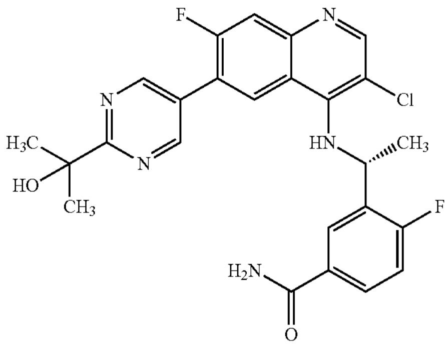 [SMILES: C[C@@H](Nc1c(Cl)cnc2cc(F)c(-c3cnc(C(C)(C)O)nc3)cc12)c1cc(C(N)=O)ccc1F] | 498 | 1.63 | A |
| 393 | 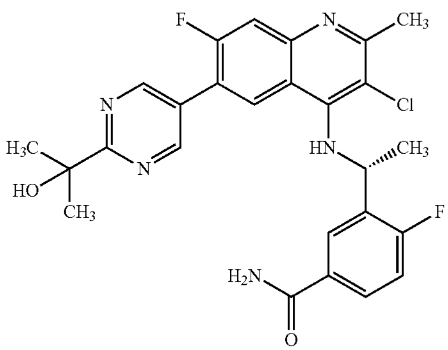 [SMILES: Cc1nc2cc(F)c(-c3cnc(C(C)(C)O)nc3)cc2c(N[C@H](C)c2cc(C(N)=O)ccc2F)c1Cl] | 512 | 1.71 | A |
| 394 | 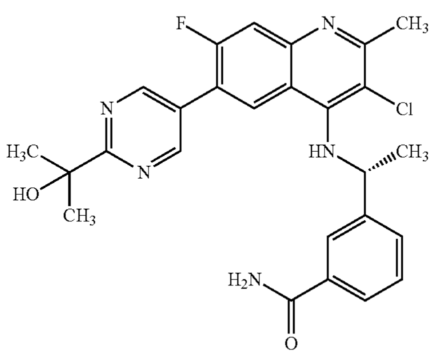 [SMILES: Cc1nc2cc(F)c(-c3cnc(C(C)(C)O)nc3)cc2c(N[C@H](C)c2cccc(C(N)=O)c2)c1Cl] | 494 | 1.61 | A |
| 395 | 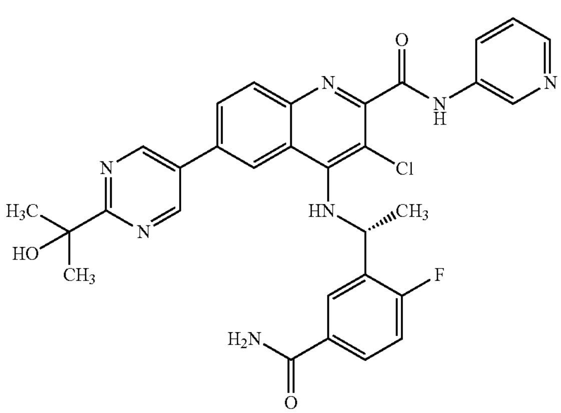 [SMILES: C[C@@H](Nc1c(Cl)c(C(=O)Nc2cccnc2)nc2ccc(-c3cnc(C(C)(C)O)nc3)cc12)c1cc(C(N)=O)ccc1F] | 600 | 0.67 | C |

Example 396

(R)-2-(5-(4-((1-(5-benzyl-2-fluorophenyl)ethyl)amino)-3-chloro-2-methylquinolin-6-yl)pyrimidin-2-yl)propan-2-ol (396)

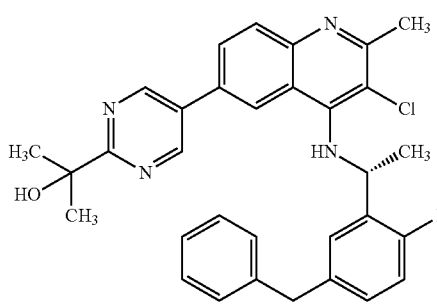

To a stirred THF (0.5 mL) suspension of lithium chloride (37 mg, 0.877 mmol) and zinc (57 mg, 0.877 mmol) in a vial was added ethylene dibromide (2.5 μL, 0.029 mmol) at room temperature. The mixture was heated at 60° C. for 5 min and allowed to cool to room temperature. TMS-Cl (0.8 μL, 5.85 μmol) was added and the mixture was stirred for 20 min. Benzyl bromide (70 μL, 0.585 mmol) was added dropwise to the activated zinc suspension at room temperature (slightly exothermic) and the mixture was stirred overnight. After the excess zinc settled, the upper cloudy solution (0.256 mL, approximately 0.3 mmol) was transferred to a degassed, stirred DMF (0.5 mL) solution of Example 316 (17 mg, 0.032 mmol), Pd(OAc)$_2$ (0.7 mg, 3.2 μmol) and 2-(dicyclohexylphosphino)-2',4',6'-triisopropylbiphenyl (X-Phos, 3 mg, 6.42 μmol) at room temperature. The mixture was heated in a sealed vial at 60° C. for 2 h. The mixture was neutralized with 1 M HCl (128 μL), diluted with MeOH (1 mL) and filtered. The filtrate was purified via preparative LC/MS (Condition A: Gradient: 50-100% B over 25 minutes, then a 5-minute hold at 100% B) to give (R)-2-(5-(4-((1-(5-benzyl-2-fluorophenyl)ethyl)amino)-3-chloro-2-methylquinolin-6-yl)pyrimidin-2-yl)propan-2-ol (4.5 mg, 25% yield). LC/MS (M+H): 541; LC retention time: 2.56 min (Method A); $^1$H NMR (500 MHz, DMSO-d$_6$) δ 9.20 (s, 2H), 8.56 (s, 1H), 8.09 (d, J=8.6 Hz, 1H), 7.92 (d, J=8.7 Hz, 1H), 7.47 (d, J=6.7 Hz, 1H), 7.15-7.05 (m, 3H), 7.03-6.88 (m, 4H), 6.38 (d, J=9.1 Hz, 1H), 5.67-5.57 (m, 1H), 3.78 (s, 2H), 2.60 (s, 3H), 1.66 (d, J=6.6 Hz, 3H), 1.56 (s, 6H).

Example 397

1-(3-((R)-1-((3-chloro-6-(2-(2-hydroxypropan-2-yl)pyrimidin-5-yl)-2-methylquinolin-4-yl)amino)ethyl)-4-fluorophenyl)ethane-1,2-diol (Diastereomeric Mixture)

(397)

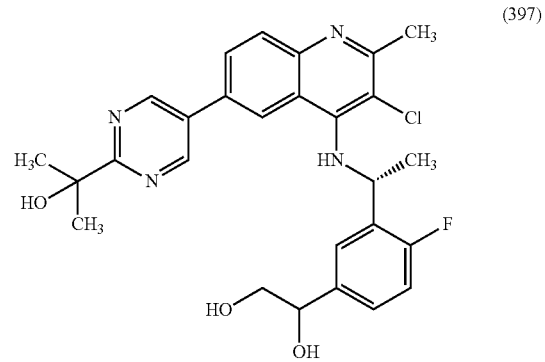 [SMILES: Cc1nc2ccc(-c3cnc(C(C)(C)O)nc3)cc2c(N[C@H](C)c2cc(C(O)CO)ccc2F)c1Cl]

A 2.5 wt % solution of osmium tetroxide in t-BuOH (10 μL, 1 μmol) was added to a stirred THF (0.5 mL) solution of Example 330 (16 mg, 34 μmol) and 50 wt % NMO in water (0.014 mL, 0.067 mmol) at room temperature. After 3 h, the mixture was filtered. Half of the filtrate (approximately 17 μmol) was purified via preparative LC/MS (Condition A: Gradient: 15-100% B over 19 minutes, then a 5-minute hold at 100% B) to give 1-(3-((R)-1-((3-chloro-6-(2-(2-hydroxypropan-2-yl)pyrimidin-5-yl)-2-methylquinolin-4-yl)amino)ethyl)-4-fluorophenyl)ethane-1,2-diol (2.7 mg, 31% yield). LC/MS (M+H): 511; LC retention time: 1.53 min (Method A); $^1$H NMR (500 MHz, DMSO-d$_6$) δ 9.13 (d, J=7.9 Hz, 2H), 8.48 (d, J=12.8 Hz, 1H), 8.04 (d, J=8.8 Hz, 1H), 7.93-7.88 (m, 1H), 7.59 (t, J=7.0 Hz, 1H), 7.16 (d, J=7.3 Hz, 1H), 7.02-6.94 (m, 1H), 6.37 (dd, J=9.0, 4.1 Hz, 1H), 5.62-5.51 (m, 1H), 5.28-5.20 (m, 1H), 4.43 (dd, J=10.4, 4.9 Hz, 1H), 3.29-3.20 (m, 2H), 2.61 (s, 3H), 1.64 (d, J=6.7 Hz, 3H), 1.55 (s, 6H).

The examples in Table 18 below were prepared according to the general procedures used in the preparation of Example 397.

TABLE 18

| Ex. No. | Structure | MS observed (M$^{+1}$) | HPLC ret. Time (min.) | HPLC method |
|---|---|---|---|---|
| 398 | (structure shown; Diastereomeric mixture) | 497 | 1.45 | A |

TABLE 18-continued

| Ex. No. | Structure | MS observed ($M^{+1}$) | HPLC ret. Time (min.) | HPLC method |
|---|---|---|---|---|
| 399 | Diastereomeric mixture | 511 | 1.64 | A |
| 400 | Diastereomer 1 | 497 | 1.45 | A |
| 401 | Diastereomer 2 | 497 | 1.56 | A |
| 402 | Diastereomeric mixture | 547 | 1.57 | A |

TABLE 18-continued

| Ex. No. | Structure | MS observed ($M^{+1}$) | HPLC ret. Time (min.) | HPLC method |
|---|---|---|---|---|
| 403 | 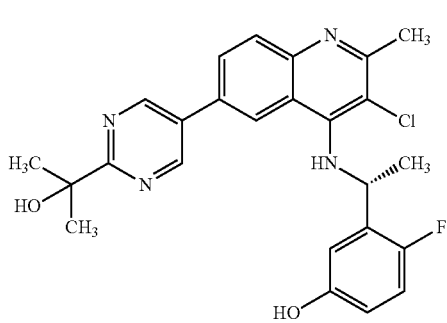 Diastereomeric mixture | 525 | 1.62 | A |

Example 404

(R)-3-(1-((3-chloro-6-(2-(2-hydroxypropan-2-yl)pyrimidin-5-yl)-2-methylquinolin-4-yl)amino)ethyl)-4-fluorophenol

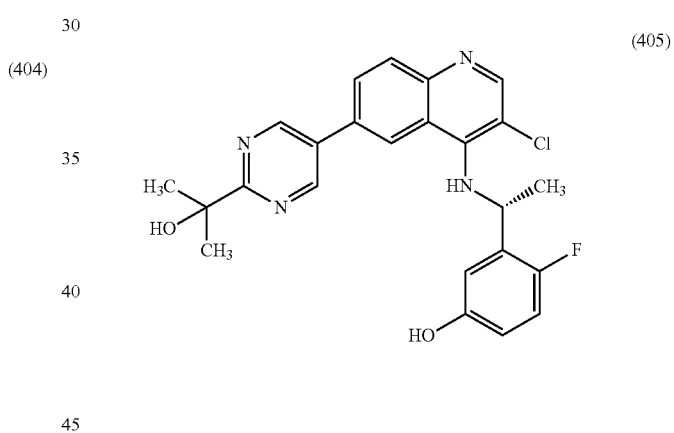

(404)

(405)

Example 405

(R)-3-(1-((3-chloro-6-(2-(2-hydroxypropan-2-yl)pyrimidin-5-yl)quinolin-4-yl)amino)ethyl)-4-fluorophenol A stirred dioxane (0.25 mL)-water (0.25 mL) solution of Example 316 (15 mg, 28 mol), 2-di-tert-butylphosphino-2',4',6'-triisopropylbiphenyl (2.4 mg, 5.7 μmol), KOH (6.4 mg, 0.11 mmol) and $Pd_2(dba)_3$ (2.6 mg, 2.8 μmol) was pumped under vacuum and backfilled with nitrogen twice. The sealed tube was then heated at 95° C. for 1 h, neutralized with 1 M HCl (113 μL), diluted with MeOH (1 mL) and filtered. The filtrate was purified via preparative LC/MS (Condition A: Gradient: 30-70% B over 19 minutes, then a 5-minute hold at 100% B) to give (R)-3-(1-((3-chloro-6-(2-(2-hydroxypropan-2-yl)pyrimidin-5-yl)-2-methylquinolin-4-yl)amino)ethyl)-4-fluorophenol (2.7 mg, 31% yield). LC/MS (M+H): 467; LC retention time: 1.81 min (Method A); $^1$H NMR (500 MHz, DMSO-$d_6$) δ 9.17 (s, 2H), 8.65 (br. s., 1H), 8.25 (d, J=8.8 Hz, 1H), 7.99 (d, J=8.7 Hz, 1H), 6.97-6.90 (m, 2H), 6.65-6.59 (m, 1H), 5.83 (br. s., 1H), 2.69 (s, 3H), 1.67 (d, J=6.6 Hz, 3H), 1.56 (s, 6H).

Using a procedure similar to the synthesis of Example 404, Example 318 (3.8 mg, 7.3 μmol) was converted to (R)-3-(1-((3-chloro-6-(2-(2-hydroxypropan-2-yl)pyrimidin-5-yl)quinolin-4-yl)amino)ethyl)-4-fluorophenol (0.7 mg, 21% yield). LC/MS (M+H): 453; LC retention time: 1.75 min (Method A); $^1$H NMR (500 MHz, DMSO-$d_6$) δ 9.25 (s, 2H), 8.73 (s, 1H), 8.46 (s, 1H), 8.12 (d, J=9.0 Hz, 1H), 7.98 (d, J=8.7 Hz, 1H), 6.88 (d, J=8.2 Hz, 2H), 6.74 (d, J=8.7 Hz, 1H), 6.56 (br. s., 1H), 5.74 (d, J=7.4 Hz, 1H), 1.63 (d, J=6.6 Hz, 3H), 1.56 (s, 6H).

Example 406

(R)-2-(5-(3-chloro-4-((1-(5-chloro-2-fluorophenyl)ethyl)amino)-2-methylquinolin-6-yl)pyrimidin-2-yl)propan-2-ol

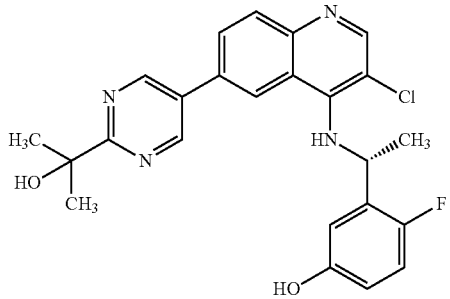

(406)

An NMP (0.5 mL) solution of Example 316 (10 mg, 0.019 mmol) and copper(I) chloride (1.9 mg, 0.019 mmol) was microwaved at 220° C. for 15 min. The mixture was diluted with MeOH (1 mL) and filtered. The filtrate was purified via preparative LC/MS (Condition A: Gradient: 45-90% B over 19 minutes, then a 5-minute hold at 100% B) to give (R)-2-(5-(3-chloro-4-((1-(5-chloro-2-fluorophenyl)ethyl)amino)-2-methylquinolin-6-yl)pyrimidin-2-yl)propan-2-ol (4.5 mg, 49% yield). LC/MS (M+H): 485; LC retention time: 2.32 min (Method A); $^1$H NMR (500 MHz, DMSO-d$_6$) δ 9.21 (br. s., 2H), 8.47 (br. s., 1H), 8.06 (br. s., 1H), 7.93 (d, J=8.1 Hz, 1H), 7.76 (br. s., 1H), 7.29 (br. s., 1H), 7.13 (t, J=9.2 Hz, 1H), 6.47 (d, J=9.0 Hz, 1H), 5.52 (br. s., 1H), 2.62 (s, 3H), 1.63 (m, 9H).

Example 407

(R)-3-(1-((3-chloro-6-(2-(2-hydroxypropan-2-yl)pyrimidin-5-yl)-2-methylquinolin-4-yl)amino)ethyl)-4-fluorobenzoic acid

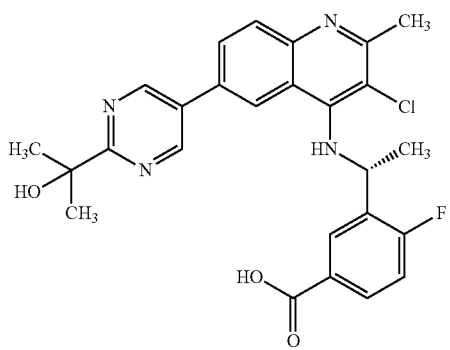

(407)

Intermediate 407A: (R)-3-(1-((3-chloro-6-(2-(2-hydroxypropan-2-yl)pyrimidin-5-yl)-2-methylquinolin-4-yl)amino)ethyl)-4-fluorobenzaldehyde

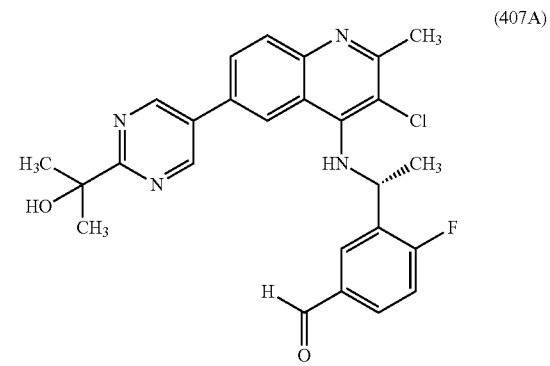 [SMILES: Cc1nc2ccc(-c3cnc(C(C)(C)O)nc3)cc2c(N[C@H](C)c2cc(C=O)ccc2F)c1Cl]

(407A)

To the other half of the filtrate from Example 397 (approximately 17 μmol) was added sodium periodate (29 mg, 0.14 mmol) and water (0.1 mL). After 30 min, the mixture was diluted with MeOH (1 mL) and filtered. Half of the filtrate (approximately 8.5 μmol) was concentrated and used in the next step.

Example 407

Sodium chlorite (3.8 mg, 0.042 mmol) was added to a mixture of (R)-3-(1-((3-chloro-6-(2-(2-hydroxypropan-2-yl)pyrimidin-5-yl)-2-methylquinolin-4-yl)amino)ethyl)-4-fluorobenzaldehyde (approximately 8.5 μmol), sodium dihydrogen phosphate (5 mg, 42 μmol), water (50 μL) and 2 M 2-methyl-2-butene in THF (146 μL, 0.292 mmol). The mixture was stirred at room temperature for 2 h, diluted with MeOH (1 mL) and filtered. The filtrate was purified via preparative LC/MS (condition A: Gradient: 15-55% B over 20 minutes, then a 5-minute hold at 100% B) to give (R)-3-(1-((3-chloro-6-(2-(2-hydroxypropan-2-yl)pyrimidin-5-yl)-2-methylquinolin-4-yl)amino)ethyl)-4-fluorobenzoic acid (3.9 mg, 93% yield). LC/MS (M+H): 495; LC retention time: 1.26 min (Method A); $^1$H NMR (500 MHz, DMSO-d$_6$) δ 9.20 (s, 2H), 8.60 (s, 1H), 8.32 (d, J=6.9 Hz, 1H), 8.07 (d, J=8.6 Hz, 1H), 7.91 (d, J=8.7 Hz, 1H), 7.79 (br. s., 1H), 7.13 (t, J=9.3 Hz, 1H), 6.62 (d, J=9.1 Hz, 1H), 5.66-5.57 (m, 1H), 2.61 (s, 3H), 1.66 (d, J=6.6 Hz, 3H), 1.56 (s, 6H).

Example 408

(R)-2-(5-(3-chloro-4-((1-(2-fluoro-5-(2-hydroxypropan-2-yl)phenyl)ethyl)amino)-2-methylquinolin-6-yl)pyrimidin-2-yl)propan-2-ol, TFA Salt

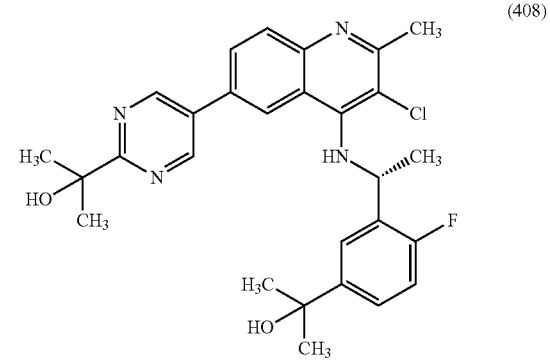 [SMILES: Cc1nc2ccc(-c3cnc(C(C)(C)O)nc3)cc2c(N[C@H](C)c2cc(C(C)(C)O)ccc2F)c1Cl]

(408)

359

Intermediate 408A: (R)-1-(3-(1-((3-chloro-6-(2-(2-hydroxypropan-2-yl)pyrimidin-5-yl)-2-methylquinolin-4-yl)amino)ethyl)-4-fluorophenyl)ethanone

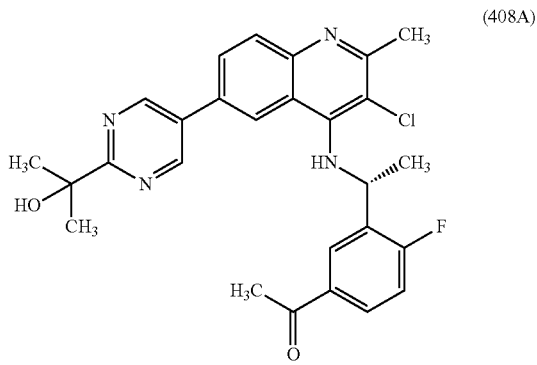 [SMILES: CC(=O)c1ccc(F)c([C@@H](C)Nc2c(Cl)c(C)nc3ccc(-c4cnc(C(C)(C)O)nc4)cc23)c1]

(408A)

A stirred dioxane (0.5 mL) solution of Example 316 (15 mg, 28 µmol), tributyl(1-ethoxyvinyl)stannane (11 mg, 31 µmol) and bis(triphenylphosphine)palladium(II) chloride (1.9 mg, 2.8 µmol) was pumped under vacuum and backfilled with nitrogen twice. The sealed tube was then heated at 90° C. for 16 h. The crude material was purified by silica gel column chromatography (4 g ISCO cartridge, 0-100% EtOAc/Hex) to give (R)-1-(3-(1-((3-chloro-6-(2-(2-hydroxypropan-2-yl)pyrimidin-5-yl)-2-methylquinolin-4-yl)amino)ethyl)-4-fluorophenyl)ethanone (8 mg, 57% yield). LC/MS (M+H): 493; LC retention time: 0.70 min (Method C).

Example 418

An ether (0.5 mL) solution of (R)-1-(3-(1-((3-chloro-6-(2-(2-hydroxypropan-2-yl)pyrimidin-5-yl)-2-methylquinolin-4-yl)amino)ethyl)-4-fluorophenyl)ethanone (Intermediate 418A, 8 mg, 16 µmol) was added to a 3 M ether solution of methylmagnesium bromide (0.05 mL, 0.15 mmol) at −20° C. The resulting solution was stirred for 1 h, quenched with saturated NH₄Cl (2 mL) and extracted with EtOAc (2×2 mL). The combined EtOAc extracts were concentrated, dissolved in MeOH (1.5 mL) and filtered. The filtrate was purified via preparative LC/MS (Condition B: Gradient: 15-55% B over 19 minutes, then a 5-minute hold at 100% B) to give (R)-2-(5-(3-chloro-4-((1-(2-fluoro-5-(2-hydroxypropan-2-yl)phenyl)ethyl)amino)-2-methylquinolin-6-yl)pyrimidin-2-yl)propan-2-ol, TFA salt (4.7 mg, 39% yield). LC/MS (M+H): 509; LC retention time: 1.95 min (Method A); $^1$H NMR (500 MHz, DMSO-d₆) δ 9.17 (s, 2H), 8.69 (br. s., 1H), 8.27 (d, J=8.4 Hz, 1H), 8.00 (d, J=8.6 Hz, 1H), 7.71 (d, J=6.1 Hz, 1H), 7.33 (d, J=6.4 Hz, 1H), 7.02 (t, J=9.5 Hz, 1H), 5.94 (br. s., 1H), 2.70 (s, 3H), 1.73 (d, J=6.5 Hz, 3H), 1.56 (s, 6H), 1.29 (s, 3H), 1.24 (s, 3H).

Example 409

(R)-1-(3-(1-((3-chloro-6-(2-(2-hydroxypropan-2-yl)pyrimidin-5-yl)quinolin-4-yl)amino)ethyl)-4-fluorophenyl)ethan-1-one

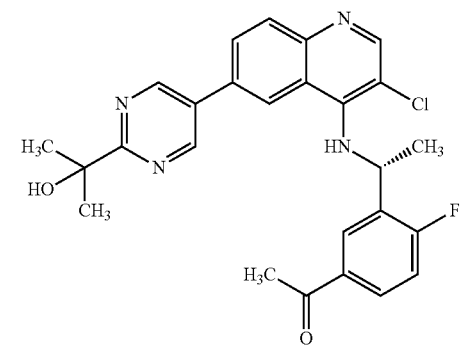

(409)

Following procedure analogous to the synthesis of Intermediate 408A, Example 318 was converted to (R)-1-(3-(1-((3-chloro-6-(2-(2-hydroxypropan-2-yl)pyrimidin-5-yl) quinolin-4-yl)amino)ethyl)-4-fluorophenyl)ethan-1-one. LC/MS (M+H): 479; LC retention time: 1.91 min (Method A); $^1$H NMR (500 MHz, DMSO-d₆) δ 9.28 (s, 2H), 8.81 (s, 1H), 8.62 (s, 1H), 8.26-8.18 (m, 2H), 8.02 (d, J=8.5 Hz, 1H), 7.91 (br. s., 1H), 7.29 (t, J=9.3 Hz, 1H), 5.95-5.88 (m, 1H), 2.46 (s, 3H), 1.72 (d, J=6.4 Hz, 3H), 1.57 (s, 6H).

Example 410

(R)-2-(5-(3-chloro-4-((1-(2-fluoro-5-(2-hydroxypropan-2-yl)phenyl)ethyl)amino)quinolin-6-yl)pyrimidin-2-yl)propan-2-ol

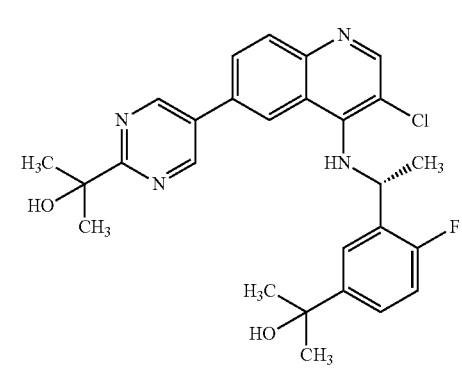

(410)

Following procedure analogous to the synthesis of Example 408, Example 409 (8 mg, 17 µmol) was converted to (R)-2-(5-(3-chloro-4-((1-(2-fluoro-5-(2-hydroxypropan-2-yl)phenyl)ethyl)amino)quinolin-6-yl)pyrimidin-2-yl)propan-2-ol (0.5 mg, 6% yield). LC/MS (M+H): 495; LC retention time: 1.70 min (Method A).

Example 411

(R)-2-(5-(3-chloro-4-((1-(2-fluoro-5-(phenylethynyl)phenyl)ethyl)amino)quinolin-6-yl)pyrimidin-2-yl)propan-2-ol

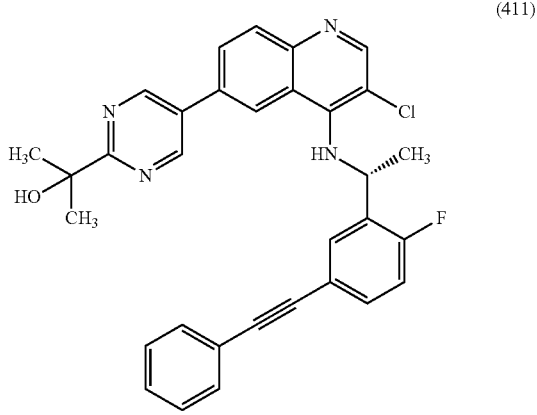 [SMILES: C[C@@H](Nc1c(Cl)cnc2ccc(-c3cnc(C(C)(C)O)nc3)cc12)c1cc(C#Cc2ccccc2)ccc1F]

(411)

A stirred toluene (0.5 mL) suspension of Example 318 (10 mg, 19 μmol), ethynylbenzene (3 mg, 29 μmol), bis(triphenylphosphine)palladium(II) chloride (3 mg, 4 mol) and copper(I) iodide (0.4 mg, 2 μmol) was pumped under vacuum and backfilled with nitrogen twice. TEA (5.40 μL, 39 μmol) was added. The mixture was again pumped under vacuum and backfilled with nitrogen twice and heated in a sealed safety vial at 90° C. for 18 h. The solvent was evaporated. The residue was dissolved in MeOH (2 mL) and filtered. The filtrate was purified via preparative LC/MS (Condition B: Gradient: 20-60% B over 19 minutes, then a 5-minute hold at 100% B) to give (R)-2-(5-(3-chloro-4-((1-(2-fluoro-5-(phenylethynyl)phenyl)ethyl)amino)quinolin-6-yl)pyrimidin-2-yl)propan-2-ol TFA salt (0.8 mg, 6% yield). LC/MS (M+H): 537; LC retention time: 2.50 min (Method A); $^1$H NMR (500 MHz, DMSO-$d_6$) δ 9.28 (s, 2H), 8.79 (br. s., 1H), 8.64 (s, 1H), 8.21 (d, J=9.2 Hz, 1H), 8.03 (d, J=8.8 Hz, 1H), 7.90 (d, J=5.8 Hz, 1H), 7.51-7.44 (m, 3H), 7.39 (d, J=3.7 Hz, 3H), 7.23-7.19 (m, 1H), 5.86 (br. s., 1H), 1.71 (d, J=6.7 Hz, 3H), 1.55 (s, 6H).

Example 412

(R)-2-(5-(3-chloro-4-((1-(2-fluoro-5-(1H-tetrazol-5-yl)phenyl)ethyl)amino)-2-methylquinolin-6-yl)pyrimidin-2-yl)propan-2-ol

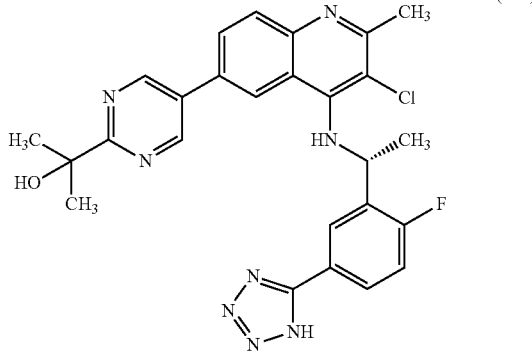

(412)

An NMP (0.5 mL) solution of Example 375 (20 mg, 42 μmol) and azidotributylstannane (28 mg, 84 μmol) was microwaved at 180° C. for 1 h. The mixture was filtered and the filtrate was purified via preparative LC/MS (Condition A: Gradient: 10-70% B over 19 minutes, then a 5-minute hold at 100% B) to give (R)-2-(5-(3-chloro-4-((1-(2-fluoro-5-(1H-tetrazol-5-yl)phenyl)ethyl)amino)-2-methylquinolin-6-yl)pyrimidin-2-yl)propan-2-ol (2.4 mg, 10% yield). LC/MS (M+H): 519; LC retention time: 1.53 min (Method A); $^1$H NMR (500 MHz, DMSO-$d_6$) δ 9.18 (s, 2H), 8.57 (s, 1H), 8.43 (d, J=6.1 Hz, 1H), 8.07 (d, J=8.8 Hz, 1H), 7.94-7.85 (m, 2H), 7.29 (t, J=9.3 Hz, 1H), 6.61 (d, J=9.2 Hz, 1H), 5.67-5.58 (m, 1H), 2.62 (s, 3H), 1.71 (d, J=6.7 Hz, 3H), 1.56 (s, 6H).

Example 413

(R)-2-(5-(3-chloro-4-((1-(2-fluoro-5-(2-methyl-2H-tetrazol-5-yl)phenyl)ethyl)amino)quinolin-6-yl)pyrimidin-2-yl)propan-2-ol

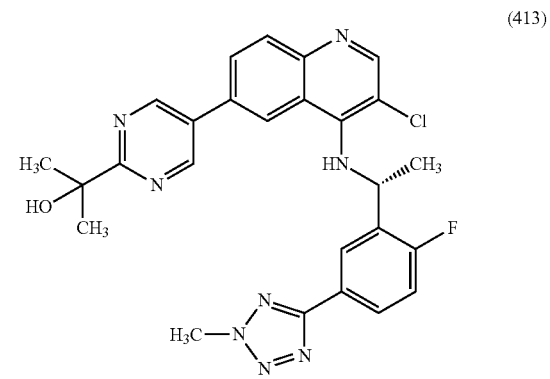 [SMILES: C[C@@H](Nc1c(Cl)cnc2ccc(-c3cnc(C(C)(C)O)nc3)cc12)c1cc(-c2nnn(C)n2)ccc1F]

(413)

Intermediate 413A: (R)-2-(5-(3-chloro-4-((1-(2-fluoro-5-(1H-tetrazol-5-yl)phenyl)ethyl)amino)quinolin-6-yl)pyrimidin-2-yl)propan-2-ol

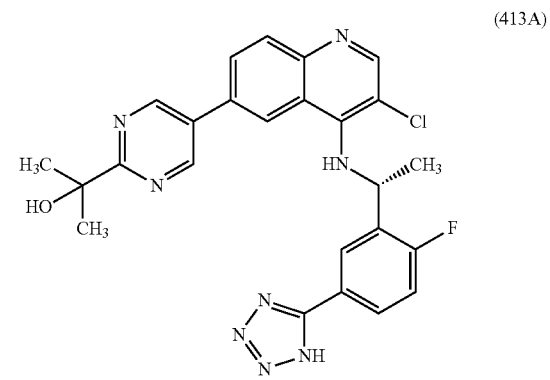 [SMILES: C[C@@H](Nc1c(Cl)cnc2ccc(-c3cnc(C(C)(C)O)nc3)cc12)c1cc(-c2nnn[nH]2)ccc1F]

(413A)

Following procedure analogous to the synthesis of Examples 375 and 412, Example 318 (30 mg, 58 μmol) was converted in two steps to a crude NMP solution of (R)-2-(5-(3-chloro-4-((1-(2-fluoro-5-(1H-tetrazol-5-yl)phenyl)ethyl)amino)quinolin-6-yl)pyrimidin-2-yl)propan-2-ol. LC/MS (M+H): 505; LC retention time: 0.67 min (Method C).

Example 413

Potassium carbonate (54 mg, 0.391 mmol) and iodomethane (0.036 mL, 0.582 mmol) were added to the crude NMP solution or Intermediate 413A. The mixture was stirred at room temperature for 1 h and filtered. The filtrate was purified via preparative LC/MS (Condition A: Gradient: 30-100% B over 20 minutes, then a 5-minute hold at 100% B) to give (R)-2-(5-(3-chloro-4-((1-(2-fluoro-5-(2-methyl-2H-tetrazol-5-yl)phenyl)ethyl)amino)quinolin-6-yl)pyrimidin-2-yl)propan-2-ol (2.8 mg, 9% yield). LC/MS (M+H): 519; LC retention time: 1.96 min (Method A); $^1$H NMR (500 MHz, DMSO-$d_6$) δ 9.24 (s, 2H), 8.78 (s, 1H), 8.49 (s, 1H), 8.41 (d, J=6.1 Hz, 1H), 8.10 (d, J=8.8 Hz, 1H), 7.97 (d, J=8.7 Hz, 1H), 7.91 (br. s., 1H), 7.29 (t, J=9.3 Hz, 1H), 6.98 (d, J=9.3 Hz, 1H), 5.88-5.77 (m, 1H), 4.34 (s, 3H), 1.72 (d, J=6.6 Hz, 3H), 1.56 (s, 6H).

Example 414

(R)-2-(5-(3-chloro-4-((1-(2-fluoro-5-(1H-1,2,4-triazol-5-yl)phenyl)ethyl)amino)quinolin-6-yl)pyrimidin-2-yl)propan-2-ol

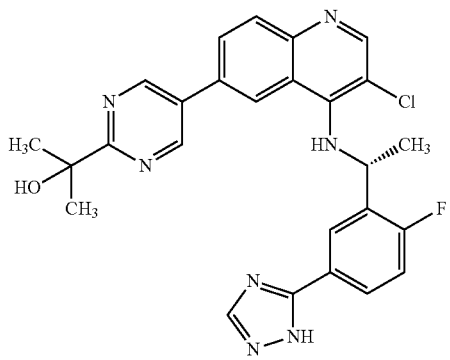

(414)

A 1,1-dimethoxy-N,N-dimethylmethanamine (0.5 mL, 4 mmol) solution of Example 388 (35 mg, 73 μmol) was heated at 120° C. for 2 h in a sealed safety vial. The excess 1,1-dimethoxy-N,N-dimethylmethanamine was removed by evaporation. The residue was dissolved in acetic acid (0.5 mL, 9 mmol). To the solution was added aqueous 35 wt % hydrazine solution (66 μL, 0.7 mmol). The mixture was heated at 90° C. for 2 h. The crude material was diluted with MeOH (1 mL) and filtered. The filtrate was purified via preparative LC/MS (Condition A: Gradient: 18-58% B over 20 minutes, then a 5-minute hold at 100% B) to give (R)-2-(5-(3-chloro-4-((1-(2-fluoro-5-(4H-1,2,4-triazol-3-yl)phenyl)ethyl)amino)quinolin-6-yl)pyrimidin-2-yl)propan-2-ol (7.6 mg, 21% yield). LC/MS (M+H): 504; LC retention time: 1.69 min (Method A); $^1$H NMR (500 MHz, DMSO-$d_6$) δ 9.28 (s, 2H), 8.80 (s, 1H), 8.49 (s, 1H), 8.37 (d, J=7.3 Hz, 2H), 8.12 (d, J=8.6 Hz, 1H), 7.98 (d, J=8.6 Hz, 1H), 7.87 (br. s., 1H), 7.22 (t, J=9.4 Hz, 1H), 6.99 (d, J=9.1 Hz, 1H), 5.87-5.77 (m, 1H), 1.71 (d, J=6.6 Hz, 3H), 1.57 (s, 6H).

Example 415

Methyl (R)-3-(1-((3-chloro-6-(2-(2-hydroxypropan-2-yl)pyrimidin-5-yl)quinolin-4-yl)amino)ethyl)-4-fluorobenzoate

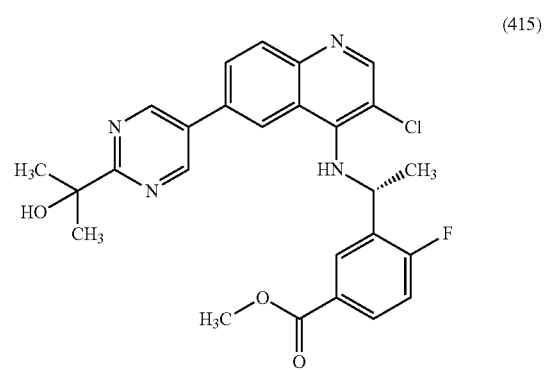 [SMILES: COC(=O)c1ccc(F)c([C@@H](C)Nc2c(Cl)cnc3ccc(-c4cnc(C(C)(C)O)nc4)cc23)c1]

(415)

A stirred DMF (0.5 mL) solution of Example 318 (50 mg, 97 μmol) and PdCl$_2$(dppf)-CH$_2$Cl$_2$ adduct (8 mg, 9.7 μmol) was pumped under vacuum and backfilled with carbon monoxide twice. TEA (41 μL, 0.29 mmol) and MeOH (39 μL, 0.97 mmol) were added. The mixture was again pumped under vacuum and backfilled with carbon monoxide twice. The reaction tube was sealed and microwaved at 100° C. for 1 h. The resulting mixture was treated with 10% LiCl (4 mL) and filtered. The solid was collected and purified by silica gel column chromatography (4 g ISCO cartridge, 0-100% EtOAc-Hexanes) to give methyl (R)-3-(1-((3-chloro-6-(2-(2-hydroxypropan-2-yl)pyrimidin-5-yl)quinolin-4-yl)amino)ethyl)-4-fluorobenzoate (18.6 mg, 39% yield). LC/MS (M+H): 495; LC retention time: 2.08 min (Method A). $^1$H NMR (500 MHz, DMSO-$d_6$) δ 9.27 (s, 2H), 8.75 (s, 1H), 8.50 (s, 1H), 8.32 (d, J=5.5 Hz, 1H), 8.13 (d, J=8.2 Hz, 1H), 7.99 (d, J=8.9 Hz, 1H), 7.85 (d, J=6.1 Hz, 1H), 7.26 (t, J=9.3 Hz, 1H), 6.92 (d, J=9.2 Hz, 1H), 5.83-5.71 (m, 1H), 3.75 (s, 3H), 1.69 (d, J=6.7 Hz, 3H), 1.57 (s, 6H).

Example 416

(R)-3-(1-((3-chloro-6-(2-(2-hydroxypropan-2-yl)pyrimidin-5-yl)quinolin-4-yl)amino)ethyl)-4-fluoro-N-methylbenzamide

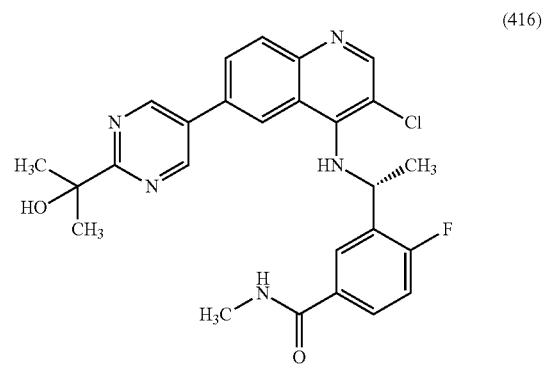 [SMILES: CNC(=O)c1ccc(F)c([C@@H](C)Nc2c(Cl)cnc3ccc(-c4cnc(C(C)(C)O)nc4)cc23)c1]

(416)

Intermediate 418A: (R)-3-(1-((3-chloro-6-(2-(2-hydroxypropan-2-yl)pyrimidin-5-yl)quinolin-4-yl)amino)ethyl)-4-fluorobenzoic acid

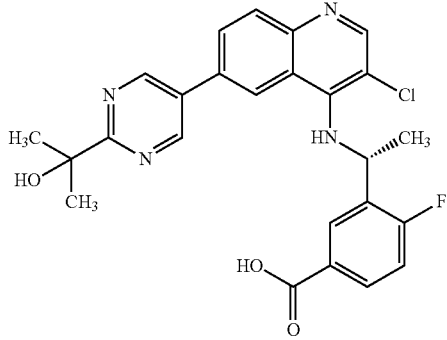

(418A)

1 M NaOH solution (250 μL, 250 μmol) was added to a MeOH (0.5 mL) solution of Example 415 (15 mg, 30 μmol) and the mixture was stirred at room temperature for 4 h. The solvent was evaporated. The resulting white residue was triturated with HCl solution (0.25 mL 1M HCl diluted with 4 mL water) then filtered. The solid was washed with water (2 mL) and dried in vacuum to obtain (R)-3-(1-((3-chloro-6-(2-(2-hydroxypropan-2-yl)pyrimidin-5-yl)quinolin-4-yl)amino)ethyl)-4-fluorobenzoic acid (10.4 mg, 22 μmol, 71% yield). LC/MS (M+H): 481; LC retention time: 0.66 min (Method C).

Example 418

An acetonitrile (0.5 mL) solution of Intermediate 418A (5 mg, 10.4 μmol), 8 M methanamine in EtOH (13 μL, 104 μmol) and BOP (8 mg, 18 μmol) was stirred at room temperature for 1 h. The resulting mixture was diluted with MeOH (1 mL) and filtered. The filtrate was purified via preparative LC/MS (Condition A: Gradient: 20-60% B over 20 minutes, then a 5-minute hold at 100% B) to give (R)-3-(1-((3-chloro-6-(2-(2-hydroxypropan-2-yl)pyrimidin-5-yl)quinolin-4-yl)amino)ethyl)-4-fluoro-N-methylbenzamide (2.9 mg, 56% yield). LC/MS (M+H): 494; LC retention time: 1.71 min (Method A); $^1$H NMR (500 MHz, DMSO-$d_6$) δ 9.25 (s, 2H), 8.72 (s, 1H), 8.48 (s, 1H), 8.36 (d, J=4.3 Hz, 1H), 8.18-8.11 (m, 2H), 7.99 (d, J=8.5 Hz, 1H), 7.71 (d, J=5.2 Hz, 1H), 7.19 (t, J=9.3 Hz, 1H), 6.84 (d, J=8.8 Hz, 1H), 5.82-5.73 (m, 1H), 2.71 (d, J=4.6 Hz, 3H), 1.68 (d, J=6.7 Hz, 3H), 1.57 (s, 6H).

Example 417

(R)-3-(1-((3-chloro-6-(2-(2-hydroxypropan-2-yl)pyrimidin-5-yl)quinolin-4-yl)amino)ethyl)-4-fluoro-N,N-dimethylbenzamide

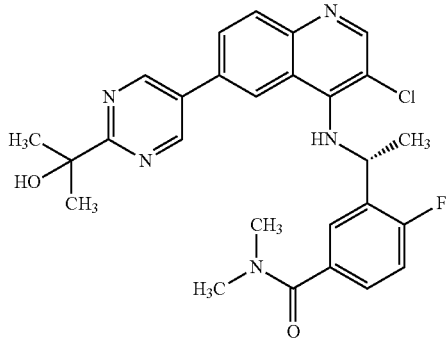

(417)

An acetonitrile (0.5 mL) solution of Intermediate 416A (5 mg, 10.4 μmol), 2 M dimethylamine in MeOH (0.052 mL, 104 μmol) and BOP (8 mg, 18 μmol) was stirred at room temperature for 1 h. The resulting mixture was diluted with MeOH (1 mL) and filtered. The filtrate was purified via preparative LC/MS (Condition A: Gradient: 20-70% B over 20 minutes, then a 5-minute hold at 100% B) to give (R)-3-(1-((3-chloro-6-(2-(2-hydroxypropan-2-yl)pyrimidin-5-yl)quinolin-4-yl)amino)ethyl)-4-fluoro-N,N-dimethylbenzamide (3.8 mg, 72% yield). LC/MS (M+H): 508; LC retention time: 1.72 min (Method A); $^1$H NMR (500 MHz, DMSO-$d_6$) δ 9.26 (br. s., 2H), 8.73 (br. s., 1H), 8.52 (br. s., 1H), 8.14 (d, J=9.1 Hz, 1H), 8.00 (d, J=8.5 Hz, 1H), 7.64 (d, J=6.5 Hz, 1H), 7.27 (br. s., 1H), 6.88 (d, J=8.9 Hz, 1H), 5.81 (t, J=7.3 Hz, 1H), 2.83 (br. s., 3H), 1.90 (s, 3H), 1.69 (d, J=6.6 Hz, 3H), 1.57 (br. s., 6H).

Example 418

(S)-2-(5-(3-chloro-4-((2,2-difluoro-1-(2-fluoro-5-(2-hydroxypropan-2-yl)phenyl)ethyl)amino)-2-methylquinolin-6-yl)pyrimidin-2-yl)propan-2-ol

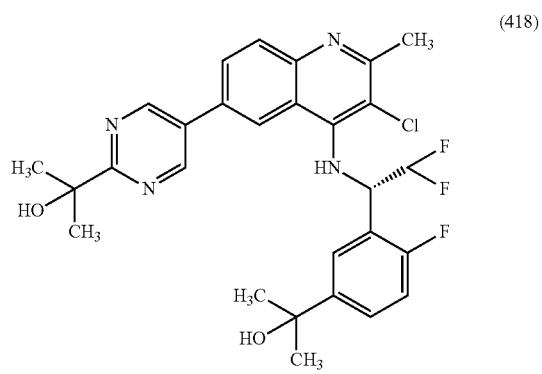 [SMILES: Cc1nc2ccc(-c3cnc(C(C)(C)O)nc3)cc2c(N[C@@H](c2cc(C(C)(C)O)ccc2F)C(F)F)c1Cl]

(418)

Following the general procedure of the 2-step synthesis of Example 408, Example 320 (17 mg, 30 μmol) was converted to (S)-2-(5-(3-chloro-4-((2,2-difluoro-1-(2-fluoro-5-(2-hydroxypropan-2-yl)phenyl)ethyl)amino)-2-methylquinolin-6-yl)pyrimidin-2-yl) propan-2-ol (3.4 mg, 20% yield). LC/MS (M+H): 545; LC retention time: 1.90 min (Method A); $^1$H NMR (500 MHz, DMSO-$d_6$) δ 9.19 (s, 2H), 8.52 (s, 1H), 8.11 (d, J=8.7 Hz, 1H), 7.97 (d, J=8.7 Hz, 1H), 7.91 (d, J=5.6 Hz, 1H), 7.42 (br. s., 1H), 7.06 (t, J=9.3 Hz, 1H), 6.80 (d, J=10.4 Hz, 1H), 6.67-6.40 (m, 1H), 5.64 (d, J=6.6 Hz, 1H), 2.66 (s, 3H), 1.56 (s, 6H), 1.32 (s, 3H), 1.22 (s, 3H).

Example 419

(R)-2-(5-(3-chloro-4-((1-(2-fluoro-5-(1H-1,2,3-triazol-4-yl)phenyl)ethyl)amino)quinolin-6-yl)pyrimidin-2-yl)propan-2-ol

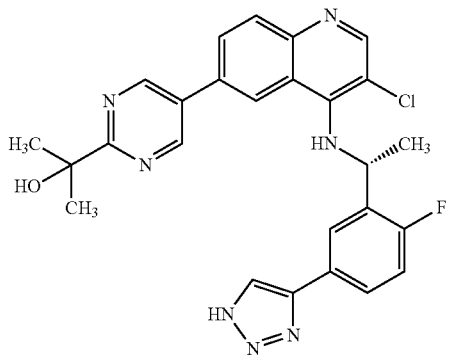

(419)

Intermediate 419A: (R)-2-(5-(3-chloro-4-((1-(2-fluoro-5-((trimethylsilyl)ethynyl)phenyl)ethyl)amino)quinolin-6-yl)pyrimidin-2-yl)propan-2-ol

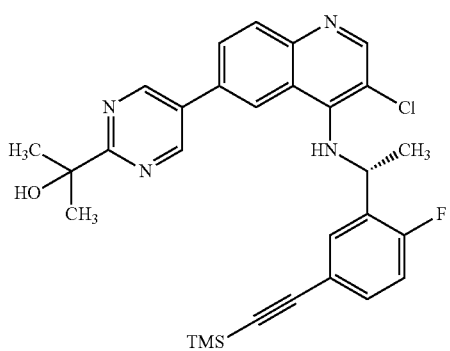

(419A)

Intermediate 419A was prepared according to the general procedure analogous of Example 411 by converting Example 318 (50 mg, 97 μmol) to (R)-2-(5-(3-chloro-4-((1-(2-fluoro-5-((trimethylsilyl) ethynyl)phenyl)ethyl)amino) quinolin-6-yl)pyrimidin-2-yl) propan-2-ol (31 mg, 59% yield). LC/MS (M+H): 533; LC retention time: 0.93 min (Method C).

Example 419

A MeOH (0.28 mL)-THF (0.28 mL) solution of (R)-2-(5-(3-chloro-4-((1-(2-fluoro-5-((trimethylsilyl)ethynyl)phenyl)ethyl)amino)quinolin-6-yl)pyrimidin-2-yl)propan-2-ol (Intermediate 419A, 15 mg, 28 μmol) was added to an aqueous (0.14 mL) solution of L-ascorbic acid (2 mg, 11 μmol), sodium azide (2 mg, 31 μmol), copper(II) sulfate (0.9 mg, 5.6 μmol) and potassium carbonate (7 mg, 51 μmol). The mixture was stirred at room temperature for 24 h. Two fifths of the crude product (approximately 11.2 μmol) was filtered. The filtrate was purified via preparative LC/MS (Condition B: Gradient: 10-50% B over 20 minutes, then a 5-minute hold at 100% B) to give (R)-2-(5-(3-chloro-4-((1-(2-fluoro-5-(1H-1,2,3-triazol-4-yl)phenyl)ethyl)amino)quinolin-6-yl)pyrimidin-2-yl)propan-2-ol (1.5 mg, 25% yield). LC/MS (M+H): 504; LC retention time: 1.79 min (Method A); $^1$H NMR (500 MHz, DMSO-$d_6$) δ 9.25 (br. s., 2H), 8.78 (br. s., 1H), 8.56 (br. s., 1H), 8.16 (d, J=7.9 Hz, 2H), 8.00 (d, J=8.3 Hz, 1H), 7.71 (br. s., 1H), 7.24-7.18 (m, 1H), 5.84 (br. s., 1H), 1.73 (d, J=6.5 Hz, 3H), 1.57 (br. s., 6H).

Examples 420 and 421

(R)-2-(5-(3-chloro-4-((1-(2-fluoro-5-(1-methyl-1H-1,2,3-triazol-4-yl)phenyl)ethyl)amino)quinolin-6-yl)pyrimidin-2-yl)propan-2-ol (420) and (R)-2-(5-(3-chloro-4-((1-(2-fluoro-5-(1-methyl-1H-1,2,3-triazol-5-yl)phenyl)ethyl)amino)quinolin-6-yl)pyrimidin-2-yl)propan-2-ol (421)

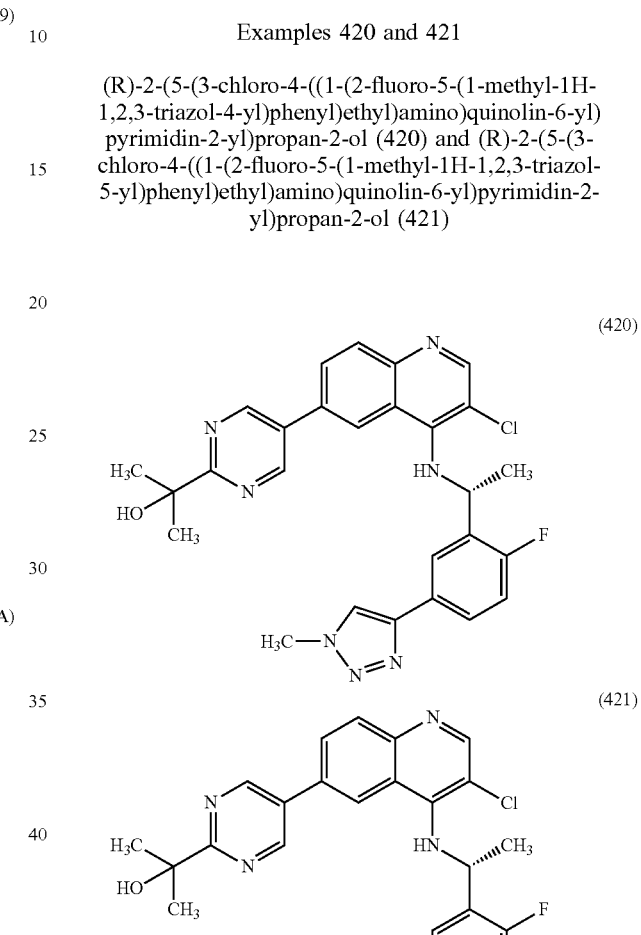

Iodomethane (1.9 μL, 31 μmol) and pyridine (11 μL, 141 μmol) was added to three fifths of the crude product solution from Intermediate 419B (approximately 16.8 μmol). The mixture was stirred at room temperature for 24 h, diluted with MeOH (1 mL) and filtered. The filtrate was purified via preparative LC/MS (Condition B: Gradient: 10-55% B over 19 minutes, then a 5-minute hold at 100% B) to give pure first eluting isomer and impure second eluting isomer. The impure second eluding isomer was further purified via preparative LC/MS (Condition A: Gradient: 40-80% B over 19 minutes, then a 5-minute hold at 100% B). The absolute structural assignments of the two eluting isomers were not made.

Analytical data for the first eluting isomer (2.2 mg, 25% yield): LC/MS (M+H): 518; LC retention time: 1.81 min (Method A); $^1$H NMR (500 MHz, DMSO-$d_6$) δ 9.26 (br. s., 2H), 8.83 (s, 1H), 8.67 (s, 1H), 8.42 (s, 1H), 8.26-8.16 (m, 2H), 8.03 (d, J=8.7 Hz, 1H), 7.79-7.65 (m, 1H), 7.25-7.21 (m, 1H), 5.94 (br. s., 1H), 4.05 (s, 2H), 1.75 (d, J=6.6 Hz, 3H), 1.57 (s, 6H).

Analytical data for the second eluting isomer (1.5 mg, 20% yield): LC/MS (M+H): 518; LC retention time: 2.01 min (Method A); $^1$H NMR (500 MHz, DMSO-$d_6$) δ 9.27 (s, 2H), 8.80 (s, 1H), 8.51 (s, 1H), 8.22-7.91 (m, 4H), 7.67 (d, J=5.9 Hz, 1H), 7.18 (t, J=9.3 Hz, 1H), 6.90 (d, J=9.3 Hz, 1H), 5.87-5.75 (m, 1H), 4.11 (s, 3H), 1.72 (d, J=6.6 Hz, 3H), 1.57 (s, 6H).

Examples 422 and 423

Diastereomers of 5-(3-((R)-1-((3-chloro-6-(2-(2-hydroxypropan-2-yl)pyrimidin-5-yl)quinolin-4-yl)amino)ethyl)-4-fluorophenyl)imidazolidine-2,4-dione

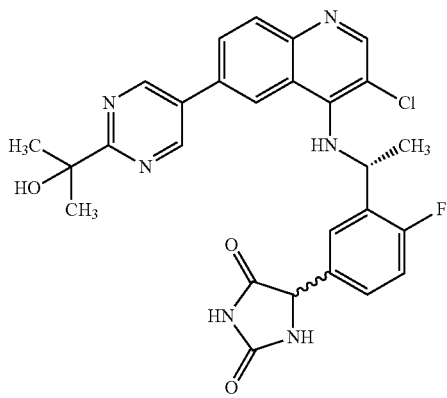

(422 and 423)

Intermediate 422A: (R)-2-(5-(3-chloro-4-((1-(2-fluoro-5-vinylphenyl)ethyl)amino)quinolin-6-yl)pyrimidin-2-yl)propan-2-ol

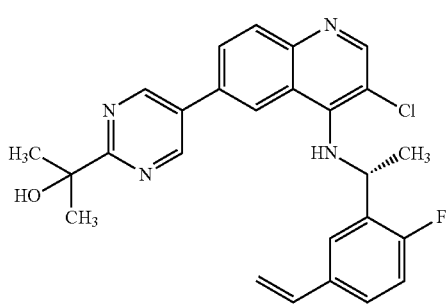

(422A)

Following procedure analogous to the synthesis of Example 330, Example 318 (100 mg, 194 μmol) was converted to (R)-2-(5-(3-chloro-4-((1-(2-fluoro-5-vinylphenyl)ethyl)amino)quinolin-6-yl)pyrimidin-2-yl)propan-2-ol (60 mg, 67% yield). LC/MS (M+H): 463; LC retention time: 0.77 min (Method C).

Intermediate 422B: (R)-3-(1-((3-chloro-6-(2-(2-hydroxypropan-2-yl)pyrimidin-5-yl)quinolin-4-yl)amino)ethyl)-4-fluorobenzaldehyde

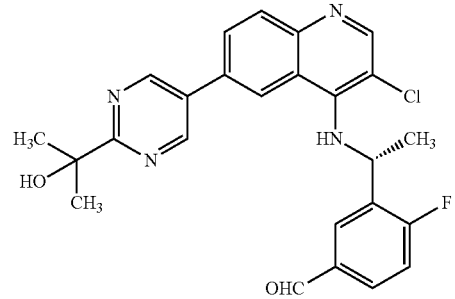

(422B)

Following procedure analogous to Intermediate 407A, (R)-2-(5-(3-chloro-4-((1-(2-fluoro-5-vinylphenyl)ethyl)amino)quinolin-6-yl)pyrimidin-2-yl)propan-2-ol (60 mg, 130 μmol) was converted to (R)-3-(1-((3-chloro-6-(2-(2-hydroxypropan-2-yl)pyrimidin-5-yl)quinolin-4-yl)amino)ethyl)-4-fluorobenzaldehyde (48 mg, 80% yield). LC/MS (M+H): 465; LC retention time: 0.71 min (Method C). $^1$H NMR (400 MHz, chloroform-d) δ 9.95 (s, 1H), 8.83 (s, 2H), 8.68 (s, 1H), 8.14 (d, J=8.7 Hz, 1H), 8.09 (dd, J=7.3, 2.0 Hz, 1H), 8.01 (d, J=1.8 Hz, 1H), 7.89-7.80 (m, 2H), 5.48-5.37 (m, 1H), 5.13 (d, J=8.9 Hz, 1H), 4.65 (s, 1H), 1.75 (d, J=6.7 Hz, 3H), 1.67 (s, 6H).

Examples 422 and 423

A stirred EtOH (0.4 mL)-water (0.1 mL) solution of the aldehyde from Intermediate 422B (10 mg, 22 μmol), sodium cyanide (1.3 mg, 26 μmol) and ammonium bicarbonate (4.59 mg, 0.058 mmol) was heated in a sealed safety vial at 90° C. for 50 min. The reaction mixture was diluted with MeOH (1 mL) and filtered. The filtrate was purified via preparative LC/MS (Condition A: Gradient: 15-55% B over 25 minutes, then a 5-minute hold at 100% B) to give partially separated two diastereomers. Analytical data for the first diastereomer (1.3 mg, 11% yield, contaminated with ~10% second diastereomer): LC/MS (M+H): 535; LC retention time: 1.40 min (Method A); $^1$H NMR (500 MHz, DMSO-$d_6$) δ 9.27-9.21 (m, 2H), 8.74-8.66 (m, 1H), 8.46 (br. s., 1H), 8.30 (s, 1H), 8.12 (d, J=8.2 Hz, 1H), 7.99 (d, J=8.6 Hz, 1H), 7.63-7.53 (m, 1H), 7.22-7.13 (m, 2H), 6.86 (d, J=8.7 Hz, 1H), 5.77 (t, J=7.4 Hz, 1H), 5.07 (s, 1H), 1.69-1.62 (m, 3H), 1.57 (s, 6H). Analytical data for the second diastereomer (1.5 mg, 12% yield, contaminated with ~50% first diastereomer): LC/MS (M+H): 535; LC retention time: 1.40 min (Method A). The absolute stereochemistry of the two product peaks was not determined).

Example 424

(R)-3-(1-((3-chloro-6-(2-(2-hydroxypropan-2-yl)pyrimidin-5-yl)quinolin-4-yl)amino)ethyl)-4-fluorobenzaldehyde oxime

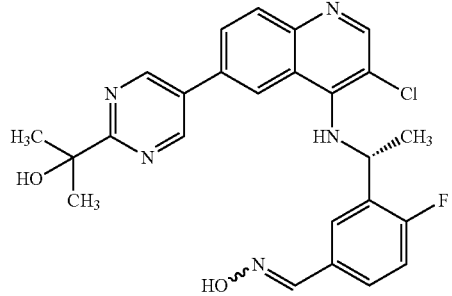
(424)

An EtOH (0.5 mL) solution of (R)-3-(1-((3-chloro-6-(2-(2-hydroxypropan-2-yl)pyrimidin-5-yl)quinolin-4-yl)amino)ethyl)-4-fluorobenzaldehyde (Intermediate 422B, 10 mg, 22 µmol) and hydroxylamine hydrochloride (1.8 mg, 26 µmol) was stirred at room temperature for 18 h. Half of the solution (approximately 11 µmol) was purified via preparative LC/MS (Condition A: Gradient: 30-70% B over 20 minutes, then a 5-minute hold at 100% B) to give (R)-3-(1-((3-chloro-6-(2-(2-hydroxypropan-2-yl)pyrimidin-5-yl)quinolin-4-yl)amino)ethyl)-4-fluorobenzaldehyde oxime (2 mg, 40% yield). LC/MS (M+H): 480; LC retention time: 1.87 min (Method A); $^1$H NMR (500 MHz, DMSO-$d_6$) δ 9.25 (br. s., 2H), 8.71 (s, 1H), 8.47 (s, 1H), 8.13 (d, J=8.9 Hz, 1H), 8.05 (s, 1H), 7.99 (d, J=8.9 Hz, 1H), 7.86 (d, J=6.1 Hz, 1H), 7.48-7.42 (m, 1H), 7.16 (t, J=9.3 Hz, 1H), 6.84 (d, J=8.9 Hz, 1H), 5.80-5.69 (m, 1H), 1.68 (d, J=6.7 Hz, 3H), 1.57 (s, 6H).

Example 425

(R)-2-(5-(3-chloro-4-((1-(2-fluoro-5-(methylsulfonyl)phenyl)ethyl)amino)quinolin-6-yl)pyrimidin-2-yl)propan-2-ol

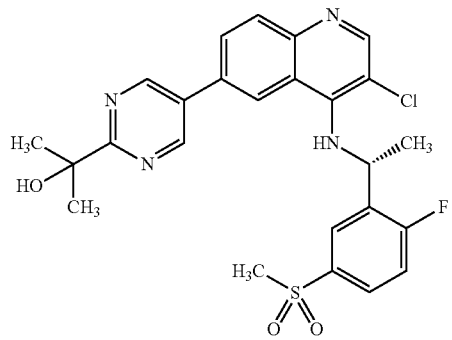
(425)

Intermediate 425A: 3-((R)-1-((3-chloro-6-(2-(2-hydroxypropan-2-yl)pyrimidin-5-yl)quinolin-4-yl)amino)ethyl)-4-fluorobenzenesulfinic acid

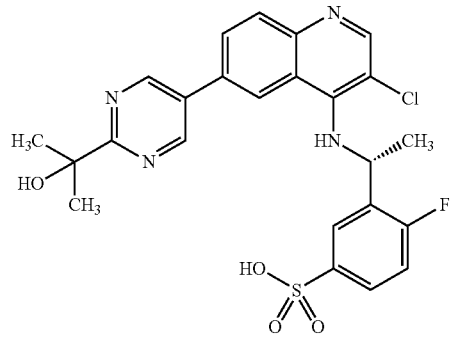
(425A)

A solution of Example 318 (30 mg, 58 µmol), bis(triphenylphosphine) palladium(II) chloride (4 mg, 5.8 µmol), potassium metabisulfite (26 mg, 116 µmol), potassium formate (11 mg, 128 µmol), tetrabutylammonium bromide (21 mg, 64 µmol) and 1,10-phenanthroline (3 mg, 17 µmol) in DMSO (1 mL) was pumped under vacuum and backfilled with nitrogen twice. The sealed tube was heated at 70° C. for 9.5 h. One third of the resulting mixture (approximately 19.3 µmol) was used in the next step.

Example 425

Iodomethane (13 mg, 87 µmol) was added to one third of the crude reaction solution (Intermediate 425A, approximately 19.3 µmol). After stirring at room temperature for 1 h, the mixture was diluted with MeOH (1 mL) and filtered. The filtrate was purified via preparative LC/MS (Condition B: Gradient: 10-50% B over 20 minutes, then a 5-minute hold at 100% B) to give (R)-2-(5-(3-chloro-4-((1-(2-fluoro-5-(methylsulfonyl)phenyl)ethyl)amino)quinolin-6-yl)pyrimidin-2-yl)propan-2-ol TFA salt (1.8 mg, 13% yield). LC/MS (M+H): 515; LC retention time: 1.81 min (Method A).

Example 426

(R)-3-(1-((3-chloro-6-(2-(2-hydroxypropan-2-yl)pyrimidin-5-yl)quinolin-4-yl)amino)ethyl)-4-fluorobenzenesulfonamide

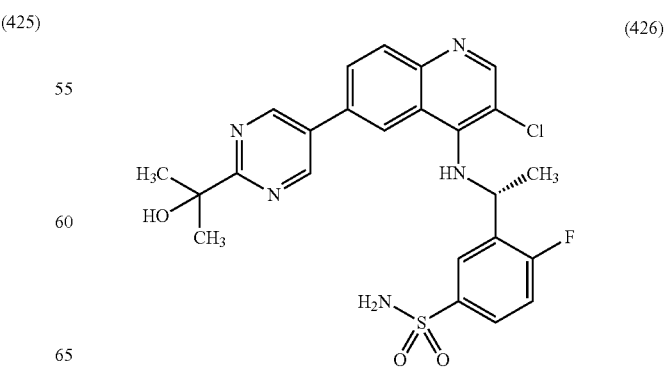
(426)

Hydroxylamine-O-sulfonic acid (26 mg, 233 µmol) was added to the remaining two thirds of the crude solution of Intermediate 425A (approximately 38.7 µmol) and the mixture was stirred at room temperature for 16 h. The mixture was diluted with MeOH (1 mL) and filtered. The filtrate was purified via preparative LC/MS (Condition B: Gradient: 0-40% B over 19 minutes, then a 5-minute hold at 100% B) to give (R)-3-(1-((3-chloro-6-(2-(2-hydroxypropan-2-yl)pyrimidin-5-yl)quinolin-4-yl)amino)ethyl)-4-fluorobenzenesulfonamide TFA salt (0.7 mg, 3% yield). LC/MS (M+H): 516; LC retention time: 1.50 min (Method A).

Example 427

Methyl (R)-3-((3-(1-((3-chloro-6-(2-(2-hydroxypropan-2-yl)pyrimidin-5-yl)quinolin-4-yl)amino)ethyl)-4-fluorophenyl)sulfonyl)propanoate (427)

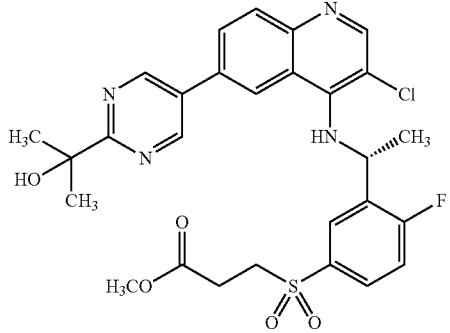

A DMSO (0.5 mL) solution of Example 318 (20 mg, 39 µmol), sodium 3-methoxy-3-oxopropane-1-sulfinate (20 mg, 116 µmol) and copper(I) iodide (22 mg, 116 mol) was heated in a sealed safety vial at 120° C. for 4.5 h. The resulting mixture was diluted with MeOH (1 mL) and filtered. The filtrate was purified via preparative LC/MS (Condition A: Gradient: 20-60% B over 20 minutes, then a 5-minute hold at 100% B) to give (R)-methyl 3-((3-(1-((3-chloro-6-(2-(2-hydroxypropan-2-yl)pyrimidin-5-yl)quinolin-4-yl)amino)ethyl)-4-fluorophenyl)sulfonyl)propanoate (3 mg, 13% yield). LC/MS (M+H): 587; LC retention time: 1.87 min (Method A). $^1$H NMR (500 MHz, DMSO-$d_6$) δ 9.26 (s, 2H), 8.75 (s, 1H), 8.49 (s, 1H), 8.18-8.11 (m, 2H), 8.00 (d, J=8.8 Hz, 1H), 7.80 (br. s., 1H), 7.44 (t, J=9.3 Hz, 1H), 6.93 (d, J=8.5 Hz, 1H), 5.86-5.78 (m, 1H), 2.42-2.32 (m, 4H), 1.71 (d, J=6.7 Hz, 3H), 1.56 (s, 6H).

Example 428

(R)-3-(3-(1-((3-chloro-6-(2-(2-hydroxypropan-2-yl)pyrimidin-5-yl)quinolin-4-yl)amino)ethyl)-4-fluorophenyl)-1H-pyrazole-5-carboxylic acid (428)

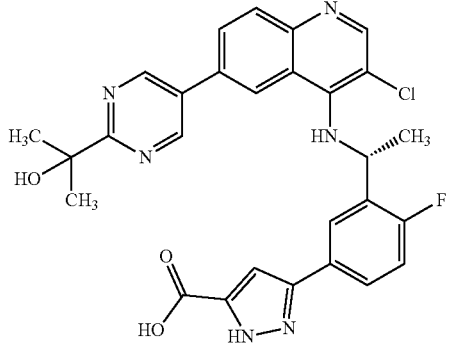

A dioxane (0.5 mL) solution of Example 318 (50 mg, 97 µmol), ethyl 3-(tributylstannyl)-1H-pyrazole-5-carboxylate (75 mg, 175 µmol) and bis(triphenylphosphine)palladium (II) chloride (7 mg, 10 µmol) was pumped under vacuum and backfilled with nitrogen twice. The sealed tube was heated at 90° C. for 17 h. After cooling to room temperature, the reaction mixture was divided into two equal parts. A 1 M NaOH solution (0.5 mL, 0.5 mmol) was added to one half of the reaction mixture (approximately 48.5 µmol). The resulting solution was stirred at room temperature for 1 h, diluted with MeOH (1 mL) and filtered. The filtrate was purified via preparative LC/MS (Condition A: Gradient: 10-50% B over 20 minutes, then a 5-minute hold at 100% B) to give (R)-3-(3-(1-((3-chloro-6-(2-(2-hydroxypropan-2-yl)pyrimidin-5-yl)quinolin-4-yl)amino)ethyl)-4-fluorophenyl)-1H-pyrazole-5-carboxylic acid (0.9 mg, 3% yield). LC/MS (M+H): 547; LC retention time: 1.42 min (Method A). $^1$H NMR (500 MHz, DMSO-$d_6$) δ 9.25 (br. s., 2H), 8.75 (br. s., 1H), 8.48 (s, 1H), 8.14-8.04 (m, 2H), 7.98 (d, J=8.3 Hz, 1H), 7.60 (br. s., 1H), 7.10 (t, J=9.3 Hz, 1H), 6.90 (d, J=8.7 Hz, 1H), 6.60 (br. s., 1H), 5.77 (br. s., 1H), 1.69 (d, J=6.0 Hz, 3H), 1.56 (br. s., 6H).

Examples 429 and 430

(R)-2-(5-(4-((1-(5-(aminomethyl)-2-fluorophenyl)ethyl)amino)-3-chloroquinolin-6-yl)pyrimidin-2-yl)propan-2-ol (429) and (R)-2-(5-(3-chloro-4-((1-(2-fluoro-5-(hydroxymethyl)phenyl)ethyl)amino)quinolin-6-yl)pyrimidin-2-yl)propan-2-ol (430)

(429)

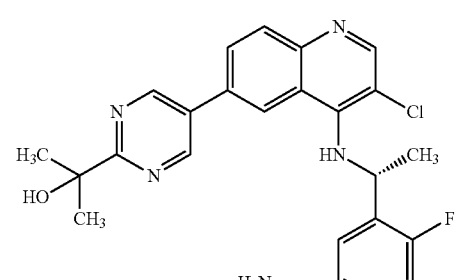

(430)

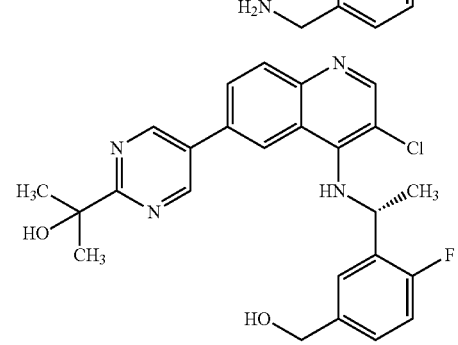

An ethanol (1 mL) solution of (R)-3-(1-((3-chloro-6-(2-(2-hydroxypropan-2-yl)pyrimidin-5-yl)quinolin-4-yl)amino)ethyl)-4-fluorobenzaldehyde (Intermediate 422B, 33 mg, 71 µmol), ammonium acetate (72 mg, 934 µmol) and sodium cyanoborohydride (15 mg, 239 µmol) was microwaved at 130° C. for 10 min. The crude was diluted with MeOH (1 mL) and filtered. The filtrate was purified via preparative LC/MS (Condition A: Gradient: 10-60% B over 20 minutes, then a 5-minute hold at 100% B) to give (R)-2-(5-(4-((1-(5-(aminomethyl)-2-fluorophenyl)ethyl)

amino)-3-chloroquinolin-6-yl)pyrimidin-2-yl)propan-2-ol (Example 429, 8.1 mg, 22% yield) as the first eluting product and (R)-2-(5-(3-chloro-4-((1-(2-fluoro-5-(hydroxymethyl)phenyl)ethyl)amino)quinolin-6-yl)pyrimidin-2-yl)propan-2-ol (Example 430, 1.5 mg, 4% yield) as the second eluding product. Analytical data for Example 429: LC/MS (M+H): 466; LC retention time: 1.41 min (Method A). $^1$H NMR (500 MHz, DMSO-$d_6$) δ 9.23 (s, 2H), 8.67 (s, 1H), 8.48 (s, 1H), 8.11 (d, J=8.4 Hz, 1H), 7.98 (d, J=8.7 Hz, 1H), 7.60 (d, J=6.6 Hz, 1H), 7.24 (br. s., 1H), 7.06 (t, J=9.4 Hz, 1H), 6.76 (d, J=8.8 Hz, 1H), 5.77-5.68 (m, 1H), 1.65 (d, J=6.6 Hz, 3H), 1.56 (s, 6H). Analytical data for Example 430: LC/MS (M+H): 467; LC retention time: 1.71 min (Method A). $^1$H NMR (500 MHz, DMSO-$d_6$) δ 9.24 (s, 2H), 8.72 (s, 1H), 8.47 (s, 1H), 8.12 (d, J=8.8 Hz, 1H), 7.98 (d, J=8.7 Hz, 1H), 7.57 (d, J=7.0 Hz, 1H), 7.16 (br. s., 1H), 7.05 (t, J=9.4 Hz, 1H), 6.81 (d, J=8.8 Hz, 1H), 5.81-5.72 (m, 1H), 4.37 (s, 2H), 1.65 (d, J=6.6 Hz, 3H), 1.57 (s, 6H).

Examples 431 and 432

(R)-2-(5-(3-chloro-4-((1-(2-fluoro-5-(hydroxymethyl)phenyl)ethyl)amino)-2-methylquinolin-6-yl)pyrimidin-2-yl)propan-2-ol and (R)-2-(5-(3-chloro-4-((1-(2-fluoro-5-(hydroxymethyl)phenyl)ethyl)amino)-2-methylquinolin-6-yl)-4,5-dihydropyrimidin-2-yl)propan-2-ol

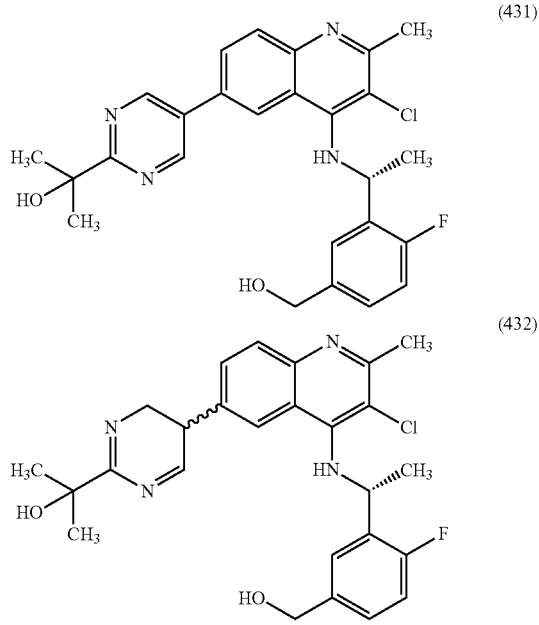

NaBH$_4$ (6.6 mg, 174 μmol) was added to an EtOH (0.5 mL) solution of (R)-3-(1-((3-chloro-6-(2-(2-hydroxypropan-2-yl)pyrimidin-5-yl)-2-methylquinolin-4-yl)amino)ethyl)-4-fluorobenzaldehyde (Intermediate 407A, 24.6 mg, 51 μmol) at 0° C. The mixture was stirred at 0° C. for 40 min, quenched with saturated NH$_4$Cl (0.5 mL) and stirred at room temperature overnight. The resulting mixture was extracted with EtOAc (2×1 mL). The combined organic extracts were concentrated, dissolved in MeOH (6 mL) and filtered. One third of the filtrate (2 mL) was purified via preparative LC/MS (Condition A: Gradient: 10-60% B over 20 minutes, then a 5-minute hold at 100% B) to give (R)-2-(5-(3-chloro-4-((1-(2-fluoro-5-(hydroxymethyl)phenyl)ethyl)amino)-2-methylquinolin-6-yl)pyrimidin-2-yl)propan-2-ol (Example 431, 2.1 mg, 8% yield). The remaining filtrate (4 mL) was purified via preparative HPLC (Condition C: Gradient: 0-100% B over 10 minutes, then a 2-minute hold at 100% B) to give additional (R)-2-(5-(3-chloro-4-((1-(2-fluoro-5-(hydroxymethyl)phenyl)ethyl)amino)-2-methylquinolin-6-yl)pyrimidin-2-yl)propan-2-ol TFA salt (5.8 mg, 17% yield) as the second eluting product and 2-(5-(3-chloro-4-(((R)-1-(2-fluoro-5-(hydroxymethyl)phenyl)ethyl)amino)-2-methylquinolin-6-yl)-4,5-dihydropyrimidin-2-yl)propan-2-ol TFA salt (Example 432, 6.1 mg, 18% yield) as the first eluting product.

Analytical data for Example 431: LC/MS (M+H): 481; LC retention time: 0.66 min (Method C). $^1$H NMR (400 MHz, 1:1 mixture of CDCl$_3$—CD$_3$OD) δ 8.84 (s, 2H), 8.36 (s, 1H), 8.16 (dd, J=8.7, 1.8 Hz, 1H), 8.03 (d, J=8.8 Hz, 1H), 7.53 (dd, J=7.4, 2.0 Hz, 1H), 7.36-7.30 (m, 1H), 7.11 (dd, J=10.3, 8.4 Hz, 1H), 5.93 (q, J=6.6 Hz, 1H), 4.56 (s, 2H), 2.86 (s, 3H), 1.83 (d, J=6.6 Hz, 3H), 1.64 (s, 6H).

Analytical data for Example 432: LC/MS (M+H): 483; LC retention time: 0.56 min (Method C). $^1$H NMR (400 MHz, 1:1 mixture of CDCl$_3$—CD$_3$OD) δ 8.00-7.95 (m, 1H), 7.93-7.86 (m, 2H), 7.52 (dd, J=7.4, 1.9 Hz, 1H), 7.37-7.28 (m, 1H), 7.14 (dd, J=10.4, 8.4 Hz, 1H), 6.81 (s, 1H), 5.87 (q, J=6.5 Hz, 1H), 4.59-4.54 (m, 3H), 4.53-4.31 (m, 2H), 2.82 (s, 3H), 1.82 (d, J=6.6 Hz, 3H), 1.56 (s, 6H).

Example 433

2-(5-(3-chloro-4-(((1R)-1-(2-fluoro-5-(1-hydroxyethyl)phenyl)ethyl)amino)-2-methylquinolin-6-yl)pyrimidin-2-yl)propan-2-ol

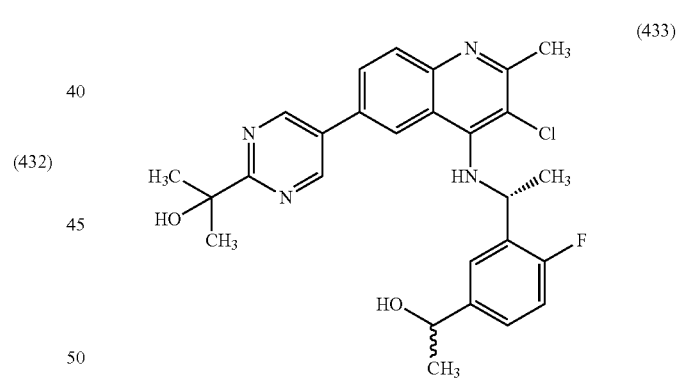

Following procedure analogous to the synthesis of Example 431, (R)-1-(3-(1-((3-chloro-6-(2-(2-hydroxypropan-2-yl)pyrimidin-5-yl)-2-methyl quinolin-4-yl)amino)ethyl)-4-fluorophenyl)ethanone (Intermediate 408A, 15 mg, 31 μmol) was converted to a diastereomeric mixture of 2-(5-(3-chloro-4-(((1R)-1-(2-fluoro-5-(1-hydroxyethyl)phenyl)ethyl)amino)-2-methylquinolin-6-yl)pyrimidin-2-yl)propan-2-ol TFA salt (5.4 mg, 26% yield). LC/MS (M+H): 495; LC retention time: 0.69 min (Method C). $^1$H NMR (400 MHz, 1:1 mixture of CDCl$_3$—CD$_3$OD) δ 8.81 (s, 2H), 8.34 (s, 1H), 8.13 (dd, J=9.0, 1.5 Hz, 1H), 8.03 (dd, J=8.8, 1.6 Hz, 1H), 7.54 (dd, J=5.0, 2.3 Hz, 1H), 7.37-7.29 (m, 1H), 7.08 (dd, J=10.3, 8.5 Hz, 1H), 5.89 (d, J=4.0 Hz, 1H), 4.79 (quin, J=6.1 Hz, 1H), 2.85 (d, J=1.2 Hz, 3H), 1.83 (dd, J=6.6, 2.0 Hz, 3H), 1.64 (s, 6H), 1.37 (dd, J=11.1, 6.5 Hz, 3H).

Example 434

2-(5-(4-(((1 S)-1-(5-(1-amino-2-hydroxyethyl)-2-fluorophenyl)-2,2-difluoroethyl)amino)-3-chloro-2-methylquinolin-6-yl)pyrimidin-2-yl)propan-2-ol

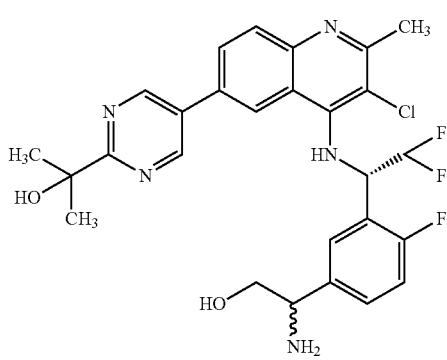
(434)

Intermediate 434A: tert-butyl (1-(3-((S)-1-((3-chloro-6-(2-(2-hydroxypropan-2-yl)pyrimidin-5-yl)-2-methyl quinolin-4-yl)amino)-2,2-difluoroethyl)-4-fluorophenyl)-2-hydroxyethyl)carbamate

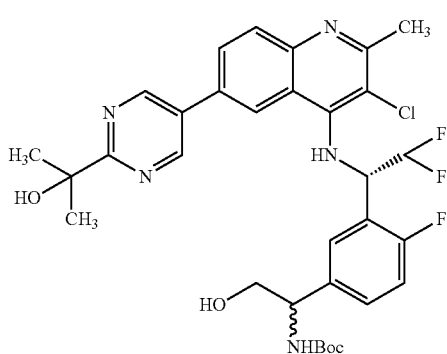
(434A)

A 2.5 wt % t-BuOH solution of osmium tetroxide (27 µL, 2.7 µmol) was added to an acetonitrile (0.25 mL) solution of tert-butyl (4-chlorobenzoyl)oxycarbamate (25 mg, 93 µmol). After stirring at room temperature for 10 min, the resulting solution was added to an acetonitrile (0.25 mL) suspension of Example 352 (34 mg, 66 µmol) followed by addition of water (0.1 mL). The resulting mixture was stirred at room temperature for 16 h. In a separate vial, additional 2.5 wt % osmium tetroxide in t-BuOH (127 µL, 12.7 mol) was added to an acetonitrile (0.25 mL) solution of tert-butyl (4-chlorobenzoyl)oxycarbamate (25 mg, 93 µmol). After stirring at room temperature for 1 h, this solution was added to the reaction mixture. After 8 days, the crude material was purified by silica gel column chromatography (4 g ISCO cartridge, 0-100% EtOAc/hexanes then 0-10% MeOH/CH₂Cl₂) to give tert-butyl (1-(3-((S)-1-((3-chloro-6-(2-(2-hydroxypropan-2-yl)pyrimidin-5-yl)-2-methyl quinolin-4-yl)amino)-2,2-difluoroethyl)-4-fluorophenyl)-2-hydroxyethyl)carbamate (14 mg, 33% yield). The regiochemistry of the aminohydroxylation reaction was tentatively assigned. LC/MS (M+H): 646; LC retention time: 0.77 min (Method C).

Example 434

A 4 M dioxane solution of HCl (0.25 mL, 1 mmol) was added to a CH₂Cl₂ (0.25 mL) solution of tert-butyl (1-(3-((S)-1-((3-chloro-6-(2-(2-hydroxypropan-2-yl)pyrimidin-5-yl)-2-methylquinolin-4-yl)amino)-2,2-difluoroethyl)-4-fluorophenyl)-2-hydroxyethyl) carbamate (Intermediate 434A, 12.3 mg, 19 µmol). After stirring at room temperature for 30 min, the mixture was diluted with MeOH (1.5 mL) and filtered. The filtrate was purified via preparative LC/MS (Condition A: Gradient: 15-55% B over 20 minutes, then a 5-minute hold at 100% B) to give 2-(5-(4-(((1S)-1-(5-(1-amino-2-hydroxyethyl)-2-fluorophenyl)-2,2-difluoroethyl)amino)-3-chloro-2-methylquinolin-6-yl)pyrimidin-2-yl)propan-2-ol (5.2 mg, 50% yield). LC/MS (M+H): 546; LC retention time: 1.37 min (Method A). ¹H NMR (400 MHz, methanol-d₄) δ 9.05 (br. s., 2H), 8.48-8.41 (m, 1H), 8.36 (dd, J=8.8, 1.6 Hz, 1H), 8.14 (d, J=8.7 Hz, 1H), 8.03-7.91 (m, 1H), 7.69-7.53 (m, 1H), 7.42-7.25 (m, 1H), 6.62-6.10 (m, 2H), 4.95 (dt, J=9.9, 3.1 Hz, 1H), 3.25-3.15 (m, 1H), 3.08-2.96 (m, 1H), 2.92 (s, 3H), 1.67 (s, 6H).

Example 435

(R)-2-(5-(3-chloro-4-((1-(2-fluoro-5-(2-hydroxyethoxy)phenyl)ethyl)amino)-2-methylquinolin-6-yl)pyrimidin-2-yl)propan-2-ol

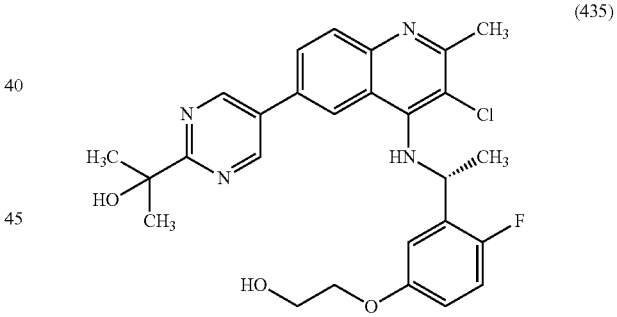
(435)

An ethylene glycol (0.5 mL, 9 mmol) suspension of Example 316 (20 mg, 38 µmol), K₂CO₃ (16 mg, 113 µmol) and copper(II) chloride (1.4 mg, 10.4 µmol) was heated in a sealed safety vial at 130° C. for 20 h. The resulting mixture was purified by preparative HPLC (Condition C: Gradient: 0-100% solvent B in 10 min then a 5-minute hold at 100% B) to give impure product. Further purification by silica gel column chromatography (2×4 g ISCO cartridge, 0-10% MeOH/CH₂Cl₂) gave (R)-2-(5-(3-chloro-4-((1-(2-fluoro-5-(2-hydroxyethoxy)phenyl)ethyl)amino)-2-methylquinolin-6-yl)pyrimidin-2-yl)propan-2-ol (3.1 mg, 15% yield). LC/MS (M+H): 511; LC retention time: 0.71 min (Method C). ¹H NMR (400 MHz, chloroform-d) δ 8.84 (s, 2H), 8.05 (dd, J=5.4, 3.3 Hz, 2H), 7.80 (dd, J=8.8, 2.0 Hz, 1H), 7.12-7.00 (m, 2H), 6.82 (dt, J=8.9, 3.5 Hz, 1H), 5.19 (br. s., 2H), 4.74 (s, 1H), 4.09-4.04 (m, 2H), 3.96 (q, J=3.9 Hz, 2H), 2.80 (s, 3H), 1.69 (d, J=5.6 Hz, 3H), 1.67 (d, J=1.6 Hz, 6H).

Example 436

(R)-2-(3-(1-((3-chloro-6-(2-(2-hydroxypropan-2-yl)pyrimidin-5-yl)-2-methylquinolin-4-yl)amino)ethyl)-4-fluorophenyl)acetic acid

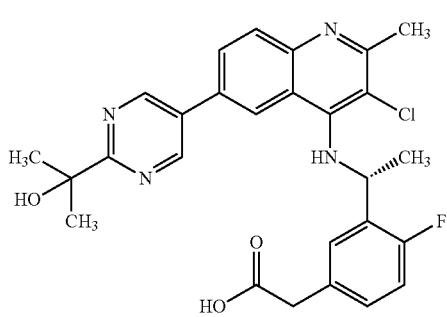

(436)

Dess-Martin periodinane (6.4 mg, 0.015 mmol) was added to a CH$_2$Cl$_2$ (0.5 mL) solution of Example 323 (6.7 mg, 0.014 mmol). After stirring at room temperature for 1.5 h, saturated NaHCO$_3$ (2 mL) was added. The resulting mixture was vigorously stirred for 0.5 h. The organic layer was separated and concentrated. The resulting solid residue was mixed with sodium dihydrogen phosphate (8.12 mg, 0.068 mmol), sodium chlorite (6.12 mg, 0.068 mmol) and 2 M THF solution of 2-methyl-2-butene (0.237 mL, 0.474 mmol). After stirring at room temperature for 1 h, the mixture was diluted with MeOH (1.5 mL) and filtered. The filtrate was purified by preparative reverse-phase HPLC (Condition C, 0-100% solvent B in 10 min then a 2-min hold at 100% B) to give (R)-2-(3-(1-((3-chloro-6-(2-(2-hydroxypropan-2-yl)pyrimidin-5-yl)-2-methylquinolin-4-yl)amino)ethyl)-4-fluorophenyl)acetic acid TFA salt (2.3 mg, 23% yield). LC/MS (M+H): 509; LC retention time: 0.68 min (Method C); $^1$H NMR (400 MHz, 1:1 mixture of CDCl$_3$—CD$_3$OD) δ 8.85 (s, 2H), 8.38 (s, 1H), 8.15 (dd, J=8.9, 1.7 Hz, 1H), 8.01 (d, J=8.8 Hz, 1H), 7.42 (dd, J=7.2, 2.2 Hz, 1H), 7.30-7.23 (m, 1H), 7.08 (dd, J=10.4, 8.4 Hz, 1H), 5.97-5.89 (m, 1H), 3.56 (s, 2H), 2.85 (s, 3H).

Additional examples prepared according to the procedures used to prepare Examples 1-436 or similar procedures are shown in Table 19

TABLE 19

| Ex. No. | Structure | MS observed (M$^{+1}$) | HPLC ret. Time (min.) | HPLC method |
|---|---|---|---|---|
| 437 | 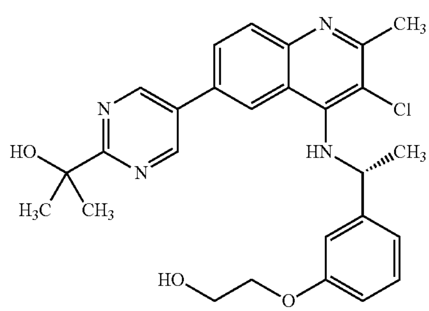 [SMILES: Cc1nc2ccc(-c3cnc(C(C)(C)O)nc3)cc2c(N[C@H](C)c2cccc(OCCO)c2)c1Cl] | 493 | 0.66 | C |
| 438 | 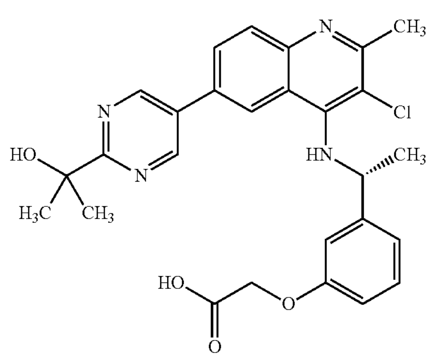 [SMILES: Cc1nc2ccc(-c3cnc(C(C)(C)O)nc3)cc2c(N[C@H](C)c2cccc(OCC(=O)O)c2)c1Cl] | 507 | 0.66 | C |

TABLE 19-continued

| Ex. No. | Structure | MS observed (M$^{+1}$) | HPLC ret. Time (min.) | HPLC method |
|---|---|---|---|---|
| 439 | 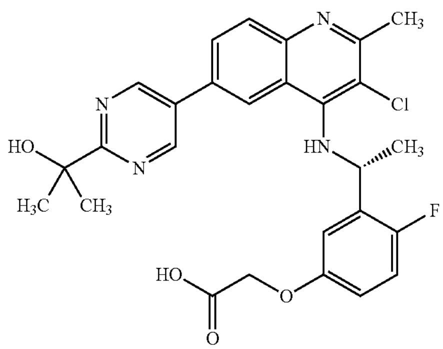 [SMILES: Cc1nc2ccc(-c3cnc(C(C)(C)O)nc3)cc2c(N[C@H](C)c2cc(OCC(=O)O)ccc2F)c1Cl] | 509 | 0.68 | C |
| 440 | 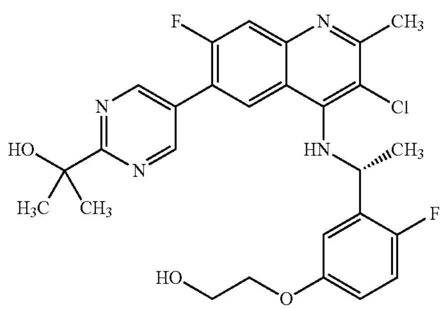 [SMILES: Cc1nc2cc(F)c(-c3cnc(C(C)(C)O)nc3)cc2c(N[C@H](C)c2cc(OCCO)ccc2F)c1Cl] | 529 | 0.69 | C |
| 441 | 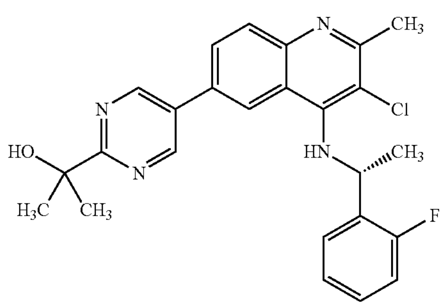 [SMILES: Cc1nc2ccc(-c3cnc(C(C)(C)O)nc3)cc2c(N[C@H](C)c2ccccc2F)c1Cl] | 451 | 2.112 | A |
| 442 | 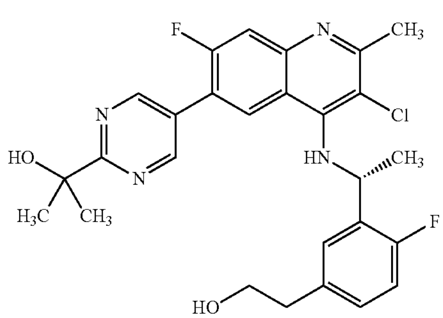 [SMILES: Cc1nc2cc(F)c(-c3cnc(C(C)(C)O)nc3)cc2c(N[C@H](C)c2cc(CCO)ccc2F)c1Cl] | 513 | 1.925 | A |

TABLE 19-continued

| Ex. No. | Structure | MS observed (M+1) | HPLC ret. Time (min.) | HPLC method |
|---|---|---|---|---|
| 443 | 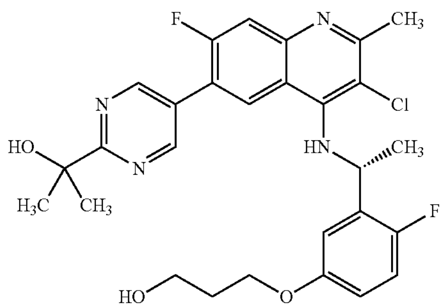 [SMILES: Cc1nc2cc(F)c(-c3cnc(C(C)(C)O)nc3)cc2c(N[C@H](C)c2cc(OCCCO)ccc2F)c1Cl] | 543 | 2.018 | A |
| 444 | 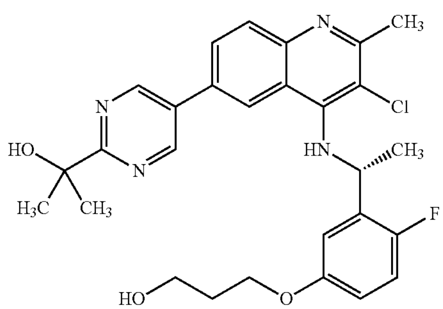 [SMILES: Cc1nc2ccc(-c3cnc(C(C)(C)O)nc3)cc2c(N[C@H](C)c2cc(OCCCO)ccc2F)c1Cl] | 525 | 1.816 | A |
| 445 | 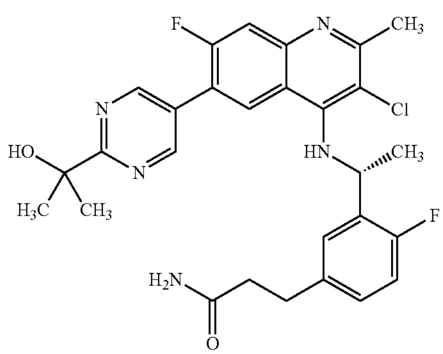 [SMILES: Cc1nc2cc(F)c(-c3cnc(C(C)(C)O)nc3)cc2c(N[C@H](C)c2cc(CCC(N)=O)ccc2F)c1Cl] | 540 | 0.66 | C |
| 446 | 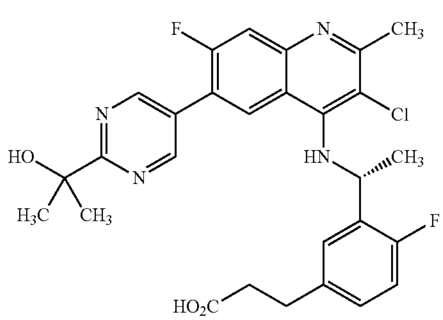 [SMILES: Cc1nc2cc(F)c(-c3cnc(C(C)(C)O)nc3)cc2c(N[C@H](C)c2cc(CCC(=O)O)ccc2F)c1Cl] | 541 | 0.71 | C |

TABLE 19-continued

| Ex. No. | Structure | MS observed (M$^{+1}$) | HPLC ret. Time (min.) | HPLC method |
|---|---|---|---|---|
| 447 | 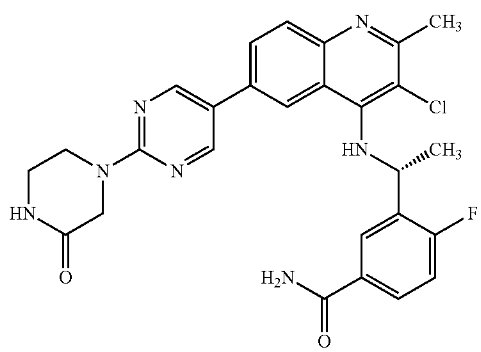 [SMILES: Cc1nc2ccc(-c3cnc(N4CCNC(=O)C4)nc3)cc2c(N[C@H](C)c2cc(C(N)=O)ccc2F)c1Cl] | 533.9 | 1.47 | A |
| 448 | 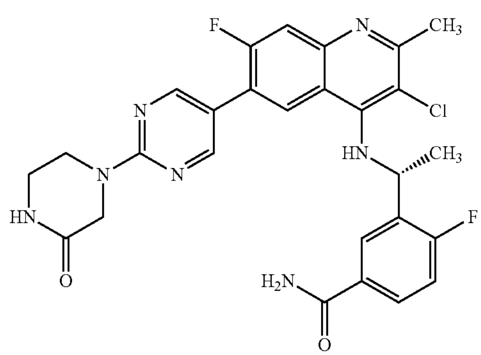 [SMILES: Cc1nc2cc(F)c(-c3cnc(N4CCNC(=O)C4)nc3)cc2c(N[C@H](C)c2cc(C(N)=O)ccc2F)c1Cl] | 551.7 | 1.58 | A |
| 449 | 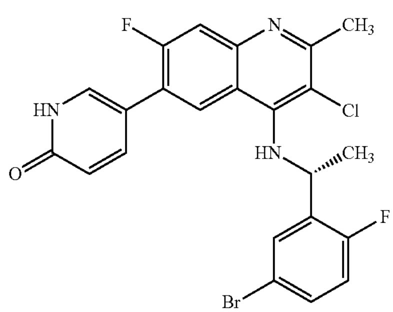 [SMILES: Cc1nc2cc(F)c(-c3ccc(=O)[nH]c3)cc2c(N[C@H](C)c2cc(Br)ccc2F)c1Cl] | 503.7 | 0.71 | C |
| 450 | 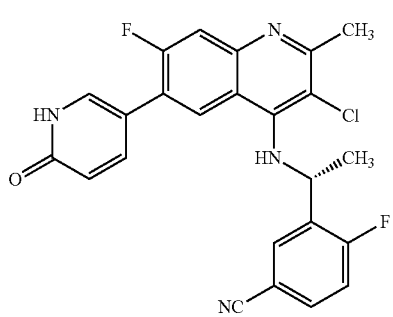 | 450.8 | 0.65 | C |

TABLE 19-continued

| Ex. No. | Structure | MS observed (M$^{+1}$) | HPLC ret. Time (min.) | HPLC method |
|---|---|---|---|---|
| 451 | 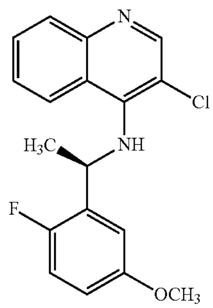 [SMILES: COc1ccc(F)c([C@@H](C)Nc2c(Cl)cnc3ccccc23)c1] | 330.7 | 0.73 | C |
| 452 | 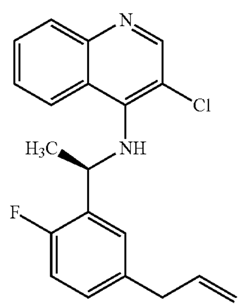 [SMILES: C=CCc1ccc(F)c([C@@H](C)Nc2c(Cl)cnc3ccccc23)c1] | 340.8 | 0.82 | C |
| 453 | 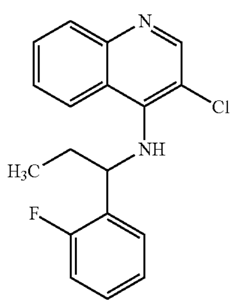 [SMILES: CCC(Nc1c(Cl)cnc2ccccc12)c1ccccc1F] | 315.2 | 2.21 | F |
| 454 | 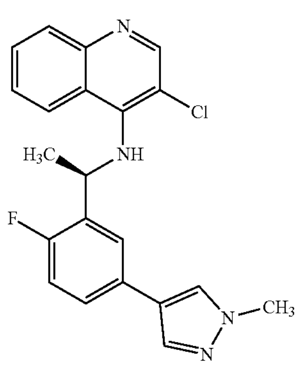 [SMILES: C[C@@H](Nc1c(Cl)cnc2ccccc12)c1cc(-c2cnn(C)c2)ccc1F] | 380.9 | 1.91 | F |

TABLE 19-continued

| Ex. No. | Structure | MS observed (M$^{+1}$) | HPLC ret. Time (min.) | HPLC method |
|---|---|---|---|---|
| 455 | 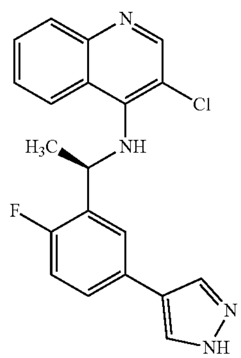 [SMILES: C[C@@H](Nc1c(Cl)cnc2ccccc12)c1cc(-c2cn[nH]c2)ccc1F] | 367.2 | 1.87 | F |
| 456 | 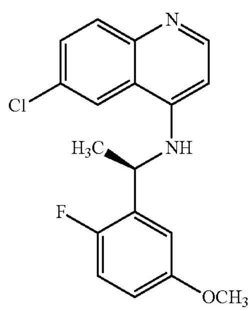 [SMILES: COc1ccc(F)c([C@@H](C)Nc2ccnc3ccc(Cl)cc23)c1] | 331.1 | 1.81 | F |
| 457 | 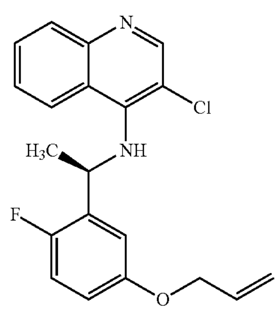 [SMILES: C=CCOc1ccc(F)c([C@@H](C)Nc2c(Cl)cnc3ccccc23)c1] | 356.7 | 0.78 | C |
| 458 | 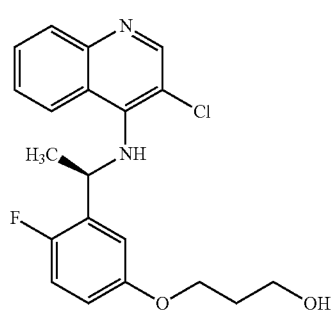 [SMILES: C[C@@H](Nc1c(Cl)cnc2ccccc12)c1cc(OCCCO)ccc1F] | 375.0 | 1.77 | F |

TABLE 19-continued

| Ex. No. | Structure | MS observed (M+1) | HPLC ret. Time (min.) | HPLC method |
|---|---|---|---|---|
| 459 | 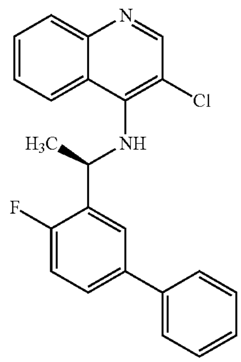 [SMILES: C[C@@H](Nc1c(Cl)cnc2ccccc12)c1cc(-c2ccccc2)ccc1F] | 377.0 | 2.47 | F |
| 460 | 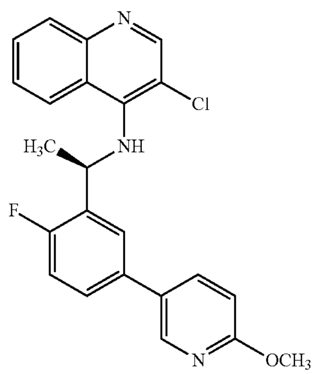 [SMILES: COc1ccc(-c2ccc(F)c([C@@H](C)Nc3c(Cl)cnc4ccccc34)c2)cn1] | 408.0 | 2.23 | F |
| 461 | 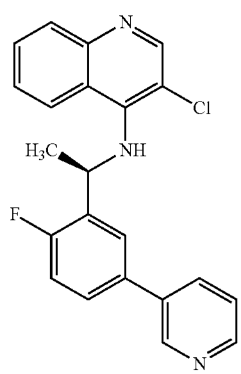 [SMILES: C[C@@H](Nc1c(Cl)cnc2ccccc12)c1cc(-c2cccnc2)ccc1F] | 378.3 | 1.90 | F |
| 462 | 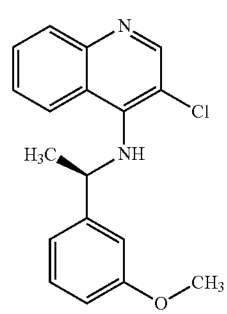 [SMILES: COc1cccc([C@@H](C)Nc2c(Cl)cnc3ccccc23)c1] | 313.3 | 1.96 | F |

TABLE 19-continued
| Ex. No. | Structure | MS observed (M$^{+1}$) | HPLC ret. Time (min.) | HPLC method |
|---|---|---|---|---|
| 463 | 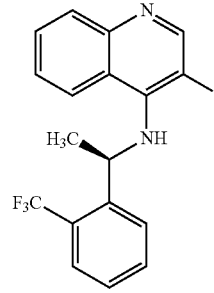 | 351.1 | 2.26 | F |
| 464 | 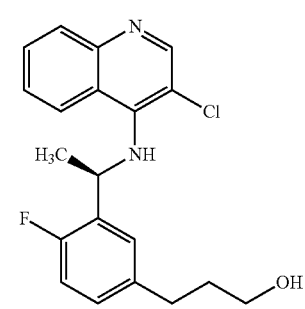 [SMILES: C[C@@H](Nc1c(Cl)cnc2ccccc12)c1cc(CCCO)ccc1F] | 359.2 | 1.77 | F |
| 465 | 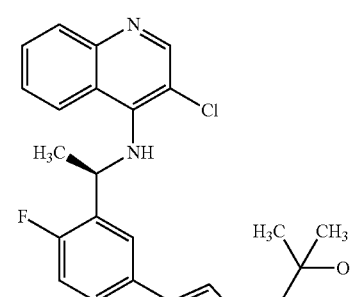 | 439.1 | 1.92 | F |
| 466 | 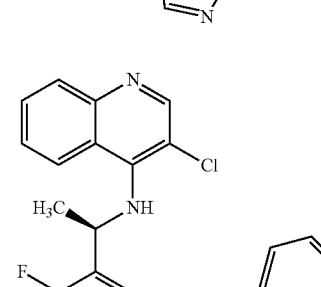 | 457.3 | 2.21 | F |

TABLE 19-continued

| Ex. No. | Structure | MS observed (M$^{+1}$) | HPLC ret. Time (min.) | HPLC method |
|---|---|---|---|---|
| 467 | 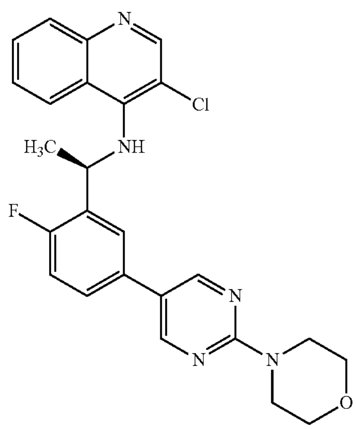 [SMILES: C[C@@H](Nc1c(Cl)cnc2ccccc12)c1cc(-c2cnc(N3CCOCC3)nc2)ccc1F] | 454.3 | 2.12 | F |
| 468 | 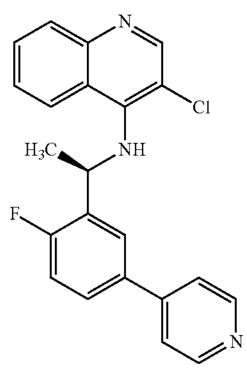 [SMILES: C[C@@H](Nc1c(Cl)cnc2ccccc12)c1cc(-c2ccncc2)ccc1F] | 378.1 | 1.97 | F |
| 469 | 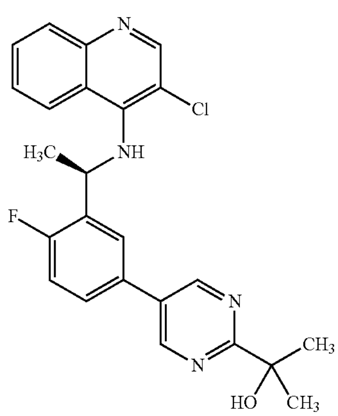 [SMILES: C[C@@H](Nc1c(Cl)cnc2ccccc12)c1cc(-c2cnc(C(C)(C)O)nc2)ccc1F] | 437.1 | 1.99 | F |
| 470 | 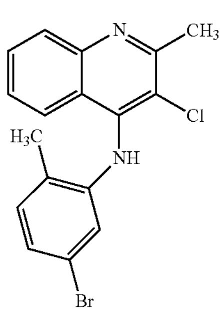 [SMILES: Cc1ccc(Br)cc1Nc1c(Cl)c(C)nc2ccccc12] | 360.7, 362.7 | 0.75 | C |

TABLE 19-continued

| Ex. No. | Structure | MS observed (M$^{+1}$) | HPLC ret. Time (min.) | HPLC method |
|---|---|---|---|---|
| 471 | 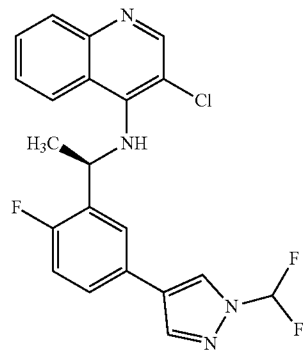 [SMILES: C[C@@H](Nc1c(Cl)cnc2ccccc12)c1cc(-c2cnn(C(F)F)c2)ccc1F] | 417.0 | 2.11 | F |
| 472 | 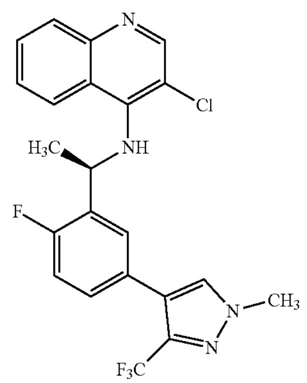 [SMILES: C[C@@H](Nc1c(Cl)cnc2ccccc12)c1cc(-c2cn(C)nc2C(F)(F)F)ccc1F] | 449.2 | 2.16 | F |
| 473 | 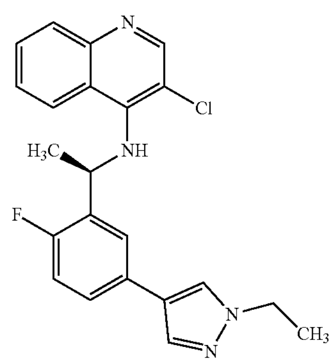 [SMILES: CCn1cc(-c2ccc(F)c([C@@H](C)Nc3c(Cl)cnc4ccccc34)c2)cn1] | 395.2 | 1.96 | F |
| 474 | 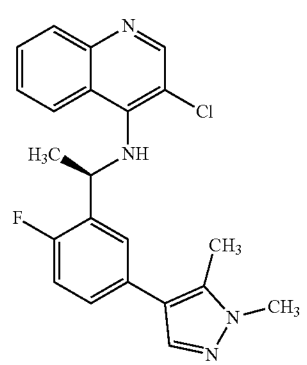 [SMILES: Cc1c(-c2ccc(F)c([C@@H](C)Nc3c(Cl)cnc4ccccc34)c2)cnn1C] | 395.3 | 1.96 | F |

TABLE 19-continued

| Ex. No. | Structure | MS observed (M$^{+1}$) | HPLC ret. Time (min.) | HPLC method |
|---|---|---|---|---|
| 475 | 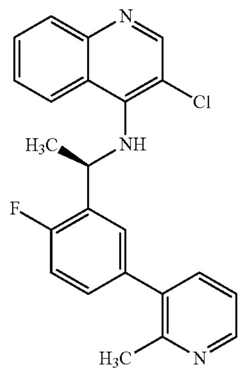 [SMILES: Cc1ncccc1-c1ccc(F)c([C@@H](C)Nc2c(Cl)cnc3ccccc23)c1] | 392.2 | 1.95 | F |
| 476 | 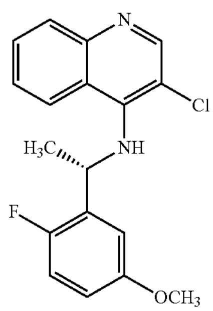 [SMILES: COc1ccc(F)c([C@H](C)Nc2c(Cl)cnc3ccccc23)c1] | 331.1 | 2.08 | F |
| 477 | 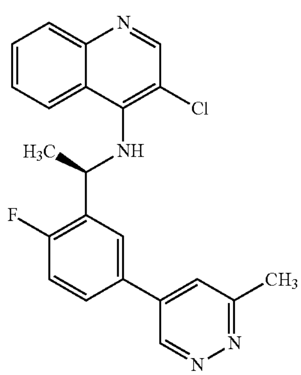 | 393.2 | 1.69 | F |
| 478 | 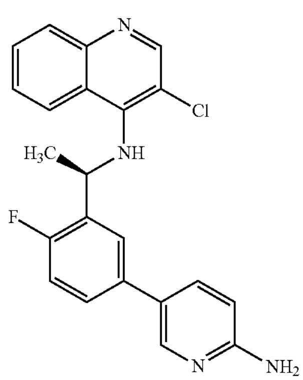 [SMILES: C[C@@H](Nc1c(Cl)cnc2ccccc12)c1cc(-c2ccc(N)nc2)ccc1F] | 393.2 | 1.78 | F |

TABLE 19-continued

| Ex. No. | Structure | MS observed (M$^{+1}$) | HPLC ret. Time (min.) | HPLC method |
|---|---|---|---|---|
| 479 | 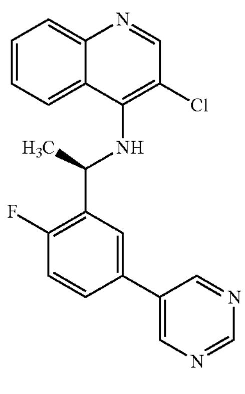 [SMILES: C[C@@H](Nc1c(Cl)cnc2ccccc12)c1cc(-c2cncnc2)ccc1F] | 379.0 | 1.78 | F |
| 480 | 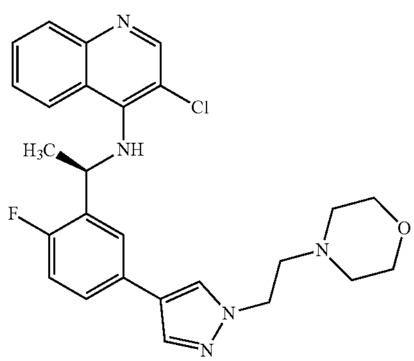 [SMILES: C[C@@H](Nc1c(Cl)cnc2ccccc12)c1cc(-c2cnn(CCN3CCOCC3)c2)ccc1F] | 480.1 | 1.80 | F |
| 481 | 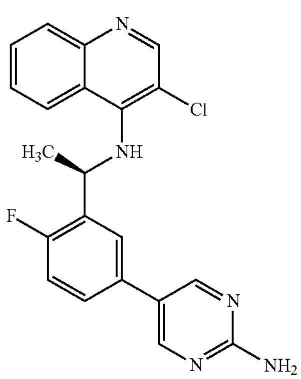 [SMILES: C[C@@H](Nc1c(Cl)cnc2ccccc12)c1cc(-c2cnc(N)nc2)ccc1F] | 394.2 | 1.66 | F |
| 482 | 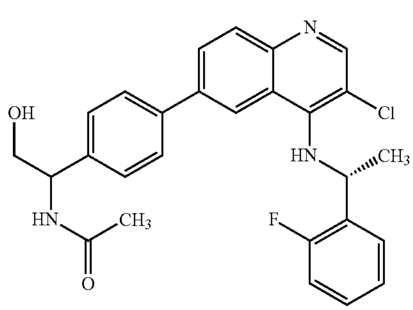 [SMILES: CC(=O)NC(CO)c1ccc(-c2ccc3ncc(Cl)c(N[C@H](C)c4ccccc4F)c3c2)cc1] | 478.0 | 1.739 | A |

TABLE 19-continued

| Ex. No. | Structure | MS observed (M+1) | HPLC ret. Time (min.) | HPLC method |
|---|---|---|---|---|
| 483 | 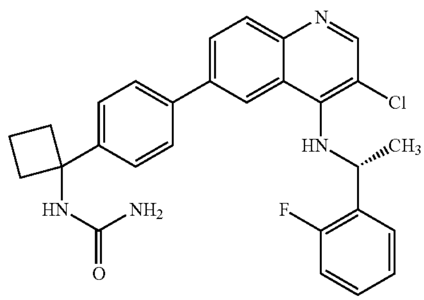 | 489.4 | 2.015 | A |
| 484 | 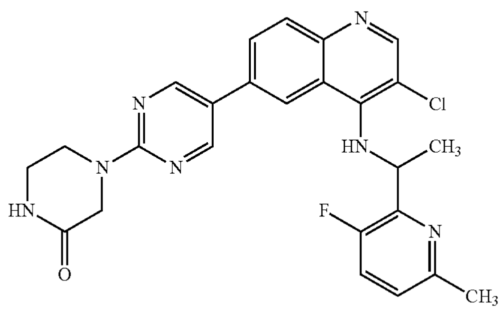 [SMILES: Cc1ccc(F)c(C(C)Nc2c(Cl)cnc3ccc(-c4cnc(N5CCNC(=O)C5)nc4)cc23)n1] | 503.0 | 1.661 | A |
| 485 | 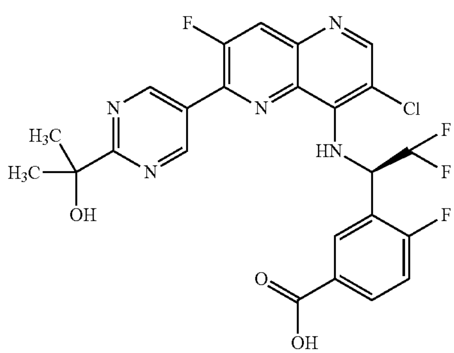 [SMILES: CC(C)(O)c1ncc(-c2nc3c(N[C@H](c4cc(C(=O)O)ccc4F)C(F)F)c(Cl)cnc3cc2F)cn1] | 536.1 (M + H)+ | 0.84 | C |
| 486 | 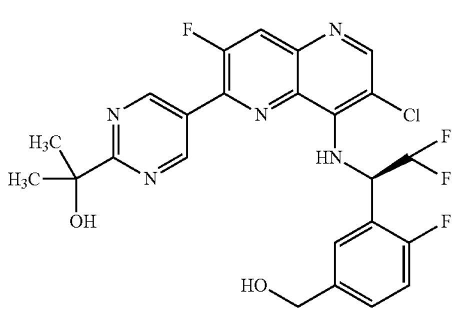 [SMILES: CC(C)(O)c1ncc(-c2nc3c(N[C@H](c4cc(CO)ccc4F)C(F)F)c(Cl)cnc3cc2F)cn1] | 522.2 (M + H)+ | 0.85 | C |

TABLE 19-continued

| Ex. No. | Structure | MS observed (M$^{+1}$) | HPLC ret. Time (min.) | HPLC method |
|---|---|---|---|---|
| 487 | 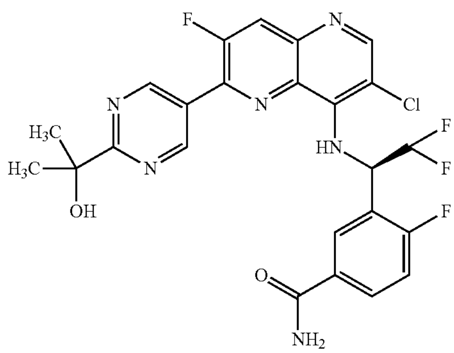 [SMILES: CC(C)(O)c1ncc(-c2nc3c(N[C@H](c4cc(C(N)=O)ccc4F)C(F)F)c(Cl)cnc3cc2F)cn1] | 535.1 (M + H)$^+$ | 0.77 | C |
| 488 | 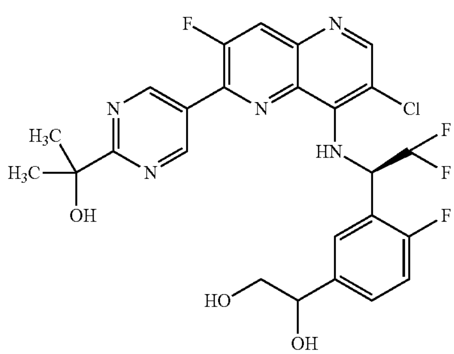 [SMILES: CC(C)(O)c1ncc(-c2nc3c(N[C@H](c4cc(C(O)CO)ccc4F)C(F)F)c(Cl)cnc3cc2F)cn1] | 552.1 (M + H)$^+$ | 0.76 | C |
| 489 | 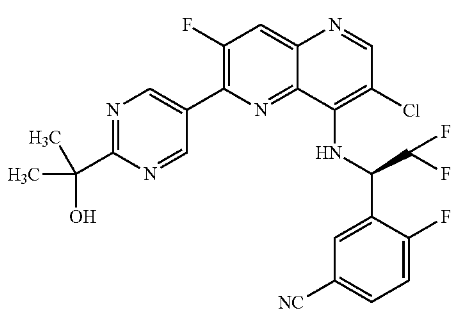 [SMILES: CC(C)(O)c1ncc(-c2nc3c(N[C@H](c4cc(C#N)ccc4F)C(F)F)c(Cl)cnc3cc2F)cn1] | 517.1 (M + H)$^+$ | 0.91 | C |
| 490 | 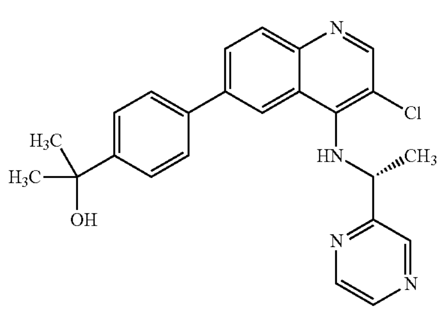 [SMILES: C[C@@H](Nc1c(Cl)cnc2ccc(-c3ccc(C(C)(C)O)cc3)cc12)c1cnccn1] | 419.0 (M + H)$^+$ | 0.67 | C |

TABLE 19-continued

| Ex. No. | Structure | MS observed (M+1) | HPLC ret. Time (min.) | HPLC method |
|---|---|---|---|---|
| 491 | 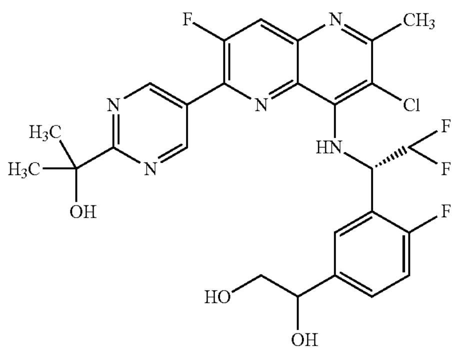 [SMILES: Cc1nc2cc(F)c(-c3cnc(C(C)(C)O)nc3)nc2c(N[C@@H](c2cc(C(O)CO)ccc2F)C(F)F)c1Cl] | 566.1 (M + H)+ | 0.71 | C |
| 492 | 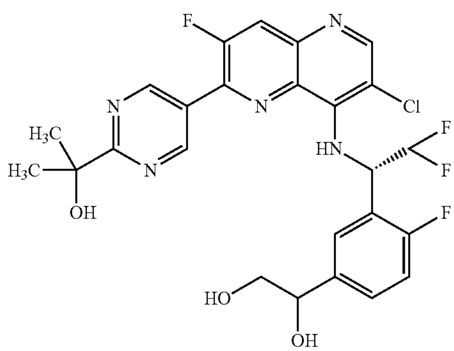 [SMILES: CC(C)(O)c1ncc(-c2nc3c(N[C@@H](c4cc(C(O)CO)ccc4F)C(F)F)c(Cl)cnc3cc2F)cn1] | 552.1 (M + H)+ | 0.77 | C |
| 493 | 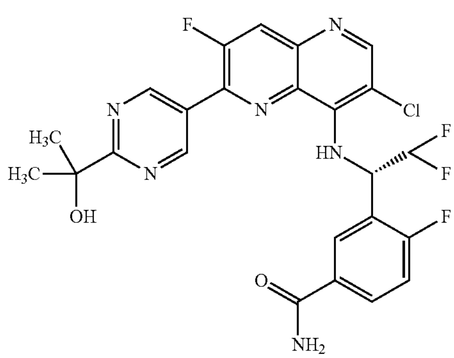 [SMILES: CC(C)(O)c1ncc(-c2nc3c(N[C@@H](c4cc(C(N)=O)ccc4F)C(F)F)c(Cl)cnc3cc2F)cn1] | 535.1 (M + H)+ | 0.79 | C |
| 494 | 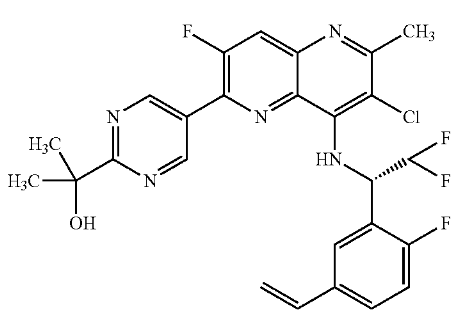 [SMILES: C=Cc1ccc(F)c([C@H](Nc2c(Cl)c(C)nc3cc(F)c(-c4cnc(C(C)(C)O)nc4)nc23)C(F)F)c1] | 532.1 (M + H)+ | 0.93 | C |

TABLE 19-continued

| Ex. No. | Structure | MS observed (M$^{+1}$) | HPLC ret. Time (min.) | HPLC method |
|---|---|---|---|---|
| 495 | 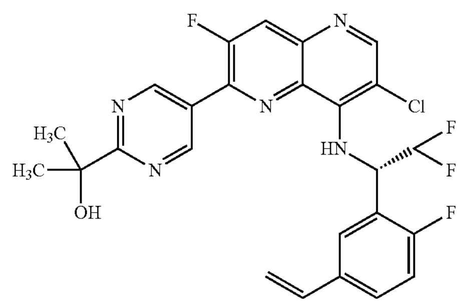 [SMILES: C=Cc1ccc(F)c([C@H](Nc2c(Cl)cnc3cc(F)c(-c4cnc(C(C)(C)O)nc4)nc23)C(F)F)c1] | 518.1 (M + H)$^+$ | 1.01 | C |
| 496 | 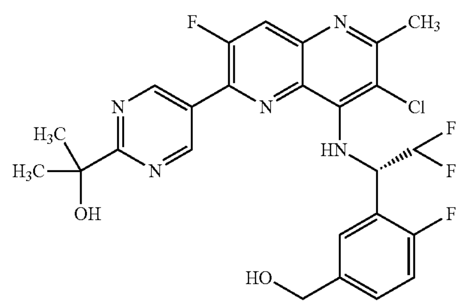 [SMILES: Cc1nc2cc(F)c(-c3cnc(C(C)(C)O)nc3)nc2c(N[C@@H](c2cc(CO)ccc2F)C(F)F)c1Cl] | 536.1 (M + H)$^+$ | 0.78 | C |
| 497 | 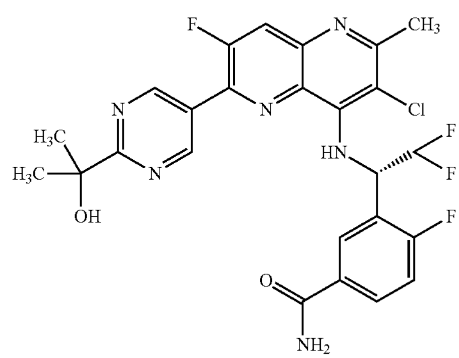 [SMILES: Cc1nc2cc(F)c(-c3cnc(C(C)(C)O)nc3)nc2c(N[C@@H](c2cc(C(N)=O)ccc2F)C(F)F)c1Cl] | 549.1 (M + H)$^+$ | 0.73 | C |
| 498 | 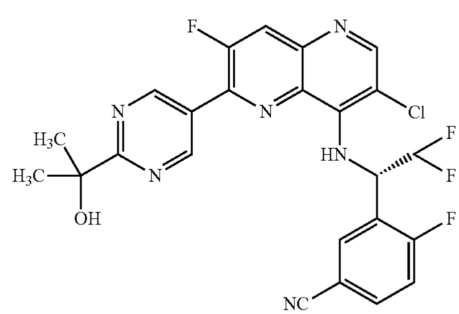 [SMILES: CC(C)(O)c1ncc(-c2nc3c(N[C@@H](c4cc(C#N)ccc4F)C(F)F)c(Cl)cnc3cc2F)cn1] | 517.2 (M + H)$^+$ | 0.93 | C |

TABLE 19-continued

| Ex. No. | Structure | MS observed (M$^{+1}$) | HPLC ret. Time (min.) | HPLC method |
|---|---|---|---|---|
| 499 | 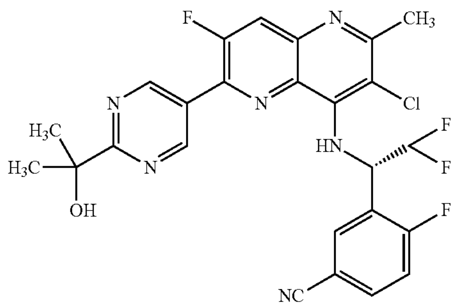 [SMILES: Cc1nc2cc(F)c(-c3cnc(C(C)(C)O)nc3)nc2c(N[C@@H](c2cc(C#N)ccc2F)C(F)F)c1Cl] | 531.3 (M + H)$^+$ | 0.87 | C |
| 500 | 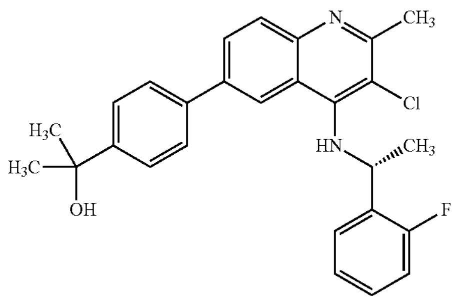 [SMILES: Cc1nc2ccc(-c3ccc(C(C)(C)O)cc3)cc2c(N[C@H](C)c2ccccc2F)c1Cl] | 449.1 (M + H)$^+$ | 0.80 | C |
| 501 | 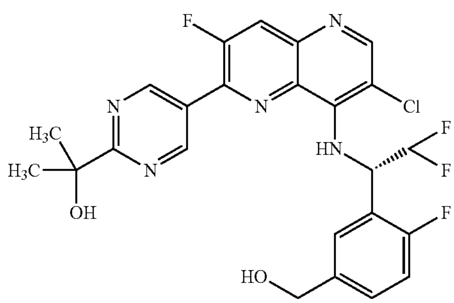 [SMILES: CC(C)(O)c1ncc(-c2nc3c(N[C@@H](c4cc(CO)ccc4F)C(F)F)c(Cl)cnc3cc2F)cn1] | 522.2 (M + H)$^+$ | 0.85 | C |
| 502 | 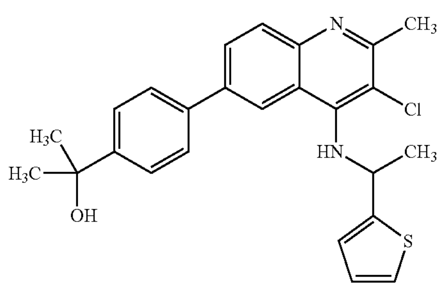 [SMILES: Cc1nc2ccc(-c3ccc(C(C)(C)O)cc3)cc2c(NC(C)c2cccs2)c1Cl] | 437.3 (M + H)$^+$ | 0.81 | C |
| 503 | 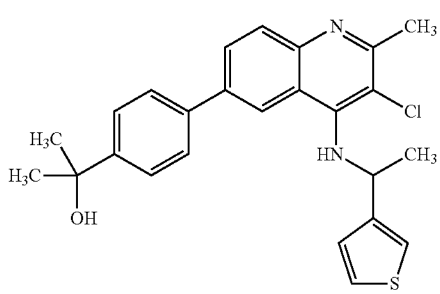 [SMILES: Cc1nc2ccc(-c3ccc(C(C)(C)O)cc3)cc2c(NC(C)c2ccsc2)c1Cl] | 437.1 (M + H)$^+$ | 0.82 | C |

TABLE 19-continued

| Ex. No. | Structure | MS observed (M$^{+1}$) | HPLC ret. Time (min.) | HPLC method |
|---|---|---|---|---|
| 504 | 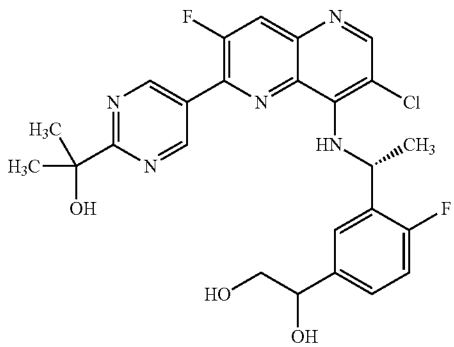 [SMILES: C[C@@H](Nc1c(Cl)cnc2cc(F)c(-c3cnc(C(C)(C)O)nc3)nc12)c1cc(C(O)CO)ccc1F] | 516.2 (M + H)$^+$ | 0.70 | C |
| 505 | 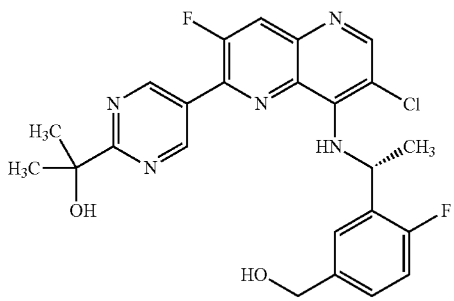 [SMILES: C[C@@H](Nc1c(Cl)cnc2cc(F)c(-c3cnc(C(C)(C)O)nc3)nc12)c1cc(CO)ccc1F] | 486.2 (M + H)$^+$ | 0.75 | C |
| 506 | 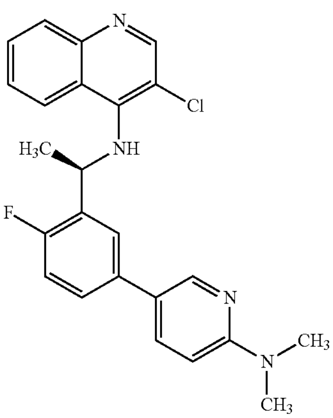 [SMILES: C[C@@H](Nc1c(Cl)cnc2ccccc12)c1cc(-c2ccc(N(C)C)nc2)ccc1F] | 419.0 | 2.282 | F |
| 507 | 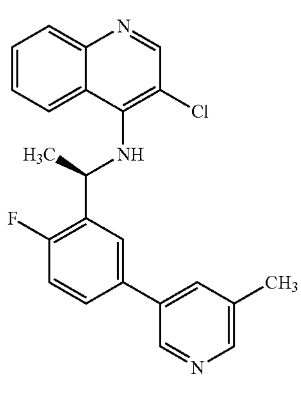 | 392.2 | 2.007 | F |

TABLE 19-continued

| Ex. No. | Structure | MS observed (M+1) | HPLC ret. Time (min.) | HPLC method |
|---|---|---|---|---|
| 508 | 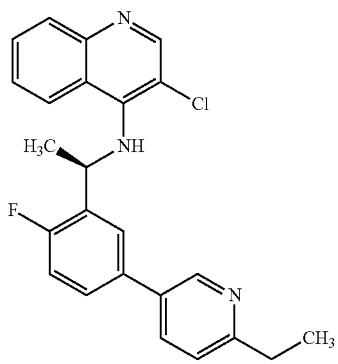 [SMILES: CCc1ccc(-c2ccc(F)c([C@@H](C)Nc3c(Cl)cnc4ccccc34)c2)cn1] | 404.0 | 2.209 | F |
| 509 | 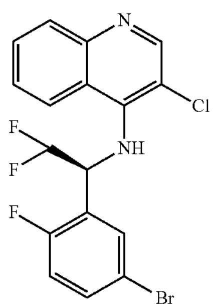 [SMILES: Fc1ccc(Br)cc1[C@H](Nc1c(Cl)cnc2ccccc12)C(F)F] | 416.9 | 2.156 | F |
| 510 | 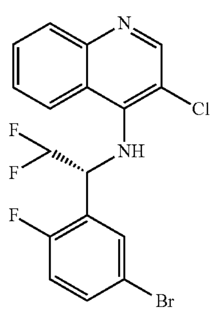 [SMILES: Fc1ccc(Br)cc1[C@@H](Nc1c(Cl)cnc2ccccc12)C(F)F] | 416.7 | 2.155 | F |
| 511 | 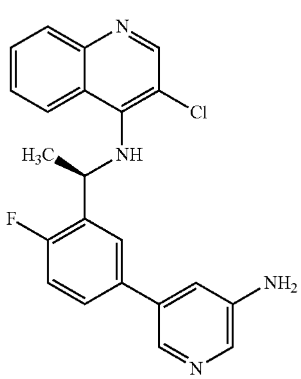 [SMILES: C[C@@H](Nc1c(Cl)cnc2ccccc12)c1cc(-c2cncc(N)c2)ccc1F] | 393.1 | 1.690 | F |

TABLE 19-continued

| Ex. No. | Structure | MS observed (M+1) | HPLC ret. Time (min.) | HPLC method |
|---|---|---|---|---|
| 512 | 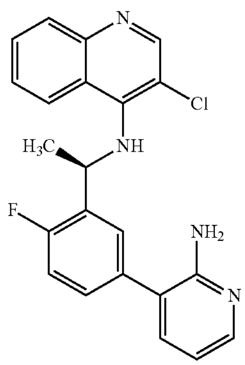 [SMILES: C[C@@H](Nc1c(Cl)cnc2ccccc12)c1cc(-c2cccnc2N)ccc1F] | 393.0 | 1.832 | F |
| 513 | 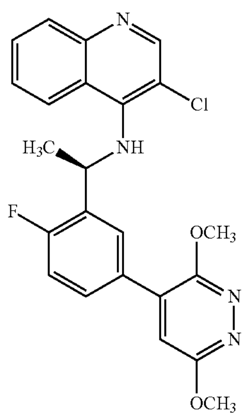 [SMILES: COc1cc(-c2ccc(F)c([C@@H](C)Nc3c(Cl)cnc4ccccc34)c2)c(OC)nn1] | 439.2 | 2.093 | F |
| 514 | 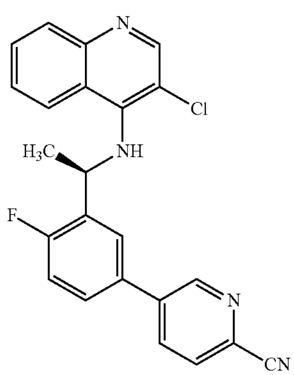 [SMILES: C[C@@H](Nc1c(Cl)cnc2ccccc12)c1cc(-c2ccc(C#N)nc2)ccc1F] | 403.1 | 2.089 | F |
| 515 | 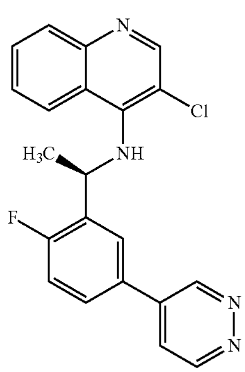 [SMILES: C[C@@H](Nc1c(Cl)cnc2ccccc12)c1cc(-c2ccnnc2)ccc1F] | 379.1 | 1.631 | F |

TABLE 19-continued
| Ex. No. | Structure | MS observed (M+1) | HPLC ret. Time (min.) | HPLC method |
|---|---|---|---|---|
| 516 | 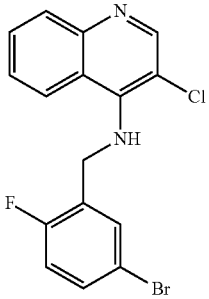 [SMILES: Fc1ccc(Br)cc1CNc1c(Cl)cnc2ccccc12] | 366.6 | 2.093 | F |
| 517 | 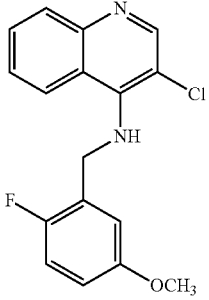 | 316.7 | 1.876 | F |
| 518 | 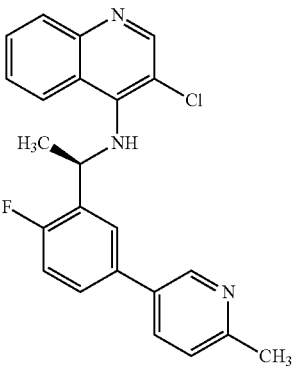 | 392.0 | 2.019 | F |
| 519 | 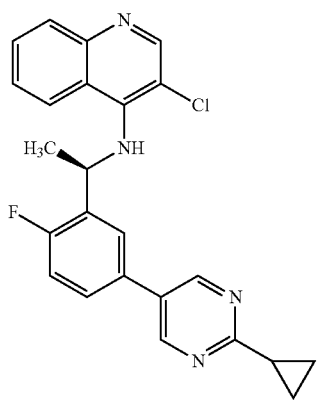 [SMILES: C[C@@H](Nc1c(Cl)cnc2ccccc12)c1cc(-c2cnc(C3CC3)nc2)ccc1F] | 419.1 | 2.141 | F |

TABLE 19-continued

| Ex. No. | Structure | MS observed (M+1) | HPLC ret. Time (min.) | HPLC method |
|---|---|---|---|---|
| 520 | 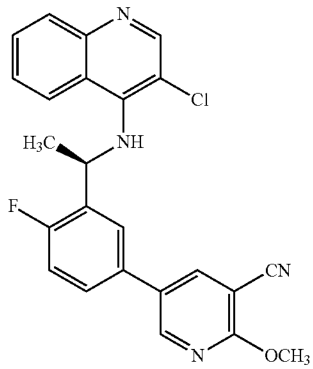 [SMILES: COc1ncc(-c2ccc(F)c([C@@H](C)Nc3c(Cl)cnc4ccccc34)c2)cc1C#N] | 433.0 | 2.278 | F |
| 521 | 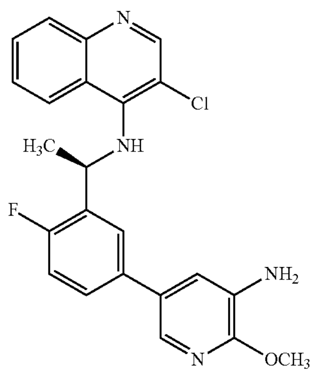 [SMILES: COc1ncc(-c2ccc(F)c([C@@H](C)Nc3c(Cl)cnc4ccccc34)c2)cc1N] | 423.2 | 1.981 | F |
| 522 | 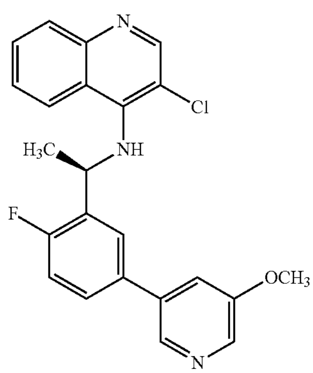 [SMILES: COc1cncc(-c2ccc(F)c([C@@H](C)Nc3c(Cl)cnc4ccccc34)c2)c1] | 406.0 | 2.028 | F |
| 523 | 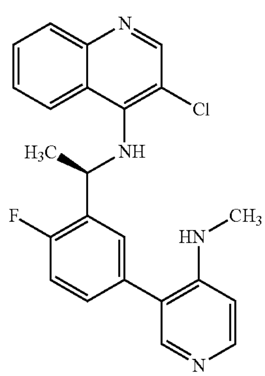 [SMILES: CNc1ccncc1-c1ccc(F)c([C@@H](C)Nc2c(Cl)cnc3ccccc23)c1] | 407.2 | 1.378 | F |

TABLE 19-continued
| Ex. No. | Structure | MS observed ($M^{+1}$) | HPLC ret. Time (min.) | HPLC method |
|---|---|---|---|---|
| 524 | 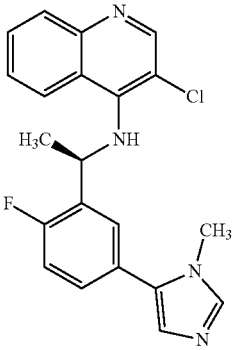 [SMILES: C[C@@H](Nc1c(Cl)cnc2ccccc12)c1cc(-c2cncn2C)ccc1F] | 381.2 | 1.754 | F |
| 525 | 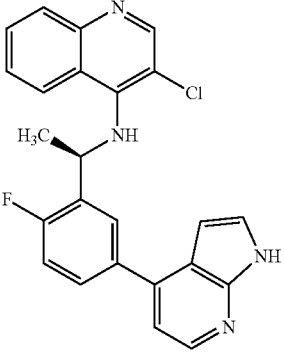 [SMILES: C[C@@H](Nc1c(Cl)cnc2ccccc12)c1cc(-c2ccnc3[nH]ccc23)ccc1F] | 417.1 | 1.971 | F |
| 526 | 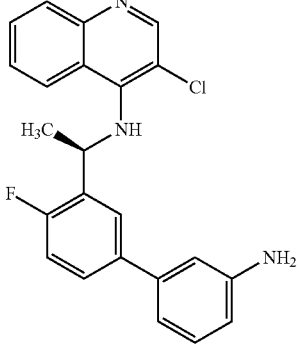 | 392.2 | 2.054 | F |
| 527 | 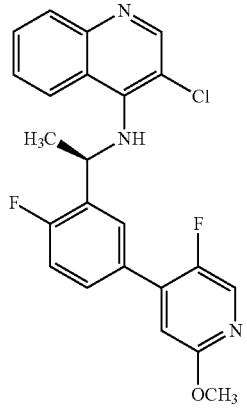 | 426.2 | 2.319 | F |

TABLE 19-continued

| Ex. No. | Structure | MS observed (M+1) | HPLC ret. Time (min.) | HPLC method |
|---|---|---|---|---|
| 528 | 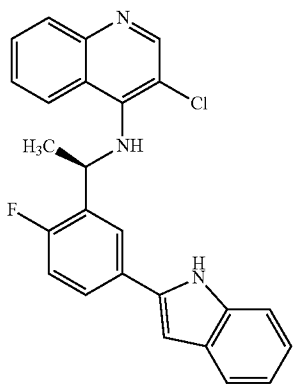 [SMILES: C[C@@H](Nc1c(Cl)cnc2ccccc12)c1cc(-c2cc3ccccc3[nH]2)ccc1F] | 416.1 | 2.364 | F |
| 529 | 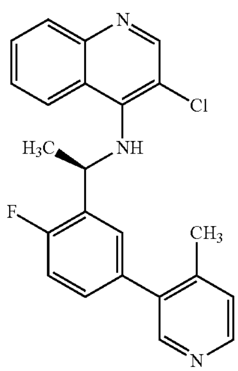 | 392.2 | 2.127 | F |
| 530 | 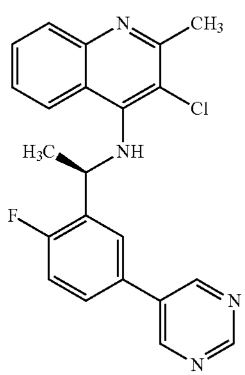 [SMILES: Cc1nc2ccccc2c(N[C@H](C)c2cc(-c3cncnc3)ccc2F)c1Cl] | 392.9 | 1.917 | F |
| 531 | 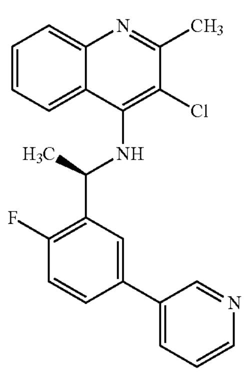 [SMILES: Cc1nc2ccccc2c(N[C@H](C)c2cc(-c3cccnc3)ccc2F)c1Cl] | 390.0 | 2.072 | F |

TABLE 19-continued

| Ex. No. | Structure | MS observed (M+1) | HPLC ret. Time (min.) | HPLC method |
|---|---|---|---|---|
| 532 | 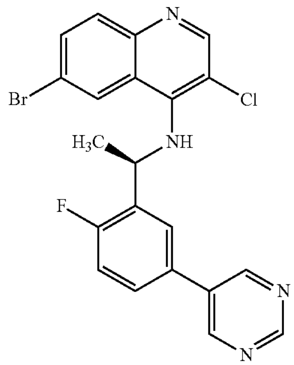 [SMILES: C[C@@H](Nc1c(Cl)cnc2ccc(Br)cc12)c1cc(-c2cncnc2)ccc1F] | 456.9 | 2.071 | F |
| 533 | 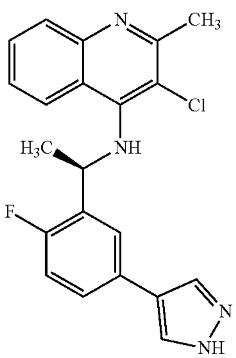 [SMILES: Cc1nc2ccccc2c(N[C@H](C)c2cc(-c3cn[nH]c3)ccc2F)c1Cl] | 379.0 | 1.894 | F |
| 534 | 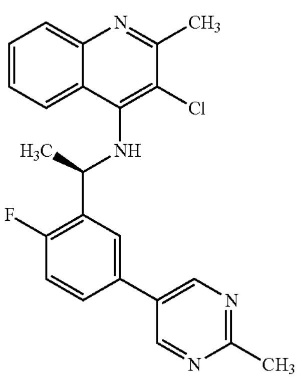 [SMILES: Cc1ncc(-c2ccc(F)c([C@@H](C)Nc3c(Cl)c(C)nc4ccccc34)c2)cn1] | 406.9 | 1.996 | F |
| 535 | 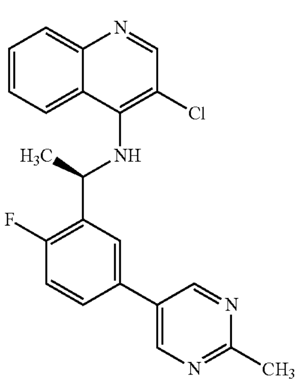 | 393.2 | 1.763 | F |

TABLE 19-continued

| Ex. No. | Structure | MS observed (M$^{+1}$) | HPLC ret. Time (min.) | HPLC method |
|---|---|---|---|---|
| 536 | 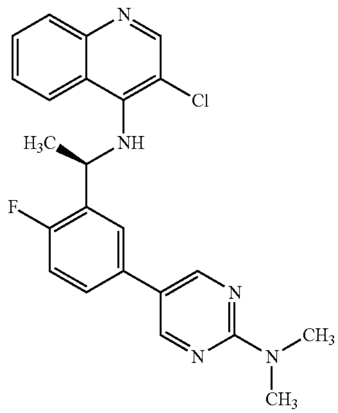 [SMILES: C[C@@H](Nc1c(Cl)cnc2ccccc12)c1cc(-c2cnc(N(C)C)nc2)ccc1F] | 422.1 | 2.226 | F |
| 537 | 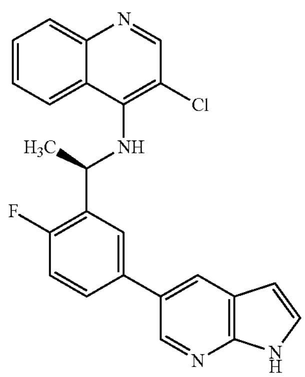 [SMILES: C[C@@H](Nc1c(Cl)cnc2ccccc12)c1cc(-c2cnc3[nH]ccc3c2)ccc1F] | 417.1 | 2.016 | F |
| 538 | 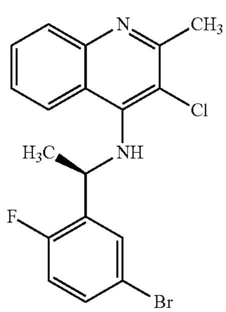 [SMILES: Cc1nc2ccccc2c(N[C@H](C)c2cc(Br)ccc2F)c1Cl] | 392.7, 394.7 | 0.78 | C |
| 539 | 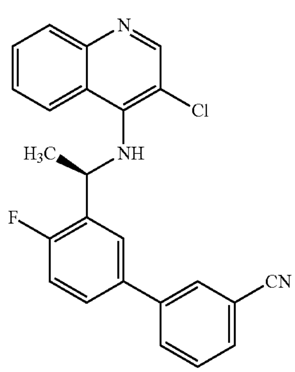 [SMILES: C[C@@H](Nc1c(Cl)cnc2ccccc12)c1cc(-c2cccc(C#N)c2)ccc1F] | 402.3 | 2.279 | F |

TABLE 19-continued

| Ex. No. | Structure | MS observed ($M^{+1}$) | HPLC ret. Time (min.) | HPLC method |
|---|---|---|---|---|
| 540 | 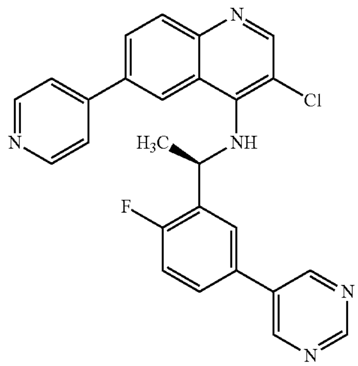 [SMILES: C[C@@H](Nc1c(Cl)cnc2ccc(-c3ccncc3)cc12)c1cc(-c2cncnc2)ccc1F] | 456.1 | 1.699 | F |
| 541 | 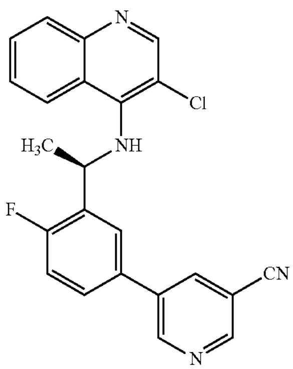 [SMILES: C[C@@H](Nc1c(Cl)cnc2ccccc12)c1cc(-c2cncc(C#N)c2)ccc1F] | 403.0 | 1.943 | F |
| 542 | 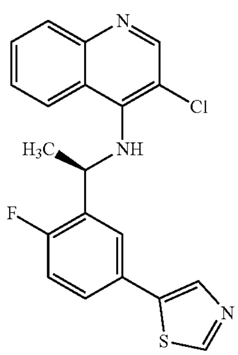 [SMILES: C[C@@H](Nc1c(Cl)cnc2ccccc12)c1cc(-c2cncs2)ccc1F] | 382.2 | 2.139 | F |
| 543 | 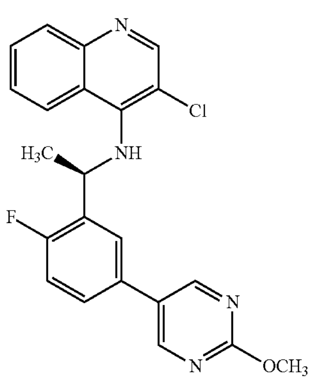 [SMILES: COc1ncc(-c2ccc(F)c([C@@H](C)Nc3c(Cl)cnc4ccccc34)c2)cn1] | 409.1 | 1.986 | F |

TABLE 19-continued

| Ex. No. | Structure | MS observed (M+1) | HPLC ret. Time (min.) | HPLC method |
|---|---|---|---|---|
| 544 | 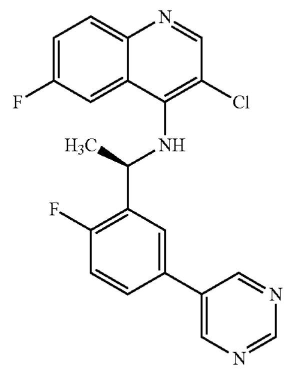 [SMILES: C[C@@H](Nc1c(Cl)cnc2ccc(F)cc12)c1cc(-c2cncnc2)ccc1F] | 397.1 | 1.827 | F |
| 545 | 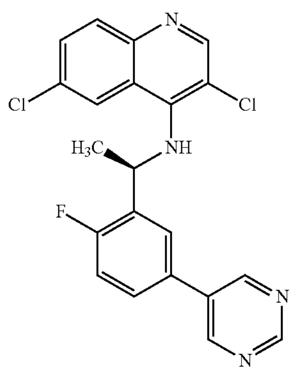 [SMILES: C[C@@H](Nc1c(Cl)cnc2ccc(Cl)cc12)c1cc(-c2cncnc2)ccc1F] | 413.3 | 2.162 | F |
| 546 | 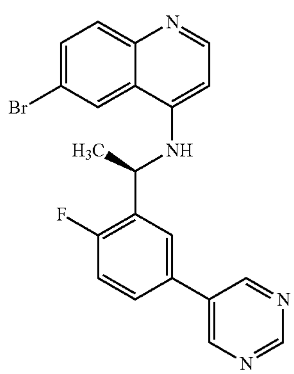 [SMILES: C[C@@H](Nc1ccnc2ccc(Br)cc12)c1cc(-c2cncnc2)ccc1F] | 423.1 | 1.351 | F |
| 547 | 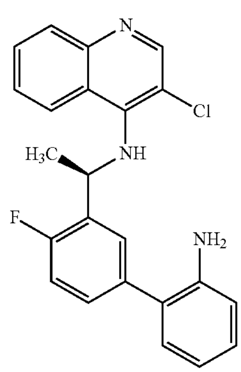 | 392.2 | 2.155 | F |

TABLE 19-continued

| Ex. No. | Structure | MS observed (M+1) | HPLC ret. Time (min.) | HPLC method |
|---|---|---|---|---|
| 548 | 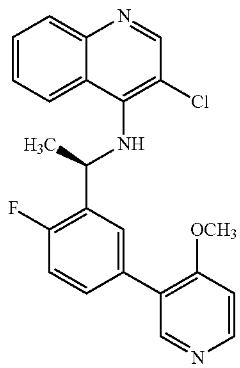 [SMILES: COc1ccncc1-c1ccc(F)c([C@@H](C)Nc2c(Cl)cnc3ccccc23)c1] | 408.1 | 1.934 | F |
| 549 | 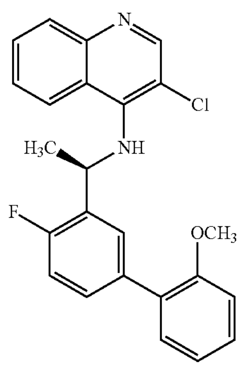 [SMILES: COc1ccccc1-c1ccc(F)c([C@@H](C)Nc2c(Cl)cnc3ccccc23)c1] | 407.3 | 2.385 | F |
| 550 | 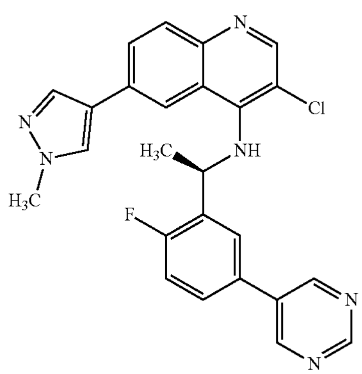 [SMILES: C[C@@H](Nc1c(Cl)cnc2ccc(-c3cnn(C)c3)cc12)c1cc(-c2cncnc2)ccc1F] | 459.3 | 1.641 | F |
| 551 | 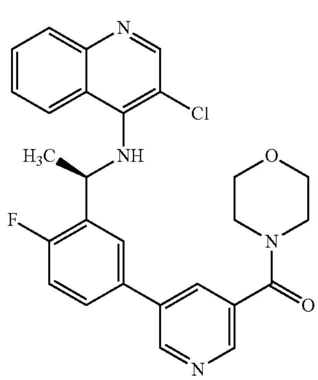 [SMILES: C[C@@H](Nc1c(Cl)cnc2ccccc12)c1cc(-c2cncc(C(=O)N3CCOCC3)c2)ccc1F] | 491.2 | 1.692 | F |

TABLE 19-continued
| Ex. No. | Structure | MS observed (M+1) | HPLC ret. Time (min.) | HPLC method |
|---|---|---|---|---|
| 552 | 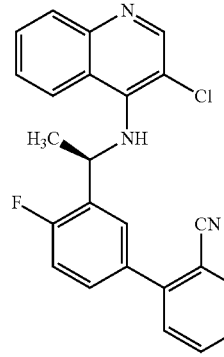 | 402.1 | 2.195 | F |
| 553 | 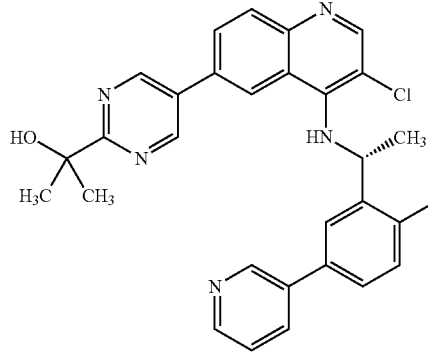 | 514.2 | 1.909 | F |
| 554 | 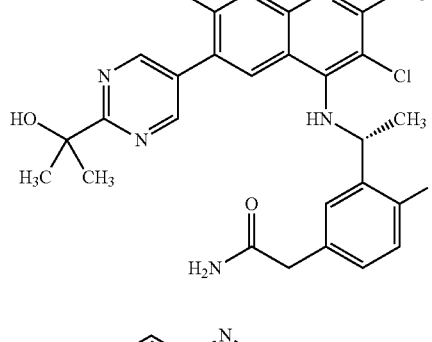 | 525.8 | 0.67 | C |
| 555 | 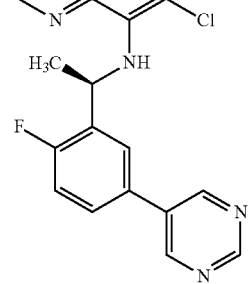 | 379.7 | 0.68 | C |

TABLE 19-continued
| Ex. No. | Structure | MS observed ($M^{+1}$) | HPLC ret. Time (min.) | HPLC method |
|---|---|---|---|---|
| 556 | 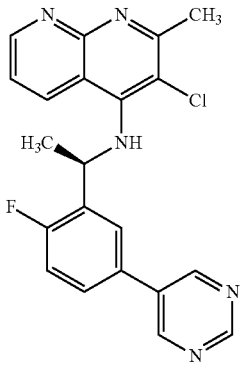 | 393.8 | 0.63 | C |
| 557 | 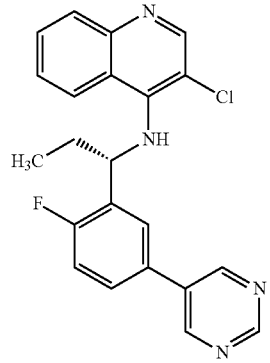 [SMILES: CC[C@H](Nc1c(Cl)cnc2ccccc12)c1cc(-c2cncnc2)ccc1F] | 393.2 | 1.882 | F |
| 558 | 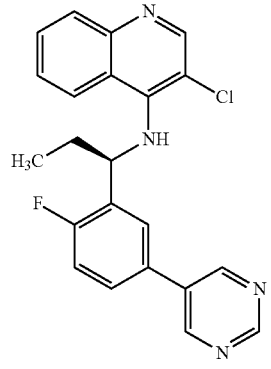 [SMILES: CC[C@@H](Nc1c(Cl)cnc2ccccc12)c1cc(-c2cncnc2)ccc1F] | 393.3 | 1.805 | F |
| 559 | 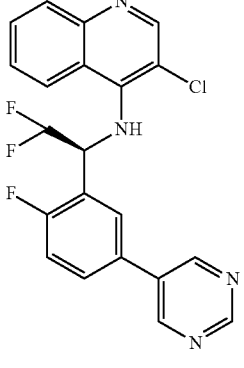 | 415.2 | 1.705 | F |

TABLE 19-continued

| Ex. No. | Structure | MS observed (M$^{+1}$) | HPLC ret. Time (min.) | HPLC method |
|---|---|---|---|---|
| 560 | 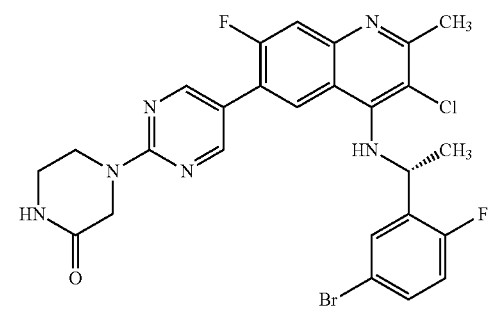 [SMILES: Cc1nc2cc(F)c(-c3cnc(N4CCNC(=O)C4)nc3)cc2c(N[C@H](C)c2cc(Br)ccc2F)c1Cl] | 586.7 588.8 | 0.74 | C |
| 561 | 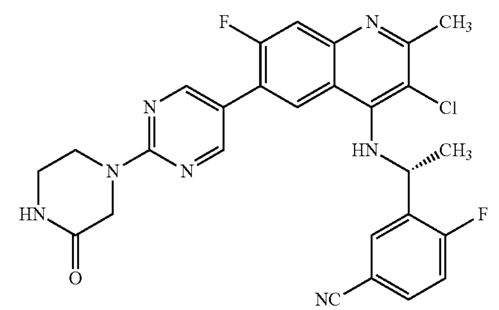 [SMILES: Cc1nc2cc(F)c(-c3cnc(N4CCNC(=O)C4)nc3)cc2c(N[C@H](C)c2cc(C#N)ccc2F)c1Cl] | 533.7 | 0.68 | C |
| 562 | 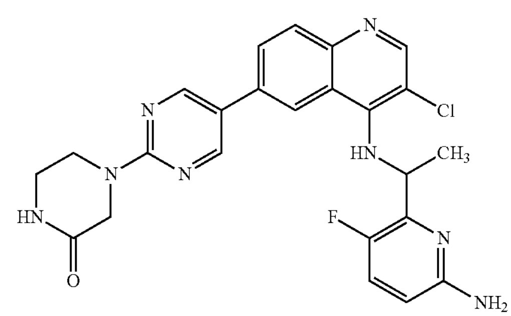 [SMILES: CC(Nc1c(Cl)cnc2ccc(-c3cnc(N4CCNC(=O)C4)nc3)cc12)c1nc(N)ccc1F] | 493.0 | 1.630 | A |
| 563 | 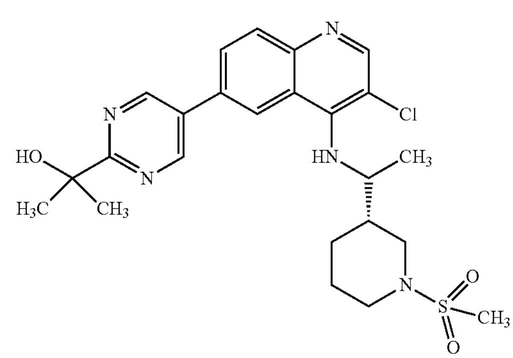 [SMILES: CC(Nc1c(Cl)cnc2ccc(-c3cnc(C(C)(C)O)nc3)cc12)[C@H]1CCCN(S(C)(=O)=O)C1] | 504.0 | 1.617 | A |

TABLE 19-continued

| Ex. No. | Structure | MS observed (M+1) | HPLC ret. Time (min.) | HPLC method |
|---|---|---|---|---|
| 564 | 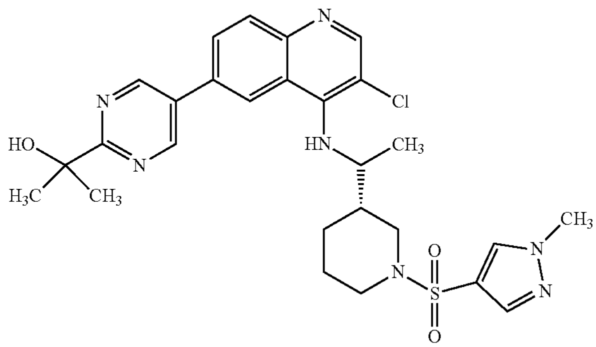 [SMILES: CC(Nc1c(Cl)cnc2ccc(-c3cnc(C(C)(C)O)nc3)cc12)[C@H]1CCCN(S(=O)(=O)c2cnn(C)c2)C1] | 570.0 | 1.631 | A |
| 565 | 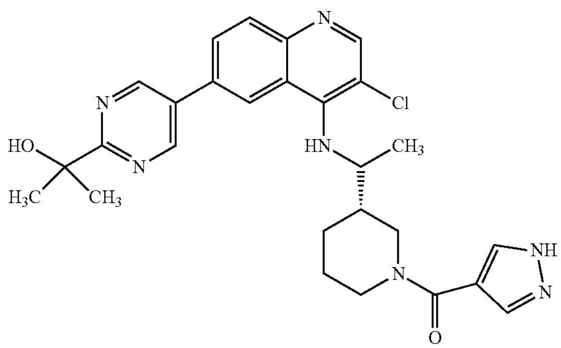 [SMILES: CC(Nc1c(Cl)cnc2ccc(-c3cnc(C(C)(C)O)nc3)cc12)[C@H]1CCCN(C(=O)c2cn[nH]c2)C1] | 520.0 | 1.498 | A |
| 566 | 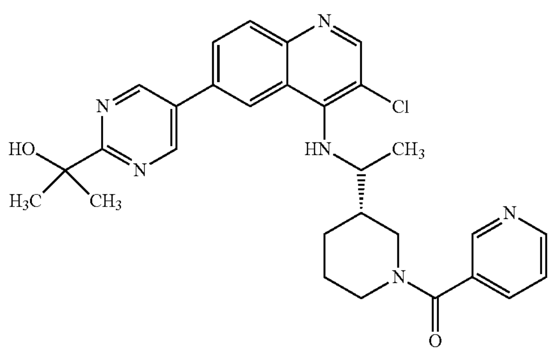 [SMILES: CC(Nc1c(Cl)cnc2ccc(-c3cnc(C(C)(C)O)nc3)cc12)[C@H]1CCCN(C(=O)c2cccnc2)C1] | 531.2 | 1.581 | A |
| 567 | 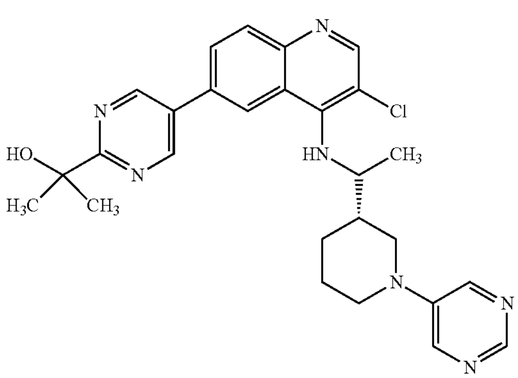 [SMILES: CC(Nc1c(Cl)cnc2ccc(-c3cnc(C(C)(C)O)nc3)cc12)[C@H]1CCCN(c2cncnc2)C1] | 504.5 | 1.612 | A |

TABLE 19-continued

| Ex. No. | Structure | MS observed (M$^{+1}$) | HPLC ret. Time (min.) | HPLC method |
|---|---|---|---|---|
| 568 | 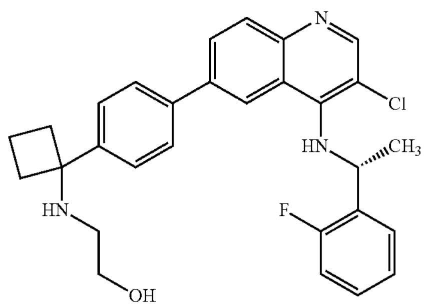 [SMILES: C[C@@H](Nc1c(Cl)cnc2ccc(-c3ccc(C4(NCCO)CCC4)cc3)cc12)c1ccccc1F] | 490.1 | 1.771 | A |
| 569 | 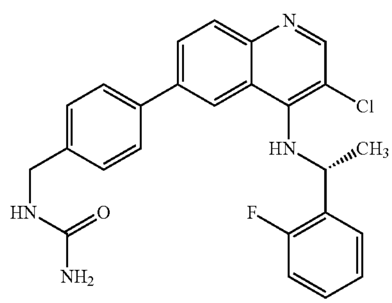 [SMILES: C[C@@H](Nc1c(Cl)cnc2ccc(-c3ccc(CNC(N)=O)cc3)cc12)c1ccccc1F] | 449.3 | 1.749 | A |
| 570 | 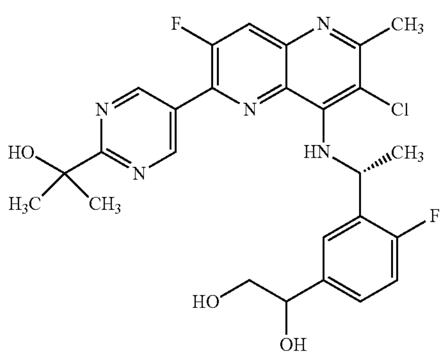 [SMILES: Cc1nc2cc(F)c(-c3cnc(C(C)(C)O)nc3)nc2c(N[C@H](C)c2cc(C(O)CO)ccc2F)c1Cl] | 530.0 (M + H)$^{F,}$ CH=CH2 | 0.66 | C |
| 571 | 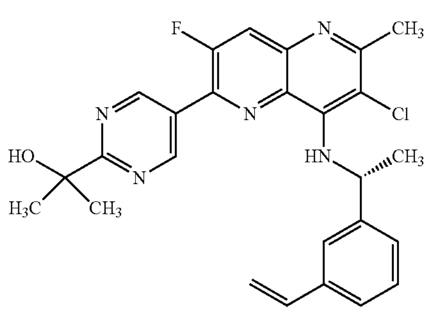 [SMILES: C=Cc1cccc([C@@H](C)Nc2c(Cl)c(C)nc3cc(F)c(-c4cnc(C(C)(C)O)nc4)nc23)c1] | 478.3 (M + H)$^+$ | 0.85 | C |

TABLE 19-continued

| Ex. No. | Structure | MS observed (M+1) | HPLC ret. Time (min.) | HPLC method |
|---|---|---|---|---|
| 572 | 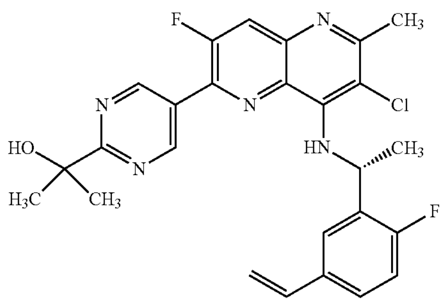 [SMILES: C=Cc1ccc(F)c([C@@H](C)Nc2c(Cl)c(C)nc3cc(F)c(-c4cnc(C(C)(C)O)nc4)nc23)c1] | 496.3 (M + H)+ | 0.86 | C |
| 573 | 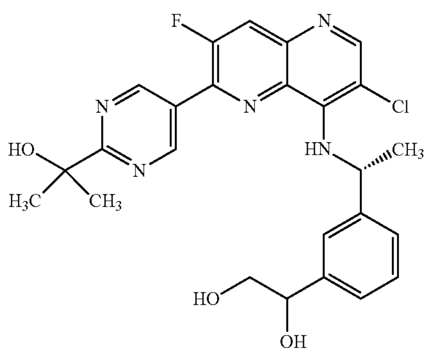 [SMILES: C[C@@H](Nc1c(Cl)cnc2cc(F)c(-c3cnc(C(C)(C)O)nc3)nc12)c1cccc(C(O)CO)c1] | 498.2 (M + H)+ | 0.66 | C |
| 574 | 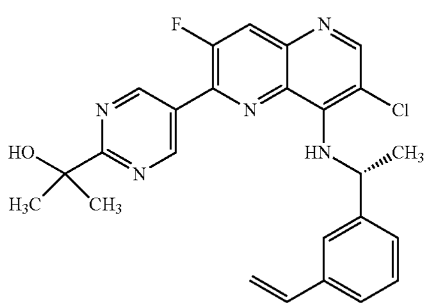 [SMILES: C=Cc1cccc([C@@H](C)Nc2c(Cl)cnc3cc(F)c(-c4cnc(C(C)(C)O)nc4)nc23)c1] | 464.3 (M + H)+ | 0.89 | C |
| 575 | 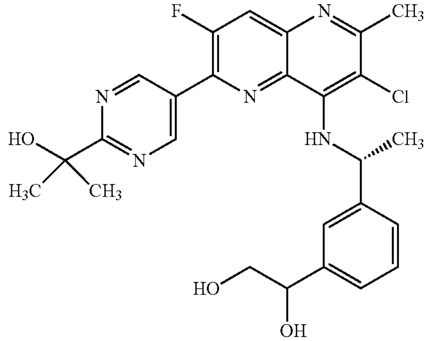 [SMILES: Cc1nc2cc(F)c(-c3cnc(C(C)(C)O)nc3)nc2c(N[C@H](C)c2cccc(C(O)CO)c2)c1Cl] | 512.2 (M + H)+ | 0.64 | C |

TABLE 19-continued
| Ex. No. | Structure | MS observed (M⁺¹) | HPLC ret. Time (min.) | HPLC method |
|---|---|---|---|---|
| 576 | 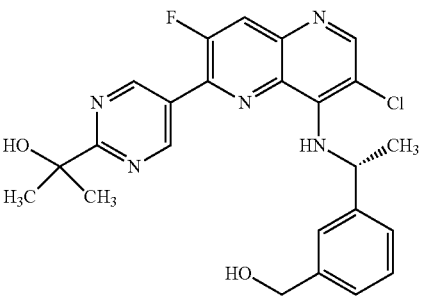 [SMILES: C[C@@H](Nc1c(Cl)cnc2cc(F)c(-c3cnc(C(C)(C)O)nc3)nc12)c1cccc(CO)c1] | 467.8 (M + H)+ | 0.72 | C |
| 577 | 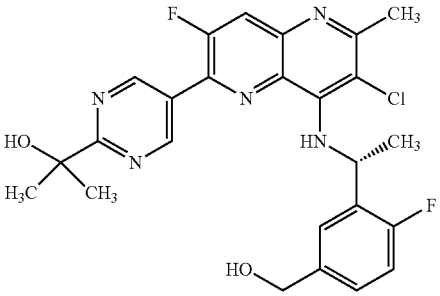 [SMILES: Cc1nc2cc(F)c(-c3cnc(C(C)(C)O)nc3)nc2c(N[C@H](C)c2cc(CO)ccc2F)c1Cl] | 499.8 (M + H)+ | 0.71 | C |
| 578 | 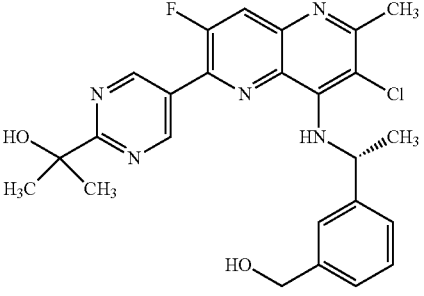 [SMILES: Cc1nc2cc(F)c(-c3cnc(C(C)(C)O)nc3)nc2c(N[C@H](C)c2cccc(CO)c2)c1Cl] | 481.8 (M + H)+ | 0.67 | C |
| 579 | 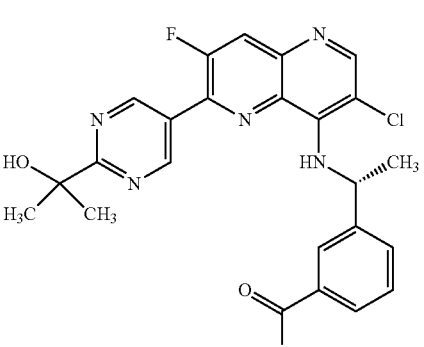 | 500.1 (M + H)+ | 0.77 | C |

TABLE 19-continued
| Ex. No. | Structure | MS observed ($M^{+1}$) | HPLC ret. Time (min.) | HPLC method |
|---|---|---|---|---|
| 580 | 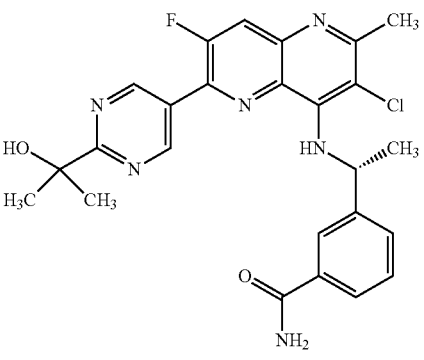 [SMILES: Cc1nc2cc(F)c(-c3cnc(C(C)(C)O)nc3)nc2c(N[C@H](C)c2cccc(C(N)=O)c2)c1Cl] | 495.3 (M + H)+ | 0.65 | C |
| 581 | 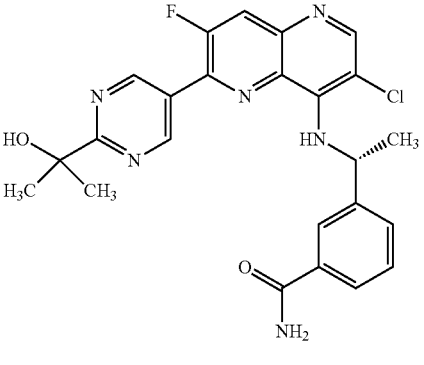 [SMILES: C[C@@H](Nc1c(Cl)cnc2cc(F)c(-c3cnc(C(C)(C)O)nc3)nc12)c1cccc(C(N)=O)c1] | 481.2 (M + H)+ | 0.67 | C |
| 582 | 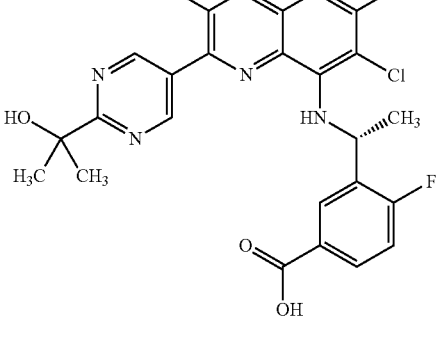 | 514.2 (M + H)+ | 0.72 | C |
| 583 | 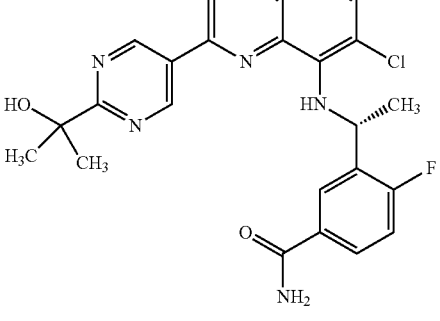 | 499.2 (M + H)+ | 0.70 | C |

TABLE 19-continued

| Ex. No. | Structure | MS observed (M$^{+1}$) | HPLC ret. Time (min.) | HPLC method |
|---|---|---|---|---|
| 584 | 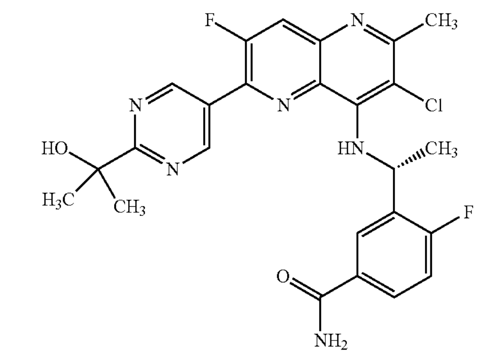 [SMILES: Cc1nc2cc(F)c(-c3cnc(C(C)(C)O)nc3)nc2c(N[C@H](C)c2cc(C(N)=O)ccc2F)c1Cl] | 513.2 (M + H)+ | 0.68 | C |
| 585 | 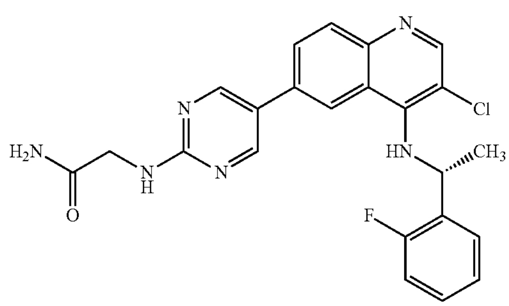 [SMILES: C[C@@H](Nc1c(Cl)cnc2ccc(-c3cnc(NCC(N)=O)nc3)cc12)c1ccccc1F] | 450.8 (M + H)+ | 0.64 | C |
| 586 | 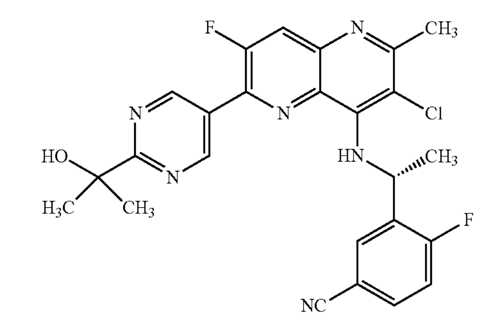 [SMILES: Cc1nc2cc(F)c(-c3cnc(C(C)(C)O)nc3)nc2c(N[C@H](C)c2cc(C#N)ccc2F)c1Cl] | 495.3 (M + H)+ | 0.80 | C |
| 587 | 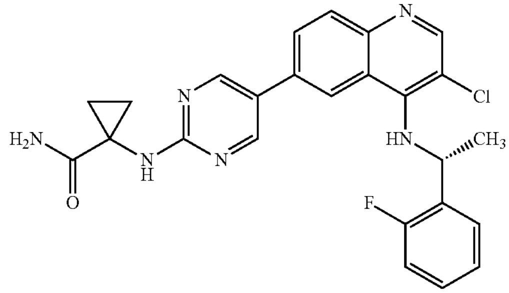 [SMILES: C[C@@H](Nc1c(Cl)cnc2ccc(-c3cnc(NC4(C(N)=O)CC4)nc3)cc12)c1ccccc1F] | 477.1 (M + H)+ | 0.69 | C |

TABLE 19-continued

| Ex. No. | Structure | MS observed (M+1) | HPLC ret. Time (min.) | HPLC method |
|---|---|---|---|---|
| 588 | 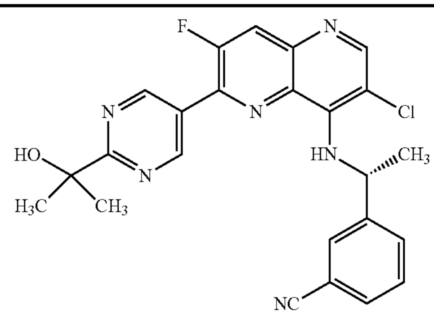 | 463.2 (M + H)+ | 0.82 | C |
| 589 | 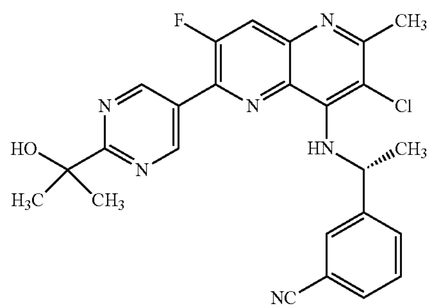 [SMILES: Cc1nc2cc(F)c(-c3cnc(C(C)(C)O)nc3)nc2c(N[C@H](C)c2cccc(C#N)c2)c1Cl] | 477.3 (M + H)+ | 0.77 | C |
| 590 | 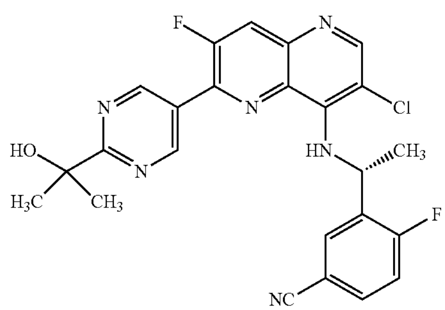 [SMILES: C[C@@H](Nc1c(Cl)cnc2cc(F)c(-c3cnc(C(C)(C)O)nc3)nc12)c1cc(C#N)ccc1F] | 481.2 (M + H)+ | 0.86 | C |
| 591 | 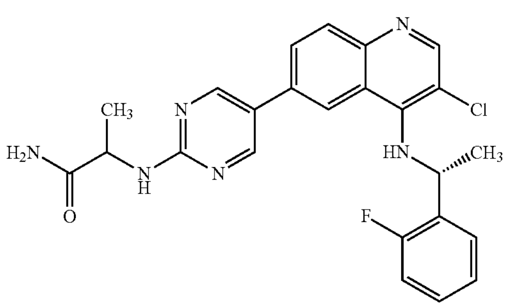 [SMILES: CC(Nc1ncc(-c2ccc3ncc(Cl)c(N[C@H](C)c4ccccc4F)c3c2)cn1)C(N)=O] | 465.3 (M + H)+ | 0.70 | C |
| 592 | 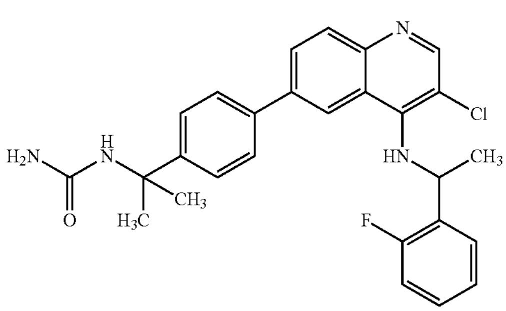 [SMILES: CC(Nc1c(Cl)cnc2ccc(-c3ccc(C(C)(C)NC(N)=O)cc3)cc12)c1ccccc1F] | 476.3 (M + H)+ | 0.83 | C |

TABLE 19-continued

| Ex. No. | Structure | MS observed (M+1) | HPLC ret. Time (min.) | HPLC method |
|---|---|---|---|---|
| 593 | 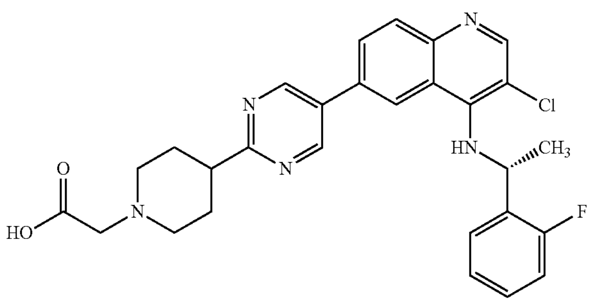 | 520.2 (M + H)+ | 0.66 | C |
| 594 | 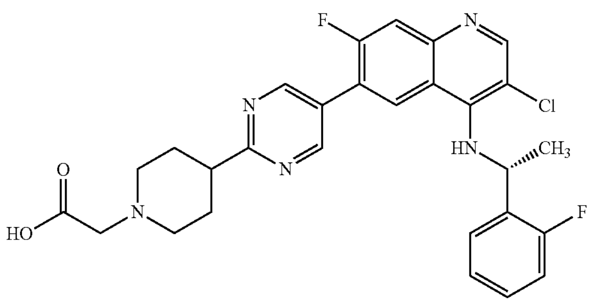 | 538.2 (M + H)+ | 0.68 | C |
| 595 | Homochiral prepared peak 4 of Intermediate I-43 | 455 | 0.74 | C |
| 596 | Homochiral prepared from peak 4 of Intermediate I-43 | 457 | 0.64 | C |

TABLE 19-continued

| Ex. No. | Structure | MS observed (M$^{+1}$) | HPLC ret. Time (min.) | HPLC method |
|---|---|---|---|---|
| 597 | Homochiral prepared from peak 4 of Intermediate I-43 | 457 | 0.64 | C |
| 598 | Diastereomeric mixture prepared from peak 4 of Intermediate I-43 | 480 | 0.69 | C |
| 599 | Diastereomeric mixture | 480 | 0.69 | C |
| 600 | Diastereomeric mixture prepared from peak 4 of Intermediate I-43 | 468 | 0.67 | C |

TABLE 19-continued
| Ex. No. | Structure | MS observed (M+1) | HPLC ret. Time (min.) | HPLC method |
|---|---|---|---|---|
| 601 | 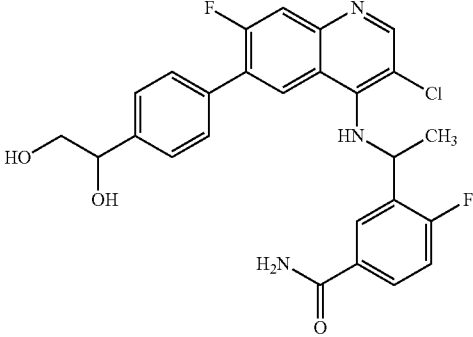 [SMILES: CC(Nc1c(Cl)cnc2cc(F)c(-c3ccc(C(O)CO)cc3)cc12)c1cc(C(N)=O)ccc1F]<br>Diastereomeric mixture prepared from peak 4 of Intermediate I-43 | 498 | 0.61 | C |
| 602 | 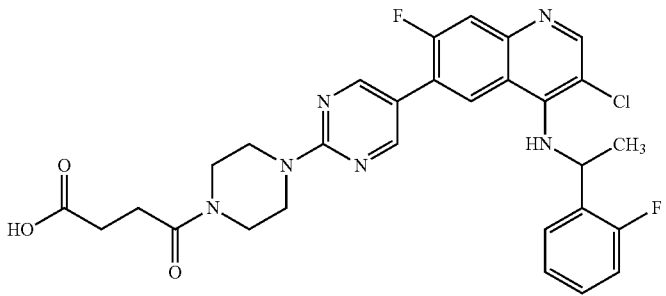 [SMILES: CC(Nc1c(Cl)cnc2cc(F)c(-c3cnc(N4CCN(C(=O)CCC(=O)O)CC4)nc3)cc12)c1ccccc1F]<br>Homochiral prepared from peak 4 of Intermediate I-43 | 581 | 0.72 | C |
| 603 | 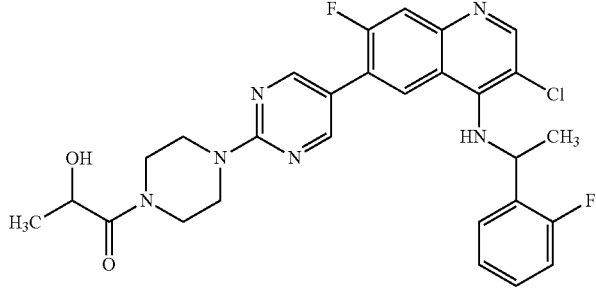 [SMILES: CC(O)C(=O)N1CCN(c2ncc(-c3cc4c(NC(C)c5ccccc5F)c(Cl)cnc4cc3F)cn2)CC1]<br>Diastereomeric mixture prepared from peak 4 of Intermediate I-43 | 553 | 0.73 | C |
| 604 | 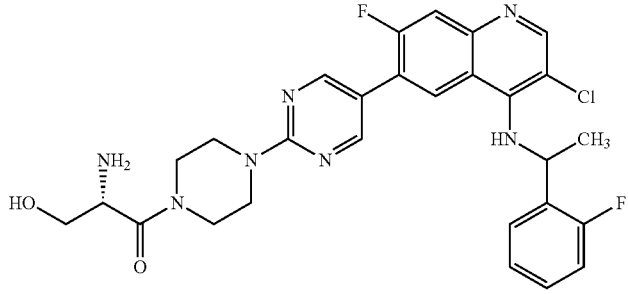 [SMILES: CC(Nc1c(Cl)cnc2cc(F)c(-c3cnc(N4CCN(C(=O)[C@@H](N)CO)CC4)nc3)cc12)c1ccccc1F]<br>Homochiral prepared from peak 4 of Intermediate I-43 | 568 | 0.66 | C |

TABLE 19-continued

| Ex. No. | Structure | MS observed (M+1) | HPLC ret. Time (min.) | HPLC method |
|---|---|---|---|---|
| 605 | Homochiral prepared from peak 4 of Intermediate I-43 | 596 | 0.66 | C |
| 606 | Homochiral prepared from peak 4 of Intermediate I-43 | 568 | 0.66 | C |
| 607 | Homochiral prepared from peak 4 of Intermediate I-43 | 596 | 0.66 | C |
| 608 | Homochiral prepared from peak 4 of Intermediate I-43 | 480 | 0.67 | C |

TABLE 19-continued

| Ex. No. | Structure | MS observed (M+1) | HPLC ret. Time (min.) | HPLC method |
|---|---|---|---|---|
| 609 | 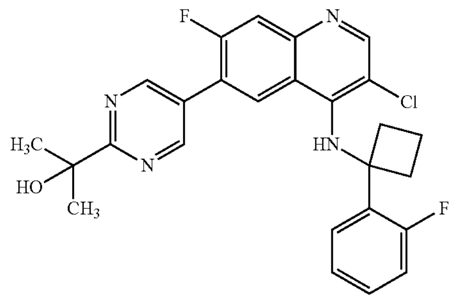 [SMILES: CC(C)(O)c1ncc(-c2cc3c(NC4(c5ccccc5F)CCC4)c(Cl)cnc3cc2F)cn1] | 481 | 0.78 | C |
| 610 | Diastereomeric mixture prepared from peak 4 of Intermediate I-43 | 566 | 0.66 | C |
| 611 | Homochiral prepared from peak 4 of Intermediate I-43 | 550 | 0.79 | C |
| 612 | Homochiral | 533 | 0.90 | C |

TABLE 19-continued

| Ex. No. | Structure | MS observed ($M^{+1}$) | HPLC ret. Time (min.) | HPLC method |
|---|---|---|---|---|
| 613 | (structure) | 547 | 0.76 | C |

Biological Assays

The pharmacological properties of the compounds of this invention may be confirmed by a number of biological assays. The exemplified biological assays, which follow, have been carried out with compounds of the invention.

TNF or CD40L-Induced HEK-Blue Assay

Test compounds serially diluted in DMSO were plated in an assay plate (LABCYTE, Cat. # LP-0200) at final concentrations ranging from 0.004 μM to 25 μM. TNFα (final concentration 0.5 ng/mL) or CD40L (final concentration 30 ng/mL) in assay buffer [DMEM, 4.5 g/l glucose (Gibco, Cat. 21063-029), 10% FBS (Sigma, F4135), 1% Penicillin-Streptomycin (Gibco, Cat. 15140-122), 1% Anti-Anti (Gibco, Cat. 15240-112) and 2 mM L-glutamine (Gibco, Cat. 25030-081)] was then added to the assay plate. After a 30 minute pre-incubation at 37° C. and 5% $CO_2$, HEK-Blue™-CD40L cells (INVIVOGEN, Cat. Code hkb-cd40) containing a NF-kB-driven secreted alkaline phosphatase reporter gene were seeded into the assay plate at a density of 20,000 cells per well. This plate was then incubated for 18 h at 37° C. and 5% $CO_2$. Secreted alkaline phosphatase expression was measured using QUANTI-Blue™ (INVIVOGEN, Cat. Code rep-qb1) according to manufacturer's specifications and the assay plate was read on a PerkinElmer Envision at 620 nm.

Inhibition data for the test compound over a range of concentrations was plotted as percentage inhibition of the test compound (100%=maximum inhibition). $IC_{50}$ values were determined after correcting for background [(sample read-mean of low control)/(mean of high control-mean of low control)] where by the low control is DMSO without stimulation and high control is DMSO with stimulation. The $IC_{50}$ is defined as the concentration of test compound which produces 50% inhibition and was quantified using the 4 parameter logistic equation to fit the data.

Table 20 lists the $IC_{50}$ values measured in the TNF induced HEK-Blue assay for Examples 1 to 612 of this invention. The results in Table 20 are reported as: "A" represents an $IC_{50}$ value of less than 1 μM, "B" represents an $IC_{50}$ value in the range of 1 μM to less than 10 μM; and "C" represents an $IC_{50}$ value in the range of 10 μM to 25 μM. The compounds of the present invention, as exemplified by Examples 1 to 612 showed $IC_{50}$ values measured in the TNF induced HEK-Blue assay of 25 μM or less.

TABLE 20

TNF induced HEK-Blue assay $IC_{50}$ value (nM)

| Ex. No. | $IC_{50}$ value |
|---|---|
| 1 | A |
| 2 | C |
| 3 | B |
| 4 | A |
| 5 | B |
| 6 | B |
| 7 | A |
| 8 | A |
| 9 | C |
| 10 | A |
| 11 | C |
| 12 | B |
| 13 | C |
| 14 | A |
| 15 | A |
| 16 | A |
| 17 | C |
| 18 | B |
| 19 | C |
| 20 | C |
| 21 | B |
| 22 | C |
| 23 | A |
| 24 | A |
| 25 | B |
| 26 | A |
| 27 | A |
| 28 | A |
| 29 | B |
| 30 | C |
| 31 | B |
| 32 | A |
| 33 | B |
| 34 | B |
| 35 | B |
| 36 | A |
| 37 | C |
| 38 | B |
| 39 | A |
| 40 | B |
| 41 | B |
| 42 | B |
| 43 | B |
| 44 | A |
| 45 | A |
| 46 | A |
| 47 | A |
| 48 | A |
| 49 | A |

TABLE 20-continued

TNF induced HEK-Blue assay $IC_{50}$ value (nM)

| Ex. No. | $IC_{50}$ value |
|---|---|
| 50 | A |
| 51 | A |
| 52 | A |
| 53 | B |
| 54 | A |
| 55 | A |
| 55a | A |
| 56 | C |
| 57 | A |
| 58 | A |
| 59 | C |
| 60 | B |
| 61 | B |
| 62 | B |
| 63 | A |
| 64 | A |
| 65 | B |
| 66 | B |
| 67 | B |
| 68 | A |
| 69 | A |
| 70 | A |
| 71 | A |
| 72 | A |
| 73 | B |
| 74 | B |
| 75 | A |
| 76 | A |
| 77 | A |
| 78 | A |
| 79 | A |
| 80 | A |
| 81 | B |
| 82 | A |
| 83 | A |
| 84 | A |
| 85 | B |
| 86 | A |
| 87 | A |
| 88 | B |
| 89 | A |
| 90 | A |
| 91 | A |
| 92 | A |
| 93 | B |
| 94 | A |
| 95 | B |
| 96 | C |
| 97 | A |
| 98 | C |
| 99 | B |
| 100 | B |
| 101 | C |
| 102 | A |
| 103 | B |
| 104 | B |
| 105 | A |
| 106 | B |
| 107 | A |
| 108 | B |
| 109 | B |
| 110 | A |
| 111 | C |
| 112 | A |
| 113 | C |
| 114 | A |
| 115 | B |
| 116 | B |
| 117 | A |
| 118 | A |
| 119 | A |
| 120 | A |
| 121 | A |
| 122 | C |
| 123 | A |
| 124 | A |
| 125 | A |
| 126 | A |
| 127 | A |
| 128 | B |
| 129 | A |
| 130 | A |
| 131 | B |
| 132 | B |
| 133 | A |
| 134 | B |
| 135 | A |
| 136 | A |
| 137 | B |
| 138 | C |
| 139 | A |
| 140 | A |
| 141 | C |
| 142 | C |
| 143 | C |
| 144 | B |
| 145 | C |
| 146 | A |
| 147 | B |
| 148 | B |
| 149 | B |
| 150 | C |
| 151 | A |
| 152 | A |
| 153 | A |
| 154 | A |
| 155 | B |
| 156 | B |
| 157 | C |
| 158 | A |
| 159 | C |
| 160 | A |
| 161 | B |
| 162 | A |
| 163 | B |
| 164 | B |
| 165 | A |
| 166 | C |
| 167 | A |
| 168 | A |
| 169 | A |
| 170 | A |
| 171 | A |
| 172 | C |
| 173 | B |
| 174 | C |
| 175 | A |
| 176 | A |
| 177 | A |
| 178 | A |
| 179 | A |
| 180 | C |
| 181 | C |
| 182 | C |
| 183 | A |
| 184 | A |
| 185 | C |
| 186 | C |
| 187 | A |
| 188 | A |
| 189 | A |
| 190 | A |
| 191 | A |
| 192 | A |
| 193 | A |
| 194 | A |
| 195 | C |
| 196 | A |
| 197 | C |
| 198 | A |
| 199 | A |
| 200 | B |

TABLE 20-continued

TNF induced HEK-Blue assay IC$_{50}$ value (nM)

| Ex. No. | IC$_{50}$ value |
|---|---|
| 201 | C |
| 202 | A |
| 203 | A |
| 204 | A |
| 205 | A |
| 206 | C |
| 207 | A |
| 208 | A |
| 209 | A |
| 210 | A |
| 211 | A |
| 212 | A |
| 213 | A |
| 214 | A |
| 215 | A |
| 216 | A |
| 217 | A |
| 218 | A |
| 219 | A |
| 220 | C |
| 221 | A |
| 222 | A |
| 223 | C |
| 224 | A |
| 225 | A |
| 226 | A |
| 227 | A |
| 228 | A |
| 229 | C |
| 230 | A |
| 231 | C |
| 232 | A |
| 233 | A |
| 234 | C |
| 235 | C |
| 236 | C |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | C |
| 249 | B |
| 250 | B |
| 251 | A |
| 252 | A |
| 253 | A |
| 254 | A |
| 255 | B |
| 256 | A |
| 257 | A |
| 258 | B |
| 259 | C |
| 260 | A |
| 261 | A |
| 262 | B |
| 263 | B |
| 264 | A |
| 265 | A |
| 266 | A |
| 267 | A |
| 268 | A |
| 269 | A |
| 270 | A |
| 271 | B |
| 272 | A |
| 273 | A |
| 274 | B |
| 275 | A |
| 276 | B |
| 277 | A |
| 278 | A |
| 279 | B |
| 280 | A |
| 281 | A |
| 282 | B |
| 283 | A |
| 284 | B |
| 285 | A |
| 286 | A |
| 287 | C |
| 288 | B |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | C |
| 302 | A |
| 303 | A |
| 304 | A |
| 305 | A |
| 306 | A |
| — | — |
| 307 | A |
| 308 | A |
| 309 | A |
| 310 | A |
| 311 | A |
| 312 | A |
| 313 | A |
| 314 | A |
| 315 | C |
| 316 | A |
| 317 | A |
| 318 | A |
| 319 | A |
| 320 | A |
| 321 | C |
| 322 | C |
| 323 | A |
| 324 | A |
| 325 | A |
| 326 | A |
| 327 | A |
| 328 | B |
| 329 | B |
| 330 | A |
| 331 | A |
| 332 | A |
| 333 | A |
| 334 | A |
| 335 | A |
| 336 | A |
| 337 | B |
| 338 | A |
| 339 | A |
| 340 | A |
| 341 | A |
| 342 | A |
| 343 | A |
| 344 | A |
| 345 | A |
| 346 | B |
| 347 | A |
| 348 | A |
| 349 | A |
| 350 | A |
| 351 | A |

TABLE 20-continued

TNF induced HEK-Blue assay IC$_{50}$ value (nM)

| Ex. No. | IC$_{50}$ value |
|---|---|
| 352 | A |
| 353 | B |
| 354 | A |
| 355 | B |
| 356 | C |
| 357 | B |
| 358 | C |
| 359 | A |
| 360 | A |
| 361 | A |
| 362 | A |
| 363 | B |
| 364 | A |
| 365 | A |
| 366 | A |
| 367 | A |
| 368 | C |
| 369 | A |
| 370 | A |
| 371 | A |
| 372 | A |
| 373 | A |
| 374 | A |
| 375 | A |
| 376 | A |
| 377 | A |
| 378 | C |
| 379 | A |
| 380 | A |
| 381 | A |
| 382 | A |
| 383 | A |
| 384 | B |
| 385 | B |
| 386 | A |
| 387 | A |
| 388 | A |
| 389 | A |
| 390 | A |
| 391 | A |
| 392 | A |
| 393 | A |
| 394 | A |
| 395 | B |
| 396 | A |
| 397 | A |
| 398 | A |
| 399 | A |
| 400 | A |
| 401 | A |
| 402 | A |
| 403 | A |
| 404 | A |
| 405 | A |
| 406 | A |
| 407 | C |
| 408 | A |
| 409 | A |
| 410 | B |
| 411 | B |
| 412 | C |
| 413 | A |
| 414 | A |
| 415 | A |
| 416 | B |
| 417 | A |
| 418 | A |
| 419 | A |
| 420 | A |
| 421 | A |
| 422 | A |
| 423 | A |
| 424 | A |
| 425 | A |
| 426 | A |
| 427 | B |
| 428 | C |
| 429 | A |
| 430 | A |
| 431 | A |
| 432 | A |
| 433 | A |
| 434 | A |
| 435 | A |
| 436 | A |
| 437 | A |
| 438 | B |
| 439 | A |
| 440 | A |
| 441 | A |
| 442 | A |
| 443 | A |
| 444 | A |
| 445 | A |
| 446 | B |
| 447 | A |
| 448 | A |
| 449 | A |
| 450 | A |
| 451 | B |
| 452 | B |
| 453 | B |
| 454 | A |
| 455 | A |
| 456 | C |
| 457 | B |
| 458 | B |
| 459 | A |
| — | — |
| 460 | A |
| 461 | A |
| 462 | C |
| 463 | C |
| 464 | B |
| 465 | B |
| 466 | C |
| 467 | B |
| 468 | B |
| 469 | B |
| 470 | C |
| 471 | B |
| 472 | B |
| 473 | A |
| 474 | A |
| 475 | B |
| 476 | B |
| 477 | B |
| 478 | A |
| 479 | A |
| 480 | C |
| 481 | A |
| 482 | C |
| 483 | B |
| 484 | A |
| 485 | B |
| 486 | A |
| 487 | A |
| 488 | A |
| 489 | A |
| 490 | A |
| 491 | A |
| 492 | A |
| 493 | A |
| 494 | A |
| 495 | A |
| 496 | A |
| 497 | A |
| 498 | A |
| 499 | A |
| 500 | A |
| 501 | A |
| 502 | B |

TABLE 20-continued

TNF induced HEK-Blue assay IC$_{50}$ value (nM)

| Ex. No. | IC$_{50}$ value |
|---|---|
| 503 | B |
| 504 | A |
| 505 | A |
| 506 | A |
| 507 | A |
| 508 | A |
| 509 | B |
| 510 | B |
| 511 | A |
| 512 | C |
| 513 | B |
| 514 | A |
| 515 | B |
| 516 | C |
| 517 | B |
| 518 | A |
| 519 | B |
| 520 | A |
| 521 | A |
| 522 | A |
| 523 | A |
| 524 | A |
| 525 | B |
| 526 | B |
| 527 | B |
| 528 | B |
| 529 | A |
| 530 | A |
| 531 | A |
| 532 | A |
| 533 | A |
| 534 | A |
| 535 | A |
| 536 | B |
| 537 | A |
| 538 | B |
| 539 | A |
| 540 | A |
| 541 | B |
| 542 | A |
| 543 | C |
| 544 | A |
| 545 | A |
| 546 | C |
| 547 | B |
| 548 | A |
| 549 | B |
| 550 | A |
| 551 | B |
| 552 | A |
| 553 | A |
| 554 | A |
| 555 | A |
| 556 | C |
| 557 | B |
| 558 | A |
| 559 | A |
| 560 | B |
| 561 | A |
| 562 | A |
| 563 | B |
| 564 | B |
| 565 | C |
| 566 | B |
| 567 | B |
| 568 | A |
| 569 | A |
| 570 | B |
| 571 | A |
| 572 | B |
| 573 | A |
| 574 | A |
| 575 | A |
| 576 | A |
| 577 | A |
| 578 | A |

TABLE 20-continued

TNF induced HEK-Blue assay IC$_{50}$ value (nM)

| Ex. No. | IC$_{50}$ value |
|---|---|
| 579 | B |
| 580 | A |
| 581 | C |
| 582 | C |
| 583 | A |
| 584 | A |
| 585 | C |
| 586 | A |
| 587 | A |
| 588 | A |
| 589 | A |
| 590 | A |
| 591 | A |
| 592 | B |
| 593 | B |
| 594 | A |
| 595 | A |
| 596 | A |
| 597 | B |
| 598 | B |
| 599 | A |
| 600 | A |
| 601 | A |
| 602 | A |
| 603 | A |
| 604 | A |
| 605 | A |
| 606 | A |
| 607 | A |
| 608 | A |
| 609 | B |
| 610 | A |
| 611 | A |
| 612 | A |
| — | — |

What is claimed is:

1. A compound of Formula (I):

$$
\text{(I)}
$$

or a salt thereof, wherein:

A is CR$_1$;
B is CR$_3$;
D is CR$_4$;
X is —NR$_8$—;
L$_1$ is a bond or —CH$_2$;
L$_2$ is a bond, —CH$_2$—, —CH(CH$_3$)—, —C(CH$_3$)$_2$—, —CH(CH$_2$F)—, —CH(CHF$_2$)—, —CH(CF$_3$)—, —CH(CH$_2$CH$_3$)—, —CH(CH$_2$CH$_2$F)—, —CH(CH$_2$CHF$_2$)—, —CH(CH$_2$CF$_3$)—, —CH(CH$_2$CH$_2$OH)—, —CH(CH$_2$N(CH$_3$)$_2$)—, —CH(C(CH$_3$)$_2$OH)—, —CH(CH$_2$CH=CH$_2$)—, —CH(CH$_3$)CH$_2$—, —CH(cyclopropyl)-, —CH(CH(CH$_3$)$_2$)—, —CH(C(CH$_3$)$_2$F)—, —CH(CH$_3$)CH$_2$CH$_2$—, —CH(CH$_3$)CH$_2$C(OH)(phenyl)-, cyclopropyl, or cyclobutyl;
Z is a cyclic group selected from C$_{3-6}$ cycloalkyl, cyclopentenyl, phenyl, furanyl, imidazolyl, indolinyl, isoquinolinyl, isothiazolyl, isoxazolyl, oxazolyl, piperidinyl, pyrazinyl, pyrazolyl, pyridinyl, pyrimidinyl, thiazolyl, and thiophenyl, wherein said cyclic group is substituted with zero to 3 R$_a$;

$R_1$ is H or F;

$R_2$ is (i) F, Cl, or Br; or (ii) dihydropyridinonyl, phenyl, piperidinyl, pyrazinyl, pyrazolyl, pyridinyl, or pyrimidinyl, each substituted with zero to 3 $R_{1a}$;

$R_3$ is H, F, or Cl;

$R_4$ is H, F, or Cl;

$R_5$ is H, —OH, —$CH_3$, —$CH_2OH$, —$CH_2NH_2$, —$CH_2N_3$, —C(O)OH, —C(O)NH($CH_3$), —C(O)N($CH_3$)$_2$, —$CH_2$NH(dimethylphenyl), —C(O)NH(pyridinyl), —C(O)NH(phenyl), or —$CH_2$O(pyridinyl);

$R_6$ is F, Cl, or —$CH_3$;

$R_8$ is H, —$CH_3$, or —$CH_2CH_3$;

each $R_{1a}$ is independently F, —CN, —$CH_3$, —$CH_2CH_3$, —$CH_2OH$, —C($CH_3$)$_2$OH, —CH(OH)$CH_2OH$, —CH($CH_3$)(OH)$CH_2OH$, —C($CH_2F$)$_2$OH, —C($CH_3$)$_2$NHC(O)$CH_3$, —C(O)$NH_2$, —C(O)NH$CH_2CH_2CH_2CH_2NH_2$, —C(O)NH$CH_3$, —C(O)OH, —CH(C(O)O$CH_3$)$CH_2NH_2$, —CH($CH_2$OH)NHC(O)$CH_3$, —CH($NH_2$)$CH_2$OH, —CH($NH_2$)$CH_2$C(O)OH, —$CH_2$CH($NH_2$)C(O)OH, —$CH_2$NH($CH_2CH_3$), —$CH_2$NHC(O)$CH_3$, —$CH_2$NHC(O)$NH_2$, —CH(OH)$CH_2$NH($CH_3$), —NH($CH_3$), —NH$CH_2CH_2$OH, —NH$CH_2$CH(OH)$CH_2$OH, —NH$CH_2$C($CH_3$)$_2$OH, —NH$CH_2$CH(OH)$CH_2$OH, —NH$CH_2$C(O)$NH_2$, —NH$CH_2$C(O)OH, —NH$CH($CH_3$)C(O)$NH_2$, —NH$CH_2$CH(OH)$CH_2$OH, —N($CH_3$)C(O)CH=$CH_2$, —O$CH_2CH_3$, —S(O)$_2CH_3$, —S(O)$_2$NH($CH_3$), —$CH_2$(azetidinyl), —$CH_2$(piperazinyl), —$CH_2$(butoxycarbonylpiperazinyl), —CH(OH)(cyclopropyl), —CH(OH)$CH_2$(morpholinyl), —CH(OH)$CH_2$(carboxypyrrolidinyl), —NH(carbamoylcyclopropyl), $C_{3-6}$ cycloalkyl substituted with 1 to 2 substituents independently selected from —OH, —$NH_2$, —NHC(O)$NH_2$, —NHC(O)$CH_3$, —NH$CH_2CH_2$OH, —NHS(O)$_2CH_3$, —$CH_2$OH, —C(O)OH, and —C(O)$CH_3$; hydroxybutanonyl, hydroxypyrrolidinyl, carboxypyrrolidinyl, methoxycarbonylpyrrolidinyl, hydroxypropylpyrrolidinyl, hydroxypyranyl, hydroxyoxetanyl, hydroxymethylmorpholinyl, dioxohydroxytetrahydrothiopyranyl, piperidinyl substituted with 1 to 2 substituents independently selected from —$NH_2$, —C(O)OH, —$CH_2$C(O)OH, —C($CH_3$)$_2$OH, and —C(O)O$CH_2CH_3$; piperazinyl substituted with zero or 1 substituent selected from —$CH_2$OH, —$CH_2$CN, —$CH_2$C(O)OH, —$CH_2$C(O)O$CH_3$, —$CH_2$C(O)$NH_2$, —$CH_2$C(O)NH$CH_3$, —CH(C(O)O$CH_3$)$CH_2$NHC(O)$CH_3$, —CH(C(O)OH)$CH_2NH_2$, —$CH_2$C(O)NHS(O)$_2CH_3$, —$CH_2$C(O)NH$CH_2$C(O)OH, —CH(C(O)OH)$CH_2$NHC(O)$CH_3$, —CH(C(O)OH)$CH_2$NHC(O)OC($CH_3$)$_3$, —C(O)OH, —C(O)CH($CH_3$)OH, —C(O)CH($NH_2$)$CH_2$C(O)OH, —C(O)CH($NH_2$)$CH_2$OH, —C(O)$CH_2CH_2$C(O)OH, —C(O)CH=$CH_2$, —C(O)C≡CH, —$CH_2$(tetrazolyl), and pyrrolidinonyl; piperazinonyl, carboxymethylpiperazinonyl, morpholinyl, dioxothiomorpholinyl, carboxyazabicyclo[3.2.1]octanyl, or pyridinyl;

each $R_a$ is independently F, Cl, Br, —CN, —OH, —$CH_3$, —$CH_2CH_3$, —CH=$CH_2$, —C≡C(phenyl), —$CF_3$, —$CH_2$OH, —$CH_2CH_2$OH, —CH($CH_3$)OH, —$CH_2CH_2CH_2$OH, —C($CH_3$)$_2$OH, —CH(OH)$CH_2$OH, —C($CH_3$)(OH)$CH_2$OH, —CH(OH)CH($CH_3$)$CH_2$C($CH_3$)$_2$, —$CH_2NH_2$, —CH($NH_2$)$CH_2$OH, —CH($NH_2$)CH($CH_3$)$CH_2CH_2CH_3$, —$CH_2$C(O)$NH_2$, —$CH_2$C(O)$NH_2$, —$CH_2$(phenyl), —C(O)$CH_3$, —C(O)$NH_2$, —C(O)NH($CH_3$), —C(O)NH($CH_2CH_3$), —C(O)N($CH_3$)$_2$, —C(O)CH($CH_3$)$CH_2CH_2CH_3$, —C(O)(pyrazolyl), —C(O)(pyridinyl), —C(O)NH(phenyl), —C(O)OH, —$CH_2$C(O)OH, —$CH_2CH_2$C(O)OH, —C(O)O$CH_3$, —C(O)OC($CH_3$)$_3$, —CH=NOH, —OCH$F_2$, —O$CH_3$, —O$CF_3$, —O$CH_2CH_2$OH, —O$CH_2CH_2CH_2$OH, —O$CH_2$C(O)OH, —OCH=$CH_2$, —$NH_2$, —NHC(O)OC($CH_3$)$_3$, —NHCH($CH_3$)$CH_2$CH($CH_3$)$CH_3$, —S(O)$_2CH_3$, —S(O)$_2NH_2$, —S(O)$_2CH_2CH_2$C(O)O$CH_3$, —S(O)$_2$(methylpyrazolyl), oxazolidinonyl, cyclopentenyl, imidazolidine-2,4-dionyl, imidazolinonyl, methylimidazolyl, indolyl, morpholinonyl, morpholinyl, pyrazinyl, pyridazinyl, methylpyridazinyl, dimethoxypyridazinyl, pyrrolidinonyl, pyrrolidinyl, pyrrolo[2,3-b]pyridinyl, tetrahydropyridinyl, tetrazolyl, methyltetrazolyl, thiazolyl, triazolyl, methyltriazolyl, phenyl substituted with zero to 2 substituents independently selected from F, Cl, —CN, —$CH_3$, —$NH_2$, —O$CH_3$, and —OC(O)C($CH_3$)$_3$; pyrazolyl substituted with zero to 2 substituents independently selected from —$CH_3$, —$CH_2CH_3$, —CH$F_2$, —$CF_3$, —C(O)OH, —$CH_2$C(O)OH, —$CH_2$C($CH_3$)$_2$OH, —$CH_2$(phenyl), and —$CH_2CH_2$(morpholinyl); pyridinyl substituted with zero to 2 substituents independently selected from —CN, —$CH_3$, —$CH_2CH_3$, —O$CH_3$, —$NH_2$, —NH($CH_3$), —N($CH_3$)$_2$, and —C(O)(morpholinyl); or pyrimidinyl substituted with zero to 1 substituent selected from —$CH_3$, —C($CH_3$)$_2$OH, —O$CH_3$, —$NH_2$, —N($CH_3$)$_2$, cyclopropyl, and morpholinyl.

2. The compound according to claim 1 or a salt thereof, wherein:

X is —$NR_8$—;

$L_1$ is a bond;

$L_2$ is —$CH_2$—, —CH($CH_3$)—, —C($CH_3$)$_2$—, —CH($CH_2F$)—, —CH(CH$F_2$)—, —CH($CF_3$)—, —CH($CH_2CH_3$)—, —CH($CH_2CH_2F$)—, —CH($CH_2$CH$F_2$)—, —CH($CH_2CF_3$)—, —CH($CH_2CH_2$OH)—, —CH($CH_2$N($CH_3$)$_2$)—, —CH(C($CH_3$)$_2$OH)—, —CH($CH_3$)$CH_2$—, —CH(cyclopropyl)-, —CH(CH($CH_3$)$_2$)—, —CH(C($CH_3$)$_2$F)—, or —CH($CH_3$)$CH_2CH_2$—;

Z is a cyclic group selected from piperidinyl, pyrazinyl, pyrazolyl, pyridinyl, or pyrimidinyl, each substituted with zero to 3 $R_a$;

each $R_a$ is independently F, Cl, Br, —CN, —OH, $C_{1-2}$ alkyl, —$CF_3$, —CH=$CH_2$, —$CH_2$OH, —$CH_2CH_2$OH, —CH($CH_3$)OH, —$CH_2CH_2CH_2$OH, —C($CH_3$)$_2$OH, —C($CH_3$)(OH)$CH_2$OH, —CH(OH)$CH_2$OH, —$CH_2$CH(OH)$CH_2$OH, —$CH_2CH_2$C(O)OH, —CH($NH_2$)$CH_2$OH, —$CH_2$(phenyl), —$CH_2$C(O)$NH_2$, —$CH_2$C(O)OH, —$CH_2CH_2$C(O)$NH_2$, —O$CH_3$, —OCH$F_2$, —O$CF_3$, —O$CH_2CH_2$OH, —O$CH_2CH_2CH_2$OH, —O$CH_2$C(O)OH, —OCH=$CH_2$, —C≡C(phenyl), —CH=N—OH, —C(O)OH, —C(O)$CH_3$, —C(O)O$CH_3$, —C(O)OC($CH_3$)$_3$, —C(O)$NH_2$, —C(O)NH($CH_3$), —C(O)NH($CH_2CH_3$), —C(O)N($CH_3$)$_2$, —C(O)NH(phenyl), —C(O)(pyrazolyl), —C(O)(pyridinyl), —$NH_2$, —$CH_2NH_2$, —NHC(O)OC($CH_3$)$_3$, —S(O)$_2CH_3$, —S(O)$_2NH_2$, —S(O)$_2CH_2CH_2$C(O)O$CH_3$, —S(O)$_2$(methylpyrazolyl), cyclopentenyl, phenyl, methylphenyl, cyanophenyl, aminophenyl, butoxycarbonyl phenyl, methoxyphenyl, oxazolidinonyl, indolyl, methylimidazolyl, imidazolinonyl, imidazolidine-2,4-dionyl, pyrazinyl, pyridazinyl, methylpyridazinyl, dimethoxypyridazinyl, pyrrolidinyl, pyrrolidinonyl, chlorophenyl, fluorophenyl, morpholinyl, morpholinonyl, methyltriazolyl, triazolyl, tetrazolyl, methyltetrazolyl, tetrahydropyridinyl, pyrrolo[2,3-b]pyridinyl, pyrazolyl substituted with zero to 2 substituents independently selected from —$CH_3$, —$CH_2CH_3$, —$CHF_2$, —$CF_3$, —$CH_2C(CH_3)_2OH$, —$CH_2C(O)OH$, —$CH_2$(phenyl), —C(O)OH, and —$CH_2CH_2$(morpholinyl); pyrimidinyl substituted with zero to one substituent selected from —$NH_2$, —$N(CH_3)_2$, —$CH_3$, —$C(CH_3)_2OH$, —$OCH_3$, cyclopropyl, and morpholinyl; or pyridinyl substituted with zero to 2 substituents independently selected from —CN, —$CH_3$, —$CH_2CH_3$, —$OCH_3$, —$NH_2$, —$NH(CH_3)$, —$N(CH_3)_2$, and —C(O)(morpholinyl);

$R_2$ is dihydropyridinonyl, phenyl, piperidinyl, pyrazinyl, pyrazolyl, pyridinyl, or pyrimidinyl, each substituted with zero to 3 $R_{1a}$; and $R_8$ is H, —$CH_3$, or —$CH_2CH_3$.

3. A pharmaceutical composition comprising one or more compounds according to claim 1 or a salt thereof; and a pharmaceutically acceptable carrier or diluent.

4. The compound according to claim 1 or a salt thereof, where said compound is:

2-(5-(3-chloro-4-((2,5-dimethylphenyl)amino)-2-methylquinolin-6-yl)pyrimidin-2-yl)propan-2-ol (1);

3-chloro-N-(2,5-dimethylphenyl)-2-(((2,5-dimethylphenyl)amino)methyl)-6-(1-methyl-1H-pyrazol-4-yl)quinolin-4-amine (2);

5-(3-chloro-4-((2,5-dimethylphenyl)amino)-2-(((2,5-dimethylphenyl)amino)methyl)quinolin-6-yl)picolinonitrile (3);

2-(5-(3-chloro-4-((2,5-dimethylphenyl)amino)-2-(hydroxymethyl)quinolin-6-yl)pyrimidin-2-yl)propan-2-ol (4);

tert-butyl 4-(4-(3-chloro-4-((2,5-dimethylphenyl)amino)-2-methylquinolin-6-yl)benzyl)piperazine-1-carboxylate (6);

3-chloro-N-(2,5-dimethylphenyl)-2-methyl-6-(4-(piperazin-1-ylmethyl)phenyl)quinolin-4-amine (7);

5-(3-chloro-4-((2,5-dimethylphenyl)amino)-2-methylquinolin-6-yl)-N-methylpicolinamide (8);

5-(3-chloro-4-((2,5-dimethylphenyl)amino)-2-methylquinolin-6-yl)picolinic acid (9);

2-(5-(3-chloro-4-((2-fluoro-1-(2-fluorophenyl)ethyl)amino)quinolin-6-yl)pyrimidin-2-yl)propan-2-ol (10);

2-(5-(3-chloro-4-((phenylamino)methyl)quinolin-6-yl)pyrimidin-2-yl)propan-2-ol (11);

2-(5-(3-chloro-4-((2-(dimethylamino)-1-(2-fluorophenyl)ethyl)amino)quinolin-6-yl)pyrimidin-2-yl)propan-2-ol (12);

(S)-(4-(3-chloro-4-((2,2-difluoro-1-(2-fluorophenyl)ethyl)amino)quinolin-6-yl)benzyl)glycine (13);

methyl (S)-2-(4-(5-(3-chloro-4-((2,2-difluoro-1-(2-fluorophenyl)ethyl)amino)quinolin-6-yl) pyrimidin-2-yl)piperazin-1-yl)acetate (14);

(S)-2-(4-(5-(3-chloro-4-((2,2-difluoro-1-(2-fluorophenyl)ethyl)amino)quinolin-6-yl)pyridin-2-yl)piperazin-1-yl)acetic acid (15);

(S)-2-(4-(4-(3-chloro-4-((2,2-difluoro-1-(2-fluorophenyl)ethyl)amino)quinolin-6-yl)phenyl)piperazin-1-yl)acetic acid (16);

(R)-3-chloro-N-(1-(2-fluorophenyl)ethyl)-6-(2-(methylamino)pyrimidin-5-yl)quinolin-4-amine (17);

4-(5-(3,8-dichloro-4-((1-(2-fluorophenyl)ethyl)amino)quinolin-6-yl)pyrimidin-2-yl)piperazin-2-one (18);

3,8-dichloro-N-(1-(2-fluorophenyl)ethyl)-6-(2-(methylamino)pyrimidin-5-yl)quinolin-4-amine (19);

3,8-dichloro-N-(1-(2-fluorophenyl)ethyl)-6-(1-methyl-1H-pyrazol-4-yl)quinolin-4-amine (20);

2-(4-(3,8-dichloro-4-((1-(2-fluorophenyl)ethyl)amino)quinolin-6-yl)phenyl)propan-2-ol (21);

4-(3,8-dichloro-4-((1-(2-fluorophenyl)ethyl)amino)quinolin-6-yl)-N-methylbenzenesulfonamide (22);

6-(1-((3-chloro-6-(2-(3-oxopiperazin-1-yl)pyrimidin-5-yl)quinolin-4-yl)amino)propyl)-5-fluoropicolinamide (23);

6-(1-((3-chloro-6-(4-(2-hydroxypropan-2-yl)phenyl)quinolin-4-yl)amino)propyl)-5-fluoropicolinamide (24);

6-(1-((3-chloro-6-(2-(3-oxopiperazin-1-yl)pyrimidin-5-yl)quinolin-4-yl)amino)ethyl)-5-fluoropicolinamide (25 and 26);

6-(1-((3-chloro-6-(4-(2-hydroxypropan-2-yl)phenyl)quinolin-4-yl)amino)ethyl)-5-fluoropicolinamide (27);

6-(1-((3-chloro-6-(2-(2-hydroxypropan-2-yl)pyrimidin-5-yl)quinolin-4-yl)amino)ethyl)-5-fluoropicolinamide (28);

(R)-3-chloro-6-(4-((ethylamino)methyl)phenyl)-N-(1-(2-fluorophenyl)ethyl)quinolin-4-amine (29);

(R)-6-(4-(azetidin-1-ylmethyl)phenyl)-3-chloro-N-(1-(2-fluorophenyl)ethyl)quinolin-4-amine (30);

3-chloro-6-(6-cyanopyridin-3-yl)-4-((2,5-dimethylphenyl)amino)quinoline-2-carboxylic acid (31);

3-chloro-6-(6-cyanopyridin-3-yl)-4-((2,5-dimethylphenyl)amino)-N-(pyridin-3-yl)quinoline-2-carboxamide (32);

3-chloro-6-(6-cyanopyridin-3-yl)-4-((2,5-dimethylphenyl)amino)-N-methylquinoline-2-carboxamide (33);

3-chloro-6-(6-cyanopyridin-3-yl)-4-((2,5-dimethylphenyl)amino)-N,N-dimethylquinoline-2-carboxamide (34);

3-chloro-6-(6-cyanopyridin-3-yl)-4-((2,5-dimethylphenyl)amino)-N-phenylquinoline-2-carboxamide (35);

3-chloro-6-(6-cyanopyridin-3-yl)-4-((2,5-dimethylphenyl)amino)-N-(pyridin-4-yl)quinoline-2-carboxamide (36);

6-(6-carbamoylpyridin-3-yl)-3-chloro-4-((2,5-dimethylphenyl)amino)-N-(pyridin-3-yl)quinoline-2-carboxamide (37);

6-(1-((3-chloro-6-(2-(3-oxopiperazin-1-yl)pyrimidin-5-yl)quinolin-4-yl)amino)ethyl)-5-fluoro-N-phenylpicolinamide (38);

6-(1-((3-chloro-6-(2-(3-oxopiperazin-1-yl)pyrimidin-5-yl)quinolin-4-yl)amino)ethyl)-N-ethyl-5-fluoropicolinamide (39);

5-(3-chloro-4-((2,5-dimethylphenyl)amino)-2-(hydroxymethyl)quinolin-6-yl)picolinonitrile (40);

5-(3-chloro-4-((2,5-dimethylphenyl)amino)-2-((pyridin-3-yloxy)methyl)quinolin-6-yl)picolinonitrile (41);

5-(2-(azidomethyl)-3-chloro-4-((2,5-dimethylphenyl)amino)quinolin-6-yl)picolinonitrile (42);

5-(2-(aminomethyl)-3-chloro-4-((2,5-dimethylphenyl)amino)quinolin-6-yl)picolinonitrile (43);

2-(5-(3-chloro-4-((2,5-dimethylphenyl)amino)-2-(hydroxymethyl)quinolin-6-yl)pyrimidin-2-yl)propan-2-ol (44);

2-(4-(5-(2-amino-3-chloro-4-((2,5-dimethylphenyl)amino)quinolin-6-yl)pyrimidin-2-yl) piperazin-1-yl)acetic acid (45);

2-(4-(5-(2-amino-3-chloro-4-((1-(2-fluorophenyl)ethyl)amino)quinolin-6-yl)pyrimidin-2-yl)piperazin-1-yl)acetic acid (46);

2-(5-(3-chloro-4-(indolin-1-ylamino)quinolin-6-yl)pyrimidin-2-yl)propan-2-ol (47);

2-(5-(3-chloro-4-((2-methylindolin-1-yl)amino)quinolin-6-yl)pyrimidin-2-yl)propan-2-ol (48);
1-((3-chloro-6-(2-(2-hydroxypropan-2-yl)pyrimidin-5-yl)quinolin-4-yl)amino)-1-(2-fluorophenyl)-2-methylpropan-2-ol (49);
2-(5-(3-chloro-4-((1-cyclobutylpropyl)amino)quinolin-6-yl)pyrimidin-2-yl)propan-2-ol (50);
2-(5-(3-chloro-4-((2-methyl-1-(pyridin-2-yl)propyl)amino)quinolin-6-yl)pyrimidin-2-yl)propan-2-ol (51);
2-(5-(3-chloro-4-((1-(pyridin-2-yl)propyl)amino)quinolin-6-yl)pyrimidin-2-yl)propan-2-ol (52);
(R)-2-(5-(3-chloro-4-((1-(2-chloro-5-fluoropyridin-4-yl)ethyl)amino)quinolin-6-yl)pyrimidin-2-yl)propan-2-ol (53);
2-(5-(3-chloro-4-(2-methyl-2-phenylhydrazinyl)quinolin-6-yl)pyrimidin-2-yl)propan-2-ol (54);
2-(5-(3-chloro-4-((2,2-difluoro-1-(2-fluorophenyl)ethyl)amino)quinolin-6-yl)pyrimidin-2-yl)propan-2-ol (55);
2-(5-(4-((4-bromo-2-(1H-pyrazol-1-yl)benzyl)amino)-3-chloroquinolin-6-yl)pyrimidin-2-yl) propan-2-ol (56);
2-(5-(3-chloro-4-((2,2-difluoro-1-phenylethyl)amino)quinolin-6-yl)pyrimidin-2-yl)propan-2-ol (57);
(R)-2-(5-(3-chloro-4-((1-cyclohexylethyl)amino)quinolin-6-yl)pyrimidin-2-yl)propan-2-ol (58);
(S)-2-(5-(3-chloro-4-((1-cyclohexylethyl)amino)quinolin-6-yl)pyrimidin-2-yl)propan-2-ol (59);
tert-butyl (S)-3-((S)-1-((3-chloro-6-(2-(2-hydroxypropan-2-yl)pyrimidin-5-yl)quinolin-4-yl)amino)ethyl)piperidine-1-carboxylate (60);
tert-butyl (R)-3-((R)-1-((3-chloro-6-(2-(2-hydroxypropan-2-yl)pyrimidin-5-yl)quinolin-4-yl)amino)ethyl)piperidine-1-carboxylate (61);
2-(5-(3-chloro-4-((1-(4-chloropyridin-2-yl)ethyl)amino)quinolin-6-yl)pyrimidin-2-yl)propan-2-ol (62);
(R)-2-(5-(3-chloro-4-((1-(4-chloropyridin-2-yl)but-3-en-1-yl)amino)quinolin-6-yl)pyrimidin-2-yl)propan-2-ol (63);
2-(5-(4-((1-(6-bromo-3-fluoropyridin-2-yl)propyl)amino)-3-chloroquinolin-6-yl)pyrimidin-2-yl)propan-2-ol (64);
N-(4-aminobutyl)-5-(3-chloro-4-((2,5-dimethylphenyl)amino)-2-methylquinolin-6-yl)picolinamide (65);
2-(5-(3-chloro-4-((ethyl(phenyl)amino)methyl)quinolin-6-yl)pyrimidin-2-yl)propan-2-ol (66);
2-(5-(3-chloro-4-(((2-fluorophenyl)(methyl)amino)methyl)quinolin-6-yl)pyrimidin-2-yl)propan-2-ol (67);
2-(5-(3-chloro-4-((ethyl(2-fluorophenyl)amino)methyl)quinolin-6-yl)pyrimidin-2-yl)propan-2-ol (68);
1-((5-(2-amino-3-chloro-4-((2,5-dimethylphenyl)amino)quinolin-6-yl)pyrimidin-2-yl)amino)-2-methylpropan-2-ol (69);
2-((5-(2-amino-3-chloro-4-((2,5-dimethylphenyl)amino)quinolin-6-yl)pyrimidin-2-yl)amino)ethan-1-ol (70);
2-((5-(2-amino-3-chloro-4-((2,5-dimethylphenyl)amino)quinolin-6-yl)pyrimidin-2-yl)amino) propane-1,3-diol (71);
4-(5-(2-amino-3-chloro-4-((2,5-dimethylphenyl)amino)quinolin-6-yl)pyrimidin-2-yl)piperazin-2-one (72);
3-((5-(2-amino-3-chloro-4-((2,5-dimethylphenyl)amino)quinolin-6-yl)pyrimidin-2-yl)amino)propane-1,2-diol (73);
(S)-4-(5-(3-chloro-4-(((S)-2,2-difluoro-1-(2-fluorophenyl)ethyl)amino)quinolin-6-yl)pyrimidin-2-yl)piperazine-2-carboxylic acid (74);
(S)-4-amino-1-(5-(3-chloro-4-((2,2-difluoro-1-(2-fluorophenyl)ethyl)amino)quinolin-6-yl)pyrimidin-2-yl)piperidine-4-carboxylic acid (75);
(S)-2-(4-(5-(3-chloro-4-((2,2-difluoro-1-(2-fluorophenyl)ethyl)amino)quinolin-6-yl)pyrimidin-2-yl)-2-oxopiperazin-1-yl)acetic acid (76);
2-(4-(5-(3-chloro-4-(((S)-2,2-difluoro-1-(2-fluorophenyl)ethyl)amino)quinolin-6-yl)pyrimidin-2-yl)piperazin-2-yl)acetic acid (77);
(S)-2-(1-(5-(3-chloro-4-((2,2-difluoro-1-(2-fluorophenyl)ethyl)amino)quinolin-6-yl)pyrimidin-2-yl)piperidin-4-yl)acetic acid (78);
(S)-4-(5-(3-chloro-4-((2,2-difluoro-1-(2-fluorophenyl)ethyl)amino)quinolin-6-yl)pyrimidin-2-yl)piperazin-2-one (79);
(S)-1-((5-(3-chloro-4-((2,2-difluoro-1-(2-fluorophenyl)ethyl)amino)quinolin-6-yl)pyrimidin-2-yl)amino)-2-methylpropan-2-ol (80);
(R)-2-(4-(5-(3-chloro-4-((1-(2-fluorophenyl)ethyl)amino)quinolin-6-yl)pyridin-2-yl)-2-oxopiperazin-1-yl)acetic acid (81);
(R)-2-(1-(5-(3-chloro-4-((1-(2-fluorophenyl)ethyl)amino)quinolin-6-yl)pyridin-2-yl)piperidin-4-yl)acetic acid (82);
((R)-4-(5-(3-chloro-4-(((R)-1-(2-fluorophenyl)ethyl)amino)quinolin-6-yl)pyridin-2-yl)morpholin-2-yl)methanol (83);
((S)-4-(5-(3-chloro-4-(((R)-1-(2-fluorophenyl)ethyl)amino)quinolin-6-yl)pyridin-2-yl)piperazin-2-yl)methanol (84);
((R)-4-(5-(3-chloro-4-(((R)-1-(2-fluorophenyl)ethyl)amino)quinolin-6-yl)pyridin-2-yl)morpholin-3-yl)methanol (85);
((S)-4-(5-(3-chloro-4-(((S)-2,2-difluoro-1-(2-fluorophenyl)ethyl)amino)quinolin-6-yl)pyrimidin-2-yl)piperazin-2-yl)methanol (86);
((S)-4-(5-(3-chloro-4-(((S)-2,2-difluoro-1-(2-fluorophenyl)ethyl)amino)quinolin-6-yl)pyrimidin-2-yl)morpholin-2-yl)methanol (87);
(R)-3-chloro-N-(1-(2-fluorophenyl)ethyl)-6-(6-(piperazin-1-yl)pyridin-3-yl)quinolin-4-amine (88);
(R)-2-(4-(5-(3-chloro-4-((1-(2-fluorophenyl)ethyl)amino)quinolin-6-yl)pyrimidin-2-yl)piperazin-1-yl)-N-methylacetamide (89);
(R)-2-(4-(5-(3-chloro-4-((1-(2-fluorophenyl)ethyl)amino)quinolin-6-yl)pyrimidin-2-yl)piperazin-1-yl)acetamide (90);
(R)-2-(4-(5-(3-chloro-4-((1-(2-fluorophenyl)ethyl)amino)quinolin-6-yl)pyrimidin-2-yl)piperazin-1-yl)-N-(methylsulfonyl)acetamide (91);
(S)-2-(4-(5-(3-chloro-4-((2,2-difluoro-1-(2-fluorophenyl)ethyl)amino)quinolin-6-yl)pyrimidin-2-yl)piperazin-1-yl)acetic acid (92);
(S)-3-((tert-butoxycarbonyl)amino)-2-(4-(5-(3-chloro-4-(((R)-1-(2-fluorophenyl)ethyl)amino) quinolin-6-yl)pyrimidin-2-yl)piperazin-1-yl)propanoic acid (93);
(S)-3-amino-2-(4-(5-(3-chloro-4-(((R)-1-(2-fluorophenyl)ethyl)amino)quinolin-6-yl)pyrimidin-2-yl)piperazin-1-yl) propanoic acid (94);
(S)-3-acetamido-2-(4-(5-(3-chloro-4-(((R)-1-(2-fluorophenyl)ethyl)amino)quinolin-6-yl)pyrimidin-2-yl)piperazin-1-yl)propanoic acid (95);
2-(5-(3-chloro-4-(((S)-1-((S)-piperidin-3-yl)ethyl)amino)quinolin-6-yl)pyrimidin-2-yl)propan-2-ol (96 and 97);
(R)-2-(5-(3-chloro-4-((1-(piperidin-3-yl)ethyl)amino)quinolin-6-yl)pyrimidin-2-yl)propan-2-ol (98);
methyl (S)-3-amino-2-(4-(5-(3-chloro-4-(((R)-1-(2-fluorophenyl)ethyl)amino)quinolin-6-yl)pyrimidin-2-yl)piperazin-1-yl)propanoate (99);

2-amino-2-(4-(3-chloro-4-(((R)-1-(2-fluorophenyl)ethyl)amino)quinolin-6-yl)phenyl)ethan-1-ol (100);
(R)—N-(4-aminobutyl)-5-(3-chloro-4-((1-(2-fluorophenyl)ethyl)amino)quinolin-6-yl)picolinamide (101);
(R)-6-(4-(1-aminocyclopropyl)phenyl)-3-chloro-N-(1-(2-fluorophenyl)ethyl)quinolin-4-amine (102);
(S)-3-((S)-1-((3-chloro-6-(2-(2-hydroxypropan-2-yl)pyrimidin-5-yl)quinolin-4-yl)amino)ethyl)piperidine-1-carboxamide (103);
(R)-3-((R)-1-((3-chloro-6-(2-(2-hydroxypropan-2-yl)pyrimidin-5-yl)quinolin-4-yl)amino)ethyl)piperidine-1-carboxamide (104);
2-(5-(3-chloro-4-(((S)-1-((S)-1-ethylpiperidin-3-yl)ethyl)amino)quinolin-6-yl)pyrimidin-2-yl)propan-2-ol (105);
3-((S)-3-((S)-1-((3-chloro-6-(2-(2-hydroxypropan-2-yl)pyrimidin-5-yl)quinolin-4-yl)amino)ethyl)piperidin-1-yl)propane-1,2-diol (106);
1-((S)-3-((S)-1-((3-chloro-6-(2-(2-hydroxypropan-2-yl)pyrimidin-5-yl)quinolin-4-yl)amino)ethyl)piperidin-1-yl)ethanone (107);
1-((R)-3-((R)-1-((3-chloro-6-(2-(2-hydroxypropan-2-yl)pyrimidin-5-yl)quinolin-4-yl)amino)ethyl)piperidin-1-yl)ethan-1-one (108);
methyl (S)-3-acetamido-2-(4-(5-(3-chloro-4-(((R)-1-(2-fluorophenyl)ethyl)amino)quinolin-6-yl)pyrimidin-2-yl)piperazin-1-yl)propanoate (109);
(R)—N-(4-(3-chloro-4-((1-(2-fluorophenyl)ethyl)amino)quinolin-6-yl)benzyl)acetamide (110);
(R)—N-(1-(4-(3-chloro-4-((1-(2-fluorophenyl)ethyl)amino)quinolin-6-yl)phenyl)cyclobutyl) methanesulfonamide (111);
3-(4-(5-(3-chloro-4-(((R)-1-(2-fluorophenyl)ethyl)amino)quinolin-6-yl)pyrimidin-2-yl)piperazin-1-yl)pyrrolidin-2-one (112);
(R)—N-(1-(4-(3-chloro-4-((1-(2-fluorophenyl)ethyl)amino)quinolin-6-yl)phenyl)cyclobutyl) acetamide (113);
(R)-4-(5-(3-chloro-4-((1-(2-fluorophenyl)ethyl)amino)quinolin-6-yl)pyrimidin-2-yl)-4-hydroxycyclohexan-1-one (114);
3-amino-3-(4-(3-chloro-4-(((R)-1-(2-fluorophenyl)ethyl)amino)quinolin-6-yl)phenyl)propanoic acid (115);
2-amino-3-(4-(3-chloro-4-(((R)-1-(2-fluorophenyl)ethyl)amino)quinolin-6-yl)phenyl)propanoic acid (116);
(R)-2-(4-(3-chloro-4-((1-(2-fluorophenyl)ethyl)amino)quinolin-6-yl)phenyl)-1,3-difluoropropan-2-ol (117);
(R)-6-(4-(1-aminocyclobutyl)phenyl)-3-chloro-N-(1-(2-fluorophenyl)ethyl)quinolin-4-amine (118);
(R)-3-amino-3-(4-(3-chloro-4-((1-(2-fluorophenyl)ethyl)amino)quinolin-6-yl)phenyl)cyclobutan-1-ol ((119);
(R)-1-(5-(3-chloro-4-((1-(2-fluorophenyl)ethyl)amino)quinolin-6-yl)pyrimidin-2-yl)cyclopentan-1-ol (120);
(1R,2R)-1-(5-(3-chloro-4-(((R)-1-(2-fluorophenyl)ethyl)amino)quinolin-6-yl)pyrimidin-2-yl)cyclopentane-1,2-diol (121);
6-bromo-3,8-dichloro-N-(1-(2-fluorophenyl)ethyl)quinolin-4-amine (122);
(R)-1-(4-(5-(3-chloro-4-((1-(2-fluorophenyl)ethyl)amino)quinolin-6-yl)pyridin-2-yl)piperazin-1-yl)prop-2-en-1-one (123);
(R)—N-(5-(3-chloro-4-((1-(2-fluorophenyl)ethyl)amino)quinolin-6-yl)pyrimidin-2-yl)-N-methylacrylamide (124);
(R)-1-(4-(5-(3-chloro-4-((1-(2-fluorophenyl)ethyl)amino)quinolin-6-yl)pyridin-2-yl)piperazin-1-yl)but-2-yn-1-one (125);
2-(5-(3-chloro-4-((1-(3-fluoro-6-vinylpyridin-2-yl)propyl)amino)quinolin-6-yl)pyrimidin-2-yl)propan-2-ol (126);
1-(6-(1-((3-chloro-6-(2-(2-hydroxypropan-2-yl)pyrimidin-5-yl)quinolin-4-yl)amino)propyl)-5-fluoropyridin-2-yl)ethane-1,2-diol (127);
6-(1-((3-chloro-6-(2-(2-hydroxypropan-2-yl)pyrimidin-5-yl)quinolin-4-yl)amino)propyl)-5-fluoropicolinic acid (128);
6-(1-((3-chloro-6-(2-(2-hydroxypropan-2-yl)pyrimidin-5-yl)quinolin-4-yl)amino)propyl)-5-fluoropicolinamide (129);
2-(5-(3-chloro-4-((1-(3-fluoro-6-(hydroxymethyl)pyridin-2-yl)propyl)amino)quinolin-6-yl)pyrimidin-2-yl)propan-2-ol (130);
(R)—N-(4-(5-(3-chloro-4-((1-(2-fluorophenyl)ethyl)amino)quinolin-6-yl)pyrimidin-2-yl)-4-hydroxycyclohexyl)acetamide (131 and 132);
2-(5-(3-chloro-4-((1-(furan-2-yl)propan-2-yl)amino)quinolin-6-yl)pyrimidin-2-yl)propan-2-ol (133);
2-(5-(3-chloro-4-((1-(2,3,3-trimethylcyclopent-1-en-1-yl)propan-2-yl)amino)quinolin-6-yl)pyrimidin-2-yl)propan-2-ol (134);
(R)-2-(5-(3-chloro-4-((1-(3-morpholinophenyl)ethyl)amino)quinolin-6-yl)pyrimidin-2-yl)propan-2-ol (136);
2-(5-(3-chloro-4-((1-(4-(trifluoromethoxy)phenyl)propan-2-yl)amino)quinolin-6-yl)pyrimidin-2-yl)propan-2-ol (137);
4-(2-((3-chloro-6-(2-(2-hydroxypropan-2-yl)pyrimidin-5-yl)quinolin-4-yl)amino)propyl)-2-methylisoquinolin-1(2H)-one (138);
2-(5-(3-chloro-4-((1-cyclopentylpropan-2-yl)amino)quinolin-6-yl)pyrimidin-2-yl)propan-2-ol (140);
2-(5-(3-chloro-4-((4-(6-methyl-1H-indol-3-yl)butan-2-yl)amino)quinolin-6-yl)pyrimidin-2-yl)propan-2-ol (141);
2-(5-(3-chloro-4-((1-(1-(4-chlorophenyl)cyclopentyl)ethyl)amino)quinolin-6-yl)pyrimidin-2-yl)propan-2-ol (142);
3-((3-chloro-6-(2-(2-hydroxypropan-2-yl)pyrimidin-5-yl)quinolin-4-yl)amino)-1,1-diphenylbutan-1-ol (143);
2-(5-(4-((1-(1H-indol-4-yl)propan-2-yl)amino)-3-chloroquinolin-6-yl)pyrimidin-2-yl)propan-2-ol (144);
2-(5-(3-chloro-4-(4-(trifluoromethyl)benzylamino)quinolin-6-yl)pyrimidin-2-yl)propan-2-ol (145);
2-(5-(3-chloro-4-((2-(trifluoromethyl)benzyl)amino)quinolin-6-yl)pyrimidin-2-yl)propan-2-ol (146);
2-(5-(3-chloro-4-((1-(3-(trifluoromethyl)phenyl)ethyl)amino)quinolin-6-yl)pyrimidin-2-yl)propan-2-ol (147);
2-(5-(3-chloro-4-((4-(difluoromethoxy)benzyl)amino)quinolin-6-yl)pyrimidin-2-yl)propan-2-ol (148);
2-(5-(3-chloro-4-((1-(2,5-dimethylphenyl)ethyl)amino)quinolin-6-yl)pyrimidin-2-yl)propan-2-ol (149);
2-(5-(3-chloro-4-((1-(4-(trifluoromethyl)phenyl)ethyl)amino)quinolin-6-yl)pyrimidin-2-yl)propan-2-ol (150);
2-(5-(3-chloro-4-((1-(2-(trifluoromethyl)phenyl)ethyl)amino)quinolin-6-yl)pyrimidin-2-yl) propan-2-ol (151);
2-(5-(3-chloro-4-((1-(2-fluorophenyl)ethyl)amino)quinolin-6-yl)pyrimidin-2-yl)propan-2-ol (152);
2-(5-(3-chloro-4-((1-(2-chlorophenyl)ethyl)amino)quinolin-6-yl)pyrimidin-2-yl)propan-2-ol (153);
(R)-2-(5-(3-chloro-4-((1-phenylethyl)amino)quinolin-6-yl)pyrimidin-2-yl)propan-2-ol (154);

2-(5-(3-chloro-4-((1-(3-fluorophenyl)ethyl)amino)quinolin-6-yl)pyrimidin-2-yl)propan-2-ol (155);
2-(5-(3-fluoro-4-((1-(2-fluorophenyl)ethyl)amino)quinolin-6-yl)pyrimidin-2-yl)propan-2-ol (156);
2-(5-(3-chloro-4-((1-(4-fluorophenyl)ethyl)amino)quinolin-6-yl)pyrimidin-2-yl)propan-2-ol (157);
2-(5-(3-chloro-4-((1-(2-fluorophenyl)cyclopropyl)amino)quinolin-6-yl)pyrimidin-2-yl)propan-2-ol (158);
2-(5-(3-fluoro-4-((1-(2-fluorophenyl)ethyl)amino)-2-methylquinolin-6-yl)pyrimidin-2-yl)propan-2-ol (159);
2-(5-(3-chloro-4-((1-(2,5-difluorophenyl)ethyl)amino)quinolin-6-yl)pyrimidin-2-yl)propan-2-ol (160);
2-(5-(3-chloro-4-((1-phenylcyclopropyl)amino)quinolin-6-yl)pyrimidin-2-yl)propan-2-ol (161);
2-(5-(3-chloro-4-((1-(3-fluoropyridin-4-yl)ethyl)amino)quinolin-6-yl)pyrimidin-2-yl)propan-2-ol (162);
2-(5-(3-chloro-4-((1-(2,4-difluorophenyl)ethyl)amino)quinolin-6-yl)pyrimidin-2-yl)propan-2-ol (163);
2-(5-(3-chloro-4-((2,2,2-trifluoro-1-(2-fluorophenyl)ethyl)amino)quinolin-6-yl)pyrimidin-2-yl)propan-2-ol (164);
2-(5-(3-chloro-4-((3,3,3-trifluoro-1-phenylpropyl)amino)quinolin-6-yl)pyrimidin-2-yl)propan-2-ol (165);
2-(4-(3-chloro-4-((1-(pyridin-3-yl)ethyl)amino)quinolin-6-yl)phenyl)propan-2-ol (166);
3-((3-chloro-6-(2-(2-hydroxypropan-2-yl)pyrimidin-5-yl)quinolin-4-yl)amino)-3-(2-fluorophenyl)propan-1-ol (167);
2-(5-(3-chloro-4-((3,3-difluoro-1-(2-fluorophenyl)propyl)amino)quinolin-6-yl)pyrimidin-2-yl)propan-2-ol (168);
2-(5-(3-chloro-4-((3,3,3-trifluoro-1-(2-fluorophenyl)propyl)amino)quinolin-6-yl)pyrimidin-2-yl)propan-2-ol (169);
2-(4-(3-chloro-4-((1-(3-fluoropyridin-2-yl)ethyl)amino)quinolin-6-yl)phenyl)propan-2-ol (170);
2-(5-(3-chloro-4-((1-(3-fluoropyridin-2-yl)ethyl)amino)quinolin-6-yl)pyrimidin-2-yl)propan-2-ol (171);
2-(4-(3-chloro-4-((1-(isothiazol-4-yl)ethyl)amino)quinolin-6-yl)phenyl)propan-2-ol (172);
2-(4-(3-chloro-4-((1-(pyrimidin-4-yl)ethyl)amino)quinolin-6-yl)phenyl)propan-2-ol (173);
2-(4-(3-chloro-4-((1-(isoxazol-3-yl)ethyl)amino)quinolin-6-yl)phenyl)propan-2-ol (174);
2-(4-(3-chloro-4-((1-(pyridin-2-yl)ethyl)amino)quinolin-6-yl)phenyl)propan-2-ol (175);
2-(4-(3-chloro-4-((1-(pyridin-4-yl)ethyl)amino)quinolin-6-yl)phenyl)propan-2-ol (176);
2-(4-(3-chloro-4-((1-(pyrimidin-2-yl)ethyl)amino)quinolin-6-yl)phenyl)propan-2-ol (177);
2-(4-(3-chloro-4-((1-(4-methylpyrimidin-2-yl)ethyl)amino)quinolin-6-yl)phenyl)propan-2-ol (178);
2-(4-(3-chloro-4-((1-(oxazol-2-yl)ethyl)amino)quinolin-6-yl)phenyl)propan-2-ol (179);
2-(5-(4-(2,5-dimethylphenylamino)-2-methoxy-3-methylquinolin-6-yl)pyrimidin-2-yl)propan-2-ol (180);
4-((2,5-dimethylphenyl)amino)-6-(2-(2-hydroxypropan-2-yl)pyrimidin-5-yl)-3-methylquinolin-2-ol (181);
2-(5-(3-chloro-4-((2-(3-(trifluoromethyl)phenyl)propan-2-yl)amino)quinolin-6-yl)pyrimidin-2-yl)propan-2-ol (182);
2-(5-(4-((2,5-dimethylphenyl)amino)-3-fluoro-2-methylquinolin-6-yl)pyrimidin-2-yl)propan-2-ol (183);
2-(5-(4-((2,5-dimethylphenyl)amino)-2,3-dimethylquinolin-6-yl)pyrimidin-2-yl)propan-2-ol (184);
2-(5-(3-chloro-4-((2-(4-(trifluoromethyl)phenyl)propan-2-yl)amino)quinolin-6-yl)pyrimidin-2-yl)propan-2-ol (185);
5-(4-((2,5-dimethylphenyl)amino)-3-fluoro-2-methylquinolin-6-yl)-N-methylpicolinamide (186);
2-(4-(5-(4-((2,5-dimethylphenyl)amino)-3-fluoro-2-methylquinolin-6-yl)pyrimidin-2-yl)piperazin-1-yl)acetic acid (187);
(R)-2-(5-(7-chloro-3-fluoro-8-((1-(2-fluoro-5-vinylphenyl)ethyl)amino)-1,5-naphthyridin-2-yl)pyrimidin-2-yl)propan-2-ol (188);
2-(5-(3-chloro-4-((1-(2-fluorophenyl)-2-methylpropyl)amino)quinolin-6-yl)pyrimidin-2-yl) propan-2-ol (189);
2-(5-(3-chloro-4-((1-(2-fluorophenyl)propyl)amino)quinolin-6-yl)pyrimidin-2-yl)propan-2-ol (190);
2-(5-(3-chloro-4-((cyclopropyl(2-fluorophenyl)methyl)amino)quinolin-6-yl)pyrimidin-2-yl)propan-2-ol (191);
2-(4-(3-chloro-4-((1-(furan-2-yl)ethyl)amino)quinolin-6-yl)phenyl)propan-2-ol (192);
2-(4-(3-chloro-4-((1-(thiazol-2-yl)ethyl)amino)quinolin-6-yl)phenyl)propan-2-ol (194);
2-(4-(3-chloro-4-((1-(1-methyl-1H-pyrazol-5-yl)ethyl)amino)quinolin-6-yl)phenyl)propan-2-ol (195);
2-(4-(3-chloro-4-((1-(thiophen-3-yl)ethyl)amino)quinolin-6-yl)phenyl)propan-2-ol (196);
2-(4-(3-chloro-4-((1-(1-methyl-1H-pyrazol-4-yl)ethyl)amino)quinolin-6-yl)phenyl)propan-2-ol (197);
2-(4-(3-chloro-4-((1-(pyrazin-2-yl)ethyl)amino)quinolin-6-yl)phenyl)propan-2-ol (198);
2-(4-(3-chloro-4-((1-(thiophen-2-yl)ethyl)amino)quinolin-6-yl)phenyl)propan-2-ol (199);
2-(4-(3-chloro-4-((1-(1-methyl-1H-pyrazol-3-yl)ethyl)amino)quinolin-6-yl)phenyl)propan-2-ol (200);
2-(4-(3-chloro-4-((1-(1-methyl-1H-imidazol-2-yl)ethyl)amino)quinolin-6-yl)phenyl)propan-2-ol (201);
2-(4-(3-chloro-4-((1-(thiazol-4-yl)ethyl)amino)quinolin-6-yl)phenyl)propan-2-ol (202);
2-(4-(3-chloro-4-((1-(oxazol-5-yl)ethyl)amino)quinolin-6-yl)phenyl)propan-2-ol (203);
2-(4-(3-chloro-4-((1-(furan-3-yl)ethyl)amino)quinolin-6-yl)phenyl)propan-2-ol (204);
2-(4-(3-chloro-4-((1-(1-methyl-1H-imidazol-4-yl)ethyl)amino)quinolin-6-yl)phenyl)propan-2-ol (205);
2-(4-(3-chloro-4-((1-(oxazol-4-yl)ethyl)amino)quinolin-6-yl)phenyl)propan-2-ol (206);
2-(4-(3-chloro-4-((1-(1-methyl-1H-imidazol-5-yl)ethyl)amino)quinolin-6-yl)phenyl)propan-2-ol (210);
2-(4-(3-chloro-4-((1-(thiazol-5-yl)ethyl)amino)quinolin-6-yl)phenyl)propan-2-ol (211);
(R)-2-(5-(3-chloro-4-(1-(2-fluorophenyl)ethylamino)quinolin-6-yl)pyrimidin-2-yl)propan-2-ol (217);
2-(5-(3-chloro-4-((1-(2-fluorophenyl)ethyl)amino)-2-methylquinolin-6-yl)pyrimidin-2-yl)propan-2-ol (218);
(R)-3-chloro-N-(1-(2-fluorophenyl)ethyl)-6-(2-morpholinopyrimidin-5-yl)quinolin-4-amine (219);
(R)-(4-(3-chloro-4-((1-(2-fluorophenyl)ethyl)amino)quinolin-6-yl)phenyl)methanol (220);
(R)-3-chloro-N-(1-(2-fluorophenyl)ethyl)-6-(6-(methylsulfonyl)pyridin-3-yl)quinolin-4-amine (221);
(R)-3-chloro-6-(2-ethoxypyrimidin-5-yl)-N-(1-(2-fluorophenyl)ethyl)quinolin-4-amine (222);
(R)-3-chloro-6-(2-ethylpyrimidin-5-yl)-N-(1-(2-fluorophenyl)ethyl)quinolin-4-amine (223);

methyl (R)-2-(4-(5-(3-chloro-4-((1-(2-fluorophenyl) ethyl)amino)quinolin-6-yl)pyrimidin-2-yl)piperazin-1-yl)acetate (224);
(R)-4-(5-(3-chloro-4-((1-(2-fluorophenyl)ethyl)amino) quinolin-6-yl)pyrimidin-2-yl)thiomorpholine 1,1-dioxide (225);
(R)-4-(5-(3-chloro-4-((1-(2-fluorophenyl)ethyl)amino) quinolin-6-yl)pyrimidin-2-yl)piperazin-2-one (226);
(R)-3-(5-(3-chloro-4-((1-(2-fluorophenyl)ethyl)amino) quinolin-6-yl)pyrimidin-2-yl)oxetan-3-ol (227);
(R)-2-(4-(3-chloro-4-((1-(2-fluorophenyl)ethyl)amino) quinolin-6-yl)phenyl)propan-2-ol (228);
2-(5-(3-chloro-4-((2-fluoro-1-(2-fluorophenyl)-2-methylpropyl)amino)quinolin-6-yl)pyrimidin-2-yl)propan-2-ol (229);
2-(5-(3-chloro-4-((3-fluoro-1-(2-fluorophenyl)propyl) amino)quinolin-6-yl)pyrimidin-2-yl)propan-2-ol (230);
2-(4-(3-chloro-4-((3-fluoro-1-(2-fluorophenyl)propyl) amino)quinolin-6-yl)phenyl)propan-2-ol (232);
(R)-2-(4-(5-(3-chloro-4-((1-(2-fluorophenyl)ethyl) amino)quinolin-6-yl)pyrimidin-2-yl)piperazin-1-yl)acetonitrile (233);
(R)-6-(2-(4-((2H-tetrazol-5-yl)methyl)piperazin-1-yl)pyrimidin-5-yl)-3-chloro-N-(1-(2-fluorophenyl)ethyl) quinolin-4-amine (237);
(R)-2-(5-(3-chloro-4-((3-fluoro-1-(2-fluorophenyl)propyl)amino)quinolin-6-yl)pyrimidin-2-yl)propan-2-ol (238);
(R)-2-(5-(4-((1-(2-fluorophenyl)ethyl)amino)-3-methylquinolin-6-yl)pyrimidin-2-yl)propan-2-ol (240);
2-(5-(3-chloro-7-fluoro-4-((1-(2-fluorophenyl)ethyl) amino)quinolin-6-yl)pyrimidin-2-yl)propan-2-ol (241);
2-(4-(5-(3-chloro-7-fluoro-4-((1-(2-fluorophenyl)ethyl) amino)quinolin-6-yl)pyrimidin-2-yl)piperazin-1-yl) acetic acid (242);
ethyl-1-(5-(3-chloro-7-fluoro-4-((1-(2-fluorophenyl) ethyl)amino)quinolin-6-yl)pyrimidin-2-yl)piperidine-4-carboxylate (243);
1-(5-(3-chloro-7-fluoro-4-((1-(2-fluorophenyl)ethyl) amino)quinolin-6-yl)pyrimidin-2-yl)piperidine-4-carboxylic acid (244);
2-(1-(5-(3-chloro-7-fluoro-4-((1-(2-fluorophenyl)ethyl) amino)quinolin-6-yl)pyrimidin-2-yl)piperidin-4-yl) propan-2-ol (245);
2-(5-(3-chloro-7-fluoro-4-((1-(2-fluorophenyl)ethyl) amino)quinolin-6-yl)pyrimidin-2-yl)propan-2-ol (246);
2-(5-(3-chloro-8-fluoro-4-((1-(2-fluorophenyl)ethyl) amino)quinolin-6-yl)pyrimidin-2-yl) propan-2-ol (247);
2-(5-(3-chloro-7-fluoro-4-((1-(2-fluorophenyl)ethyl) amino)quinolin-6-yl)pyrimidin-2-yl)propan-2-ol (248);
2-(5-(3-chloro-7-fluoro-4-((1-(2-fluorophenyl)ethyl) amino)quinolin-6-yl)pyrimidin-2-yl)propan-2-ol (249);
2-(5-(3-chloro-7-fluoro-4-((1-(2-fluorophenyl)ethyl) amino)quinolin-6-yl)pyrimidin-2-yl)propan-2-ol (250);
4-(4-(3-chloro-7-fluoro-4-((1-(2-fluorophenyl)ethyl) amino)quinolin-6-yl)phenyl)-4-hydroxycyclohexane-1-carboxylic acid (251);
2-(5-(3-chloro-7-fluoro-4-((1-(2-fluorophenyl)ethyl) amino)quinolin-6-yl)pyrimidin-2-yl)propan-2-ol (252);
2-(5-(3-chloro-5-fluoro-4-((1-(2-fluorophenyl)ethyl) amino)quinolin-6-yl)pyrimidin-2-yl) propan-2-ol (253);
2-(5-(3-chloro-7-fluoro-4-((1-(2-fluorophenyl)ethyl) amino)quinolin-6-yl)pyrimidin-2-yl)propane-1,2-diol (254);
5-(3-chloro-7-fluoro-4-((1-(2-fluorophenyl)ethyl)amino) quinolin-6-yl)pyrimidine-2-carbonitrile (255);
1-(4-(3-chloro-7-fluoro-4-((1-(2-fluorophenyl)ethyl) amino)quinolin-6-yl)phenyl)ethane-1,2-diol (256);
2-(5-(3-chloro-7-fluoro-4-((1-(2-fluorophenyl)ethyl) amino)quinolin-6-yl)pyrimidin-2-yl)propane-1,2-diol (257);
2-(4-(3-chloro-7-fluoro-4-((1-(2-fluorophenyl)ethyl) amino)quinolin-6-yl)-2-fluorophenyl)propan-2-ol (258);
2-(5-(3-chloro-7-fluoro-4-((1-(2-fluorophenyl)ethyl) amino)quinolin-6-yl)pyrimidin-2-yl)propane-1,2-diol (259);
(4-(3-chloro-7-fluoro-4-((1-(2-fluorophenyl)ethyl)amino) quinolin-6-yl)phenyl)(cyclopropyl)methanol (260);
(4-(3-chloro-7-fluoro-4-((1-(2-fluorophenyl)ethyl)amino) quinolin-6-yl)phenyl)(cyclopropyl) methanol (261);
(4-(3-chloro-7-fluoro-4-((1-(2-fluorophenyl)ethyl)amino) quinolin-6-yl)phenyl)(cyclopropyl) methanol (262);
(4-(3-chloro-7-fluoro-4-((1-(2-fluorophenyl)ethyl)amino) quinolin-6-yl)phenyl)(cyclopropyl)methanol (263);
(1-(4-(3-chloro-7-fluoro-4-((1-(2-fluorophenyl)ethyl) amino)quinolin-6-yl)phenyl)cyclopropyl) methanol (264);
(1-(4-(3-chloro-7-fluoro-4-((1-(2-fluorophenyl)ethyl) amino)quinolin-6-yl)phenyl)cyclopropyl) methanol (265);
2-(1-(5-(3-chloro-7-fluoro-4-((1-(2-fluorophenyl)ethyl) amino)quinolin-6-yl)pyrimidin-2-yl)piperidin-4-yl) acetic acid (266);
2-(4-(3-chloro-7-fluoro-4-((1-(2-fluorophenyl)ethyl) amino)quinolin-6-yl)-2,6-difluorophenyl)propan-2-ol (267);
2-(4-(3-chloro-7-fluoro-4-((1-(2-fluorophenyl)ethyl) amino)quinolin-6-yl)-2,6-difluorophenyl) propan-2-ol (268);
(S)-2-(5-(3-chloro-4-((2,2-difluoro-1-(2-fluorophenyl) ethyl)amino)-7-fluoroquinolin-6-yl)pyrimidin-2-yl) propan-2-ol (269);
(S)-2-(5-(3-chloro-4-((2,2-difluoro-1-(2-fluorophenyl) ethyl)amino)-7-fluoroquinolin-6-yl)pyridin-2-yl)propan-2-ol (270);
2-(5-(3-chloro-7-fluoro-4-(((1S,2R)-2-phenylcyclopropyl)amino)quinolin-6-yl)pyrimidin-2-yl)propan-2-ol (271);
1-(4-(3-chloro-7-fluoro-4-((1-(2-fluorophenyl)ethyl) amino)quinolin-6-yl)phenyl)-2-morpholinoethan-1-ol (272);
1-(5-(3-chloro-7-fluoro-4-((1-(2-fluorophenyl)ethyl) amino)quinolin-6-yl)pyrazin-2-yl)-2-morpholinoethan-1-ol (273);
1-(5-(3-chloro-7-fluoro-4-((1-(2-fluorophenyl)ethyl) amino)quinolin-6-yl)pyrazin-2-yl)-2-morpholinoethan-1-ol (274);
1-(5-(3-chloro-7-fluoro-4-((1-(2-fluorophenyl)ethyl) amino)quinolin-6-yl)pyrazin-2-yl)-2-morpholinoethan-1-ol (275);
1-(5-(3-chloro-7-fluoro-4-((1-(2-fluorophenyl)ethyl) amino)quinolin-6-yl)pyrazin-2-yl)-2-morpholinoethan-1-ol (276);

1-(4-(3-chloro-7-fluoro-4-((1-(2-fluorophenyl)ethyl)amino)quinolin-6-yl)phenyl)-2-morpholinoethan-1-ol (277);
2-(5-(3-chloro-7-fluoro-4-((1-(2-fluorophenyl)cyclopropyl)amino)quinolin-6-yl)pyrimidin-2-yl)propan-2-ol (278);
2-(4-(3-chloro-7-fluoro-4-((1-(2-fluorophenyl)cyclopropyl)amino)quinolin-6-yl)phenyl)propan-2-ol (279);
(R)-2-(4-(4-(3-chloro-7-fluoro-4-((1-(2-fluorophenyl)ethyl)amino)quinolin-6-yl)phenyl)piperazin-1-yl)acetic acid (280);
methyl 1-(5-(3-chloro-7-fluoro-4-(((R)-1-(2-fluorophenyl)ethyl)amino)quinolin-6-yl)pyrimidin-2-yl)pyrrolidine-3-carboxylate (281);
1-(5-(3-chloro-7-fluoro-4-(((R)-1-(2-fluorophenyl)ethyl)amino)quinolin-6-yl)pyrimidin-2-yl)pyrrolidine-3-carboxylic acid (282);
2-(1-(5-(3-chloro-7-fluoro-4-(((R)-1-(2-fluorophenyl)ethyl)amino)quinolin-6-yl)pyrimidin-2-yl)pyrrolidin-3-yl)propan-2-ol (283);
1-(5-(3-chloro-7-fluoro-4-((1-(2-fluorophenyl)ethyl)amino)quinolin-6-yl)pyrazin-2-yl)pyrrolidin-3-ol (284);
(R)-2-(4-(5-(3-chloro-4-((1-(2-fluorophenyl)ethyl)amino)quinolin-6-yl)pyrimidin-2-yl)piperazin-1-yl)acetic acid (285);
1-(4-(3-chloro-7-fluoro-4-((1-(2-fluorophenyl)ethyl)amino)quinolin-6-yl)phenyl)-2-morpholinoethan-1-ol (286);
4-(5-(7-fluoro-4-((1-(2-fluorophenyl)ethyl)amino)quinolin-6-yl)pyrimidin-2-yl)tetrahydro-2H-pyran-4-ol (287);
1-(4-(3-chloro-7-fluoro-4-((1-(2-fluorophenyl)ethyl)amino)quinolin-6-yl)phenyl)-2-morpholinoethan-1-ol (288);
4-(5-(3-chloro-7-fluoro-4-((1-(2-fluorophenyl)ethyl)amino)quinolin-6-yl)pyrimidin-2-yl)-4-hydroxytetrahydro-2H-thiopyran 1,1-dioxide (289);
1-(4-(3-chloro-7-fluoro-4-((1-(2-fluorophenyl)ethyl)amino)quinolin-6-yl)phenyl)ethane-1,2-diol (290);
1-(4-(3-chloro-7-fluoro-4-((1-(2-fluorophenyl)ethyl)amino)quinolin-6-yl)phenyl)ethane-1,2-diol (291);
2-(5-(3-chloro-7-fluoro-4-((1-(2-fluorophenyl)ethyl)amino)quinolin-6-yl)pyrimidin-2-yl)-1-methoxypropan-2-ol (292);
2-(5-(3-chloro-7-fluoro-4-((1-(2-fluorophenyl)ethyl)amino)quinolin-6-yl)pyrimidin-2-yl)-1-methoxypropan-2-ol (293);
2-(5-(3-chloro-7-fluoro-4-((1-(2-fluorophenyl)ethyl)amino)quinolin-6-yl)pyrazin-2-yl)propan-2-ol (294);
4-(5-(3-chloro-7-fluoro-4-((1-(2-fluorophenyl)ethyl)amino)quinolin-6-yl)pyrimidin-2-yl)-4-hydroxycyclohexane-1-carboxylic acid (295);
2-(5-(3,5-dichloro-4-((1-(2-fluorophenyl)ethyl)amino)quinolin-6-yl)pyrimidin-2-yl)propan-2-ol (296);
(S)-2-(5-(3-chloro-4-((2,2-difluoro-1-(2-fluorophenyl)ethyl)amino)-8-fluoroquinolin-6-yl) pyrimidin-2-yl)propan-2-ol (297);
2-(5-(3-chloro-8-fluoro-4-((1-(2-fluorophenyl)ethyl)amino)-2-methylquinolin-6-yl)pyrimidin-2-yl)propan-2-ol (298);
(S)-2-(5-(3-chloro-4-((2,2-difluoro-1-(2-fluorophenyl)ethyl)amino)-8-fluoro-2-methylquinolin-6-yl)pyrimidin-2-yl)propan-2-ol (299);
1-(5-(3-chloro-7-fluoro-4-((1-(2-fluorophenyl)ethyl)amino)quinolin-6-yl)pyrimidin-2-yl)ethane-1,2-diol (300);
2-(5-(3-chloro-8-fluoro-4-((1-(4-fluorophenyl)ethyl)amino)-2-methylquinolin-6-yl)pyrimidin-2-yl)propan-2-ol (301);
(R)-3-(1-((3-chloro-8-fluoro-6-(2-(2-hydroxypropan-2-yl)pyrimidin-5-yl)-2-methylquinolin-4-yl)amino)ethyl)-4-fluorobenzonitrile (302);
(R)-3-(1-((3-chloro-8-fluoro-6-(2-(2-hydroxypropan-2-yl)pyrimidin-5-yl)-2-methylquinolin-4-yl)amino)ethyl)-4-fluorobenzamide (303);
(R)-(2-(4-(5-(3-chloro-7-fluoro-4-((1-(2-fluorophenyl)ethyl)amino)quinolin-6-yl)pyrimidin-2-yl) piperazin-1-yl)acetyl)glycine (304);
(S)-2-(4-(3-chloro-4-((2,2-difluoro-1-(2-fluorophenyl)ethyl)amino)-8-fluoro-2-methylquinolin-6-yl)phenyl)propan-2-ol (305);
2-(5-(3-chloro-8-fluoro-2-methyl-4-((1-phenylethyl)amino)quinolin-6-yl)pyrimidin-2-yl)propan-2-ol (306);
2-(5-(3-chloro-8-fluoro-4-((1-(3-fluorophenyl)ethyl)amino)-2-methylquinolin-6-yl)pyrimidin-2-yl)propan-2-ol (307);
±2-(4-(3-chloro-4-((1-(2-fluorophenyl)ethyl)amino)-2-methylquinolin-6-yl)phenyl)propan-2-ol (308);
2-(4-(5-(3-chloro-4-((1-(2-fluorophenyl)ethyl)amino)-2-methylquinolin-6-yl)pyrimidin-2-yl)piperazin-1-yl)acetic acid (309);
4-(5-(3-chloro-4-((1-(2-fluorophenyl)ethyl)amino)-2-methylquinolin-6-yl)pyrimidin-2-yl)thiomorpholine 1,1-dioxide (310);
3-chloro-N-(1-(2-fluorophenyl)ethyl)-2-methyl-6-(2-morpholinopyrimidin-5-yl)quinolin-4-amine (311);
(R)-3-(1-((3-chloro-6-(4-(2-hydroxypropan-2-yl)phenyl)-2-methylquinolin-4-yl)amino)ethyl)-4-fluorobenzamide (312);
(R)-3-(1-((3-chloro-2-methyl-6-(2-morpholinopyrimidin-5-yl)quinolin-4-yl)amino)ethyl)-4-fluorobenzamide (313);
(R)-4-fluoro-3-(1-((6-(2-(2-hydroxypropan-2-yl)pyrimidin-5-yl)-2,3-dimethylquinolin-4-yl)amino)ethyl)benzonitrile (314);
(R)-4-fluoro-3-(1-((6-(2-(2-hydroxypropan-2-yl)pyrimidin-5-yl)-2,3-dimethylquinolin-4-yl)amino)ethyl)benzamide (315);
(R)-2-(5-(4-((1-(5-bromo-2-fluorophenyl)ethyl)amino)-3-chloro-2-methylquinolin-6-yl)pyrimidin-2-yl)propan-2-ol (316);
2-(5-(3-chloro-4-((1-(2,5-difluorophenyl)ethyl)amino)-2-methylquinolin-6-yl)pyrimidin-2-yl)propan-2-ol (317);
(R)-2-(5-(4-((1-(5-bromo-2-fluorophenyl)ethyl)amino)-3-chloroquinolin-6-yl)pyrimidin-2-yl)propan-2-ol (318);
(R)-2-(5-(4-((1-(3-bromophenyl)ethyl)amino)-3-chloroquinolin-6-yl)pyrimidin-2-yl)propan-2-ol (319);
(S)-2-(5-(4-((1-(5-bromo-2-fluorophenyl)-2,2-difluoroethyl)amino)-3-chloro-2-methylquinolin-6-yl)pyrimidin-2-yl)propan-2-ol (320);
(R)-2-(5-(4-((1-(5-bromo-2-fluorophenyl)-2,2-difluoroethyl)amino)-3-chloro-2-methylquinolin-6-yl)pyrimidin-2-yl)propan-2-ol (321);
(R)-2-(5-(3-chloro-2-methyl-4-((1-phenylethyl)amino)quinolin-6-yl)pyrimidin-2-yl)propan-2-ol (322);
(R)-2-(5-(3-chloro-4-((1-(2-fluoro-5-(2-hydroxyethyl)phenyl)ethyl)amino)-2-methylquinolin-6-yl)pyrimidin-2-yl)propan-2-ol (323);
(R)-2-(5-(3-chloro-7-fluoro-4-((1-(2-fluoro-5-(2-hydroxyethoxy)phenyl)ethyl)amino)-2-methylquinolin-6-yl)pyrimidin-2-yl)propan-2-ol (324);

(R)-2-(5-(3-chloro-7-fluoro-4-((1-(2-fluoro-5-(2-hy-droxyethyl)phenyl)ethyl)amino)-2-methylquinolin-6-yl)pyrimidin-2-yl)propan-2-ol (325);

(R)-2-(5-(3-chloro-4-((1-(2-fluoro-5-methoxyphenyl)ethyl)amino)-2-methylquinolin-6-yl)pyrimidin-2-yl)propan-2-ol (326);

(R)-2-(5-(3-chloro-4-((1-(2-fluoro-5-methoxyphenyl)ethyl)amino)quinolin-6-yl)pyrimidin-2-yl)propan-2-ol (327);

(R)-6-bromo-3-chloro-N-(1-(2-fluoro-5-methoxyphenyl)ethyl)-2-methylquinolin-4-amine (328);

(R)-2-(5-(3-chloro-4-((1-(2-fluoro-5-vinylphenyl)ethyl)amino)-2-methylquinolin-6-yl)pyrimidin-2-yl)propan-2-ol (330);

(R)-2-(5-(3-chloro-4-((1-(4-fluoro-[1,1'-biphenyl]-3-yl)ethyl)amino)-2-methylquinolin-6-yl)pyrimidin-2-yl)propan-2-ol (331);

(R)-2-(5-(3-chloro-4-((1-(4-fluoro-2'-methyl-[1,1'-biphenyl]-3-yl)ethyl)amino)-2-methylquinolin-6-yl)pyrimidin-2-yl)propan-2-ol (332);

(R)-2-(5-(3-chloro-4-((1-(5-(cyclopent-1-en-1-yl)-2-fluorophenyl)ethyl)amino)-2-methylquinolin-6-yl)pyrimidin-2-yl)propan-2-ol (333);

(R)-2-(5-(3-chloro-4-((1-(2-fluoro-5-methylphenyl)ethyl)amino)-2-methylquinolin-6-yl)pyrimidin-2-yl)propan-2-ol (334);

(R)-2-(5-(3-chloro-4-((1-(2-fluoro-5-(1H-pyrazol-4-yl)phenyl)ethyl)amino)-2-methylquinolin-6-yl)pyrimidin-2-yl)propan-2-ol (335);

(R)-2-(5-(3-chloro-4-((1-(2-fluoro-5-(1H-pyrazol-3-yl)phenyl)ethyl)amino)-2-methylquinolin-6-yl)pyrimidin-2-yl)propan-2-ol (336);

tert-butyl (R)-4-(3-(1-((3-chloro-6-(2-(2-hydroxypropan-2-yl)pyrimidin-5-yl)quinolin-4-yl)amino)ethyl)-4-fluorophenyl)-3,6-dihydropyridine-1(2H)-carboxylate (337);

(R)-2-(5-(3-chloro-4-((1-(2-fluoro-5-(1,2,3,6-tetrahydropyridin-4-yl)phenyl)ethyl)amino)quinolin-6-yl)pyrimidin-2-yl)propan-2-ol (338);

(R)-2-(5-(3-chloro-4-((1-(2-fluoro-5-(1-methyl-1H-pyrazol-4-yl)phenyl)ethyl)amino)quinolin-6-yl)pyrimidin-2-yl)propan-2-ol (339);

(R)-2-(5-(3-chloro-4-((1-(2-fluoro-5-(pyrimidin-5-yl)phenyl)ethyl)amino)quinolin-6-yl)pyrimidin-2-yl)propan-2-ol (340);

(R)-2-(5-(3-chloro-4-((1-(2-fluoro-5-(pyrazin-2-yl)phenyl)ethyl)amino)quinolin-6-yl)pyrimidin-2-yl)propan-2-ol (341);

(R)-2-(4-(5-(3-chloro-4-((1-(2-fluoro-5-(1H-pyrazol-4-yl)phenyl)ethyl)amino)-2-methylquinolin-6-yl)pyrimidin-2-yl)piperazin-1-yl)acetic acid (342);

(R)-2-(5-(3-chloro-4-((1-(2-fluoro-5-(2-(2-hydroxypropan-2-yl)pyrimidin-5-yl)phenyl)ethyl)amino)-2-methylquinolin-6-yl)pyrimidin-2-yl)propan-2-ol (343);

(R)-2-(5-(3-chloro-4-((1-(2-fluoro-5-(1-methyl-1H-pyrazol-4-yl)phenyl)ethyl)amino)-2-methylquinolin-6-yl)pyrimidin-2-yl)propan-2-ol (344);

(R)-2-(5-(3-chloro-4-((1-(2-fluoro-5-(pyrimidin-2-yl)phenyl)ethyl)amino)quinolin-6-yl)pyrimidin-2-yl)propan-2-ol (345);

(R)-2-(4-(3-(1-((3-chloro-6-(2-(2-hydroxypropan-2-yl)pyrimidin-5-yl)quinolin-4-yl)amino)ethyl)-4-fluorophenyl)-1H-pyrazol-1-yl)acetic acid (346);

(R)-2-(5-(3-chloro-4-((1-(2-fluoro-5-(thiazol-5-yl)phenyl)ethyl)amino)quinolin-6-yl)pyrimidin-2-yl)propan-2-ol (347);

(R)-2-(5-(4-((1-(5-(6-aminopyridin-3-yl)-2-fluorophenyl)ethyl)amino)-3-chloroquinolin-6-yl)pyrimidin-2-yl)propan-2-ol (348);

(R)-1-(4-(3-(1-((3-chloro-6-(2-(2-hydroxypropan-2-yl)pyrimidin-5-yl)quinolin-4-yl)amino) ethyl)-4-fluorophenyl)-1H-pyrazol-1-yl)-2-methylpropan-2-ol (349);

(R)-2-(5-(4-((1-(5-(2-aminopyridin-4-yl)-2-fluorophenyl)ethyl)amino)-3-chloroquinolin-6-yl)pyrimidin-2-yl)propan-2-ol (350);

(S)-2-(5-(3-chloro-4-((2,2-difluoro-1-(2-fluoro-5-methylphenyl)ethyl)amino)-2-methylquinolin-6-yl)pyrimidin-2-yl)propan-2-ol (351);

(S)-2-(5-(3-chloro-4-((2,2-difluoro-1-(2-fluoro-5-vinylphenyl)ethyl)amino)-2-methylquinolin-6-yl)pyrimidin-2-yl)propan-2-ol (352);

2-(5-(4-([1,1'-biphenyl]-2-yl)-3-chloro-2-methylquinolin-6-yl)pyrimidin-2-yl)propan-2-ol (353);

(S)-methyl 3-((S)-1-((3-chloro-6-(2-(2-hydroxypropan-2-yl)pyrimidin-5-yl)quinolin-4-yl)amino)ethyl)piperidine-1-carboxylate (354);

tert-Butyl (R)-(3-(1-((3-chloro-6-(2-(2-hydroxypropan-2-yl)pyrimidin-5-yl)-2-methylquinolin-4-yl)amino) ethyl)-4-fluorophenyl)carbamate (359);

(R)-2-(5-(4-((1-(5-amino-2-fluorophenyl)ethyl)amino)-3-chloro-2-methylquinolin-6-yl)pyrimidin-2-yl)propan-2-ol (360);

(R)-1-(3-(1-((3-chloro-6-(2-(2-hydroxypropan-2-yl)pyrimidin-5-yl)-2-methylquinolin-4-yl)amino)ethyl)-4-fluorophenyl)pyrrolidin-2-one (361);

(R)-1-(3-(1-((3-chloro-6-(2-(2-hydroxypropan-2-yl)pyrimidin-5-yl)quinolin-4-yl)amino)ethyl)-4-fluorophenyl)pyrrolidin-2-one (362);

(R)-1-(3-(1-((3-chloro-6-(2-(2-hydroxypropan-2-yl)pyrimidin-5-yl)quinolin-4-yl)amino)ethyl) phenyl)pyrrolidin-2-one (363);

(R)-2-(5-(3-chloro-4-((1-(2-fluoro-5-(pyrrolidin-1-yl)phenyl)ethyl)amino)quinolin-6-yl)pyrimidin-2-yl)propan-2-ol (364);

(R)-2-(5-(3-chloro-4-((1-(2-fluoro-5-(1H-pyrazol-1-yl)phenyl)ethyl)amino)-2-methylquinolin-6-yl)pyrimidin-2-yl)propan-2-ol (365);

(R)-2-(5-(3-chloro-4-((1-(2-fluoro-5-(1H-pyrazol-1-yl)phenyl)ethyl)amino)quinolin-6-yl)pyrimidin-2-yl)propan-2-ol (366);

(R)-3-(3-(1-((3-chloro-6-(2-(2-hydroxypropan-2-yl)pyrimidin-5-yl)quinolin-4-yl)amino)ethyl)-4-fluorophenyl)oxazolidin-2-one (367);

(R)-2-(5-(4-((1-(3-(1H-pyrazol-1-yl)phenyl)ethyl)amino)-3-chloroquinolin-6-yl)pyrimidin-2-yl)propan-2-ol (368);

(R)-4-(3-(1-((3-chloro-6-(2-(2-hydroxypropan-2-yl)pyrimidin-5-yl)quinolin-4-yl)amino)ethyl)-4-fluorophenyl)morpholin-3-one (369);

(R)-1-(3-(1-((3-chloro-6-(2-(2-hydroxypropan-2-yl)pyrimidin-5-yl)quinolin-4-yl)amino)ethyl)-4-fluorophenyl)imidazolidin-2-one (370);

(R)-2-(5-(3-chloro-4-((1-(2-fluoro-5-(4H-1,2,4-triazol-4-yl)phenyl)ethyl)amino)quinolin-6-yl)pyrimidin-2-yl)propan-2-ol (371);

(S)-1-(3-(1-((3-chloro-6-(2-(2-hydroxypropan-2-yl)pyrimidin-5-yl)-2-methylquinolin-4-yl)amino)-2,2-difluoroethyl)-4-fluorophenyl)imidazolidin-2-one (372);

(R)-1-(3-(1-((3-chloro-6-(2-(2-hydroxypropan-2-yl)pyrimidin-5-yl)-2-methylquinolin-4-yl)amino)ethyl)-4-fluorophenyl)imidazolidin-2-one (373);

(R)-2-(5-(4-((1-(5-amino-2-fluorophenyl)ethyl)amino)-3-chloroquinolin-6-yl)pyrimidin-2-yl)propan-2-ol (374);

(R)-3-(1-((3-chloro-6-(2-(2-hydroxypropan-2-yl)pyrimidin-5-yl)-2-methylquinolin-4-yl)amino)ethyl)-4-fluorobenzonitrile (375);

(R)-3-(1-((3-chloro-6-(2-(2-hydroxypropan-2-yl)pyrimidin-5-yl)quinolin-4-yl)amino)ethyl)-4-fluorobenzonitrile (376);

(R)-2-(4-(5-(3-chloro-4-((1-(5-cyano-2-fluorophenyl)ethyl)amino)-2-methylquinolin-6-yl)pyrimidin-2-yl)piperazin-1-yl)acetic acid (377);

(R)-3-(1-((3-chloro-6-(2-(2-hydroxypropan-2-yl)pyrimidin-5-yl)-2-methylquinolin-4-yl)amino)-2,2-difluoroethyl)-4-fluorobenzonitrile (378);

(R)-3-(1-((3-chloro-7-fluoro-6-(2-(2-hydroxypropan-2-yl)pyrimidin-5-yl)quinolin-4-yl)amino)ethyl)-4-fluorobenzonitrile (379);

(S)-3-(1-((3-chloro-6-(2-(2-hydroxypropan-2-yl)pyrimidin-5-yl)-2-methylquinolin-4-yl)amino)-2,2-difluoroethyl)-4-fluorobenzonitrile (380);

(S)-3-(1-((3-chloro-7-fluoro-6-(2-(2-hydroxypropan-2-yl)pyrimidin-5-yl)quinolin-4-yl)amino)-2,2-difluoroethyl)-4-fluorobenzonitrile (381);

(R)-3-(1-((3-chloro-7-fluoro-6-(2-(2-hydroxypropan-2-yl)pyrimidin-5-yl)-2-methylquinolin-4-yl)amino)ethyl)-4-fluorobenzonitrile (382);

(R)-3-(1-((3-chloro-7-fluoro-6-(2-(2-hydroxypropan-2-yl)pyrimidin-5-yl)-2-methylquinolin-4-yl)amino)ethyl)benzonitrile (383);

(R)-3-chloro-4-((1-(5-cyano-2-fluorophenyl)ethyl)amino)-6-(2-(2-hydroxypropan-2-yl)pyrimidin-5-yl)-N-(pyridin-3-yl)quinoline-2-carboxamide (385);

(R)-3-(1-((3-chloro-6-(2-(2-hydroxypropan-2-yl)pyrimidin-5-yl)-2-methylquinolin-4-yl)amino)ethyl)benzonitrile (386);

(R)-3-(1-((3-chloro-6-(2-(2-hydroxypropan-2-yl)pyrimidin-5-yl)-2-methylquinolin-4-yl) amino)ethyl)-4-fluorobenzamide (387);

(R)-3-(1-((3-chloro-6-(2-(2-hydroxypropan-2-yl)pyrimidin-5-yl)quinolin-4-yl)amino)ethyl)-4-fluorobenzamide (388);

(R)-2-(4-(5-(4-((1-(5-carbamoyl-2-fluorophenyl)ethyl)amino)-3-chloro-2-methylquinolin-6-yl)pyrimidin-2-yl)piperazin-1-yl)acetic acid (389);

(S)-3-(1-((3-chloro-6-(2-(2-hydroxypropan-2-yl)pyrimidin-5-yl)-2-methylquinolin-4-yl)amino)-2,2-difluoroethyl)-4-fluorobenzamide (390);

(S)-3-(1-((3-chloro-7-fluoro-6-(2-(2-hydroxypropan-2-yl)pyrimidin-5-yl)quinolin-4-yl)amino)-2,2-difluoroethyl)-4-fluorobenzamide (391);

(R)-3-(1-((3-chloro-7-fluoro-6-(2-(2-hydroxypropan-2-yl)pyrimidin-5-yl)quinolin-4-yl) amino)ethyl)-4-fluorobenzamide (392);

(R)-3-(1-((3-chloro-7-fluoro-6-(2-(2-hydroxypropan-2-yl)pyrimidin-5-yl)-2-methylquinolin-4-yl)amino)ethyl)-4-fluorobenzamide (393);

(R)-3-(1-((3-chloro-7-fluoro-6-(2-(2-hydroxypropan-2-yl)pyrimidin-5-yl)-2-methylquinolin-4-yl)amino)ethyl)benzamide (394);

(R)-4-((1-(5-carbamoyl-2-fluorophenyl)ethyl)amino)-3-chloro-6-(2-(2-hydroxypropan-2-yl)pyrimidin-5-yl)-N-(pyridin-3-yl)quinoline-2-carboxamide (395);

(R)-2-(5-(4-((1-(5-benzyl-2-fluorophenyl)ethyl)amino)-3-chloro-2-methylquinolin-6-yl)pyrimidin-2-yl)propan-2-ol (396);

1-(3-((R)-1-((3-chloro-6-(2-(2-hydroxypropan-2-yl)pyrimidin-5-yl)-2-methylquinolin-4-yl)amino)ethyl)-4-fluorophenyl)ethane-1,2-diol (397);

1-(3-((R)-1-((3-chloro-6-(2-(2-hydroxypropan-2-yl)pyrimidin-5-yl)quinolin-4-yl)amino)ethyl)-4-fluorophenyl)ethane-1,2-diol (398);

3-(3-((R)-1-((3-chloro-6-(2-(2-hydroxypropan-2-yl)pyrimidin-5-yl)quinolin-4-yl)amino)ethyl)-4-fluorophenyl)propane-1,2-diol (399);

1-(3-((R)-1-((3-chloro-6-(2-(2-hydroxypropan-2-yl)pyrimidin-5-yl)quinolin-4-yl)amino)ethyl)-4-fluorophenyl)ethane-1,2-diol (400);

1-(3-((R)-1-((3-chloro-6-(2-(2-hydroxypropan-2-yl)pyrimidin-5-yl)quinolin-4-yl)amino)ethyl)-4-fluorophenyl)ethane-1,2-diol (401);

1-(3-((S)-1-((3-chloro-6-(2-(2-hydroxypropan-2-yl)pyrimidin-5-yl)-2-methylquinolin-4-yl)amino)-2,2-difluoroethyl)-4-fluorophenyl)ethane-1,2-diol (402);

2-(3-((R)-1-((3-chloro-6-(2-(2-hydroxypropan-2-yl)pyrimidin-5-yl)-2-methylquinolin-4-yl)amino)ethyl)-4-fluorophenyl)propane-1,2-diol (403);

(R)-3-(1-((3-chloro-6-(2-(2-hydroxypropan-2-yl)pyrimidin-5-yl)-2-methylquinolin-4-yl)amino)ethyl)-4-fluorophenol (404);

(R)-3-(1-((3-chloro-6-(2-(2-hydroxypropan-2-yl)pyrimidin-5-yl)quinolin-4-yl)amino)ethyl)-4-fluorophenol (405);

(R)-2-(5-(3-chloro-4-((1-(5-chloro-2-fluorophenyl)ethyl)amino)-2-methylquinolin-6-yl)pyrimidin-2-yl)propan-2-ol (406);

(R)-3-(1-((3-chloro-6-(2-(2-hydroxypropan-2-yl)pyrimidin-5-yl)-2-methylquinolin-4-yl) amino)ethyl)-4-fluorobenzoic acid (407);

(R)-2-(5-(3-chloro-4-((1-(2-fluoro-5-(2-hydroxypropan-2-yl)phenyl)ethyl)amino)-2-methylquinolin-6-yl)pyrimidin-2-yl)propan-2-ol, TFA salt (408);

(R)-1-(3-(1-((3-chloro-6-(2-(2-hydroxypropan-2-yl)pyrimidin-5-yl)quinolin-4-yl)amino)ethyl)-4-fluorophenyl)ethan-1-one (409);

(R)-2-(5-(3-chloro-4-((1-(2-fluoro-5-(2-hydroxypropan-2-yl)phenyl)ethyl)amino)quinolin-6-yl)pyrimidin-2-yl)propan-2-ol (410);

(R)-2-(5-(3-chloro-4-((1-(2-fluoro-5-(phenylethynyl)phenyl)ethyl)amino)quinolin-6-yl)pyrimidin-2-yl)propan-2-ol (411);

(R)-2-(5-(3-chloro-4-((1-(2-fluoro-5-(1H-tetrazol-5-yl)phenyl)ethyl)amino)-2-methylquinolin-6-yl)pyrimidin-2-yl)propan-2-ol (412);

(R)-2-(5-(3-chloro-4-((1-(2-fluoro-5-(2-methyl-2H-tetrazol-5-yl)phenyl)ethyl)amino)quinolin-6-yl)pyrimidin-2-yl)propan-2-ol (413);

(R)-2-(5-(3-chloro-4-((1-(2-fluoro-5-(1H-1,2,4-triazol-5-yl)phenyl)ethyl)amino)quinolin-6-yl)pyrimidin-2-yl)propan-2-ol (414);

Methyl (R)-3-(1-((3-chloro-6-(2-(2-hydroxypropan-2-yl)pyrimidin-5-yl)quinolin-4-yl)amino)ethyl)-4-fluorobenzoate (415);

(R)-3-(1-((3-chloro-6-(2-(2-hydroxypropan-2-yl)pyrimidin-5-yl)quinolin-4-yl)amino)ethyl)-4-fluoro-N-methylbenzamide (416);

(R)-3-(1-((3-chloro-6-(2-(2-hydroxypropan-2-yl)pyrimidin-5-yl)quinolin-4-yl)amino)ethyl)-4-fluoro-N,N-dimethylbenzamide (417);

(S)-2-(5-(3-chloro-4-((2,2-difluoro-1-(2-fluoro-5-(2-hydroxypropan-2-yl)phenyl)ethyl)amino)-2-methylquinolin-6-yl)pyrimidin-2-yl)propan-2-ol (418);

(R)-2-(5-(3-chloro-4-((1-(2-fluoro-5-(1H-1,2,3-triazol-4-yl)phenyl)ethyl)amino)quinolin-6-yl)pyrimidin-2-yl)propan-2-ol (419);

(R)-2-(5-(3-chloro-4-((1-(2-fluoro-5-(1-methyl-1H-1,2,3-triazol-4-yl)phenyl)ethyl)amino) quinolin-6-yl)pyrimidin-2-yl)propan-2-ol (420);

(R)-2-(5-(3-chloro-4-((1-(2-fluoro-5-(1-methyl-1H-1,2,3-triazol-5-yl)phenyl)ethyl)amino)quinolin-6-yl)pyrimidin-2-yl)propan-2-ol (421);

5-(3-((R)-1-((3-chloro-6-(2-(2-hydroxypropan-2-yl)pyrimidin-5-yl)quinolin-4-yl)amino)ethyl)-4-fluorophenyl)imidazolidine-2,4-dione (422 and 423);

(R)-3-(1-((3-chloro-6-(2-(2-hydroxypropan-2-yl)pyrimidin-5-yl)quinolin-4-yl)amino)ethyl)-4-fluorobenzaldehyde oxime (424);

(R)-2-(5-(3-chloro-4-((1-(2-fluoro-5-(methylsulfonyl)phenyl)ethyl)amino)quinolin-6-yl)pyrimidin-2-yl)propan-2-ol (425);

(R)-3-(1-((3-chloro-6-(2-(2-hydroxypropan-2-yl)pyrimidin-5-yl)quinolin-4-yl)amino)ethyl)-4-fluorobenzenesulfonamide (426);

Methyl (R)-3-((3-(1-((3-chloro-6-(2-(2-hydroxypropan-2-yl)pyrimidin-5-yl)quinolin-4-yl)amino)ethyl)-4-fluorophenyl)sulfonyl)propanoate (427);

(R)-3-(3-(1-((3-chloro-6-(2-(2-hydroxypropan-2-yl)pyrimidin-5-yl)quinolin-4-yl)amino)ethyl)-4-fluorophenyl)-1H-pyrazole-5-carboxylic acid (428);

(R)-2-(5-(4-((1-(5-(aminomethyl)-2-fluorophenyl)ethyl)amino)-3-chloroquinolin-6-yl)pyrimidin-2-yl)propan-2-ol (429);

(R)-2-(5-(3-chloro-4-((1-(2-fluoro-5-(hydroxymethyl)phenyl)ethyl)amino)quinolin-6-yl)pyrimidin-2-yl)propan-2-ol (430);

(R)-2-(5-(3-chloro-4-((1-(2-fluoro-5-(hydroxymethyl)phenyl)ethyl)amino)-2-methylquinolin-6-yl)pyrimidin-2-yl)propan-2-ol (431);

(R)-2-(5-(3-chloro-4-((1-(2-fluoro-5-(hydroxymethyl)phenyl)ethyl)amino)-2-methylquinolin-6-yl)-4,5-dihydropyrimidin-2-yl)propan-2-ol (432);

2-(5-(3-chloro-4-(((1R)-1-(2-fluoro-5-(1-hydroxyethyl)phenyl)ethyl)amino)-2-methylquinolin-6-yl)pyrimidin-2-yl)propan-2-ol (433);

2-(5-(4-(((1S)-1-(5-(1-amino-2-hydroxyethyl)-2-fluorophenyl)-2,2-difluoroethyl)amino)-3-chloro-2-methylquinolin-6-yl)pyrimidin-2-yl)propan-2-ol (434);

(R)-2-(5-(3-chloro-4-((1-(2-fluoro-5-(2-hydroxyethoxy)phenyl)ethyl)amino)-2-methylquinolin-6-yl)pyrimidin-2-yl)propan-2-ol (435);

(R)-2-(3-(1-((3-chloro-6-(2-(2-hydroxypropan-2-yl)pyrimidin-5-yl)-2-methylquinolin-4-yl)amino)ethyl)-4-fluorophenyl)acetic acid (436);

(R)-2-(5-(3-chloro-4-((1-(3-(2-hydroxyethoxy)phenyl)ethyl)amino)-2-methylquinolin-6-yl)pyrimidin-2-yl)propan-2-ol (437);

(R)-2-(3-(1-((3-chloro-6-(2-(2-hydroxypropan-2-yl)pyrimidin-5-yl)-2-methylquinolin-4-yl)amino)ethyl)phenoxy)acetic acid (438);

(R)-2-(3-(1-((3-chloro-6-(2-(2-hydroxypropan-2-yl)pyrimidin-5-yl)-2-methylquinolin-4-yl)amino)ethyl)-4-fluorophenoxy)acetic acid (439);

(R)-2-(5-(3-chloro-7-fluoro-4-((1-(2-fluoro-5-(2-hydroxyethoxy)phenyl)ethyl)amino)-2-methylquinolin-6-yl)pyrimidin-2-yl)propan-2-ol (440);

(R)-2-(5-(3-chloro-4-((1-(2-fluorophenyl)ethyl)amino)-2-methylquinolin-6-yl)pyrimidin-2-yl)propan-2-ol (441);

(R)-2-(5-(3-chloro-7-fluoro-4-((1-(2-fluoro-5-(2-hydroxyethyl)phenyl)ethyl)amino)-2-methylquinolin-6-yl)pyrimidin-2-yl)propan-2-ol (442);

(R)-3-(3-(1-((3-chloro-7-fluoro-6-(2-(2-hydroxypropan-2-yl)pyrimidin-5-yl)-2-methylquinolin-4-yl)amino)ethyl)-4-fluorophenoxy)propan-1-ol (443);

(R)-3-(3-(1-((3-chloro-6-(2-(2-hydroxypropan-2-yl)pyrimidin-5-yl)-2-methylquinolin-4-yl)amino)ethyl)-4-fluorophenoxy)propan-1-ol (444);

(R)-3-(3-(1-((3-chloro-7-fluoro-6-(2-(2-hydroxypropan-2-yl)pyrimidin-5-yl)-2-methylquinolin-4-yl)amino)ethyl)-4-fluorophenyl)propanamide (445);

(R)-3-(3-(1-((3-chloro-7-fluoro-6-(2-(2-hydroxypropan-2-yl)pyrimidin-5-yl)-2-methylquinolin-4-yl)amino)ethyl)-4-fluorophenyl)propanoic acid (446);

(R)-3-(1-((3-chloro-2-methyl-6-(2-(3-oxopiperazin-1-yl)pyrimidin-5-yl)quinolin-4-yl)amino)ethyl)-4-fluorobenzamide (447);

(R)-3-(1-((3-chloro-7-fluoro-2-methyl-6-(2-(3-oxopiperazin-1-yl)pyrimidin-5-yl)quinolin-4-yl)amino)ethyl)-4-fluorobenzamide (448);

(R)-5-(4-(((1-(5-bromo-2-fluorophenyl)ethyl)amino)-3-chloro-7-fluoro-2-methylquinolin-6-yl)pyridin-2(1H)-one (449);

(R)-3-(1-((3-chloro-7-fluoro-2-methyl-6-(6-oxo-1,6-dihydropyridin-3-yl)quinolin-4-yl)amino)ethyl)-4-fluorobenzonitrile (450);

(R)-6-chloro-N-(1-(2-fluoro-5-methoxyphenyl)ethyl)quinolin-4-amine (456);

N-(1-(4-(3-chloro-4-(((R)-1-(2-fluorophenyl)ethyl)amino)quinolin-6-yl)phenyl)-2-hydroxyethyl)acetamide (482);

(R)-1-(1-(4-(3-chloro-4-((1-(2-fluorophenyl)ethyl)amino)quinolin-6-yl)phenyl)cyclobutyl)urea (483);

4-(5-(3-chloro-4-((1-(3-fluoro-6-methylpyridin-2-yl)ethyl)amino)quinolin-6-yl)pyrimidin-2-yl)piperazin-2-one (484);

(R)-2-(4-(3-chloro-4-((1-(pyrazin-2-yl)ethyl)amino)quinolin-6-yl)phenyl)propan-2-ol (490);

(R)-2-(4-(3-chloro-4-((1-(2-fluorophenyl)ethyl)amino)-2-methylquinolin-6-yl)phenyl)propan-2-ol (500);

2-(4-(3-chloro-2-methyl-4-((1-(thiophen-2-yl)ethyl)amino)quinolin-6-yl)phenyl)propan-2-ol (502);

2-(4-(3-chloro-2-methyl-4-((1-(thiophen-3-yl)ethyl)amino)quinolin-6-yl)phenyl)propan-2-ol (503);

(R)-6-bromo-3-chloro-N-(1-(2-fluoro-5-(pyrimidin-5-yl)phenyl)ethyl)quinolin-4-amine (532);

(R)-3-chloro-N-(1-(2-fluoro-5-(pyrimidin-5-yl)phenyl)ethyl)-6-(pyridin-4-yl)quinolin-4-amine (540);

(R)-3-chloro-6-fluoro-N-(1-(2-fluoro-5-(pyrimidin-5-yl)phenyl)ethyl)quinolin-4-amine (544);

(R)-3,6-dichloro-N-(1-(2-fluoro-5-(pyrimidin-5-yl)phenyl)ethyl)quinolin-4-amine (545);

(R)-6-bromo-N-(1-(2-fluoro-5-(pyrimidin-5-yl)phenyl)ethyl)quinolin-4-amine (546);

(R)-3-chloro-N-(1-(2-fluoro-5-(pyrimidin-5-yl)phenyl)ethyl)-6-(1-methyl-1H-pyrazol-4-yl)quinolin-4-amine (550);

(R)-2-(5-(3-chloro-4-((1-(2-fluoro-5-(pyridin-3-yl)phenyl)ethyl)amino)quinolin-6-yl)pyrimidin-2-yl)propan-2-ol (553);

(R)-2-(3-(1-((3-chloro-7-fluoro-6-(2-(2-hydroxypropan-2-yl)pyrimidin-5-yl)-2-methylquinolin-4-yl)amino)ethyl)-4-fluorophenyl)acetamide (554);

(R)-4-(5-(4-((1-(5-bromo-2-fluorophenyl)ethyl)amino)-3-chloro-7-fluoro-2-methylquinolin-6-yl)pyrimidin-2-yl)piperazin-2-one (560);

(R)-3-(1-((3-chloro-7-fluoro-2-methyl-6-(2-(3-oxopiperazin-1-yl)pyrimidin-5-yl)quinolin-4-yl)amino)ethyl)-4-fluorobenzonitrile (561);

4-(5-(4-((1-(6-amino-3-fluoropyridin-2-yl)ethyl)amino)-3-chloroquinolin-6-yl)pyrimidin-2-yl)piperazin-2-one (562);

2-(5-(3-chloro-4-(((S)-1-((S)-1-(methylsulfonyl)piperidin-3-yl)ethyl)amino)quinolin-6-yl)pyrimidin-2-yl)propan-2-ol (563);

2-(5-(3-chloro-4-(((S)-1-((S)-1-((1-methyl-1H-pyrazol-4-yl)sulfonyl)piperidin-3-yl)ethyl)amino)quinolin-6-yl)pyrimidin-2-yl)propan-2-ol (564);

((S)-3-((S)-1-((3-chloro-6-(2-(2-hydroxypropan-2-yl)pyrimidin-5-yl)quinolin-4-yl)amino)ethyl)piperidin-1-yl)(1H-pyrazol-4-yl)methanone (565);

2-(5-(3-chloro-4-(((S)-1-((S)-1-(pyrimidin-5-yl)piperidin-3-yl)ethyl)amino)quinolin-6-yl)pyrimidin-2-yl)propan-2-ol (567);

(R)-2-((1-(4-(3-chloro-4-((1-(2-fluorophenyl)ethyl)amino)quinolin-6-yl)phenyl)cyclobutyl)amino)ethan-1-ol (568);

(R)-1-(4-(3-chloro-4-((1-(2-fluorophenyl)ethyl)amino)quinolin-6-yl)benzyl)urea (569);

(R)-2-((5-(3-chloro-4-((1-(2-fluorophenyl)ethyl)amino)quinolin-6-yl)pyrimidin-2-yl)amino)acetamide (585);

(R)-1-((5-(3-chloro-4-((1-(2-fluorophenyl)ethyl)amino)quinolin-6-yl)pyrimidin-2-yl)amino)cyclopropane-1-carboxamide (587);

2-((5-(3-chloro-4-(((R)-1-(2-fluorophenyl)ethyl)amino)quinolin-6-yl)pyrimidin-2-yl)amino)propanamide (591);

N-(2-(4-(3-chloro-4-((1-(2-fluorophenyl)ethyl)amino)quinolin-6-yl)phenyl)propan-2-yl)acetamide (592);

(R)-2-(4-(5-(3-chloro-4-((1-(2-fluorophenyl)ethyl)amino)quinolin-6-yl)pyrimidin-2-yl)piperidin-1-yl)acetic acid (593);

(R)-2-(4-(5-(3-chloro-7-fluoro-4-((1-(2-fluorophenyl)ethyl)amino)quinolin-6-yl)pyrimidin-2-yl)piperidin-1-yl)acetic acid (594);

2-(5-(3-chloro-7-fluoro-4-((1-(2-fluorophenyl)ethyl)amino)quinolin-6-yl)pyrazin-2-yl)propan-2-ol (595);

1-(5-(3-chloro-7-fluoro-4-((1-(2-fluorophenyl)ethyl)amino)quinolin-6-yl)pyrimidin-2-yl)ethane-1,2-diol (596);

1-(5-(3-chloro-7-fluoro-4-((1-(2-fluorophenyl)ethyl)amino)quinolin-6-yl)pyrimidin-2-yl)ethane-1,2-diol (597);

3-chloro-7-fluoro-N-(1-(2-fluorophenyl)ethyl)-6-(4-(morpholin-3-yl)phenyl)quinolin-4-amine (598);

3-(1-((3-chloro-6-(4-(1,2-dihydroxyethyl)phenyl)-7-fluoroquinolin-4-yl)amino)ethyl)-4-fluorobenzonitrile (599);

1-(4-(3-chloro-7-fluoro-4-((1-(2-fluorophenyl)ethyl)amino)quinolin-6-yl)phenyl)-2-(methylamino)ethan-1-ol (600);

3-(1-((3-chloro-6-(4-(1,2-dihydroxyethyl)phenyl)-7-fluoroquinolin-4-yl)amino)ethyl)-4-fluorobenzamide (601);

4-(4-(5-(3-chloro-7-fluoro-4-((1-(2-fluorophenyl)ethyl)amino)quinolin-6-yl)pyrimidin-2-yl) piperazin-1-yl)-4-oxobutanoic acid (602);

1-(4-(5-(3-chloro-7-fluoro-4-((1-(2-fluorophenyl)ethyl)amino)quinolin-6-yl)pyrimidin-2-yl)piperazin-1-yl)-2-hydroxypropan-1-one (603);

(2S)-2-amino-1-(4-(5-(3-chloro-7-fluoro-4-((1-(2-fluorophenyl)ethyl)amino)quinolin-6-yl)pyrimidin-2-yl)piperazin-1-yl)-3-hydroxypropan-1-one (604);

(3S)-3-amino-4-(4-(5-(3-chloro-7-fluoro-4-((1-(2-fluorophenyl)ethyl)amino)quinolin-6-yl)pyrimidin-2-yl)piperazin-1-yl)-4-oxobutanoic acid (605);

(2R)-2-amino-1-(4-(5-(3-chloro-7-fluoro-4-((1-(2-fluorophenyl)ethyl)amino)quinolin-6-yl)pyrimidin-2-yl)piperazin-1-yl)-3-hydroxypropan-1-one (606);

(3R)-3-amino-4-(4-(5-(3-chloro-7-fluoro-4-((1-(2-fluorophenyl)ethyl)amino)quinolin-6-yl)pyrimidin-2-yl)piperazin-1-yl)-4-oxobutanoic acid (607);

3-chloro-7-fluoro-N-(1-(2-fluorophenyl)ethyl)-6-(2-(piperazin-1-yl)pyrimidin-5-yl)quinolin-4-amine (608);

2-(5-(3-chloro-7-fluoro-4-((1-(2-fluorophenyl)cyclobutyl)amino)quinolin-6-yl)pyrimidin-2-yl)propan-2-ol (609);

1-(2-(5-(3-chloro-7-fluoro-4-((1-(2-fluorophenyl)ethyl)amino)quinolin-6-yl)pyrimidin-2-yl)-2-hydroxyethyl)piperidine-4-carboxylic acid (610);

(1R,5S,8r)-3-(5-(3-chloro-7-fluoro-4-((1-(2-fluorophenyl)ethyl)amino)quinolin-6-yl)pyrimidin-2-yl)-3-azabicyclo[3.2.1]octane-8-carboxylic acid (611); or 2-(5-(4-((1-(5-bromo-2-fluorophenyl)ethyl)amino)-3-chloro-8-fluoroquinolin-6-yl)pyrimidin-2-yl)propan-2-ol (612).

* * * * *